United States Patent
Ludlow et al.

(10) Patent No.: US 9,271,824 B2
(45) Date of Patent: Mar. 1, 2016

(54) CELL SCAFFOLD CONSTRUCTS

(71) Applicants: John W. Ludlow, Carrboro, NC (US); Manuel J. Jayo, Winston-Salem, NC (US); Joydeep Basu, Winston-Salem, NC (US); Timothy A. Bertram, Winston-Salem, NC (US); Christopher W. Genheimer, Colfax, NC (US); Kelly I. Guthrie, Winston-Salem, NC (US); Roger M. Ilagan, Burlington, NC (US); Deepak Jain, Winston-Salem, CA (US); Oluwatoyin A. Knight, Winston-Salem, NC (US); Richard Payne, Winston-Salem, NC (US); Sarah F. Quinlan, Clemmons, NC (US); H. Scott Rapoport, Winston-Salem, NC (US); Namrata D. Sangha, Winston-Salem, NC (US)

(72) Inventors: John W. Ludlow, Carrboro, NC (US); Manuel J. Jayo, Winston-Salem, NC (US); Joydeep Basu, Winston-Salem, NC (US); Timothy A. Bertram, Winston-Salem, NC (US); Christopher W. Genheimer, Colfax, NC (US); Kelly I. Guthrie, Winston-Salem, NC (US); Roger M. Ilagan, Burlington, NC (US); Deepak Jain, Winston-Salem, CA (US); Oluwatoyin A. Knight, Winston-Salem, NC (US); Richard Payne, Winston-Salem, NC (US); Sarah F. Quinlan, Clemmons, NC (US); H. Scott Rapoport, Winston-Salem, NC (US); Namrata D. Sangha, Winston-Salem, NC (US)

(73) Assignee: REGENMEDTX, LLC, Winston-Salem, NC (US)

(*) Notice: Subject to any disclaimer, the term of this patent is extended or adjusted under 35 U.S.C. 154(b) by 0 days.

(21) Appl. No.: 13/682,614

(22) Filed: Nov. 20, 2012

(65) Prior Publication Data
US 2013/0173015 A1 Jul. 4, 2013

Related U.S. Application Data

(62) Division of application No. 12/612,606, filed on Nov. 4, 2009, now Pat. No. 8,337,485.

(60) Provisional application No. 61/201,555, filed on Dec. 10, 2008, provisional application No. 61/201,554,
(Continued)

(51) Int. Cl.
A61F 2/04 (2013.01)
A61M 27/00 (2006.01)
(Continued)

(52) U.S. Cl.
CPC ............ *A61F 2/042* (2013.01); *A61L 27/18* (2013.01); *A61L 27/3804* (2013.01); *A61L 27/3826* (2013.01); *A61L 27/3882* (2013.01); *A61L 2430/22* (2013.01)

(58) Field of Classification Search
CPC ............................ A61F 2/04; A61M 27/00
USPC .............................. 623/23.64–23.7
See application file for complete search history.

(56) References Cited

U.S. PATENT DOCUMENTS

| 4,182,339 A | 1/1980 | Hardy |
| 4,520,821 A | 6/1985 | Schmidt et al. |

(Continued)

FOREIGN PATENT DOCUMENTS

| WO | WO 99/22781 | 5/1999 |
| WO | WO 03/022988 | 3/2003 |

(Continued)

OTHER PUBLICATIONS

Amann et al. "Urinary levels of monocyte chemo-attract protein-1 correlate with tumor stage and gradein patients with bladder cancer" British J. of Urol. 82:118-121, (1998).
(Continued)

*Primary Examiner* — Suzette J Gherbi
(74) *Attorney, Agent, or Firm* — Christopher DeVry; Arnold & Porter LLP

(57) ABSTRACT

The present invention relates to the regeneration, reconstruction, repair, augmentation or replacement of organs or tissue structures using scaffolds and autologous cells that are not derived from such organs or tissues.

14 Claims, 120 Drawing Sheets
(86 of 120 Drawing Sheet(s) Filed in Color)

Related U.S. Application Data filed on Dec. 10, 2008, provisional application No. 61/201,550, filed on Dec. 10, 2008, provisional application No. 61/114,382, filed on Nov. 13, 2008, provisional application No. 61/114,388, filed on Nov. 13, 2008, provisional application No. 61/114,021, filed on Nov. 12, 2008, provisional application No. 61/113,542, filed on Nov. 11, 2008, provisional application No. 61/111,242, filed on Nov. 4, 2008.

(51) Int. Cl.
*A61L 27/18* (2006.01)
*A61L 27/38* (2006.01)

(56) References Cited

U.S. PATENT DOCUMENTS

| | | | |
|---|---|---|---|
| 5,399,352 A * | 3/1995 | Hanson | 424/423 |
| 5,514,378 A | 5/1996 | Mikos et al. | |
| 5,567,612 A | 10/1996 | Vacanti et al. | |
| 5,586,438 A | 12/1996 | Fahy | |
| 5,654,273 A | 8/1997 | Gallo et al. | |
| 5,759,830 A | 6/1998 | Vacanti et al. | |
| 5,762,966 A | 6/1998 | Knapp | |
| 5,770,417 A | 6/1998 | Vacanti et al. | |
| 5,851,833 A | 12/1998 | Atala | |
| 5,855,610 A | 1/1999 | Vacanti et al. | |
| 5,863,531 A | 1/1999 | Naughton et al. | |
| 5,902,336 A * | 5/1999 | Mishkin | 623/11.11 |
| 6,039,749 A * | 3/2000 | Marin et al. | 623/1.11 |
| 6,171,344 B1 | 1/2001 | Atala | |
| 6,187,039 B1 * | 2/2001 | Hiles et al. | 623/1.44 |
| 6,296,668 B1 * | 10/2001 | Desgrandchamps et al. | 623/23.65 |
| 6,358,284 B1 * | 3/2002 | Fearnot et al. | 623/23.72 |
| 6,371,992 B1 * | 4/2002 | Tanagho et al. | 623/23.72 |
| 6,376,244 B1 | 4/2002 | Atala | |
| 6,416,995 B1 | 7/2002 | Wolfinbarger | |
| 6,428,802 B1 | 8/2002 | Atala | |
| 6,576,019 B1 | 6/2003 | Atala | |
| 6,939,381 B2 | 9/2005 | Stark et al. | |
| 7,131,996 B2 | 11/2006 | Wasserman et al. | |
| 7,306,627 B2 * | 12/2007 | Tanagho et al. | 623/14.13 |
| 7,479,161 B1 | 1/2009 | Wassermann et al. | |
| 7,531,355 B2 | 5/2009 | Rodriguez et al. | |
| 7,531,503 B2 * | 5/2009 | Atala et al. | 514/1.1 |
| 7,811,332 B2 | 10/2010 | Atala | |
| 7,918,897 B2 | 4/2011 | Bertram et al. | |
| 7,935,096 B2 * | 5/2011 | Johansson et al. | 604/338 |
| 8,337,485 B2 * | 12/2012 | Ludlow et al. | 604/544 |
| 2002/0183853 A1 | 12/2002 | Mitchell et al. | |
| 2004/0029266 A1 | 2/2004 | Barbera-Guillem | |
| 2005/0002982 A1 | 1/2005 | Mooney et al. | |
| 2006/0002972 A1 | 1/2006 | Atala et al. | |
| 2007/0276507 A1 * | 11/2007 | Bertram et al. | 623/23.65 |
| 2008/0033569 A1 | 2/2008 | Ferren et al. | |
| 2008/0051624 A1 | 2/2008 | Bonutti | |
| 2008/0183299 A1 | 7/2008 | Monga et al. | |
| 2009/0125100 A1 | 5/2009 | Mead | |
| 2009/0269310 A1 | 10/2009 | Le Ricousse et al. | |
| 2010/0152861 A1 | 6/2010 | Chung | |
| 2010/0285587 A1 | 11/2010 | Ollerenshaw et al. | |
| 2011/0015475 A1 | 1/2011 | Hanuka et al. | |
| 2011/0035023 A1 | 2/2011 | Maquet et al. | |
| 2011/0066254 A1 * | 3/2011 | Forsell | 623/23.64 |
| 2011/0196324 A1 | 8/2011 | Johansson et al. | |
| 2013/0204216 A1 * | 8/2013 | Matar | 604/342 |
| 2013/0231689 A1 * | 9/2013 | Binmoeller et al. | 606/153 |

FOREIGN PATENT DOCUMENTS

| | | |
|---|---|---|
| WO | WO 2005/085424 | 9/2005 |
| WO | WO 2007/095192 | 8/2007 |
| WO | WO 2007/095193 | 8/2007 |

OTHER PUBLICATIONS

Ashkar et al. "The Silastic Bladder Patch", J. Urol. vol. 98, pp. 679-683 (1967).
Ashijian et al. "In vitro differentiation of human processed lipoaspirate cells into early neural progenitors" Plast. Reconstr. Surg. 11 1:1922-1931, (2003).
Atala et al., "Tissue-engineered autologous bladders for patients needing cystoplasty", The Lancet, pp. 1-6, published online Apr. 4, 2006.
Atala et al. "Formation of Urothelial Structures in Vivo from Disassociated Cells attached to Biodegradable Polymer Scaffolds in Vitro", J. Urol. vol. 148 (2 pt 2) pp. 658-662 (1992).
Atala et al. "Implantation in Vivo and Retrieval of Artificial Structures Consisting of Rabbit and Human Urothelium and Human Bladder Muscle", J. Urol. vol. 150 (2 pt 2) pp. 608-612 (1993).
Atala et al "Tissue engineering for bladder substitution", World J. Urol. vol. 18:364-370 (2000).
Atala, A. "Commentary on the replacement of urologic associated mucosa", J. of Urol. vol. 156, 338-339, (1996).
Atala et al. "Tissue Engineering for the Replacement Organ Function in the Genitourinary System" Am J. Transplant 4 Suppl 6:58-73, 2004.
Aust et al. "Yield of human adipose-derived adult stem cells from liposuction aspirates", Cytotherapy vol. 6:7-14, (2004).
Awad et al. "Effects of Transforming Growth Factor β1 and Dexamethasone on the Growth and Chondrogenic Differentiation of Adipose-Derived Stromal Cells", Tissue Engineering vol. 9:1301-1312, (2003).
Barr et al. "Assessment and management of stomal complications: A framework for clinical decision making", Ostomy Wound Management, vol. 50, Issue 9, pp. 50-67, (2004).
Berman et al. "Comparative cost analysis of collagen injection and fascia lata sling cystourethropexy for the treatment of type III incontinence in women", J. of Urology, vol. 157:122-124 (1997).
Craig et al. "A biological comparison of polyglactin 910 and polyglycolic acid synthetic absorbable sutures" Surg. vol. 141, No. 1 pp. 1-7 (1975).
Contreras-Shannon et al. "Fat accumulation with altered inflammation and regeneration in skeletal muscle of CCR2−/− mice following ischemic injury". Am. J. Physiol Cell Physiol 292: C953-C967, (2007).
De Ugarte et al. "Comparison of Multi-Lineage Cells from Human Adipose Tissue and Bone Marrow" Cells Tissues Organs. 174:101-109, (2003).
Deonarine et al. "Gene expression profiling of cutaneous wound healing" Journal of Transl. Med. 5: 1-11, (2007).
Erickson et al. "Chondrogenic potential of adipose tissue-derived stromal cells in vitro and vivo" Biochemical and Biophysical Research Communications 290:763-769, (2002).
Fauza et al "Videofetoscopically Assisted Fetal Tissue Engineering: Bladder Augmentation", J. Ped. Surg. vol. 33, pp. 7-12 (1998).
Gimble et al. "Adipose-derived adult stem cells: isolation, characterization, and differentiation potential" Cyrotherapy vol. 5:362-369, (2003).
Gronthos et al. "Surface protein characterization of human adipose tissue-derived stromal cells" Journal of Cellular Physiology 189:54-63, (2001).
Halvorsen et al. "Thiazolidinediones and glucocorticoids synergistically induce differentiation of human adiposse tissue stromal cells: Biochemical, cellular, and molecular analysis", Metabolism 50:407-413, (2001).
Halvorsen et al. "Extracellular Matrix Mineralization and Osteoblast Gene Expression by Human Adipose Tissue-Derived Stromal Cells", Tissue Engineering vol. 7, No. 6:729-741, (2001).
Harp et al. "Differential Expression of Signal Transducers and Activators of Transciption during Human Adipogenesis", Biochemical and Biophysical Research Communication 281:907-912, (2001).
Herschorn et al. "Followup of Intraurethral Collagen for Female Stress Urinary Incontinence", J. of Urology, vol. 156:1305-1309 (1996).
Herzog et al. "Urinary Incontinence: Medical and Psychosocial Aspects" Ann. Rev. Gerontol. Geriatrics, 9:74-119, (1989).

(56) References Cited

OTHER PUBLICATIONS

Hicok et al. "Human Adipose-Derived Adult Stem Cells Produce Osteoid in Vivo", Tissue Engineering vol. 10:371-380, (2004).
Ishaug et al "Bone Formation by Three-Dimensional Stromal Osteoblast Culture in Biodegradable Polymer Scaffolds", J. Biomed Mater Res. 36(1): 17-28 (1997).
Jack et al "Urinary Bladder Smooth Muscle Engineered from Adipose Stem Cells and a Three Dimensional Synthetic Compossite" Biomaterials, pp. 3259-3270, (2009).
Jayo et al. "Long-term Durability, Tissue Regeneration and Neo-Organ Growth during Skeletal Maturation with a Neo-bladder Augmentation Construct", Regen. Med. 3(5), 671-682, (2008).
Jayo et al. "Early Cellular and Stromal Responses in Regeneration Versus Repair of a Mammalian Bladder Using Autologous Cell and Biodegradable Scaffold Technologies", J. of Urol. 180:392-397, (2008).
Kakizoe, T. "Development and Progression of Urothelial Carcinoma", Cancer Sci. 97(9) 821-828, (2006).
Kassis et al. "Isolation of Mesenchymal Stem Cells from G-CSF-mobilized human peripheral blood using fibrin microbeads", Bone marrow transplant, 37: 967-976, (2006).
Kelami et al "Experimental Investigations of Bladder Regeneration Using Teflon-Felt as a bladder wall substitute" J, Urol. vol. 104, No. 5, pp. 693-698(1970).
Kelami et al "Lyophilized Human Dura as a Bladder Wall Substitute: Experimental and Clinical Results", J. Urol. vol. 105, No. 4, pp. 518-522 (1971).
Khullar et al. "GAX collagen in the treatment of urinary incontinence in elderly women: a two year follow up", British J. Obstetrics & Gynecology, 104:96-99 (1996).
Kirker-Head, C.A., "Recombinanat Bone Morphogenetic Proteins: Novel Substances for Enhancing Bone Healing", Vet. Surg. vol. 24, pp. 408-419 (1995).
Kudish "The use of polyvinyl sponge for experimental cystoplasty" J. Urol. vol. 78, No. 3, pp. 232-235 (1957).
Klutke et al. "Early results with antegrade collagen injection for post-radical prostatectomy stress urinary incontinence", J. Urology, 156:1703-1706 (1996).
Koerner et al. "Equine peripheral blood-derived progenitors in comparison to bone marrow-derived mesenchymal stem cells", Stem cells, 24:1613-1619, (2006).
Kondo et al. "Bladder neck support prosthesis: A nonoperative treatment fo rstress or mixed urinary incontinence", J. Urology, 157:824-827 (1997).
Laurencin et al. "A Highly Porous 3-Dimentional Polyphosphazene Polymer Matrix for Skeletal Tissue Regeneration" J. Biomed Mater . Res. vol. 30 pp. 133-138 (1996).
Leonard et al. "Treatment of urinary incontinence in children by endoscopically directed bladder neck injection of collagen", J. Urology, 156:637-640 (1996).
Levenberg et al. "Differentiation of human embryonic stem cells on three-dimensional polymer scaffolds", PNAS, vol. 100: 12741-12746, (2003).
Levesque et al. "Ten-year experience with the artificial urinary sphincter in children", J. Urology, 156:625-628 (1996).
Lewis et al. "The Clam: Indications and Complications" British J. Urol.; 65:488-491, (1990).
Lima et al. "Combined use of enterocystoplasty and a new type of artificial sphincter in the treatment of urinary incontinence", J. Urology, 156:622-624 (1996).
Lumeng et al. "Obesity induces a phenotypic switch in adipose tissue macrophage polarization" J Clin. Invest. 117(1): 175-184, (2007).
McCelland et al. "Evaluation of antibody class in response to bovine collagen treatment in patients with urinary incontinence", J. Urology 155, 2068-2073 (1996).
Mizuno et al. "Myogenic differentiation by human processed lipoaspirate cells", Plast Reconstr Surg. 109:199-209, (2002).
Morizono et al. "Multilineage cells from adipose tissue as gene delivery vehicles", Hum Gene Therapy 14:59-66, (2003).
Oberpenning et al., "De novo reconstitution of a functional mammalian urinary bladder by tissue engineering", Nature Biotechnology, vol. 17, pp. 149-155, (1999).
Perez et al. "Submucosal bladder neck injection of bovine dermal collagen for stress urinary incontinence in the pediatric population", J. Urology, 156:633-636 (1996).
Roth et al., "Temporal differentiation and maturation of regenerated rat urothelium", BJU International,103: 836-841, (2008).
Safford et al. "Characterization of neuronal/glial defferentiation of murine adipose-derived adult stromal cells" Experimental Neurology 187:319-328, (2004).
Safford et al. "Neurogenic differentiation of murine and human adipose-derived stromal cells" Biochem Biophys Res Commun. 294(2):371-379, (2002).
Schecter et al. "MCP-1-dependent signaling in CCR2 aortic smooth muscle cells" J. Leukocyte Biol.75:1079-1085, (2004).
Selzman et al. "Monocyte chemotactic protein-1 directly induces human vascular smooth muscle proliferation", Am J Physiol Heart Circ Physiol. 283(4); H1455-H1461, (2002).
Sen et al. "Adipogenic potential of human adipose derived stromal cells from multiple donors is hereterogeneous", Journal of Cellular Biochemistry 81:312-319, (2001).
Shireman et al. "MCP-1 Parallels inflammatory and regenerative responses in ischemic muscle", J. Surg. Res. 134(1): 145-157, (2006).
Sigal et al. "Characterization and enrichment of fetal rat hepatoblasts by immunoadsorption ("Panning") and fluorescene-activated cell sorting", Hepatology 19: 999-1006, (1994).
Simper et al. "Smooth muscle progenitor cells in human blood", Circulation, 106: 1199-1204, (2002).
Warren et al. "Chemokine receptor CCR2 involvement in skeletal muscle regeneration", FASEB J.19: 1-23, (2005).
Wein, Alan J "Pharmacology of Incontinence", Urol. Clinic of N. America vol. 22:557-577, (1995).
Wickham et al. "Multipotent stromal cells derived from the infrapatellar fat pad of the knee", Clinic Orthopedics and Related Research 412:196-212, (2003).
Winter et al. "Cartilage-Like gene expression in differentiated human stem cell spheroids", Arthritis & Rheum. 48:418-429, (2003).
Zdrahala "Small Caliber Vascular Grafts Part I: State of the Art", J. Biomater. Appl. vol. 10, pp. 309-329, 1996.
Zuk et al. "Human adipose tissue is a source of multipotent stem cells", Mol Biol Cell 13:4279-4295, (2002).
Zuk et al. "Multilineage cells from human adipose tissue: Implications for cell-based therapies", Tissue Eng 7:211-228; (2001).
Kwon et al. "Local and systemic effects of a tissue engineered neobladder in a canine cystoplasty model", J. Urology 179: 2035-2041, May 2008.
Champeau, R. "UCLA researchers transform stem cells found in human fat into smooth muscle cells", University of California, Jul. 24, 2006.
Williams et al. "Liposuction-derived human fat used for vascular graft sodding contains endothelial cells and not mesothelial cells as the major cell type", J Vasc Surg.19:916-923, 1994.
Yang et al. "Blood-derived smooth muscle cells as a target for gene delivery", J Vasc. Surg. 47:432-440, 2008.

* cited by examiner

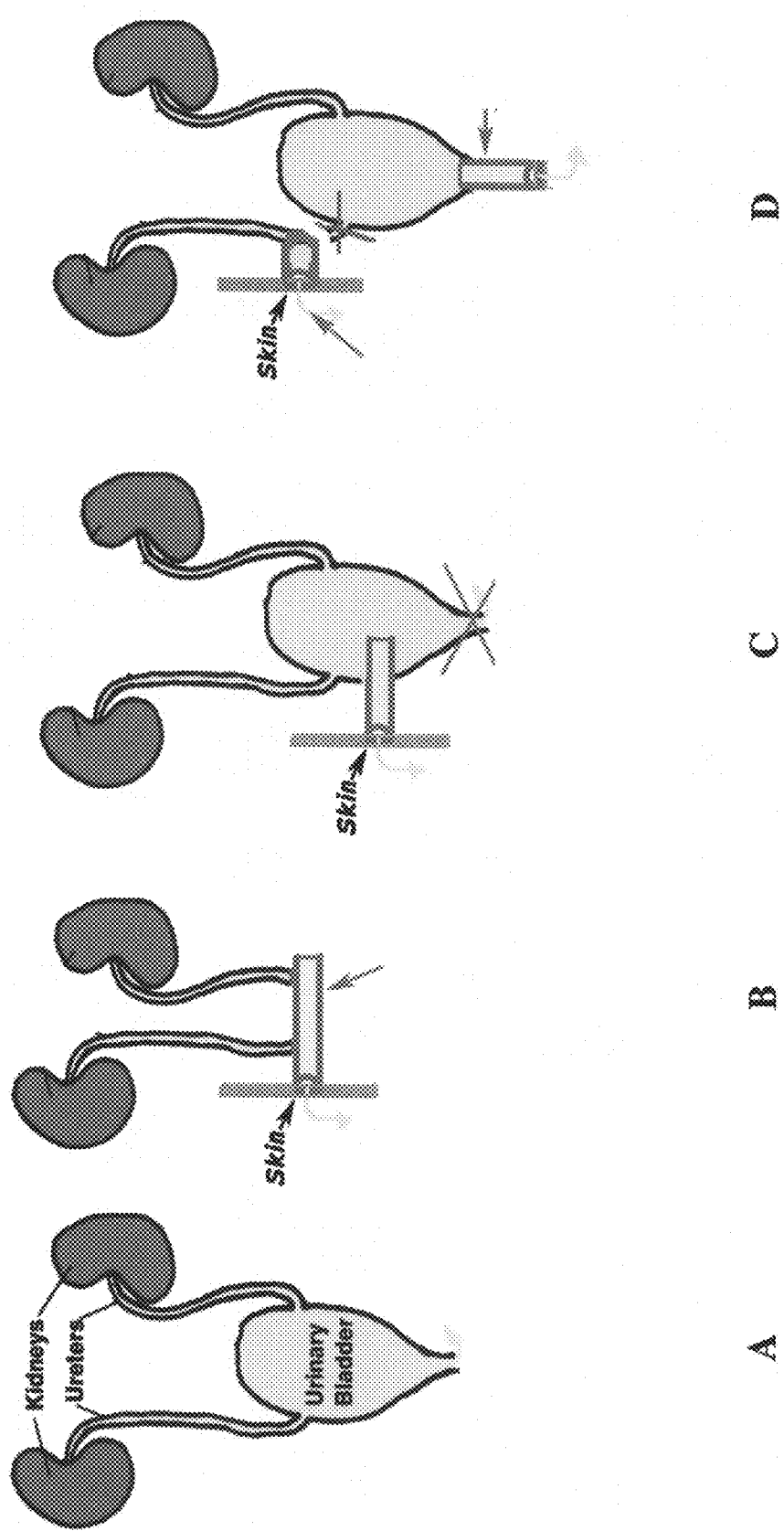

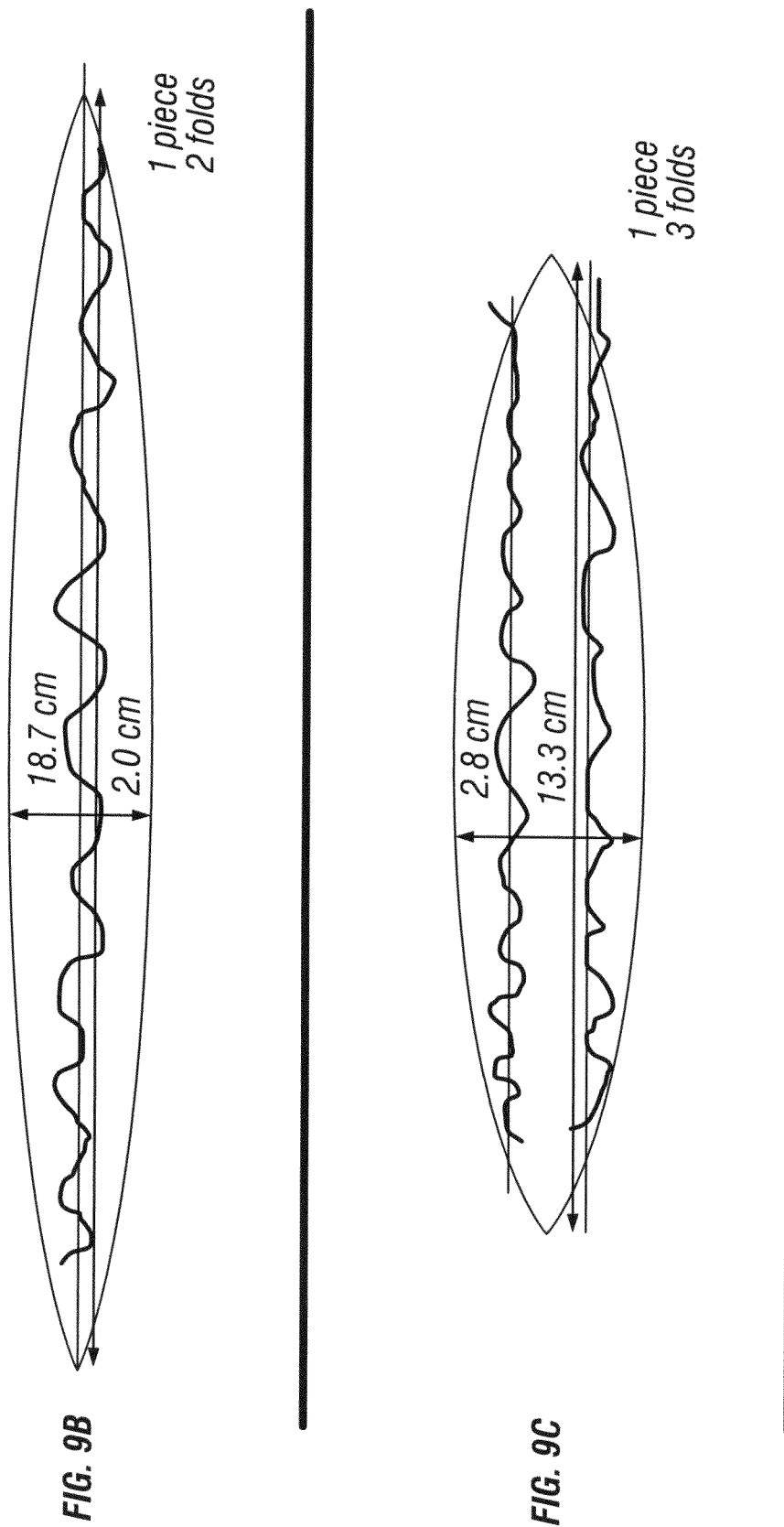

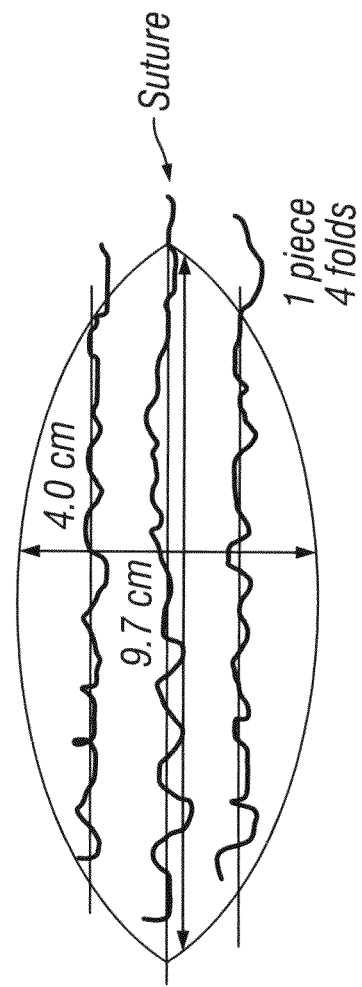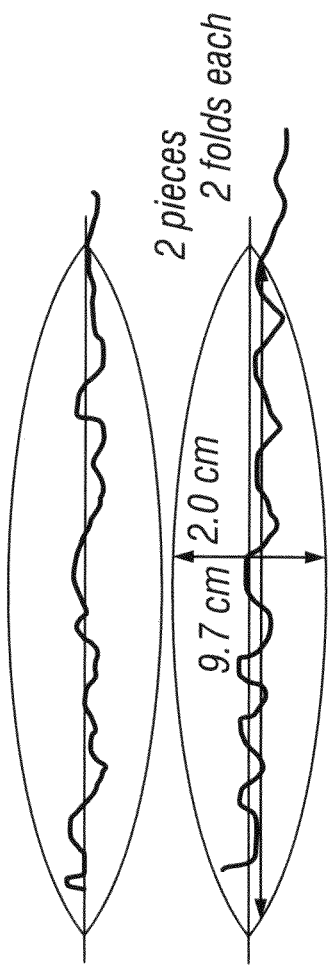

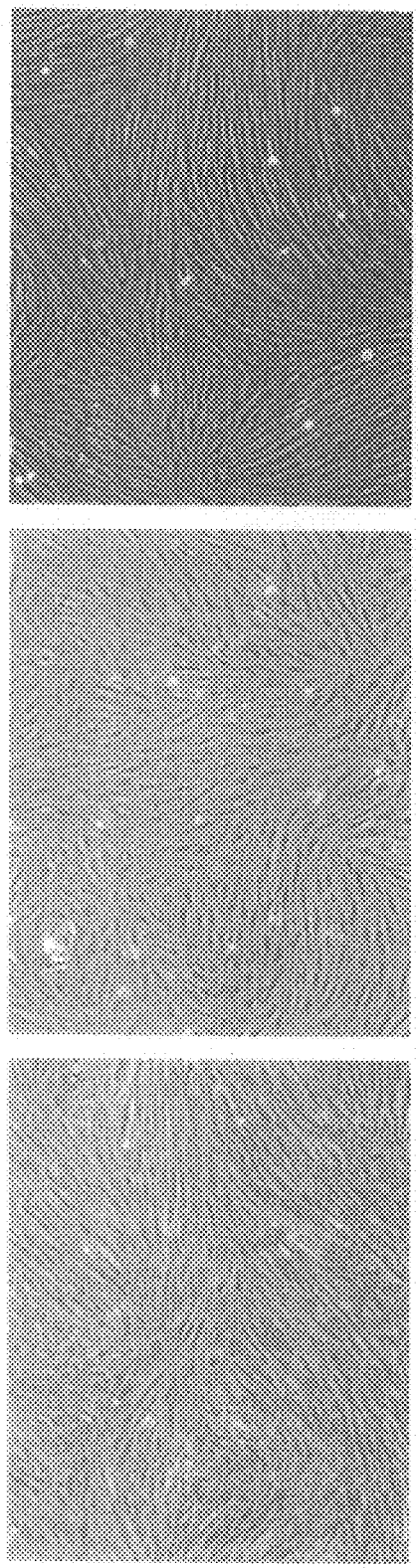
Fig. 68: Isolation of smooth muscle cells from porcine bladder, adipose and peripheral blood
A) Bladder  B) Adipose  C) Peripheral Blood

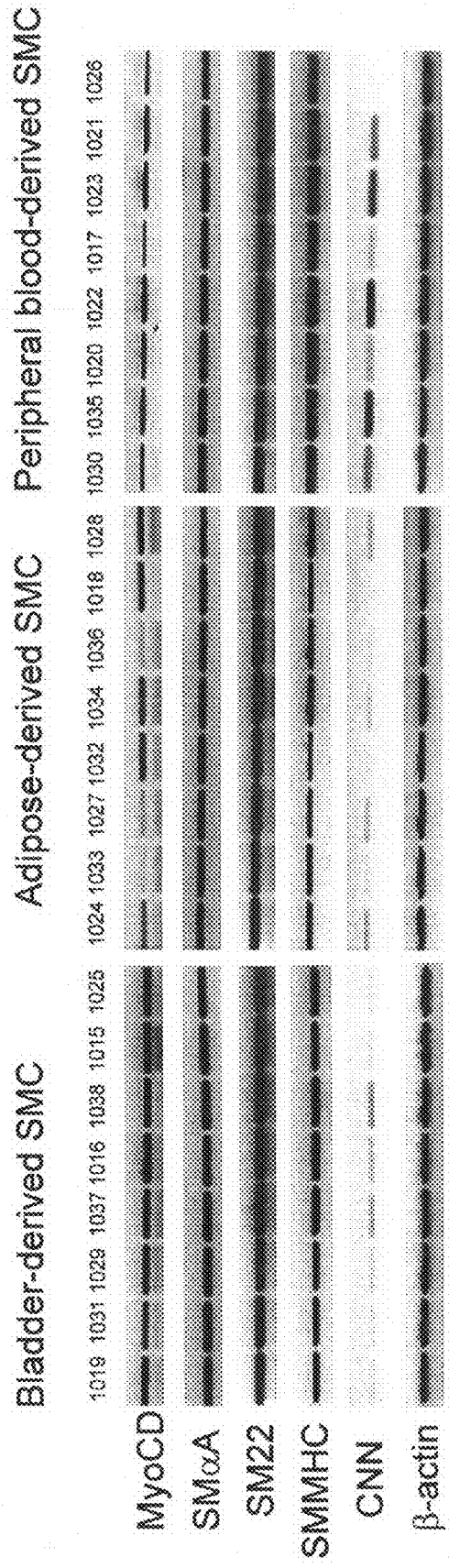
Fig. 69: RT-PCR analysis of smooth muscle marker expression from bladder, peripheral blood or adipose-derived smooth muscle cells

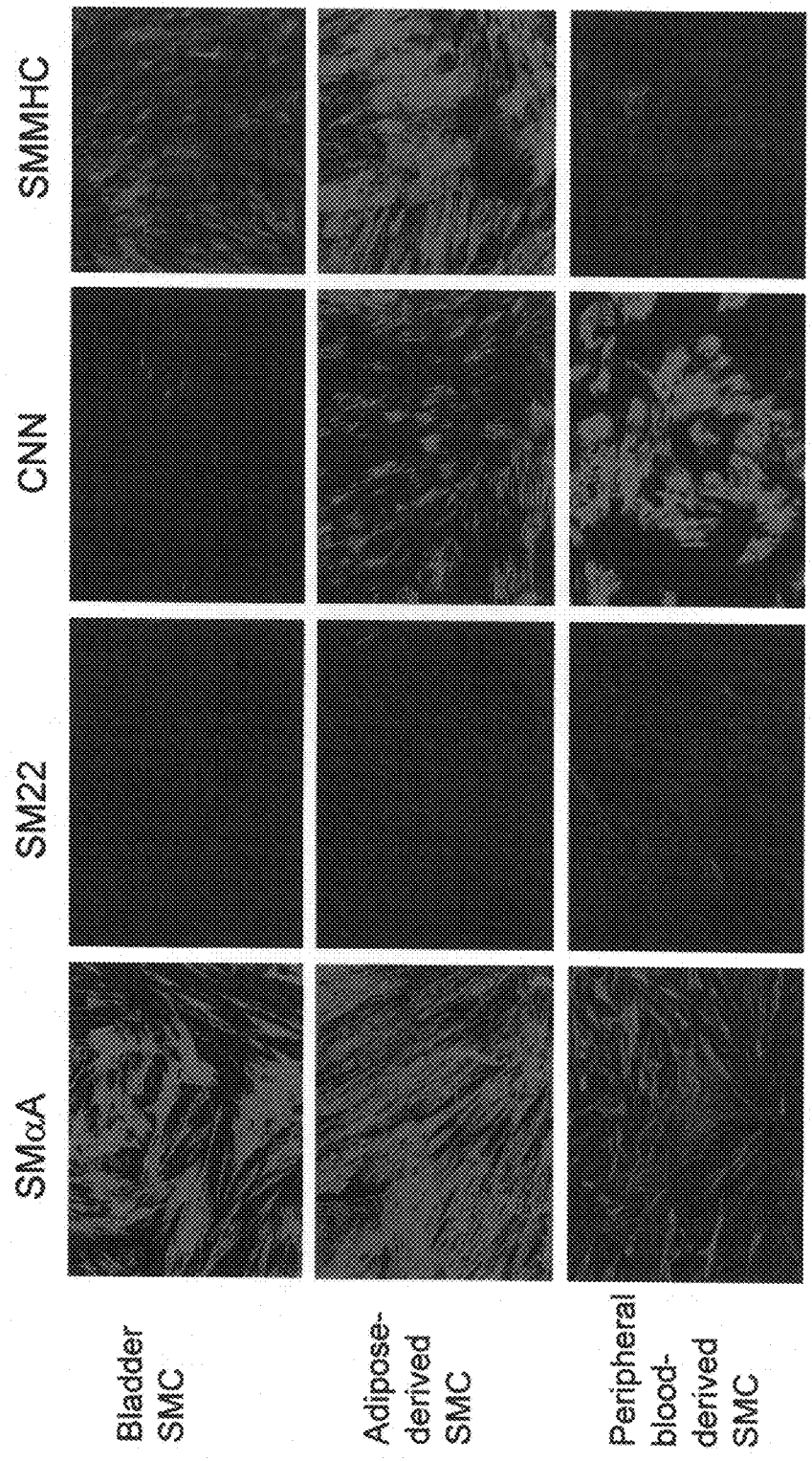
Fig. 70: Immuno-fluorescence analysis of smooth muscle marker expression in porcine bladder, adipose and peripheral blood-derived smooth muscle cells

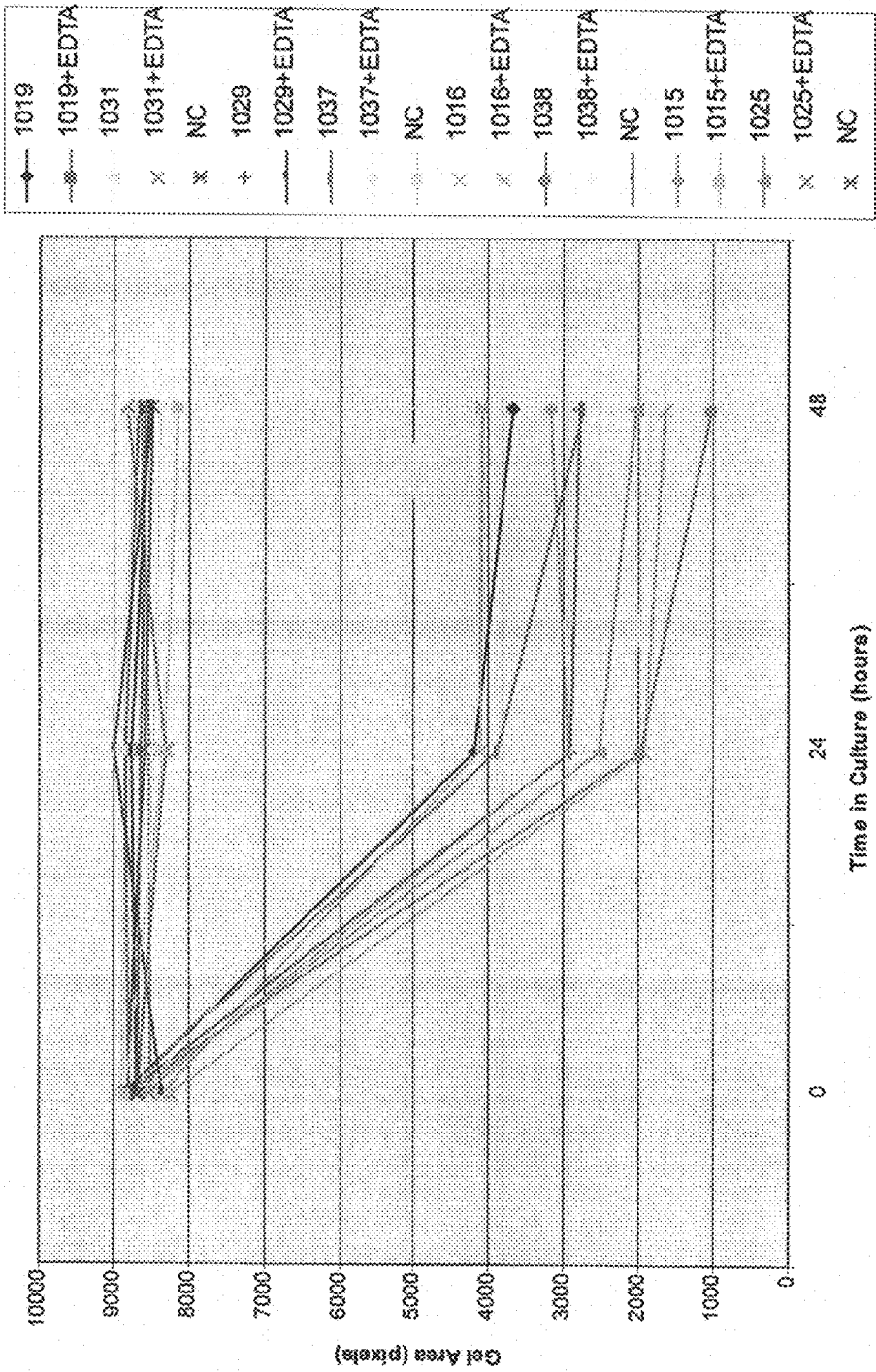
Fig. 71A: Contractility of Porcine Bladder-derived smooth muscle cells

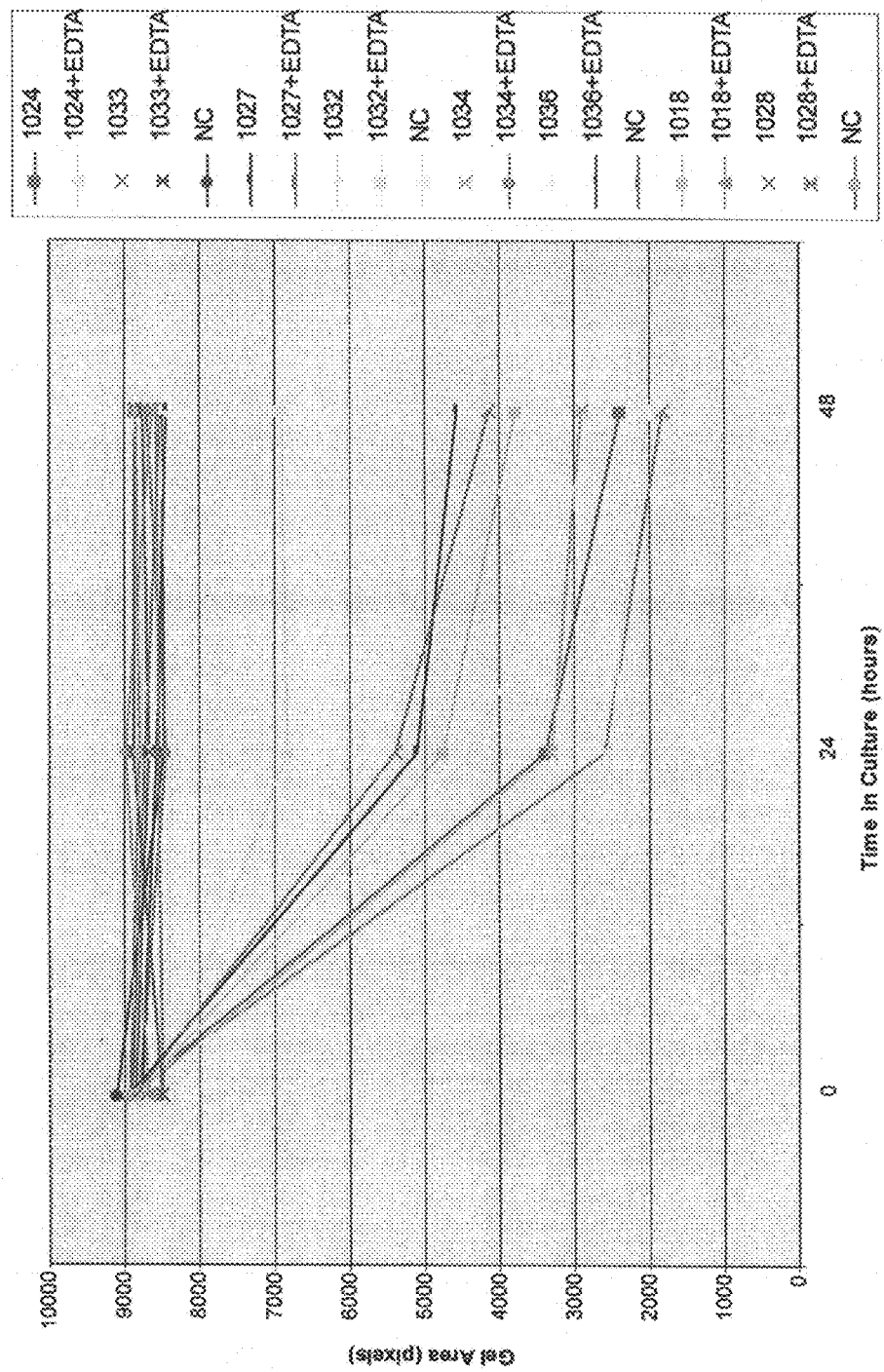
Fig. 71B: Contractility of Porcine Adipose-derived smooth muscle cells

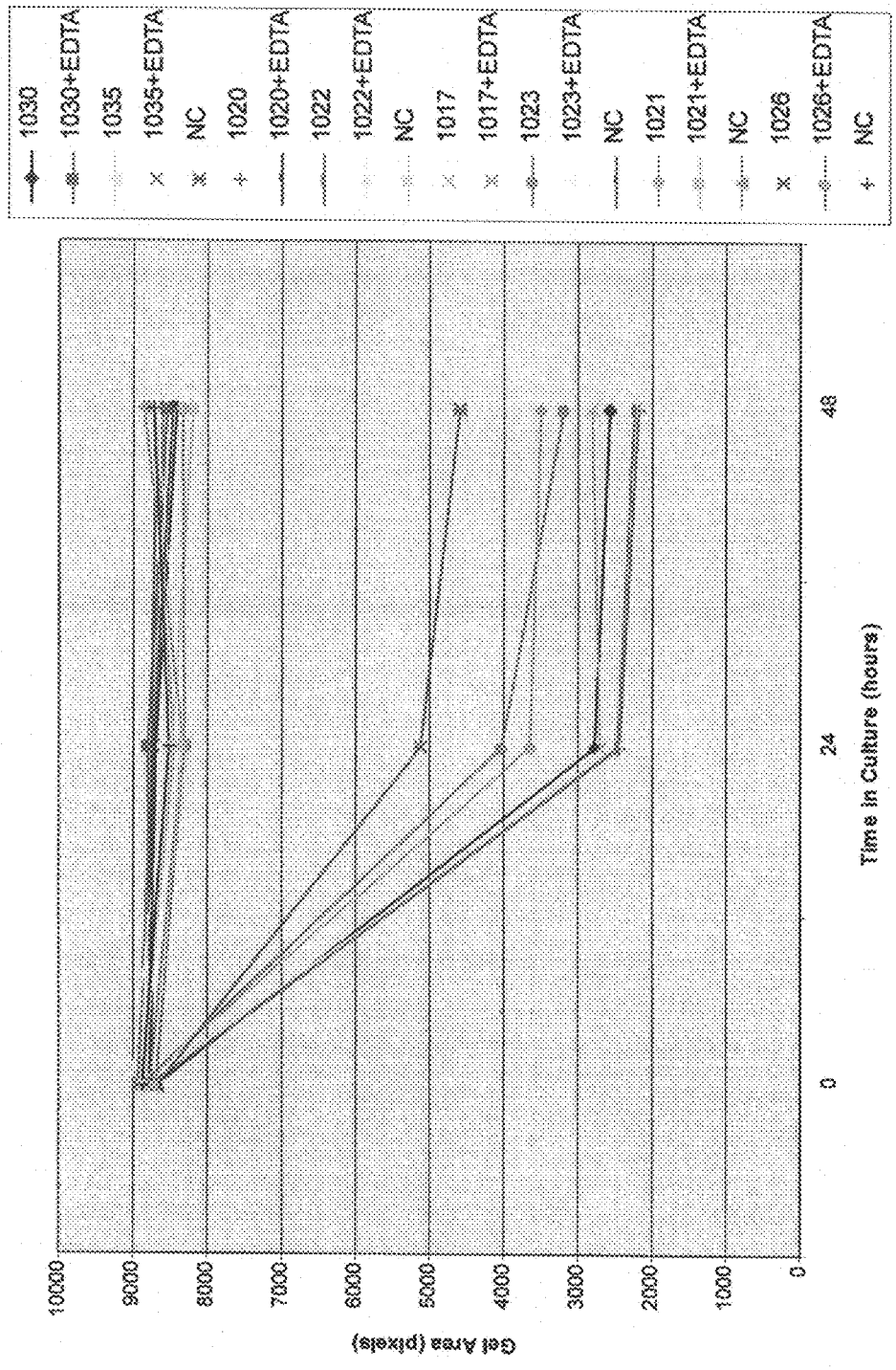
Fig. 71C: Contractility of Porcine Peripheral blood-derived smooth muscle cells

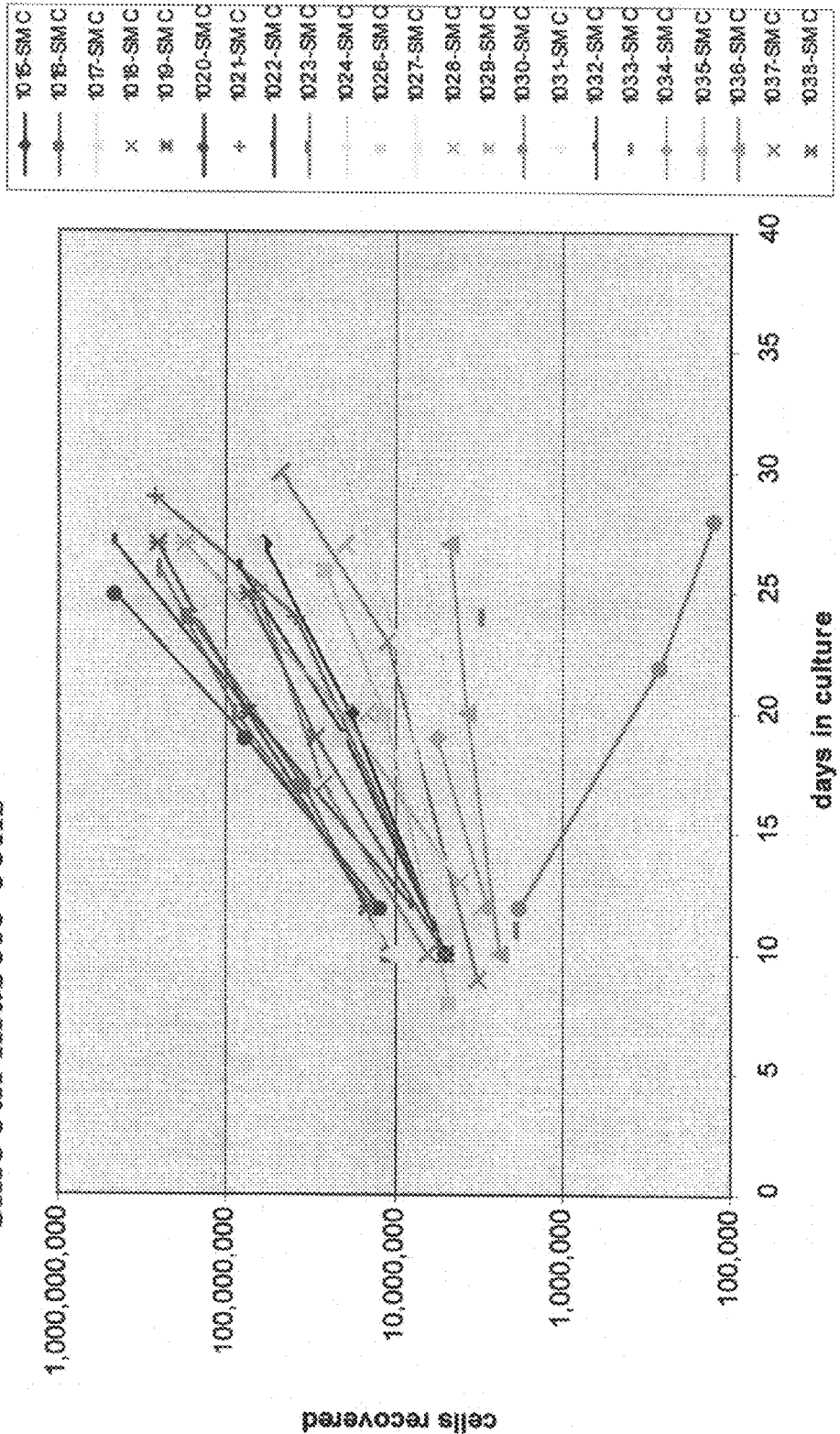

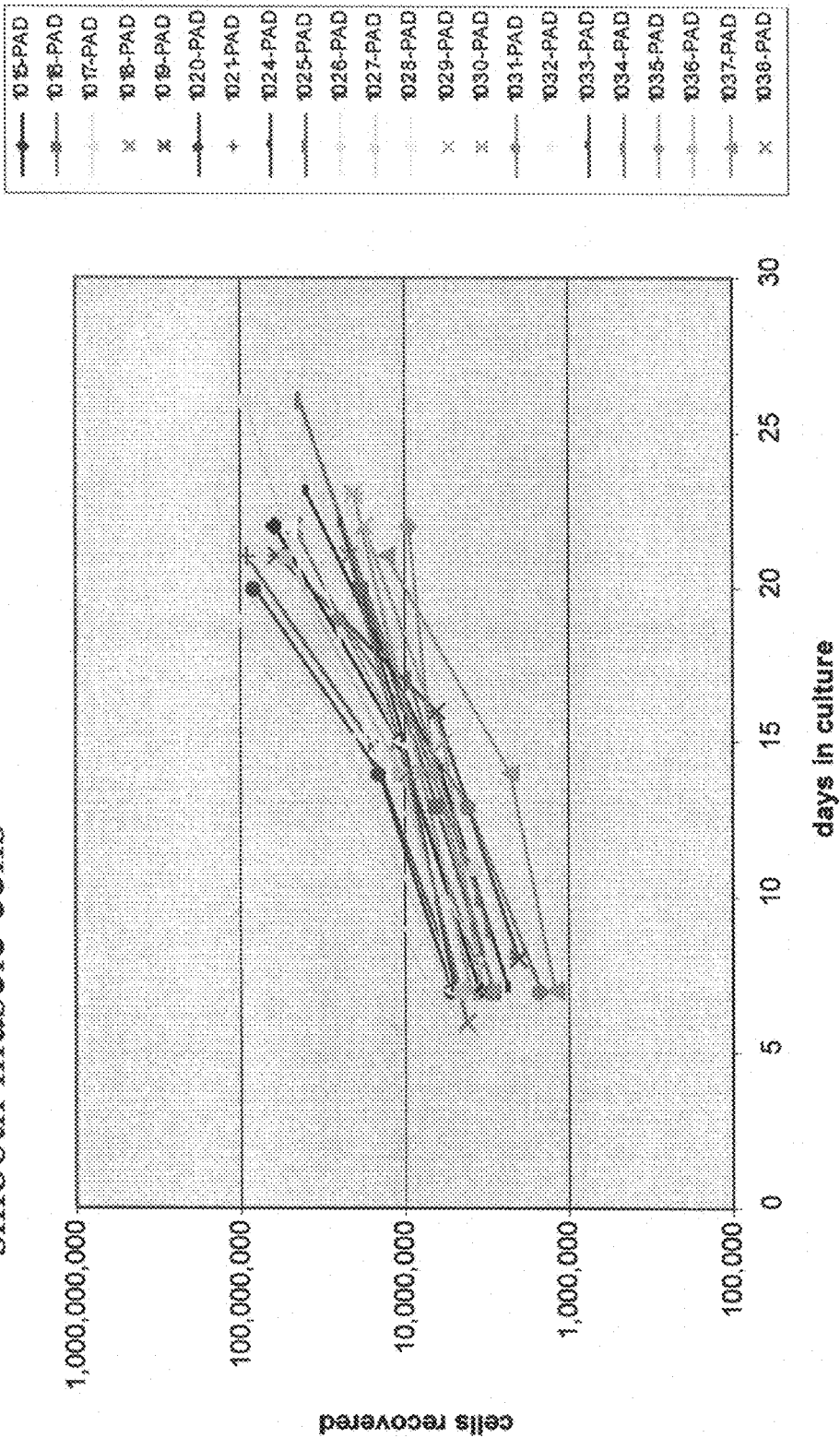
Fig. 72B: Growth kinetics of Porcine Adipose-derived smooth muscle cells

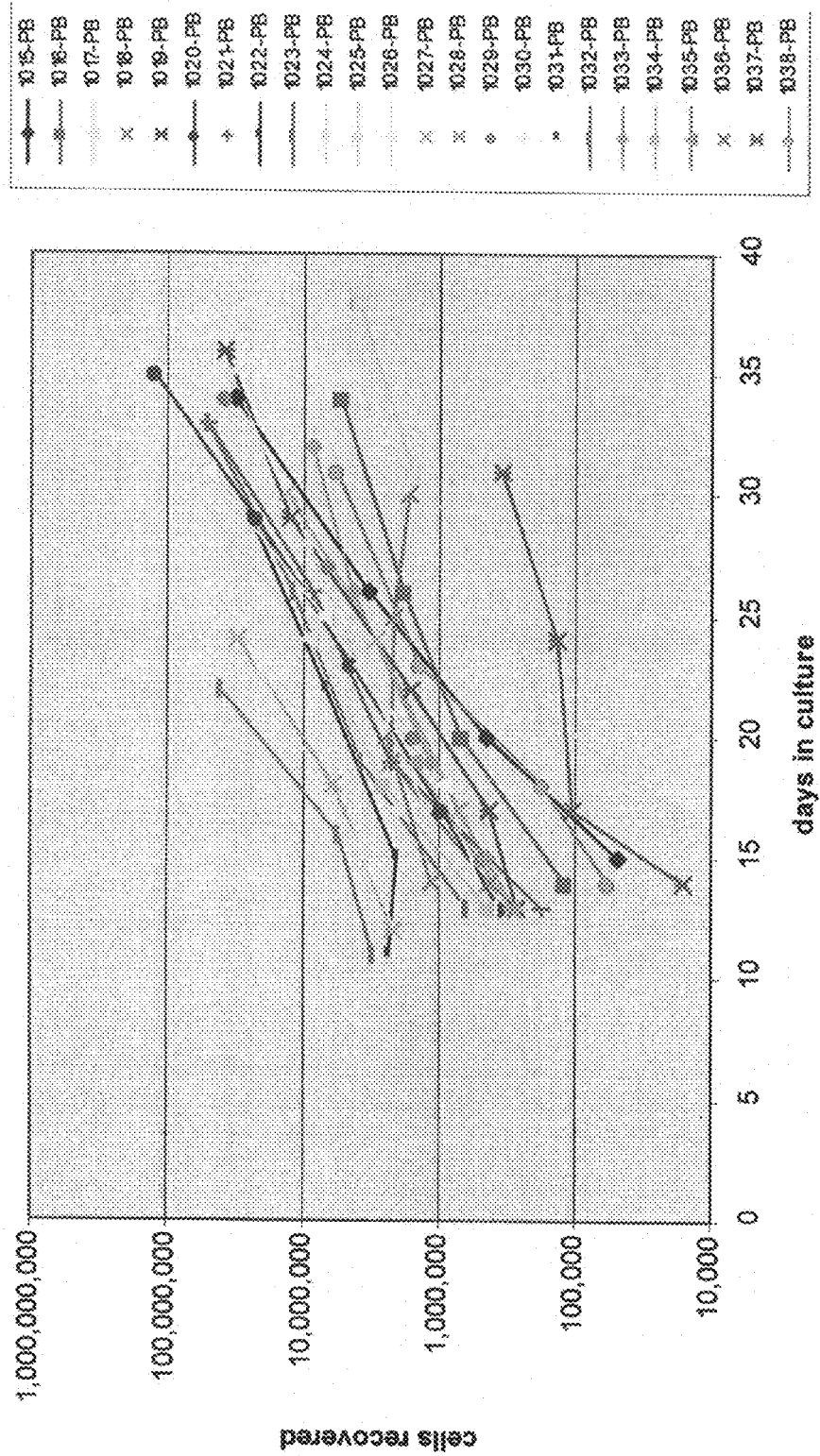
Fig. 72C: Growth kinetics of Porcine Peripheral blood-derived smooth muscle cells

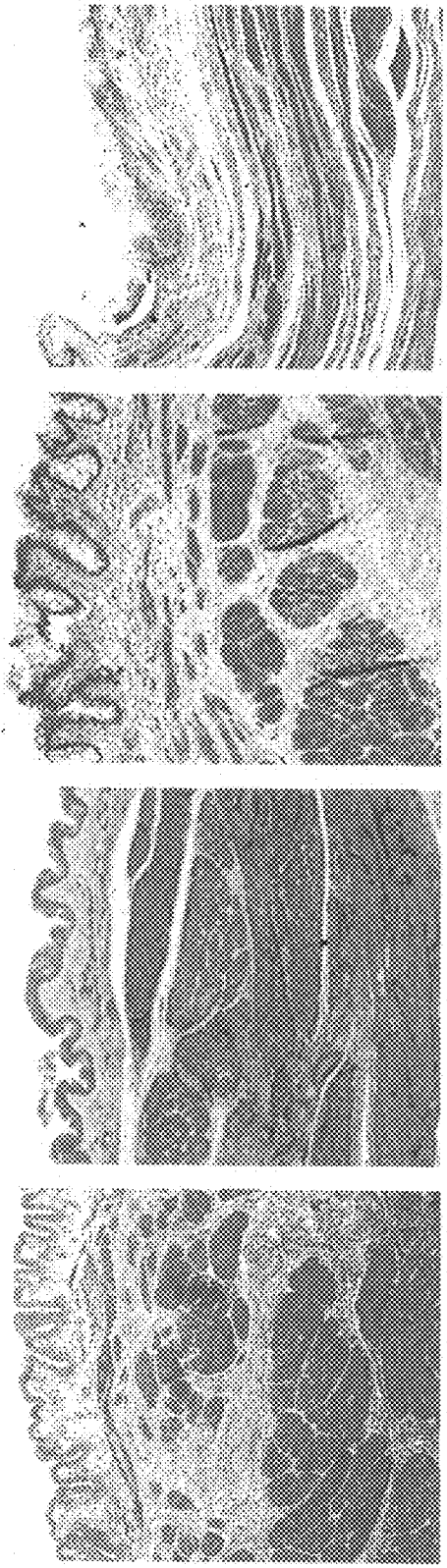
Fig. 73: Histopathology of Neo-Urinary Conduits seeded with bladder, adipose & peripheral blood-derived smooth muscle cells A
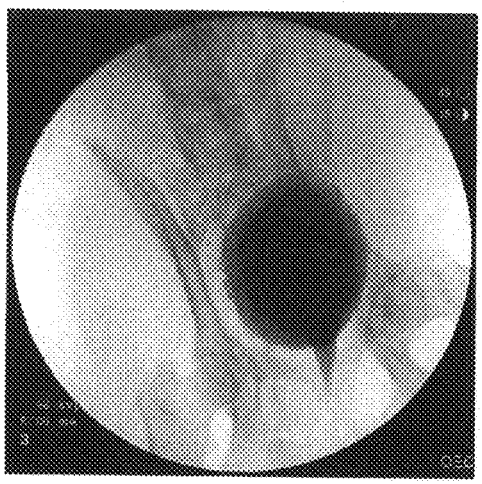
B
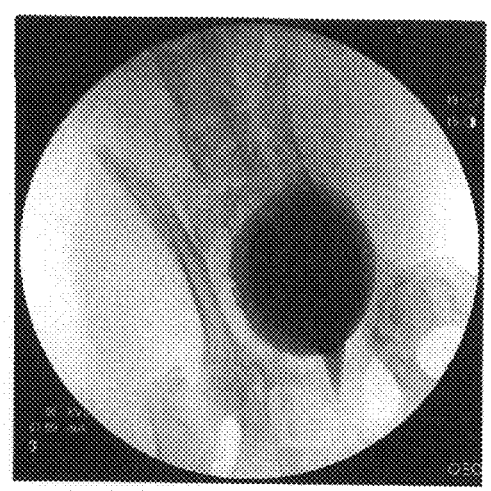
C
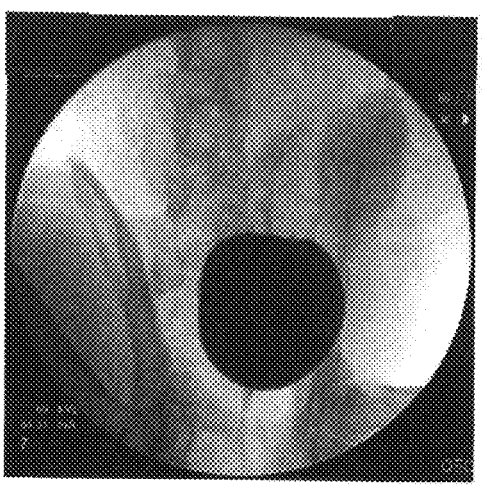
D
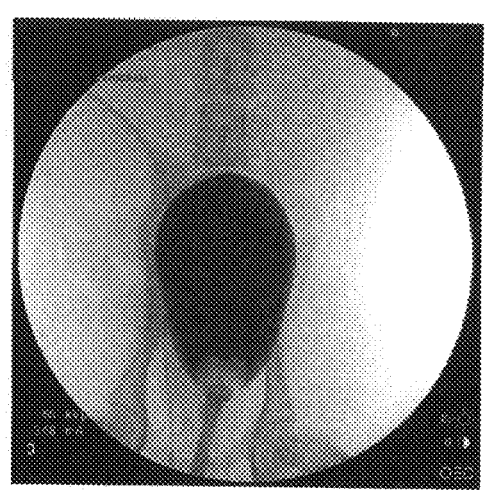
Figure 75

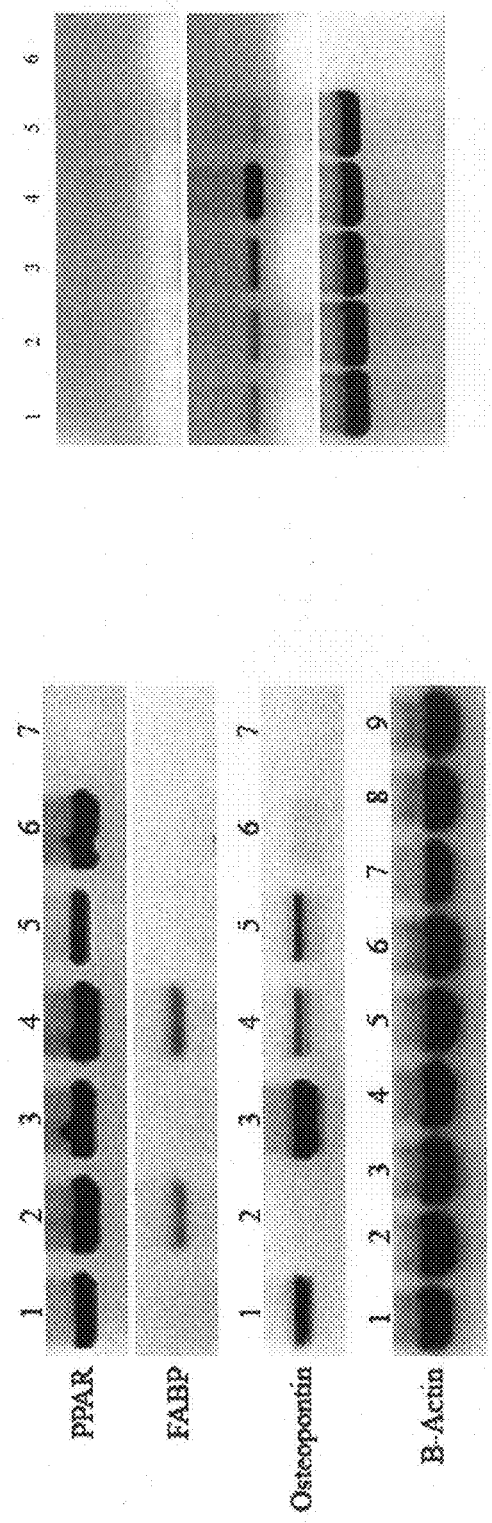

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttctacaatg agctgcgtgt g                                             21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgttcacact tcatgatgga gt                                            22

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatccaactg gtttatgaag aaagc                                         25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctaactgat gatctgccga ggtc                                          24

<210> SEQ ID NO 5
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccagcagatg tggatcagca                                             20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagcatttgc ggtggacaat                                             20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctcagaaag tttgccacct c                                           21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcctgctcca ggatgaacat                                             20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catgtcctct gctcacttca ac                                          22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccctcgatc cactctctca                                             20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagagcacag ggtctcctca                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actccgagtc atttgctgct                                              20
```

CELL SCAFFOLD CONSTRUCTS

RELATED APPLICATIONS

This application is a divisional of, and claims the benefit under 35 U.S.C. §120 of U.S. application Ser. No. 12/612,606, filed Nov. 4, 2009, which claims priority to under 35 U.S.C. §119(e) and the benefit of U.S. Provisional Application Ser. Nos. 61/111,242 filed on Nov. 4, 2008; 61/113,542 filed on Nov. 11, 2008; 61/114,021 filed on Nov. 12, 2008; 61/114,382 filed on Nov. 13, 2008; 61/114,388 filed on Nov. 13, 2008; 61/201,555 filed on Dec. 10, 2008; 61/201,550 filed on Dec. 10, 2008; and 61/201,554 filed on Dec. 10, 2008, the specifications of which are incorporated by reference herein in their entirety.

The instant application contain a Sequence Listing which has been submitted via EFS-Web and is hereby incorporated by reference in its entirety. Said ASCII copy, created on Jan. 11, 2010, is named TGN1014U.txt, and is 3,513 bytes in size.

FIELD OF THE INVENTION

The present invention relates to the regeneration, reconstruction, repair, augmentation or replacement of laminarly organized luminal organs or tissue structures using scaffolds seeded with cells obtained from autologous sources.

BACKGROUND OF THE INVENTION

Several anomalies can cause the bladder to develop abnormally and require surgical augmentation. Conditions such as posterior urethral valves, bilateral ectopic ureters, bladder extrophy, cloacal extrophy, and spina bifida (ie, myelomeningocele) may cause the bladder to be noncompliant, resulting in a small capacity bladder that generates high pressures. Clinically this causes patients to suffer from incontinence while increasing their risk for renal failure due to the high pressures in the genitourinary system. The current standard of therapy for these pediatric patients is bladder augmentation through enterocystoplasty (Lewis et al. Br. J. Urol. (1990); 65:488-491). Bladder augmentation involves the removal of a section of large bowel from the patient who then has that tissue connected to the existing bladder to increase compliance, decrease pressure, and improve capacity. The surgeries are relatively complex and expensive. Even in patients with a good technical result, the procedure is associated with numerous immediate risks and chronic complications. The invasiveness, cost, and complications of these surgeries limit their use to only the most severe bladder deficiencies. A similar surgical procedure is performed in adults who require a bladder replacement, many as a result of bladder cancer. In adults, the entire bladder is resected and replaced with large bowel. Despite the risk of adverse effects, there are approximately 10,000 of these procedures performed per year in the United States, including about 10% in children with congenital abnormalities and 90% in adults with acquired disorders such as bladder cancer. There is clearly a compelling medical need for an improved approach that would eliminate or at least substantially reduce the adverse effects associated with the current standard of care.

The human urinary bladder is a musculomembranous sac, situated in the anterior part of the pelvic cavity that serves as a reservoir for urine, which it receives through the ureters and discharges through the urethra. In a human the bladder is found in the pelvis behind the pelvic bone (pubic symphysis) and is above and posteriorly connected to a drainage tube, called the urethra, that exits to the outside of the body. The urinary bladder is subject to numerous maladies and injuries which cause deterioration of the urinary bladder in patients. For example, bladder deterioration may result from infectious diseases, neoplasms and developmental abnormalities. Further, bladder deterioration may also occur as a result of trauma such as, for example, car accidents and sports injury. Urinary diversions are often necessary in bladder cancer patients. There are over 54,000 new bladder cancer cases each year in the United States of America. Most bladder cancers are of epithelial origin, and worldwide, there are approximately 336,000 new cases of urothelial carcinomas (transitional cell carcinomas (TCC)) annually (Kakizoe (2006) Cancer Sci. 97(9) 821).

Urinary diversion is a way to route and excrete urine from the body when an individual is unable to urinate due to a damaged or non-functional urinary system. In general, any condition that blocks the flow of urine and increases pressure in the ureters and/or kidneys may require a urinary diversion. Some common indications for diversion include cancer of the bladder requiring a cystectomy, a neurogenic bladder that impact renal function, radiation injury to the bladder, intractable incontinence that occurs in women, and chronic pelvic pain syndromes. In general, two major strategies exist for urinary diversion: a urostomy and a continent diversion. A urostomy involves the creation of a stoma in the abdomen which is connected to a conduit inside the body such as a short segment of the small intestine submucosa (SI) such as the ileum, colon or jejunum. In this procedure, the other end of the short SI is connected to the ureters which normally carry urine from the kidney to the bladder. Urine flows through the ureters into the short SI and out the stoma to an external collection reservoir. An alternative of this procedure is the attach the ureters directly to a stoma, also called a ureterostomy. A continent diversion involves the creation of a pouch or reservoir inside the body from a section of the stomach or small or large intestine and the use of a stoma may or may not be required. For example, a continent cutaneous reservoir may be created by obtaining a segment of the bowel and modifying it into a more spherical shape. One end of the modified segment is connected to the ureters and the other to a stoma that leads to an external collection reservoir. Finally, an orthotopic diversion may created by placing the re-shaped segment in place of the original bladder by connecting one end to the ureters and the other end to the urethra so the individual may urinate through the urethra instead of through a stoma.

Although small intestinal submucosa (SI) may be used for urinary diversion, it has been reported that the removal of the mucosa and submucosa may lead to retraction of the intestinal segment (see, e.g., Atala, A., J. Urol. 156:338 (1996)). Other problems have been reported with the use of certain gastrointestinal segments for bladder surgery including stone formation, increased mucus production, neoplasia, infection, metabolic disturbances, long term contracture and resorption. The use of natural materials for urinary diversion has shown that bladder tissue, with its specific muscular elastic properties and urothelial impermeability functions, cannot be easily replaced. In addition, the use of a patient's own bowel segments for urinary diversion requires at least two different surgical procedures where a first surgery is performed to remove a segment and a second surgery to install the urinary diversion. The requirement of multiple surgeries increases the overall cost of the procedures, the risk to the patient, and patient's overall comfort.

Therefore, due to the multiple complications associated with the use of gastrointestinal segments for urinary diversion and requirement for multiple surgical procedures, there exists a need for methods and devices for providing urinary diversion systems to patients in need of such a system.

Urinary incontinence is a prevalent problem that affects people of all ages and levels of physical health, both in the community at large and in healthcare settings. Medically, urinary incontinence predisposes a patient to urinary tract infections, pressure ulcers, perineal rashes, and urosepsis. Socially and psychologically, urinary incontinence is associated with embarrassment, social stigmatization, depression, and especially for the elderly, an increased risk of institutionalization (Herzo et al., Ann. Rev. Gerontol. Geriatrics, 9:74 (1989)). Economically, the costs are astounding; in the United States alone, over ten billion dollars per year is spent managing incontinence.

Incontinence can be attributed to genuine urinary stress (bladder and urethra hypermobility), to intrinsic sphincter deficiency ("ISD"), or both. It is especially prevalent in women, and to a lesser extent incontinence is present in children (in particular, ISD), and in men following radical prostatectomy.

Stress incontinence is an involuntary loss of urine that occurs during physical activities which increase intra-abdominal pressure, such as coughing, sneezing, laughing, or exercise. A person can suffer from one or both types of incontinence, and when suffering from both, it is called mixed incontinence. Despite all of the knowledge associated with incontinence, the majority of cases of urge incontinence are idiopathic, which means a specific cause cannot be identified. Urge incontinence may occur in anyone at any age, and it is more common in women and the elderly.

The detrusor is the bladder wall muscle that contracts to expel the urine from the bladder. Consequences of detrusor malfunction such as hyperreflexia include poor bladder compliance, high intravesical pressure, and reduction in bladder capacity, all of which may result in deterioration of the upper urinary tract.

One current treatment for urge incontinence is injection of neurotoxins, such as botulinum toxin, e.g., Botox®. It is thought that botulinum toxin exerts its effect on bladder hyperactivity by paralyzing the detrusor muscle in the bladder wall or possibly impacting afferent pathways in the bladder and reducing sensory receptors in suburothelial nerves. The large size of the botulinum toxin molecule can limit its ability to diffuse, and thus prohibits it from reaching both afferent and efferent nerve fibers. As a result, current methods of administration for overactive bladder (OAB), for example, require many injections (typically 20 to 50) of botulinum toxin into the bladder muscle wall, thus increasing the number of doctor visits and associated cost of treatment. Moreover, the safety of chronic long-term impact of inhibition of sensory neurotransmitter release from bladder has not yet been determined.

Further approaches for treatment of urinary incontinence involve administration of drugs with bladder relaxant properties, with anticholinergic medications representing the mainstay of such drugs. For example, anticholinergics such as propantheline bromide, and combination smooth muscle relaxant/anticholinergics such as racemic oxybutynin and dicyclomin, have been used to treat urge incontinence. (See, e.g., A. J. Wein, Urol. Clin. N. Am., 22:557 (1995)). Often, however, such drug therapies do not achieve complete success with all classes of incontinent patients, and often results in the patient experiencing significant side effects.

Besides drug therapies, other options used by the skilled artisan prior to the present invention include the use of artificial sphincters (Lima S. V. C. et al., J. Urology, 156:622-624 (1996), Levesque P. E. et al., J. Urology, 156:625-628 (1996)), bladder neck support prosthesis (Kondo A. et al., J. Urology, 157:824-827 (1996)), injection of cross-linked collagen (Berman C. J. et al., J. Urology, 157:122-124 (1997), Perez L. M. et al., J. Urology, 156:633-636 (1996); Leonard M. P. et al., J. Urology, 156:637-640 (1996)), and injection of polytetrafluoroethylene (Perez L. M. et al., J. Urology, 156:633-636 (1996)).

A recent well known approach for the treatment of urinary incontinence associated with ISD is to subject the patient to periurethral endoscopic collagen injections. This augments the bladder muscle in an effort to reduce the likelihood of bladder leakage or stress incontinence.

Existing solutions to circumvent incontinence have well known drawbacks. While endoscopically directed injections of collagen around the bladder neck has a quite high success rate in sphincter deficiency with no significant morbidity, the use of collagen can result in failures that occur after an average of two years and considerations need to be given to its cost effectiveness (Khullar V. et al., British J. Obstetrics & Gynecology, 104:96-99 (1996)). In addition, deterioration of patient continency, probably due to the migration phenomena (Perez L. M. et al.) may require repeated injections in order to restore continency (Herschorn S. et al., J. Urology, 156:1305-1309 (1996)).

The results with using collagen following radical prostatectomy for the treatment of stress urinary incontinence have also been generally disappointing (Klutke C. G. et al., J. Urology, 156:1703-1706 (1996)). Moreover, one study provides evidence that the injection of bovine dermal collagen produced specific antibodies of IgG and IgA class. (McCell and, M. and Delustro, F., J. Urology 155, 2068-2073 (1996)). Thus, possible patient sensitization to the collagen could be expected over the time.

Despite of the limited success rate, transurethral collagen injection therapy remains an acceptable treatment for intrinsic sphincter deficiency, due to the lack other suitable alternatives.

At present, individuals who suffer from Overactive Bladder Disorders or Urge Incontinence are initially treated by physicians with non-invasive pharmaceutical medical products. However, if these non-invasive pharmaceutical products fail, physicians offer a more invasive solution.

Thus, a need exists for a minimally invasive method of enlarging an existing laminarily organized luminal organ or tissue structure, e.g., a bladder.

Tissue engineering principles have been applied to successfully provide implantable cell-seeded matrices for use in the reconstruction, repair, augmentation or replacement of laminarily organized luminal organs or tissue structures, such as a bladder, a portion of a bladder, or a bladder component. As described in Atala U.S. Pat. No. 6,576,019, cells may be derived from the patient's own tissue, including the bladder, urethra, ureter, and other urogenital tissue. However, there are challenges associated with a dependence upon the development and maintenance of cell culture systems from the primary organ site as the basic unit for developing new and healthy engineered tissues. For example, the treatment of a defective bladder poses a particular challenge regarding cell sourcing because it stands to reason that culturing bladder cells from a defective bladder will result in the cultured cells also being defective. Such cells are not a wise choice for populating an implantable neo-bladder scaffold or matrix. As such there is a need for alternative sources of cells that are suitable for seeding on implantable neo-organ/tissue structure scaffold or matrix.

There is a wealth of literature supporting the notion that human adipose tissue is a rich source of adult stem cells (Devlin et al. (2004), Cytotherapy 6:7-14; Awad, et al. (2003), Tissue Engineering 9:1301-12; Erickson et al. (2002), Biochemical and Biophysical Research Communications 290: 763-769; Gronthos et al. (2001), Journal of Cellular Physiology 189:54-63; Halvorsen et al. (2001); Metabolism 50:407-413; Halvorsen et al. (2001), Tissue Eng. 6:729-41; Harp et al. (2001), Biochemical and Biophysical Research Communication 281:907-912; Hicok et al. (2004), Tissue Engineering 10:371-380; Safford et al. (2002), Jun. 7, 294(2):371-9; Safford et al, (2004), Experimental Neurology 187:319-28; Sen et al. (2004), Journal of Cellular Biochemistry 81:312-319; Sigal et al. (1994), Hepatology 19:999-1006; Wickham et al. (2003), Clinical Orthopedics and Related Research, 412:196-212; Ashijian et al. (2003), Plast Reconstr Surg. 111:1922-31; De Ugarte et al. (2003), Cells Tissues Organs. 174:101-9; Mizumo et al. (2002), Plast Reconstr Surg. 109:199-209; Morizono et al. (2003), Hum Gene Ther. 14:59-66; Winter et al. (2003), Arthritis Rheum. 48:418-29; Zuk et al. (2001), Tissue Eng 7:211-228; Zuk et al. (2002), Mol Biol 13: 4279-4295, reviewed in Gimble et al. (2003), Cytotherapy 5:362-369). These cells, termed Adipose-Derived Adult Stem (ADAS) cells, exhibit an immunophenotype and differentiation potential comparable to that of MSCs (Gronthos et al. (2001), Journal of Cellular Physiology 189:54-63; Safford et al. (2002), Biochem Biophys Res Commun. 294(2):371-9; Zuk et al. (2002), Mol Biol Cell 13:4279-4295).

Reproducible and efficient methods to isolate adult stem cells from human liposuction specimens are available in the public domain (Aust et al. (2004), Cytotherapy 6:7-14; Halvorsen et al. (2001), Metabolism 50:407-413). The procedure involves collagenase digestion of the tissue, differential centrifugation, and expansion in culture. A single gram of tissue can yield between 50,000 to 100,000 stromal cells within 24 hours of culture (Sen et al. (2001), J Cellular Biochemistry 81:312-319). Analysis of specimens obtained from 20 individual donors resulted in a consistent recovery a mean of 401,000 cells with a viability of 94% from a single ml of liposuction waste (Aust et al. (2004), Cytotherapy 6:7-14). Expansion of these cells can result in a population greater than 500 million cells within a 2 week period from a standard lipoaspirate.

In the presence of dexamethasone, insulin, isobutylmethylxanthine and a thiazolidinedione, the ADAS cells undergo adipogenesis (Sen et al. (2001) Journal of Cellular Biochemistry 81:312-319). The differentiation potential of the ADAS cells is not limited to the adipocyte lineage. Conditions that promote ADAS cell differentiation along the chondrocyte and osteoblast pathways have been reported (Awad, et al. (2003), Tissue Engineering 9:1301-12; Erickson et al. (2002), Biochemical and Biophysical Research Communications 290: 763-769; Halvorson et al. (2001), Metabolism 50:407-413; Hicok et al. (2004), Tissue Engineering 10:371-380; Wickham et al. (2003), Clinic Orthopedics and Related Research 412:196-212). In vivo, human ADAS cells combined with a hydroxyapatite biomaterial synthesize osteoid matrix when implanted subcutaneously into immunodeficient mice (Hikok et al. (2004), Tissue Engineering 10:371-380). Substantial data are available to demonstrate that murine or human adipose derived adult stem cells (muADAS and huADAS respectively) cultured in the presence of antioxidants and other mediators undergo morphologic and phenotypic changes consistent with neuronal differentiation (De Ugarte (2003) Cells Tissues Organs. 174:101-9; Safford et al. (2002), 294(2):371-9; Safford et al. (2004), Experimental Neurology 187:319-28).

As described by Jayo et al. Regen. Med. (2008) 3(5), 671-682 (hereinafter referred to as "Jayo I"), attempts to repair organs or tissue have been characterized by incomplete tissue replacement frequently with collagen deposition, and in some cases scar tissue formation. Jayo et al. also observed a more desirable outcome of tissue engineering is regeneration of the original structure and function of a tissue structure or organ. See also Jayo et al., J. Urol. (2008) 180; 392-397 (hereinafter referred to as "Jayo II"). Certain molecules are believed to be associated with the regenerative process in vivo. For example, the chemokine MCP-1 is best known for its ability to recruit mononuclear cells. However, it also appears to be a potent mitogen for vascular smooth muscle cell proliferation. MCP-1 recruits circulating monocytes to the area of vessel injury, which in turn are typically transformed to macrophages that can serve as reservoirs for cytokines and growth factors. Macrophages also ingest cholesterol and oxidize lipids. Macrophages and muscle precursor cells are both believed to be targets for MCP-1 signaling. The CCR-2 receptor is the ligand for MCP-1 (CCL2) and CCR-2 deficient mice show a regeneration defect with enhanced adipogenesis/fibrosis. Sections from CCR-2 deficient mice when challenged with skeletal muscle regeneration demonstrated the following in comparison to normal mice: more interstitial space, a high number of inflammatory cells, large round swollen myofibers, more fibroblast accumulation in interstitial space, fat infiltration with collagen distribution around fat deposits, and fibrosis accompanied by calcium deposition (Warren et al. (2005), FASEB J. 19:413-415; Selzman et al. (2002), Am J Physiol Heart Circ Physiol. 283(4); H1455-H1461; Shannon et al. (2007), Am. J. Cell Physiol. 292:C953-C967; Shireman et al. (2006), J. Surg. Res. 134(1):145-57. Epub 2006 Feb. 20; Amann et al. (1998), Brit. J. Urol. 82:118-121; Schecter et al. (2004), J. Leukocyte Biol.75:1079-1085; Deonarine et al., (2007), Transl Med. 5:11; Lumeng et al. (2007), J. Clin. Invest. 117(1): 175-184).

The present invention concerns cell populations derived from autologous sources that are different from the organ or tissue structure that is the subject of the regeneration, reconstruction, repair, augmentation or replacement described herein, methods of isolating such cells, neo-organ/tissue structure scaffolds or matrices seeded with such cells (constructs) and methods of making the same, as well as methods of treating a patient in need using such neo-organ/tissue structure constructs.

SUMMARY OF THE INVENTION

The present invention relates to the regeneration, reconstruction, repair, augmentation or replacement of laminarly organized luminal organs or tissue structures in a subject in need using scaffolds seeded with autologous cells derived from the subject.

In one aspect, the present invention provides urinary diversion constructs and methods of making and using the same. In one embodiment, the urinary diversion is for a defective bladder in a subject and includes (a) a first implantable, biocompatible construct comprising a tubular scaffold having a first end configured to connect to an abdominal wall section, a second closed end, and at least a first side opening configured to connect to a first ureter; and (b) an autologous cell population that is not derived from the defective bladder, deposited on or in a surface of the scaffold. In another embodiment, the urinary diversion is for a defective bladder in a subject and includes (a) an implantable, biocompatible tubular scaffold adapted for temporary storage and passage of urine that comprises a first end configured to connect to an opening in the subject's abdominal wall, a second closed end, and at least a first side opening adapted to connect to a first ureter to allow passage of urine from the first ureter to the interior of the tubular scaffold; and (b) an autologous cell population that is not derived from the defective bladder, deposited on or in a surface of the scaffold.

In one embodiment, the present invention provides a method of preparing a urinary diversion construct for a defective bladder in a subject in need that includes the steps of a) providing a first implantable biocompatible scaffold comprising a tubular scaffold having a first end configured to contact an abdominal wall section, a second closed end, and at least a first side opening configured to connect to a first ureter; and b) depositing an autologous cell population that is not derived from the defective bladder on or in a first area of the scaffold to form a urinary diversion construct. In another embodiment, the method includes the steps of a) providing an implantable, biocompatible tubular scaffold adapted for temporary storage and passage of urine that comprises a first end configured to connect to an opening in the subject's abdominal wall, a second closed end, and at least a first side opening adapted to connect to a first ureter to allow passage of urine from the first ureter to the interior of the tubular scaffold; and b) depositing an autologous cell population that is not derived from the defective bladder on or in a surface of the scaffold to form a urinary diversion construct.

In one other embodiment, the present invention provides a method of providing a urinary diversion for a defective bladder in a subject in need that includes the steps of a) providing a first implantable biocompatible scaffold comprising a tubular scaffold having a first end configured to connect to an abdominal wall section, a second closed end, and at least a first side opening configured to connect to a first ureter; and b) depositing an autologous cell population that is not derived from the defective bladder on or in a first area of the scaffold to form a urinary diversion construct; and c) implanting the construct into the subject for the formation of the urinary diversion. In another embodiment, the method includes the steps of a) providing an implantable, biocompatible tubular scaffold adapted for temporary storage and passage of urine that comprises a first end configured to connect to an opening in the subject's abdominal wall, a second closed end, and at least a first side opening adapted to connect to a first ureter to allow passage of urine from the first ureter to the interior of the tubular scaffold; b) depositing an autologous cell population that is not derived from the defective bladder on or in a surface of the scaffold to form a urinary diversion construct; and c) implanting the construct into the subject for the formation of the urinary diversion. In one other embodiment, the method includes the step of implanting into the subject a urinary diversion construct comprising (a) a tubular scaffold having a first end configured to contact an abdominal wall section, a second closed end, and at least a first side opening configured to connect to a first ureter; and (b) an autologous cell population that is not derived from the defective bladder, deposited on or in a surface of the scaffold, for the formation of the urinary diversion.

In all embodiments, the urinary diversion scaffold may further comprise a second side opening configured to connect to a second ureter. In all embodiments, the first end may be configured to be positioned flush with the abdominal wall. In all embodiments, the first end may be configured to be sutured to the skin of the subject. In all embodiments, the first end may be configured to form a stoma. In all embodiments, the stoma may further comprise a stoma button. In all embodiments, the scaffold further comprises a washer ring configured to form a stoma. In all embodiments, the biocompatible scaffold is biodegradable. In all embodiments, the scaffold may comprise a material selected from the group consisting of polyglycolic acid, polylactic acid, and a copolymer of polyglycolic acid and polylactic acid. In all embodiments, the cell population is a smooth muscle cell population. In all embodiments, the diversion may be a replacement for the defective bladder. In all embodiments, the diversion may be temporary. In all embodiments, the diversion may be permanent. In all embodiments, the tubular scaffold may have a rectangular cross-section configuration or a triangular cross-section configuration, or a circular cross-section configuration. In all embodiments, the diversion may be free of urothelial cells. In all embodiments, the methods of the present invention may provide a neo-urinary conduit characterized by urinary-like tissue regeneration. In all embodiments, the regenerated tissue may be characterized by the presence of one or more of the following: urothelium, lamina propria, and smooth muscle bundles. In all embodiments, the regenerated tissue can be observed at one or more of the following: ureter-conduit junction (UCJ), cranial portion of the conduit, and mid-atrium portion of the conduit. In all embodiments, the regenerated tissue may be characterized by the presence of one or more of the following: mucosa, submucosa, and smooth muscle with a fibrovascular stroma. In all embodiments, the regenerated tissue is continuous urothelium with underlying smooth muscle. In all embodiments, the urinary conduit forms an epithelialized mucosa upon implantation.

In one aspect, the present invention concerns isolated smooth muscle cell populations. In one embodiment, the cell populations are derived from peripheral blood and contain one or more cells having contractile function, that are positive for a smooth muscle cell marker. In another embodiment, the cell populations are derived from adipose tissue and contain one or more cells having contractile function that are positive for a smooth muscle cell marker.

In all embodiments, the cell populations may be characterized by one or more smooth muscle cell markers selected from the following: myocardin, alpha-smooth muscle actin, calponin, myosin heavy chain, BAALC, desmin, myofibroblast antigen, and SM22. In all embodiments, the cell populations may express myocardin (MYOCD). In all embodiments, the term "MYOCD" includes a nucleic acid encoding a MYOCD polypeptide and a MYOCD polypeptide.

In all embodiments, the contractile function of the cell populations may be calcium-dependent.

In another aspect, the present invention provides a smooth muscle cell (SMC) population derived directly from human adipose tissue. In one embodiment, at least one biomarker selected from the group consisting of Oct4B, osteopontin, BMP6, CD44, and IL-1B, GDF5, HGF, LIF, MCAM, RUNX2, VCAM1, PECAM, vWF, and Flk-1 is differentially expressed in the SMC population, relative to its level of expression in human bone marrow-derived MSCs. In another embodiment, at least one of GDF5, HGF, LIF, MCAM, RUNX2, VCAM1, PECAM, vWF, and Flk-1 is under-expressed in the SMC population, relative to its level of expression in MSCs. In one other embodiment, at least one of Oct4B, osteopontin, BMP6, CD44, and IL-1B is over-expressed in the SMC population, relative to its level of expression in human bone marrow-derived MSCs.

In another embodiment, the present invention provides a smooth muscle cell population derived directly from human adipose tissue characterized by (a) under-expression of at least one of GDF5, HGF, LIF, MCAM, RUNX2, VCAM1, PECAM, vWF, and Flk-1, and (b) over-expression of at least one of Oct4B, osteopontin, BMP6, CD44, and IL-1B, relative to the expression level thereof in human bone marrow-derived MSCs. In yet another embodiment, the SMC population is characterized by (a) under-expression of all of GDF5, HGF, LIF, MCAM, RUNX2, VCAM1, PECAM, vWF, and Flk-1, and (b) over-expression of all of Oct4B, osteopontin, BMP6, CD44, and IL-1B, relative to the expression level thereof in human bone marrow-derived MSCs.

In one other embodiment, the present invention provides a smooth muscle cell population derived directly from adipose tissue that comprises one or more cells that are CD45+ and/or one or more cells that are CD117+.

In another embodiment, the present invention provides a smooth muscle cell population derived directly from human adipose tissue having a shorter proliferative lifespan than human bone marrow-derived MSCs.

In one other embodiment, the present invention provides a smooth muscle cell population derived directly from adipose tissue that exhibits contact-dependant inhibition of proliferation in culture.

In yet another embodiment, the present invention provides a smooth muscle cell population derived directly from adipose tissue characterized by down-regulation of at least one smooth muscle cell (SMC) marker in response to a thromboxane A2 mimetic. In one embodiment, the SMC marker is selected from the group consisting of myocardin and myosin heavy chain-smooth muscle isoform (SMMHC). In another embodiment, the myocardin and SMMHC are down-regulated in response to a thromboxane A2 mimetic.

In one embodiment, the smooth muscle cell populations described herein are purified cell populations.

In one aspect, the present invention provides a preparation or population of cells derived from adipose tissue. In another embodiment, the population is derived from the SVF of adipose tissue. In another embodiment, the SVF contains a cell population that is heterogeneous. In one other embodiment, the population of cells comprises fully differentiated smooth muscle cells. In yet another embodiment, the present invention provides a population of human adipose-derived smooth muscle cells that is distinct from a population of human bone marrow-derived mesenchymal stem cells (MSCs). In one embodiment, the distinction is based upon transcriptomic, proteomic, and functional attributes that are different in the human adipose-derived SMC population, as compared to a population of human bone marrow-derived MSCs. In one embodiment, the cell population is derived from adipose tissue obtained from an autologous source.

In another aspect, the present invention provides methods of isolating smooth muscle cell populations from autologous peripheral blood or adipose sources.

In one embodiment, the method includes the steps of (a) contacting a peripheral blood sample with a density gradient material; (b) centrifuging the sample to define a density gradient comprising a mononuclear fraction; (c) extracting the mononuclear fraction from the density gradient, wherein the fraction contains a cell population having one or more smooth muscle cells having contractile function that are positive for a smooth muscle cell marker. In another embodiment, the method further includes the step of (d) culturing the cell population. In one embodiment, the cultured cell population forms smooth muscle cell colonies in culture. In yet another embodiment, the colonies form about 5 to about 10 days after culture. In a further embodiment, the cell population does not form endothelial colonies. In other embodiments, the method further comprises expanding the cell population of step (d). In another embodiment, the expanded cell population is a purified cell population.

In another embodiment, the method includes the steps of (a) digesting an adipose tissue sample with collagenase; (b) centrifuging the sample to define a stromal vascular fraction (SVF); and (c) extracting the SVF from the sample, wherein the fraction contains a cell population having one or more smooth muscle cells having contractile function that are positive for a smooth muscle cell marker. In another embodiment, the method further includes the step of (d) culturing the cell population. In other embodiments, the method further includes the step of expanding the cell population from step (d). In one other embodiment, the expanded cell population is a purified cell population.

In a further embodiment, the present invention provides a method of providing an isolated smooth muscle cell population that includes the steps of a) culturing a heterogenous smooth muscle cell preparation derived from a human adipose SVF without the use of smooth muscle cell differentiation inductive media; and b) isolating a fully differentiated smooth muscle cell population from the cultured cell preparation. In one other embodiment, the culturing step is preceded by the step of enzymatically digesting adipose tissue. In another embodiment, the culturing step is preceded by the step of centrifuging the digested adipose tissue to provide the SW. In other embodiments, the culturing step is preceded by the step of washing and plating the SVF. In another embodiment, the culturing step comprises selecting for cells that are adherent to a cell culture support. In yet another embodiment, the culturing step does not comprise the use of media containing components for inducing smooth muscle cell differentiation. In one other embodiment, the culturing step comprises the use of cell culture media containing serum, such as fetal bovine serum (FBS), which contains several endogenous growth factors. In another embodiment, the culturing step does not comprise the selection and addition of specific, exogenous growth factors to the cell culture media. In general, an "exogenous" growth factor is a growth factor that is selected and added to a cell culture media in addition to the endogenous growth factors that are typically already provided by the serum component of the media, such as from FBS. Exogenous growth factors may be recombinant growth factors. In one embodiment, the culturing step does not comprise the use of cell culture media containing exogenous growth factors. In another embodiment, the culturing step does not comprise the use of cell culture media containing recombinant growth factors.

In all embodiments, the smooth muscle cell population is not an adipose-derived stem cell population and/or the smooth muscle cell population is not a mesenchymal stem cell population.

In one other aspect, the present invention provides constructs for providing a new laminarily organized luminal organ or tissue structure to a subject in need. In one embodiment, the construct includes (a) an implantable construct comprising a polymeric matrix or scaffold; and (b) an autologous cell population deposited on or in a surface of the polymeric matrix that is not derived from a native organ or tissue corresponding to the new organ or tissue structure.

In another aspect, the present invention provides constructs for providing a neo-bladder or portion thereof to a subject in need. In one embodiment, the construct includes (a) an implantable construct comprising a polymeric matrix or scaffold; and (b) an autologous cell population that is not derived from the subject's bladder deposited on or in a surface of the polymeric matrix.

In certain embodiments, the shaped polymeric matrix construct has an ellipsoid shape. In some embodiments, the shaped polymeric matrix construct is formed into a folded configuration at the time of implantation. In one embodiment, the shaped polymeric matrix construct is treated prior to the time of implantation such that flexibility of the shaped polymeric matrix construct is more flexible at the time of implantation. In another embodiment, the shaped polymeric matrix construct is about 10 cm in maximal length. In one embodiment, the shaped polymeric matrix construct is about 4 cm in maximal length. In another embodiment, the shaped polymeric matrix construct is about 3 cm in maximal length. In yet another embodiment, the shaped polymeric matrix construct is about 4 cm in maximal width. In one embodiment, the shaped polymeric matrix construct has a 2D surface area of about 30 cm$^2$. In another embodiment, the shaped polymeric matrix construct has a 2D surface area of about 25 cm$^2$.

In other embodiments, the constructs contain cell populations having one or more peripheral blood-derived smooth muscle cells having contractile function that are positive for a smooth muscle cell marker, or cell populations having one or more adipose tissue-derived smooth muscle cells having contractile function that are positive for a smooth muscle cell marker. In one embodiment, the cell population of the construct has calcium-dependent contractile function.

In all embodiments, the construct may be free of other cell populations. In all embodiments, the construct may be free of urothelial cells. In all embodiments, the autologous cell population deposited on the matrix is a human adipose-derived smooth muscle cell population as described herein. In all embodiments, the human adipose-derived SMC population may be derived directly from the SVF and is fully differentiated. In all embodiments, the human adipose-derived SMC population seeded on the matrix may have the capacity to produce MCP-1 upon implantation of the construct in the subject at a site in need. In one embodiment, the MCP-1 is an attractant for native mesenchymal stem cells to the site of implantation.

In another aspect, the present invention provides methods for preparing a new organ or tissue structure construct suitable for implantation into a subject in need. In one embodiment, the method includes the steps of a) obtaining a human adipose tissue sample; b) isolating a fully differentiated smooth muscle cell population from the sample; c) culturing the cell population; and d) contacting the cell population with a shaped polymeric matrix cell construct, wherein steps a), b), c) and d) are performed in about 45 days or less. In all embodiments, the human adipose tissue sample is obtained from an autologous source. In one other embodiment, the method further includes the step of detecting expression of a smooth muscle cell marker. In another embodiment, expression is mRNA expression. In a further embodiment, the expression is polypeptide expression. In one embodiment, the polypeptide expression is detected by intracellular immunofluorescence.

In one other aspect, the present invention provides methods for providing a laminarily organized luminal organ or tissue structure to a subject in need. In one embodiment, the method includes the steps of a) providing a biocompatible synthetic or natural polymeric matrix shaped to conform to at least a part of the organ or tissue structure in need of the treatment; b) depositing on or in a first area of the polymeric matrix an autologous cell population that is not derived from a native organ or tissue corresponding to the new organ or tissue structure; and c) implanting the shaped polymeric matrix cell construct into the subject for the formation of a laminarily organized luminal organ or tissue structure. In one other aspect, the present invention provides methods for providing a neo-bladder or portion thereof to a subject in need. In one embodiment, the method includes a) providing a biocompatible synthetic or natural polymeric matrix shaped to conform to a bladder or portion thereof; b) depositing an autologous cell population that is not derived from the subject's bladder on or in a first area of the polymeric matrix; and c) implanting the shaped polymeric matrix cell construct into the subject for the formation of the neo-bladder or portion thereof. In another embodiment, the cell population of step b) of the methods described herein contains one or more peripheral blood-derived smooth muscle cells having contractile function that are positive for a smooth muscle cell marker, or the cell population of step b) contains one or more adipose tissue-derived smooth muscle cells having contractile function that are positive for a smooth muscle cell marker. In one other embodiment, the contractile function of the cell population is calcium-dependent. In all embodiments, the autologous cell population deposited on the matrix is a human adipose-derived smooth muscle cell population as described herein. In all embodiments, the human adipose-derived SMC population seeded on the matrix has the capacity to produce MCP-1 upon implantation of the construct in the subject at a site in need. In one embodiment, the MCP-1 is an attractant for native mesenchymal stem cells to the site of implantation.

In one embodiment, the methods of the present invention further include the step of wrapping the implanted conduit construct with the subject's omentum, mesentery, muscle fascia, and/or peritoneum to allow for vascularization.

The present invention further relates to the enlargement of laminarly organized luminal organs or tissue structures in a subject in need using scaffolds seeded with autologous cells derived from the subject. In one aspect, the present invention provides methods of expanding an existing laminarily organized luminal organ or tissue structure in a subject in need of such treatment by providing a polymeric matrix or scaffold shaped to conform to at least a part of the organ or tissue structure in need of the treatment and of a sufficient size to be laparoscopically implanted, depositing an autologous cell population that is not derived from the organ or tissue structure on or in a first area of the polymeric matrix, and laparoscopically implanting the shaped polymeric matrix construct into the subject at the site of the treatment such that the existing laminarily organized luminal organ or tissue structure is expanded. In certain embodiments, the luminal organ or tissue structure is a bladder or a part of a bladder.

In another aspect, the instant invention provides methods for increasing bladder volumetric capacity of a bladder in a subject in need of such treatment by providing a biocompatible synthetic or natural polymeric matrix shaped to conform to at least a part of the bladder in need of such treatment and of a sufficient size to be laparoscopically implanted, depositing an autologous cell population that is not derived from the subject's bladder on or in a first area of the polymeric matrix, and laparoscopically implanting the shaped polymeric matrix construct laparoscopically into the subject at the site of the treatment such that bladder volume capacity is increased. In one embodiment, the bladder volume capacity is increased about 50 mL. In another embodiment, the bladder volume capacity is increased about 100 mL.

In yet another aspect, the present invention provides methods for expanding a bladder incision site in a bladder of a subject in need of such treatment by providing a biocompatible synthetic or natural polymeric matrix shaped to conform to at least a part of the bladder in need of the treatment and of a sufficient size to be laparoscopically implanted, depositing an autologous cell population that is not derived from the bladder on or in a first area of the polymeric matrix, and laparoscopically implanting the shaped polymeric matrix construct laparoscopically into the subject at the site of the treatment such that the bladder incision site is expanded.

In still another aspect, the present invention provides methods for the treatment of urinary incontinence in a subject in need of such treatment by providing a biocompatible synthetic or natural polymeric matrix shaped to conform to at least a part of the subject's bladder and of a sufficient size to be laparoscopically implanted, depositing an autologous cell population that is not derived from the bladder on or in a first area of the polymeric matrix, laparoscopically implanting the shaped polymeric matrix construct laparoscopically into the subject at the site of the treatment such that bladder volume capacity is increased.

The present invention further provides kits comprising the polymeric matrix or scaffold of the invention and instructions for use.

In another aspect, the present invention provides a prognostic method for monitoring regeneration of a new organ or tissue structure in a subject following implantation. In one embodiment, the method includes the step of detecting the level of MCP-1 expression in a test sample obtained from the subject and in a control sample, wherein a higher level of expression of MCP-1 in the test sample, as compared to the control sample, is prognostic for regeneration in the subject. In another embodiment, wherein the new organ or tissue structure is derived from an autologous smooth muscle cell population described herein. In one other embodiment, MCP-1 polypeptide expression is detected. In another embodiment, MCP-1 polypeptide expression is detected using an anti-MCP-1 agent. In one other embodiment, the anti-MCP-1 agent is an antibody. In another embodiment, MCP-1 polypeptide expression is detected using immunohistochemistry. In one embodiment, the detecting step is preceded by the step of obtaining the test sample from the subject. In another embodiment, the test sample is blood.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIG. 4 shows different applications of a urinary diversion or conduit construct.

FIG. 7 depicts different muscle equivalent scaffolds and representative methods of implantation.

FIG. 9B depicts one scaffold of 18.7 cm in length by 2.0 cm in width having 2 folds.

FIG. 9C depicts one scaffold of 13.3 cm in length by 2.8 cm in width having 3 folds.

FIG. 9D depicts one scaffold of 9.7 cm in length by 4.0 cm in width having 4 folds.

FIG. 9E depicts one scaffold comprised of two pieces, 2 folds each, of 9.7 cm in length and 2.0 cm in width.

FIG. 68 shows morphological features of porcine (A) bladder-, (B) adipose-, and (C) peripheral blood-derived smooth muscle cells.

FIG. 69 shows RT-PCR analysis of smooth muscle cell associated markers from porcine bladder-, adipose-, and peripheral blood-derived smooth muscle cells.

FIG. 70 shows immuno-fluorescence analysis of smooth muscle cell associated markers from porcine bladder, adipose & peripheral blood-derived smooth muscle cells.

FIG. 71 shows contractility of porcine (A) bladder-, (B) adipose-, and (C) peripheral blood-derived smooth muscle cells.

FIG. 72 shows the growth kinetics of (A) bladder-, (B) adipose-, and (C) peripheral blood-derived smooth muscle cells.

FIG. 73 shows the histological characteristics of the regenerated urological tissue formed from implanted neo-urinary conduit constructs.

FIG. 75 shows cystograms for implanted neo-bladder constructs at 4 months. A—Bladder-derived SMCs; B—Blood-derived SMCs; C—Adipose tissue-derived SMCs; D—Native bladder baseline.

FIG. 101 shows the results of RT-PCR analysis of mesodermal differentiation markers.

FIG. 102 shows the results of RT-PCR analysis of Oct4A/Oct4B expression in MSC/AdSMC.

DETAILED DESCRIPTION OF THE INVENTION

Figure 1:
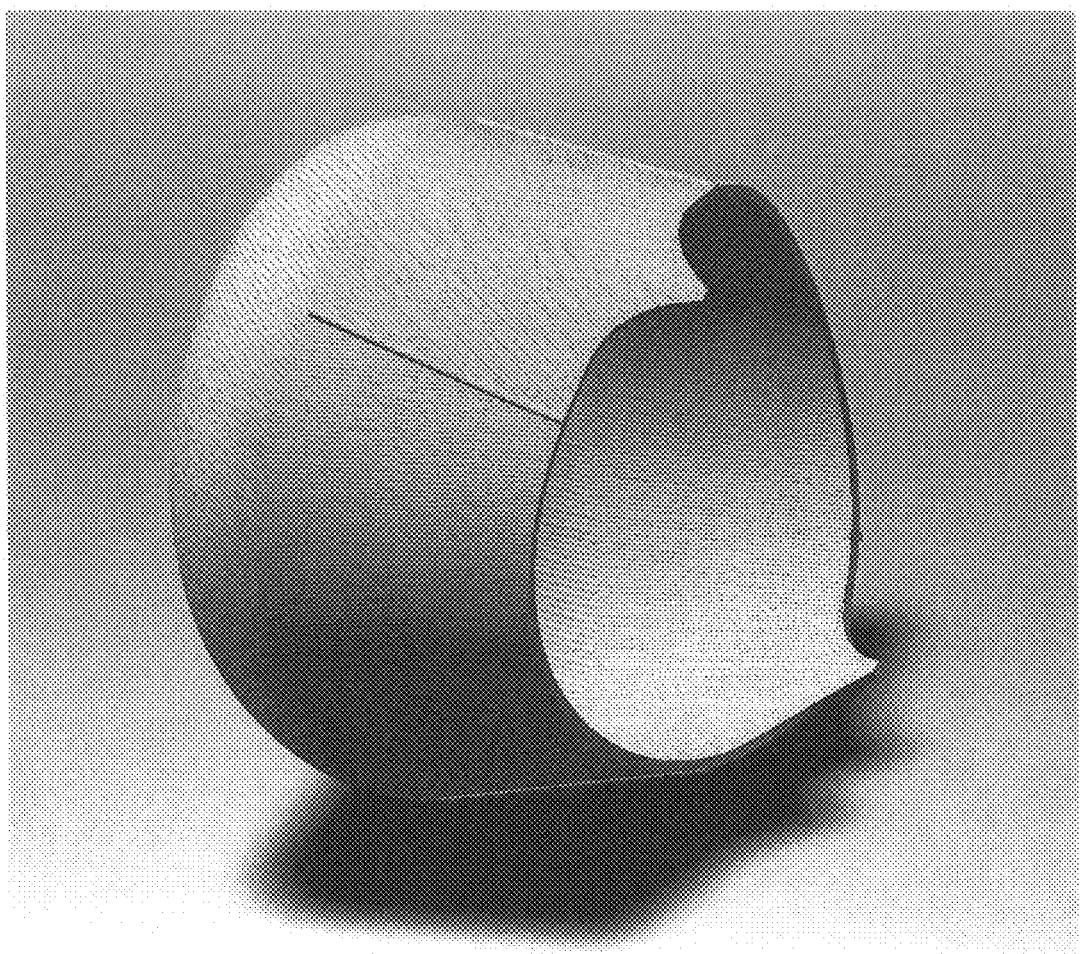
FIG. 1 shows an example of a bladder augmentation scaffold.

The present invention concerns cell populations derived from sources that are different from the organ or tissue structure that is the subject of the reconstruction, repair, augmentation or replacement described herein, methods of isolating such cells, neo-organ/tissue structure scaffolds or matrices seeded with such cells (constructs) and methods of making the same, and methods of treating a patient in need using such neo-organ/tissue structure constructs.

1. Definitions

Unless defined otherwise, technical and scientific terms used herein have the same meaning as commonly understood by one of ordinary skill in the art to which this invention belongs. *Principles of Tissue Engineering*, $3^{rd}$ Ed. (Edited by R Lanza, R Langer, & J Vacanti), 2007 provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "smooth muscle cell" or "SMC" as used herein refers to a contractile cell that is derived from a source that is different from the native organs or tissues that are the subject of the reconstruction, repair, augmentation or replacement constructs and methods as described herein. The SMCs may be derived from peripheral blood or adipose tissue. For adipose tissue, the SMCs may be derived from a SVF containing vascular tissue. Thus, the SMCs may be derived from the capillaries, arterioles, and venules of the adipose-derived vascular bed, or the SMCs may be derived from the perivascular niche containing pericytes. The smooth muscle cells provided by the present invention, once seeded and cultured on the scaffolds or matrices described herein, are capable of forming the non-striated muscle that is found in the walls of hollow organs (e.g. bladder, abdominal cavity, gastrointestinal tract, etc.) and characterized by the ability to contract and relax. Those of ordinary skill in the art will appreciate other attributes of smooth muscle cells.

The term "cell population" as used herein refers to a number of cells obtained by isolation directly from a suitable mammalian tissue source and subsequent culturing in vitro. Those of ordinary skill in the art will appreciate that various methods for isolating and culturing cell populations for use with the present invention and the various numbers of cells in a cell population that are suitable for use in the present invention and the various numbers of cells in a cell population that are suitable for use in the present invention. The cell population may be an adipose-derived smooth muscle cell population (SMC) that is substantially free of adipocytes or non-adherent adipose cells. The SMC population may be characterized by the expression of markers associated with smooth muscle cells. The SMC population may also be a purified cell population. The SMC population may be derived from an autologous source.

The term "autologous" refers to derived or transferred from the same individual's body. An autologous smooth muscle cell population is derived from the subject who will be recipient of an implantable construct as described herein.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. In general, the term cell "marker" or "biomarker" refers to a molecule expressed in a cell population described herein that is typically expressed by a native cell. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function.

The term "smooth muscle cell marker" refers to generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a smooth muscle cell. In general, the term smooth muscle cell (SMC) "marker" or "biomarker" refers to a molecule that is typically expressed by a native smooth muscle cell. The marker may be a polypeptide expressed by the cell or an identifiable physical location on a chromosome, such as a gene, a restriction endonuclease recognition site or a nucleic acid encoding a polypeptide expressed by the SMC. The marker may be an expressed region of a gene referred to as a "gene expression marker", or some segment of DNA with no known coding function. Such markers contemplated by the present invention include, but are not limited to, one or more of the following: myocardin, alpha-smooth muscle actin, calponin, myosin heavy chain, BAALC, desmin, myofibroblast antigen, SM22, and any combination thereof.

The terms "differentially expressed gene," "differential gene expression" and their synonyms, which are used interchangeably, refer to a gene whose expression is activated to a higher or lower level in a first cell or cell population, relative to its expression in a second cell or cell population. The terms also include genes whose expression is activated to a higher or lower level at different stages over time during passage of the first or second cell in culture. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between the first cell and the second cell. Differential expression includes both quantitative, as well as qualitative, differences in the temporal or cellular expression pattern in a gene or its expression products among, for example, the first cell and the second cell. For the purpose of this invention, "differential gene expression" is considered to be present when there is an at least about one-fold, at least about 1.5-fold, at least about 2-fold, at least about 2.5-fold, at least about 3-fold, at least about 3.5 fold, at least about 4-fold, at least about 4.5-fold, at least about 5-fold, at least about 5.5-fold, at least about 6-fold, at least about 7-fold, at least about 8-fold, at least about 9-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, or at least about 15-fold difference between the expression of a given gene in the first cell and the second cell, or at different stages over time during passage of the cells in culture. The differential expression of a marker may be in an adipose-derived cell (the first cell) relative to expression in a mesenchymal stem cell or MSC (the second cell).

The terms "inhibit", "down-regulate", "under-express" and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls. The under-expression may be in an adipose-derived cell relative to expression in an MSC.

The term "up-regulate" or "over-express" is used to mean that the expression of a gene, or level of RNA molecules or equivalent RNA molecules encoding one or more proteins or protein subunits, or activity of one or more proteins or protein subunits, is elevated relative to one or more controls, such as, for example, one or more positive and/or negative controls. The over-expression may be in an adipose-derived cell relative to expression in an MSC.

The term "contractile function" refers to smooth muscle contractile function involving the interaction of sliding actin and myosin filaments, which is initiated by calcium-activated phosphorylation of myosin thus making contraction dependent on intracellular calcium levels.

The term "contact-dependent inhibition" refers to the halting of cell growth when two or more cells come into contact with each other. The absence of this property can be observed in cell culture where cells whose growth is not inhibited by contact can be observed piling on top of each other, similar to foci formation in transformed cell culture. Mesenchymal stem cells do not exhibit this property. In contrast, cells having the contact-dependent inhibition property will not be observed to pile on top of each other in culture.

The term "peripheral blood" shall generally mean blood circulating throughout the body.

The term "adipose tissue" or "fat" shall generally mean loose connective tissue made up primarily of adipocytes. Adipose tissue can be obtained from various places in the body including, without limitation, beneath the skin (subcutaneous fat) and around internal organs (visceral fat).

The term "construct" refers to at least one cell population deposited on or in a surface of a scaffold or matrix made up of one or more synthetic or naturally-occurring biocompatible materials. The cell population may be combined with a scaffold or matrix in vitro or in vivo.

The term "sample" or "patient sample" or "biological sample" shall generally mean any biological sample obtained from an individual, body fluid, body tissue, cell line, tissue culture, or other source. The term includes body fluids such as, for example, blood such as peripheral blood or venous blood, urine and other liquid samples of biological origin, such as lipoaspirates, and solid tissue biopsies such as a biopsy specimen (e.g., adipose tissue biopsy), or tissue cultures or cells derived therefrom, and the progeny thereof. The definition also includes samples that have been manipulated in any way after they are obtained from a source, such as by treatment with reagents, solubilization, or enrichment for certain components, such as proteins or polynucleotides. The definition also encompasses a clinical sample, and also includes cells in culture, cell supernatants, cell lysates, serum, plasma, biological fluid, and tissue samples. The source of a sample may be solid tissue, such as from fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in the development of the subject. The biological sample may contain compounds which are not naturally present with or in the tissue in nature such as preservatives, anticoagulants, buffers, fixatives, nutrients, antibiotics, or the like. The sample can be used for a diagnostic or monitoring assay. Methods for obtaining samples from mammals are well known in the art. If the term "sample" is used alone, it shall still mean that the "sample" is a "biological sample" or "patient sample", i.e., the terms are used interchangeably. A sample may also be a test sample.

The term "test sample" refers to a sample from a subject following implantation of a construct described herein. The test sample may originate from various sources in the mammalian subject including, without limitation, blood, serum, urine, semen, bone marrow, mucosa, tissue, etc.

The term "control" or "control sample" refers a negative control in which a negative result is expected to help correlate a positive result in the test sample. Alternatively, the control may be a positive control in which a positive result is expected to help correlate a negative result in the test sample. Controls that are suitable for the present invention include, without limitation, a sample known to have normal levels of a cytokine, a sample obtained from a mammalian subject known not to have been implanted with a construct described herein, and a sample obtained from a mammalian subject known to be normal. A control may also be a sample obtained from a subject prior to implantation of a construct described herein. In addition, the control may be a sample containing normal cells that have the same origin as cells contained in the test sample. Those of skill in the art will appreciate other controls suitable for use in the present invention.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "subject" shall mean any single human subject, including a patient, eligible for treatment, who is experiencing or has experienced one or more signs, symptoms, or other indicators of a deficient organ function or failure, including a deficient, damaged or non-functional urinary system. Such subjects include, without limitation, subjects who are newly diagnosed or previously diagnosed and now experiencing a recurrence or relapse, or are at risk for deficient organ function or failure, no matter the cause. The subject may have been previously treated for a condition associate with deficient organ function or failure, or not so treated. Subjects may be candidates for a urinary diversion including, without limitation, subjects having cancer of the bladder requiring a cystectomy, subjects having a neurogenic bladder that impacts renal function, subjects having radiation injury to the bladder, and subjects having intractable incontinence. The subject may be newly diagnosed as requiring a urinary diversion, or previously diagnosed as requiring a urinary diversion and now experiencing complications, or at risk for a deficient, damaged or non-functional urinary system, no matter the cause. The subject may have been previously treated for a condition associated with a deficient, damaged or non-functional urinary system, or not so treated.

The term "urinary diversion" or "conduit" refers to the resulting organ or tissue structure resulting from the subject's interaction over time with an implanted urinary diversion construct, anastomosed ureters, and adjacent atrium. The atrium is the anterior connecting chamber that allows for urine passage through the abdominal wall and may be made by the most anterior tube-like portion of a peritoneal wrap connecting the caudal end of the construct (located in the intra-abdominal cavity) to the skin.

The terms "caudal" and "cranial" are descriptive terms relating to the urinary production and flow. The term "caudal" refers to the end of the urinary diversion construct that upon implantation is closest to the stoma, while the term "cranial" refers to the end of the urinary diversion construct that upon implantation is closest to the kidneys and ureters.

The term "detritis" refers to debris formed during the healing and regenerative process that occurs following implantation of a urinary diversion construct. Detritis can be made up of exfoliated tissue cells, inflammatory exudate and scaffold biodegradation. If the conduit is obstructed (improper outflow) by such debris, then the stagnated debris forms a detritis or semisolid bolus within the lumen of the conduit.

The term "debridement" refers to surgical or non-surgical removal of foreign matter, or lacerated, devitalized, contaminated or dead tissue from a conduit in order to prevent infection, prevent obstruction, and to promote the healing process. The debridement may involved the removal of detritis.

The term "stoma" refers to a surgically created opening used to pass urine from the draining outflow end of a urinary diversion construct to outside the body. The urine is typically collected in a reservoir outside the body.

The term "stoma port" or "stoma button" refers to means, such as a device used to maintain the integrity of the stoma opening.

The term "expanding" or "enlarging" as used herein refers to increasing the size of the existing laminarily organized luminal organ or tissue structure. For example, in one aspect of the invention, the existing laminarily organized luminal organ or tissue structure may be enlarged by 10, 11, 12, 13, 14, 15, 16, 17, 18, 19, 20, 21, 22, 23, 24, 25, 26, 27, 28, or 29 percent. In another aspect of the invention, the existing laminarily organized luminal organ or tissue structure may be enlarged such as to increase the existing volumetric capacity of the existing laminarily organized luminal organ or tissue structure.

The term "volumetric capacity" as used herein refers to the amount of liquid capable of being contained in a defined area.

"Regeneration prognosis" or "regenerative prognosis" generally refers to a forecast or prediction of the probable course or outcome of the implantation of a construct described herein. As used herein, regeneration prognosis includes the forecast or prediction of any one or more of the following: development or improvement of a functional bladder after bladder replacement or augmentation, development of a functional urinary diversion after conduit implantation, development of improved bladder capacity, and development of improved bladder compliance. As used herein, "prognostic for regeneration" means providing a forecast or prediction of the probable course or outcome of the implantation of a new organ or tissue structure. In some embodiments, "prognostic for regeneration" comprises providing the forecast or prediction of (prognostic for) any one or more of the following: development or improvement of a functional bladder after bladder replacement or augmentation, development of a functional urinary diversion after conduit implantation, development of bladder capacity or improved bladder capacity, and development of bladder compliance or improved bladder compliance.

"Regenerated tissue" refers to the tissue of a new organ or tissue structure that develops after implantation of a construct as described herein. The organ or tissue structure may be a bladder or a part of a bladder. The regenerated tissue may include a continuos urothelium with underlying smooth muscle.

2. Cell Populations

The present invention provides populations of smooth muscle cells for use in the reconstruction, repair, augmentation or replacement of laminarly organized luminal organs or tissue structures in which the cell population comprises at least one cell that has contractile function and is positive for one or more smooth muscle cell markers.

As discussed herein, tissue engineering principles have been successfully applied to provide implantable cell-seeded matrices for use in the reconstruction, repair, augmentation or replacement of laminarily organized luminal organs and tissue structures, such as a bladder or a bladder component, typically composed of urothelial and smooth muscle layers. (Becker et al. *Eur. Urol.* 51, 1217-1228 (2007); Frimberger et al. *Regen. Med.* 1, 425-435 (2006); Roth et al. *Curr. Urol. Rep.* 10, 119-125 (2009); Wood et al. *Curr. Opin. Urol.* 18, 564-569). Smooth muscle cells may be derived from the patient's own tissue, including the bladder, urethra, ureter and other urogenital tissue. However, there are challenges associated with dependence upon the development and maintenance of cell culture systems from the primary organ site as the basic unit for developing new and healthy engineered tissues, as for example during treatment of cancerous bladder tissue. Clearly, such cancerous cells are inappropriate for populating an implantable neo-bladder scaffold or matrix.

The present invention provides cell populations that are derived from sources that are different from the organ or tissue structure that is the subject of the reconstruction, repair, augmentation or replacement. In one embodiment, the source is an autologous source.

In another aspect, the cell population expresses markers consistent with or typical of a smooth muscle cell population.

In one other aspect, the present invention provides smooth muscle cell populations isolated from sources that are different from the luminal organ or tissue structure that is the subject of the reconstruction, repair, augmentation or replacement. In a preferred embodiment, the luminal organ or tissue structure is a bladder or portion of a bladder.

In one aspect, the source is peripheral blood. In one embodiment, the peripheral blood-derived smooth muscle cell population is derived from a patient sample. The patient sample may be venous blood.

In one aspect, the source is adipose tissue. In one embodiment, the adipose tissue-derived smooth muscle cell population is derived from a patient sample. The patient sample may be adipose tissue removed during an abdominalplasty procedure, or lipoaspirates. In a preferred embodiment, the patient sample In yet one other embodiment, the isolated cell populations of the present invention, upon culturing, can develop various smooth muscle cell characteristics including, but not limited to, hill-and-valley morphology, expression of one or more smooth muscle cell markers, contractile function, filament formation, and cytokine synthesis.

In one aspect, the cultured cell population is characterized by its hill-and-valley morphology. The cells having a hill-and-valley morphology may have various characteristics including, without limitation, spindly shaped, flattened and fibroblast-like upon passage, elongated and arranged in parallel rows, a "whirled" appearance of growth, and any combination thereof. In one embodiment, the cell population upon culturing in the appropriate media develops a "hill-and-valley morphology" that is typical of cultured smooth muscle cells.

In another aspect, the cultured cell population is characterized by the presence of one or more smooth muscle cell markers. In one embodiment, the cell population upon culturing in the appropriate media develops detectable smooth muscle cell markers including, without limitation, one or more of the following myocardin, alpha-smooth muscle actin, calponin, myosin heavy chain, BAALC, desmin, myofibroblast antigen, SM22, and any combination thereof.

In another aspect, the cultured cell population is characterized by the presence of one or more cells that express one or more cell surface markers. In one embodiment, the cell population upon culturing in the appropriate media contains one or more cells that are positive for cell surface markers including, without limitation, one or more of the following CD73, CD90, CD105, CD166, CD31, CD54, CD56, CD117, and any combination thereof. In another embodiment, the cell population upon culturing in the appropriate media contains one or more cells that are CD45+, CD31+, CD54+, CD56+, CD90+, and CD105+.

In one other aspect, the cultured cell population is characterized by the presence of one or more cells having contractile function. In one embodiment, the cell population upon culturing in the appropriate media develops contractile function. In another embodiment, the contractile function is calcium dependent. In one other embodiment, the calcium-dependent contractile function is demonstrated by inhibition of contraction with a calcium chelator. In another embodiment, the calcium chelator is EDTA. Those of ordinary skill in the art will appreciate that other chelators known in the art may be suitable.

In yet another aspect, the cultured cell population is characterized by filament formation. In one embodiment, the cell population upon culturing in the appropriate media undergoes filament formation.

In one aspect, the cell population includes at least one cell expressing one or more cytokines. In one embodiment, the cytokine is selected from the group consisting of MCP-1, oncostatin M, IL-8, and GRO.

In one aspect, the cell populations of the present invention have a finite proliferative lifespan in culture following isolation. In other embodiments, the cell population has a lifespan of about 1 passage, about 2 passages, about 3 passages, about 4 passages, about 5 passages, about 6 passages, about 7 passages, about 8 passages, about 9 passages, about 10 passages, about 11 passages, about 12 passages, about 13 passages, about 14 passages, about 15 passages, about 16 passages, about 17 passages, or about 18 passages. In a preferred embodiment, the cell population has a lifespan in culture of no more than 5 passages. The adipose-derived SMCs can generally be cultured 3-5 days between passages and the blood-derived SMCs can generally be cultured 14 days before the first passage and then 3-5 days for additional passages (see Example 1 for more details)

In one aspect, the present invention provides a regenerative cell population containing at least one regenerative cell that when deposited on a scaffold or matrix as described herein and implanted into a subject in need, provides a regenerative effect for the organ or tissue structure that is the subject of the reconstruction, repair, augmentation, or replacement contemplated herein. A regenerative cell population has the ability to stimulate or initiate regeneration of laminarly organized luminal organs or tissue structures upon implantation into a patient in need. In general, the regeneration of an organ or tissue structure is characterized by the restoration of cellular components, tissue organization and architecture, function, and regulative development. In addition, a regenerative cell population minimizes the incompleteness or disorder that tends to occur at the implantation site of a cell-seeded luminal organ or tissue structure construct. Disorganization at the site of implantation can manifest itself as increased collagen deposition and/or scar tissue formation, each of which can be minimized through the use of a regenerative cell population. In addition, certain cellular events are indicative of the regenerative process. In the case of a regenerated bladder or portion of a bladder using the cell populations and scaffolds described herein, a regenerating organ or tissue structure is composed of a smooth muscle parenchyma with fibrovascular tissue radiating around numerous microvessels that extend toward the luminal surface, as well as stromal elements having well developed blood vessels aligned to the mucosal surface (see Jayo II supra). A regenerating bladder or portion of a bladder is also characterized by the presence of spindloid/mesenchymal cells and αSMA positive muscle precursor cells. In one embodiment, the αSMA positive spindloid cells are observed in neostromal tissues and around multiple neo-vessels (arterioles).

In one embodiment, the present invention provides a cell population that when deposited on a scaffold or matrix as described herein and implanted into a subject in need, provides a reparative effect for the organ or tissue structure that is the subject of the reconstruction, repair, augmentation, or replacement contemplated herein. In other embodiments, a reparative effect is characterized by scar tissue formation and/or collagen deposition. Those of skill in the art will appreciate other characteristics of repair that are known in the art.

In another aspect, the regenerative cell population provides a regenerative effect characterized by the adaptive regulation of the size of a restored laminarly organized luminal organ or tissue structure. In one embodiment, the regenerative cell population's regenerative effect is the establishment of adaptive regulation that is specific to the subject that receives the scaffold or matrix seeded with the regenerative cell population. In one embodiment, the adaptive regulation is the replacement or augmentation of a bladder in a subject using a construct described herein such that the neo-bladder grows and develops to a size that is proportional to the subject's body size.

In one embodiment, the cell population capable of regenerative stimulation is an MCP-1 producing cell population, which contains at least one cell that expresses the chemokine product MCP-1. MCP-1 regenerative stimulation is characterized by the recruitment of certain cell types to the site of implantation. In one embodiment, MCP-1 recruits muscle progenitor cells to the site of implantation to proliferate within the neo-bladder. In another embodiment, MCP-1 recruits monocytes to the site of implantation which in turn produce various cytokines and/or chemokines to facilitate the regenerative process. In one other embodiment, MCP-1 induces omental cells to develop into muscle cells.

In one aspect, the present invention provides the use of specific cytokines, such as MCP-1, as a surrogate marker for tissue regeneration. Such a marker could be used in conjunction with an assessment of regeneration based on whether function has been reconstituted. Monitoring a surrogate marker over the time course of regeneration may also serve as a prognostic indicator of regeneration.

In another embodiment, the cell population is a purified cell population. A purified cell population as described herein is characterized by a phenotype based on one or more of morphology, the expression of markers, and function. The phenotype includes without limitation, one or more of hill-and-valley morphology, expression of one or more smooth muscle cell markers, expression of cytokines, a finite proliferative lifespan in culture, contractile function, and ability to induce filament formation. The phenotype may include other features described herein or known to those of ordinary skill in the art. In another embodiment, the purified populations are substantially homogeneous for a smooth muscle cell population as described herein. A purified population that is substantially homogeneous is typically at least about 90% homogeneous, as judged by one or more of morphology, the expression of markers, and function. In other embodiments, the purified populations are at least about 95% homogeneous, at least about 98% homogeneous, or at least about 99.5% homogeneous.

In another embodiment, the smooth muscle cell population is derived directly from human adipose tissue and is characterized by differential expression of one or more of the following osteopontin, Oct4B, growth differentiation factor 5 (GDF5), hepatocyte growth factor (HGF), leukemia inhibitory factor (LIF), melanoma cell adhesion molecule (MCAM), vascular cell adhesion molecule 1 (VCAM1), PECAM, vWF, Flk-1, runt-related transcription factor 2 (RUNX2), bone morphogenetic protein 6 (BMP6), CD44, and IL-1B, relative to its level of expression in human bone marrow-derived mesenchymal stem cells (MSCs). In one other embodiment, the SMC population (a) under-expresses one or more of GDF5, HGF, LIF, MCAM, RUNX2, VCAM1, PECAM, vWF, and Flk-1 and/or (b) over-expression one or more of Oct4B, osteopontin, BMP6, CD44, and IL-1B, relative to the expression level thereof in human bone marrow-derived MSCs. In one other embodiment, the SMC population (a) under-expresses all of GDF5, HGF, LIF, MCAM, RUNX2, VCAM1, PECAM, vWF, and Flk-1 and/or (b) over-expression all of Oct4B, osteopontin, BMP6, CD44, and IL-1B, relative to the expression level thereof in human bone marrow-derived MSCs.

In another embodiment, the smooth muscle cell population derived directly from adipose tissue that comprises one or more cells that are CD45+ and/or one or more cells that are CD117+.

In other embodiments, the present invention provides a smooth muscle cell population derived directly from human adipose tissue having a shorter proliferative lifespan than human bone marrow-derived MSCs. In another embodiment, the SMC population exhibits contact-dependant inhibition of proliferation in culture. In one other embodiment, the SMC population derived directly from adipose tissue characterized by down-regulation of at least one smooth muscle cell (SMC) marker in response to a thromboxane A2 mimetic. In other embodiments, the SMC marker is selected from the group consisting of myocardin and myosin heavy chain-smooth muscle isoform (SMMHC). In another embodiment, the myocardin and SMMHC are down-regulated in response to a thromboxane A2 mimetic.

In all embodiments, the SMC population is derived from an autologous source.

In one aspect, the present invention contemplates the application of the smooth muscle cell populations described herein for respiratory disorders. Airway smooth muscle is present in the bronchial tree of most vertebrates. A respiratory ocular disorder is one in which the subject has a defective respiratory system due to improper function of the muscles of the lung. It has been reported that certain cell populations may provide beneficial effects when administered to the lung (e.g., Ohnishi et al. Int J Chron Obstruct Pulmon Dis. 2008 December; 3(4): 509-514). Individuals with respiratory disorders such as asthma, emphysema, or chronic obstructive pulmonary disease (COPD) could benefit from these SMC populations. Individuals with lung cancer could also benefit. In one embodiment, an autologous SMC cell population could be isolated from the adipose tissue or peripheral blood of a subject in need. The cell population could be seeded onto a scaffold suitable for implantation at a site within the lung of the subject. An advantage of the cell populations of the present invention is that suitable SMCs may not be available for sourcing from the subject's lung if the subject has a defective respiratory system, e.g., lung cancer. The cell populations may be used in cases where part or all of a subject's lung is removed, such as in the case of lung cancer. Upon removal of a lung or a part of a lung in a subject, an autologous SMC population could be isolated from a biopsy, cultured, seeded on a suitable scaffold, and implanted into the subject to provide a new lung or new lung tissue structure.

In another aspect, the present invention contemplates the application of the SMC populations described herein for ocular disorders. An ocular disorder is one in which the subject has a defective eye due to improper function of the muscles of the eye. Smooth muscle is present as ciliary muscle in the eye and controls the eye's accommodation for viewing objects at varying distances and regulates the flow of aqueous humour through Schlemm's canal. Smooth muscle is also present in then iris of the eye. Individuals with ocular disorders such as presbyopia and hyperopia could benefit from these SMC populations. Individuals with lung cancer could also benefit. In one embodiment, an autologous SMC cell population could be isolated from the adipose tissue or peripheral blood of a subject in need. The cell population could be seeded onto a scaffold suitable for implantation at a site within the eye of the subject. An advantage of the cell populations of the present invention is that suitable SMCs may not be available for sourcing from the subject's eye if the subject has a defective eye or due to the limited availability of eye tissue. An autologous SMC population could be isolated from a biopsy, cultured, seeded on a suitable scaffold, and implanted into the subject to provide new eye tissue.

In another embodiment, the smooth muscle cell populations of the present invention may be administered to a subject having a respiratory disorder or an ocular disorder without the use of a scaffold, such as by engraftment. Those of ordinary skill in the art will appreciate suitable methods of engraftment.

In one embodiment, an autologous SMC cell population could be isolated from the adipose tissue or peripheral blood of a subject in need. The cell population could be seeded onto a scaffold suitable for implantation at a site within the lung of the subject. An advantage of the cell populations of the present invention is that suitable SMCs may not be available for sourcing from the subject's lung if the subject has a defective respiratory disorder, e.g., lung cancer. The cell populations may be used in cases where part or all of a subject's lung is removed, such as in the case of lung cancer. Upon removal of a lung or a part of a lung in a subject, an autologous SMC population could be isolated from a biopsy, cultured, seeded on a suitable scaffold, and implanted into the subject to provide a new lung or lung tissue structure. In another embodiment, the smooth muscle cell populations of the present invention may be administered to a subject having a respiratory disorder without the use of a scaffold, such as by engraftment. Those of ordinary skill in the art will appreciate suitable methods of engraftment.

3. Methods of Isolating Cell Populations

Autologous cell populations are derived directly from the subjects in need of treatment. The subject's source tissue is generally not the same as the organ or tissues structure that is in need of the treatment. An autologous population of cells may be derived from the patient's own tissue such as, for example, from adipose tissue or peripheral blood. The autologous cells may be isolated in biopsies. In addition, the cells may be frozen or expanded before use.

To prepare for construction of a cell-seeded scaffold, sample(s) obtained from a subject containing smooth muscle cells are dissociated into appropriate cell suspension(s). Methods for the isolation and culture of cells were discussed in issued U.S. Pat. No. 5,567,612 which is herein specifically incorporated by reference. Dissociation of the cells to the single cell stage is not essential for the initial primary culture because single cell suspension may be reached after a period, such as, a week, of in vitro culture. Tissue dissociation may be performed by mechanical and enzymatic disruption of the extracellular matrix and the intercellular junctions that hold the cells together. Autologous cells can be cultured in vitro, if desired, to increase the number of cells available for seeding on scaffold.

Cells may be transfected prior to seeding with genetic material. Smooth muscle cells could be transfected with specific genes prior to polymer seeding. The cell-polymer construct could carry genetic information required for the long term survival of the host or the tissue engineered neo-organ.

Cell cultures may be prepared with or without a cell fractionation step. Cell fractionation may be performed using techniques, which is known to those of skill in the art. Cell fractionation may be performed based on cell size, DNA content, cell surface antigens, and viability. For example, smooth muscle cells may be enriched from adipose tissue, while endothelial cells and adipocytes may be reduced for smooth muscle cell collection. While cell fractionation may be used, it is not necessary for the practice of the invention.

Another optional procedure in the methods described herein is cryopreservation. Cryogenic preservation may be useful, for example, to reduce the need for multiple invasive surgical procedures. Cells taken from a biopsy or sample from the subject may be amplified and a portion of the amplified cells may be used and another portion may be cryogenically preserved. The ability to amplify and preserve cells may minimize the number of surgical procedures required. Another example of the utility of cryogenic preservation is in tissue banks. Autologous cells may be stored, for example, in a donor tissue bank. As cells are needed for new organs or tissue structures, the cryopreserved supply of cells may be used as needed. Patients who have a disease or undergoing treatment which may endanger their existing organs or tissue structures may cryogenically preserve one or more biopsies. Later, if the patient's own organ or tissue structure fails, the cryogenically preserved autologous cells may be thawed and used for treatment. For example, if a cancer reappeared in a new organ or tissue structure after treatment, cryogenically preserved cells may be used for reconstruction of the organ or tissue structure without the need for additional biopsies.

Smooth muscle cells may be isolated from adipose or peripheral blood based on the following general protocols. An adipose biopsy specimen of suitable weight (e.g., in grams) and/or area (e.g., $cm^2$) can be obtained. An appropriate volume of peripheral blood (e.g., ml) can be obtained prior to the planned implantation of a new organ or tissue structure construct.

The following is a representative example of a protocol suitable for the isolation of smooth muscle cells from the stromal vascular fraction (SVF) of adipose, which represents a heterogenous cell population composed of multiple cell types, including endothelial and smooth muscle cells as well as cells that are MSC-like as defined by the International Society for Cellular Therapy (ISCT) criteria (Domini et al. 2006 Cytotherapy 8:4, 315-317). A suitable gram weight of adipose tissue (e.g., 7-25 g) can be obtained by biopsy and washed with PBS (e.g., 3 times), minced with a scalpel and scissors, transferred into a 50 mL conical tube and incubated at 37° C. for 60 minutes in a solution of collagenase (e.g., 0.1 to 0.3%) (Worthington) and 1% BSA in DMEM-HG. The tubes may be either continually rocked or periodically shaken to facilitate digestion. The SVF can be pelleted by centrifugation at 600 g for 10 minutes and resuspended in DMEM-HG+10% FBS. The stromal-vascular fraction may then be used to seed passage zero.

The following is a representative example of a protocol suitable for the isolation of smooth muscle cells from peripheral blood. A suitable volume of peripheral blood (e.g. 25 ml) may be diluted 1:1 in PBS and layered with 25 ml Histopaque-1077 (Sigma) in a 50 mL conical tube. Following centrifugation (e.g., 800 g, 30 min), the mononuclear fraction can be collected, washed once with PBS and resuspended in α-MEM/10% FBS (Invitrogen) to seed passage zero.

Those of ordinary skill in the art will appreciate additional methods for the isolation of smooth muscle cells.

In one aspect, the present invention provides methods for isolating an isolated smooth muscle cell population from SVF without the need for conditions that induce differentiation to smooth muscle cells. In one embodiment, the method comprises a) obtaining adipose tissue, b) digesting the adipose tissue, c) centrifuging the digested adipose tissue to provide a stromal vascular fraction (SW), d) culturing the SVF without the need for conditions that induce differentiation to smooth muscle cells, and e) isolating a smooth muscle cell population from the adipose tissue-derived SVF. In one embodiment, the culturing step comprises washing the SVF, re-suspending the SVF in a cell culture media, and plating the re-suspended SVF. In another embodiment, the culturing step comprises providing a cell population that is adherent to the cell culture support, such as a plate or container. In another embodiment, the method further comprises expanding the cultured cell population. In other embodiments, the method further comprises analyzing the smooth muscle cell population for smooth muscle cell characteristics. In one embodiment, the adipose tissue is derived from an autologous source.

In one embodiment, the culturing conditions do not require the use of cell culture components for inducing differentiation of the adipose tissue SVF-derived cell population to smooth muscle cells. Jack et al., J Biomaterials 30 (2009) 3529-3270 report that undifferentiated adipose stem cells derived from SVF were incubated in inductive media containing heparin for 6 weeks in order to differentiate the stem cells into smooth muscle cells (see also Rodriguez U.S. Pat. No. 7,531,355). The stem cells reported by Jack et al. did not require splitting during this incubation period. In another embodiment, the culturing conditions do not require the use of inductive media, including inductive media containing heparin. In one other embodiment, the methods of the present invention comprise the use of culturing conditions that do not require the use of exogenous growth factors for differentiating a cell population into smooth muscle cells or for culturing and expanding a cell population.

The advantages of the methods of the present invention over other reported methods include the elimination of the step of differentiating adipose derived stem cells into smooth muscle cells, which reduces the time between obtaining an adipose biopsy and isolating a smooth muscle cell population therefrom. In addition, the elimination of the need for other cell culture media components for inducing differentiation, such as exogenous growth factors, is advantageous in terms of cost.

In one other aspect, the present invention provides methods of isolating and culturing populations of smooth muscle cells that contain at least one cell that has contractile function and is positive for one or more smooth muscle cell markers. In one embodiment, the method includes the step of obtaining a sample from a patient in need of the reconstruction, repair, augmentation or replacement of a laminarily organized luminal organ or tissue structure, where the sample is not obtained from the luminal organ or tissue structure that is in need of the reconstruction, repair, augmentation or replacement. In another embodiment, smooth muscle cells are derived from the patient sample. In one other embodiment, the luminal organ or tissue structure is a bladder or portion of a bladder. In one embodiment, the sample is an autologous sample. In another embodiment, the sample is a peripheral blood sample. In yet another embodiment, the sample is an adipose tissue sample. The adipose tissue may be tissue removed from a subject as a result of an abdominalplasty procedure.

In another embodiment, the obtaining step is followed by a separation step.

In the case of a peripheral blood sample, the separation step includes contacting the sample with a density gradient material, centrifuging the sample to define a density gradient that has a mononuclear fraction, and extracting the mononuclear fraction from the density gradient. The separation step may be followed by a culturing step in which cells from the extracted fraction are cultured.

In the case of an adipose tissue sample, the purification step includes digestion of the sample with collagenase, centrifuging the digested sample, mixing of the centrifuged sample to separate stromal cells from primary adipocytes, centrifuging the mixed sample to obtain a stromal-vascular fraction that can be resuspended for subsequent culturing.

In one aspect, the present invention provides a method of providing an isolated smooth muscle cell (SMC) population without the use of differentiation inductive cell culture media. In one embodiment, the method includes the steps of a) obtaining an adipose tissue biopsy, b) enzymatically digesting the adipose tissue, c) centrifuging the digested adipose tissue to provide a stromal vascular fraction (SVF) that contains a heterogenous population of cells, d) washing and plating the heterogeneous population of cells; e) culturing the population of cells without the use of smooth muscle cell differentiation inductive media, f) isolating a fully differentiated SMC population from the cultured cells. In one other embodiment, the culturing step e) includes selecting for cells that are adherent to a cell culture support. In another embodiment, the culturing step e) does not include the use of cell culture media that contains exogenous growth factors. In one embodiment, the culturing method includes the use of cell culture media containing minimal essential medium (e.g., DMEM or α-MEM) and fetal bovine serum (e.g., 10% FBS) by standard conditions known to those of ordinary skill in the art. In another embodiment, the smooth muscle cell population is not an adipose-derived stem cell population. In one other embodiment, the smooth muscle cell population is not a mesenchymal stem cell population.

4. Scaffolds

As described in Atala U.S. Pat. No. 6,576,019 (incorporated herein by reference in its entirety), scaffolds or polymeric matrices may be composed of a variety of different materials. In general, biocompatible material and especially biodegradable material is the preferred material for the construction of the scaffolds described herein. The scaffolds are implantable, biocompatible, synthetic or natural polymeric matrices with at least two separate surfaces. The scaffolds are shaped to conform to a at least a part of the luminal organ or tissue structure in need or treatment. The biocompatible materials are biodegradable. Biocompatible refers to materials which do not have toxic or injurious effects on biological functions. Biodegradable refers to material that can be absorbed or degraded in a patient's body. Examples of biodegradable materials include, for example, absorbable sutures. Representative materials for forming the scaffolds include natural or synthetic polymers, such as, for example, collagen, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polyglactin, developed as absorbable synthetic suture material. Polyglycolic acid and polyglactin fibers may be used as supplied by the manufacturer. Other scaffold materials include cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

Other scaffold materials that are biodegradable include synthetic suture material manufactured by Ethicon Co. (Ethicon Co., Somerville, N.J.), such as MONOCRYL™ (copolymer of glycolide and epsilon-caprolactone), VICRYL™ or Polyglactin 910 (copolymer of lactide and glycolide coated with Polyglactin 370 and calcium stearate), and PANACRYL™ (copolymer of lactide and glycolide coated with a polymer of caprolactone and glycolide). (Craig P. H., Williams J. A., Davis K. W., et al.: A Biological Comparison of Polyglactin 910 and Polyglycolic Acid Synthetic Absorbable Sutures. Surg. 141; 1010, (1975)) and polyglycolic acid. These materials can be used as supplied by the manufacturer.

In yet another embodiment, the matrix or scaffold can be created using parts of a natural decellularized organ. Biostructures, or parts of organs can be decellularized by removing the entire cellular and tissue content from the organ. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components and the nuclear components.

Preferably, the biostructure, e.g., part of an organ is decellularized by removing the cell membrane and cellular debris surrounding the part of the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ part, agitating the organ part, or stirring the organ in a suitable volume of fluid, e.g., distilled water. In one preferred embodiment, the gentle mechanical disruption method includes stirring the organ part in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of nonionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl-D-glucopuranoside, n-heptyl-D-glucopyranoside, n-Octyl-D-glucopyranoside and Nonidet P40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem. R., Hoechst Celanese Corp., 1987. In one preferred embodiment, the non-ionic surfactant is the Triton. series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentration ranges of non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, which includes the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

Still other biocompatible materials that may be used include stainless steel, titanium, silicone, gold and silastic.

The polymeric matrix or scaffold can be reinforced. For example, reinforcing materials may be added during the formation of a synthetic matrix or scaffold or attached to the natural or synthetic matrix prior to implantation. Representative materials for forming the reinforcement include natural or synthetic polymers, such as, for example, collagen, poly (alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration.

The biodegradable polymers can be characterized with respect to mechanical properties, such as tensile strength using an Instron tester, for polymer molecular weight by gel permeation chromatography (GPC), glass, transition temperature by differential scanning calorimetry (DSC) and bond structure by infrared (IR) spectroscopy; with respect to toxicology by initial screening tests involving Ames assays and in vitro teratogenicity assays and implantation studies in animals for immunogenicity, inflammation, release and degradation studies. In vitro cell attachment and viability can be assessed using scanning electron microscopy, histology and quantitative assessment with radioisotopes. The biodegradable material may also be characterized with respect to the amount of time necessary for the material to degrade when implanted in a patient. By varying the construction, such as, for example, the thickness and mesh size, the biodegradable material may substantially biodegrade between about 2 years or about 2 months, preferably between about 18 months and about 4 months, most preferably between about 15 months and about 8 months and most preferably between about 12 months and about 10 months. If necessary, the biodegradable material may be constructed so as not to degrade substantially within about 3 years, or about 4 years or about five or more years.

The polymeric matrix or scaffold may be fabricated with controlled pore structure as described above. The size of the pores may be used to determine the cell distribution. For example, the pores on the polymeric matrix or scaffold may be large to enable cells to migrate from one surface to the opposite surface. Alternatively, the pores may be small such that there is fluid communication between the two sides of the polymeric matrix or scaffold but cells cannot pass through. Suitable pore size to accomplish this objective may be about 0.04 micron to about 10 microns in diameter, preferably between about 0.4 micron to about 4 microns in diameter. In some embodiments, a surface of the polymeric matrix or scaffold may comprise pores sufficiently large to allow attachment and migration of a cell population into the pores. The pore size may be reduced in the interior of the polymeric matrix or scaffold to prevent cells from migrating from one side of the polymeric matrix or scaffold to the opposite side. One embodiment of a polymeric matrix or scaffold with reduced pore size is a laminated structure of a small pore material sandwiched between two large pore material. Polycarbonate membranes are especially suitable because they can be fabricated in very controlled pore sizes such as, for example, about 0.01 microns, about 0.05 micron, about 0.1 micron, about 0.2 micron, about 0.45 micron, about 0.6 micron, about 1.0 micron, about 2.0 microns and about 4.0 microns. At the submicron level the polymeric matrix or scaffold may be impermeable to bacteria, viruses and other microbes.

The following characteristics or criteria, among others, are taken into account in the design of each discrete matrix, or part thereof: (i) shape, (ii) strength, (iii) stiffness and rigidity, and (iv) suturability (the degree to which the matrix, or part thereof, is readily sutured or otherwise attached to adjacent tissue). As used herein, the stiffness of a given matrix or scaffold is defined by the modulus of elasticity, a coefficient expressing the ratio between stress per unit area acting to deform the scaffold and the amount of deformation that results from it. (See e.g., Handbook of Biomaterials evaluation, Scientific, Technical, and Clinical Testing of Implant Materials, 2nd edition, edited by Andreas F. von Recum, (1999); Ratner, et al., Biomaterials Science: An Introduction to Materials in Medicine, Academic Press (1996)). The rigidity of a scaffold refers to the degree of flexibility (or lack thereof) exhibited by a given scaffold.

Each of these criteria is a variable that can be changed (through, among other things, the choice of material and the manufacturing process) to allow the matrix, or part thereof to best placed and modified to address the medical indication and the physiological function for which it is intended. For example, the material comprising the matrix or scaffold for bladder replacement, reconstruction and/or augmentation must be sufficiently strong to support sutures without tearing, while being sufficient compliant so as to accommodate fluctuating volumes of urine.

Optimally, the matrix or scaffold should be shaped such that after its biodegradation, the resulting reconstructed bladder is collapsible when empty in a fashion similar to a natural bladder and the ureters will not be obstructed while the urinary catheter has been removed from the new organ or tissue structure without leaving a leak point. The bioengineered bladder construct can be produced as one piece or each part can be individually produced or combinations of the sections can be produced as specific parts. Each specific matrix or scaffold part may be produced to have a specific function. Otherwise specific parts may be produced for manufacturing ease. Specific parts may be constructed of specific materials and may be designed to deliver specific properties. Specific part properties may include tensile strength similar to the native tissue (e.g. ureters) of 0.5 to 1.5 MPa.sup.2 and an ultimate elongation of 30 to 100% or the tensile strength may range from 0.5 to 28 MPa.sup.2, ultimate elongations may range from 10-200% and compression strength may be <12.

A mesh-like structure formed of fibers, which may be round, scalloped, flattened, star shaped, solitary or entwined with other fibers is preferred. The use of branching fibers is based upon the same principles which nature has used to solve the problem of increasing surface area proportionate to volume increases. All multicellular organisms utilize this repeating branching structure. Branching systems represent communication networks between organs, as well as the functional units of individual organs. Seeding and implanting this configuration with cells allows implantation of large numbers of cells, each of which is exposed to the environment of the host, providing for free exchange of nutrients and waste while neovascularization is achieved. The polymeric matrix or scaffold may be made flexible or rigid, depending on the desired final form, structure and function.

In one preferred embodiment, the polymeric matrix or scaffold is formed with a polyglycolic acid with an average fiber diameter of 15.mu.m and configured into a bladder shaped mold using 4-0 polyglactin 910 sutures. The resulting structure is coated with a liquefied copolymer, such as, for example, pol-DL-lactide-co-glycolide 50:50, 80 milligram per milliliter methylene chloride, in order to achieve adequate mechanical characteristics and to set its shape.

In a further embodiment, the scaffolds of the present invention are coated with a biocompatible and biodegradable shape-setting material. In one embodiment, the shape-setting material contains a poly-lactide-co-glycolide copolymer. In another embodiment, the shape setting material is liquefied.

In one other aspect, the scaffolds of the present invention may be treated with additives or drugs prior to implantation (before or after the polymeric matrix or scaffold is seeded with cells), e.g., to promote the regeneration of new tissue after implantation. Thus, for example, growth factors, cytokines, extracellular matrix or scaffold components, and other bioactive materials can be added to the polymeric matrix or scaffold to promote graft healing and regeneration of new tissue. Such additives will in general be selected according to the tissue or organ being reconstructed, replaced or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, when polymeric matrices (optionally seeded with endothelial cells) are used to augment vascular tissue, vascular endothelial growth factor (VEGF), (see, e.g., U.S. Pat. No. 5,654,273) can be employed to promote the regeneration of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the regeneration of new tissue of a type appropriate to the tissue or organ, which is to be repaired, replaced or augmented (e.g., by causing or accelerating infiltration of host cells into the graft). Other useful additives include antibacterial agents such as antibiotics.

One preferred supporting matrix or scaffold is composed of crossing filaments which can allow cell survival by diffusion of nutrients across short distances once the cell support is implanted. The cell support matrix or scaffold becomes vascularized in concert with expansion of the cell mass following implantation.

The building of three-dimensional structure constructs in vitro, prior to implantation, facilitates the eventual terminal differentiation of the cells after implantation in vivo, and minimizes the risk of an inflammatory response towards the matrix, thus avoiding graft contracture and shrinkage.

The polymeric matrix or scaffold may be sterilized using any known method before use. The method used depend on the material used in the polymeric matrix. Examples of sterilization methods include steam, dry heat, radiation, gases such as ethylene oxide, gas and boiling.

The synthetic materials that make up the scaffolds may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the construct. Next a solvent is used to dissolve away one of the components, resulting in pore formation. (See Mikos, U.S. Pat. No. 5,514,378, hereby incorporated by reference.) In nucleation, thin films in the shape of a scaffold are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix or scaffold may be weaved, compression molded and glued together. Furthermore different polymeric materials shaped by different processes may be joined together to form a composite shape. The composite shape may be a laminar structure. For example, a polymeric matrix or scaffold may be attached to one or more polymeric matrixes to form a multilayer polymeric matrix or scaffold structure. The attachment may be performed by gluing with a liquid polymer or by suturing. In addition, the polymeric matrix or scaffold may be formed as a solid block and shaped by laser or other standard machining techniques to its desired final form. Laser shaping refers to the process of removing materials using a laser.

In a preferred embodiment, the scaffolds are formed from nonwoven polyglycolic acid (PGA) felts and poly(lactic-co-glycolic acid) polymers (PLGA). In another preferred embodiment, the scaffold is a urinary diversion scaffold.

As described in Bertram et al. U.S. Published Application 20070276507 (incorporated herein by reference in its entirety), the polymeric matrix or scaffold of the present invention may be shaped into any number of desirable configurations to satisfy any number of overall system, geometry or space restrictions. The matrices may be three-dimensional matrices shaped to conform to the dimensions and shapes of a laminarily organized luminal organ or tissue structure. For example, in the use of the polymeric matrix for bladder reconstruction, a three-dimensional matrix may be used that has been shaped to conform to the dimensions and shapes of the whole or a part of a bladder. Naturally, the polymeric matrix may be shaped in different sizes and shapes to conform to the bladders of differently sized patients. Optionally, the polymeric matrix should be shaped such that after its biodegradation, the resulting reconstructed bladder may be collapsible when empty in a fashion similar to a natural bladder. The polymeric matrix may also be shaped in other fashions to accommodate the special needs of the patient. For example, a previously injured or disabled patient, may have a different abdominal cavity and may require a bladder replacement scaffold, a bladder augmentation scaffold, a bladder conduit scaffold, and a detrusor muscle equivalent scaffold adapted to fit.

In one aspect, the present invention contemplates additional scaffolds suitable for use with the smooth muscle cell populations described herein. For example, scaffolds suitable for implantation into the lung may be provided.

A. Augmentation or Replacement Scaffolds

In one other aspect, the polymeric matrix or scaffold is shaped to conform to part of a bladder. In one embodiment, the shaped matrix is conformed to replace at least about 50%, at least about 60%, at least about 70%, at least about 80%, at least about 90%, or at least about 95% of the existing bladder of a recipient. In one other aspect, the polymeric matrix or scaffold is shaped to conform to 100% or all of a bladder.

In one embodiment, the polymeric matrix comprises a first implantable, biocompatible, synthetic or natural polymeric matrix or scaffold having at least two separate surfaces, and a second implantable, biocompatible, synthetic or natural polymeric matrix or scaffold having at least two separate surfaces, which are adapted to mate to each other and shaped to conform to at least a part of the luminal organ or tissue structure in need of the treatment when mated. The first and second polymeric matrices may be formed from one integral unit subdivided into two or more distinct parts, or from two or more distinct parts, adapted to mate. In some embodiments, the first and second polymeric matrices once mated may be used for reconstruction, repair, augmentation, or replacement of a luminal organ or tissue structure.

Figure 2:
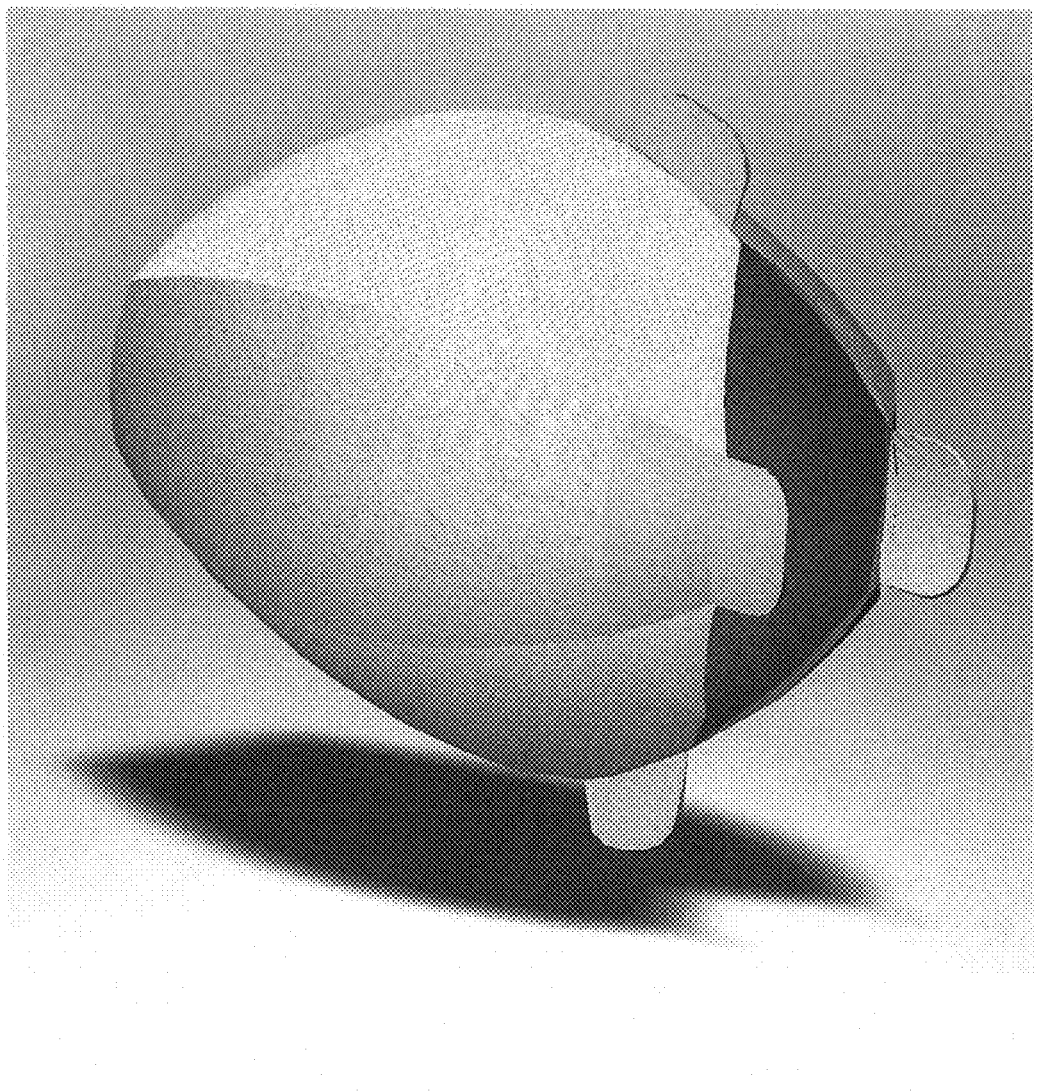
FIG. 2 shows an example of a bladder replacement scaffold.

In some embodiments, the first and second polymeric matrices are symmetrical, while in other embodiments, the first and second polymeric matrices are asymmetrical. In one embodiment, the first polymeric matrix or scaffold has a hemispherical or quasi-hemispherical shape having a closed, domed end and an open, equatorial border, and the second polymeric matrix or scaffold is a collar adapted to mate with the equatorial border of the first polymeric matrix. In another embodiment, the first and second polymeric matrices are each hemispherical or quasi-hemispherical in shape, having a closed, domed end and an open, equatorial border. In yet another embodiment, the first and second polymeric matrices each comprise a circular or semi-circular base and at least 2 petals radially extending from each base. In this embodiment, the bases and petal shaped portions of the first and the second polymeric matrices are mated to create a hollow spherical or quasi-spherical matrix or scaffold such that a flanged longitudinal, elliptical opening is created on one side of the mated polymeric matrices, and a circular opening is created on the side opposite the longitudinal opening. In another embodiment, the first and second polymeric matrices are made from 3 parts comprising a top, a front and a sidepiece, adapted to mate. In this embodiment, the 3 distinct parts are mated using at least 3, preferably four vertical seams, thereby forming a crown shaped neo-bladder construct. The crown shaped constructs are preferably used alone as a device for luminal organ reconstruction, repair, augmentation, or replacement. In one embodiment, the construct is a bladder augmentation scaffold. One example of a bladder augmentation scaffold is depicted in FIG. 1. In another embodiment, the construct is a bladder replacement scaffold. One example of a bladder replacement scaffold is depicted in FIG. 2.

Additionally, the first polymeric matrix, the second polymeric matrix, or both, may contain at least one receptacle or port adapted to receive a tubular vessel or insert where the connection of the construct to a native vessel or tube is necessary. The vessels or inserts are themselves, for example, cylindrical or tubular shaped polymer matrices, each having at least one flange located at a first end of the cylindrical polymer. The vessels or inserts are, preferably, composed of the same biocompatible material as the first or second polymeric matrices described above. In some embodiments, the vessel or insert also contains a washer adapted to fit around the cylindrical or tubular vessel or insert polymer matrix. For example, the washer is a hydrogel. The cylindrical or tubular vessel or insert may optionally contain a washer. The washer may be hydrogel. Additionally, the cylindrical or tubular insert may be self-stabilizing.

In another embodiment, the receptacles or ports adapted to receive tubular vessels or inserts where the connection of the scaffold or matrix (once seeded with cells) to a native vessel or tube is necessary also applies to other the matrices discussed below.

B. Urinary Diversions

The present invention provides neo-urinary diversion or conduit scaffolds that can be seeded with cells and used as a replacement for gastrointestinal tissue in the construction of a urinary diversion in a subject. For example, the neo-urinary diversions described herein may have application after radical cystectomy for the treatment of patients who would otherwise undergo an ileal loop diversion.

In one aspect, the present invention contemplates conduit scaffolds or matrices suitable for use as urinary diversions in a subject in need formed from the methods described herein. One end of the conduit scaffold may be connected to one or more ureters and the other end may be connected to a urine reservoir that is external to the subject's body. In one embodiment, the conduit may exit the subject's body via a stoma. In another embodiment, the polymeric matrix comprises a first implantable, biocompatible, synthetic polymeric matrix or scaffold provided in a tubular form. In some embodiments, the tubular scaffold comprises a first end configured to connect to a ureter of the subject. In another embodiment, the first scaffold further includes a second end configured to form a stoma or sphincter in the subject. In another embodiment, the first scaffold further includes at least one side opening configured to connect to a least one ureter. In some embodiments, the first scaffold includes a first side opening configured to attach to a first ureter and a second side opening configured to attach to a second ureter.

In one other embodiment, the tubular structure comprises a first end comprising an even edge and a second end comprising a non-uniform or uneven edge. The non-uniform edge may include a circular base with a number of petals radially extending from the base. The number of petals may be 1, 2, 3, 4, 5, or 6. The uneven edge may comprise a series of petals such as, for example, those shown in FIG. 3. In one embodiment, the tubular structure has a form suitable for use as a urinary diversion system or a conduit in a patient in need. In another embodiment, the system diverts urine from one or more ureters to an abdominal wall section such as, for example, in the case of a ureterostomy. In other embodiments, the system diverts urine from the bladder to an abdominal wall section such as, for example, in the case of a cystostomy. In one other embodiment, the system connects the bladder to the urethra. In yet another embodiment, a first system may divert urine from one or more ureters to an abdominal wall section and a second system may divert urine from the bladder to an abdominal wall section. In all embodiments, the system may divert urine from one or more ureters to an abdominal wall section such as, for example, in the formation of a stoma.

In another embodiment, the tubular matrix or scaffold is a urinary diversion or conduit scaffold.

In one embodiment, the tubular structure of the urinary diversion system is of rectangular, circular, or triangular cross sectional area. FIG. 3A illustrates some of the different cross sectional configurations contemplated herein.

In another embodiment, tubular structure retains sufficient rigidity to remain patent following implantation. In one other embodiment, the tubular structure's rigidity is retained with or without the use of a catheter in its lumen. Where a catheter is used, it can be placed into the luminal space of the tubular structure to provide additional patency.

In one other embodiment, the conduit scaffold may further include a second scaffold in the form of a round or ovoid connector configured to connect the first end of the first scaffold to a ureter. In yet another embodiment, the conduit scaffold may further include a third scaffold in the form of a washer-ring configured to form a stoma or sphincter with the second end of the first tubular scaffold to create a stoma in a subject. FIG. 3B illustrates variations of a urinary diversion construct (A—open claim ovoid; B—open claim ovoid receptacle; C—closed ovoid receptacle and three tubes).

In some embodiments, the tubular structure may include a washer structure for connection to a tissue, organ or body part to achieve anastomosis for the creation of a continent stoma or sphincter. In another embodiment, the washer is provided with a thickness of about less than 1 mm, about less than 1.5 mm, about less than 2 mm, about less than 2.5 mm, about less than 3 mm, about less than 3.5 mm, about less than 4 mm, about less than 4.5 mm, or about less than 5 mm.

Figure 3:
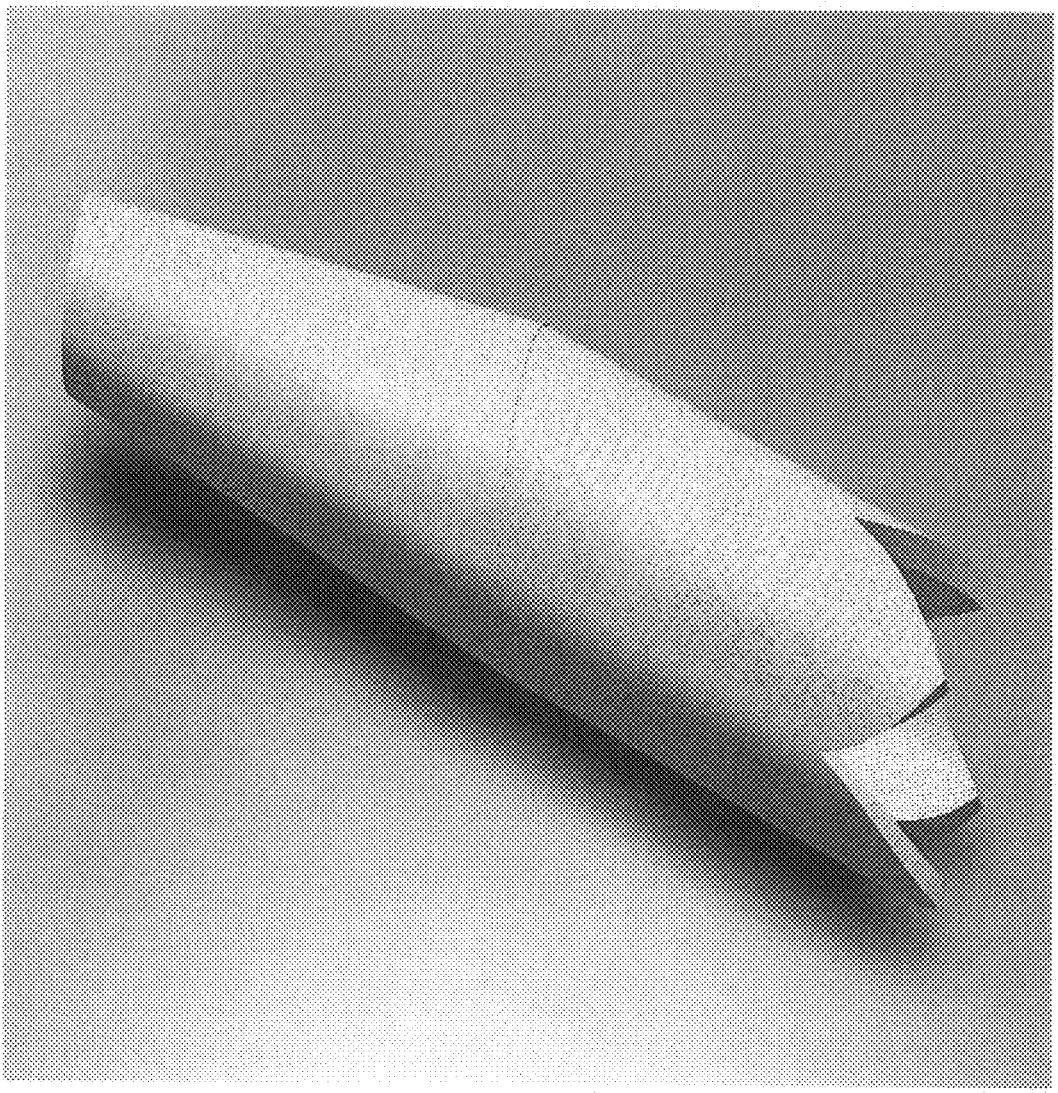
FIG. 3 shows an example of a urinary diversion or conduit scaffold.
Figure 3A:
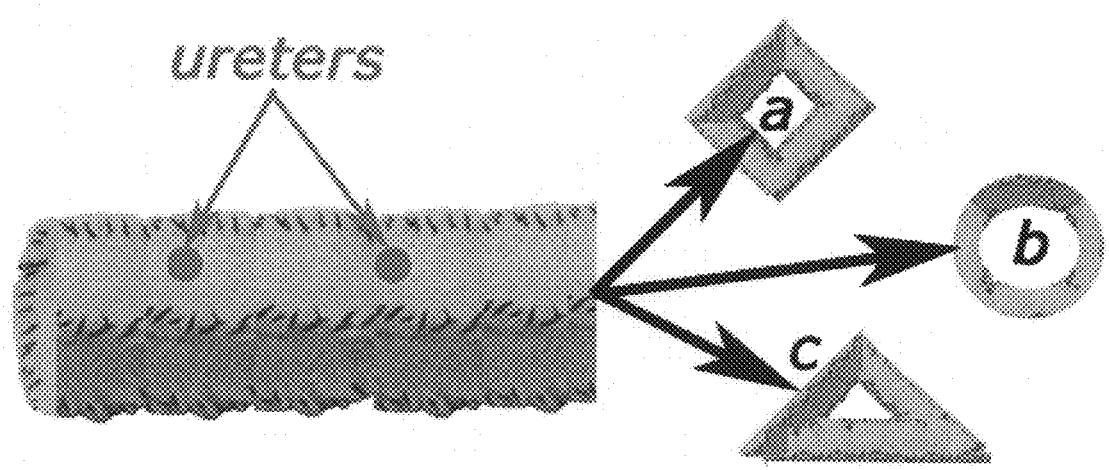
FIG. 3A shows an example of a urinary diversion construct having different types of cross-sectional areas, as well as potential positions for openings that may be configured to connect to ureter(s).
Figure 3B:
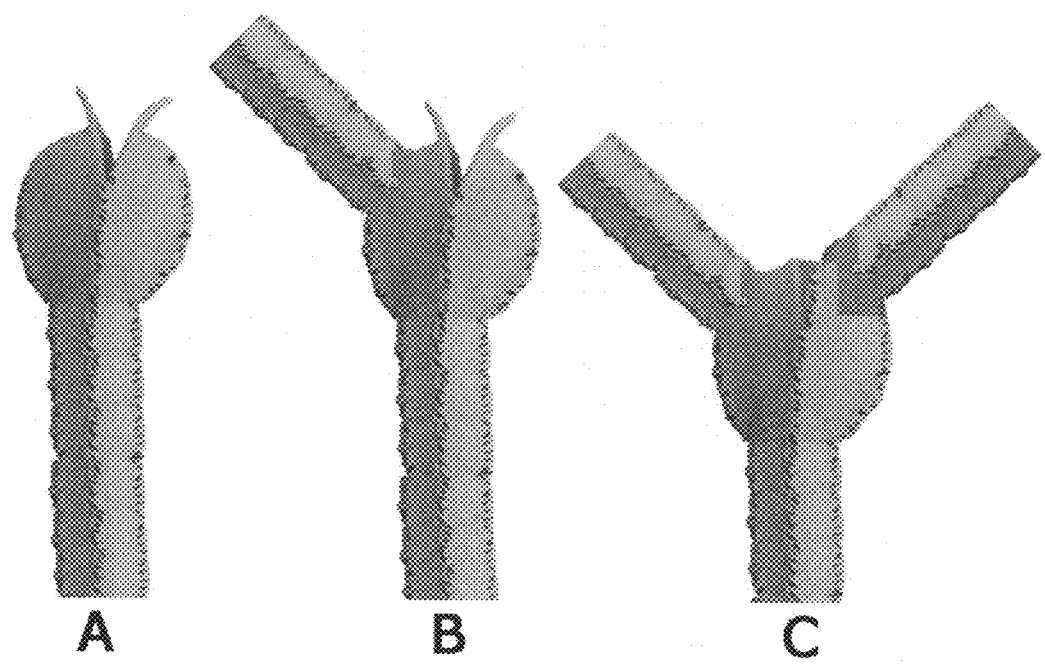
FIG. 3B illustrates variations of a urinary diversion construct (A—open claim ovoid; B—open claim ovoid receptacle; C—closed ovoid receptacle and three tubes).

In one embodiment, the urinary diversion or conduit scaffold is shaped into the configuration shown in FIG. 3.

In one other embodiment, the tubular structure comprises a first end comprising an even edge and a second end comprising a non-uniform or uneven edge. The non-uniform edge may include one or more fasteners configured for attachment to an external region of the subject, such as in the formation of a stoma external to the subject. In one embodiment, the first and second ends of the tubular structure may be in the form illustrated in FIG. 3. The number of fasteners may be 1, 2, 3, 4, 5, or 6.

Figure 27:
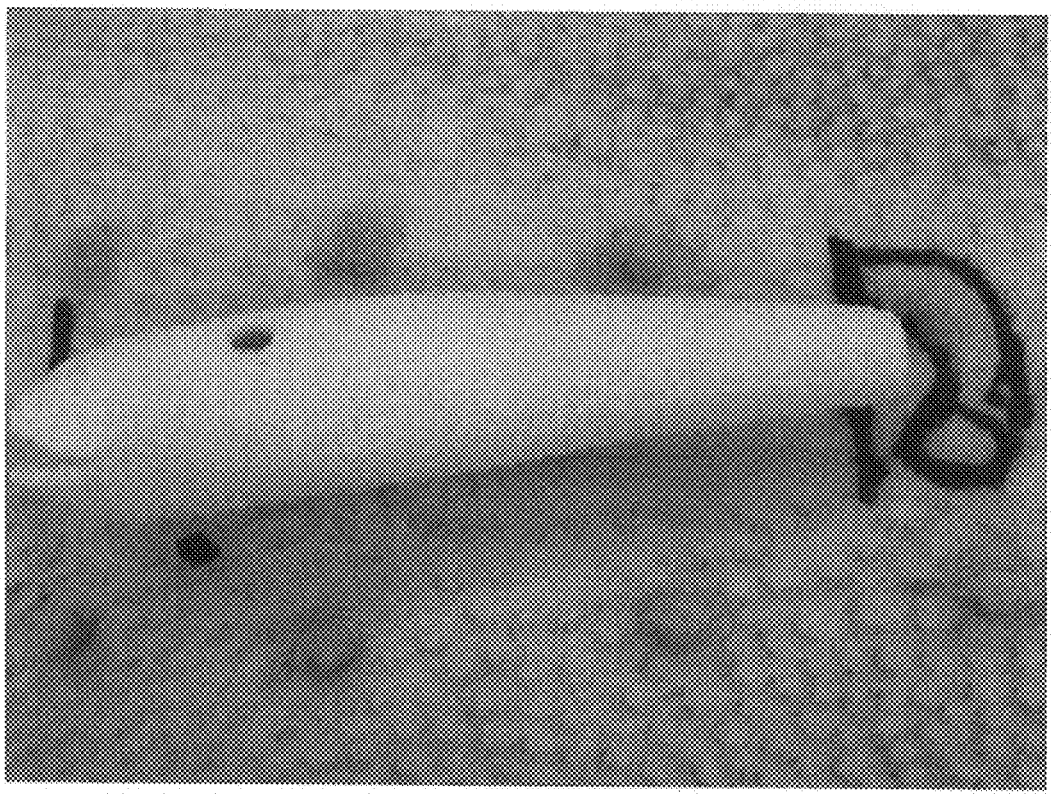
FIG. 27 shows a neo-conduit construct.

In another embodiment, the tubular scaffold is in the form depicted in FIG. 27.

FIG. 4A depicts a part of the normal anatomy for the human urinary system.

In one embodiment, the tubular structure has a form suitable for use as a urinary diversion or a conduit in a patient in need. In another embodiment, the conduit diverts urine from one or more ureters to an abdominal wall section such as, for example, in the case of a ureterostomy (FIG. 4D). In other embodiments, the conduit diverts urine from the bladder to an abdominal wall section such as, for example, in the case of a cystostomy (FIG. 4B). In one other embodiment, the conduit connects the bladder to the urethra (FIG. 4D). In yet another embodiment, a first conduit may divert urine from one or more ureters to an abdominal wall section and a second conduit may divert urine from the bladder to an abdominal wall section. In all embodiments, the conduit may divert urine from one or more ureters to an abdominal wall section (FIG. 4B). In all embodiments, the conduit may be configured to form a stoma.

In one embodiment, the tubular structure of the urinary diversion or conduit scaffold is of rectangular, circular, or triangular cross sectional area. In another embodiment, the tubular structure retains sufficient rigidity to remain patent following implantation. In one other embodiment, the tubular structure's rigidity is retained with or without the use of a catheter in its lumen. In some embodiments, a urinary diversion scaffolds further include a catheter configured to be placed in the luminal space of tubular structure upon implantation. In one embodiment, the catheter is a Foley-like balloon catheter. Where a catheter is used, it can be placed into the luminal space of the tubular structure to provide additional patency. Those of ordinary skill in the art will appreciate that other catheters known in the art may be suitable for use with the present invention.

In another embodiment, the thickness of the tubular wall of the scaffolds will be less than about 2 mm, less than about 2.5 mm, less than about 3.5 mm, less than about 4 mm, less than about 4.5 mm, less than about 5 mm, less than about 5.5 mm, or less than about 6 mm.

In some embodiments, the scaffolds may have variable outer and inner diameters. In one embodiment, the ends of the scaffold may be flared, non-flared, sealed, or rounded.

In other embodiments, the scaffold is permeable to urine. In one embodiment, the scaffold's pore size is about greater than about 0 microns to about 500 microns. In another embodiment, the pore size is from about 100 microns to about 200 microns. In another embodiment, the pore size is from about 150 microns to about 200 microns. In other embodiments, the pore size is about 100 microns, about 110 microns, about 120 microns, about 130 microns, about 140 microns, about 150 microns, about 160 microns, about 170 microns, about 180 microns, about 190 microns, or about 200 microns. In some embodiments, the pore size is about 100 microns, about 200 microns, about 300 microns, about 400 microns, about 500 microns, or about 600 microns. In other embodiments, the scaffold includes a pore architecture that is a single pore size distribution, multiple pore size distribution, or a pore gradient distribution.

In another embodiment, the scaffold material is suturable and may form connections with tissue that are resistant to leakage.

In other embodiments, the tubular scaffold material is selected to maintain patency throughout the duration of implantation use, support cell attachment and the in-growth of host tissue, and retain flexibility. In another embodiment, the material will have a burst strength that exceeds the pressures to which it will be exposed during normal in vivo fluid cycling. In other embodiments, the material will have a degradation time commensurate with host tissue in-growth.

C. Muscle Equivalents

In one aspect, the polymeric matrix or scaffold of the present invention is a muscle equivalent scaffold. In one embodiment, the muscle equivalent scaffold is a detrusor muscle equivalent scaffold. In another embodiment, the scaffold is suitable for laparoscopic implantation.

In one aspect, the polymeric matrix comprises a polymeric matrix or scaffold shaped to conform to at least a part of the organ or tissue structure in need of said treatment and of a sufficient size to be laparoscopically implanted. In certain embodiments, the polymeric matrix or scaffold of the invention is between about 3 and about 20 cm in length. In one embodiment the polymeric matrix or scaffold is about 20 cm in maximal length. In another embodiment, the polymeric matrix or scaffold is about 15 cm in maximal length. In another embodiment, the polymeric matrix or scaffold is about 10 cm in maximal length. In another embodiment, the polymeric matrix or scaffold is about 8 cm in maximal length. In another embodiment, the polymeric matrix or scaffold is about 4 cm in maximal length. In yet another embodiment, the polymeric matrix or scaffold is about 3 cm in maximal length. In certain embodiments, the polymeric matrix or scaffold of the invention is between about 1 and about 8 cm in width. In some embodiments, the polymeric matrix or scaffold is about 4 cm in maximal width. In other embodiments, the polymeric matrix or scaffold is about 3 cm in maximal width. In yet other embodiments, the polymeric matrix or scaffold is about 5 cm in maximal width.

In one embodiment, the polymeric matrix or scaffold has a three-dimensional (3-D) shape. In another embodiment, the polymeric matrix or scaffold has a flat shape. In one embodiment, the flat-shaped polymeric matrix or scaffold comprises pre-treated areas to allow more flexibility. In certain embodiments, the pre-treated areas are coated in the areas to be creased. In one embodiment, the polymeric matrix or scaffold is sufficiently malleable to be rolled, folded, or otherwise shaped for implantation through a laparoscope tube and/or port. In such embodiments, the polymeric matrix or scaffold is sufficiently malleable to be unrolled, unfolded, or otherwise returned to shape following insertion through the laparoscope tube and/or port. In one embodiment, the polymeric matrix or scaffold is cut into 2, 3, 4, 5, 6, 7, 8, 9 or 10 strips prior to implantation through a laparoscope tube and/or port. In certain embodiments, the 2, 3, 4, 5, 6, 7, 8, 9 or 10 strips are mated prior to implantation through a laparoscope tube and/or port. The 2, 3, 4, 5, 6, 7, 8, 9 or 10 strips may be mated using glue, staples, sutures, or other technique known to one of ordinary skill in the art. In such embodiments the 2, 3, 4, 5, 6, 7, 8, 9 or 10 mated strips are folded and/or stacked to pass through a laparoscope tube and/or port. In such embodiments, the 2, 3, 4, 5, 6, 7, 8, 9 or 10 strips are unfolded and/or unstacked following insertion through the laparoscope tube and/or port. In some embodiments, the previously placed mating means are tightened as appropriate following insertion through the laparoscope tube and/or port.

In one embodiment, the polymeric matrix comprises a first implantable, biocompatible, synthetic or natural polymeric matrix or scaffold provided in the form of a patch or in the form of a strip. In one embodiment, the patch has a form suitable for use as a detrusor muscle equivalent in the bladder of a patient in need. In one other embodiment, the patch has a form suitable for increasing the volume capacity of the existing bladder of a patient in need. In certain embodiments, the patch increases the bladder size between about 50 mL and about 500 mL. In some embodiments, the patch would increase bladder size in increments of 50 mL. In some embodiments, the patch increases the bladder size about 450 mL. In one embodiment, a surface area increase of 30 $cm^2$ increases the volume of a 200 mL bladder to 250 mL. In another embodiment, an increase of 25 $cm^2$ increases the volume of a 350 mL bladder to 400 mL. In one embodiment, the scaffold has a two-dimensional surface area of about 30 $cm^2$. In another embodiment, the scaffold has a two-dimensional surface area of about 25 $cm^2$. In one embodiment, the patch is in the form of a strip, disc, square, ellipsoid, or any other appropriate configuration. In other embodiments, the patch is provide in a pre-folded form, e.g., like an accordion.

Figure 5A:
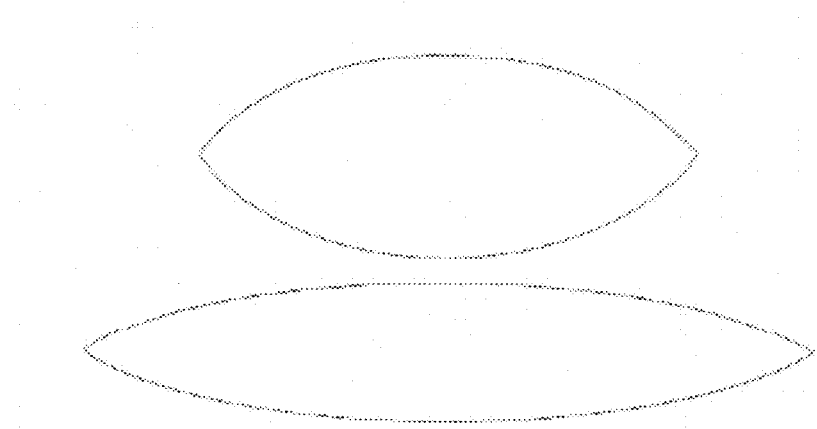
FIG. 5A-B show examples of a muscle equivalent scaffold.
Figure 5B:
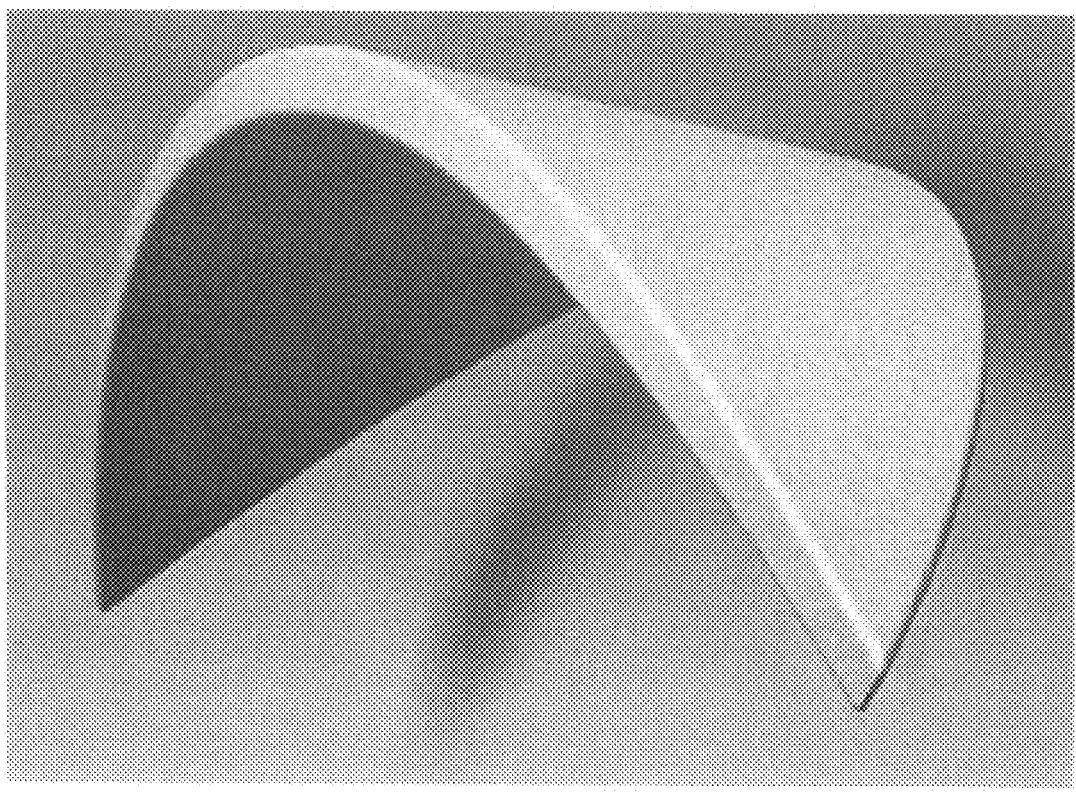
Figure 6:
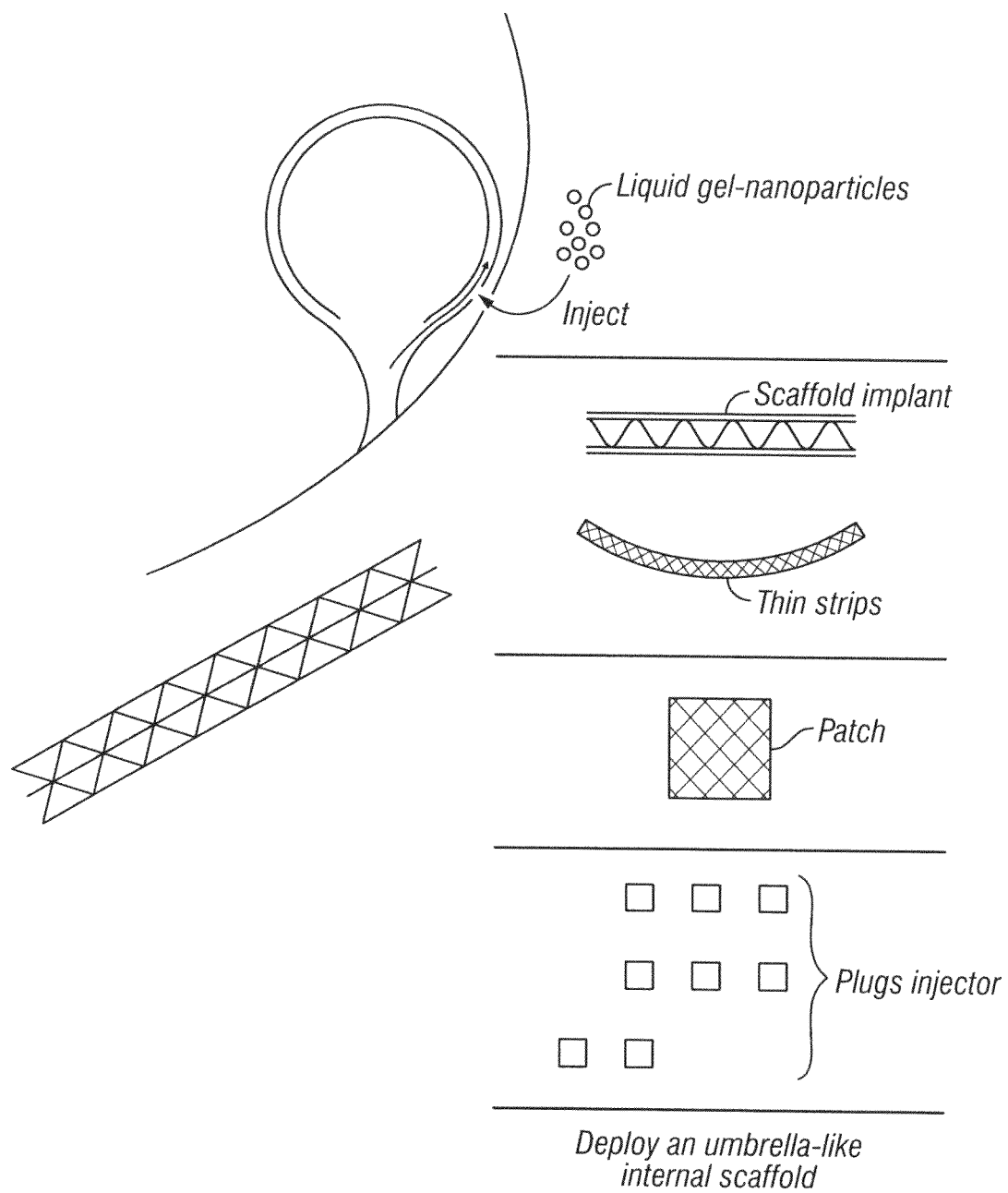
FIG. 6 depicts images of various muscle equivalent scaffolds in the form of patches or strips.

FIG. 5A-B show examples of a muscle equivalent scaffold or polymeric matrix. In one embodiment, the polymeric matrix or scaffold is in the shape of a double wedge, e.g., the shape shown in FIG. 5A. In another embodiment, the polymeric matrix is shaped into one of the configurations shown in FIGS. 6-9.

In all embodiments, the polymeric matrix or scaffold is shaped so as to minimize the strain on both the bladder and matrix or scaffold.

In another embodiment, the polymeric matrix comprises a first implantable, biocompatible, synthetic or natural polymeric matrix or scaffold provided in the form of a patch or in the form of a strip.

In one embodiment, the patch has a form suitable for use as a detrusor muscle equivalent in the bladder of a patient in need. In one other embodiment, the patch has a form suitable for increasing the volume capacity of the existing bladder of a patient in need. In some embodiments, the patch would increase bladder size in increments of 50 mL. In one embodiment, the patch is in the form of a strip, disc, square, ellipsoid, or any other appropriate configuration. In other embodiments, the patch is provide in a pre-folded form, e.g., like an accordion.

In one embodiment, the polymeric matrix is shaped into one of the configurations shown in FIG. 1-9 or 27.

In all embodiments, the biocompatible material used for these matrices or scaffolds is, for example, biodegradable. In all the embodiments, the biocompatible material may be polyglycolic acid.

In all embodiments, the polymeric matrix or scaffold is coated with a biocompatible and biodegradable shaped setting material. In one embodiment, the shape setting material may comprise a liquid copolymer. In another embodiment, the liquid co-polymer may comprise a liquefied lactide/glycolide copolymer. In one embodiment, the liquid co-polymer may comprise poly-DL-lactide-co-glycolide.

5. Constructs

In one aspect, the invention provides one or more polymeric scaffolds or matrices that are seeded with at least one cell population. Such scaffolds that have been seeded with a cell population and may be referred to herein as "constructs". In one embodiment, the cell-seeded polymeric matrix or matrices form a neo-bladder construct selected from the group consisting of a bladder replacement construct, a bladder augmentation construct, a bladder conduit construct, and a detrusor muscle equivalent construct.

Those of skill in the art will appreciate that the seeding or deposition of one or more cell populations described herein may be achieved by various methods known in the art. For example, bioreactor incubation and culturing, (Bertram et al. U.S. Published Application 20070276507; McAllister et al. U.S. Pat. No. 7,112,218; Auger et al. U.S. Pat. No. 5,618,718; Niklason et al. U.S. Pat. No. 6,537,567); pressure-induced seeding (Torigoe et al. (2007) Cell Transplant., 16(7):729-39; Wang et al. (2006) Biomaterials. May; 27(13):2738-46); and electrostatic seeding (Bowlin et al. U.S. Pat. No. 5,723,324) may be used. In addition, a recent technique that simultaneously coats electrospun fibers with an aerosol of cells may be suitable for seeding or deposition (Stankus et al. (2007) Biomaterials, 28:2738-2746).

In one embodiment, the deposition of cells includes the step of contacting a scaffold with a cell attachment enhancing protein. In another embodiment, the enhancing protein is one or more of the following: fibronection, collagen, and MATRIGEL™. In one other embodiment, the scaffold is free of a cell attachment enhancing protein. In another embodiment, the deposition of cells includes the step of culturing after contacting a scaffold with a cell population. In yet another embodiment, the culturing may include conditioning by pulsatile and/or steady flow in a bioreactor.

Smooth muscle cell populations isolated from adipose or peripheral blood as described herein may then be seeded on a scaffold described herein.

The following is a representative example of a protocol for seeding cells on a scaffold. Adipose- or peripheral blood-derived smooth muscle cells may be expanded for up to 7 weeks to generate the quantity of cells required for seeding a scaffold. The density of cells suitable for seeding a scaffold is described below. Adipose-derived smooth muscle cells may be expanded for 2 passages before harvesting of cells for seeding of scaffolds to produce a construct. Peripheral blood-derived smooth muscle cell cultures may be expanded to P3-4 before harvesting for scaffold seeding. To prepare a scaffold for cell seeding, a suitable material (e.g., PGA felt) may be cut to size, sutured into the appropriate shape, and coated with material (e.g., PLGA). The scaffold may then be sterilized using a suitable method (e.g., ethylene oxide). On the day prior to cell seeding, the sterilized scaffold may be serially pre-wetted by saturation with 60% ethanol/40% D-PBS, 100% D-PBS, D-MEM/10% FBS or α-MEM/10% FBS followed by incubation in D-MEM/10% FBS or α-MEM/10% FBS at room temperature overnight. The scaffold can then be seeded with adipose-, or peripheral blood-derived smooth muscle cells and the seeded construct matured in a humidified 37° C. incubator at 5% $CO_2$ until implantation in a subject (e.g., by day 7). Those of ordinary skill in the art will appreciate additional methods for preparing scaffolds for seeding of cells and seeding of cells onto scaffolds.

In one aspect, the present invention provides methods of preparing a construct in a reduced time frame, which is advantageous to the subject awaiting implantation of a construct. It has been reported that undifferentiated adipose stem cells derived from SVF must be incubated in inductive media for 6 weeks prior to differentiation into smooth muscle cells (Jack et al. 2009 supra). In one embodiment, the method includes the steps of a) obtaining a human adipose tissue sample; b) isolating a fully differentiated smooth muscle cell population from the sample; c) culturing the cell population; and d) contacting the cell population with a shaped polymeric matrix cell construct, wherein steps a), b), c) and d) are performed in about 45 days or less. In another embodiment, the isolating step is performed without cell selection. In another embodiment, the isolating step b) is performed about 72 hours or less after obtaining step a). In yet another embodiment, the culturing step c) is performed in about 4 weeks or less. In other embodiments, the contacting step d) is performed in about 10 days or less. In another embodiment, steps a), b), c) and d) are performed in about 28 days or less. In one other embodiment, the isolating step b) is performed about 48 hours or less after obtaining step a). In one embodiment, the culturing step c) is performed in about 2 weeks or less. In another embodiment, the contacting step d) is performed in about 5 days or less. In all embodiments, the human adipose tissue sample is obtained from an autologous source. In one other embodiment, the method further includes the step of detecting expression of a smooth muscle cell marker. In another embodiment, expression is mRNA expression. In a further embodiment, the expression is polypeptide expression. In one embodiment, the polypeptide expression is detected by intracellular immunofluorescence.

In one embodiment, the scaffold comprises a cell population as described herein. In another embodiment, the scaffold consists essentially of a cell population as described herein. In one other embodiment, the scaffold consists of a cell population as described herein.

The first polymeric matrix or the second polymeric matrix, if any, or both, comprise at least one cell population deposited on or in a first surface of the first polymeric matrix, a first surface of the second polymeric matrix, or both, to form a construct of matrix or scaffold plus cells, wherein at least one cell population comprises substantially a muscle cell population. The muscle cell population is, e.g., a smooth muscle cell population. In a preferred embodiment, the first surface and the second surface are each the outer surface of the first and second polymeric matrices.

In another embodiment, the construct containing the matrix and cells is free of any other cell populations. In a preferred embodiment, the construct is free of urothelial cells.

These constructs are used to provide a luminal organ or tissue structures such as genitourinary organs, including for example, the urinary bladder, ureters and urethra, to a subject in need. The subject may require the reconstruction, repair, augmentation or replacement of such organs or tissues. In one embodiment, the luminal organ or tissue structure is a bladder or portion thereof, and the polymeric matrix or scaffold has smooth muscle cells deposited on a surface of the matrix. The constructs may also be used to provide a urinary diversion or conduit, or a detrusor muscle equivalent.

In one aspect, the invention provides urinary diversion or conduit scaffolds or matrices that are seeded with a cell population described herein. Such scaffolds that have been seeded with a cell population and may be referred to herein as "constructs". In one embodiment, the urinary diversion or bladder conduit construct is made up of one or more scaffolds as described herein and a cell population deposited on one or more surfaces of the one or more scaffolds as described herein.

In one aspect, the present invention provides muscle equivalent constructs that may be used to enhance an existing luminal organ or tissue structures such as genitourinary organs, including for example, the urinary bladder, to a subject in need. The subject may require expansion or treatment of such organs or tissues. In one embodiment, the luminal organ or tissue structure is a bladder or portion thereof, and the polymeric matrix or scaffold has smooth muscle cells deposited on a surface of the matrix. In one embodiment, the constructs are used to provide a detrusor muscle equivalent.

Those of ordinary skill in the art will appreciate there are several suitable methods for depositing cell populations upon matrices or scaffolds.

In one aspect, the constructs are suitable for implantation into a subject in need of a new organ or tissue structure. In one embodiment, the construct comprises a population of cells that produce the cytokine MCP-1. In another embodiment, the MCP-1 elicits the migration of the subject's or recipient's native mesenchymal stem cells to the site of implantation. In one embodiment, the migrating recipient native mesenchymal stem cells assist in the regeneration of the new organ or tissue structure.

In one other aspect, the invention provides scaffolds seeded with cells at particular cell densities. In one embodiment, a scaffold is seeded with a smooth muscle cell population at a cell density of about $20 \times 10^6$ to about $30 \times 10^6$ cells. In another embodiment, the cell density is about $1 \times 10^6$ to about $40 \times 10^6$, about $1 \times 10^6$ to about $30 \times 10^6$, about $1 \times 10^6$ to about $20 \times 10^6$, about $1 \times 10^6$ to about $10 \times 10^6$, or about $1 \times 10^6$ to about $5 \times 10^6$.

In a further embodiment, the density is about $20 \times 10^6$ to about $98 \times 10^6$ cells. In yet further embodiments, the density is about $21 \times 10^6$ to about $97 \times 10^6$, about $22 \times 10^6$ to about $95 \times 10^6$, about $23 \times 10^6$ to about $93 \times 10^6$, about $24 \times 10^6$ to about $91 \times 10^6$, about $25 \times 10^6$ to about $89 \times 10^6$, about $26 \times 10^6$ to about $87 \times 10^6$, about $28 \times 10^6$ to about $85 \times 10^6$, about $29 \times 10^6$ to about $83 \times 10^6$, about $30 \times 10^6$ to about $80 \times 10^6$, about $35 \times 10^6$ to about $75 \times 10^6$, about $40 \times 10^6$ to about $70 \times 10^6$, about $45 \times 10^6$ to about $65 \times 10^6$, or about $50 \times 10^6$ to about $60 \times 10^6$. In a preferred embodiment, the density is about $24 \times 10^6$ to about $91 \times 10^6$ cells In another embodiment, the density is about $2.5 \times 10^6$ to about $40 \times 10^6$, about $5 \times 10^6$ to about $40 \times 10^6$, about $7.5 \times 10^6$ to about $35 \times 10^6$, about $10 \times 10^6$ to about $30 \times 10^6$, about $15 \times 10^6$ to about $25 \times 10^6$, and about $17.5 \times 10^6$ to about $22.5 \times 10^6$. In another embodiment, the cell density is about $1 \times 10^6$, about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, about $10 \times 10^6$, about $11 \times 10^6$, about $12 \times 10^6$, about $13 \times 10^6$, about $14 \times 10^6$, about $15 \times 10^6$, about $16 \times 10^6$, about $17 \times 10^6$, about $18 \times 10^6$, about $19 \times 10^6$, about $20 \times 10^6$, about $21 \times 10^6$, about $22 \times 10^6$, about $23 \times 10^6$, about $24 \times 10^6$, about $25 \times 10^6$, about $26 \times 10^6$, about $27 \times 10^6$, about $28 \times 10^6$, about $29 \times 10^6$, about $30 \times 10^6$, about $31 \times 10^6$, about $32 \times 10^6$, about $33 \times 10^6$, about $34 \times 10^6$, about $35 \times 10^6$, about $36 \times 10^6$, about $37 \times 10^6$, about $38 \times 10^6$, about $39 \times 10^6$, about $40 \times 10^6$, about $41 \times 10^6$, about $42 \times 10^6$, about $43 \times 10^6$, about $44 \times 10^6$, about $45 \times 10^6$, about $46 \times 10^6$, about $47 \times 10^6$, about $48 \times 10^6$, about $49 \times 10^6$, about $50 \times 10^6$, about $51 \times 10^6$, about $52 \times 10^6$, about $53 \times 10^6$, about $54 \times 10^6$, about $55 \times 10^6$, about $56 \times 10^6$, about $57 \times 10^6$, about $58 \times 10^6$, about $59 \times 10^6$, about $60 \times 10^6$, about $61 \times 10^6$, about $62 \times 10^6$, about $63 \times 10^6$, about $64 \times 10^6$, about $65 \times 10^6$, about $66 \times 10^6$, about $67 \times 10^6$, about $68 \times 10^6$, about $69 \times 10^6$, about $70 \times 10^6$, about $71 \times 10^6$, about $72 \times 10^6$, about $73 \times 10^6$, about $74 \times 10^6$, about $75 \times 10^6$, about $76 \times 10^6$, about $77 \times 10^6$, about $78 \times 10^6$, about $79 \times 10^6$, about $80 \times 10^6$, about $81 \times 10^6$, about $82 \times 10^6$, about $83 \times 10^6$, about $84 \times 10^6$, about $85 \times 10^6$, about $86 \times 10^6$, about $87 \times 10^6$, about $88 \times 10^6$, about $89 \times 10^6$, about $90 \times 10^6$, about $91 \times 10^6$, about $92 \times 10^6$, about $93 \times 10^6$, about $94 \times 10^6$, about $95 \times 10^6$, about $96 \times 10^6$, about $97 \times 10^6$, about $98 \times 10^6$, or about $99 \times 10^6$.

In a further aspect, the invention provides scaffolds seeded with cells at particular cell densities per $cm^2$ of a scaffold. In one embodiment, the density is about 3,000 cells/$cm^2$ to about 15,000 cells/$cm^2$, about 3,500 cells/$cm^2$ to about 14,500 cells/$cm^2$, about 4,000 cells/$cm^2$ to about 14,000 cells/$cm^2$, about 4,500 cells/$cm^2$ to about 13,500 cells/$cm^2$, about 5,000 cells/$cm^2$ to about 13,000 cells/$cm^2$, about 4,500 cells/$cm^2$ to about 13,500 cells/$cm^2$, about 5,000 cells/$cm^2$ to about 13,000 cells/$cm^2$, about 5,500 cells/$cm^2$ to about 12,500 cells/$cm^2$, about 6,000 cells/$cm^2$ to about 12,000 cells/$cm^2$, about 6,500 cells/$cm^2$ to about 11,500 cells/$cm^2$, about 7,000 cells/$cm^2$ to about 11,000 cells/$cm^2$, about 7,500 cells/$cm^2$ to about 10,500 cells/$cm^2$, about 8,000 cells/$cm^2$ to about 10,000 cells/$cm^2$, about 7,500 cells/$cm^2$ to about 9,500 cells/$cm^2$, or about 8,000 cells/$cm^2$ to about 9,000 cells/$cm^2$. In a preferred embodiment, the density is about 3,000 cells/$cm^2$ to about 7,000 cells/$cm^2$, or about 9,000 cells/$cm^2$ to about 15,000 cells/$cm^2$.

In one aspect, the constructs of the present invention are adapted to provide particular features to the subject following implantation. In one embodiment, the constructs are adapted to provide regeneration to the subject following implantation. In another embodiment, the constructs are adapted to promote regeneration in a subject at the site of implantation. For example, following implantation, regenerated tissue may form from the construct itself at the site of implantation. In another embodiment, the construct may impart functional attributes to the subject following implantation. For example, a urinary diversion construct may be adapted to allow the passage of a subject's urine from a first ureter (e.g., first side opening) to the interior of the tubular scaffold, and/or adapted to provide temporary storage and passage of urine (e.g., tubular scaffold) out of a subject. In one embodiment, a urinary diversion construct may be adapted to provide an epithelialized mucosa upon implantation. In another embodiment, a construct may be adapted to provide homeostatic regulative development of a new organ or tissue structure in a subject.

6. Methods of Use

In one aspect, the present invention contemplates methods for providing a laminarily organized luminal organ or tissue structure to a subject in need of such treatment. In one embodiment, the subject may be in need of reconstruction, repair, augmentation, or replacement of an organ or tissue. In one embodiment, the method includes the step of providing a biocompatible synthetic or natural polymeric matrix shaped to conform to at least a part of the organ or tissue structure in need of an organ or tissue structure. The providing step may be followed by depositing at least one cell population that is not derived from the organ or tissue structure that is the subject of the reconstruction, repair, augmentation or replacement. The depositing step may include culturing the cell population on the polymeric matrix. After depositing the cell population on the matrix to provide a construct, it can be implanted into a patient at the site of treatment for the formation of the desired laminarily organized luminal organ or tissue structure. In one embodiment, the laminarly organized luminal organ or tissue structure is a bladder or a part of a bladder.

In one other aspect, the present invention provides methods for providing a laminarily organized luminal organ or tissue structure to a subject in need. In one embodiment, the method includes the steps of a) providing a biocompatible synthetic or natural polymeric matrix shaped to conform to at least a part of the organ or tissue structure in need of said treatment; b) depositing on or in a first area of the polymeric matrix an autologous cell population that is not derived from a native organ or tissue corresponding to the new organ or tissue structure; and c) implanting the shaped polymeric matrix cell construct into said the subject for the formation of laminarily organized luminal organ or tissue structure. In one other aspect, the present invention provides methods for providing a neo-bladder or portion thereof to a subject in need. In one embodiment, the method includes a) providing a biocompatible synthetic or natural polymeric matrix shaped to conform to a bladder or portion thereof; b) depositing an autologous cell population that is not derived from the subject's bladder on or in a first area of the polymeric matrix; and c) implanting the shaped polymeric matrix cell construct into the subject for the formation of the neo-bladder or portion thereof. In another embodiment, the cell population of step b) of the methods described herein contains one or more peripheral blood-derived smooth muscle cells having contractile function that are positive for a smooth muscle cell marker, or the cell population of step b) contains one or more adipose tissue-derived smooth muscle cells having contractile function that are positive for a smooth muscle cell marker. In one other embodiment, the contractile function of the cell population is calcium-dependent.

In one embodiment, the methods of the present invention further include the step of wrapping the implanted conduit construct with the subject's omentum, mesentery, muscle fascia, and/or peritoneum to allow for vascularization.

In one other aspect, the present invention provides methods for providing a urinary diversion or conduit for a defective bladder in a subject in need. In one embodiment, the method for providing a urinary diversion to a subject in need includes the steps of (a) providing a biocompatible conduit scaffold; (b) depositing a first cell population on or in a first area of said scaffold, said first cell population being substantially a muscle cell population; and (c) implanting the scaffold of step (b) into said subject to form a conduit that allows urine to exit the subject. In another embodiment, the biocompatible material is biodegradable. In other embodiments, the biocompatible material is polyglycolic acid. In yet another embodiment, the first cell population is substantially a smooth muscle cell population.

In one embodiment, the method includes the step of providing a urinary diversion or conduit scaffold as described herein. In other additional embodiments, the urinary diversion or conduit scaffold is provided in multiple parts, such as a first, second, and third scaffold, as described herein. In another embodiment, the method further includes the step of depositing a cell population that is not derived from the defective bladder to form a urinary diversion or conduit construct.

In one other embodiment, the depositing step may include culturing the cell population on the scaffold. In some embodiments, the methods further includes the step of implanting the urinary diversion construct into a patient in need. In another embodiment, the implantation is at the site of the defective bladder.

In one embodiment, an open end of the construct (e.g., a first end configured to connect to the abdominal wall) is anastomosed to the skin (ostomy) through the abdominal or suprapubic wall to form a stoma or sphincter. In another embodiment, a catheter is inserted through stoma opening and into the lumen of the construct to provide urine outflow.

Figure 10:
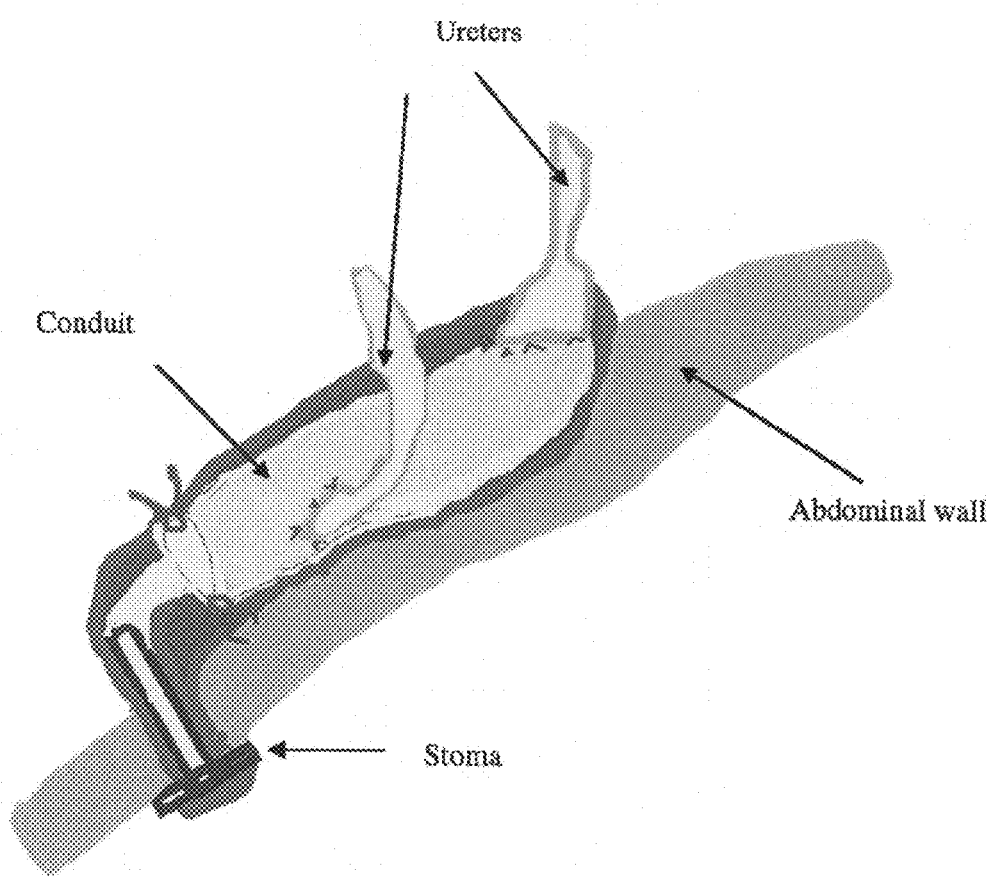
FIG. 10 shows an example of a configuration for an implanted conduit construct.

FIG. 10 illustrates a configuration for an implanted conduit construct.

In another embodiment, the methods of the present invention further include the step of monitoring the conduit for the presence of an obstruction following implantation of the urinary diversion construct. The obstruction may be caused by the build-up of detritus. The method may further include the step of removing detritus from the lumen of the conduit if an obstruction is detected.

Figure 11:
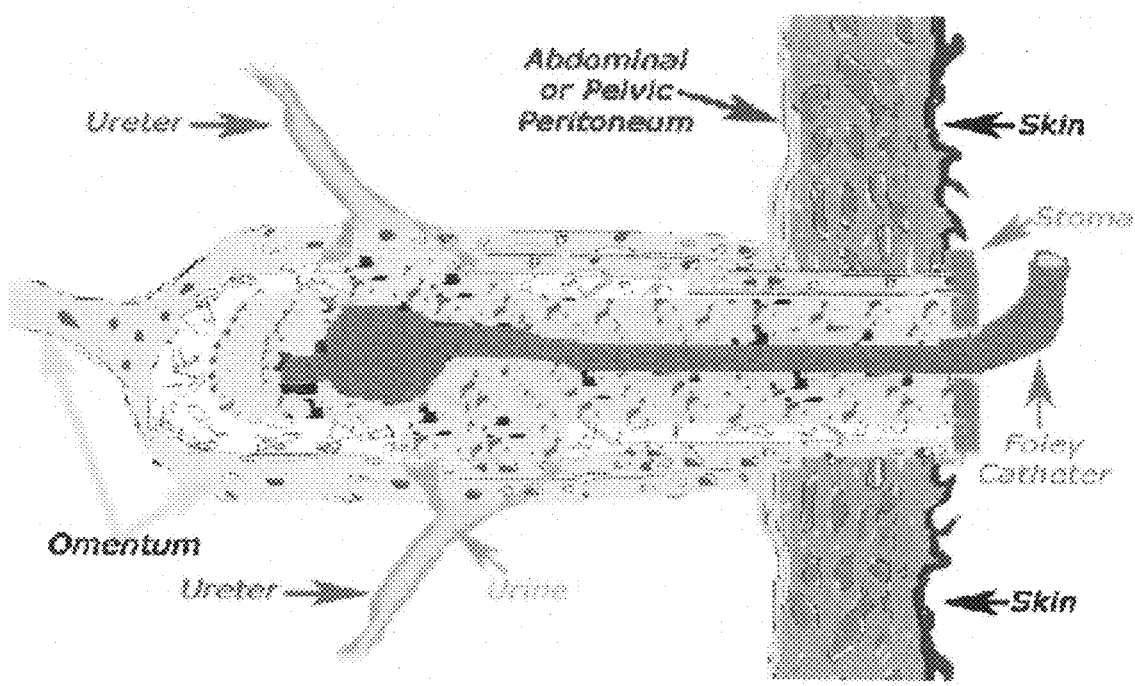
FIG. 11 shows an example of the implanted components of a temporary urinary diversion construct.

In one aspect, the present invention provides a urinary diversion to a subject in need on a temporary basis. In one embodiment, a temporary urinary diversion or conduit construct is implanted into a subject to form a stoma opening, and a catheter or other device is temporarily inserted through the stoma to the lumen of the conduit construct. A temporary conduit provides the advantage of allowing urine to exit the subject while a permanent solution to the defective bladder is attempted. For example, the implantation of a conduit construct could be performed prior to, following, or simultaneous with the implantation of a neo-bladder construct seeded with a cell population (see for example Bertram et al. supra). FIG. 11 shows an example of the implanted components of a temporary urinary diversion construct.

In one embodiment, the methods of the present invention further include the step of wrapping the implanted urinary diversion or conduit construct with the subject's omentum, mesentery, muscle fascia, and/or peritoneum to allow for vascularization.

Figure 12:
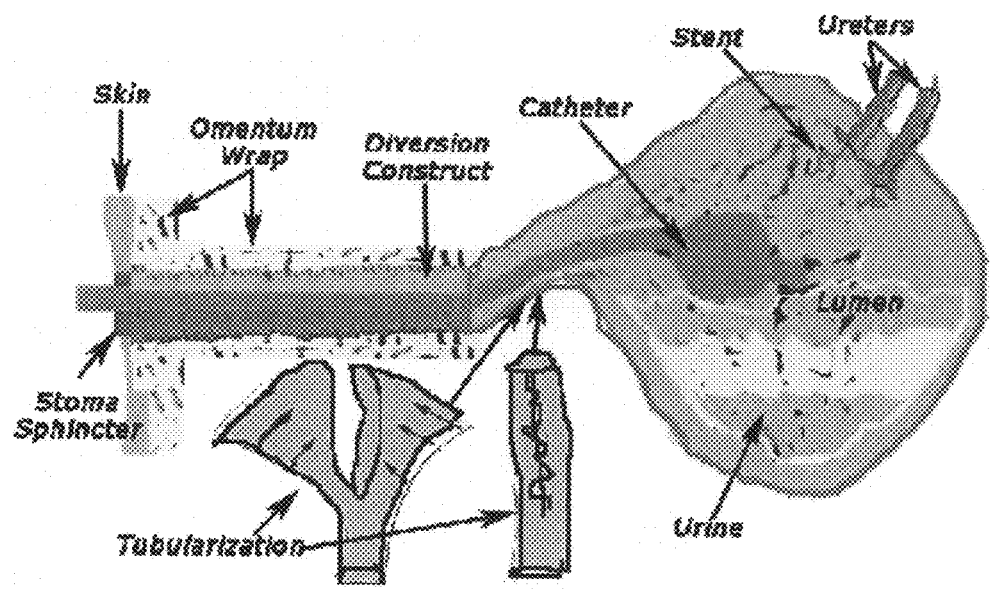
FIG. 12 shows an example of the implanted components of a permanent urinary diversion construct.

In one aspect, the present invention provides a urinary diversion to a subject in need on a permanent basis. FIG. 12 shows an example of the implanted components of a permanent urinary diversion construct.

Figure 13:
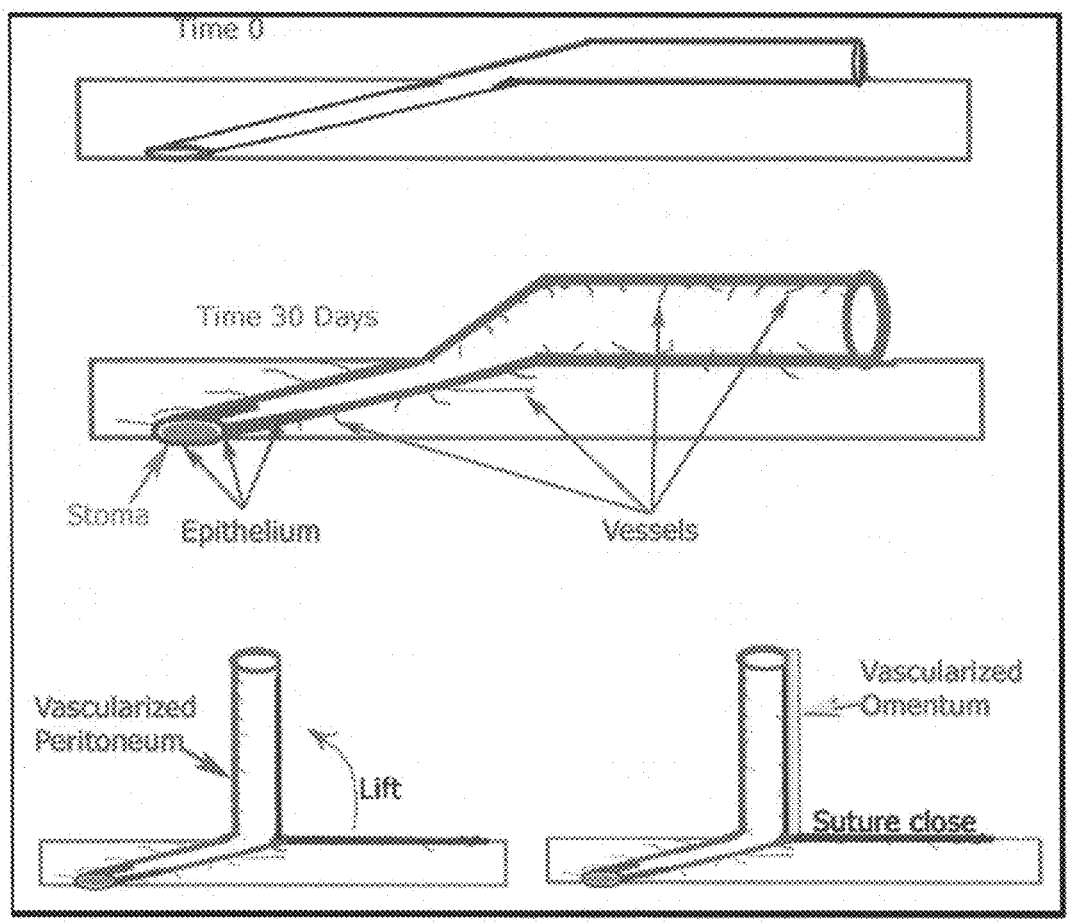
FIG. 13 depicts other applications of the urinary diversion constructs.

In one embodiment, the constructs described herein may be used for a prostatic urethra replacement and urinary diversion. Such a procedure is necessary for subjects requiring a radical prostatectomy to remove the prostatic urethra. In other embodiments, the constructs may be used for a percutaneous diversion tube to form a continent tube with a valve-like kink. In an additional embodiment, the constructs may be used as a bladder neck sling and wrapping materials used in bladder neck surgery and urinary outlets with continent channels or catherizable openings. Examples of such embodiments are depicted in FIG. 13.

In one aspect, the urinary diversion constructs of the present invention provide an epithelialized mucosa. In one embodiment, the construct is adapted to form an epithelialized mucosa upon implantation. In one embodiment, the epithelialized mucosa comprises a vestibular region and a mucocutaneous region. In another embodiment, the vestibular region is adjacent to the mucocutaneous region. In another embodiment, the mucocutaneous region is located at the stromal end of the construct connected to the abdominal wall and skin of the subject. In general, naturally-occurring mucocutaneous regions are characterized by the presence of mucosa and cutaneous skin and typically exist near the orifices of the body where the external skin ends and the mucosa that covers the inside of the body starts. The epithelialized mucosa provided by the constructs and methods of the present invention develops at the first end of the urinary diversion construct following implantation into the subject. In a further embodiment, the epithelialized mucosa is characterized by the presence of an epithelium that first appears in the vestibular region and gradually expands or increases through the mucocutaneous region towards the stomal end of the construct. In another embodiment, the epithelium is characterized by expression of an epithelial cell marker. In a further embodiment, the epithelial cell marker is cytokeratin. The cytokeratin may be one or more of the cytokeratins known in the art including, without limitation, cytokeratins 1 through 19. In one other embodiment, the cytokeratin is detectable with AE-1/AE3 antibody.

Grafting of scaffolds to an organ or tissue to be enlarged can be performed according to the methods described in the Examples or according to art-recognized methods. The matrix or scaffold can be grafted to an organ or tissue of the subject by suturing the graft material to the target organ.

The described techniques may be used to expand an existing laminarily organized luminal organ or tissue structure in a patient in need of such treatment. For example, an existing laminarily organized luminal organ or tissue structure may be enlarged by providing a polymeric matrix or scaffold shaped to conform to at least a part of the organ or tissue structure in need of said treatment and of a sufficient size to be laparoscopically implanted, depositing an autologous cell population that is not derived from the organ or tissue structure on or in a first area of said polymeric matrix; and laparoscopically implanting the shaped polymeric matrix construct into said patient at the site of said treatment such that the existing laminarily organized luminal organ or tissue structure is expanded.

Figure 7A:
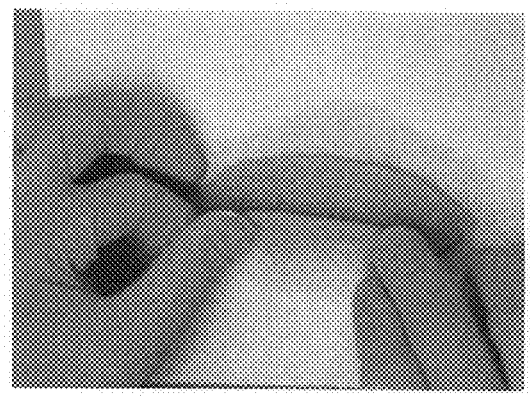
FIG. 7a depicts formation of a flat sheet of scaffold.
Figure 7B:
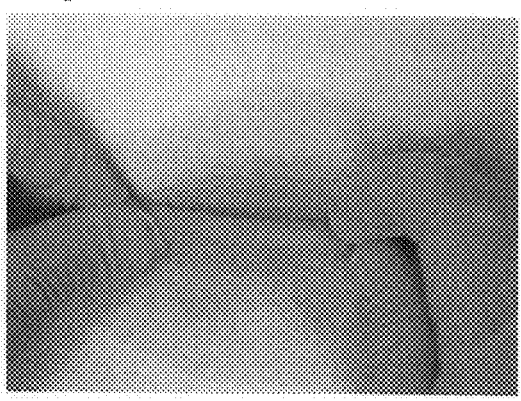
FIG. 7b depicts a laparoscopically-suited scaffold which can be rolled at the time of implantation and fed through a laparoscopic tube and unrolled in the abdominal cavity.
Figure 7C:
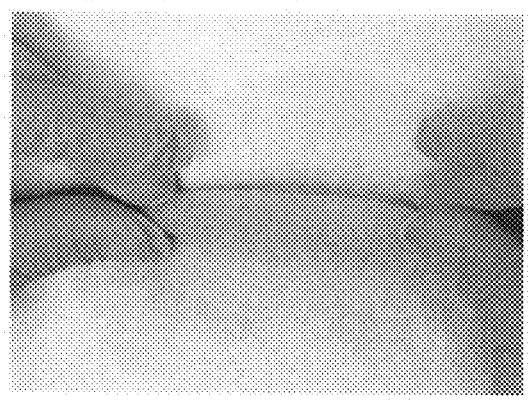
FIG. 7c depicts formation of a laparoscopically-suited scaffold sheet in a rolled configuration to facilitate insertion through a laparoscopic tube, after which it is unrolled in the abdominal cavity.
Figure 7D:
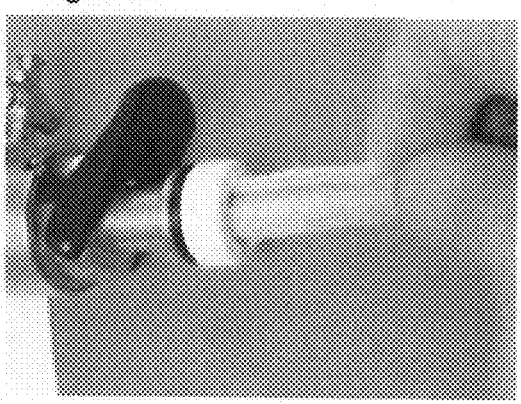
FIG. 7d depicts formation of a laparoscopically-suited scaffold sheet in a folded configuration or accordion style to facilitate insertion through the tube, after which it is unfolded in the abdominal cavity.
Figure 7E:
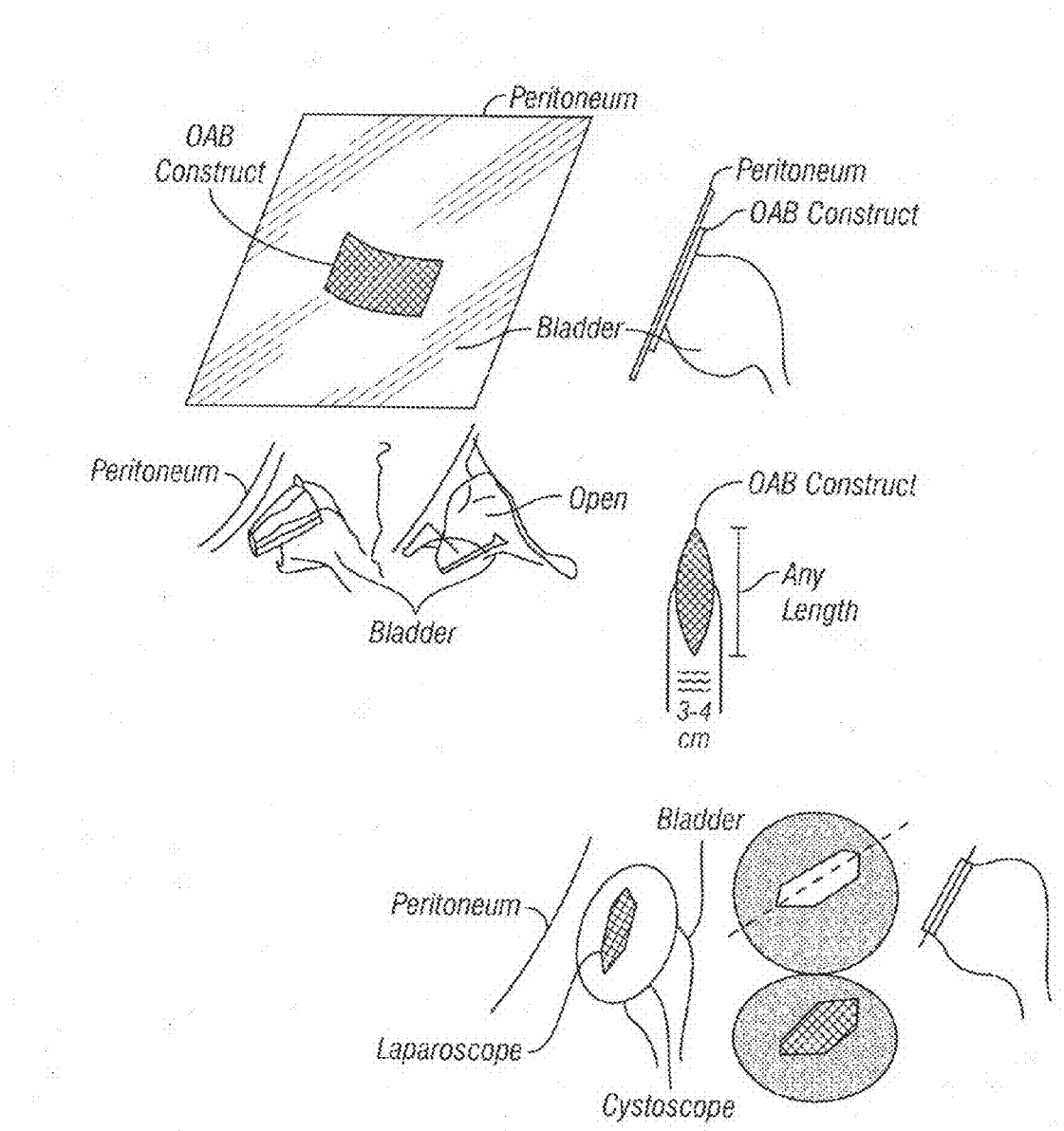
FIG. 7e depicts possible surgical methods for the implantation of a muscle equivalent scaffold.
Figure 7F:
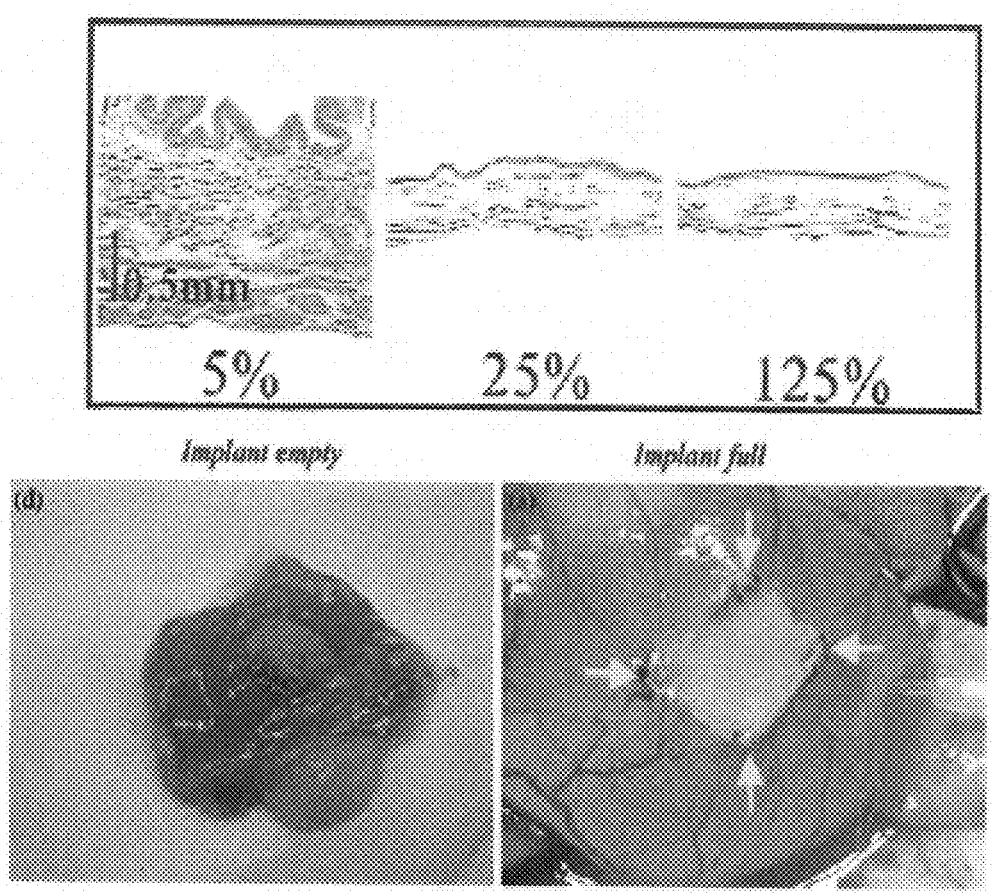
FIG. 7f depicts implantation sites on an empty and full bladder.
Figure 7G:
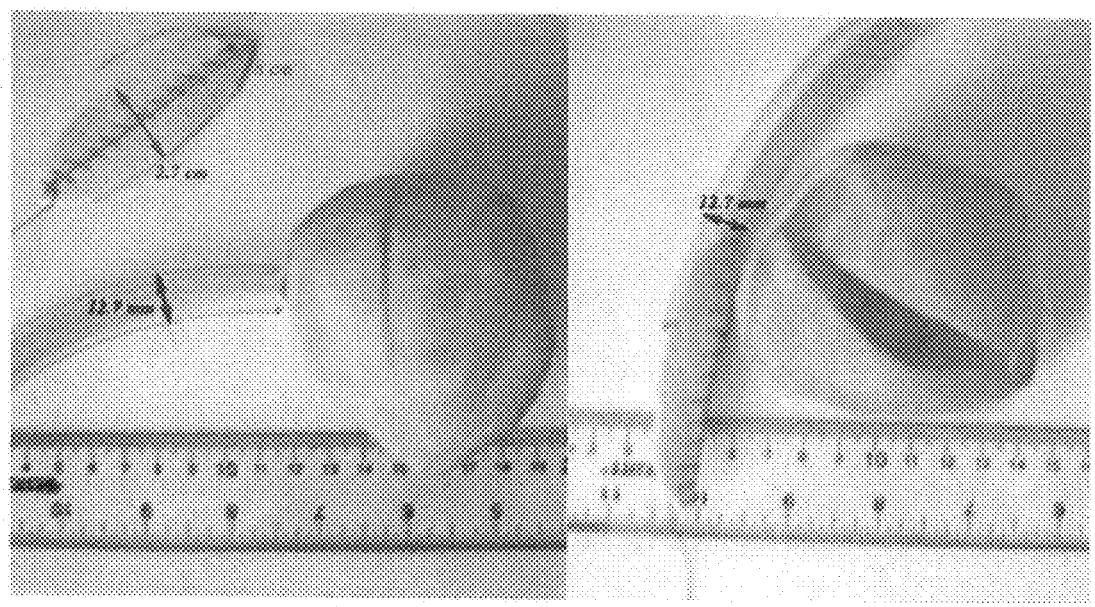
FIG. 7g depicts a urinary bladder model with surgical slit showing ellipsoid created upon sectioning of surface.

FIG. 7e depicts possible surgical methods for the implantation of a muscle equivalent scaffold described herein. FIG. 7f depicts implantation sites on an empty and full bladder. FIG. 7g depicts a urinary bladder model with surgical slit showing ellipsoid created upon sectioning of surface. A plastic tube may be used as a model of the limited space available in order to pass the folded or rolled polymeric matrices or scaffolds of the invention.

The described techniques may also be used to increase bladder volumetric capacity in a patient in need of such treatment. For example, bladder volumetric capacity may be increased by providing a biocompatible synthetic or natural polymeric matrix shaped to conform to at least a part of the organ or tissue structure in need of said treatment and of a sufficient size to be laparoscopically implanted; depositing an autologous cell population that is not derived from the organ or tissue structure on or in a first area of said polymeric matrix; and laparoscopically implanting the shaped polymeric matrix construct laparoscopically into said patient at the site of said treatment such that bladder volume capacity is increased. In one embodiment, the matrix or scaffold of the instant invention is suitable for increasing bladder volume capacity about 50 mL. In other embodiments, the matrix or scaffold of the instant invention is suitable for increasing bladder volume capacity about 100 mL. In other embodiments, the matrix or scaffold of the instant invention is suitable for increasing bladder volume capacity about 60, about 70, about 80, or about 90 mL.

The described techniques may further be used to expand a bladder incision site in a patient in need of such treatment. For example, a bladder incision site may be expanded by providing a biocompatible synthetic or natural polymeric matrix shaped to conform to at least a part of the organ or tissue structure in need of said treatment and of a sufficient size to be laparoscopically implanted; b) depositing an autologous cell population that is not derived from the organ or tissue structure on or in a first area of said polymeric matrix; and c) laparoscopically implanting the shaped polymeric matrix construct laparoscopically into said patient at the site of said treatment such that the bladder incision site is expanded.

Another non-limiting use of the invention includes methods for the treatment of urinary incontinence in a patient in need of such treatment. For example, urinary incontinence may be treated by providing a biocompatible synthetic or natural polymeric matrix shaped to conform to at least a part of the organ or tissue structure in need of said treatment and of a sufficient size to be laparoscopically implanted; depositing an autologous cell population that is not derived from the organ or tissue structure on or in a first area of said polymeric matrix; and laparoscopically implanting the shaped polymeric matrix construct laparoscopically into said patient at the site of said treatment such that bladder volume capacity is increased.

In one embodiment, the scaffolds, cell populations, and methods described herein may further be used for the preparation of a medicament useful in the treatment of a disorder described herein. The disorders include any condition in a subject that requires the regeneration, reconstruction, repair, augmentation or replacement of laminarly organized luminal organs or tissue structures. In another embodiment, the organ or tissue structure is a bladder or a part of the bladder.

In another embodiment, the cells deposited on the implanted construct produce MCP-1 and release it at the site of implantation, which stimulates native mesenchymal stem cells (MSCs) to migrate to the site of implantation. In one other embodiment, the native MSCs facilitate and/or enhance regeneration of the implanted construct at the site of implantation.

In one embodiment, the cell population deposited is a smooth muscle cell (SMC) population derived from peripheral blood or from adipose tissue as described herein. In another embodiment, the SMC population includes at least one cell that has contractile function and is positive for a smooth muscle cell marker, such as myocardin, alpha-smooth muscle actin, calponin, myosin heavy chain, BAALC, desmin, myofibroblast antigen, SM22, and any combination thereof. In other embodiments, the SMC population includes at least one cell that demonstrates myocardin (MYOCD) expression. The MYOCD expression may be expression of a nucleic acid encoding a MYOCD polypeptide or a MYOCD polypeptide. In another embodiment, the contractile function of the SMC is calcium-dependent. In one embodiment, the laminarily organized luminal organ or tissue structure that is the subject of reconstruction, repair, augmentation or replacement is a bladder or a portion of a bladder. In another embodiment, the polymeric matrix is free of urothelial cells.

In all embodiments, the methods of the present invention utilize a construct for implantation that is based upon a bladder replacement scaffold, a bladder augmentation scaffold, a bladder conduit scaffold, or a detrusor muscle equivalent scaffold that has been seeded with a cell population as described herein.

In another embodiment, the methods for the regeneration, reconstruction, repair, augmentation or replacement of laminarly organized luminal organs or tissue structures described herein include the steps of a) providing a biocompatible synthetic or natural polymeric matrix shaped to conform to at least a part of the luminal organ or tissue structure in need of said treatment; b) depositing a first cell population on or in a first area of said polymeric matrix at a cell density described herein, said first cell population being substantially a muscle cell population; and c) implanting the shaped polymeric matrix cell construct into said patient at the site of said treatment for the formation of the laminarily organized luminal organ or tissue structure. In one other embodiment, the laminarily organized luminal organ or tissue structure formed in vivo exhibits the compliance of natural bladder tissue.

In one other aspect, the present invention provides methods for the regeneration of a neo-bladder following implantation into a subject in need thereof based upon biomechanical stimulation or cycling. In one aspect, the methods are suitable for use in promoting the regeneration of an implanted neo-bladder construct that has been implanted for the augmentation or replacement of a bladder or a portion of a bladder. In one embodiment, the neo-bladder construct is formed from seeding cells on a neo-bladder matrix or scaffold. In another embodiment, the neo-bladder scaffold is a bladder replacement scaffold, a bladder augmentation scaffold, a bladder conduit scaffold, or a detrusor muscle equivalent scaffold.

In one aspect, the method of the present invention applies to implanted neo-bladder constructs formed from seeding neo-bladder scaffolds with at least one cell population. In one embodiment, the cell-seeded polymeric matrix (or matrices) is a bladder replacement scaffold, a bladder augmentation scaffold, a bladder conduit scaffold, or a detrusor muscle equivalent scaffold. In one embodiment, the at least one cell population comprises substantially a muscle cell population. In another embodiment, the muscle cell population may be a smooth muscle cell population. Different densities of cells for seeding may be appropriate as described herein.

In one aspect, the methods of the present invention are performed at different times and for different durations following the implantation of the neo-bladder. In one embodiment, the cycling is performed on a daily basis over a period of time, on a weekly basis over a period of time, or every other week. In another embodiment, the duration of the daily cycling regimen is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or longer than 14 weeks.

In one embodiment, a daily cycling protocol for a subject may include the steps of filling the neo-bladder for about an hour, draining the filled neo-bladder for about an hour, and allowing the neo-bladder to drain freely, typically overnight. This protocol can be performed on day one of the cycling regimen in the subject. This daily sequence can be performed for a number of consecutive days after the first day. In one embodiment, the cycling protocol may be performed on a day after day one in which the duration of the filling step is increased to about two hours, about three hours, about four hours, or more than about four hours. In another embodiment, the filling and draining steps may be repeated more than once daily before allowing the neo-bladder to drain freely.

In another embodiment, the subjects are catheterized post-implantation, and the cycling time is controlled by clamping and unclamping the subject's catheter.

Those of ordinary skill in the art will appreciate that additional cycling regimens are contemplated herein.

An example of a cycling protocol is as follows. Following implantation of a neo-bladder construct formed by seeding a neo-bladder matrix or scaffold with cells as described herein, cycling will be performed every 2 weeks (14±2 day intervals) starting approximately 1 month after implantation and continuing until approximately Day 90. Cycling will be completed after certain types of assessment, such as compliance measurement of the implanted neo-bladder, but before other types of assessment such as fluoroscopic imaging. Cycling will be performed by re-inflating the bladder with sterile saline (warmed by incubator) after the completion of compliance measurement at a rate of 10-25 mL/min. The cycling will be repeated at least 5-10 times. The starting pressure of 0-10 mmHg will be achieved and recorded along with the start time. Time, volume of isotonic solution delivered, and the pressure obtained will be recorded for each cycle at the time leakage is observed around the catheter (a.k.a. leak point), or when the volume delivered is equal to that of the compliance measurement just performed, whichever comes first.

In one embodiment, the present invention provides a method of promoting regeneration of a neo-bladder implanted in a subject that includes the steps of (a) filling the implanted neo-bladder with a fluid; (b) emptying the filled neo-bladder of step (a). In another embodiment, the method includes step (c) repeating steps (a) and (b). In one other embodiment, the method is commenced within the first 2 weeks post-implantation. In one embodiment, the steps (a) and (b) are performed once daily, once weekly, or once every other week. In some other embodiments, the filling step (a) is performed for about one hour and the emptying step (b) is performed for about one hour. In yet another embodiment, steps a) and b) are performed at least until about six weeks post-implantation. In one other embodiment, steps a) and b) are not performed for more than about ten weeks post-implantation. In another embodiment, steps a) and b) are performed for more than about ten weeks post-implantation. In other embodiments, the filling comprises expanding the neo-bladder. In another embodiment, the regeneration comprises an increase in the capacity of the neo-bladder as compared to a neo-bladder in a subject that has not undergone cycling. In one other embodiment, the regeneration comprises an increase in compliance of the neo-bladder as compared to a neo-bladder in a subject that has not undergone cycling. In other embodiments, the regeneration comprises an increase in extracellular matrix development in the neo-bladder as compared to a neo-bladder in a subject that has not undergone cycling. In one embodiment, the increase in extracellular matrix development comprises the development of elastin fibers.

In one other aspect, the present invention concerns methods for providing homeostatic regulative development of neo-bladders in mammals such that implanted neo-bladders are responsive to the needs of the recipient. In one embodiment, the implanted neo-bladder grows to a size proportionate to the recipient. In another embodiment, the methods for providing homeostatic regulative development of a neo-bladder in a subject include the steps of (a) providing a biocompatible polymeric scaffold; (b) depositing an a first cell population on or in a first area of said scaffold, said first cell population being substantially a muscle cell population; and (c) implanting the scaffold of step (b) into said subject to establish homeostatic regulative development. In one other embodiment, the homeostatic regulative development comprises restoration of organ size and structure. In another embodiment, the homeostatic regulative development comprises neo-bladder capacities proportionate to body weight. In one embodiment, the proportionate neo-bladder capacity is achieved at about four months post-implantation.

In another embodiment, the method for providing homeostatic regulative development of a neo-bladder in a subject includes the step of monitoring the state of homeostatic regulative development or progress of the implanted neo-bladder. The monitoring may include a cystogram procedure to show the position and shape of the implanted neo-bladder, and/or a measurement of urodynamic compliance and capacity.

In another aspect, the invention provides methods for prognostic evaluation of a patient following implantation of a new organ or tissue structure. In one embodiment, the method includes the step of detecting the level of MCP-1 expression in a test sample obtained from said subject; (b) determining the expression level in the test sample to the level of MCP-1 expression relative to a control sample (or a control reference value); and (c) predicting regenerative prognosis of the patient based on the determination of MCP-1 expression levels, wherein a higher level of expression of MCP-1 in the test sample, as compared to the control sample (or a control reference value), is prognostic for regeneration in the subject.

In another aspect, the invention provides methods for prognostic evaluation of a patient following implantation of a new organ or tissue structure in the patient, the methods comprising: (a) obtaining a patient biological sample; and (b) detecting MCP-1 expression in the biological sample, wherein MCP-1 expression is prognostic for regeneration in the patient. In some embodiments, increased MCP-1 expression in the patient biological sample relative to a control sample (or a control reference value) is prognostic for regeneration in the subject. In some embodiments, decreased MCP-1 expression in the patient sample relative to the control sample (or control reference value) is not prognostic for regeneration in the subject. The patient sample may be a test sample comprising a bodily fluid, such as blood or urine.

In some embodiments, the determining step comprises the use of a software program executed by a suitable processor for the purpose of (i) measuring the differential level of MCP-1 expression in a test sample and a control; and/or (ii) analyzing the data obtained from measuring differential level of MCP-1 expression in a test sample and a control. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the determining step, the measurement results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment, a prognosis, prediction and/or treatment recommendation based on the level of MCP-1 expression measured in a test subject having a differential level of MCP-1 expression is communicated to the subject as soon as possible after the assay is completed and the prognosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computer, such as in case of email communications. In certain embodiments, the communication containing results of a prognosit test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, prognosis and/or prediction of regeneration, and communicating of assay results or prognoses, may be carried out in diverse (e.g., foreign) jurisdictions.

In another aspect, the prognostic methods described herein provide information to an interested party concerning the success of the implantation, and the rehabilitation/treatment protocol for regeneration. In one embodiment, the methods include the steps of detecting the level of MCP-1 expression in a test sample obtained from said subject; (b) determining the expression level in the test sample to the level of MCP-1 expression relative to a control sample (or a control reference value); and (c) predicting regenerative prognosis of the patient based on the determination of MCP-1 expression levels, wherein a higher level of expression of MCP-1 in the test sample, as compared to the control sample (or a control reference value), is indicative of the state of regeneration of a new organ or tissue structure.

Generally, as used herein, regeneration prognosis encompasses the forecast or prediction of any one or more of the following: development or improvement of a functional bladder after bladder replacement or augmentation through implantation of a construct described herein, development of a functional urinary diversion after implantation of a construct described herein, development of bladder capacity or improved bladder capacity after implantation of a construct described herein, or development of bladder compliance or improved bladder compliance after implantation of a construct described herein.

In all embodiments, the methods of providing a laminarily organized luminal organ or tissue structure to a subject in need of such treatment as described herein may include the post-implantation step of prognostic evaluation of regeneration as described above.

In all embodiments, the present invention relates to methods for providing a new organ or tissue structure to a subject in need that include certain post-implantation monitoring steps. In one embodiment, the effect and performance of an implanted constructs is monitored, such as through ultrasound imaging, pyelogram, as well as urine and blood analysis at different time-points after implantation. These monitoring steps are described in further detail in Examples 3-6.

7. Kits

The instant invention further includes kits comprising the polymeric matrices and scaffolds of the invention and related materials, and/or cell culture media and instructions for use. The instructions for use may contain, for example, instructions for culture of the cells or administration of the cells and/or cell products. The instructions for use may also contain instructions for pre-treating, folding or otherwise preparing the polymeric matrices and scaffolds of the invention for laparoscopic implantation.

In one embodiment, the present invention provides a kit comprising a scaffold as described herein and instructions. In another embodiment, the scaffold of the kit is one or more of the following: a bladder augmentation scaffold, a bladder replacement scaffold, a urinary conduit scaffold, or a muscle equivalent scaffold.

8. Reports

The methods of this invention, when practiced for commercial purposes generally produce a report or summary of the regenerative prognosis. The methods of this invention will produce a report comprising a prediction of the probable course or outcome of regeneration before and after any surgical procedure to provide a construct described herein. The report may comprise information on any indicator pertinent to the prognosis. The methods and reports of this invention can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer. The methods provided by the present invention may also be automated in whole or in part.

The following examples are offered for illustrative purposes only, and are not intended to limit the scope of the present invention in any way.

All patent, patent applications, and literature references cited in the present specification are hereby incorporated by reference in their entirety.

EXAMPLES

Example 1

Peripheral Blood and Adipose Tissue as a Source of SMCs

Blood-derived Cells

Smooth muscle cells have been successfully isolated from canine, porcine, and human peripheral blood. Briefly, a dilution of 50 ml of peripheral blood 1:1 with phosphate buffered saline (PBS; 100 mL final volume) was prepared and layered onto Histopaque, a density gradient material, and centrifuged at 1,354 xg for 20 minutes at room temperature. After centrifugation, four layers will be clearly defined in the density gradient (from top to bottom): serum, buffy coat, Histopaque, red blood cells. The mononuclear cells are located in the buffy coat, which appears as an opaque white/gray band. The buffy coat was withdrawn and transferred into a separate 50 ml conical tube. Dilute to 50 mL with PBS. Centrifuge the samples at 711 xg for 10 minutes at room temperature to pellet cells. Resuspend pellet and culture the cells. When appropriate cell numbers are reached by subsequent cell passaging, an aliquote is fixed and processed for end-point analysis including immunodetection of expressed smooth muscle cell proteins, nucleic acid detection of smooth muscle cell mRNA transcripts, cellular contraction, cytokine and enzyme synthesis.

Results

Media selection. The mononuclear fraction of a single 40-50 mL canine peripheral blood sample was resuspended in six different media formulations and seeded into 6-well Primaria or collagen-coated plates.

As shown in FIG. 14A-E, after one week of culture, small adherent colonies and small cell aggregates were observed in all conditions (DMEM media isolations are not shown) but the identity of the cell types were indiscernible. Small clusters and cell aggregates were observed on Primaria culture dishes when grown in alpha-MEM+10% FBS, EGM-2 medium with all of the accompanying supplements, and EGM-2 with selected accompanying supplements (minus VEGF and FGF2) (A, C, E) and collagen type I coated on tissue culture plastic plates grown in the same medias (B, D, F). Similar results were seen in peripheral blood cultures grown in DMEM formulations (data not shown).

Figure 15:
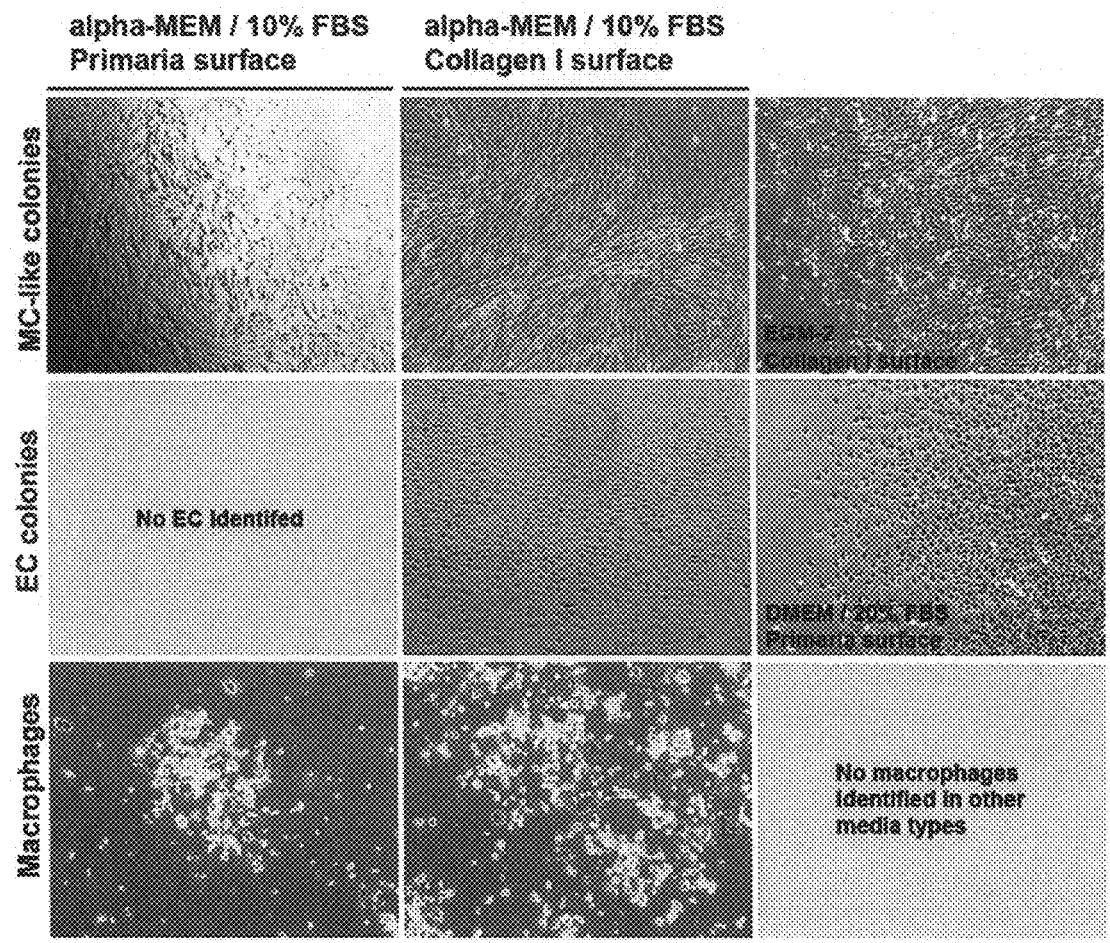
FIG. 15 shows canine peripheral blood outgrowth cells.

As shown in FIG. 15, after two weeks of culture, outgrowth colonies and small monolayers were observed in alpha-MEM on Primaria (left panels) and collagen-coated plates (middle panels). Morphologically, these colonies appeared smooth muscle (FIG. 15, top panels) or endothelial (FIG. 15, middle panels). Outgrowth colonies of smooth muscle (FIG. 15, top panels) or endothelial (FIG. 15, middle panels) morphology also formed in other media/substrate conditions (right panels). Some macrophages were initially maintained in alpha-MEM (FIG. 15, bottom left and middle panels), but did not carry over into subsequent passages. Cells isolated in αMEM with 10% FBS on Primaria plates were of smooth muscle (top left panel) or macrophage (bottom left panel) morphology. No endothelial cells were isolated under these conditions (middle left panel). Cells isolated in αMEM/10% FBS on collagen I plates were of smooth muscle (top middle panel), endothelial (middle middle panel) and macrophage (bottom middle panel) morphology. Other media/substrate formulations such as EGM-2 (top right panel) and DMEM supplemented with 20% FBS (middle right panel) also permitted outgrowth of mesenchymal- and endothelial-like cells.

Of the twelve media/substrate conditions, Primaria plates with alpha-MEM/10% FBS contained the most homogeneous isolation of smooth muscle cells (FIG. 15, top left panel) without outgrowth colonies of endothelial cells. Cells isolated on Primaria plates and expanded on Nunclon surfaces (in alpha-MEM/10% FBS) exhibited the classical 'hill and valley' morphology that is typical of smooth muscle cells (SMC), and is consistent with descriptions in other studies (Kassis et al. (2006); Koerner et al. (2006); Simper et al. (2002), supra).

Figure 16:
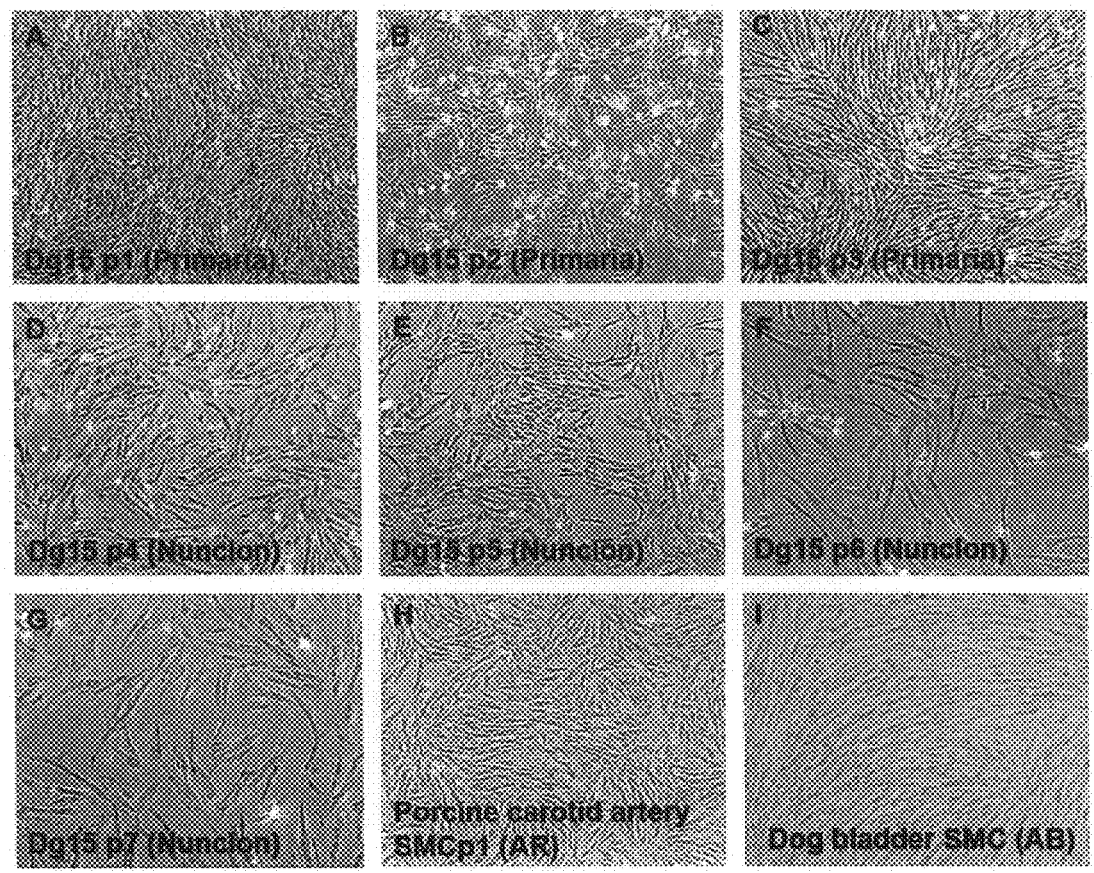
FIG. 16 shows the morphology of canine smooth muscle cells after several passages.

As shown in FIG. 16, these cells also maintained this morphology for several passages (FIG. 16A-G). Images of porcine carotid artery SMC (FIG. 16H) and dog bladder SMC (FIG. 16I) are shown for comparison. The smooth muscle cells at later passages (FIG. 16F, G) became larger and more spread out. Early passages (A-E) resemble smooth muscle cells (SMC) isolated from porcine carotid artery (H) and dog bladder (I). Later passages of smooth muscle cells (F, G) are larger and more spread out, suggesting a smooth muscle phenotype.

Adipose-derived Cells

Smooth muscle cells have been isolated from porcine adipose tissue according the following procedure. All procedures are performed in the biosafety hoods.

Obtain adipose sample. Store at room temperature or 4° C. for no more than 24 hours prior to use in biosafety container.

Prepare collagenase solution by adding 1 gm of BSA and 0.1 to 0.3 gm of collagenase per 100 ml of PBS. Filter the solution through a 0.2 μm filter unit. Warm to 37° C.

Add equivalent volume of Collagenase solution per adipose volume to each centrifuge bottle. One tissue volume of collagenase solution is required (i.e. 10 ml of collagenase solution per 10 ml adipose tissue).

Wipe the tubes with disinfectant, cap, wrap with parafilm and place in a 37° C. incubator on a rocker for 60 minutes. Alternatively, tubes may be placed in a 37° C. water bath and vigorously shaken by hand every 20 min.

Centrifuge at 300 xg at Room Temperature for 5 minutes.

Take the tubes out of the centrifuge and shake them vigorously for 10 seconds to thoroughly mix the cells. This is to complete the separation of stromal cells from the primary adipocytes.

Centrifuge again at 300 xg for 5 minutes. Carefully aspirate off the oil on top, the primary adipocytes (yellow layer of floating cells), and the collagenase solution. Leave behind approximately 10 ml of the brown collagenase solution above the pellet so that the stromal-vascular fraction (dark red cells on bottom) is not disturbed.

Resuspend the pellet of cells in PBS with 1% BSA and filter using Steri-Flip.

Centrifuge the cells at 300 xg for 5 minutes and aspirate the remaining collagenase solution. When aspirating, the tip of the pipette should aspirate from the top so that the oil is removed as thoroughly as possible. The cell pellet should be tightly packed at the bottom.

Add 10 ml of tissue culture medium to each centrifuge tube and resuspend the cells. Pool the cells to one tube and centrifuge again.

Aspirate supernatant. Suspend the cells in 10 ml of medium.

Divide the cells equally and accordingly to the appropriate number of flasks. 24-72 hours after plating, aspirate medium from flask. Wash with PBS and aspirate.

Add the original volume per flask of fresh medium.

Cells will be grown to 80-90% confluence and then either passaged or cryopreserved.

When appropriate cell numbers are reached by subsequent cell passaging, an aliquot is fixed and processed for immuno-detection of expressed smooth muscle cell proteins.

Figure 17:
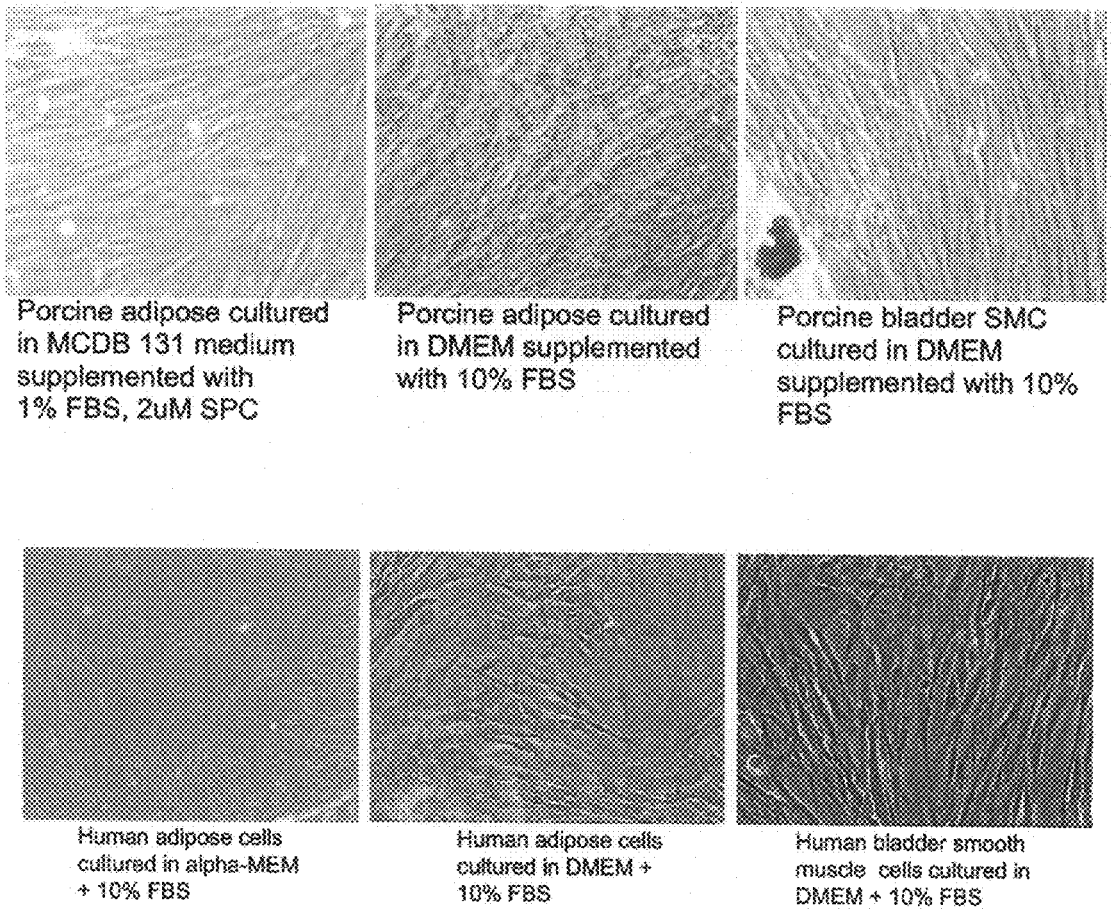
FIG. 17 shows smooth muscle cells isolated from porcine and human adipose.

FIG. 17 concerns the morphological assessment of cultures. The morphology was assessed after 3 to 5 days in culture. Human and porcine cells derived from adipose tissue exhibit smooth muscle cell morphological characteristics (FIG. 17). The cells demonstrate a hill-and-valley morphology and exhibit additional characteristics such as spindly shaped, flattened and fibroblast-like upon passage, elongated and arranged in parallel rows, and a "whirled" appearance of growth, all of which are typical of cultured smooth muscle cells.

Smooth muscle markers. Increased expression of contractile genes (and the proteins they encode) is associated with SMC maturation (Jeon et al. *J Cell Sci* 119, 4994-5005 (2006); Ross et al. *J Clin Inves.* 116, 3139-3149 (2006); Sinha et al. *Am J Physiol Cell Physiol* 287, 1560-1568 (2004)). Myocardin is a transcriptional regulator of genes that encode smooth muscle contractile proteins, among which include SM22, alpha smooth muscle actin, smooth muscle myosin heavy chain, and calponin (Qiu et al. (2005) Circ Res 983-991; Wang et al. (2003) Proc Natl. Acad Sci 100:7129-7134; Yoshida et al. (2003) Circ Res 92:856-864). Myocardin is required for smooth muscle differentiation, and is sufficient to drive smooth muscle gene expression in some cell types (Milyaysky et al. (2007) Cancer Cell 11:133-146; van Tuyn et al. (2005) supra; Wang et al. (2003), supra; Yoshida et al. (2003), supra). We determined if the smooth muscle cells isolated from blood or adipose tissue expressed the smooth muscle cell markers myocardin, smooth muscle alpha actin, SM22, myosin heavy chain, and calponin by isolating total RNA and performing semi-quantitative RT-PCR.

Figure 18:
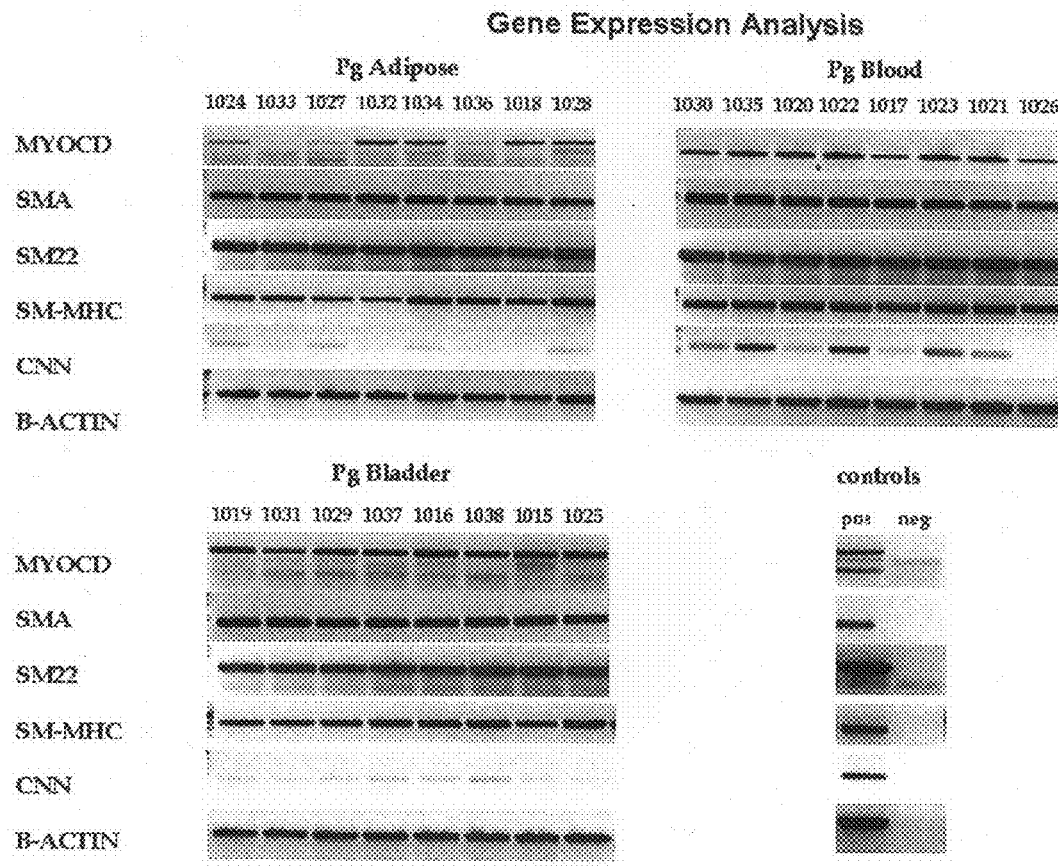
FIG. 18 shows RT-PCR analysis for gene expression of the smooth muscle cell markers.

As shown in FIG. 18, the results indicate that these cells express all of these smooth muscle cell markers at the gene level, consistent with the smooth muscle cell markers found in bladder smooth muscle cells. These data support the notion that these smooth muscle cells isolated from peripheral blood or adipose tissue have properties of smooth muscle cells.

Phenotypic characterization. We have already shown that these peripheral blood isolated smooth muscle cells express a transcriptional regulator of smooth muscle gene expression as well as specific smooth muscle contractile proteins (FIG. 18). FIG. 18 shows RT-PCR analysis for gene expression of SMC markers myocardin, smooth muscle alpha-actin, SM22, smooth muscle myosin heavy chain, and calponin. Samples were from smooth muscle cells isolated from porcine adipose, peripheral blood, and bladder (passage 4). The SMCs isolated from adipose tissue can be cultured 3-5 days between each passage, while the SMCs isolated from blood can be cultured for 14 days before the first passage and then 3-5 days for additional passage. Gene expression for beta-actin was used as an internal loading control for the gel. Expression profiles for adipose and peripheral blood cell isolates are comparable to that of the bladder SMC.

Figure 19:
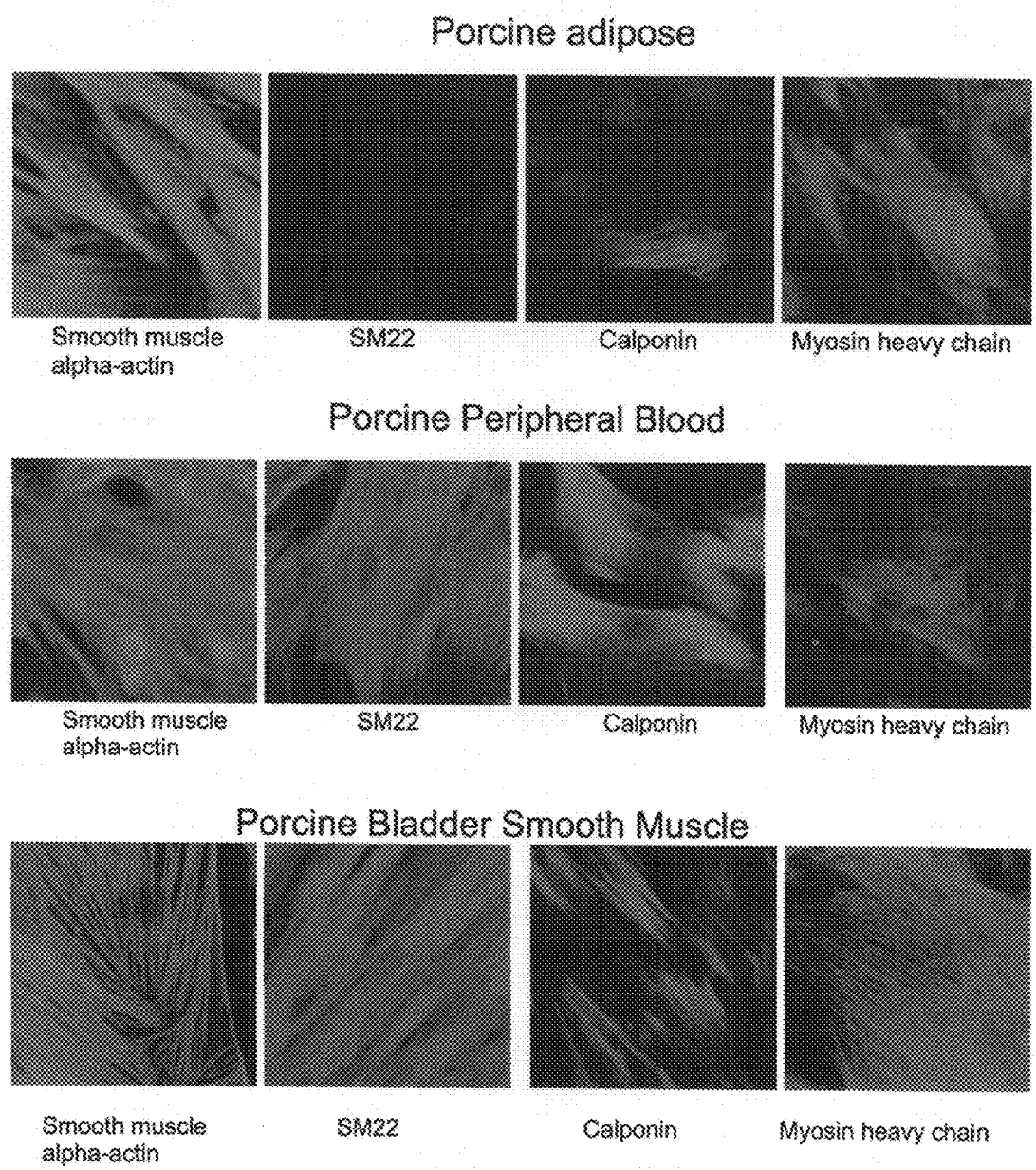
FIG. 19 shows immunofluorescence protein expression of smooth muscle cell markers.

FIG. 19 shows immunofluorescence staining that was performed utilizing a variety of antibodies directed towards smooth muscle cell expressed protein markers. The markers alpha-actin, SM22, calponin, and smooth muscle myosin heavy chain were examined in smooth muscle cells isolated from porcine adipose, peripheral blood, and bladder. These proteins are all involved in the contractile function of smooth muscle cells. Smooth muscle cells at multiple passages stained positively for smooth muscle alpha actin, SM22, calponin, and smooth muscle myosin heavy chain. Subcellular localization of these proteins was virtually identical in smooth muscle cells compared to bladder SMC. Detailed staining of these proteins in the stress fibers of the cells was noted. This pattern of staining is typical and expected for smooth muscle cells.

Figure 20:
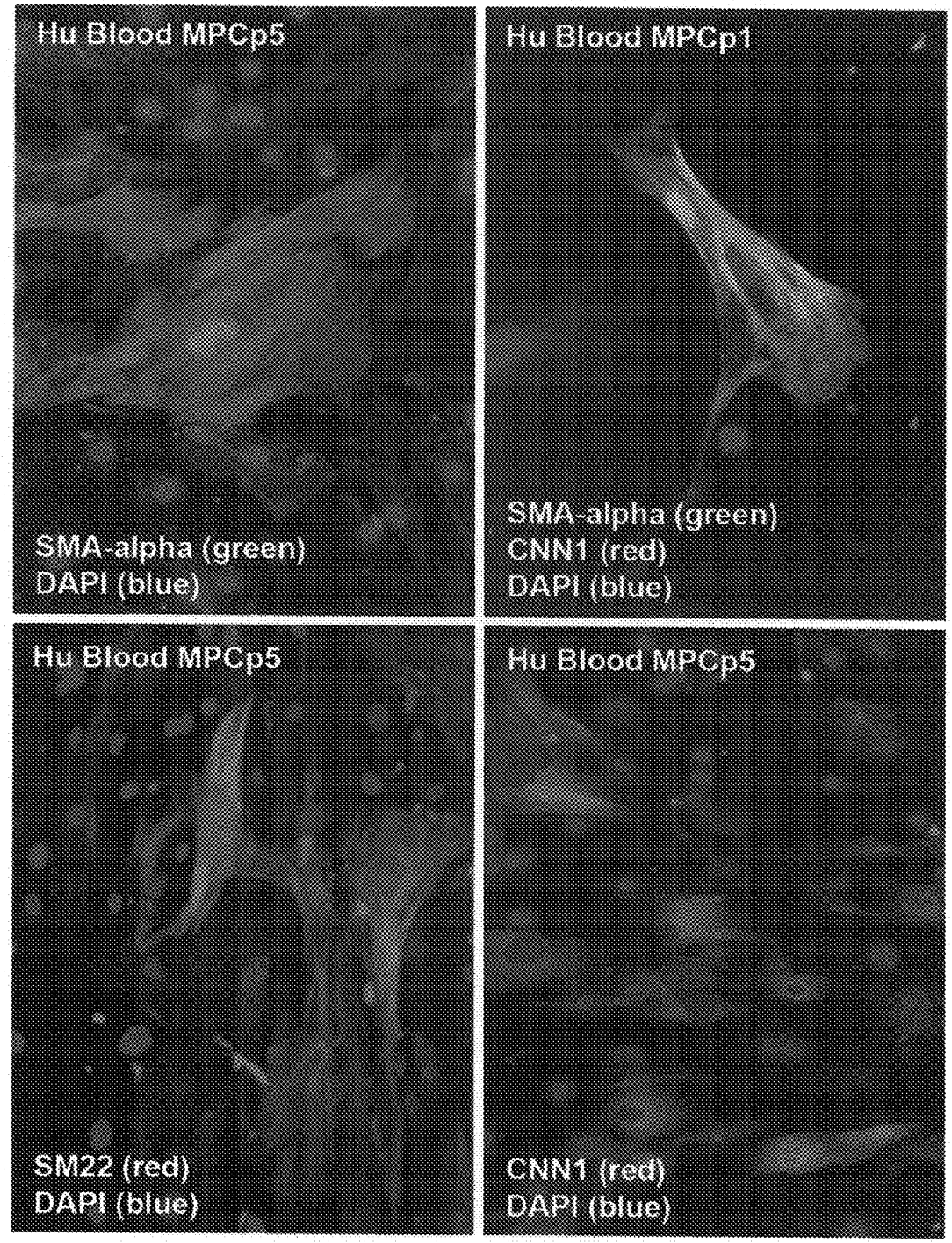
FIG. 20 shows immunostaining of smooth muscle cells isolated from human peripheral blood.

FIG. 20 shows immunostaining of smooth muscle cells isolated from human peripheral blood (passage 5). Probes for smooth muscle alpha actin, SM22, and calponin were used. Dual staining for smooth muscle alpha actin and calponin (top right panel) reveals co-expression of these two proteins within the same cells. This simultaneous expression of more than one smooth muscle cell marker in a single cell further supports the notion that these smooth muscle cells.

Contractility. Since the peripheral blood derived smooth muscle cells express smooth muscle contractile proteins, we performed a three-dimensional gel contraction assay to assess their contractile function. SMC have been shown to spontaneously induce contraction of a collagen matrix when embedded in a three-dimensional gel (Travis et al. (2001) Circ Res 88:77-83). Adipose tissue-derived smooth muscle cells were also tested for contractility.

Figure 21A:
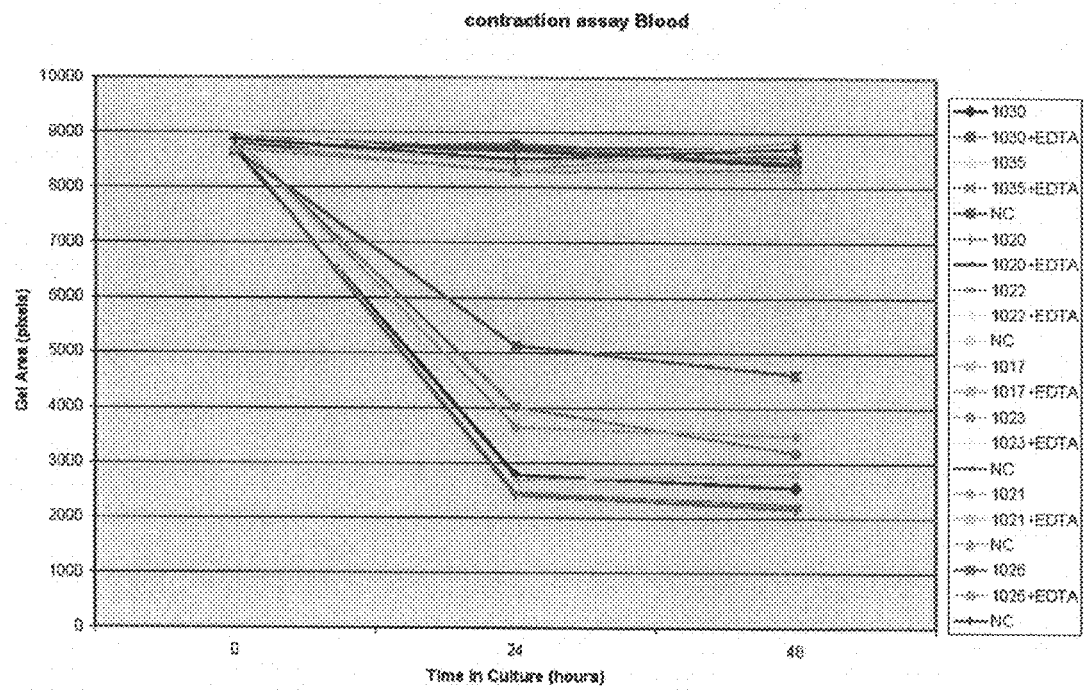
FIG. 21 shows the results of a contractility assay for porcine smooth muscle cells isolated from blood (A), adipose tissue (B), and bladder tissue (C).
Figure 21B:
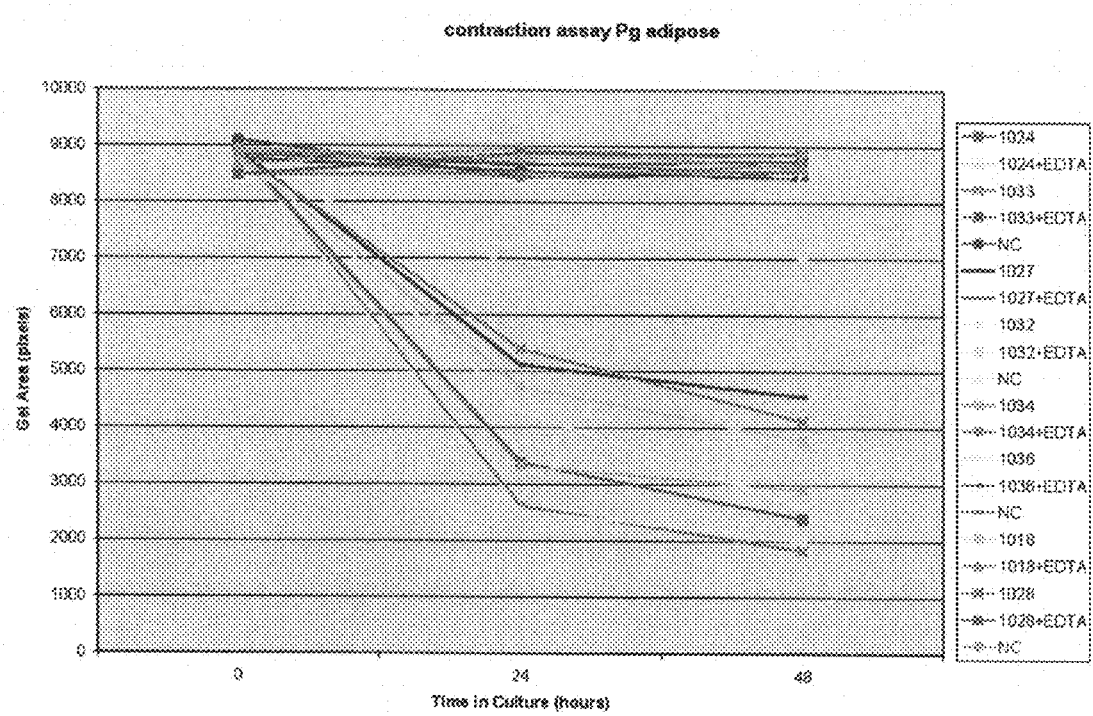
Figure 21C:
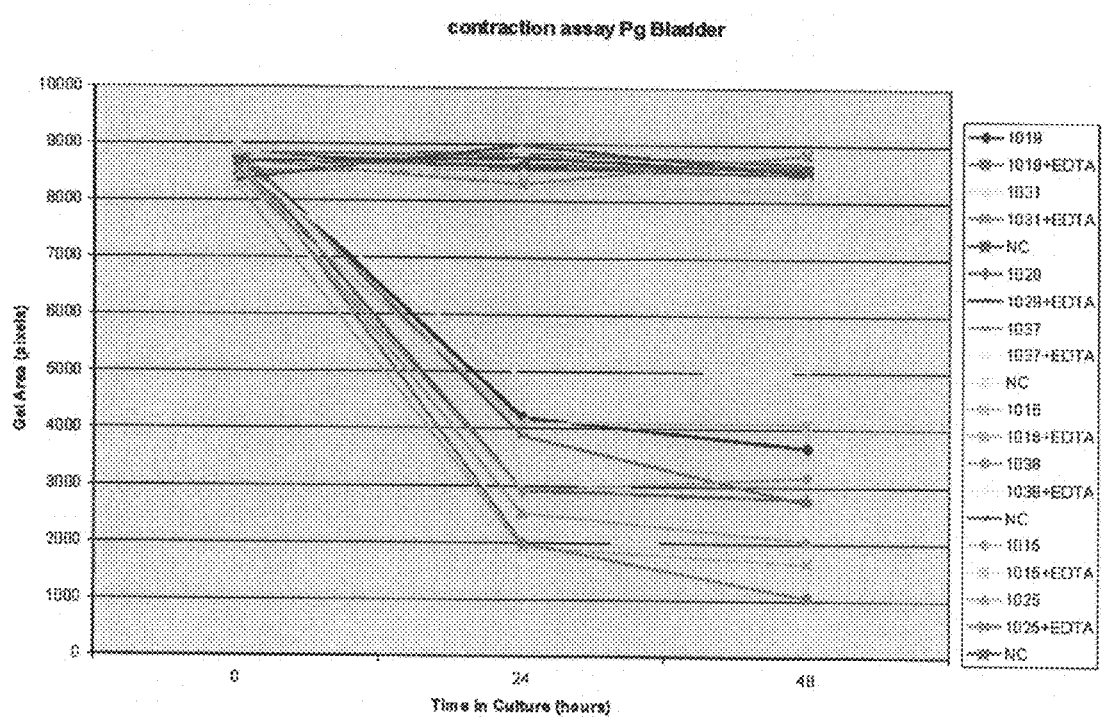

FIG. 21 shows that porcine blood-derived (A) and porcine adipose tissue-derived (B) cells contract to a degree comparable to that of bladder smooth muscle cells (C). The addition of EDTA to the mixture inhibits contraction, thus supporting the idea that the contraction is calcium dependent, another characteristic of smooth muscle cells. These data indicate that diameter reduction is dependent on contractile cells, and that the cells function in this capacity. The cells were seeded at 500,000 cells/ml and found to be capable of contraction as demonstrated by a reduction of collagen gel diameter after two days. Porcine bladder smooth muscle cells were used as a positive control. To demonstrate the calcium dependence of this contraction, the calcium chelator EDTA was added to separate samples to inhibit contraction. These results confirm the ability of the cells to contract in a calcium-dependent manner similarly to bladder-derived smooth muscle cells.

Figure 14:
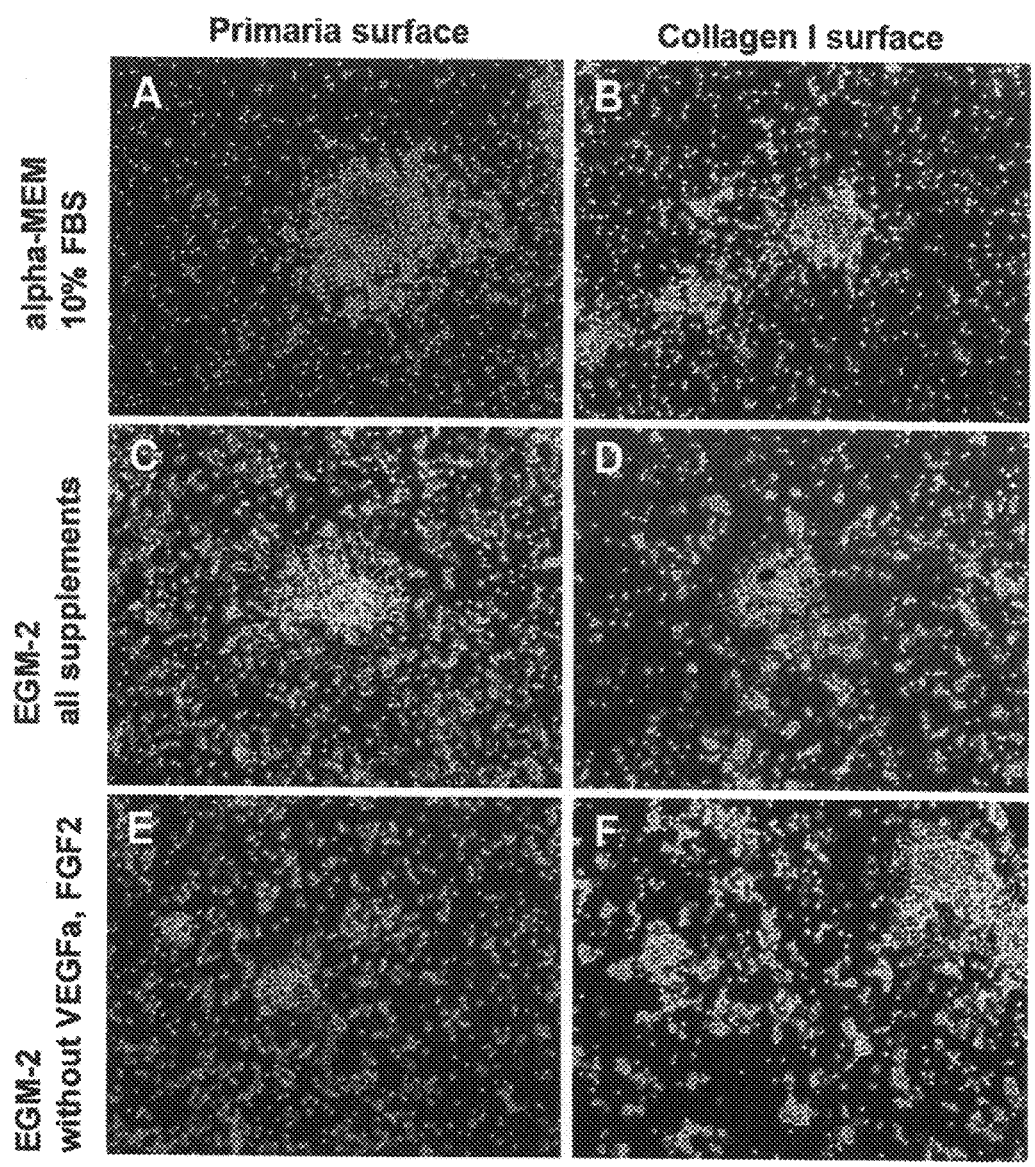
FIG. 14 shows cultures of the canine peripheral blood mononuclear fraction (buffy coat).

Growth kinetics. In order to utilize smooth muscle cells in cell therapy applications, it is important to determine if the required cell numbers can be achieved in an acceptable time frame. The results from canine and porcine studies indicate that smooth muscle colonies (from a 40 ml sample of peripheral blood) can be observed as early as 7 days post seeding, and can readily be passed within 14 days (FIGS. 14 and 15). In one study, 1.2 million cells were obtained after 18 days of culture (end of passage 2), at which time they were cryopreserved. These particular cells were thawed ~50 days later, and routinely passed when ~80% confluent to determine growth kinetics. Six days after thawing, the cell population expanded to 16.7 million cells (end of passage 3). After another 7 days of culture, the cell population reached 31.7 million cells (end of passage 4). This initial study indicates that 30 million cells can be achieved in roughly 30 days of culture.

Figure 22:
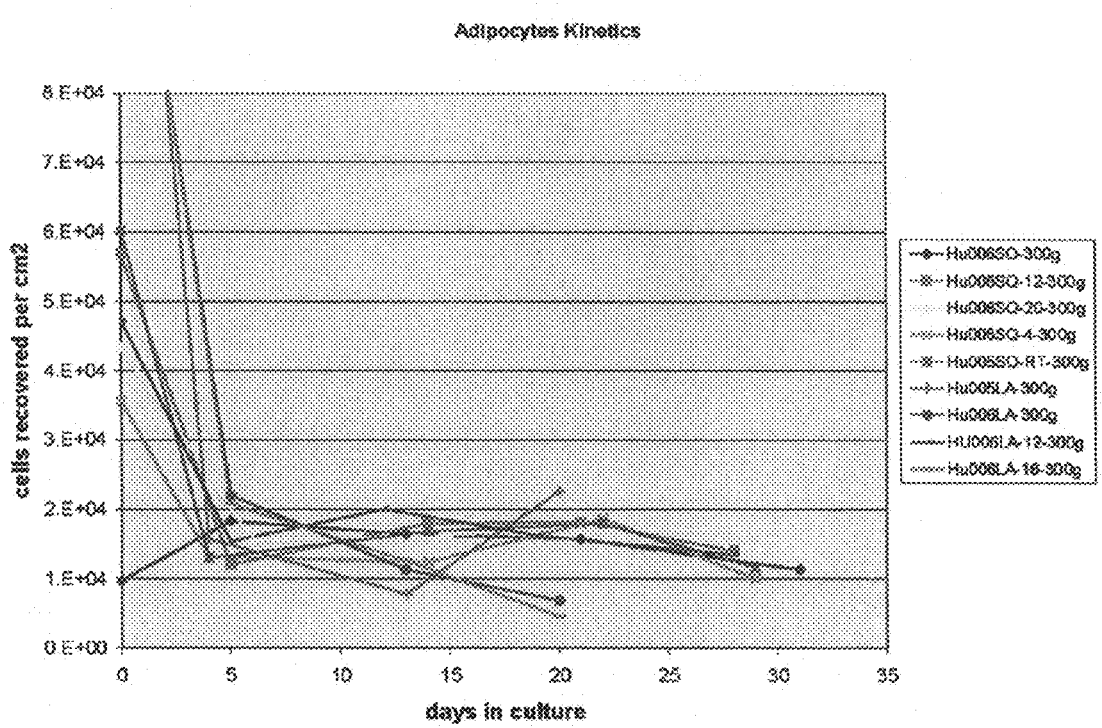
FIG. 22 shows the growth of smooth muscle cells isolated from human adipose tissue as a function of the numbers of cells recovered per unit area.

FIG. 22 concerns the limited proliferation potential of the cells. FIG. 22 shows the growth of smooth muscle cells isolated from human adipose tissue as a function of the numbers of cells recovered per unit area. These data indicate that between passages 4 and 5, the number of recovered cells begins to decline, supporting the contention that these cells have a limited and finite proliferative capacity, which is characteristic of progenitor cells, but not true stem cells.

Figure 23A:
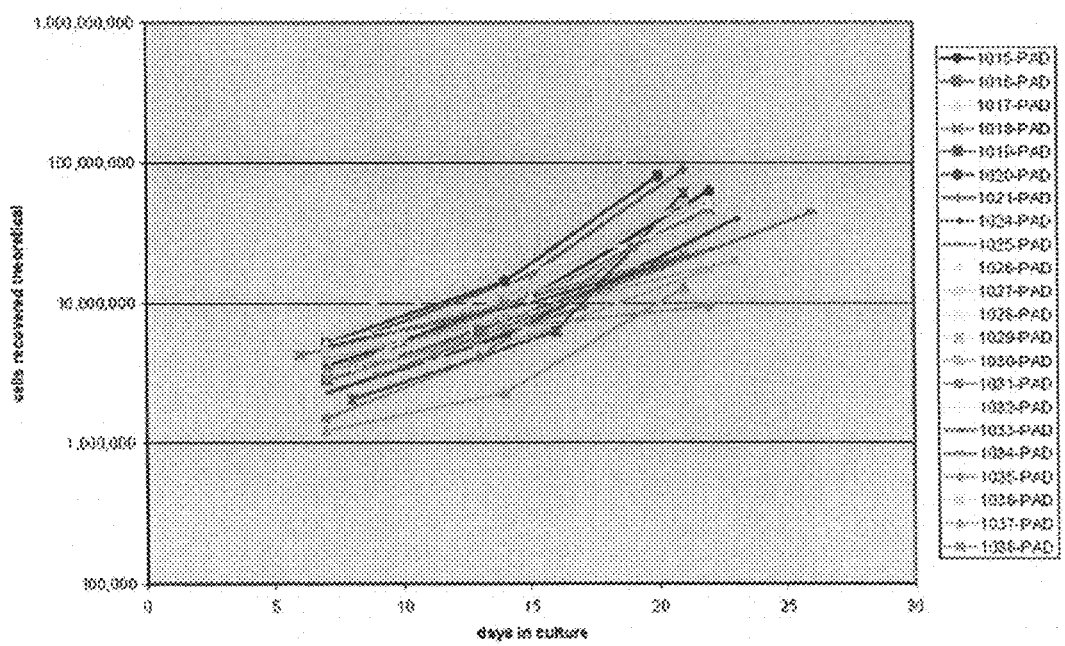
FIG. 23 shows the growth of smooth muscle cells isolated from porcine adipose (A), peripheral blood (B), and bladder smooth muscle (C) as a function of the number of recovered cells per passage.
Figure 23B:
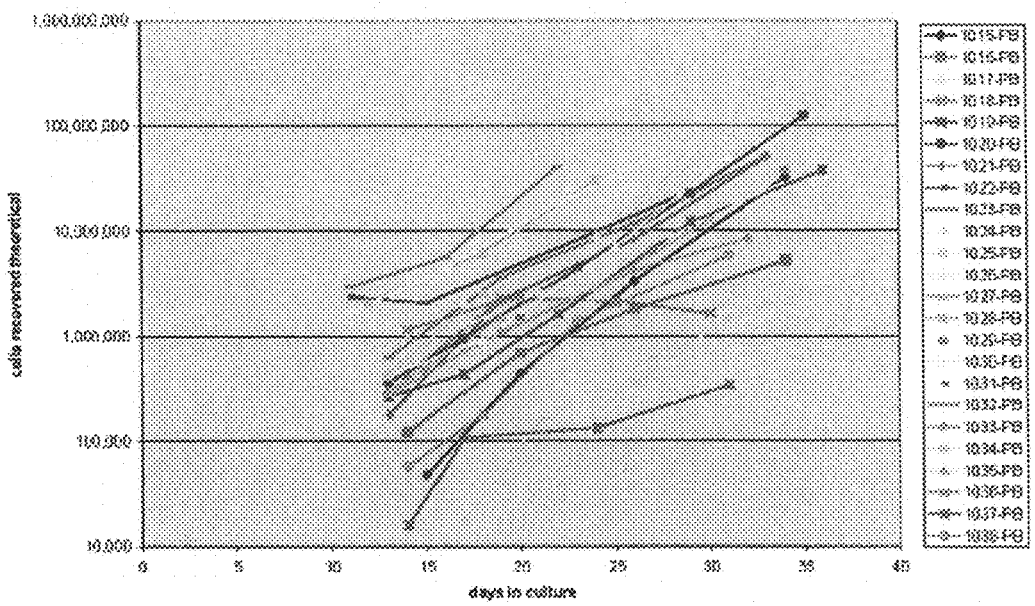
Figure 23C:
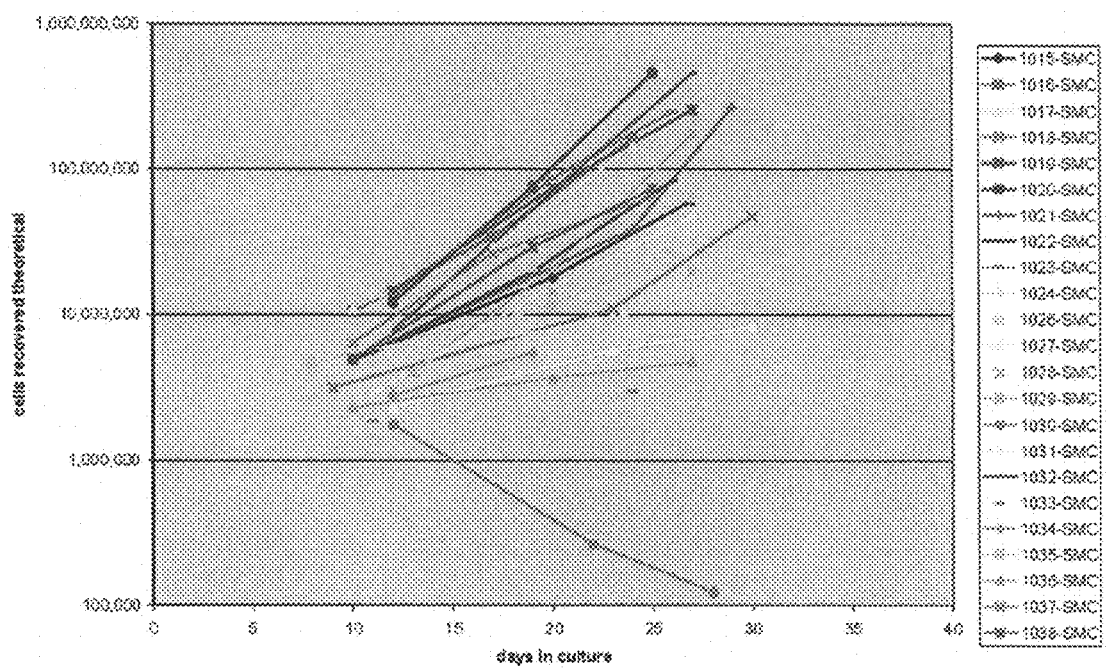

FIG. 23 shows the growth of smooth muscle cells isolated from porcine adipose, peripheral blood, and bladder smooth muscle as a function of the number of recovered cells per passage. As illustrated, dramatic expansion in cell numbers is achieved between passages 2 and 3, over a time frame of 2-4 weeks, enabling recovery of tens of millions of cells. This demonstrates the limited or finite proliferation potential of the adipose-derived cells.

Contact inhibition of proliferation. The smooth muscle cells isolated from peripheral blood and adipose tissue exhibit contact inhibition of proliferation. For example, the morphological assessment of these cells provided in FIGS. 14-17 demonstrates the presence of contact inhibition of proliferation over several passages. The cells do not continue proliferating upon contact with each other. In contrast, MSCs do not exhibit contact inhibition of proliferation and they can be observed piling on top of each other, similar to foci formation in transformed cell cultures. For example, Zhou et al. report on the isolation and culturing of MSCs from the mononuclear cell fraction of mouse bone marrow, and observe that after three passages the cultured MSCs demonstrated a loss of contact inhibition (see page 10850 and FIG. 1A) (Cancer Res. 2006; 66(22):10849-10854).

Cytokine MCP-1 production. MCP-1 is a normal product of bladder detrusor cells. In aortic smooth muscle cells, MCP-1 plays a role in regeneration. MCP-1 is best known for its ability to recruit mononuclear cells. It is however more than a chemokine; it is also a potent mitogen for vascular smooth muscle cell proliferation and recruits circulating monocytes to the area of vessel injury. Monocytes are typically transformed to macrophages which can serve as reservoirs for cytokines and growth factors. Macrophages and muscle precursor cells are both targets for MCP-1 signaling. This cytokine has been implicated in stem and progenitor cell recruiting within the body, potentially contributing to the regenerative process.

In order to quantitate MCP-1 produced by human peripheral blood smooth muscle cells, an ELISA based assay system from R&D Systems was employed. Medium samples were assayed in duplicate and compared to a standard curve to provide estimated MCP-1 levels and reported as ug/24 hr/one million cells. Expression of the cytokine MCP-1 for cells isolated from human bladder smooth muscle, adipose, peripheral blood, and bladder urothelium (negative control) was determined.

Figure 24:
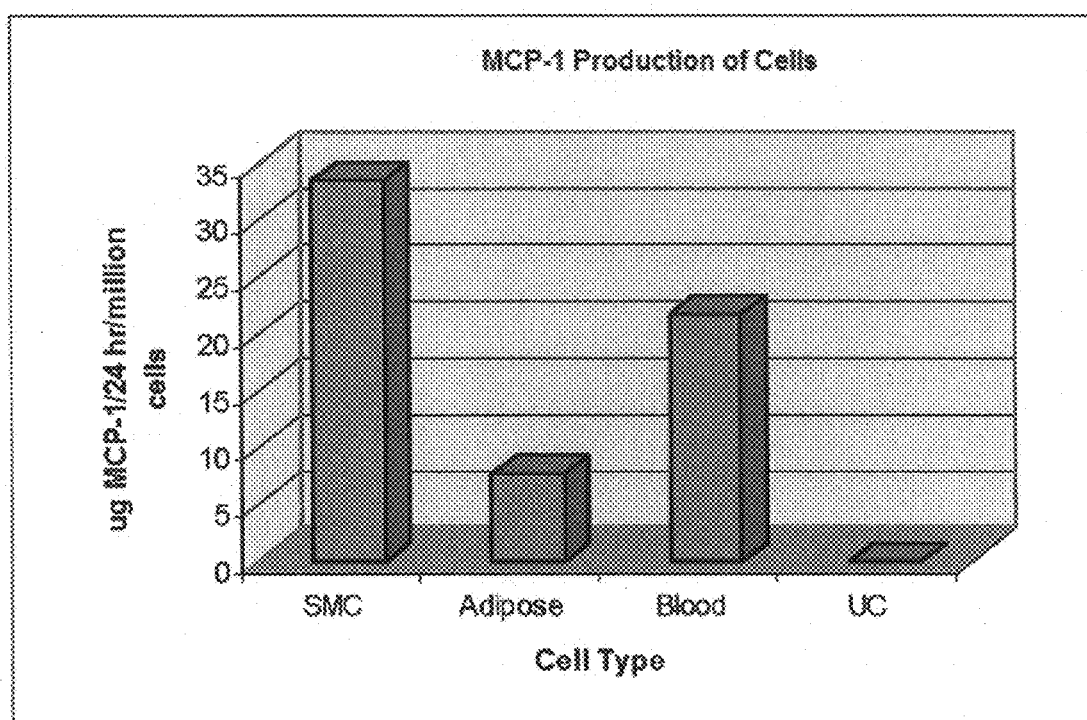
FIG. 24 shows expression of the cytokine MCP-1 for cells isolated from human bladder smooth muscle, adipose, peripheral blood, and bladder urothelium.

FIG. 24 shows the results from this analysis indicates that human peripheral blood-derived and human adipose tissue-derived smooth muscle cells produce MCP-1 at levels comparable to that of human bladder smooth muscle cells. These data support the conclusion that, just like bladder SMC, MCP-1 is expressed by the smooth muscle cells isolated from adipose and peripheral blood. In addition, these data lead us to hypothesize that the production of MCP-1 may play a critical role in regeneration by directly or indirectly causing muscle progenitor cells to be recruited/migrate or to proliferate within the construct.

Discussion. Isolated smooth muscle cells from adipose demonstrate several smooth muscle cell characteristics. Our studies have indicated that the cells can readily be isolated from adipose using standard enzymatic digestion and low-speed centrifugation protocols. Cells can be expanded very rapidly, perhaps reaching ~30 million cells within a month's time. Our studies have further demonstrated that these cells may, in fact, represent a smooth muscle cell population rather than a true stem cell population, as smooth muscle markers are present as early as passage 3. Expression of SMC marker mRNA can be observed as early as P0, as demonstrated by RTPCR. Furthermore, the smooth muscle cells isolated from are capable of contractile function as demonstrated by standard collagen gel contraction assays.

Characterization of smooth muscle cells. We have already shown that during subsequent passages, the smooth muscle cell cellular morphology is retained. There is also good correlation of smooth muscle markers at both the gene and protein levels.

Cytokine induction. Expression of MCP-1 by adipose smooth muscle cells has lead us to hypothesize that the production of MCP-1 may play a critical role in neo-organ or tissue structure regeneration by directly or indirectly causing native mesenchymal stem cells to be recruited/migrate or to proliferate within the construct.

Example 2

MCP-1 Production and Cell Density

Conditioned medium from cultures of bladder smooth muscle cells were analyzed using commercially available kits for the detection and quantitation of MCP-1. Conditioned media samples from 9 constructs (3 from each of 3 seeding levels) and the paired SMC cells used for seeding the constructs were tested for MCP-1 levels. The results are shown in Table 2.1.

TABLE 2.1

| Test ID | Sample ID | cIL2 pg/ml | cIL6 pg/ml | cIL10 pg/ml | cMCP-1 pg/ml | cIFNg pg/ml | cTNFa pg/ml | cTGFb pg/ml |
|---|---|---|---|---|---|---|---|---|
| 1 | TT1 | <1.0 | <9.8 | 1.0 | <3.7 | <2.4 | <0.2 | |
| 2 | TT2 | <1.0 | 8.8 | <2.0 | 39.6 | <2.4 | <0.2 | |

Figure 25:
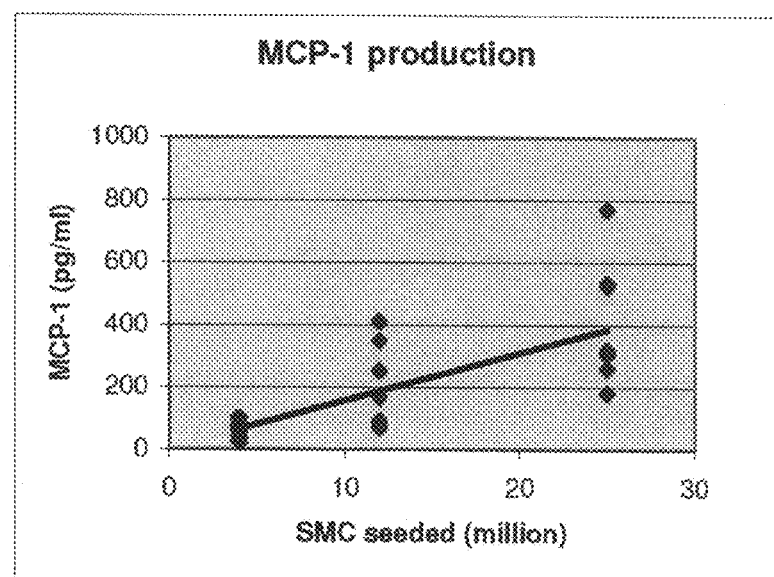
FIG. 25 shows the correlation between MCP-1 production and the density of cells seeded.

In order to quantitate MCP-1 present in the construct medium, an ELISA based assay system specific for Canine MCP-1 from R&D Systems was employed. Samples were assayed in duplicate and compared to a standard curve to provide estimated MCP-1 levels in construct medium. As shown in FIG. 25, the results from this analysis show a positive correlation between MCP-1 production and the density of cells seeded. Table 2.2 shows MCP-1 quantitation of construct medium as determined by R&D Systems ELISA.

TABLE 2.2

| Group | Construct | MCP-1 pg/ml | Group Average | Std Dev |
|---|---|---|---|---|
| 4 million | 1151 | 71 | 65 | 24 |
| | 1152 | 102 | | |
| | 1153 | 59 | | |
| | 1154 | 80 | | |
| | 1155 | 74 | | |
| | 1156 | 24 | | |
| | 1157 | 70 | | |
| | 1158 | 39 | | |
| 12 million | 1159 | 253 | 188 | 135 |
| | 1160 | 85 | | |
| | 1161 | 412 | | |
| | 1162 | 167 | | |
| | 1163 | 69 | | |
| | 1164 | 349 | | |
| | 1165 | 91 | | |
| | 1166 | 78 | | |
| 25 million | 1167 | 183 | 385 | 207 |
| | 1168 | 307 | | |
| | 1169 | 181 | | |
| | 1170 | 527 | | |
| | 1171 | 771 | | |
| | 1172 | 534 | | |
| | 1173 | 260 | | |
| | 1174 | 321 | | |

Table 2.3 shows a comparison of the average MCP-1 levels from each group in which it can been seen that the resulting ratios parallel the differences in seeding densities.

TABLE 2.3

| | Average | 4 million | | 12 million | | 25 million | |
|---|---|---|---|---|---|---|---|
| Group | MCP-1 | MCP-1 | # | MCP-1 | # | MCP-1 | Cell # |
| 4 million | 65 | | | 0.35 | 0.33 | 0.17 | 0.16 |
| 12 million | 188 | 2.89 | 3.00 | | | 0.49 | 0.48 |
| 25 million | 385 | 5.92 | 6.25 | 2.05 | 2.08 | | |

Results indicated that there was a positive correlation between cell number and MCP-1 levels detected in the media. It had been previously noted that some tissue from a regenerated canine bladder (approximately 9 million cells seeded) processed for SMC explanation contained more fat than is typically observed in native and regenerated canine tissue. The tissue when explanted was very soft and the explants when viewed contained fatty tissue in greater proportion to that observed with native tissue. The media on these explant plates also exhibited a "sheen" on the surface typically observed when fatty tissue is present. These observations suggest a role for MCP-1/CCR-2 interaction in fat deposition/adipogenesis of regenerated bladder tissue.

Example 3

Implantation of Neo-urinary Conduit Constructs in Swine

The objective of this study was to investigate the surgical implantation of the neo-urinary conduit and evaluation of the post surgical care, as well as to assess the regeneration of urinary-like tissue following implantation of the Neo-Urinary Conduit (NUC) test articles and the ability of swine peritoneum to provide a vascular supply and water-tightness to the implant.

Neo-Urinary Conduit (NUC) construct test articles were comprised of a scaffold formed from nonwoven polygycolic acid (PGA) felts and poly(lactic-co-glycolic acid) polymers (PLGA) with or without autologous smooth muscle cells (SMC). Cells previously removed from an animal were used to produce the construct that was implanted in the same animal. A construct refers to the sterile tube-shaped biomaterial comprised of a scaffold formed from nonwoven polygycolic acid (PGA) felts and poly(lactic-co-glycolic acid) polymers (PLGA) combined with autologous SMC. The term scaffold-only refers to the sterile tube-shaped biomaterial comprised of a scaffold formed from nonwoven polygycolic acid (PGA) felts and poly(lactic-co-glycolic acid) polymers (PLGA) without cells.

In this study, the constructs used correspond to test articles comprised of scaffold and SMC and scaffold only refers to a test article comprised of scaffold without SMC. Seven female Gottingen minipigs were divided into three groups: N=1 in Group 1 (scaffold-only), N=3 in Group 2 (scaffold seeded with blood derived SMC) and N=3 in Group 3 (scaffold seeded with adipose derived SMC) for implantation with the test articles.

Swine were considered a suitable animal model for evaluation of the Neo-Urinary Conduit given the similarities between swine and human abdominal and upper urinary tract anatomy, surgical manipulation strategies, stoma placement and healing, postsurgical care, and peritoneal anatomy. Swine is also a well established animal model of wound healing in skin, closely approximating the normal process of healing in humans, allowing evaluation of stoma healing. Gottingen minipigs were chosen as the breed based on their slow average growth rate during the 3-month study duration. Autologous SMCs were obtained from adipose tissue biopsies and venous blood samples from all animals approximately 10-11 weeks prior to test article implantation. Specified test articles were surgically implanted on Day 0 in each group. After surgical removal of the bladder (total cystectomy) the ureters were stented and mobilized for anastomosis to the inflow (cranial) end of the test article. Parietal peritoneum was separated from the abdominal wall starting from the linea alba at midline and bilaterally towards the right and left side of the abdominal wall. The peritoneum was transected on the left side and used to wrap the implants towards the right of midline portion which provided the vascular source and a water-tight urine channel, and formed a tubular connection (atrium) between the caudal end of the implant (located in the intra-abdominal cavity) and the skin. The implant's caudal end terminated within the peritoneal atrium approximately 5 to 7 cm away from the skin stoma. The atrium was extended using the cranial peritoneal wrap which traversed the abdominal wall and exited the skin near the xiphoid (off midline, right side). The externalized peritoneum was sutured to the skin to form a peritoneum-cutaneous junction and peritoneal-lined stoma lumen.

The suture strands that were connected to the ureteral stents were exteriorized through the stoma for future removal. The abdominal incision was closed with non-absorbable Prolene suture. The skin was closed in a routine fashion. A Foley catheter was inserted into the stoma to allow urine passage during stoma healing. The same surgical procedure was used for all animals Following removal of the Foley catheter, all animals were fitted with TRACOE® stoma ports to facilitate urine drainage. The animals were able to dislodge the stoma port, so an 8Fr Foley catheter was used to aid urine drainage. Detritus buildup in the atrium and stoma led to the use of a larger diameter modified extension set (study specific) to manage the stoma.

Stoma maintenance and replacement was scheduled weekly and was done on as needed basis. Blood samples were collected, analyzed and the results recorded at baseline, weekly during weeks 1 through 4 post-implantation, week 8, and necropsy for hematology and serum chemistry. Urine samples were collected, analyzed and the results recorded at baseline and necropsy for urinalysis. Imaging (fluoroscopy, ultrasonography, and/or endoscopy) of the constructs, ureters, and kidneys was performed at weeks 2, 4, 8 and necropsy during the study. Imaging was also performed as needed in response to adverse clinical signs (e.g. observed lack of urine flow or suspected fistula formation). A fistula refers to an abnormal duct or passage that connects an abscess, cavity or hollow organ to the body surface or to another hollow organ (for example, between intestines or between the intestines and conduit).

At necropsy, the abdominal cavity was opened, the conduit visualized and photographed before the conduit was removed en bloc with stoma, kidneys and ureters. Representative tissue samples of the entire urinary tract from kidneys to skin stoma, regional lymph nodes, and any other lesions observed grossly were obtained. All tissue samples were placed in 10% Neutral Buffered Formalin (NBF) for histological processing and evaluation. Post fixation, tissues were processed routinely to microslides and stained with hematoxylin and eosin (H&E) and Masson's trichrome. Slides were evaluated microscopically.

Results: Implantation (Surgical Methodology): All animals were recovered from implantation surgery uneventfully and the stoma was visualized to be draining urine. The animal model was considered appropriate for evaluating the surgical procedures for implanting the NUC (Neo-Urinary Conduit).

Morbidity and Mortality: Animals survived 28-83 days. One of 7 animals survived until scheduled sacrifice (Animal 4 of Group 2, 83 days). Six of 7 animals were sacrificed unscheduled: animal 5 of Group 3 was electively euthanized 28 days post-implantation for histopathological analysis and 5 animals were euthanized for poor clinical condition between 38 and 63 days post-implantation. (animal 1 of Group 1, animals 2 and 3 of Group 2, and animals 6 and 7 of Group 3). These unscheduled deaths occurred in all treatment groups and were attributed to viral infection and/or obstruction-related pathology with damage to the upper urinary tract.

Evidence of Porcine Circovirus Type-2 (PCV-2 evidence gathered during histopathology of harvested tissues) infection was observed in 3/7 animals. Two animals with PCV-2 infection were unscheduled death animals. These included animal 2 of Group 2 euthanized on day 38 and animal 7 of Group 3 euthanized on day 63. The third animal identified with PCV-2 infection (animal 4 of Group 2), survived to scheduled sacrifice (83 days). Obstruction of urine flow through the conduit and stoma contributed to the morbidity in 4/6 unscheduled deaths animals. These included animal 1 of Group 1 euthanized on day 47; animals 2 and 3 of Group 2, euthanized on days 38 and 40; and animal 6 of Group 3 euthanized on day 39.

Post-Surgical Care: Day 1-30 post-implantation: All animals required postoperative stoma management (e.g. flushing and cleaning of debris and replacement of catheter or stoma port when dislodged weekly and on as needed basis) regardless of treatment. Debris is formed during the healing and regenerative processes. Exfoliated tissue cells, inflammatory exudate and scaffold biodegradation are sources of debris. Without proper outflow (e.g., with obstruction), the stagnated debris forms a detritus: a semisolid bolus within the lumen of the conduit.

Loss of appetite and lethargy were observed in all animals. These post-operative procedures and clinical signs were not considered uncommon following abdominal surgery in swine. Based on the first 30-days post-implantation, none of the post-operative manipulations or findings were considered sufficiently considerable at the time of evaluation to change the established surgical procedures or post-surgical care.

Day 31 post-implantation to necropsy: All animals demonstrated partial or complete obstruction of the urine outflow. Obstruction of urine flow was observed with or without debris accumulation. Ventral abdomen positioning of surgically implanted test article contributed to physical obstruction of urine flow in the quadruped animal model where the weight of the overlying abdominal organs contributed to conduit closure, adhesion and fistula formation, and secondary upper urinary tract renal complications (e.g., dilation, inflammation, and/or infection of ureters or kidney). Adhesion refers to the union of two tissue surfaces. Intra-abdominal and/or pelvic adhesions are common post-surgical complications. At necropsy, adhesions to conduit or ureters were observed grossly and radiographically, and efforts for microscopic correlates were attempted.

In addition, the urine flow obstruction was exacerbated by the use of peritoneum to form the atrium, causing partial or full urinary obstruction with subsequent detritus build-up and bacterial infection. The atrium refers to the anterior connecting chamber that allowed for urine passage through the abdominal wall. This segment was made by the most anterior tube-like portion of the peritoneal wrap connecting the caudal end of the test article (located in the intra-abdominal cavity approximately 5 to 7 cm away from the skin) to the skin.

Surgical placement of the test article was the same in all study animals; therefore, obstruction-related complications had a similar pathobiological mechanism in all groups (i.e. abdominal content pressure and a peritoneal atrium contributing to detritus build up).

Regeneration: Regeneration of urinary-like tissue was evident as early as day 28, with presence of urothelium, lamina propria and smooth muscle bundles at the ureter-conduit junction (UCJ) in an electively euthanized animal 5 of Group 3(adipose-derived SMC). The regenerative process at the ureteral end of the implant resulted in urinary-like tissue formation that was comparable among animals receiving a construct implant (Groups 2 and 3). The extent of urinary-like tissue regeneration in the construct groups (Groups 2 and 3) was influenced by duration of animal survival post-implantation. The one animal surviving to scheduled sacrifice (animal 4 of Group 2 at day 83) had urothelium and smooth muscle present in the UCJ, cranial and mid portions of the conduit in spite of a detected viral infection. However, the peritoneum-only atrium was insufficient to support urinary-like tissue regeneration and the tissue formed in the atrium had a wall comprised of fibrous connective tissue without urothelial mucosal lining. The point of transition from conduit to atrium varied between animals because the caudal end of the implant floated freely within the peritoneal wrapping making the transition from conduit to atrium difficult to define at necropsy. The typical composition of the (presumed) caudal conduit was organized collagen with associated fibroblasts and/or myofibroblasts. Peritoneum atrium appears to be insufficient for urinary-like tissue regeneration, but the peritoneum does serve as a source of vascularization to NUC implants.

Conclusions: The swine animal model proved appropriate for evaluating the surgical application of the Neo-Urinary Conduit in this pilot study because all animals recovered from surgery and urinary diversion was achieved. In addition, the swine model was appropriate for evaluating post-operative care of urinary flow obstruction and its impact to the upper urinary tract. Finally, the swine model was appropriate for evaluating the ability of the test articles to regenerate urinary-like tissue in an environment complicated by detritus accumulation and bacterial colonization, viral infection, and enteric adhesions and fistulas. The surgical methodology was determined to be successful although anatomical placement of the urinary diversion on the ventral abdominal floor of a quadrupedal animal resulted in partial obstruction of urine outflow. The animal model was considered appropriate for evaluating the surgical application, postsurgical care and functionality of the Neo-Urinary Conduit.

Post-surgical findings during the first 30 days following implant surgery revealed findings that were not considered uncommon following urinary diversion surgery in the pig.

Although several confounding factors occurred during the study (i.e. surgical placement on the ventral abdominal floor, use of peritoneal atrium and viral infection), regeneration of urinary-like tissue was evident as early as day 28, with presence of urothelium, lamina propria and smooth muscle bundles at the ureterconduit junction in an electively euthanized animal (animal 5 of Group 3, adipose derived SMC).

The extent of urinary-like tissue regeneration in the construct groups (Groups 2 and 3) was influenced by duration of animal survival post-implantation. The one animal surviving to scheduled sacrifice (animal 4 of Group 2 at Day 83) had urothelium and smooth muscle present in the UCJ, cranial and mid portions of the conduit in spite of a detected viral infection.

There were no apparent differences observed in the regenerative process when scaffolds were seeded with SMC derived from blood or adipose (Groups 2 and 3, respectively) suggesting equivalence between SMC sources in promoting regeneration.

The tissue formed from peritoneum in the atrium segment of the conduit had a wall comprised of fibrous connective tissue without urothelial lining.

Experimental Design

Overview: Seven female Gottingen minipigs were divided into three groups: N=1 in Group 1 (scaffold only), N=3 in Group 2 (blood-derived SMC), and N=3 in Group 3 (adipose-derived SMC) and implanted with the test articles. Autologous SMC were obtained from adipose tissue biopsies and venous blood samples from all animals approximately 10-11 weeks prior to test article implantation. Specified test articles were surgically implanted on Day 0 in each group. After surgical removal of the bladder (total cystectomy) the ureters were stented and mobilized for anastomosis to the inflow (cranial) end of the test article. Parietal peritoneum was separated from the abdominal wall starting from the linea alba at midline and bilaterally towards the right and left side of the abdominal wall. The peritoneum was transected on the left side and used to wrap the implants towards the right of midline which provided the vascular source and a watertight urine channel, and formed a tubular connection (atrium) between the caudal end of the implant (located in the intra-abdominal cavity) and the skin. The implant's caudal end terminated within the peritoneal atrium approximately 5 to 7 cm away from the skin stoma The atrium was extended using the cranial peritoneal wrap which traversed the abdominal wall and exited the skin near the xiphoid (off midline, right side). The externalized peritoneum was sutured to the skin to form a peritoneum-cutaneous junction and peritoneal-lined stoma lumen. The suture strands that were connected to the ureteral stents were exteriorized through the stoma for future removal. The abdominal incision was closed with non-absorbable Prolene suture. The skin was closed in a routine fashion. A Foley catheter was inserted into the stoma to allow urine passage during stoma healing. The same surgical procedure was used for all animals.

Following removal of the Foley catheter, all animals were fitted with TRACOE® stoma ports to facilitate urine drainage. The animals were able to dislodge the stoma port, so an 8Fr Foley catheter was used to aid urine drainage. Detritus buildup in the atrium and stoma led to the use of a larger diameter modified extension set (study specific) to manage the stoma. Stoma maintenance and port/catheter replacement was scheduled weekly and was done on as needed basis.

Blood samples were collected, analyzed and the results recorded at baseline, weekly during weeks 1 through 4 post-implantation, week 8, and necropsy for hematology and serum chemistry. Urine samples were collected, analyzed and the results recorded at baseline and necropsy for urinalysis. Imaging (fluoroscopy, ultrasonography, and/or endoscopy) of the constructs, ureters, and kidneys was performed at weeks 2, 4, 8 and necropsy during the study. Imaging was also performed as needed in response to adverse clinical signs (e.g. observed lack of urine flow or suspected fistula formation). At necropsy, the abdominal cavity was opened, the conduit visualized and photographed before the conduit was removed en bloc with stoma, kidneys and ureters. Representative tissue samples of the entire urinary tract from kidneys to skin stoma, regional lymph nodes, and any other lesions observed grossly were obtained. All tissue samples were placed in 10% Neutral Buffered Formalin (NBF) for 24-48 hours prior to shipping to Vet Path Services, Inc. for histological processing and evaluation. Post fixation, tissues were processed routinely to microslides and stained with hematoxylin and eosin (H&E) and Masson's trichrome. Slides were evaluated microscopically. The pathology report appears in the Example below.

The following table 3.1 provides a summary of the study design.

TABLE 3.1

| Group No. | Treatment | No. of Animals | Biopsy Procedure (~Day 70) | Surgical Procedure (Day 0) | Postoperative procedures | Estimated Necropsy Time Point |
|---|---|---|---|---|---|---|
| 1 | Scaffold only | 1 | | | | |
| 2 | Autologous Blood SMC | 3 | Removal of adipose biopsy, blood collection | Cystectomy followed by neo-urinary conduit implantation with transposition of ureters to inflow end. Whole test article wrapped in peritoneum, with a peritoneal transition from | Fluoroscopic and ultrasonic examination, general health assessment and clinical treatment as necessary, clinical pathology and urinalysis | 84 ± 5 days |

TABLE 3.1-continued

| Group No. | Treatment | No. of Animals | Biopsy Procedure (~Day 70) | Surgical Procedure (Day 0) | Postoperative procedures | Estimated Necropsy Time Point |
|---|---|---|---|---|---|---|
| | | | | end of test article through skin to create incontinent stoma. | | |
| 3 | Autologous adipose SMC | 3 | | | | |

Swine were considered as the optimal animal model for evaluation of the Neo-Urinary Conduit given the similarities between swine and human abdominal and upper urinary tract anatomy, surgical manipulation strategies, stoma placement and healing, and post-surgical care. Swine is a well-established animal model of wound healing in skin, closely approximating the normal process of healing in humans, allowing evaluation of stoma healing. The omentum was previously validated for providing a blood supply and a water tight surface for urinary tissue regeneration in dogs. In the current studies, the ability of peritoneum to provide a vascular supply and watertightness for the NUC was being evaluated and swine is the only large animal species with a parietal peritoneum similar to that of humans. Gottingen minipigs were chosen as the breed of swine based on a slow average growth rate during the 3-month study duration.

Materials and Methods

Test Devices—The test articles were i) a conduit shaped scaffold comprising a synthetic lactide/glycolide polymer seeded with autologous adipose-derived pig smooth muscle cells ($2.5 \times 10^7$ cells or $2.5 \times 10^7$ cells); ii) a conduit shaped scaffold comprising a synthetic lactide/glycolide polymer seeded with autologous blood-derived pig smooth muscle cells ($2.5 \times 10^7$ cells or $2.5 \times 10^7$ cells) and iii) a conduit shaped scaffold comprising a synthetic lactide/glycolide polymer without any cells seeded.

Animals. A total of 7 animals were implanted with the test articles. The animals were initially housed in individual cages. After test article implantation, the animals were transferred into a steel pen with two pigs in each pen. The animals were fed twice daily in the morning and in the evening. The animals were provided with fresh filtered tap water ad libitum via an automatic watering system. During quarantine and the study, the animals were housed in an area where environmental controls were set to maintain a temperature of 61 to 81° F. and a relative humidity of 30 to 70%. Periodically the humidity was slightly out of range. A 12-hour light/dark cycle was employed and the room underwent a minimum of ten fresh air changes/hour. One of the seven animals implanted with the test articles (Group 3) was electively euthanized for histopathological evaluation at the one month time point (Day 28). All other animals were euthanized during the course of the study. Animals were fasted for at least 12-24 hours prior to biopsy and implantation procedures. Water was not withheld.

Preoperative Procedures.

Anesthesia and Analgesia. For biopsy and definitive surgery, animals were sedated via intramuscular (IM) injection of a cocktail containing 20 mg/kg ketamine, 2 mg/kg xylazine, and 0.040-mg/kg atropine. Each animal was then intubated and received inhalant isoflurane at 2.5%-4% for induction and 0.5-2.5% for maintenance of anesthesia, delivered through either a volume-regulated respirator or rebreathing apparatus. Lactated Ringer's solution was administered at 10 ml/kg/hr for the duration of the surgical procedure. For technical procedures, animals were sedated with the same intramuscular cocktail injection as described above. Ten ml of 10-mg/ml Propofol was also used in some animals at the discretion of the attending veterinarian. For postoperative analgesia, Fentanyl patches (75 µg/hr) were applied to provide continuous pain relief. Alternatively, Rimadyl (50 mg) or Buprenex (0.05 mg/kg) were administered as needed.

Antibiotic Therapy. Broad-spectrum antibiotic therapy (approximately 5 mg/kg Naxcel) was administered to all animals at the biopsy and implantation surgeries. The treatment continued for up to 9 days and as needed post surgery.

Surgical Preparation. For both biopsy and implantation surgery, the hair over the entire abdominal region was clipped. The animal was then positioned in dorsal recumbency. The operative area was cleaned with three alternating scrubs of povidone-iodine solution and 70% alcohol; once the alternating scrubs are complete, a final application of povidone-iodine solution was applied and allowed to dry. The area(s) was then draped for aseptic surgery.

Surgical Procedures.

Biopsy/Tissue Collection. For all animals (Groups 1-3), biopsies of adipose tissue, as well as venous blood, were obtained 10-11 weeks prior to Day 0 (implantation procedure). For tissue biopsy procedures, a midline incision was made in the abdomen beginning immediately caudal to the umbilicus. Adipose biopsies of 21-34 grams of soft, pliable subcutaneous adipose tissue (without connective tissue) were collected aseptically from this midline access point. Collected tissue samples were individually and aseptically transferred to containers with tissue culture media (supplied by the Sponsor), then packaged in a bio-shipper (supplied by the Sponsor) and shipped overnight to the Sponsor for processing. The abdominal incision was closed in layers with absorbable suture material of an appropriate size. The skin was closed in a subcuticular fashion, again using an appropriate size of absorbable suture material. Approximately six 10-ml aliquots of venous blood were collected in heparinized vacutainers, packaged in an ice-pack cooled container (~8° C.) and shipped overnight to the Sponsor for processing.

Cannulation procedure. At 12-18 days prior to test article implantation, an indwelling catheter was placed within the jugular vein of each animal to facilitate blood collection. The area surrounding the right jugular vein was shaved and prepared as described above. All animals were cannulated with a sterile 5.5-mm ID silicon catheter, which was inserted into the right external jugular vein and secured by suture to prevent movement. An extra-large DaVINCI port was attached and implanted in a subcutaneous pocket.

Test Device Implantation. A midline abdominal incision was made 5 cm cranial to the umbilicus and extended approximately 15 cm caudally. The peritoneum was identified and then carefully separated from the abdominal wall starting from the linea alba at midline and bilaterally towards the right and left side of the abdominal wall. Care was taken to ensure the tissue remained intact and vascularized. The urinary bladder was then exposed and carefully emptied of urine, ensuring no urine entered into the abdominal cavity. The arteries and veins supplying the bladder were identified and ligated. The ureters were identified, stented (two 14-cm 7Fr DaVINCI non-absorbable ureter stents, inserted in ascending fashion) and carefully transected from the bladder. The urethra was over-sewn as it was transected. The bladder was then removed. The left ureter was carefully freed from the surrounding retroperitoneal fascia extending cranially until there was enough mobility to reach the right side of test article. The right ureter was dissected free to reach the other side of the test article. The ureters were sutured on to the test article with 3-0 Vicryl in a simple continuous pattern. The peritoneum was transected on the left side and used to wrap the implants towards the right of midline portion which provided the vascular source and a watertight urine channel, and formed a tubular connection (atrium) between the caudal end of the implant (located in the intra-abdominal cavity) and the skin. The implant's caudal end terminated in the peritoneal atrium approximately 5 to 7 cm away from the skin stoma. The peritoneum was sutured with 3-0 Vicryl. The atrium was extended using the cranial peritoneal wrap which traversed the abdominal wall and exited the skin near the xiphoid (off midline, right side). The externalized peritoneum was sutured to the skin to form a peritoneum-cutaneous junction and peritoneal-lined stoma lumen. Surgical adhesive was then placed along the suture line where the peritoneum exited the body wall. The suture strands that were connected to the ureteral stents were exteriorized through the stoma for future removal. The abdominal incision was closed with non-absorbable Prolene suture. The skin was closed in a routine fashion. A Foley catheter was inserted into the stoma to allow urine passage during stoma healing. The same surgical procedure was used for all animals.

Monitoring Procedures. Vital signs (oxygen rate, oxygen $[O_2]$ saturation, pulse rate, respiration, and body temperature) were monitored at intervals of approximately 20 minutes throughout the procedure.

Post Operative Procedures

Recovery. All animals were recovered after each surgical procedure within their own cages under normal environmental conditions.

Operative Drug Therapy. In addition to the antibiotic and analgesic therapies describes previously, Flomax was also used at the discretion of the facility veterinarian following surgeries and on as needed basis in order to maintain general good health during the survival period.

Stoma Maintenance. For two weeks post implantation or until the incision site was healed, the surgical area was evaluated for any signs of dehiscence, abnormal discharge, odor, irritation or any abnormalities. The stoma area and surrounding tissue was cleaned twice daily, and the stoma catheter was observed for urine drainage. When not dripping, the catheter was flushed with sterile saline to confirm patency. If the stoma became clogged, the flocculents and clogging materials were removed by forceps following the saline flush. If these efforts did not restore the free flow of urine, a new catheter was installed and secured in place with prolene sutures. A stoma port was also installed and secured with 2-0 prolene suture.

Stent Removal. At various time points from 2-4 weeks post-implantation surgery the animals were anesthetized as described above and the ureteral stents were removed.

Jugular Port. The jugular port catheter was flushed with injectable saline and locked with Heparin (100 U/mL, ~2-3 mL) weekly until Week 4 and at each subsequent use to assure patency.

Imaging.

Ultrasonography. Ultrasound imaging of the conduit and kidneys was performed at Weeks 2, 4, 8 and prior to necropsy Cystoscopy. Cystoscopy was performed at week 4 by inserting a bladder scope (flexible optical fiber with lens like a telescope or microscope) to view the inner surfaces of the conduit and to remove ureteral stents as discussed above Animals were anesthetized for this procedure.

Observations and Health Assessments. From the time of receipt until euthanasia, the animals were observed twice daily for abnormalities of appearance and behavior that might indicate adverse effects on health. At each check (performed approximately 8 hours apart), it was confirmed whether all the animals had eaten and whether there was evidence of urine and fecal output in each pen. Physical signs such as lethargy, emaciation, abnormal vocalization, missing anatomy, and laceration, as well as abnormal behavioral signs, were noted, if present. Animals were not removed from their pen during these daily assessments. Any abnormal signs were documented.

Body weights. Body weights were recorded at baseline, weekly and prior to necropsy.

Clinical Pathology.

Blood Collection. Blood samples for analysis of hematology (CBC), coagulation, and serum chemistry parameters and were collected at scheduled time points (baseline, Week 1, 2, 3, 4, and 8, and prior to necropsy) via the indwelling port in the jugular vein.

Hematology. Hematology samples were collected in 2.0 ml EDTA tubes and stored refrigerated on or wet ice (2-8° C.) prior to shipment (on wet ice) to Idexx. Shipment was timed to facilitate analysis within 24 hours of collection, as specified in the protocol. Samples were evaluated for the hematology parameters: Total leukocyte count (WBC); Erythrocyte count (RBC); Hemoglobin concentration (HGB); Hematocrit value (HCT) 1; Mean corpuscular volume (MCV); Mean corpuscular hemoglobin (MCH) 1; Mean corpuscular hemoglobin concentration (MCHC) 1; Platelet count (PLT); Relative reticulocyte count (RTC), wherein 1=Calculated values.

Coagulation. Coagulation samples were collected in 1.8-ml sodium citrate tubes (0.2 mL of 3.8% sodium citrate) and stored on wet ice until being centrifuged at 8,000 RPM for 10-15 minutes. The plasma was removed and divided between two labelled vials, then frozen at −70° C. One vial was packaged on dry ice and sent to Idexx for analysis, and the remaining vial was stored as a reserve until the conclusion of the study. Samples were evaluated for the following parameters: Prothrombin time (PT); Activated partial thromboplastin time (APTT); Fibrinogen (FIB).

Serum Chemistry. Blood samples for serum chemistry analysis were collected in approximately 4.0-ml serum separation tubes. The blood samples were centrifuged at 10,000 RPM for 10-15 minutes and the serum was extracted using sterile technique. Serum was divided between two labeled vials and frozen at −70° C. One vial was packaged on dry ice and sent to Idexx for analysis, and the remaining vial was stored as a reserve until the conclusion of the study. Samples were evaluated for the following serum chemistry parameters: Glucose (GLU); Urea nitrogen (BUN); Creatinine (CRE); Total protein (TPR); Albumin (ALB); Globulin (GLOB) 1; Albumin/Globulin ratio (A/G) 1; Calcium (CAL); Phosphorus (PHOS); Sodium (NA); Potassium (K); Chloride (CL); Total cholesterol (CHOL); Total bilirubin (TBIL); Triglycerides (TRG); Alanine aminotransferase (ALT); Aspartate aminotransferase (AST); Alkaline phosphatase (ALK); Gamma glutamyltransferase (GGT); where 1=Calculated values.

Blood Gases. Arterial blood gas samples were collected in a syringe (~1.0 mL), and the blood was placed into a CG8+ i-STAT cartridge for in-house analysis. Samples were evaluated for the following blood gas parameters: Sodium (Na) (mmol/L) PCO2 (mm Hg); Potassium (K) (mmol/L) PO2 (mm Hg); Ionized Calcium (iCa) (mmol/L) TCO2 (mmol/L); Glucose (Glu) (mg/dL) HCO3 (mmol/L); Hematocrit (Hct) (%) BEecf (mmol/L); pH; and SO2 (%).

Urine Collection. Urine samples were collected at baseline and pre-necropsy. Approximately 1.0 mL and 3.0 mL samples were collected in sterile containers for qualitative and quantitative analysis, respectively. The qualitative analyses were done at the time of collection using Multistix® 10 SG Test Strips. The samples for quantitative comprehensive urinalysis were refrigerated and shipped to IDEXX Laboratories (North Grafton, Mass.) within 24 hours of collection. Samples were evaluated for the following qualitative urinalysis parameters: Glucose; Bilirubin; Blood; pH; Protein; Ketones; Urobilinogen; Specific Gravity; Nitrites; and Leukocytes, and for the following quantitative urinalysis: Bacterial culture; Total bacteria; glucose; and total protein.

Anatomic Pathology

Moribund and Early Death Animals. Animals unlikely to survive until the next scheduled observation (i.e., moribund animals) were weighed, euthanized, and necropsied. Animals were subjected to a limited necropsy, aimed at determining a cause of declining health or death. Tissue collection from these specimens was limited to the urogenital system. Necropsy occurred on the day of death, unless otherwise noted. An attempt was made to collect terminal samples for clinical pathology from animals that were euthanized moribund.

Physical Examination. The animals were evaluated by the Test Facility veterinarian prior to euthanasia. The general condition of the animal was recorded.

Euthanasia. Animals were injected with sodium pentobarbital (150 mg/kg, IV) to cause euthanasia.

Necropsy. For the animal that was euthanized on schedule (84±5 days), the necropsy focused specifically on the kidneys, conduit, ureters, uretero-vesical junctions, mid-conduit, conduit-skin junction, and lymph nodes (lumbar and mesenteric).

Tissue Collection. At euthanasia and necropsy, all tissues surrounding the neo-conduit implant were examined grossly and photographed in situ. The kidneys, the neo-conduit with attached ureters, and lymph nodes were harvested. The kidneys were dissected and photographed. The neoconduit with attached ureters was evaluated and pressure perfused with 10% normal buffered saline (NBF). All collected tissues were stored in 10% normal buffered saline (NBF) solution for histological processing.

Histology and Histopathology. Urinary organs were trimmed, examined, embedded in paraffin, and sectioned. Specific details regarding the sample sectioning scheme are included in the Pathology Report (below). Slides were stained with hematoxylin and eosin (H & E) and Masson's Trichrome.

Results

Biopsy. Adipose tissue biopsies (21-34 grams) and venous blood (6×10 mL aliquots in heparinized tubes) were collected as outlined in the protocol. Individual weights of adipose biopsy samples are presented in Appendix 1 (EE=Elective Euthanasia; PCV-2=Porcine Circovirus-2; SMC=Smooth Muscle Cells; S=Survivor; UD=Unscheduled Death due to poor clinical condition; X=observed).

Implantation (Surgical Methodology). All animals were recovered from implantation surgery uneventfully and the stoma was visualized to be draining urine. The animal model was considered appropriate for evaluating the surgical application, post-surgical care and functionality of the Neo-Urinary Conduit.

Figure 26:
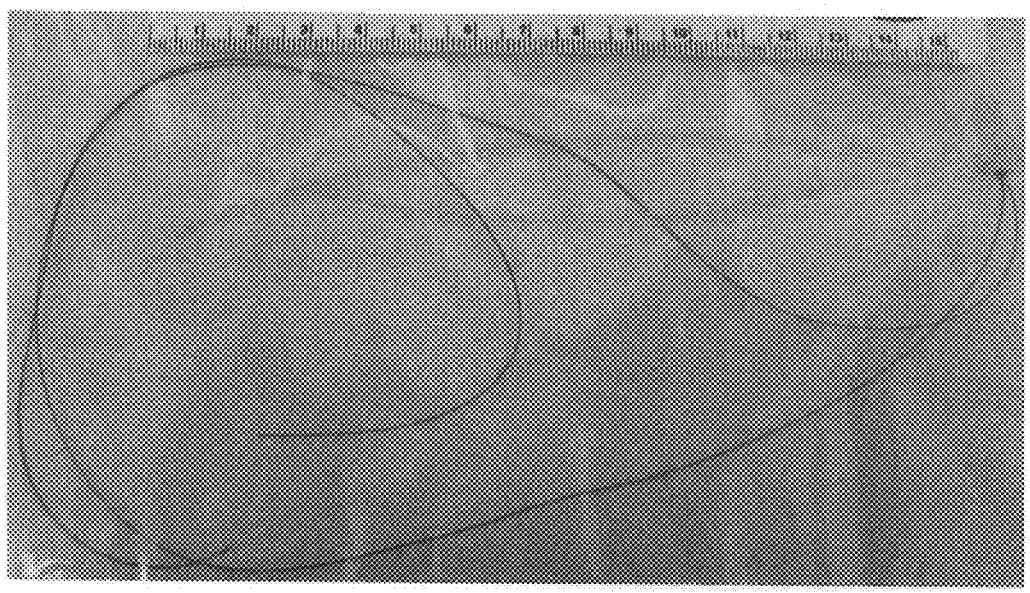
FIG. 26 shows ureteral stents.
Figure 28:
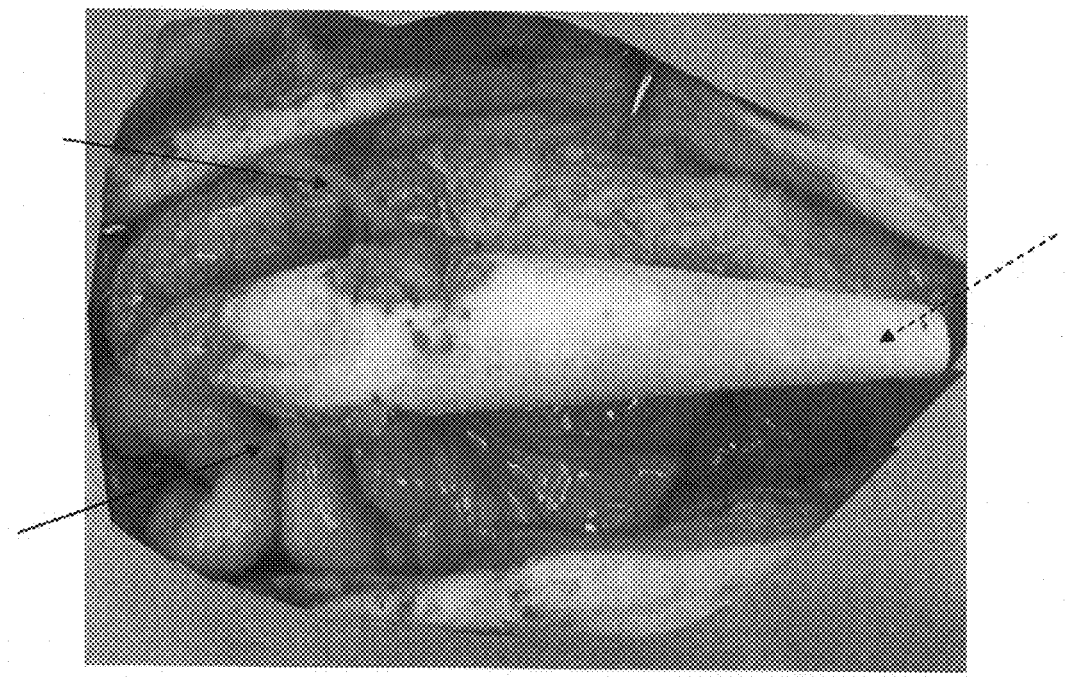
FIG. 28 shows a neo-conduit construct (dashed arrow) attached to ureters (solid arrows).
Figure 29:
FIG. 29 shows the inflow end of a construct attached to the ureters (solid arrows) and the outflow end directed towards the surgically created stoma (dashed arrow).
Figure 30:
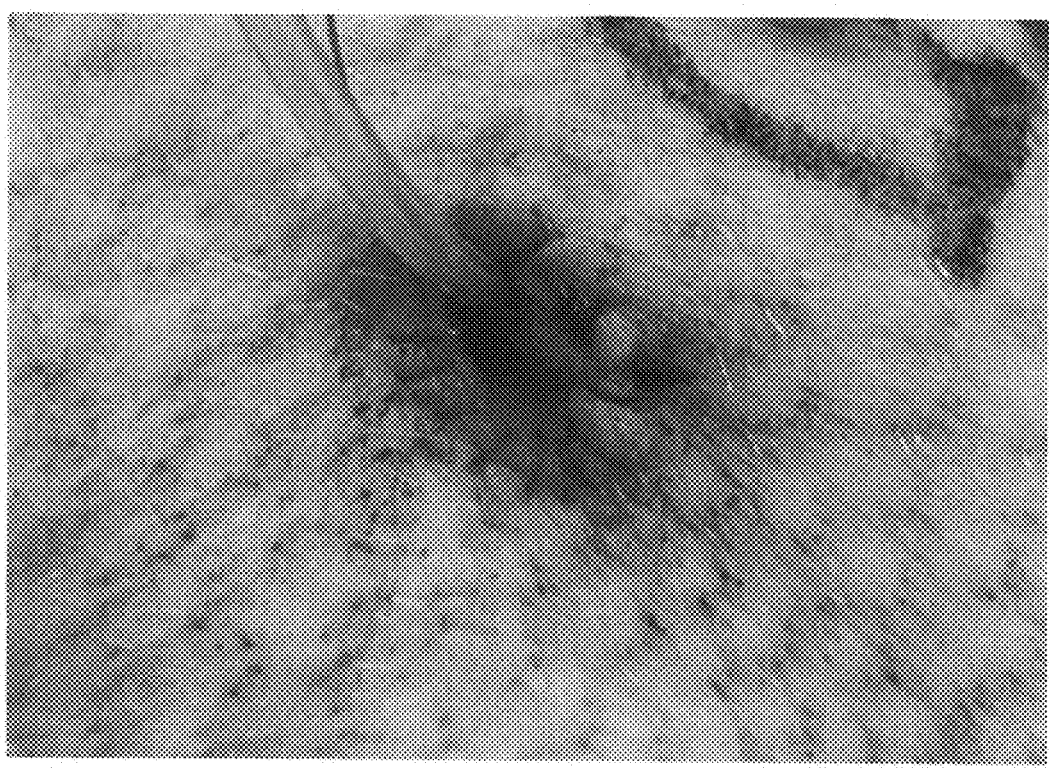
FIG. 30 shows the stoma and catheter for urine drainage.

FIG. 26 shows the ureteral stents used for the study. FIG. 27 shows the neo-conduit construct. FIG. 28 shows the neo-conduit construct attached to the ureters. FIG. 29 shows the inflow end of the construct attached to the ureters and the outflow end directed towards the surgically created stoma. FIG. 30 shows the stoma and catheter for urine drainage.

Mortality. One of 7 animals survived until scheduled sacrifice (animal 4 of Group 2, 83 days). Six of 7 animals were sacrificed unscheduled: animal 5 of Group 3 was electively euthanized 28 days post-implantation for histopathological analysis and 5 animals were euthanized for poor clinical condition between 38 and 63 days post-implantation. (animal 1 of Group 1, animals 2 and 3 of Group 2, and animals 6 and 7 of Group 3). These unscheduled deaths occurred in all treatment groups and were attributed to viral infection and/or obstruction-related pathology with damage to the upper urinary tract.

Final disposition and mortality findings for each of the 7 animals are shown in the table 3.2 below (EE=Elective Euthanasia; PCV-2=Porcine Circovirus-2; SMC=Smooth Muscle Cells; S=Survivor; UD=Unscheduled Death due to poor clinical condition; X=Observed)

TABLE 3.2

| Animal Number | Group | SMC Source | Cell Seeding Density (×10$^7$) | Adipose tissue collected (grams) | Blood collected (ml) | Implant Date (days after biopsy) | Stent Removal | Days on Study | Disposition | Mortality Findings PCV-2 | Obstruction |
|---|---|---|---|---|---|---|---|---|---|---|---|
| 1 | 1 | Scaffold Only | 0 | 24 | 60 | 74 | Week 2 (1) and week 4 (1) | 47 | UD | | X |
| 2 | 2 | Blood | 2.5 | 21 | 60 | 71 | Week 2 | 38 | UD | X | X |
| 3 | 2 | Blood | 2 | 30 | 60 | 72 | Necropsy | 40 | UD | | X |
| 4 | 2 | Blood | 2.5 | 25 | 60 | 71 | Week 2 | 83 | S | X | |
| 5 | 3 | Adipose | 2 | 34 | 60 | 73 | Week 3 | 28 | EE | | |
| 6 | 3 | Adipose | 2 | 22 | 60 | 73 | Week 2 (1) and week 3 (1) | 39 | UD | | X |
| 7 | 3 | Adipose | 2.5 | 21 | 60 | 72 | Week 4 | 63 | UD | X | |

Porcine Circovirus-2 (PCV-2) Infections. Three of 7 animals developed one or more lesions consistent with distinct pathological features ascribed to porcine dermatitis and nephropathy syndrome (PDNS), associated with PCV-2 infection. Animals were classified as PCV-2-infected if the following were observed: 1) Clinically-observed purple skin discoloration; 2) Microscopic vasculitis or vasculitis/perivasculitis affecting the kidney; 3) Kidney findings of tubular necrosis/fluid/casts/glomerulonephritis, or viral inclusions of tubular epithelial cells. By these criteria, porcine PCV-2 infection was confirmed in 3/7 animals. Two PCV-2 infected animals were unscheduled necropsy animals. These included animal 2 of Group 2 euthanized on day 38 and animal 7 of Group 3 euthanized on day 63. The third animal identified with PCV-2 infection (animal 4 of Group 2) survived to scheduled sacrifice (83 days).

Obstruction. Obstruction of urine flow through the conduit and stoma contributed to the morbidity in 4/6 unscheduled death animals. These included animal 1 of Group 1 euthanized on day 47; animals 2 and 3 of Group 2 euthanized on day 38 and day 40; and animal 6 of Group 3 euthanized on day 39. Obstruction appeared to have been facilitated by the placement of the test article in the ventral portion of the abdominal cavity of the quadruped where the weight of the overlying abdominal organs could lead to conduit closure, adhesion and fistula formation, and renal complications (e.g., dilation, inflammation, and/or infection of ureters or kidney). Obstruction was exacerbated by the use of peritoneum to form the atrium, causing partial or full urinary obstruction with subsequent detritus build-up and bacterial infection. Surgical placement of the test article was the same in all study animals; therefore, obstruction-related complications had a similar pathobiological mechanism (i.e. abdominal viscera resting on the conduit because of the quadruped anatomy) in all groups.

Clinical Heath Observations and Post-Surgical Care

Individual clinical health observations and post-surgical care for all animals were observed (data not shown). To distinguish between the protocol objective of establishing the post-surgical care following implantation of the test article and the ancillary 3-month pilot evaluation of the test article itself, the data below is broken into 2 categories: observations <30 days and observations >30 days.

Clinical Heath Observations and Post-Surgical Care <30 Days. Following test article implantation surgery for all 7 animals, an indwelling Foley catheter was placed through the stoma to facilitate urine drainage. All 7 animals required weekly and on as needed basis maintenance of this catheter during the first 30 days postimplantation (e.g., Foley catheter replacement [if dislodged], stoma flushing, and cleaning of the expected debris from anticipated scaffold biodegradation). This was performed a minimum of 8 and a maximum of 15 times overall during the first 30 days. Clinically, 7/7 animals experienced a loss of appetite (anorexia) or appeared thin during the first 30 days post-implantation. This included 1/1 animals in Group 1 (animal 1); 2/3 animals in Group 2 (animals 2 and 3) and 3/3 animals in Group 3 (5, 6, and 7). Seven of 7 animals appeared lethargic during the first 30 days post-implantation. This included 1/1 animals in Group 1 (animal 1); 3/3 animals in Group 2 (animals 2, 3, and 4) and 2/3 animals in Group 3 (animals 5 and 7). These clinical observations are not uncommon following urinary tract surgery in pigs. The following table 3.3 provides clinical health observations and post-surgical care by test group (<30 Days Post implantation).

TABLE 3.3

| Clinical Observations | Group 1 N = 1 | Group 2 N = 3 | Group 3 N = 3 | Total N = 7 |
| --- | --- | --- | --- | --- |
| Stoma Maintenance | 1/1 | 3/3 | 3/3 | 7/7 |
| Anorexia (Not Eating, Thin) | 1/1 | 3/3 | 3/3 | 7/7 |
| Lethargy | 1/1 | 3/3 | 3/3 | 7/7 |

Clinical Heath Observations and Post-Surgical Care >30 Days. Six animals were on study >30 days (animal 5 of Group 3 was electively euthanized on day 28). One important clinical observation was intermittent obstruction of the outflow of urine. Since biodegradation of the scaffold occurs during the first 30 days post-implantation, obstruction appeared to have been facilitated by the placement of the test article in the ventral portion of the abdominal cavity of the quadruped where the weight of the overlying abdominal organs could lead to conduit closure, adhesion and fistula formation, and renal complications (e.g., dilation, inflammation, and/or infection of ureters or kidney). Obstruction was exacerbated by the use of peritoneum to form the atrium, causing partial or full urinary obstruction with subsequent detritus build-up and bacterial infection. Therefore, stoma maintenance was continued for the six surviving animals from day 31 to necropsy. This was performed a minimum of 4 and a maximum of 13 times overall from day 31 to necropsy. Two of 6 animals presented with anorexia after day 30 (animal 1 of Group 1 and animal 7 of Group 3). Three of 6 animals appeared lethargic after day 30. Two animals presenting with lethargy in the first 30 days continued to present with lethargy (animal 1 of Group 1 and animal 4 of Group 2) after day 30. The one animal that did not present with lethargy in the first 30 days presented with lethargy after day 30 (animal 6 of Group 3). The following table 3.4 shows clinical health observations and post-surgical care by group (>30 Days post implantation).

TABLE 3.4

| Clinical Observations | Group 1 N = 1 | Group 2 N = 3 | Group 3 N = 2* | Total N = 6 |
| --- | --- | --- | --- | --- |
| Stoma port Maintenance | 1/1 | 3/3 | 2/2 | 6/6 |
| Anorexia (Not Eating, Thin) | 1/1 | 0/3 | 1/2 | 2/6 |
| Lethargy | 1/1 | 1/3 | 1/2 | 3/6 |

*animal 5 of Group 3 was electively euthanized at day 28.

Stent Removal. Stents were removed from anesthetized animals between 2 and 4 weeks postimplantation by stent tether or visualization by ultrasound and retrieval with cystoscope. The stents in one animal (animal 3 of Group 2) were not able to be visualized and removed and remained in place until necropsy. Individual ureteral stent removal data was collected (data not shown).

Stoma Port/Catheter. Individual data was collected (data not shown). A progression of changes was made during the study to optimize stoma management. Initially a Foley catheter was utilized. This was replaced with a TRACOE® stoma ports. When this proved to be impractical due to frequent device dislodgment by the animal, an 8Fr Foley catheter was used to aid urine drainage. This was later replaced by a modified extension set tubing with bigger diameter to reduce clogging. Maintenance or replacement was done weekly and on an as needed basis.

Body Weights. All animals lost weight post-implantation. Body weights for all animals fluctuated during the course of the study. One animal (animal 4 of Group 2) survived until scheduled sacrifice, and remained steady or gained weight from week 2 until necropsy. Individual body weight data appears in the table 3.5 below.

was generally decreased by necropsy, and potassium and sodium fluctuated. Although changes were apparent in all groups, the scaffold only animal (Group 1) appeared to have the most significant changes by necropsy.

TABLE 3.5

| Animal No. | Implant Type | Baseline | Wk 1 | Wk 2 | Wk 2 | Wk 3 | Wk 4 | Wk 5 | Wk 6 | Wk 7 | Wk 8 | Wk 9 | Wk 12 |
|---|---|---|---|---|---|---|---|---|---|---|---|---|---|
| 1 | Scaffold only | 17.8 | 16.3 | 16.4 | 15.2 | 15.4 | 16.1 | NP | 15.7 | 14.95 | | NA | |
| 2 | Blood derived SMC | 20.1 | 19.1 | NP | 17.4 | 16.5 | 17.9 | 15.9 | | | NA | | |
| 3 | Blood derived SMC | 17.4 | 15.9 | 16.3 | 16.3 | 16.6 | 17.25 | NP | 18.1 | NP | 19.6 | 19.8 | 19 |
| 4 | Blood derived SMC | 17.4 | 15.5 | 16.1 | NP | 17.1 | 19.3 | 18.1 | | | NA | | |
| 5 | Adipose-derived SMC | 18.6 | 16.9 | 15.7 | 14.4 | 15.5 | 14.9 | NP | NP | NP | 16.65 | 13.4 | NA |
| 6 | Adipose-derived SMC | 17.1 | 16.6 | 16.2 | 16.1 | 15.4 | 16.6 | NP | 17.2 | | NA | | |
| 7 | Adipose-derived SMC | 16.9 | 15.1 | 14.3 | 13.7 | 12.5 | 11.3 | | | | NA | | |

Clinical Pathology. Clinical pathology data for individual animals was collected.

Hematology. Hematology data was collected (data not shown). Postoperative blood collection for hematology revealed the development of leukocytosis for all groups. Leukocyte counts for the all groups fluctuated; however, leukocyte counts for the scaffold-only animal (Group 1) had the highest value at necropsy. Red blood cell counts (RBCs) fluctuated for all groups but remained within the reference range (8-10 MILL/uL) throughout the study. Hematocrit (%) fluctuated over the course of the study for all groups.

Serum Chemistry. Serum chemistry data was collected (data not shown). Overall, BUN, creatinine, total protein and potassium were elevated at necropsy for all animals. Albumin Coagulation. Coagulation data was collected (data not shown). The activated partial thromboplastin time increased but then returned to near baseline by necropsy for all animals except animals 5 and 7, which remained elevated. Fibrinogen was elevated for all groups at necropsy, and was highest in the scaffold only animal.

Urinalysis. Urinalysis data was collected (data not shown). Urinalysis data showed increases in protein, blood presence, white blood cell count and bacteria count for all groups between baseline and necropsy.

Imaging. Ultrasound data is presented in the following table 3.6.

TABLE 3.6

| | | Week 2 | | | | | Week 4 | | | | |
|---|---|---|---|---|---|---|---|---|---|---|---|
| | | Right Kidney | | Left Kidney | | Conduit Wall | Right Kidney | | Left Kidney | | Conduit Wall |
| Animal No. | Group Type | L | W | L | W | Thickness | L | W | L | W | Thickness |
| 1 | Scaffold only | 5.67 | 3.04 | 5.49 | 2.79 | 0.236 | 4.55 | 2.71 | 7.09 | 4.36 | 0.132 |
| 2 | Blood derived | 4.52 | 3.33 | 5.55 | 3.96 | 0.139 | 9.45 | 3.54 | 8.08 | 3.59 | 0.16 |
| 4 | | 5 | 2.91 | 6.23 | 3.94 | 0.272 | 10.5 | 4.31 | 5.2 | 3.49 | 0.17 |
| 3 | | 4.5 | 2.57 | 5.87 | 3.2 | 0.172 | 6.47 | 3.7 | 5.39 | 3.18 | 0.176 |
| 6 | Adipose derived | 4.33 | 3.07 | 5.67 | 3.58 | 0.171 | 11.7 | 5.37 | 7.09 | 4.47 | 0.334 |
| 5 | | 5.18 | 3.26 | 5.65 | 2.77 | 0.246 | 4.1 | 2.1 | 5.08 | 2.76 | 0.147 |
| 7 | | 4.82 | 2.62 | 3.57 | 2.14 | 0.233 | 10.2 | 3.5 | 7.09 | 3 | 0.403 |

| | | Week 8 | | | | | Week 12 | | | |
|---|---|---|---|---|---|---|---|---|---|---|
| | | Right Kidney | | Left Kidney | | Conduit Wall Thickness | Right Kidney | | Left Kidney | | Conduit Wall |
| Animal No. | Group Type | L | W | L | W | (cm) | L | W | L | W | Thickness |
| 1 | Scaffold only | | | NA | | | | | NA | | |
| 2 | Blood | | | NA | | | | | NA | | |
| 4 | derived | 8.05 | 3.32 | 7.05 | 4.85 | 0.22 | 7.16 | 4.19 | 8.35 | 3.59 | 0.242 |
| 3 | | | | NA | | | | | NA | | |
| 6 | Adipose | | | NA | | | | | NA | | |
| 5 | derived | | | NA | | | | | NA | | |
| 7 | | 7.51 | 4.4 | 7.09 | 3.31 | 0.211 | | | NA | | |

Figure 31:
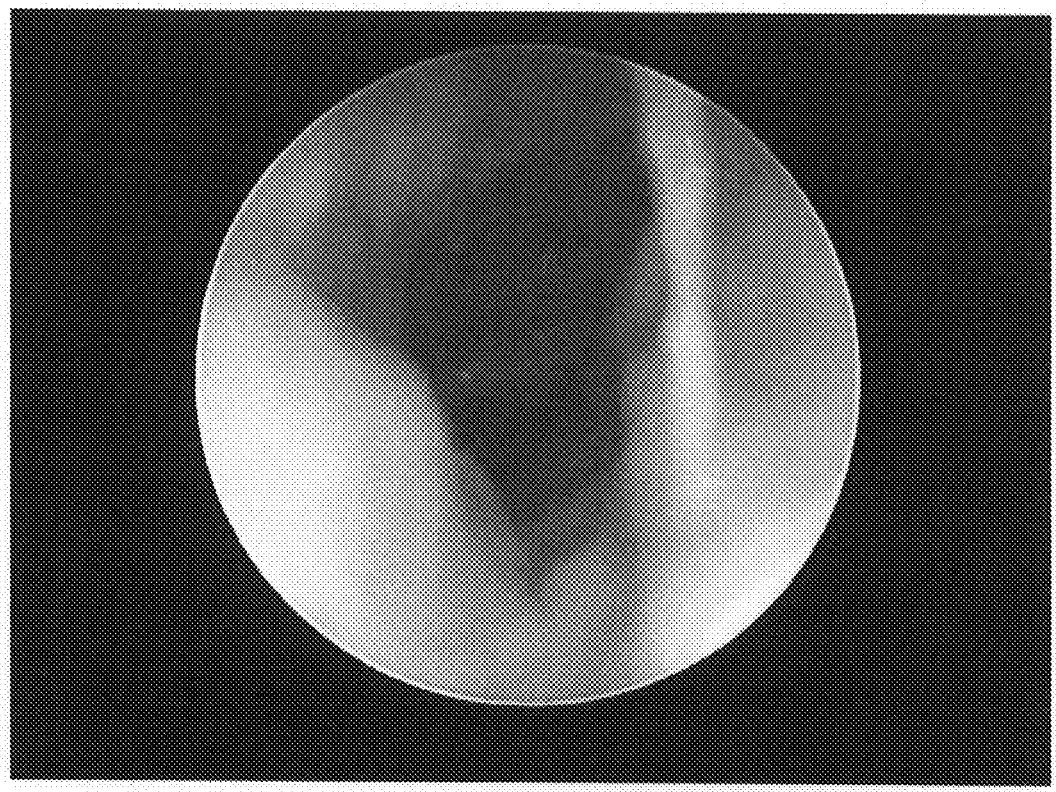
FIGS. 31-32 show the cytoscopy images of an animal implanted with a cell-free scaffold.
Figure 32:
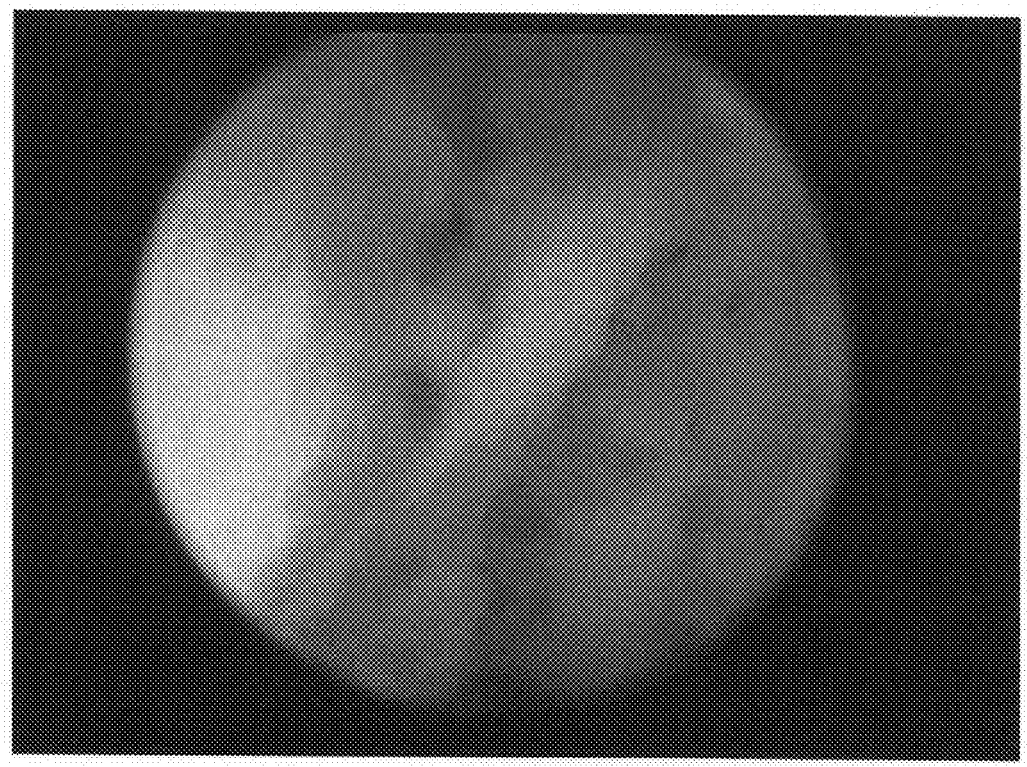

FIGS. 31-43 show representative cystoscopy images. FIG. 31 shows a cytoscopy image of animal 1 of Group 1 at week 4 (cell-free scaffold implanted). FIG. 32 shows the same animal 2 days before necropsy at the 6 week check-up.

Figure 33:
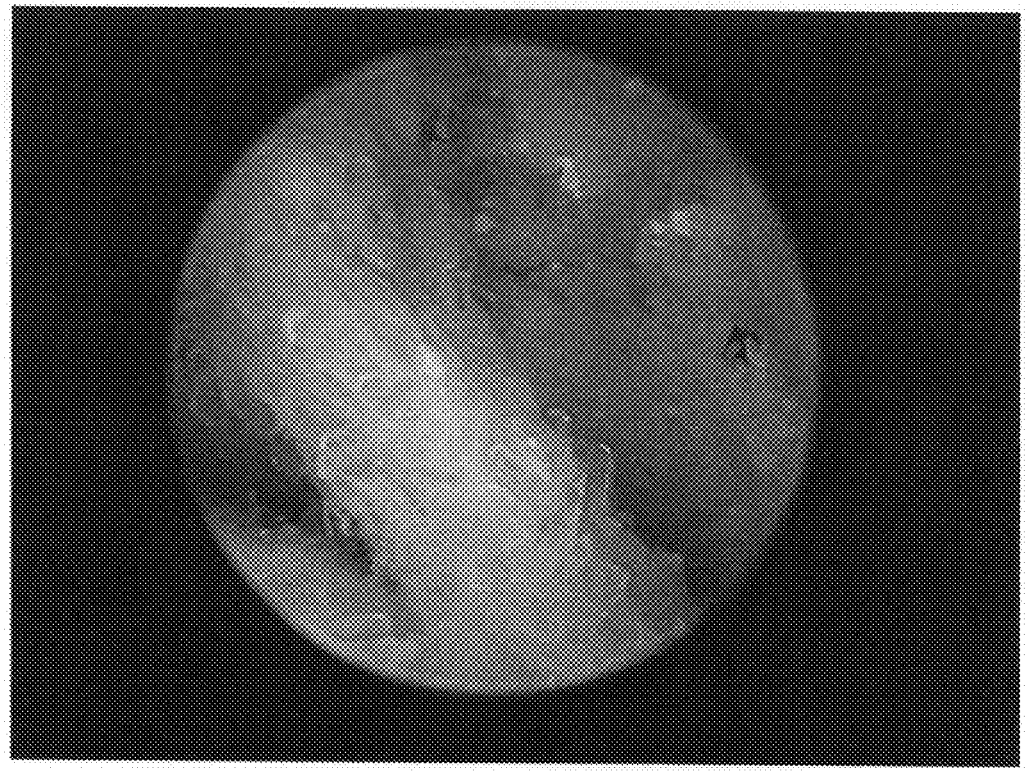
FIG. 33 shows the cytoscopy image of an animal implanted with a scaffold seeded with blood-derived SMCs.

FIG. 33 shows the cytoscopy image of animal 2 of Group 2 pre-necropsy (scaffold seeded with blood-derived SMCs).

Figure 34:
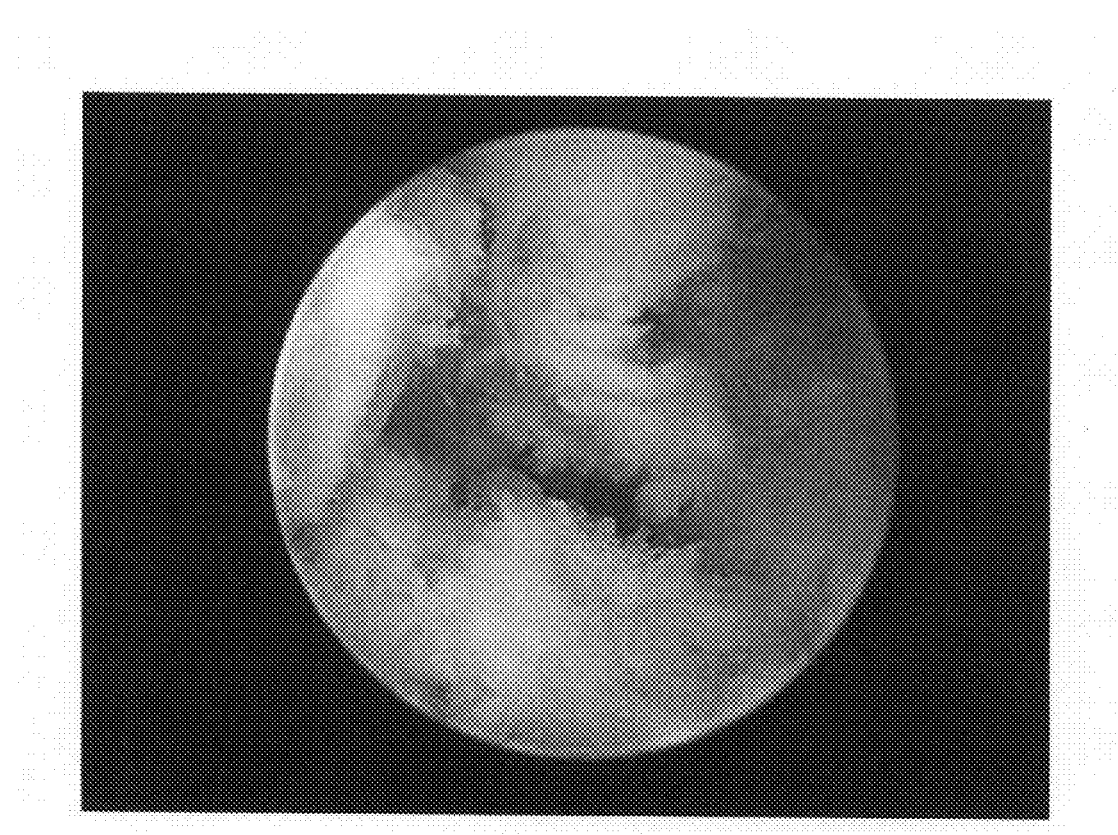
FIGS. 34-36 show the cytoscopy images of an animal implanted with a scaffold seeded with blood-derived SMCs.
Figure 35:
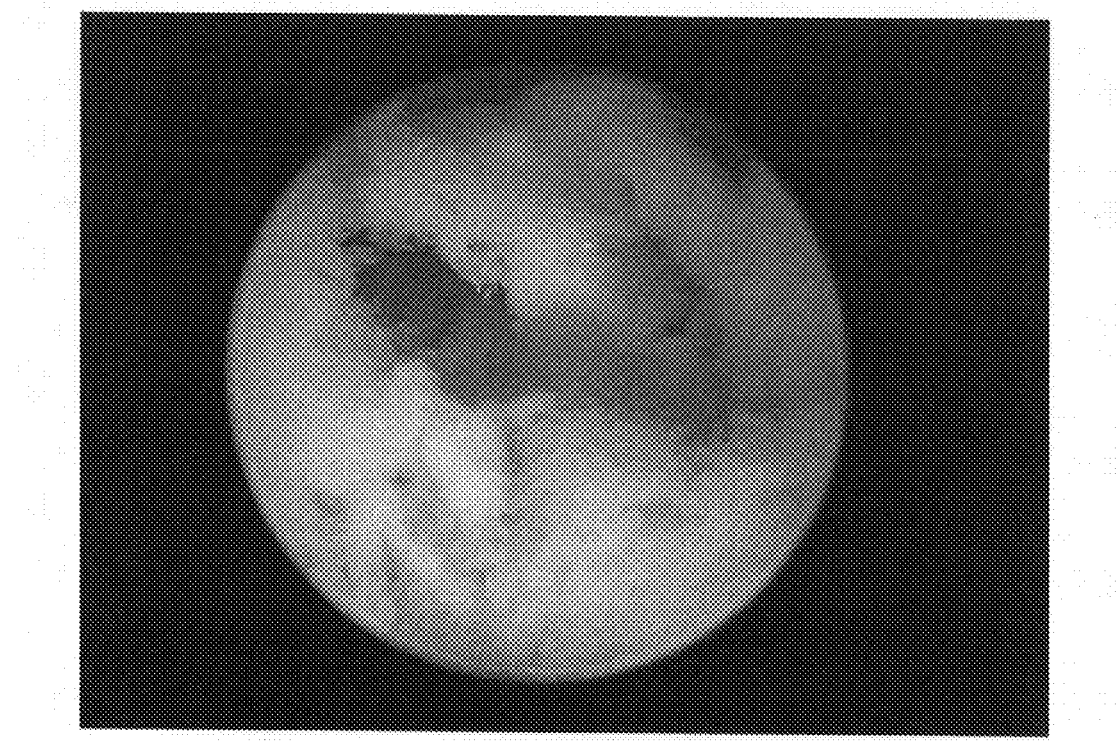
Figure 36:
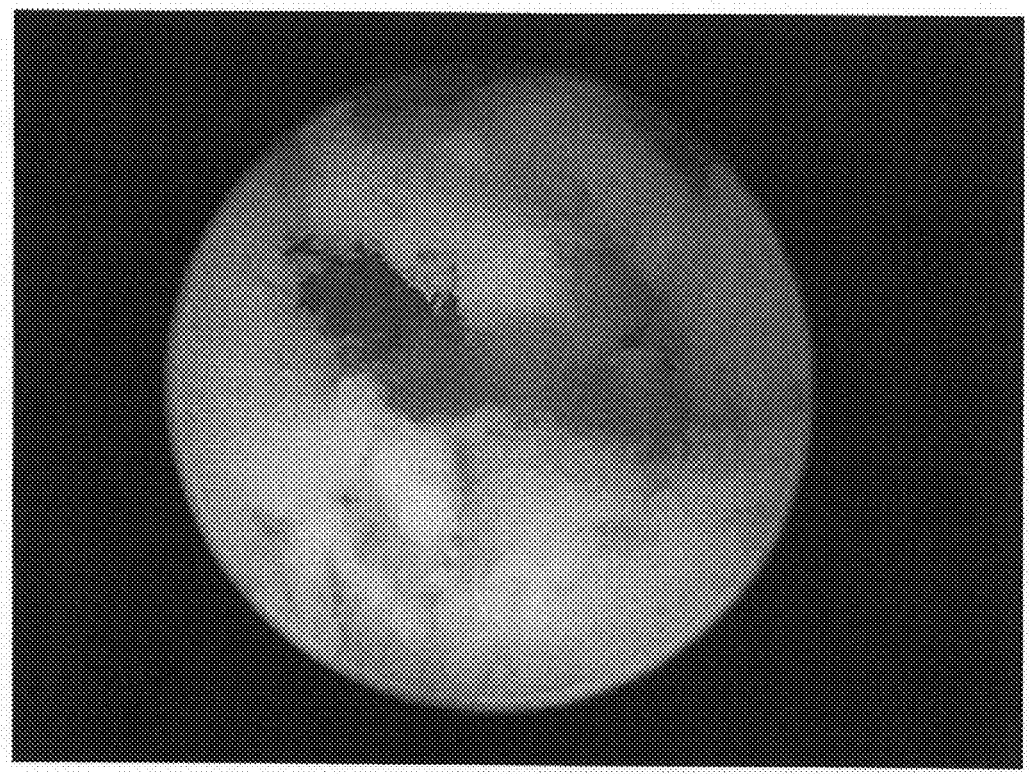

FIGS. 34-36 shows the cytoscopy image of animal 3 of Group 2 at week 4, week 5, and pre-necropsy (scaffold seeded with blood-derived SMCs).

Figure 37:
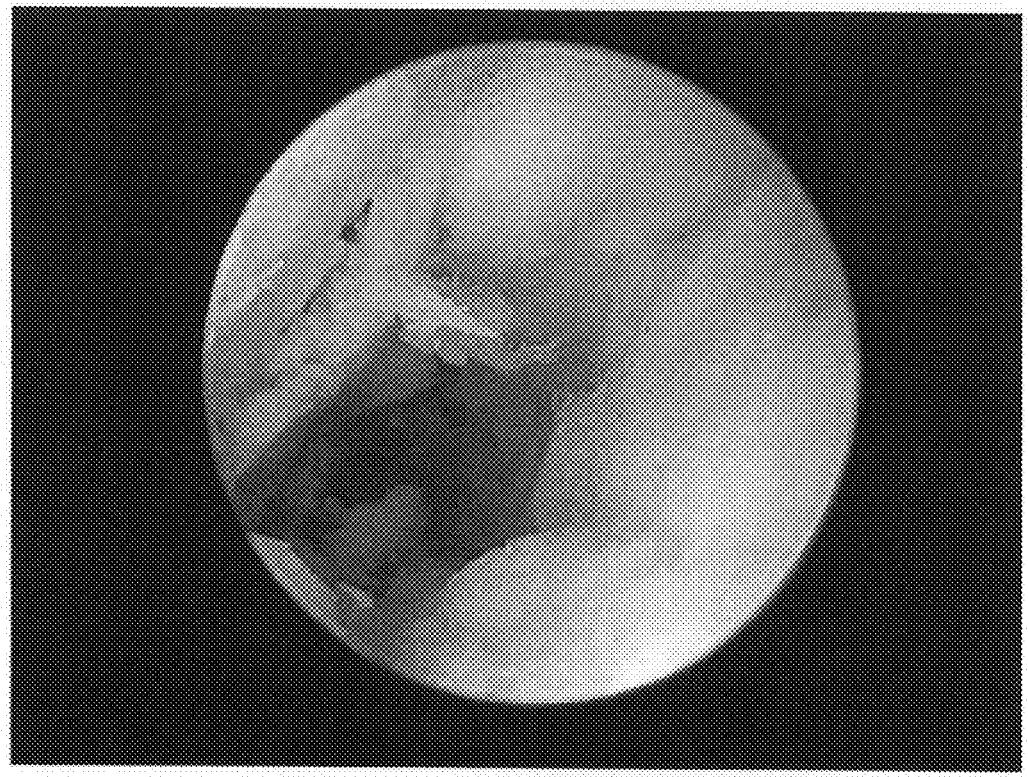
FIG. 37 shows the cytoscopy image of an animal implanted with a scaffold seeded with blood-derived SMCs.

FIG. 37 shows the cytoscopy image of animal 4 of Group 2 pre-necropsy (scaffold seeded with blood-derived SMCs).

Figure 38:
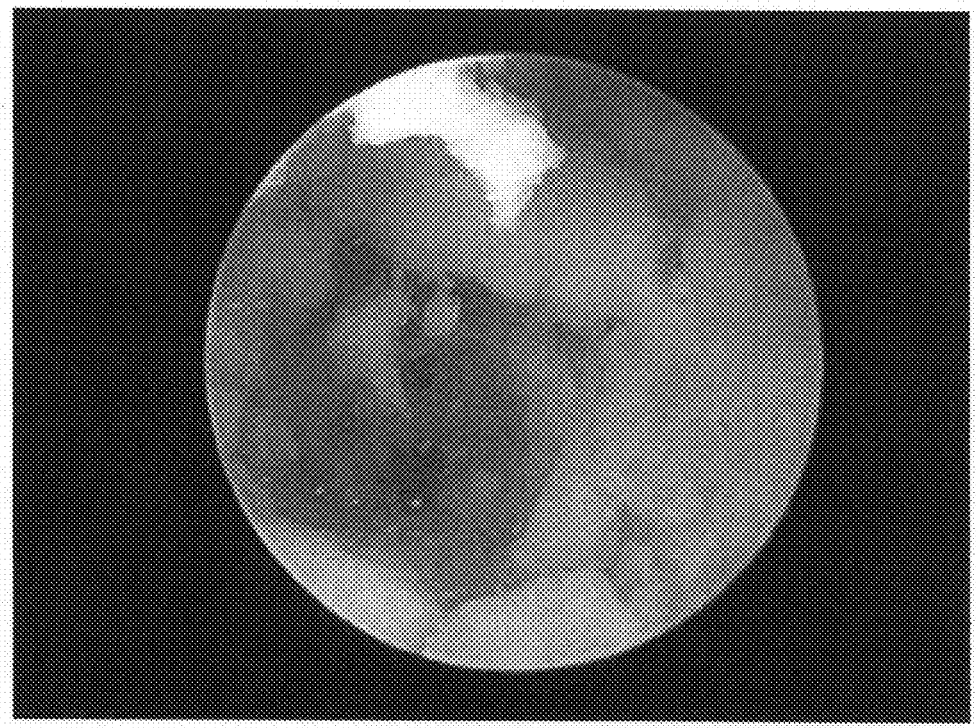
FIGS. 38-39 show the cytoscopy images of an animal implanted with a scaffold seeded with adipose-derived SMCs.
Figure 39:
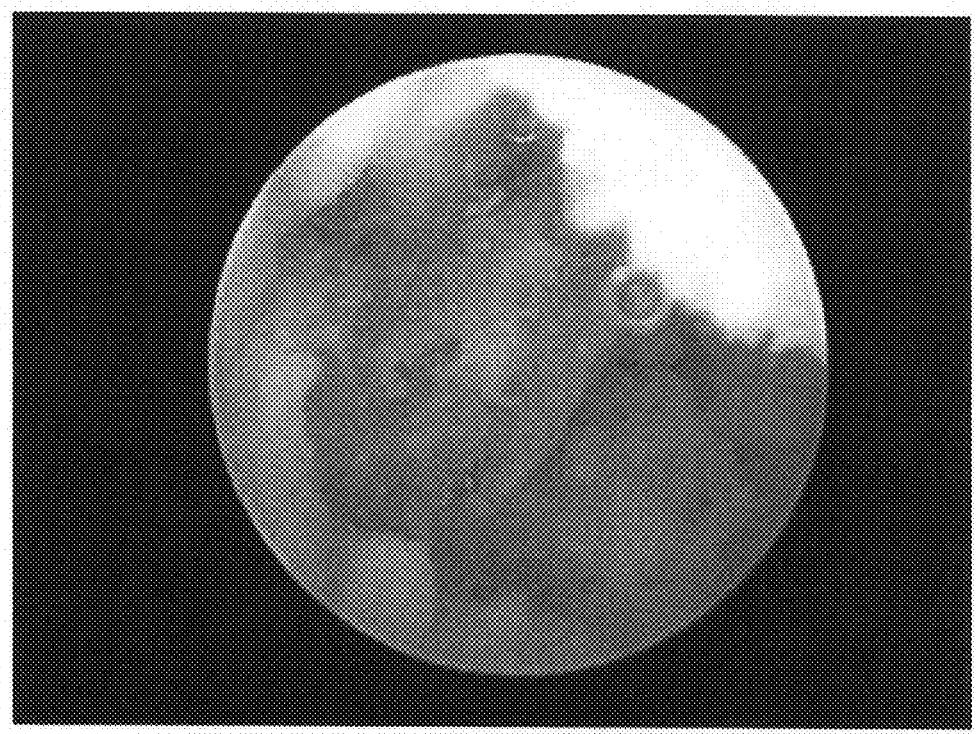

FIG. 38 shows the cytoscopy image of animal 5 of Group 3 at week 3 (scaffold seeded with adipose-derived SMCs). The image shows mucosa that is covered by white-tan amorphous granular castsof scaffold debris. FIG. 39 shows an image of the same animal at week 3. The pinkish focus near or at the ureteral anastomoses indicates where the epithelium came off with removal of the stents leaving a pink, vascularized granulation bed.

Figure 40:
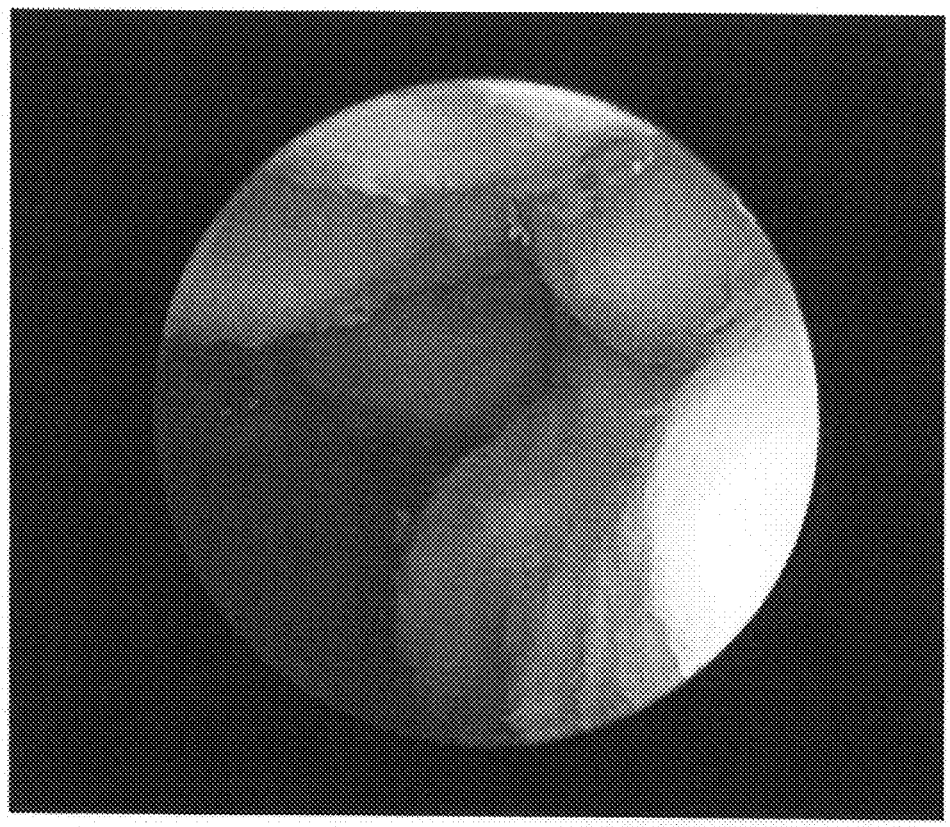
FIGS. 40-42 show the cytoscopy images of an animal implanted with a scaffold seeded with adipose-derived SMCs.
Figure 41:
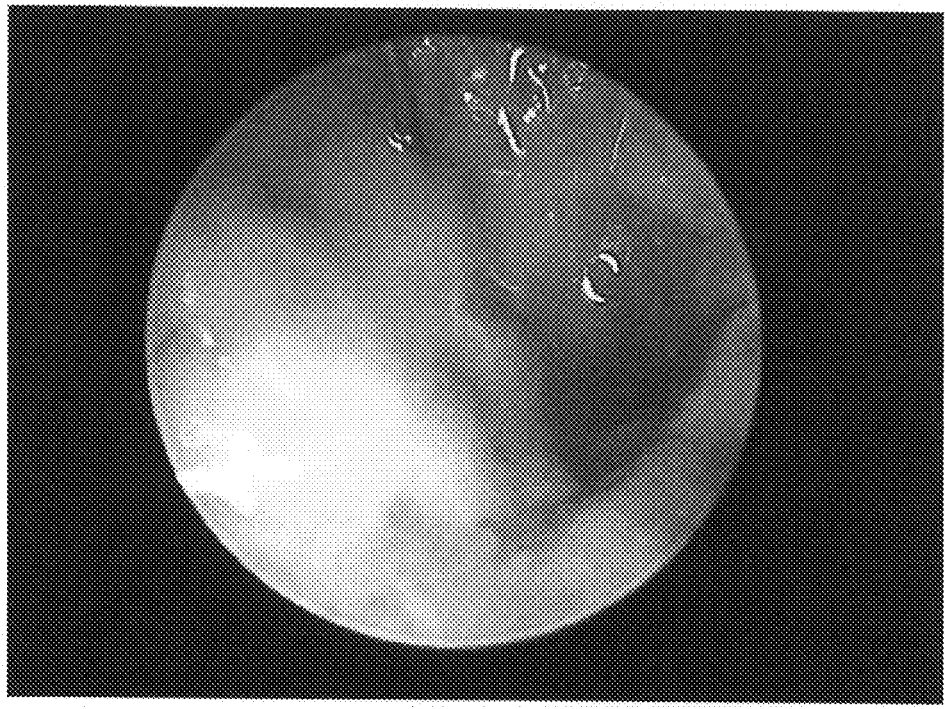
Figure 42:
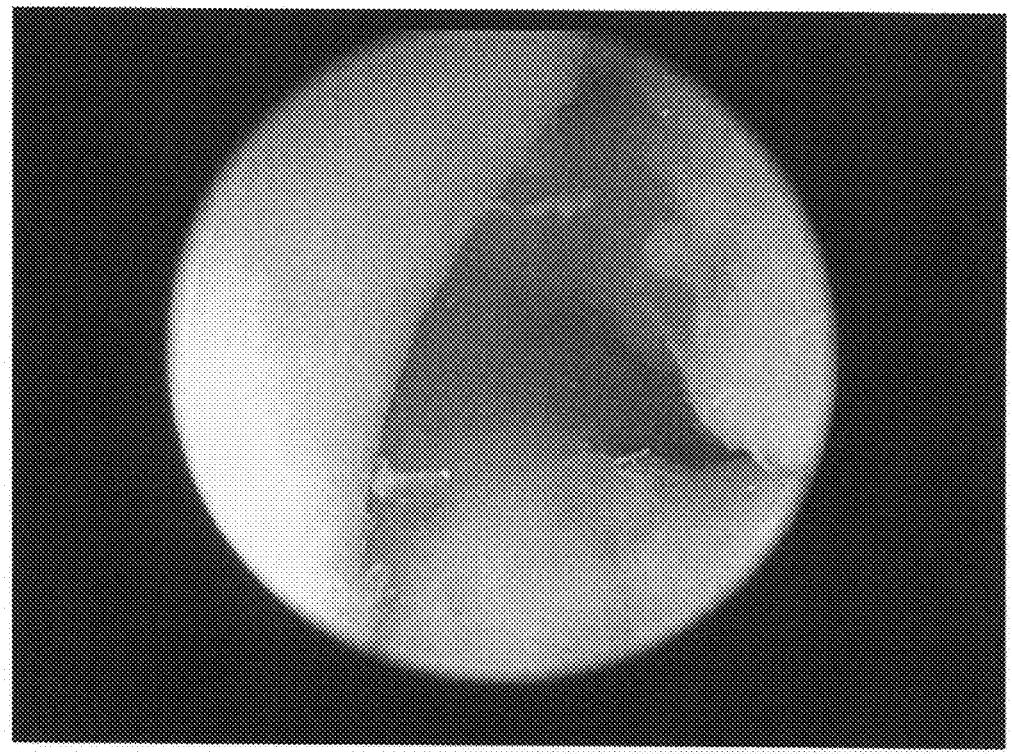

FIGS. 40-42 shows the cytoscopy image of animal 6 of Group 3 at week 3, week 4, and pre-necropsy (scaffold seeded with adipose-derived SMCs).

Figure 43:
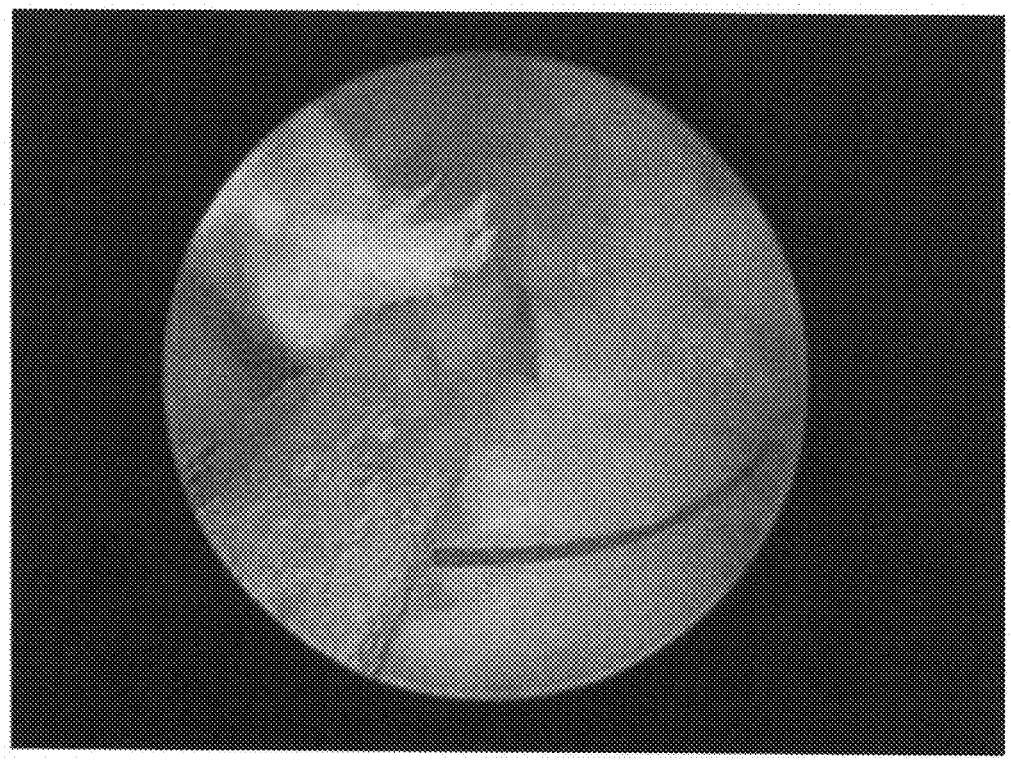
FIG. 43 shows the cytoscopy image of an animal implanted with a scaffold seeded with adipose-derived SMCs.

FIG. 43 shows the cytoscopy image of animal 7 of Group 3 at week 4 (scaffold seeded with adipose-derived SMCs). Two stents (blue material) were initially seen under ultrasound imaging and were later removed with cytoscopic guidance.

Ultrasound. Individual and group ultrasonography data are presented in the table above. Ultrasonography on the kidneys over the course of the study showed increases in surface area (length×width) indicating kidney changes (hydronephrosis) in all treatment groups. The following table 3.7 provides the kidney surface area (L×W, cm2).

TABLE 3.7

| Group No. | Group Type | Animal No. | Week 2 | Week 4 | Week 8 | Week 12 |
|---|---|---|---|---|---|---|
| Left Kidney | | | | | | |
| 1 | Scaffold only | 1 | 15.32 | 30.91 | NA | NA |
| 2 | Blood derived | 2 | 21.98 | 29.01 | NA | NA |
| 2 | Blood derived | 3 | 24.55 | 18.15 | 34.19 | 29.98 |
| 2 | Blood derived | 4 | 18.78 | 17.14 | NA | NA |
| 3 | Adipose derived | 5 | 20.30 | 31.69 | NA | NA |
| 3 | Adipose derived | 6 | 15.65 | 14.02 | NA | NA |
| 3 | Adipose derived | 7 | 7.64 | 21.27 | 23.47 | NA |
| Right Kidney | | | | | | |
| 1 | Scaffold only | 1 | 17.24 | 12.33 | NA | NA |
| 2 | Blood derived | 2 | 15.05 | 33.45 | NA | NA |
| 2 | Blood derived | 3 | 14.55 | 45.26 | 26.73 | 30.00 |
| 2 | Blood derived | 4 | 11.57 | 23.94 | NA | NA |
| 3 | Adipose derived | 5 | 13.29 | 62.83 | NA | NA |
| 3 | Adipose derived | 6 | 16.89 | 8.61 | NA | NA |
| 3 | Adipose derived | 7 | 12.63 | 35.70 | 33.04 | NA |

Ultrasonography on the implant wall thickness showed a fluctuation in thickness for all Groups. The following table 3.8 illustrates this.

TABLE 3.8

Conduit Wall Thickness (cm)

| Group No. | Group Type | Animal No. | Week 2 | Week 4 | Week 8 | Week 12 |
|---|---|---|---|---|---|---|
| 1 | Scaffold only | 1 | 0.236 | 0.132 | NA | NA |
| 2 | Blood derived | 2 | 0.139 | 0.160 | NA | NA |
| 2 | Blood derived | 3 | 0.272 | 0.170 | 0.220 | 0.242 |
| 2 | Blood derived | 4 | 0.172 | 0.176 | NA | NA |
| 3 | Adipose derived | 5 | 0.171 | 0.334 | NA | NA |
| 3 | Adipose derived | 6 | 0.246 | 0.147 | NA | NA |
| 3 | Adipose derived | 7 | 0.233 | 0.403 | 0.211 | NA |

The pathology report appears in Example 4 below.

Evidence of Porcine Circovirus Type-2 (PCV-2) infection was observed in 3/7 animals. These included animal 2 of Group 2 euthanized on day 38 and animal 7 of Group 3 euthanized on day 63. The third animal identified with PCV-2 infection, animal 4 of Group 2, survived to scheduled sacrifice (83 days). Obstruction of urine flow through the conduit and stoma contributed to the morbidity in 4/6 unscheduled death animals. These included animal 1 of Group 1, euthanized on day 47; animals 2 and 3 of Group 2 euthanized on days 38 and 40; and animal 6 of Group 3 euthanized on day 39. Ventral abdomen positioning of surgically implanted test article contributed to physical obstruction of urine flow in the quadruped animal model where the weight of the overlying abdominal organs contributed to conduit closure, adhesion and fistula formation, and secondary upper urinary tract renal complications (e.g., dilation, inflammation, and/or infection of ureters or kidney). In addition, the urine flow obstruction was exacerbated by the use of peritoneum to form the atrium, causing partial or full urinary obstruction with subsequent detritus build-up and bacterial infection. Surgical placement of the test article was the same in all study animals; therefore, obstruction-related complications had a similar pathobiological mechanism in all groups. Regeneration of urinary-like tissue was evident as early as day 28, with presence of urothelium, lamina propria and smooth muscle bundles at the ureter-conduit junction (UCJ) in an electively euthanized animal (animal 5 of Group 3, adipose-derived SMC). The regenerative process at the ureteral end of the implant resulted in urinary-like tissue formation that was comparable among animals receiving a construct implant (Groups 2 and 3). The extent of urinary-like tissue regeneration in the construct groups (Groups 2 and 3) was influenced by duration of animal survival post-implantation. The one animal surviving to scheduled sacrifice (animal 4 of Group 2 at day 83) had urothelium and smooth muscle present in the UCJ, cranial and mid portions of the conduit in spite of a detected viral infection. However, the peritoneum-only atrium was insufficient to support urinary-like tissue regeneration and the tissue formed in the atrium had a wall comprised of fibrous connective tissue without urothelial mucosal lining. The point of transition from conduit to atrium varied between animals because the caudal end of the implant floated freely within the peritoneal wrapping making the transition from conduit to atrium difficult to define at necropsy. The typical composition of (presumed) caudal conduit was organized collagen with associated fibroblasts and/or myofibroblasts. Peritoneum atrium appears to be insufficient for urinary-like tissue regeneration, but does serve as a source of vascularization to NUC implants.

CONCLUSIONS. The swine animal model proved appropriate for evaluating the surgical application of the Neo-Urinary Conduit in this study because all animals recovered from surgery and urinary diversion was achieved. In addition, the swine model was appropriate for evaluating post-operative care of urinary flow obstruction and its impact to the upper urinary tract. Finally, the swine model was appropriate for evaluating the ability of the test articles to regenerate urinary-like tissue in an environment complicated by detritus accumulation and bacterial colonization, viral infection, and enteric adhesions and fistulas.

The surgical methodology was determined to be successful although anatomical placement of the urinary diversion on the ventral abdominal floor of a quadrupedal animal resulted in partial obstruction of urine outflow. The animal model was considered appropriate for evaluating the surgical application, postsurgical care and functionality of the Neo-Urinary Conduit.

Post-surgical findings during the first 30 days following implant surgery revealed findings that were not considered uncommon following urinary diversion surgery in the pig.

Although several confounding factors occurred during the study (i.e. surgical placement on the ventral abdominal floor, use of peritoneal atrium and viral infection), regeneration of urinary-like tissue was evident as early as day 28, with presence of urothelium, lamina propria and smooth muscle bundles at the ureterconduit junction in an electively euthanized animal (animal 5 of Group 3, adipose-derived SMC).

The extent of urinary-like tissue regeneration in the construct groups (Groups 2 and 3) was influenced by duration of animal survival post-implantation. The one animal surviving to scheduled sacrifice (animal 4 of Group 2 at Day 83) had urothelium and smooth muscle present in the UCJ, cranial and mid portions of the conduit in spite of a detected viral infection.

There were no apparent differences observed in the regenerative process when scaffolds were seeded with SMC derived from blood or adipose (Groups 2 and 3, respectively), suggesting equivalence between SMC sources in promoting regeneration.

The tissue formed from peritoneum in the atrium segment of the conduit had a wall comprised of fibrous connective tissue without urothelial lining.

Example 4

Pathology of Animals Following Implantation of Neo-urinary Conduit Constructs

At the conclusion of the study described in Example 3, the anatomic pathology of the test animals was assessed.

Tissue Collection. The abdominal cavity was opened and the conduit, i.e., the outcome of implanting a construct or scaffold only test article, was visualized and digitally photographed in situ at the animal facility. The conduit was removed en bloc with the kidneys and ureters. The ureters were detached from the conduit by transverse sectioning 3-4 cm away from the anastomoses. Representative sections of the kidneys, ureters, lymph nodes, and any other lesions observed grossly were obtained. All tissue samples were placed in 10% Neutral Buffered Formalin (NBF) for 24-48 hours prior to shipping to Vet Path Services, Inc. for histological processing and evaluation.

Figure 44:
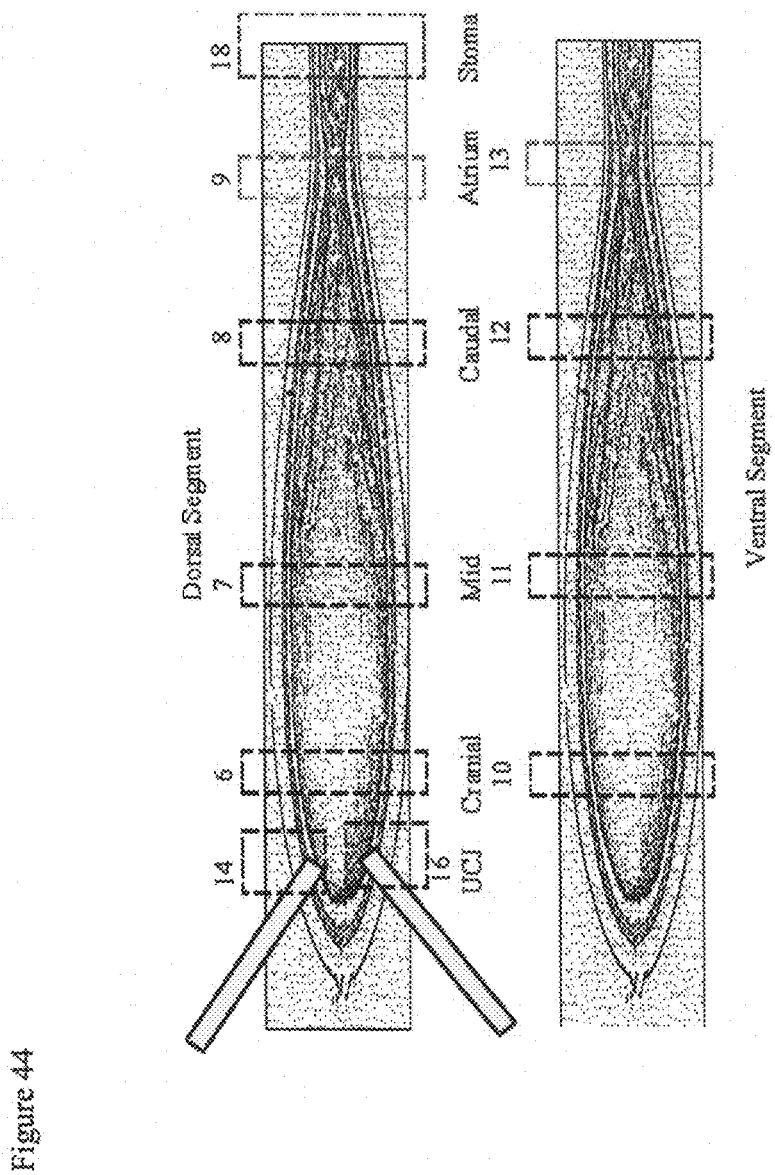
FIG. 44 shows a trimming schematic for a urinary conduit.

Histological Processing. After fixation, the conduit was opened longitudinally (parallel with the outflow) and divided into dorsal and ventral halves as illustrated in FIG. 44.

Three transverse sections were trimmed from each half (cranial, mid and caudal sections were captured for the dorsal half and the ventral half). One section from each half was taken from the conduit-atrium junction. An additional section was taken at each of the two ureterconduit junctions. One other slide was used to capture the stoma at the skin surface and the adjacent canal through the abdominal wall. When the size of the conduit permitted, this scheme resulted in 11 slides. Sections were collected from each animal. In addition, the following tissue/organ sections were obtained and submitted for histology: left kidney, right kidney, left ureter, right ureter, lumbar lymph node, mesenteric lymph nodes inguinal lymph node and any gross lesions.

During trimming of tissues at VPS, digital photographs were taken for illustration purposes. Post fixation, tissues were processed routinely to microslides and stained with hematoxylin and eosin (H&E) and Masson's trichrome. In addition, slides for the kidneys and 5 conduit sites were stained with Brown and Hopps (Gram) stain. Slides were evaluated microscopically.

Where appropriate, microscopic observations for Individual Animal Data were obtained and scored.

Results

Mortality. Animals survived 28-83 days. One of 7 animals survived until scheduled sacrifice (an animal from Group 2, 83 days). Six of 7 animals were sacrificed unscheduled: a Group 3 animal was electively euthanized at 28 days post-implantation for histopathological analysis and 5 animals were euthanized for poor clinical condition between 38 and 63 days post-implantation (a Group 1 Animal; two Group 2 Animals; and two Group 3 Animals). These unscheduled deaths occurred in all treatment groups and were attributed to viral infection and/or obstruction-related pathology with damage to the upper urinary tract. Final disposition and mortality findings for each of the 7 animals are shown in Appendix 1, Animal Information. Disposition (mortality classification) is summarized by treatment group in the following table 4.2 (Group 1=Scaffold-only, Group 2=Blood-derived SMC construct, Group 3=Adipose-derived SMC construct).

TABLE 4.2

Unscheduled and Scheduled Deaths by Group

| Mortality | Group 1 N = 1 | Group 2 N = 3 | Group 3 N = 3 | Total N = 7 |
|---|---|---|---|---|
| Unscheduled Necropsy (Euthanized) | 1/1 | 2/3 | 3/3* | 6/7 |
| Scheduled Necropsy | 0/1 | 1/3 | 0/3 | 1/7 |

Evidence of Porcine Circovirus Type 2 (PCV-2). Three of 7 animals developed one or more lesions consistent with distinct pathological features ascribed to porcine dermatitis and nephropathy syndrome (PDNS), associated with PCV-2 infection Animals were classified as PCV-2-infected if the following were observed: 1) Clinically-observed purple skin discoloration; 2) Microscopic vasculitis or vasculitis/perivasculitis affecting the kidney; 3) Kidney findings of tubular necrosis/fluid/casts/glomerulonephritis, or viral inclusions of tubular epithelial cells.

By these criteria, porcine PCV-2 infection was confirmed in 3/7 animals. Two PCV-2 infected animals were unscheduled necropsy animals. These included one animal in Group 2 (animal 2) euthanized on day 38 and another animal in Group 3 (animal 7) euthanized on day 63. The third animal identified with PCV-2 infection, animal 4 of Group 2, survived to scheduled sacrifice (83 days).

Obstruction. Obstruction of urine flow through the conduit and stoma contributed to the morbidity in 4/6 unscheduled death animals. These included animal 1 of Group 1, euthanized on day 47; animals 2 and 3 of Group 2, euthanized on days 38 and 40; and animal 6 of Group 3, euthanized on day 39. Ventral abdomen positioning of surgically implanted test article contributed to physical obstruction of urine flow in the quadruped animal model where the weight of the overlying abdominal organs contributed to conduit closure, adhesion and fistula formation, and secondary upper urinary tract renal complications (e.g., dilation, inflammation, and/or infection of ureters or kidney). In addition, the urine flow obstruction was exacerbated by the use of peritoneum to form the atrium, causing partial or full urinary obstruction with subsequent detritus build-up and bacterial infection. Surgical placement of the test article was the same in all study animals; therefore, obstruction-related complications had a similar pathobiological mechanism in all groups.

Distribution of Unscheduled and Scheduled Deaths by Underlying Findings. A summary of underlying findings in the unscheduled and scheduled deaths is presented in the following table 4.3 (Group 1=Scaffold-only, Group 2=Blood-derived SMC construct, and Group 3=Adipose-derived SMC construct).

TABLE 4.3

| Mortality Categories | Group 1 N = 1 | Group 2 N = 3 | Group 3 N = 3 | Total N = 7 |
|---|---|---|---|---|
| Evidence of PCV-2 infection (unscheduled and scheduled death) | 0 | 2*^ | 1 | 3 |
| Obstruction | 1 | 2^ | 1 | 4 |
| Elective Euthanasia | 0 | 0 | 1 | 1 |
| Total unscheduled deaths | 1 | 2^ | 3 | 6 |
| Total scheduled deaths | 0 | 1* | 0 | 1 |

*animal 4 of Group 2 survived until scheduled sacrifice (Day 83)
^animal 2 of Group 2 showed evidence of PCV-2 and obstruction related findings Surgical Care. A comprehensive list of macroscopic findings and microscopic correlates for all animals was obtained (data not shown).

Inter-group incidences for kidney, ureter and other findings are shown in the following tables. Table 4.6 below shows the intergroup incidence: kidney, ureter and other tissue findings (Number of animals with finding (of any severity)/Number of animals examined; and U=Unexamined).

TABLE 4.6

| | Group: Treatment: | | |
|---|---|---|---|
| Mean Days on Study: | 1 Scaffold Only 47 | 2 Autologous Blood SMC 54 | 3 Autologous Adipose SMC 43 |
| Left Kidney | | | |
| Hydronephrosis/chronic nephritis | 1/1 | 1/3 | 1/3 |
| Chronic nephritis (without hydronephrosis) | 0/1 | 1/3 | 0/3 |
| Pyelonephritis | 0/1 | 1/3 | 0/3 |
| Chronic-active nephritis | 0/1 | 1/3 | 3/3 |
| Regeneration, tubular epithelium | 1/1 | 2/3 | 2/3 |
| Tubular necrosis/fluid/casts/glomerulonephritis | 0/1 | 0/3 | 1/3 |
| Vasculitis/perivascular inflammation | 0/1 | 1/3 | 1/3 |
| Viral inclusions | 0/1 | 0/3 | 1/3 |
| Inflammation, chronic-active, capsule/peritoneum | 0/1 | 0/3 | 1/3 |
| Bacterial colonies, capsule/peritoneum | 0/1 | 0/3 | 1/3 |
| Right Kidney | | | |
| Hydronephrosis/chronic nephritis | 1/1 | 1/3 | 1/3 |
| Chronic nephritis (without hydronephrosis) | 0/1 | 0/3 | 0/3 |
| Pyelonephritis | 0/1 | 1/3 | 0/3 |
| Chronic-active nephritis | 1/1 | 1/3 | 1/3 |
| Regeneration, tubular epithelium | 0/1 | 2/3 | 3/3 |
| Tubular necrosis/fluid/casts/glomerulonephritis | 0/1 | 2/3 | 0/3 |
| Vasculitis/perivascular inflammation | 0/1 | 1/3 | 0/3 |
| Viral inclusions | 0/1 | 0/3 | 0/3 |
| Inflammation, chronic-active, capsule/peritoneum | 1/1 | 0/3 | 0/3 |
| Bacterial colonies, capsule/peritoneum | 1/1 | 0/3 | 0/3 |
| Left Ureter | | | |
| Dilatation | 0/1 | 1/3 | 1/3 |
| Vacuolation, transitional epithelium | 0/1 | 1/3 | 0/3 |
| Inflammation, subacute/chronic, peri-ureter mesentery | 1/1 | 2/3 | 2/3 |
| Vasculitis/necrosis, mesenteric blood vessel | 0/1 | 1/3 | 2/3 |
| Right Ureter | | | |
| Dilatation | 1/1 | 1/3 | 2/3 |
| Vacuolation, transitional epithelium | 0/1 | 0/3 | 0/3 |
| Inflammation, subacute/chronic, peri-ureter mesentery | 1/1 | 1/3 | 2/3 |
| Vasculitis, mesenteric blood vessel | 0/1 | 1/3 | 1/3 |
| Lymph Node, Inguinal (Normal) | 1/1 | 1/1 | 3/3 |
| Lymph Node, Lumbar (Normal) | U | 1/2 | 2/3 |
| Histiocytosis, sinus | U | 1/2 | 1/3 |
| Lymph Node, Mesenteric (Normal) | U | 2/2 | 2/3 |
| Infiltrate, neutrophils | U | 0/2 | 1/3 |
| Adhesions and Fistulas | | | |
| Adhesion conduit to intestines (macroscopic and microscopic) | 1/1 | 2/3 | 2/3 |
| Adhesion conduit to intestines (microscopic only) | 0/1 | 1/3 | 0/3 |
| Adhesion conduit to uterus (macroscopic) | 0/1 | 1/3 | 0/3 |
| Adhesion ureter to uterus/ovary (macroscopic) | 0/1 | 1/3 | 1/3 |
| Adhesion ureter to intestines (macroscopic) | 0/1 | 0/3 | 1/3 |
| Fistula (macroscopic) & Fistula/neutrophil tract (microscopic) | 0/1 | 2/3 | 0/3 |
| GROSS LESIONS: Skin, Inner Left Thigh & Perineum | | | |
| Vasculitis, acute, necrotizing, dermis | U | 1/1 | U |
| Hemorrhage, dermis | U | 1/1 | U |

Table 4.7 below shows the intergroup incidence: kidney, ureter and other tissue findings (Number of animals with finding (of any severity)/Number of animals examined; and U=Unexamined) (non-PCV-2 animals).

TABLE 4.7

|  | Group: Treatment: | | |
| --- | --- | --- | --- |
|  | 1 Scaffold Only | 2 Autologous Blood SMC | 3 Autologous Adipose SMC |
| Left Kidney | | | |
| Hydronephrosis/chronic nephritis | 1/1 | 0/1 | 1/2 |
| Chronic nephritis (without hydronephrosis) | 0/1 | 0/1 | 0/2 |
| Pyelonephritis | 0/1 | 0/1 | 0/2 |
| Chronic-active nephritis | 0/1 | 0/1 | 2/2 |
| Regeneration, tubular epithelium | 1/1 | 0/1 | 1/2 |
| Tubular necrosis/fluid/casts/glomerulonephritis | 0/1 | 0/1 | 0/2 |
| Vasculitis/perivascular inflammation | 0/1 | 0/1 | 1/2 |
| Viral inclusions | 0/1 | 0/1 | 0/2 |
| Inflammation, chronic-active, capsule/peritoneum | 0/1 | 0/1 | 1/2 |
| Bacterial colonies, capsule/peritoneum | 0/1 | 0/1 | 1/2 |
| Right Kidney | | | |
| Hydronephrosis/chronic nephritis | 1/1 | 0/1 | 1/2 |
| Chronic nephritis (without hydronephrosis) | 0/1 | 0/1 | 0/2 |
| Pyelonephritis | 0/1 | 0/1 | 0/2 |
| Chronic-active nephritis | 1/1 | 0/1 | 0/2 |
| Regeneration, tubular epithelium | 0/1 | 0/1 | 2/2 |
| Tubular necrosis/fluid/casts/glomerulonephritis | 0/1 | 0/1 | 0/2 |
| Vasculitis/perivascular inflammation | 0/1 | 0/1 | 0/2 |
| Viral inclusions | 0/1 | 0/1 | 0/2 |
| Inflammation, chronic-active, capsule/peritoneum | 1/1 | 0/1 | 0/2 |
| Bacterial colonies, capsule/peritoneum | 1/1 | 0/1 | 0/2 |
| Left Ureter | | | |
| Dilatation | 0/1 | 0/1 | 1//2 |
| Vacuolation, transitional epithelium | 0/1 | 1/1 | 0/2 |
| Inflammation, subacute/chronic, peri-ureter mesentery | 1/1 | 1/1 | 2/2 |
| Vasculitis/necrosis, mesenteric blood vessel | 0/1 | 0/1 | 2/2 |
| Right Ureter | | | |
| Dilatation | 1/1 | 0/1 | 2/2 |
| Vacuolation, transitional epithelium | 0/1 | 0/1 | 0/2 |
| Inflammation, subacute/chronic, peri-ureter mesentery | 1/1 | 1/1 | 2/2 |
| Vasculitis, mesenteric blood vessel | 0/1 | 1/1 | 1/1 |
| Lymph Node, Inguinal (Normal) | 1/1 | 1/1 | 2/2 |
| Lymph Node, Lumbar (Normal) | U | 1/1 | 2/2 |
| Lymph Node, Mesenteric (Normal) | U | 1/1 | 2/2 |

TABLE 4.7-continued

|  | Group: Treatment: | | |
| --- | --- | --- | --- |
|  | 1 Scaffold Only | 2 Autologous Blood SMC | 3 Autologous Adipose SMC |
| Adhesions and Fistulas | | | |
| Adhesion conduit to intestines (macroscopic and microscopic) | 1/1 | 1/1 | 1/2 |
| Adhesion conduit to intestines (microscopic only) | 0/1 | 0/1 | 0/2 |
| Adhesion conduit to uterus (macroscopic) | 0/1 | 0/1 | 0/2 |
| Adhesion ureter to uterus/ovary (macroscopic) | 0/1 | 0/1 | 1/2 |
| Adhesion ureter to intestines (macroscopic) | 0/1 | 0/1 | 1/2 |
| Fistula (macroscopic) & Fistula/neutrophil tract (microscopic) | 0/1 | 1/1 | 0/2 |

Conduits formed from implantation of a test article were variably sized and shaped tubes located in the retro-peritoneal space of the ventral abdomen. The ureters entered at the cranial end of the conduit (ureter-conduit junction, UCJ, FIG. 44). Urine flow was directed through the peritoneal-wrapped implant and the atrium and emerged at the stoma. The cranial end of the conduit (ureteral attachment) frequently had bilateral bulbous dilations, referred to as diverticula that were considered to be part of the regenerative process and reflected the intermittent obstruction of the stoma and back pressure causing a dilatation to develop in the regenerated conduit.

Adhesions and Fistulas. The ventral side of the conduit was adhered to the fascia and skeletal muscle of the abdominal wall, and the dorsal side was covered with peritoneum. At necropsy, adhesions between the conduit or ureters and other abdominal organs (e.g., gastrointestinal tract, omentum or other abdominal organs) were observed. The lumen of the conduit was filled with detritus. Abdominal adhesions, including adhesions among the various abdominal organs and adhesions between the conduit and abdominal organs, were present in 7/7 animals. The incidence of adhesions and fistulas is summarized in the following Table 4.8 below (Group 1=Scaffold-only, Group 2=Blood-derived SMC construct, and Group 3=Adipose-derived SMC construct)

TABLE 4.8

| Finding | Group 1 N = 1 | Group 2 N = 3 | Group 3 N = 3 | Total N = 7 |
| --- | --- | --- | --- | --- |
| Adhesion conduit to intestines | 1/1 | 3/3 | 2/3 | 6/7 |
| Adhesion conduit to uterus | 0/1 | 1/3 | 0/3 | 1/7 |
| Adhesion ureter to uterus or ovary | 0/1 | 1/3 | 2/3 | 3/7 |
| Adhesion ureter to intestine | 0/1 | 0/3 | 1/3 | 1/7 |
| Fistula (conduit to intestines) | 0/1 | 2/3 | 0/3 | 2/7 |

Six of 7 animals had adhesions between the conduit and intestine (macroscopically and microscopically in animal 1 of Group 1; animals 3 and 4 of Group 2 and animals 6 and 7 of Group 3; microscopically in animal 2 of Group 2). One of 7 animals also had macroscopic adhesions between the conduit and uterus and ureter to uterus or ovary (animal 4 of Group 2). One animal (animal 5 of Group 3) had an adhesion between the ureter and uterus or ovary (macroscopically). One of 7 animals had macroscopic adhesions ureter to uterus or ovary and ureter to intestine (animal 6 of Group 3). Fistulas were observed macroscopically, and fistula/neutrophil tract microscopically, between the conduit and intestinal tract in 2/7 animals (animals 2 and 3 of Group 2). Fistulas were observed macroscopically, and fistula/neutrophil tract microscopically, between the conduit and intestinal tract in 2/7 animals (animals 2 and 3 of Group 2).

Ureters and Kidneys. Thickened ureters observed macroscopically resulted from several underlying biological processes upon microscopic evaluation. Ureter dilatation (or hydroureter) was characterized by an expanded lumen with normal ureteral wall structure. Ureters were also sometimes thickened by subacute/chronic inflammation of the peri-ureter mesentery, which occurred when the mesentery surrounding the ureter was expanded by collagen and fibroblasts, with occasional lymphocytes and macrophages. Transitional cell vacuolation was characterized by round, clear vacuoles in the epithelium. This inflammation did not usually affect the muscle tunics or urothelium of the ureter. Peri-ureter inflammation could be related to adhesion between ureter and intestinal or reproductive organs; but it could also occur without adhesion. Vasculitis, with or without necrosis of blood vessels, was observed within the areas of peri-ureter inflammation. This may have been associated with the PCV-2 viral infection in animals 2 of Group 2. Microscopically, hydronephrosis was characterized by a dilatation of the renal pelvis with thinning and chronic inflammation (fibrosis, lymphocytes, plasma cells and occasional macrophages) of the renal cortex. Hydronephrosis was considered to be the result of full or partial obstruction in the lower urinary system (ureters, conduit or atrium/stoma). Chronic-active pyelonephritis, which was occasionally associated with hydronephrosis, was characterized by infiltration of neutrophils and cellular debris into the renal pelvis, often spreading into the distal medulla. Pyelonephritis was the result of bacterial infection of the lower urinary tract which ascended into the renal pelvis. Chronic nephritis (without hydronephrosis) was characterized by fibrosis with infiltration of inflammatory cells (lymphocytes, macrophages, plasma cells and occasionally neutrophils) in the renal cortex or medulla. The cortex of kidneys with chronic nephritis looked similar to those in animals with hydronephrosis/chronic nephritis; however, in chronic nephritis the pelvis was not dilated. Chronic-active nephritis was similar in appearance to chronic nephritis, but with significant infiltration of neutrophils. Tubular necrosis/fluid/casts/glomerulonephritis was a constellation of changes characterized by neutrophils, lymphocytes and macrophages in glomeruli, necrosis of individual tubular epithelial cells, proteinaceous tubular casts and/or hemorrhage in tubular lumens. Tubular necrosis/fluid/casts/glomerulonephritis was observed in animals 2 and 4 of Group 2 and animal 7 of Group 3. Also common in the kidneys of the animals with tubular necrosis/fluid/casts/glomerulonephritis was vasculitis/perivascular inflammation. Chronic-active inflammation of the capsule/peritoneum was characterized by thickening of the capsule of the kidney by fibroblasts, collagen fibers and/or fibrin, neutrophils, lymphocytes and macrophages, and was indicative of peritonitis.

Microscopic Hydroureter and Hydronephrosis and/or Pyelonephritis. Hydroureter and hydronephrosis were observed in 4 of 7 animals. The results are shown in the following table 4.9 (Group 1=Scaffold-only, Group 2=Blood-derived SMC construct, and Group 3=Adipose-derived SMC construct).

TABLE 4.9

Incidence of Hydroureter, Hydronephrosis and/or Pyelonephritis

| Finding | Group 1 N = 1 | Group 2 N = 3 | Group 3 N = 3 | Total N = 7 |
|---|---|---|---|---|
| Hydroureter, Unilateral | 1/1 | 0/3 | 1/3 | 2/7 |
| Hydroureter, Bilateral | 0/1 | 1/3 | 1/3 | 2/7 |
| Hydronephrosis, Unilateral | 0/1 | 0/3 | 2/3 | 2/7 |
| Hydronephrosis, Bilateral | 1/1 | 1/3 | 0/3 | 2/7 |
| Pyelonephritis, Unilateral | 0/1 | 0/3 | 0/3 | 0/7 |
| Pyelonephritis, Bilateral | 0/1 | 1/3 | 0/3 | 1/7 |

Unilateral hydroureter (2/7 animals): 1 animal in Group 1 (animal 1) and 1 animal in Group 3 (animal 6). Bilateral hydroureter (2/7 animals): 1 animal in Group 2 (animal 2) and 1 animal in Group 3 (animal 5). Unilateral hydronephrosis (2/7 animals): 2 animals in Group 3 (animals 5 and 6). Bilateral hydronephrosis (2/7 animals): 1 animal in Group 1 (animal 1) and 1 animal in Group 2 (animal 2). Pyelonephritis (bilateral) was observed in 1 of 7 animals; Group 2 (animal 2). The one animal that survived to the scheduled sacrifice (Group 2 animal 4, Day 83) did not have hydroureter, hydronephrosis or pyelonephritis.

Findings related to Regeneration of a Urinary Conduit. Detailed findings of tissue components observed in each section harvested was collected (data not shown).

Inter-group incidences for regenerated conduit findings are shown in the following tables. The table 4.17 below shows the NUC Summary of findings by Group.

TABLE 4.17

| | Group: Treatment: | | |
|---|---|---|---|
| | 1 Scaffold Only | 2 Autologous Blood SMC | 3 Autologous Adipose SMC |
| | Mean Days on Study: | | |
| | 47 | 54 | 43 |
| Incidence of Select Findings by Conduit Location (# animals with finding/# animals examined at that location) | | | |
| Presence of Urothelium | | | |
| Left Ureter Conduit Junction (Slide 14) | 1/1 | 1/3 | 3/3 |
| Right Ureter Conduit Junction (Slide 16) | 0/1 | 1/3 | 3/3 |
| Cranial (Ureter) End of Conduit Body (Slides 6 or 10) | 0/1 | 1/3 | 0/3 |
| Middle of Conduit Body (Slides 7 or 11) | 0/1 | 1/3 | 0/3 |
| Caudal Conduit Body/Atrium (Slides 8, 9, 12 or 13) | 0/1 | 0/3 | 0/3 |
| Atrium-Stoma-Skin Junction (Slide 18) | 0/1 | 0/3 | 0/3 |
| Presence of Squamous Epithelium in Atrium/Conduit | | | |
| Left Ureter Conduit Junction (Slide 14) | 0/1 | 0/3 | 0/3 |
| Right Ureter Conduit Junction (Slide 16) | 0/1 | 0/3 | 0/3 |
| Cranial (Ureter) End of Conduit Body (Slides 6 or 10) | 0/1 | 0/3 | 0/3 |
| Middle of Conduit Body (Slides 7 or 11) | 0/1 | 0/3 | 0/3 |

TABLE 4.17-continued

| | Group: Treatment: | | |
|---|---|---|---|
| | 1 Scaffold Only | 2 Autologous Blood SMC | 3 Autologous Adipose SMC |
| | Mean Days on Study: | | |
| | 47 | 54 | 43 |
| Incidence of Select Findings by Conduit Location (# animals with finding/# animals examined at that location) | | | |
| Caudal Conduit Body/Atrium (Slides 8, 9, 12 or 13) | 0/1 | 1/3 | 0/3 |
| Atrium-Stoma-Skin Junction (Slide 18) | 0/1 | 2/3 | 1/3 |
| Smooth Muscle | | | |
| Left Ureter Conduit Junction (Slide14) | 1/1 | 0/3 | 1/3 |
| Right Ureter Conduit Junction (Slide 16) | 0/1 | 1/3 | 1/3 |
| Cranial (Ureter) End of Conduit Body (Slides 6 or 10) | 0/1 | 1/3 | 0/3 |
| Middle of Conduit Body (Slides 7 or 11) | 0/1 | 1/3 | 0/3 |
| Caudal Conduit Body/Atrium (Slides 8, 9, 12 or 13) | 0/1 | 0/3 | 0/3 |
| Atrium-Stoma-Skin Junction (Slide 18) | 0/1 | 0/3 | 0/3 |
| Surface of Chronic-Active Inflammation/Detritus | | | |
| Left Ureter Conduit Junction (Slide14) | 0/1 | 3/3 | 1/3 |
| Right Ureter Conduit Junction (Slide 16) | 1/1 | 2/3 | 1/3 |
| Cranial (Ureter) End of Conduit Body (Slides 6 or 10) | 1/1 | 3/3 | 3/3 |
| Middle of Conduit Body (Slides 7 or 11) | 1/1 | 3/3 | 3/3 |
| Caudal Conduit Body/Atrium (Slides 8, 9, 12 or 13) | 1/1 | 3/3 | 3/3 |
| Atrium-Stoma-Skin Junction (Slide 18) | 1/1 | 3/3 | 2/3 |
| Attenuation, Urothelium | 1/1 | 0/3 | 2/3 |
| Hyperplasia, Urothelium | 0/1 | 1/3 | 1/3 |
| Vacuolation, Urothelium | 0/1 | 0/3 | 1/3 |
| Hemorrhage, Conduit Wall | 1/1 | 1/3 | 1/3 |
| Scaffold Material, Conduit Wall | 0/1 | 0/3 | 2/3 |
| Increased Collagen, Scaffold Wall | 1/1 | 0/3 | 0/3 |
| Adhered GI Tract (P = present) | 0/1 | 2/3 | 0/3 |
| Fistula/neutrophil Tract to Intestines | 0/1 | 2/3 | 0/3 |
| Acanthosis, skin, stoma | 0/1 | 2/3 | 1/3 |
| Brown and Hopps Gram Stain | | | |
| Gram positive bacteria in detritus | 1/1 | 3/3 | 3/3 |
| Gram negative bacteria in detritus | 1/1 | 3/3 | 3/3 |

Table 4.18 below shows the NUC Summary of findings by Group (Non-PCV-2 Animals).

TABLE 4.18

| | Group: Treatment: | | |
|---|---|---|---|
| | 1 Scaffold Only | 2 Autologous Blood SMC | 3 Autologous Adipose SMC |
| | Mean Days on Study: | | |
| | 47 | 40 | 34 |
| Incidence of Select Findings by Conduit Location (# animals with finding/# animals examined at that location) | | | |
| Presence of Urothelium | | | |
| Left Ureter Conduit Junction (Slide14) | 1/1 | 0/1 | 2/2 |
| Right Ureter Conduit Junction (Slide 16) | 0/1 | 0/1 | 2/2 |
| Cranial (Ureter) End of Conduit Body (Slides 6 or 10) | 0/1 | 0/1 | 0/2 |
| Middle of Conduit Body (Slides 7 or 11) | 0/1 | 0/1 | 0/2 |
| Caudal Conduit Body/Atrium (Slides 8, 9, 12 or 13) | 0/1 | 0/1 | 0/2 |
| Atrium-Stoma-Skin Junction (Slide 18) | 0/1 | 0/1 | 0/2 |
| Presence of Squamous Epithelium in Atrium/Conduit | | | |
| Left Ureter Conduit Junction (Slide14) | 0/1 | 0/1 | 0/2 |
| Right Ureter Conduit Junction (Slide 16) | 0/1 | 0/1 | 0/2 |
| Cranial (Ureter) End of Conduit Body (Slides 6 or 10) | 0/1 | 0/1 | 0/2 |
| Middle of Conduit Body (Slides 7 or 11) | 0/1 | 0/1 | 0/2 |
| Caudal Conduit Body/Atrium (Slides 8, 9, 12 or 13) | 0/1 | 0/1 | 0/2 |
| Atrium-Stoma-Skin Junction (Slide 18) | 0/1 | 1/1 | 0/2 |
| Smooth Muscle | | | |
| Left Ureter Conduit Junction (Slide14) | 1/1 | 0/1 | 1/2 |
| Right Ureter Conduit Junction (Slide 16) | 0/1 | 0/1 | 1/2 |
| Cranial (Ureter) End of Conduit Body (Slides 6 or 10) | 0/1 | 0/1 | 0/2 |
| Middle of Conduit Body (Slides 7 or 11) | 0/1 | 0/1 | 0/2 |
| Caudal Conduit Body/Atrium (Slides 8, 9, 12 or 13) | 0/1 | 0/1 | 0/2 |
| Atrium-Stoma-Skin Junction (Slide 18) | 0/1 | 0/1 | 0/2 |
| Surface of Chronic-Active Inflammation/Detritus | | | |
| Left Ureter Conduit Junction (Slide14) | 0/1 | 1/1 | 1/2 |
| Right Ureter Conduit Junction (Slide 16) | 1/1 | 1/1 | 1/2 |
| Cranial (Ureter) End of Conduit Body (Slides 6 or 10) | 1/1 | 1/1 | 2/2 |
| Middle of Conduit Body (Slides 7 or 11) | 1/1 | 1/1 | 2/2 |
| Caudal Conduit Body/Atrium (Slides 8, 9, 12 or 13) | 1/1 | 1/1 | 2/2 |
| Atrium-Stoma-Skin Junction (Slide 18) | 1/1 | 1/1 | 1/2 |
| Attenuation, Urothelium | 1/1 | 0/1 | 2/2 |

TABLE 4.18-continued

| | Group: Treatment: | | |
|---|---|---|---|
| | 1 Scaffold Only | 2 Autologous Blood SMC | 3 Autologous Adipose SMC |
| | Mean Days on Study: | | |
| | 47 | 40 | 34 |
| Incidence of Select Findings by Conduit Location (# animals with finding/# animals examined at that location) | | | |
| Hyperplasia, Urothelium | 0/1 | 0/1 | 0/2 |
| Vacuolation, Urothelium | 0/1 | 0/1 | 0/2 |
| Hemorrhage, Conduit Wall | 1/1 | 0/1 | 1/2 |
| Scaffold Material, Conduit Wall | 0/1 | 0/1 | 2/2 |
| Increased Collagen, Scaffold Wall | 1/1 | 0/1 | 0/2 |
| Adhered GI Tract (P = present) | 0/1 | 1/1 | 0/2 |
| Fistula/neutrophil Tract to Intestines | 0/1 | 1/1 | 0/2 |
| Acanthosis, skin, stoma | 0/1 | 1/1 | 1/2 |
| Brown and Hopps Gram Stain | | | |
| Gram positive bacteria in detritus | 1/1 | 1/1 | 2/2 |
| Gram negative bacteria in detritus | 1/1 | 1/1 | 2/2 |

The conduit that developed after surgical implantation of the test article consisted of a central lumen that coursed from ureters (cranial end) through the implant and atrium to the stomal opening in the skin of the ventral abdomen. The extent of urinary-like tissue regeneration in the construct groups (Groups 2 and 3) was influenced by duration of animal survival postimplantation. Since animals were sacrificed at various time points post-implantation, the observed regenerative process was in different stages and the extent of urinary-like tissue present in each group varied based on time post-implantation and presence or absence of SMC.

Ureter-Conduit Junction, Cranial and Mid-Portions of Conduit. The typical composition of tissue near the cranial end of the conduit encompassing the ureterconduit junction (UCJ; Sections 14 and 16 in FIG. 44) was urothelium overlying a variably-sized submucosa and layers of smooth muscle fibers with interspersed connective tissue (FIGS. 27-28).

Figure 45:
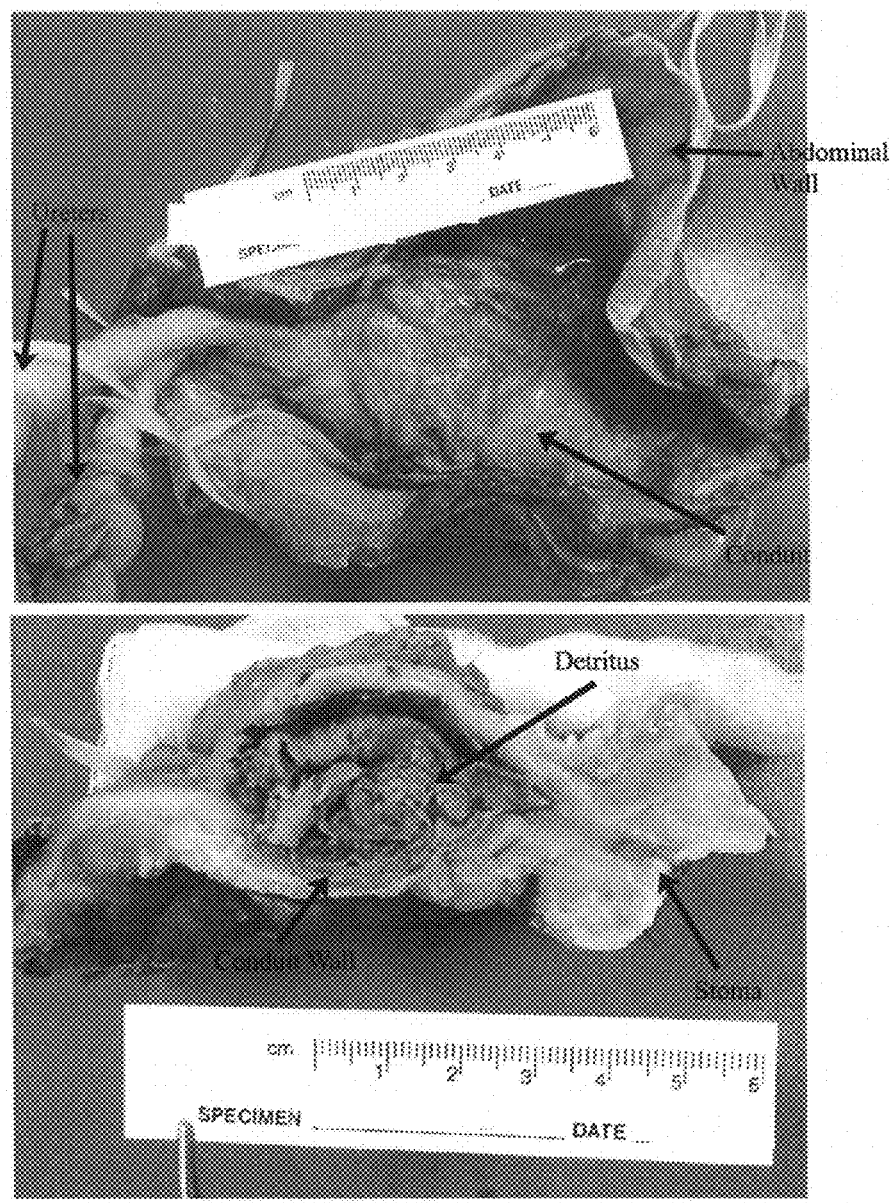
FIG. 45 shows subgross photographs of animals implanted with a neo-urinary conduit construct.

FIG. 45 shows subgross photographs of animal 6 of Group 3 (adipose-derived SMC) in the upper panel and animal 1 of Group 1 in the lower panel.

Figure 46:
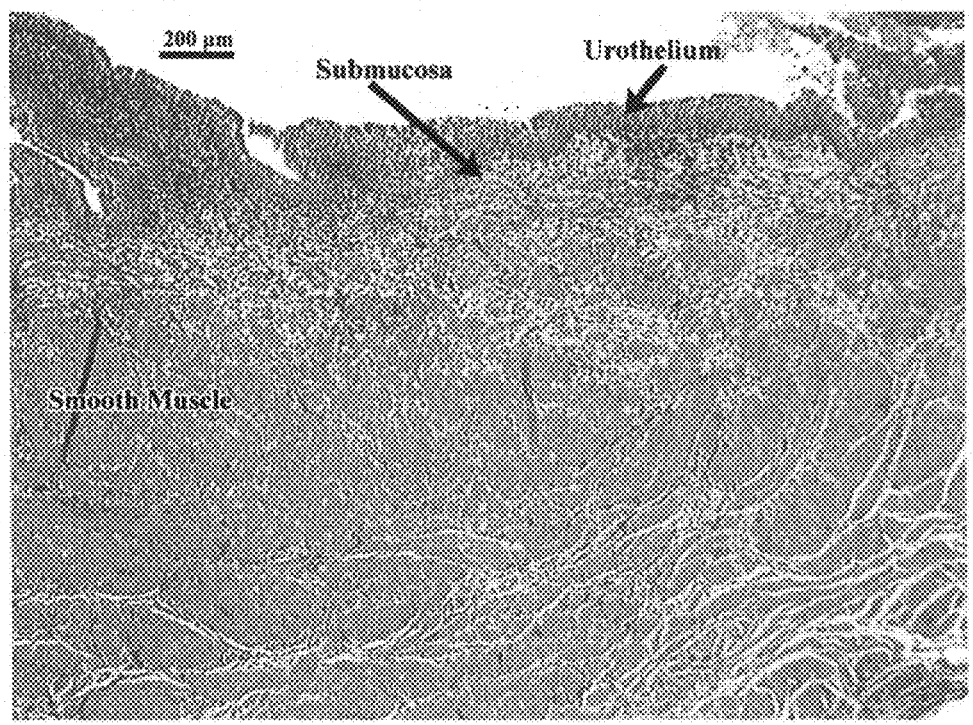
FIG. 46 shows a photomicrograph of a neo-urinary conduit near the ureter-conduit junction in an animal implanted with a neo-urinary conduit construct.

FIG. 46 shows a photomicrograph (Massons's trichrome stain) of a neo-urinary conduit near the ureter-conduit junction from Group 2 animal 4 (blood-derived SMC). The urothelium is evident over a thin submucosa and smooth muscle layers.

Figure 47:
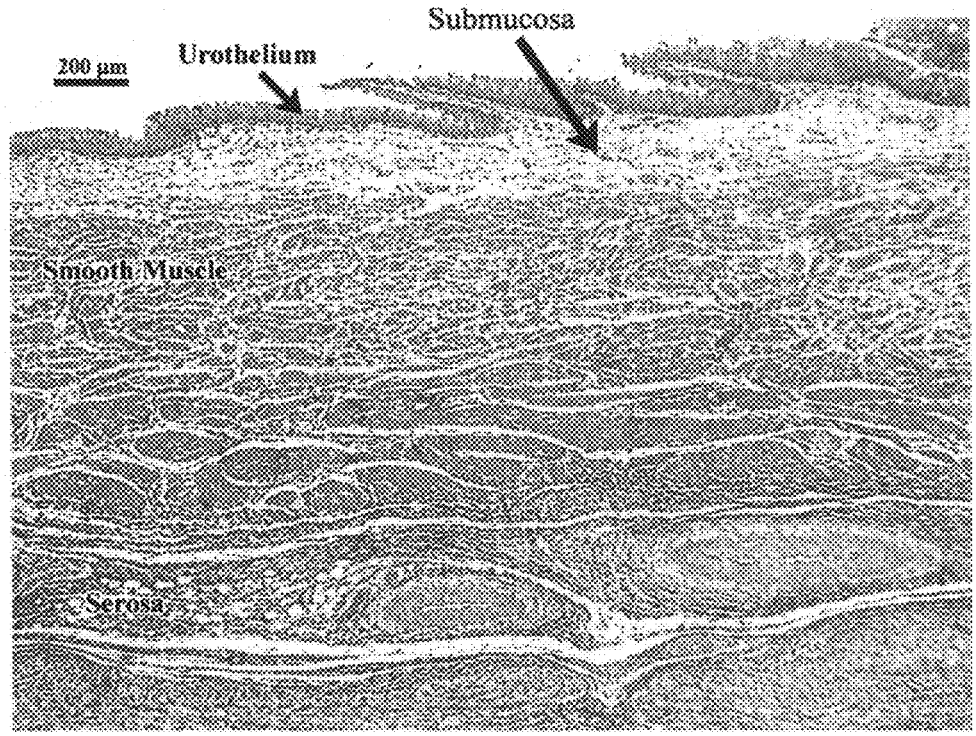
FIG. 47 shows a photomicrograph of a neo-urinary conduit near the ureter-conduit junction in an animal implanted with a neo-urinary conduit construct.

FIG. 47 shows a photomicrograph (Massons's trichrome stain) of a neo-urinary conduit near the ureter-conduit junction from Group 3 animal 6 (adipose-derived SMC). The urothelium is evident over a thin submucosa and smooth muscle layers.

Figure 48:
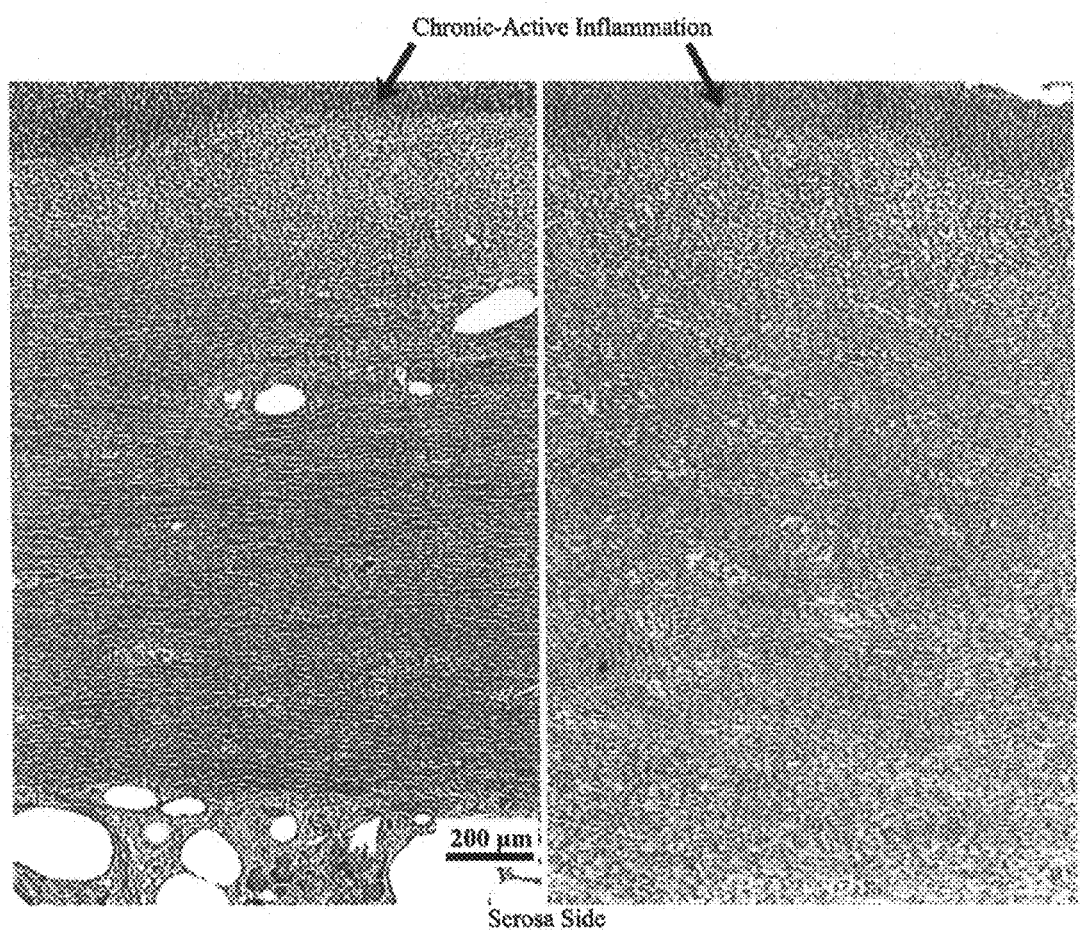
FIG. 48 shows photomicrographs of the mid-conduit walls of animals implanted with a neo-urinary conduit construct.

FIG. 48 shows photomicrographs (Massons's trichrome stain) of a mid-conduit wall of animal 1 (Group 1) (left panel) and animal 3 (Group 2) (right panel). The mid-conduit wall closest to the lumen was often lined by chronic-active inflammation. The wall of the scaffold-only (Group 1) animal is made primarily of blue-stained collagen (reparative), while the wall of the construct on the right is primarily made up of (regenerative) red-staining spindle cells (presumably myocytes, fibroblasts, and myofibroblasts).

In the animal that survived to scheduled sacrifice, portions of the cranial and mid conduit were similar in appearance. Where urothelium and smooth muscle layering were present within the conduit, they were morphologically similar to the ureters, although the conduit wall thickness was typically greater than that of the ureter, particularly within diverticula. Diverticula appeared as bi-compartmental portions of conduit projecting caudally from the left and right ureteral-conduit junctions. The typical appearance of urothelium was mildly vacuolated and variable in thickness. Urothelium thickness varied between minimally-to-moderately attenuated (especially within a large diverticulum) and mildly hyperplastic.

Urothelium was present at the ureter-conduit junction (UCJ; Sections 14 and/or 16 in FIG. 44) in 5/7 animals (Table 4.19): 1 animal in Group 1 (animal 1), 1 animal in Group 2 (animal 4) and 3 animals in Group 3 (animals 5, 6, and 7). Urothelium was present at the cranial and mid portions (Sections 6 and/or 10 in FIG. 44; Sections 7 and/or 11 in FIG. 44) in 1/7 animals: 1 animal in Group 2 (animal 4). Smooth muscle was present at the ureter-conduit junction (UCJ; Sections 14 and/or 16 in FIG. 44) in 4/7 animals: 1 animal in Group 1 (animal 1), 1 animal in Group 2 (animal 4) and 2 animals in Group 3 (animals 5 and 6). Smooth muscle was present at the cranial and mid portions (Sections 6 and/or 10 in FIG. 44 Sections 7 and/or 11 in FIG. 44) in 1/7 animals: 1 animal in Group 2 (animal 4).

The extent of urinary-like tissue regeneration was dependant upon time post-implantation. The one animal that survived to scheduled sacrifice (Group 2 animal 4, day 83) had urothelium and smooth muscle present at the UCJ, cranial and mid portions of the conduit.

The following table 4.19 shows the incidence of Urothelium and Smooth Muscle in UCJ, Cranial and Mid Conduit (Group 1=Scaffold-only, Group 2=Blood-derived SMC construct, and Group 3=Adipose-derived SMC construct).

TABLE 4.19

| Finding | Group 1 N = 1 | Group 2 N = 3 | Group 3 N = 3 | Total N = 7 |
|---|---|---|---|---|
| Presence of Urothelium | | | | |
| UCJ (slides 14 and/or 16) | 1/1 | 1/3 | 3/3 | 5/7 |
| Cranial (Ureter) End of Conduit Body (Slides 6 and/or 10) | 0/1 | 1/3 | 0/3 | 1/7 |
| Middle (Mid) of Conduit Body (Slides 7 and/or 11) | 0/1 | 1/3 | 0/3 | 1/7 |
| Presence of Smooth Muscle | | | | |
| UCJ (slides 14 and/or 16) | 1/1 | 1/3 | 2/3 | 4/7 |
| Cranial (Ureter) End of Conduit Body (Slides 6 and/or 10) | 0/1 | 1/3 | 0/3 | 1/7 |
| Middle (Mid) of Conduit Body (Slides 7 and/or 11) | 0/1 | 1/3 | 0/3 | 1/7 |

Caudal Portion of Conduit. The point of transition from conduit to atrium varied between animals because the caudal end of the implant floated freely within the peritoneal wrapping making the transition from conduit to atrium difficult to define at necropsy. The typical composition of Sections 8 and 12 (presumed caudal conduit, FIG. 44) was organized collagen with associated fibroblasts and/or myofibroblasts. Internal to the collagenous wall and closest to the lumen was a layer of chronicactive inflammation comprised of loosely arranged collagen, capillaries and abundant neutrophils with fewer lymphocytes and macrophages. Internal to the inflammation, the lumen was often filled with detritus comprised of degenerate or necrotic inflammatory cells (primarily neutrophils) and cellular debris with admixed bacterial colonies. By Brown and Hopps gram stain, bacterial colonies were both gram positive and gram negative. Most of the gram positive bacteria were cocci; however, both cocci and rod-shaped gram negative and gram positive bacteria were observed. The scaffold-only animal (Group 1) had only minimal regeneration near the ureter on one side, and the remainder of the conduit body was almost solely comprised of collagen fibers with minimal fibroblasts. In the animals receiving constructs (Groups 2 and 3), regeneration tended to be more extensive, and in other parts of the conduit, the wall was comprised of a mix of collagen, fibroblasts and other spindle cells (presumed myofibroblasts and myocytes).

Atrium and Stoma Portions of Conduit. At the region of the atrium-stomal end of the conduit (Sections 9, 13 and 18 in FIG. 44), the stoma-atrium junction was visible where the organized collagen and adnexa of the stomal dermis apposed the atrium wall. These sections consisted mainly of squamous epithelium and chronic-active inflammation/detritus. In 3/7 animals (animals 3 and 4 of Group 2, and animal 7 of Group 3), the squamous epithelium (epidermis) of the skin extended cranially for a short distance over the atrium. The external surface of the atrium was comprised of loose connective tissue of peritoneum origin. This external covering was the equivalent of a serosal layer and contained nerves, blood vessels, adipose tissue, and some areas of fibrous connective tissue (collagen fibers and fibroblasts). There was no evidence of urinary-like tissue regeneration at the atrium-stomal end of the conduit (Sections 9, 13 and 18 in FIG. 44) in any animal.

Other Findings. In 2/7 animals, scaffold material was observed in the conduit wall. This was observed in all levels of the conduit body in Group 3 animal 5 (day 28), and only in the atriumconduit junction of Group 3 animal 6 (day 39).

DISCUSSION. Animals survived 28-83 days. One of 7 animals survived until scheduled sacrifice (animal 4 of Group 2, 83 days). Six of 7 animals were sacrificed unscheduled: animal 5 (Group 3) was electively euthanized 28 days post-implantation for histopathological analysis and 5 animals were euthanized for poor clinical condition between 38 and 63 days post-implantation (Group 1 animal 1; Group 2 animals 2 and 3; and Group 3 animals 6 and 7).

PCV-2 infection was confirmed in 3/7 animals. Two PCV-2 infected animals were unscheduled necropsy animals. These included one animal in Group 2 (animal 2) euthanized on day 38 and another animal in Group 3 (animal 7) euthanized on day 63. The third animal identified with PCV-2 infection, Group 2 animal 4, survived to scheduled sacrifice (83 days). In these 3 animals, there were pathological signs compatible with concurrent infection with PCV-2 during the course of this study. A macroscopic finding related to viral infection was skin discoloration in one animal (Group 2 animal 4). Microscopic findings included renal changes consisting of tubular necrosis/fluid/casts/glomerulonephritis, eosinophilic intracellular inclusions in tubular epithelial cells in the kidney, and vasculitis/perivascular inflammation in the kidneys and ureters. These findings are among those commonly reported for pigs with PCV-2 infection. The infection with PCV-2 contributed to the poor clinical health of the animals (e.g. lethargy, diarrhea, loss of appetite) and subsequent humane early euthanasia. Obstruction of urine flow through the conduit and stoma contributed to the morbidity in 4/6 unscheduled death animals. These included Group 1 animal 1, euthanized on day 47; Group 2 animals 2 and 3, euthanized on days 38 and 40; and Group 3 animal 6, euthanized on day 39. Obstruction was caused by a combination of the surgical placement of the test article along the abdominal floor of the pig where the weight of abdominal viscera compressed the implant, and the use of peritoneum to form an atrium segment connecting the conduit to the skin resulting in detritus buildup from the external environment and mucus in the urine (normal for swine). Relevant postoperative complications that are inherent in this quadruped animal model include: (i) abdominal adhesions leading to potential fistula formation and (ii) location of the test article placement in relation to the abdominal organs. When intestines were the adhered organ, the tunica muscularis of the adhered segment of intestine was often diminished or eroded at the point of adhesion, as was the atrium wall. Test articles were placed on the ventral abdomen wrapped with peritoneum and formed a urinary conduit from the ureters to the skin surface. The test articles were anchored at the cranial end to the ureters, but floated freely within the peritoneal wrapping at the caudal end where the peritoneum formed the passage through the abdominal wall and onto the skin surface. Smooth muscle and/or urothelium formation occurred near to the conduit-ureter junctions in 5/7 animals and at the cranial end of the conduit (where the implanted test article was present within the peritoneal wrap) in the one animal surviving to scheduled sacrifice (Group 2 animal 4, day 83). The middle and caudal portions of the conduit were comprised of fibrous connective tissue walls without urothelial covering (except in Group 2 animal 4, in which urothelium and smooth muscle were observed in the middle level of the conduit). Regeneration of urinary-like tissue was evident as early as day 28, with presence of urothelium, lamina propria and smooth muscle bundles at the ureter-conduit junction (UCJ) in electively euthanized animal 5 (Group 3, adipose-derived SMC). The regenerative process at the ureteral end of the implant resulted in urinary-like tissue formation that was comparable among animals receiving a construct implant (Groups 2 and 3). The extent of urinary-like tissue regeneration in the construct groups (Groups 2 and 3) was influenced by duration of animal survival post-implantation. The one animal surviving to scheduled sacrifice (Group 2 animal 4, day 83) had urothelium and smooth muscle present in the UCJ, cranial and mid portions of the conduit in spite of a detected viral infection. However, the peritoneum-only atrium was insufficient to support urinary-like tissue regeneration and the tissue formed in the atrium had a wall comprised of fibrous connective tissue without urothelial mucosal lining. The point of transition from conduit to atrium varied between animals because the caudal end of the implant floated freely within the peritoneal wrapping making the transition from conduit to atrium difficult to define at necropsy. The typical composition of Sections 8 and 12 (presumed caudal conduit, FIG. 44) was organized collagen with associated fibroblasts and/or myofibroblasts. Peritoneum conduit without cellular construct appears to be insufficient for urinary-like tissue regeneration, but does serve as a source of vascularization to NUC implants.

Conclusions.

Regeneration of urinary-like tissue was evident as early as 28 days with presence of urothelium, lamina propria and smooth muscle bundles at the ureter-conduit junction (Animal 5, Adipose-derived SMC).

Despite complications from a viral infection and animal model, construct (Scaffold seeded with SMC derived from blood or adipose) implantation (Groups 2 and 3, respectively) resulted in the formation of a conduit having a urinary-like tissue wall composed of mucosa and smooth muscle layers.

The extent of urinary-like tissue regeneration in the construct groups (Groups 2 and 3) was influenced by duration of animal survival post-implantation. The one animal that survived to scheduled sacrifice and was infected with PCV-2 (Group 2 animal 4, day 83) had urothelium and smooth muscle present at the UCJ, cranial and mid portions of the conduit.

There were no apparent differences observed in the regenerative process when scaffolds were seeded with SMC derived from blood or adipose, (Groups 2 and 3, respectively) suggesting equivalence between SMC sources in promoting regeneration.

Animal model anatomy led to the observed complications (i.e., location of test article in abdomen, peritoneum to form the atrium, compression of the test article by abdominal contents with formation of adhesions and fistulas, and detritus buildup that lead to subsequent obstruction).

PCV-2 infection was confirmed in 3/7 animals. Two PCV-2 infected animals were unscheduled necropsy animals. Obstruction of the urinary flow as a result of surgical implantation site and abdominal content compressing the lumen contributed to 4/6 unscheduled deaths. One animal (Group 3 animal 5) was electively euthanized at day 28 for histopathological evaluation.

Example 5

Evaluation of an Implanted Neo-urinary Conduit Constructs in a Swine Model

The objective of this study was to evaluate the safety and functionality of the neo-urinary conduit seeded with autologous smooth muscle cells (SMC) derived from the urinary bladder, adipose, or blood. Additionally, a scaffold-only treatment (not seeded with SMC) was evaluated.

Methods: Neo-Urinary Conduit (NUC) test articles were comprised of a scaffold formed from nonwoven polygycolic acid (PGA) felts and poly(lactic-co-glycolic acid) polymers (PLGA) with or without autologous smooth muscle cells (SMC). Unless otherwise indicated, the protocols followed herein are essentially the same as those followed in Example 3.

The study consisted of 32 Gottingen minipigs (16 Females, 16 Males), divided into four groups of 8 animals (4 males and 4 females each group) that were assigned to receive one of the four test articles. Biopsies of urinary bladder, adipose tissue, and a sample of venous blood were obtained from animals in Groups 1, 2, and 3 (construct) 6-10 weeks prior to test article implantation. Animals in Groups 1, 2, and 3 were implanted with a test article seeded with SMC derived from bladder, adipose, or blood, respectively. Animals in Group 4 were not biopsied and were implanted with a scaffold-only test article. Animals in Groups 1-3 experienced two surgical procedures (biopsy plus test article implantation) and Group 4 animals experienced one surgical procedure (test article implantation). Test articles were surgically implanted into all animals (Groups 1-4) on Day 0 by removing the urinary bladder (radical cystectomy) and diverting the ureters to the inflow end of the test article. Test articles were placed on the ventral floor of the abdominal cavity and intra-abdominally, having no direct exposure to ambient air from the skin stoma which emptied off-midline to the right cranial abdominal quadrant near the xiphoid. Peritoneum was wrapped around the test article to provide a vascular source, water-tightness, and to channel urine to an outflow skin stoma. The peritoneal wrap extended approximately 5 to 7 cm beyond the caudal end of the test article (located in the intra-abdominal cavity) through the abdominal wall to the skin surface to form a channel for urine outflow; a structure referred to as an "atrium" in this report. Blood and urine samples were collected at designated time points, analyzed, and results recorded. Imaging (fluoroscopy, ultrasonography, and/or endoscopy) of the implants, ureters, and kidneys were performed at designated time points during the study. Imaging was also performed as needed in response to observed clinical symptoms.

The abdominal cavity was opened and the conduit (the outcome of implanting a construct or scaffold-only test article), was visualized and digitally photographed in situ at the animal facility. The conduit was removed en bloc with the skin stoma, kidneys, and ureters. The ureters were measured, and then detached from the conduit by transverse sectioning 3-4 cm away from the anastomoses. Representative tissue samples of the entire urinary tract from kidneys to skin stoma, regional lymph nodes, and any other lesions observed grossly were obtained. All tissue samples were placed in 10% Neutral Buffered Formalin (NBF) for 24-48 hours for histological processing and evaluation. Post fixation, tissues were processed routinely to microslides and stained with hematoxylin and eosin (H&E) and Masson's trichrome. Slides were evaluated microscopically.

Results

Mortality: During definitive surgery, the ureters of animal 30 (Group 4) were perforated, thus preventing test article implantation. The animal was euthanized on Day 0 and not replaced, reducing the total N of animals implanted with test articles (construct or scaffold only) to 31 and the N of Group 4 to 7 animals. All other animals were successfully implanted with test devices and recovered from surgery. Animals survived 6-84 days post-implantation. Twenty-four animals were unscheduled deaths and seven animals survived until the scheduled sacrifice.

Findings related to the safety of the Construct and Scaffold-only treatment groups: Postoperative clinical observations were similar across groups. The most common of these were stoma flow interruption (31/31 animals), loss of appetite (30/31 animals), soft feces (23/31 animals) and body weight loss (21/31 animals). During in-life clinical observations, skin lesions consistent with PCV-2 infection were observed. Twelve of the 24 unscheduled death animals developed one or more lesions, consistent with distinct pathological features ascribed to porcine dermatitis and nephropathy syndrome (PDNS), associated with PCV-2 infection. The PCV-2 animals will not be discussed in the results section as the PCV-2 condition was deemed an assignable cause of morbidity unrelated to the device. Available data for all animals was obtained (data not shown). Animals were classified as PCV-2-infected if any of the following were observed: 1) Clinically-observed purple skin discoloration; 2) Microscopic vasculitis or vasculitis/perivasculitis affecting the kidney, skin or lung; 3) Kidney findings of tubular necrosis/fluid/casts/glomerulonephritis, or viral inclusions of tubular epithelial cells; 4) Lymphocyte depletion in lumbar lymph nodes in the presence of 1, 2, or 3.

By these criteria, porcine PCV-2 infection was confirmed in 12 of the 24 unscheduled necropsy animals: 5/8 animals in Group 1, 4/8 animals in Group 2, 2/8 animals in Group 3, and 1/7 animals in Group 4. An important clinical observation in all animals was intermittent obstruction of the outflow of urine with or without atrial, stomal, or stent debris accumulation. Obstruction appeared to have been facilitated by the placement of the test article in the ventral portion of the abdominal cavity and an anatomic relationship where the weight of the overlying abdominal organs could lead to conduit closure, adhesion and fistula formation, and renal complications (e.g., dilation, inflammation, and/or infection of ureters or kidney).

Surgical placement of the test article was the same in all study animals; therefore, obstruction-related complications had a similar pathobiological mechanism (i.e., abdominal viscera resting on the conduit because of the quadruped anatomy or detritus build up in stoma) in all groups. Obstructions led to significant safety findings consisting of hydroureter, hydronephrosis, pyelonephritis, adhesions, and fistula formation. Hydroureter and hydronephrosis were linked to intermittent complete obstruction of the urine outflow. Pyelonephritis was considered secondary to the debris and detritus build-up and bacterial contamination of the stoma from feces and skin and was most prevalent in the scaffold-only group (Group 4). The surgical positioning of the test article and multiple surgeries for animals in Groups 1-3 (biopsy and test article implantation) promoted the formation of abdominal and pelvic adhesions. The debridement protocol (use of forceps in tranquilized animals), urinary flow obstruction, viral infection, and adhesions of intestinal tract to the conduit contributed to enteric-conduit fistula formation.

Findings related to Regeneration: The conduit that developed after surgical implantation of the test article consisted of a central lumen that coursed from ureters (cranial end) through the implant and atrium to the stomal opening in the skin of the ventral abdomen. The histological appearance of the conduit wall varied depending upon location of sample within the conduit and animal survival time. Urinary tissue-like regeneration characterized by mucosa, submucosa and smooth muscle with a fibrovascular stroma was observed after construct (Groups 1-3) test article implantation regardless of SMC source (i.e., bladder, adipose, or blood). Areas of urinary tract tissue, comprised of continuous urothelium with underlying smooth muscle, were observed in a majority of animals implanted with construct test articles. In contrast, a reparative process was observed following implantation of the scaffold-only test article characterized by an abnormal mucosa supported by fibrovascular stroma with limited smooth muscle. The extent of urinary-like tissue regeneration in the construct groups was influenced by duration of animal survival post-implantation.

Conclusions: Seven of 31 (23%) animals completed this study. PCV-2 viral infection and partial to full urinary obstruction of the urinary flow as a result of surgical implantation site and abdominal content compressing the lumen contributed to 23/24 unscheduled deaths. An in-life surgical procedure-related complication contributed to 1/24 unscheduled death. Safety findings associated with intermittent obstruction of the conduit were hydronephrosis, hydroureter, pyelonephritis, adhesions, and fistulas.

Healing and regeneration was observed in portions of conduits derived from any of the construct test articles while healing and repair was observed in the conduits derived from the scaffold-only test article, demonstrating that construct implantation resulted in the formation of a conduit having a native urinary-like tissue wall composed of mucosa and smooth muscle layers.

The difference in healing between the construct test articles (regeneration) and scaffold-only test article (repair) contributed to a higher incidence of significant renal findings observed with the scaffold-only test article, leading to a determination that the scaffold-only test article was unsuitable for further development.

There were no differences observed in the regenerative process and outcome between construct test articles, suggesting equivalence between SMC sources in promoting regeneration.

The objective of this study was to determine the safety and functionality of the Neo-Urinary Conduit (NUC) seeded with autologous smooth muscle cells (SMC) derived from the urinary bladder, adipose or blood. Additionally, a scaffold only treatment (not seeded with SMC) was evaluated. The goal was to regenerate a tube-like conduit structure composed of urinary-like tissue mucosa and wall after surgical removal of the bladder (total cystectomy) and ureteral reimplantation to the inflow end of the test article. The in-life phase of the study lasted about 5 months.

Experimental Design.

Overview. Thirty-two Gottingen minipigs were divided into four groups (4/sex/group). Animals in Groups 1-3 underwent a surgical biopsy procedure 6-10 weeks prior to test article (construct) implantation to isolate, characterize, and expand the SMC needed to produce a construct. Construct or scaffold only test articles (Groups 1-4) were surgically implanted on Day 0. After surgical removal of the bladder (radical cystectomy) the ureters were diverted to the inflow end of the test article. Test articles were placed on the ventral floor of the abdominal cavity and kept intra-abdominally with no direct exposure to ambient air from the skin stoma which emptied off-midline to the right upper abdominal quadrant near the xiphoid. Peritoneum was wrapped around the test article to provide a vascular source, water-tightness, and to channel urine to an outflow skin stoma. The peritoneal wrap was also extended to form a channel for urine outflow from the caudal end of the test article (located in the intra-abdominal cavity) through the abdominal wall to the skin surface, a structure referred to as an "atrium" in this report. The test articles were tube-shaped scaffolds formed from nonwoven polygycolic acid (PGA) felts and poly(lactic-co-glycolic acid) polymers (PLGA) seeded with autologous SMC (construct) or without SMC (scaffold only). Group 1 animals were implanted with constructs seeded with bladder-derived autologous SMC, Group 2 with constructs seeded with adipose-derived autologous SMC, Group 3 with constructs seeded with blood-derived autologous SMC, and Group 4 animals with scaffolds only. Table 5.1 provides a summary of the study design.

TABLE 5.1

| Group No. | Treatment | No. of Animals M | No. of Animals F | Biopsy Procedure (Day ~70 to ~40) | Surgical Procedure (Day 0) | Postoperative procedures | Intended Necropsy Time Point |
|---|---|---|---|---|---|---|---|
| 1 | Autologous Bladder SMC | 4 | 4 | Removal of urinary bladder and adipose | Cystectomy followed by neo-urinary conduit | Fluoroscopic and ultrasonic examination, | 84 ± 5 days |

TABLE 5.1-continued

| Group No. | Treatment | No. of Animals M | F | Biopsy Procedure (Day ~70 to ~40) | Surgical Procedure (Day 0) | Postoperative procedures | Intended Necropsy Time Point |
|---|---|---|---|---|---|---|---|
| 2 | Autologous adipose SMC | 4 | 4 | biopsy, blood collection | implantation with transposition of ureters to cranial end. Whole test article wrapped in peritoneum, with a peritoneal transition from end of test article through skin to create incontinent stoma. | general health assessment and clinical treatment as necessary, clinical pathology and urinalysis | |
| 3 | Autologous Blood SMC | 4 | 4 | | | | |
| 4 | Scaffold only (no cells) | 4 | 4 | | | | |

Table 5.2 provides an overview of the study (TA=Test Article NA=Not applicable M=Male F=Female N=No Y=Yes; a—Animal found dead, b—Animal died under anesthesia, c—Ureter perforated at surgery; animal not replaced, d—Spare animals not utilized in study).

TABLE 5.2

| | Sex | Group | Cell Source | Cell Seeding Density (×106) | Adipose Tissue collected (g) | Implant Date (Day 0)/ Days after biopsy | Stent Removal (Day) | Survival days following implantation/ Necropsy Date | Unscheduled death (Y/N) |
|---|---|---|---|---|---|---|---|---|---|
| 1 | F | 1 | Bladder | 40.7 | 33.0 | 67 | 11 | 81 | N |
| 2 | F | | | 35.7 | 35.0 | 66 | 12 | 68 | Y |
| 3 | F | | | 29 | 33.0 | 64 | 11 | 69 | Y |
| 4 | F | | | 29 | 32.0 | 63 | 14 | 28 | Y |
| 5 | M | | | 24.9 | 5.0 | 63 | 14 | 44 | Y |
| 6 | M | | | 29 | 7.0 | 48 | 13 | 83 | N |
| 7 | M | | | 29 | 18.0 | 49 | 12 | 42 | Y |
| 8 | M | | | 29 | 13.0 | 51 | NA | 9 | Y |
| 9 | F | 2 | Adipose | 33.1 | 29.0 | 60 | 5 | 33 | Y |
| 10 | F | | | 29 | 26.0 | 68 | 8 | 30 | Y |
| 11 | F | | | 29.0 | 30.0 | 58 | 7 | 58 | Y |
| 12 | F | | | 40 | 35.0 | 73 | 5 | 70 | Y |
| 13[a] | M | | | 29 | 7.0 | 57 | 7 | 82 | Y |
| 14 | M | | | 29 | 9.0 | 55 | 8 | 63 | Y |
| 15 | M | | | 29 | 11.0 | 57 | 6 | 81 | N |
| 16[a] | M | | | 24 | 13.0 | 56 | 6 | 63 | Y |
| 17 | F | 3 | Blood | 29 | 35.0 | 59 | 6 | 48 | Y |
| 18 | F | | | 24.25 | 25.0 | 57 | 5 | 80 | N |
| 19 | F | | | 29 | 30.0 | 57 | 7 | 70 | Y |
| 20 | F | | | 40.7 | 40.0 | 58 | 5 | 6 | Y |
| 21 | M | | | 29 | 10.0 | 41 | 8 | 73 | Y |
| 22[b] | M | | | 29 | 0.0 | 56 | 7 | 51 | Y |
| 23 | M | | | 29 | 0.0 | 57 | 6 | 81 | N |
| 24 | M | | | 29 | 11.0 | 42 | 8 | 77 | Y |
| 25 | F | 4 | Scaffold only; no autologous cells | NA | NA | 0 | 9 | 84 | N |
| 26 | F | | | NA | NA | 0 | 9 | 84 | N |
| 27 | F | | | NA | NA | 0 | 9 | 20 | Y |
| 28[a] | F | | | NA | NA | 0 | 7 | 17 | Y |
| 29 | M | | | NA | NA | 0 | 7 | 48 | Y |
| 30[c] | M | | | NA | NA | NA | NA | NA | Y |
| 31 | M | | | NA | NA | 0 | 6 | 55 | Y |
| 32 | M | | | NA | NA | 0 | 6 | 31 | Y |
| 33[d] | F | spares | NA | NA | 26.0 | NA | NA | NA | Spare |
| 34[d] | M | | | NA | 0.0 | NA | NA | NA | Spare |

Blood and urine samples were collected at designated time points, analyzed and recorded.

Imaging (fluoroscopy, ultrasonography, and/or endoscopy) of the implants, ureters, and kidneys were performed at designated time points during the study. Imaging was also performed as needed in response to observed clinical symptoms. Animals survived 6-84 days post-implantation. At necropsy, the abdominal cavity was opened, the conduit visualized and photographed before the conduit was removed en bloc with kidneys and ureters. Ureter lengths and widths were measured and then detached from the conduit by transverse sectioning 3-4 cm away from the anastomoses. Representative sections of the kidneys, ureters, lymph nodes and any other lesions observed grossly were obtained. All tissue samples were placed in 10% Neutral Buffered Formalin (NBF) for 24-48 hours for histological processing and evaluation. Post-fixation, tissues were processed routinely to microslides and stained with hematoxylin and eosin (H&E) and Masson's trichrome. Slides were evaluated by a board-certified pathologist.

The pathology report appears in the Example below.

Materials and Methods.

Test Devices

The test articles were i) a conduit shaped scaffold comprising a synthetic lactide/glycolide polymer seeded with autologous bladder-derived pig smooth muscle cells ($24.9 \times 10^6$ cells, $40.7 \times 10^6$ cells, $29 \times 10^6$ cells, $24.25 \times 10^6$ cells, or $35.7 \times 10^6$ cells); ii) a conduit shaped scaffold comprising a synthetic lactide/glycolide polymer seeded with autologous blood-derived pig smooth muscle cells ($40.7 \times 10^6$ cells or $29 \times 10^6$ cells) iii) a conduit shaped scaffold comprising a synthetic lactide/glycolide polymer seeded with autologous adipose-derived pig smooth muscle cells ($24 \times 10^6$ cells, $40 \times 10^6$ cells, $33.1 \times 10^6$ cells, or $29 \times 10^6$ cells), and iii) a conduit shaped scaffold comprising a synthetic lactide/glycolide polymer without any cells seeded.

Thirty-two Gottingen minipigs (16 female and 16 male) were received from Marshall Farms (North Rose, N.Y.) on May 13, 2008. The animals were 7 months old. Three additional minipigs (2 females and 1 male) were received from the same vendor. These additional animals, which were 6 months old, were acquired as spares. Upon receipt, animals were examined for signs of disease or injury. Following initial examination, the animals from the initial shipment were held in quarantine for 6 days from day of receipt and were released for use in the study following a physical examination. The spare animals were held in quarantine for 4 days but were not used for this study.

Identification. Each animal was identified with a unique number that was indicated by ear tag and on the pen cards.

Initial group assignment was based on average group weight. Assignment changes for animals in Groups 1-3 were made based on ex-vivo cell expansion from harvested tissues and peripheral blood.

Surgical Procedures.

Biopsy/Tissue Collection: For animals in Groups 1-3 (construct test articles), biopsies of urinary bladder and adipose tissue, as well as venous blood, were obtained 6-10 weeks prior to Day 0 (implantation procedure). Group 4 animals (scaffold-only test article) did not undergo these procedures. For tissue biopsy procedures, a midline incision was made in the abdomen beginning immediately caudal to the umbilicus. Adipose biopsies of approximately 20-50 grams of soft, pliable subcutaneous adipose tissue (without connective tissue) were collected from this midline access point, if possible. Bladder biopsies (approximately 2.5 cm×2.5 cm) were collected from the apical dome of the urinary bladder. Collected tissue samples were individually and aseptically transferred to containers with tissue culture media. The defect in the bladder was then closed in at least two layers, using absorbable suture material. The abdominal incision was closed in layers with absorbable suture material of an appropriate size. The skin was closed in a subcuticular fashion, again using an appropriate size of absorbable suture material.

Approximately six 10-ml aliquots of venous blood per animal were collected in heparinized vacutainers. The vials of blood were then packaged in an ice pack-cooled container ($\sim 8°$ C.).

Cannulation Procedure. On Day 0 (test article implantation), an indwelling catheter was placed within the jugular vein of each animal to facilitate blood collection. The area surrounding the right jugular vein was shaved and prepared as described above. All animals were cannulated with a sterile 9.0Fr silicon catheter, which was inserted into the right external jugular vein and secured by suture to prevent movement. An extra-large DaVINCI port was attached and implanted in a subcutaneous pocket.

Test Device Implantation. A midline abdominal incision was made 5 cm cranial to the umbilicus and extended approximately 15 cm caudally. The peritoneum was identified and then carefully separated from the abdominal space. Care was taken to ensure the tissue remained intact and vascularized.

The urinary bladder was then exposed and carefully emptied of urine, ensuring no urine entered into the abdominal cavity. The arteries and veins supplying the bladder were identified and ligated. The ureters were identified, stented and carefully transected from the bladder. The urethra was oversewn as it was transected. The bladder was then removed. The left ureter was carefully separated from the surrounding retroperitoneal fascia (extending cranially) until there was enough mobility to reach the right side of test article. The right ureter was dissected free until it reached the inflow (cranial) end of the test article. The ureters were sutured onto the test article with 3-0 Vicryl in a simple continuous pattern. Peritoneum was wrapped around the test article to provide a vascular source, water-tightness, and to channel urine to an outflow skin stoma. The peritoneal wrap was also extended approximately 5-7 cm from the caudal end of the test article (located in the intra-abdominal cavity) to form a channel for urine outflow through the abdominal wall to the skin surface. The peritoneum was sutured with 3-0 Vicryl.

Stoma and Stoma Port Procedures. A stoma was created on the ventral abdominal wall lateral to the mammary glands. The peritoneal atrium without construct or scaffold-only, was exteriorized and sutured to the skin. Surgical adhesive was placed along the suture line and where the peritoneum exited the body wall. The suture strands connected to the stents were exteriorized through the stoma for future removal. A stoma port (TRACOE®) was placed. Approximately 1-3 months after implantation, a study specific stoma port was used on the remaining animals. For both types, after the stoma ports were secured the abdominal incision was closed with non-absorbable Prolene suture. The skin was closed in a routine fashion.

Monitoring Procedures. Vital signs (oxygen rate, oxygen $[O_2]$ saturation, pulse rate, respiration, and body temperature) were monitored at intervals of approximately 20 minutes throughout the procedure.

Postoperative Procedures.

Postoperative Drug Therapy. Concurrent therapy was permissible to maintain good animal health with the exception of aminoglycosides, quinolones, and corticosteroids. Each drug's identification, dose, route and frequency of administration were documented and are maintained in the study file.

During the survival period, clinical symptoms developed related to the progression of the study. These were addressed by the Facility veterinarian through drug therapy. The following drugs were utilized. Buprenorphine was used to control pain in the post operative period. Rimadyl (carprofen, an anti-inflammatory) was used post operatively and then as needed (i.e., post debridement of the stomal area). Excede (ceftiofur) is a long-acting cephalosporin antibiotic. This was used prophylactically to prevent infection, especially of the urinary tract. Baytril (enrofloxacin) is a fluoroquinolone antibiotic and was used to treat pneumonia and severe UTIs that did not respond to ceftiofur. Reglan (metoclopramide) was used to treat vomiting or constipation. Yobine was used to reverse the effects of the sedative xylazine.

Stent Removal. At various time points from 5-14 days post-implantation surgery the animals were anesthetized as described above and the ureteral stents were removed.

Postoperative Management.

Stoma port. For 2 weeks following implantation, stoma port was evaluated daily for patency (urine drainage). If urine was not observed to be dripping at examination, the stoma port was flushed with saline to assess patency.

Incision Site. Incision sites were also evaluated daily for 2 weeks following implantation (or until healed) for dehiscence, abnormal discharge, odor, irritation or any abnormalities.

Debridement: A debridement procedure was initiated because a detritus/caseous material was accumulating in the conduits and potentially impeding the free flow of urine. Animals on study had reached 35-52 days post-implantation. For debridement, animals were sedated as described. If the detritus material was larger than the stoma opening, a small incision was made on the stoma to facilitate debridement. The detritus was visually identified, grasped with forceps and gently tugged. Once all visible detritus was removed, the stoma was flushed with saline solution. Stoma incisions were closed with suture(s) and a fresh Study Specific Stoma port was inserted and secured to the animal with sutures. Animals were allowed to recover as per protocol.

Jugular Port. The jugular port catheter was flushed with injectable saline and locked with Heparin (100 U/mL, ~2-3 mL) weekly until Week 4 and at each subsequent use to assure patency.

Imaging

Intravenous Pyelography. During Week 8 and prior to necropsy, pyelograms were obtained following injection of a radiopaque contrast agent directly into the renal artery under fluoroscopic guidance. Animals were sedated for the procedure, and access was gained via either the femoral artery or a peripheral vein.

Loopography (Retrograde Pyelography). Five animals [Group 2 animals 9 (day 33) and 10 (day 30); Group 3 animals 17 (day 48) and Group 4 animals 27 (day 20) and 29 (day 41)] underwent loopography to confirm the presence of fistulas. Those animals were prepared for fluoroscopic imaging by washing, rinsing and drying the stoma abdominal area. A 3:1 mixture of saline: contrast medium was injected via the stoma into the conduit. Fluoroscopic imaging was then performed.

Ultrasonography. Ultrasound imaging of the conduit and kidneys was performed at baseline (kidneys only), during Weeks 2, 6, and 10, and prior to necropsy Animals were anesthetized for this procedure.

Observations.

Health Assessments. From the time of receipt until euthanasia, the animals were observed twice daily for abnormalities of appearance and behavior that might indicate adverse effects on health. At each check (performed approximately 8 hours apart), the technician walked through study room to confirm that all animals had eaten and that there was evidence of urine and fecal output in each cage pan. Physical signs such as lethargy, emaciation, abnormal vocalization, missing anatomy, and laceration, as well as abnormal behavioral signs, were noted, if present. Animals were not removed from their cages during these daily assessments. Any abnormal signs were documented.

Body Weights. Body weights were recorded prior to biopsy (Groups 1-3), prior to implant surgery (Groups 1-4), and prior to necropsy (Groups 1-4).

Clinical Pathology.

Blood. Blood samples for analysis of hematology (CBC), coagulation, and serum chemistry parameters were collected prior to biopsy (Groups 1-3) and prior to implant surgery (Group 4), at Weeks 1, 2, 3, 4 and 8, and prior to necropsy via the indwelling port in the jugular vein (Groups 1-4). Blood samples for analysis of blood gases were collected prebiopsy (Groups 1-3) and pre-implant surgery (Group 4) via either the jugular or femoral vein.

The analysis of hematology, coagulation, serum chemistry, and blood gases were performed as described in Example 3.

Additional Analysis. Immediately prior to euthanasia, heparinized blood and serum samples were collected from animals 23, 18, 12, 6, 1, and 15. One 10-mL sample of whole blood was collected in a heparin tube. Additional blood was collected in two 4.0-mL serum separation tubes, and serum was separated as described above.

Urine. Two methods were used to collect urine samples at scheduled time points (pre-biopsy [Groups 1-3], pre-implant surgery [Group 4] and prior to necropsy): catheterization or a test tube catch method. The method used was recorded. The desired sample size was at least 3 ml, which was to be separated into three aliquots in sterile 5-ml tubes. When sample collection was difficult, the quantitative samples took precedent. Samples were evaluated for qualitative and quantitative parameters as described in Example 3.

Results.

Biopsy. Bladder tissues and blood samples were obtained according to protocol from all animals in Groups 1, 2, 3 and spares. Adipose tissue biopsies from all male animals were less than the protocol-defined minimum of 20 grams. However, sufficient SMC were expanded from the collected tissue to produce constructs for the males assigned to Group 2. No adipose tissue could be obtained from three animals (animals 22 and 23, and spare animal 34) Animals 22 and 23 were assigned to Group 3. Individual weights of adipose biopsy samples are presented in Table 5.2.

Implantation. All animals were implanted without incident with two exceptions Animal 30 (Male, Group 4), had anatomically small ureters that were perforated upon attempting to place the stents at test article implantation. This animal was euthanized and not replaced Animal 29 (Male, Group 4), also had a small ureteral perforation at test article implantation. This animal was successfully implanted and survived the surgical procedure.

Stent Removal. Individual stent removal data are presented in Table 5.2. Ureteral stents were removed 5-14 days post implantation.

Mortality. Survival days post-implant and final disposition of each of the 31 animals implanted with the test article are shown in Table 5.2 (above) and Table 5.5 (below) Animal 30 (Group 4) was not implanted with a test article because of ureteral perforations. The animal was euthanized and not replaced, reducing the total N to 31 and the N of Group 4 to 7 animals. Twenty-four animals were unscheduled deaths and seven animals survived until the scheduled sacrifice. Disposition (mortality classification) of the 24 unscheduled deaths is summarized by treatment group in Table 5.3.

TABLE 5.3

| Mortality | Group 1 | Group 2 | Group 3 | Group 4 | Total |
| --- | --- | --- | --- | --- | --- |
| Group N | 8 | 8 | 8 | 7 | 31 |
| In-life procedure-related death | 0/8 | 0/8 | 1/8 | 0/7 | 1/31 |
| Found dead | 0/8 | 2/8 | 0/8 | 1/7 | 3/31 |
| Euthanized | 6/8 | 5/8 | 5/8 | 4/7 | 20/31 |
| Total Unscheduled Necropsies | 6/8 | 7/8 | 6/8 | 5/7 | 24/31 |
| Scheduled Necropsies | 2/8 | 1/8 | 2/8 | 2/7 | 7/31 |

PCV-2 Associated Mortalities. During in-life clinical observations, skin lesions consistent with PCV-2 infection were observed. Twelve unscheduled death animals developed one or more lesions, consistent with distinct pathological features ascribed to porcine dermatitis and nephropathy syndrome (PDNS), associated with PCV-2 infection. Animals were classified as PCV-2-infected according to the criteria of Example 3. By these criteria, porcine PCV-2 infection was identified in 12 of the 24 unscheduled necropsy animals. These included 5 animals in Group 1 (animals 5, 7, 2, 4, and 3); 4 animals in Group 2 (animals 13, 16, 14, and 10); 2 animals in Group 3 (animals 20 and 19); and 1 animal in Group 4 (animal 28). The PCV-2 animals will not be discussed in the results section as the PCV-2 condition was deemed an assignable cause of morbidity unrelated to the device.

Non-PCV-2 Associated Mortalities. A total of 12 unscheduled deaths were not associated with a detected PCV-2 virus infection (including the 1 1n-life procedure-related death). The 12 unscheduled deaths not attributable to PCV-2 infection included 1 animal in Group 1 (animal 8); 3 animals in Group 2 (animals 11, 9, and 12), 4 animals in Group 3 (animals 24, 21, 22, and 17) and 4 animals in Group 4 (animals 32, 31, 29, and 27). An important event in the clinical decline of these animals was obstruction of the outflow of urine and debris through the stoma. Obstruction appeared to have been facilitated by the placement of the test article in the ventral portion of the abdominal cavity where the weight of the overlying abdominal organs could lead to conduit closure, adhesion and fistula formation, and renal complications (e.g., dilation, inflammation, and/or infection of ureters or kidney). Surgical placement of the test article was the same in all study animals; therefore, obstruction-related complications had a similar pathobiological mechanism (i.e. abdominal viscera resting on the conduit because of the quadruped anatomy) in all groups.

Distribution of Unscheduled Deaths by Underlying Findings. A summary of underlying findings in the 24 unscheduled deaths is presented in Table 5.4.

TABLE 5.4

| Mortality Categories | Group 1 | Group 2 | Group 3 | Group 4 | Total |
| --- | --- | --- | --- | --- | --- |
| Evidence of PCV-2 infection | 5 | 4 | 2 | 1 | 12 |
| Non-PCV-2 associated unscheduled deaths | 1 | 3 | 4 | 4 | 12 |
| Total unscheduled deaths | 6 | 7 | 6 | 5 | 24 |

Mortality category for each animal implanted with the test article appears in Table 5.5 (S=scheduled sacrifice; FD=found dead; E=euthanized for poor clinical condition; A=died during post-op procedural complication mid-study; SMC=Smooth Muscle Cells; NA =Not applicable; F=Female; M=Male; P=PCV-2 associated mortality; Non-P=Non-PCV-2 associated mortality; SURV=survived to scheduled sacrifice.)

TABLE 5.5

| Animal | Sex | Group | SMC Source | Days on Study | Disposition | Mortality Group |
| --- | --- | --- | --- | --- | --- | --- |
| 5 | M | 1 | Bladder | 44 | E | P |
| 2 | F | | | 68 | E | P |
| 8 | M | | | 9 | E | Non-P |
| 4 | F | | | 28 | E | P |
| 1 | F | | | 81 | S | SURV |
| 3 | F | | | 69 | E | P |
| 6 | M | | | 83 | S | SURV |
| 7 | M | | | 42 | E | P |
| 13 | M | 2 | Adipose | 82 | FD | P |

TABLE 5.5-continued

| Animal | Sex | Group | SMC Source | Days on Study | Disposition | Mortality Group |
| --- | --- | --- | --- | --- | --- | --- |
| 16 | M | | | 63 | FD | P |
| 10 | F | | | 30 | E | P |
| 9 | F | | | 33 | E | Non-P |
| 11 | F | | | 58 | E | Non-P |
| 14 | M | | | 63 | E | P |
| 12 | F | | | 70 | E | Non-P |
| 15 | M | | | 81 | S | SURV |
| 18 | F | 3 | Blood | 80 | S | SURV |
| 24 | M | | | 77 | E | Non-P |
| 21 | M | | | 73 | E | Non-P |
| 20 | F | | | 6 | E | P |
| 22 | M | | | 51 | A | Non-P |
| 23 | M | | | 81 | S | SURV |
| 19 | F | | | 70 | E | P |
| 17 | F | | | 48 | E | Non-P |
| 26 | F | 4 | Scaffold-only, no SMC | 84 | S | SURV |
| 32 | M | | | 31 | E | Non-P |
| 27 | F | | | 20 | E | Non-P |
| 31 | M | | | 55 | E | Non-P |
| 25 | F | | | 84 | S | SURV |
| 29 | M | | | 48 | E | Non-P |
| 28 | F | | | 17 | FD | P |

Findings Pertinent to Safety. Individual and group data for all 31 animals implanted with the test article was obtained (data not shown). Discussion is focused on the 7 animals surviving to scheduled necropsy and the 12 non-PCV-2 associated unscheduled deaths. The data is organized as follows:

Clinical Heath Observations and Post-Surgical Care. Individual clinical health observations and post-surgical care for all animals was observed (data not shown). To distinguish between expected post-operative clinical observations due to surgical trauma and recovery, and the clinical observations anticipated to be related to obstruction (i.e., safety signal), the data below is broken into 2 categories: observations <30 days and observations >31 days.

Clinical Heath Observations and Post-Surgical Care for 7 Surviving Animals. During the first 30 days post-implantation, debridement was not performed on any animal. Anorexia (not eating) was observed and stoma port maintenance was performed in all 7 animals. Soft feces (diarrhea) were observed in 3 of 7 animals: 2/2 in Group 1 (animal 1) and 1/2 in Group 3 (animal 23). These observations are not uncommon following an invasive surgical procedure (Table 5.6—Pertinent Clinical Health Observations and Post-Surgical Care by Group of 7 Surviving Animals (<30 Days PI)).

TABLE 5.6

| Clinical Observations | Group 1 N = 2 | Group 2 N = 1 | Group 3 N = 2 | Group 4 N = 2 | Total N = 7 |
| --- | --- | --- | --- | --- | --- |
| Debridement | 0/2 | 0/1 | 0/2 | 0/2 | 0/7 |
| Anorexia (Not Eating) | 2/2 | 1/2 | 2/2 | 2/2 | 7/7 |
| Stoma port Maintenance | 2/2 | 1/1 | 2/2 | 2/2 | 7/7 |
| Soft Feces (Diarrhea) | 2/2 | 0/1 | 1/2 | 0/2 | 3/7 |

After day 30 (i.e. day 31-84±5/necropsy), debridement was performed to remove debris/detritus in 4 of 7 animals: 1/2 in Group 1 (animal 1); 1/1 in Group 2 (animal 15); and 2/2 in Group 3 (animal 23). Animals implanted with the scaffold only (Group 4) did not undergo the debridement procedure. Anorexia (not eating) was observed in 4 of 7 animals: 1/2 in Group 1 (animal 1); 1/1 in Group 2 (animal 15); 1/2 in Group 3 (animal 18) and 1/2 in Group 4 (animal 26). Stoma port maintenance was performed on all 7 animals. Soft feces (diarrhea) were observed in 5 of 7 animals: 2/2 in Group 1 (animal 1 and 6); 1/1 in Group 2 (animal 15) and 2/2 in Group 3 (animals 23 and 18) (see Table 5.7 —Pertinent Clinical Health Observations and Post-Surgical Care by Group of 7 Surviving Animals; (>30 Days PI)).

TABLE 5.7

| Clinical Observations | Group 1 N = 2 | Group 2 N = 1 | Group 3 N = 2 | Group 4 N = 2 | Total N = 7 |
|---|---|---|---|---|---|
| Debridement | 1/2 | 1/1 | 2/2 | 0/2 | 4/7 |
| Anorexia (Not Eating) | 1/2 | 1/1 | 1/2 | 1/2 | 4/7 |
| Stoma port Maintenance | 2/2 | 1/1 | 2/2 | 2/2 | 7/7 |
| Soft Feces (Diarrhea) | 2/2 | 1/1 | 2/2 | 0/2 | 5/7 |

Clinical Heath Observations and Post-Surgical Care for 12 non-PCV-2 Unscheduled Deaths. During the first 30 days post-implantation, debridement was not performed on any animal. Anorexia (not eating) was observed in 11 of 12 animals: 1/1 in Group 1 (animal no. 8), 3/3 in Group 2 (animal nos. 9, 11 and 12), 4/4 in Group 3 (animal nos. 17, 21, 24 and 22) and 3/4 in Group 4 (animal nos. 27, 32 and 29). Stoma port maintenance was performed in all 12 animals. Soft feces (diarrhea) were observed in 5 of 12 animals: 1/1 in Group 1 (animal no. 8), 1/3 in Group 2 (animal no. 11) and 3/4 in Group 3 (animal nos. 21, 22 and 24). These observations are not uncommon following an invasive surgical procedure (see Table 5.8).

TABLE 5.8

| Clinical Observations | Group 1 N = 1 | Group 2 N = 3 | Group 3 N = 4 | Group 4 N = 4 | Total N = 12 |
|---|---|---|---|---|---|
| Debridement | 0/1 | 0/3 | 0/4 | 0/4 | 0/12 |
| Anorexia (Not Eating) | 1/1 | 3/3 | 4/4 | 3/4 | 11/12 |
| Stoma port Maintenance | 1/1 | 3/3 | 4/4 | 4/4 | 12/12 |
| Soft Feces (Diarrhea) | 1/1 | 1/3 | 3/4 | 0/4 | 5/12 |

Two animals were euthanized before day 30; Group 1 animal no 8 (day 9) and Group 4 animal no. 27 (day 20). Two animals were euthanized at day 31 and 33; Group 4 animal no. 32 and Group 2 animal no. 9, respectively. These animals are included in the >30 day analysis. After day 30 (i.e. day 31-84±5/necropsy), debridement was performed to remove debris/detritus in 5 of 12 animals: 2/3 in Group 2 (animal nos. 12 and 11) and 3/4 in Group 3 (animal nos. 21, 22 and 24). Animals implanted with the scaffold only (Group 4) were euthanized or found dead prior to implementation of the debridement procedure. Anorexia (not eating) was observed in 7 of 12 animals: 1/3 in Group 2 (animal no. 11); 4/4 in Group 3 (animal nos. 17, 21, 22 and 24) and 2/4 animals in Group 4 (animal nos. 29 and 31). Stoma port maintenance was performed on 10/12 animals: 3/3 in Group 2 (animal nos. 9, 11 and 12), 4/4 in Group 3 (animal nos. 21, 22, 17 and 24) and 3/4 in Group 4 (animal nos. 29, 31 and 32). Soft feces (diarrhea) were observed in 8 of 12 animals: 3/3 in Group 2 (animal nos. 9, 11 and 12), 4/4 in Group 3 (animal nos. 17, 21, 22 and 24) and 1/4 in Group 4 (animal no. 29). The adverse health observations were believed to be a consequence of obstruction (Table 5.9—Pertinent Clinical Health Observations and Post-Surgical Care by Group of 12 non-PCV-2— Unscheduled Deaths (>30 Days PI)).

TABLE 5.9

| Clinical Observations | Group 1 N = 1 | Group 2 N = 3 | Group 3 N = 4 | Group 4 N = 4 | Total N = 12 |
|---|---|---|---|---|---|
| Debridement | 0/1* | 2/3^ | 3/4 | 0/4♦▲ | 5/12 |
| Anorexia (Not Eating) | 0/1* | 1/3^ | 4/4 | 2/4♦▲ | 7/12 |
| Stoma Button Maintenance | 0/1* | 3/3^ | 3/4 | 3/4♦▲ | 9/12 |
| Soft Feces (Diarrhea) | 0/1* | 3/3^ | 4/4 | 1/4♦▲ | 8/12 |

*Animal no. 8 euthanized on day 9.
♦Animal no. 27 euthanized on day 20.
▲Animal no. 32 euthanized on day 31.
^Animal no. 27 euthanized on day 33.

Body Weights. Individual and group body weights for all animals are presented in Tables 5.10 and 5.11 below.

TABLE 5.10

| ANIMAL | Group No. | Group | Sex | Weight (Kg) Pre-Bx | Pre-Sx | Δ: pre Bx →pre Sx | % weight Δ pre Bx →pre Sx | Necropsy | Δ: pre SX →Nx | % weight Δ pre SX →Nx |
|---|---|---|---|---|---|---|---|---|---|---|
| 1 | 1 | bladder | F | 12.8 | 19.8 | 7.0 | 55% | 13.4 | -6.4 | -32% |
| 2 | 1 | bladder | F | 12.9 | 18.7 | 5.8 | 45% | 16.6 | -2.1 | -11% |
| 3 | 1 | bladder | F | 14.4 | 18.7 | 4.3 | 30% | 13.1 | -5.6 | -30% |
| 4 | 1 | bladder | F | 11.9 | 17.9 | 6.0 | 50% | 15.8 | -2.1 | -12% |
| 5 | 1 | bladder | M | 14.0 | 16.0 | 2.0 | 14% | 13.0 | -3.0 | -19% |
| 8 | 1 | bladder | M | 14.2 | 16.0 | 1.8 | 13% | 11.5 | -4.5 | -28% |
| 6 | 1 | bladder | M | 15.2 | 15.9 | 0.7 | 5% | 16.2 | 0.3 | 2% |
| 7 | 1 | bladder | M | 17.2 | 20.3 | 3.1 | 18% | 17.0 | -3.3 | -16% |
| | Mean | | | 14.1 | 17.9 | 3.8 | 27% | 14.6 | -3.3 | -19% |
| | Std Dev | | | 1.6 | 1.8 | 2.3 | | 2.1 | 2.1 | |
| 9 | 2 | adipose | F | 16.2 | 19.7 | 3.5 | 22% | 20.2 | 0.5 | 3% |
| 10 | 2 | adipose | F | 13.1 | 17.8 | 4.7 | 36% | 15.5 | -2.3 | -13% |
| 11 | 2 | adipose | F | 16.5 | 18.5 | 2.0 | 12% | 13.1 | -5.4 | -29% |
| 12 | 2 | adipose | F | 11.9 | 18.6 | 6.7 | 56% | 19.2 | 0.6 | 3% |
| 13 | 2 | adipose | M | 17.7 | 17.4 | -0.3 | -2% | FD | NA | NA |
| 14 | 2 | adipose | M | 14.0 | 14.3 | 0.3 | 2% | 16.4 | 2.1 | 15% |
| 15 | 2 | adipose | M | 15.4 | 17.1 | 1.7 | 11% | 15.7 | -1.4 | -8% |
| 16 | 2 | adipose | M | 17.6 | 17.2 | -0.4 | -2% | FD | NA | NA |
| | Mean | | | 15.3 | 17.6 | 2.3 | 15% | 16.7 | -1.0 | -5% |
| | Std Dev | | | 2.1 | 1.6 | 2.5 | | 2.6 | 2.7 | |

TABLE 5.11

| | | | | Weight (Kg) | | | | | | |
|---|---|---|---|---|---|---|---|---|---|---|
| ANIMAL | Group No. | Group | Sex | Pre-Bx | Pre-Sx | Δ: pre Bx →pre Sx | % weight Δ pre Bx →pre Sx | Necropsy | Δ: pre SX →Nx | % weight Δ pre SX →Nx |
| 17 | 3 | blood | F | 13.3 | 18.6 | 5.3 | 40% | 17.4 | −1.2 | −6% |
| 18 | 3 | blood | F | 13.2 | 16.8 | 3.6 | 27% | 20.1 | 3.3 | 20% |
| 19 | 3 | blood | F | 13.0 | 18.0 | 5.0 | 38% | 12.3 | −5.7 | −32% |
| 20 | 3 | blood | F | 14.8 | 20.1 | 5.3 | 36% | 19.2 | −0.9 | −4% |
| 22 | 3 | blood | M | 13.8 | 17.0 | 3.2 | 23% | 16.0 | −1.0 | −6% |
| 23 | 3 | blood | M | 13.2 | 16.6 | 3.4 | 26% | 18.7 | 2.1 | 13% |
| 21 | 3 | blood | M | 14.8 | 15.8 | 1.0 | 7% | 10.9 | −4.9 | −31% |
| 24 | 3 | blood | M | 16.2 | 18.1 | 1.9 | 12% | 15.7 | −2.4 | −13% |
| | | Mean | | 14.0 | 17.6 | 3.6 | 26% | 16.3 | −1.3 | −8% |
| | | Std Dev | | 1.1 | 1.4 | 1.6 | | 3.3 | 3.1 | |
| 25 | 4 | scaffold | F | NA | 16.5 | NA | NA | 17.3 | 0.8 | 5% |
| 26 | 4 | scaffold | F | NA | 14.0 | NA | NA | 10.9 | −3.1 | −22% |
| 27 | 4 | scaffold | F | NA | 15.0 | NA | NA | 12.8 | −2.2 | −15% |
| 28 | 4 | scaffold | F | NA | 18.4 | NA | NA | FD | NA | NA |
| 29 | 4 | scaffold | M | NA | 16.1 | NA | NA | 13.0 | −3.1 | −19% |
| 30 | 4 | scaffold | M | NA | NA | NA | NA | NA | NA | NA |
| 31 | 4 | scaffold | M | NA | 18.2 | NA | NA | 16.3 | −1.9 | −10% |
| 32 | 4 | scaffold | M | NA | 16.1 | NA | NA | 12.4 | −3.7 | −23% |
| | | Mean | | NA | 16.3 | NA | NA | 13.8 | −2.2 | −16% |
| | | Std Dev | | NA | 1.6 | NA | NA | 2.5 | 1.6 | |

Body Weights for 7 Surviving Animals. The body weight of all 7 animals fluctuated during the study due to post-surgical complications (e.g., animal model complications leading to obstruction, abdominal adhesions, fistulas and renal complications) (Table 5.12). Although the number of animals in each group is small, all animals receiving constructs (Groups 1-3) gained weight from pre-biopsy to pre-surgery. All groups except Group 3 lost weight from the time of implant until necropsy.

due to post-surgical complications (e.g., animal model complications leading to obstruction, abdominal adhesions, fistulas and renal complications) (Table 5.13). All animals receiving constructs (Groups 1-3) gained weight from pre-biopsy to pre-surgery. All groups lost weight losing the most (N=1) and Group 2 losing the least amount from the time of implant until necropsy, with Group 1

TABLE 5.12

| | Weight (Kg)--Average* | | | | | | |
|---|---|---|---|---|---|---|---|
| Group | Pre-Biopsy | Pre-Surgery | Δ: Pre-Biopsy→ Pre-Surgery | % Δ Pre-Biopsy→ Pre-Surgery | Pre-Necropsy | Δ: Pre-Surgery→ Pre-Necropsy | % Δ Pre-Surgery→ Pre-Necropsy |
| 1 (N = 2) | 14.0 | 17.9 | 3.9 | 30% | 14.8 | −3.1 | −15% |
| 2 (N = 1) | 15.4 | 17.1 | 1.7 | 11% | 15.7 | −1.4 | −8% |
| 3 (N = 2) | 13.2 | 16.7 | 3.5 | 27% | 19.4 | 2.7 | 16% |
| 4 (N = 2) | NA | 15.3 | NA | NA | 14.1 | −1.2 | −9% |

Body Weights for 12 non-PCV-2 Unscheduled Deaths. The body weight of all 12 animals fluctuated during the study for 12 Non-PCV-2 Unscheduled Deaths; NA=not applicable).

TABLE 5.13

| | Weight (Kg)--Average | | | | | | |
|---|---|---|---|---|---|---|---|
| Group | Pre-Biopsy | Pre-Surgery | Δ: Pre-Biopsy→ Pre-Surgery | % Δ Pre-Biopsy→ Pre-Surgery | Pre-Necropsy | Δ: Pre-Surgery→ Pre-Necropsy | % Δ Pre-Surgery→ Pre-Necropsy |
| 1 (N = 1) | 14.2 | 16.0 | 1.8 | 13% | 11.5 | −4.5 | −28% |
| 2 (N = 3) | 14.9 | 18.9 | 4.1 | 30% | 17.5 | −1.4 | −8% |

TABLE 5.13-continued

Weight (Kg)--Average

| Group | Pre-Biopsy | Pre-Surgery | Δ: Pre-Biopsy→ Pre-Surgery | % Δ Pre-Biopsy→ Pre-Surgery | Pre-Necropsy | Δ: Pre-Surgery→ Pre-Necropsy | % Δ Pre-Surgery→ Pre-Necropsy |
|---|---|---|---|---|---|---|---|
| 3 (N = 4) | 14.5 | 17.4 | 2.9 | 20% | 15.0 | −2.4 | −14.2% |
| 4 (N = 4) | NA | 16.4 | NA | NA | 13.6 | −2.7 | −17% |

Clinical Pathology. Clinical pathology data for individual animals is presented below (Hematology (CBC); coagulation; serum chemistry; blood gas; and urinalysis.

Hematology data can be found in Tables 5.14 (White Blood Count (THSN/UL) Ref. Range 11-22); 5.15 (Red Blood Count (MILL/UL) Ref. Range 5-8); 5.16 (Hemoglobin (%) Ref. Range 10-16); 5.17 (Hematocrit (%) Ref. Range 32-50); 5.18 (MCV (FL) Ref. Range 50-68); 5.19 (MCH (pico gram) Ref. Range 17-21); and 5.20 (PLATELET (THSN/UL) Ref. Range 325-715). This data is based on the individual values of the animals in each group (data not shown).

TABLE 5.14

| Group | Stat | Baseline | Week 1 | Week 2 | Week 3 | Week 4 | Week 8 | Pre-Necropsy |
|---|---|---|---|---|---|---|---|---|
| 1 | Mean | 8.1 | 21.6 | 26.6 | 16.6 | 23.8 | 16.5 | 18.0 |
|   | SD | 1.3 | 12.5 | 14.6 | 5.5 | 9.9 | 3.5 | 8.1 |
| 2 | Mean | 6.6 | 15.6 | 17.0 | 20.3 | 18.1 | 21.9 | 25.4 |
|   | SD | 2.0 | 6.9 | 3.7 | 6.3 | 3.8 | 9.9 | 11.7 |
| 3 | Mean | 9.4 | 14.3 | 18.8 | 17.1 | 19.7 | 22.4 | 22.0 |
|   | SD | 2.6 | 4.0 | 5.4 | 4.4 | 4.8 | 7.7 | 10.6 |
| 4 | Mean | 11.5 | 14.5 | 25.2 | 30.9 | 25.3 | 27.3 | 34.5 |

TABLE 5.15

| Group | Stat | Baseline | Week 1 | Week 2 | Week 3 | Week 4 | Week 8 | Pre-Necropsy |
|---|---|---|---|---|---|---|---|---|
| 1 | Mean | 6.75 | 6.47 | 6.08 | 6.77 | 6.81 | 5.11 | 5.66 |
|   | SD | 0.95 | 0.99 | 1.54 | 1.03 | 0.69 | 0.33 | 1.71 |
| 2 | Mean | 6.36 | 6.64 | 6.03 | 6.48 | 5.89 | 6.03 | 5.68 |
|   | SD | 0.41 | 1.19 | 1.21 | 0.99 | 0.56 | 1.24 | 2.18 |
| 3 | Mean | 6.59 | 7.39 | 7.21 | 6.37 | 6.42 | 5.42 | 5.12 |
|   | SD | 0.71 | 1.26 | 1.38 | 1.25 | 0.83 | 0.92 | 1.28 |
| 4 | Mean | 6.45 | 6.32 | 6.41 | 7.10 | 6.80 | 6.11 | 5.11 |

TABLE 5.16

| Group | Stat | Baseline | Week 1 | Week 2 | Week 3 | Week 4 | Week 8 | Pre-Necropsy |
|---|---|---|---|---|---|---|---|---|
| 1 | Mean | 11.1 | 10.9 | 10.4 | 11.7 | 11.7 | 8.6 | 9.4 |
|   | SD | 1.7 | 1.2 | 2.7 | 1.9 | 0.8 | 0.9 | 2.8 |
| 2 | Mean | 10.0 | 10.5 | 9.6 | 10.3 | 9.4 | 9.3 | 9.1 |
|   | SD | 0.9 | 2.0 | 1.5 | 1.2 | 1.0 | 1.2 | 3.2 |
| 3 | Mean | 10.4 | 12.0 | 11.9 | 10.4 | 10.5 | 8.7 | 8.0 |
|   | SD | 1.2 | 2.3 | 2.7 | 2.1 | 1.2 | 1.2 | 2.3 |
| 4 | Mean | 9.6 | 9.5 | 9.7 | 10.6 | 10.1 | 8.9 | 7.3 |
|   | SD | 0.7 | 0.6 | 1.1 | 1.9 | 2.3 | 3.6 | NA |

TABLE 5.17

| Group | Stat | Baseline | Week 1 | Week 2 | Week 3 | Week 4 | Week 8 | Pre-Necropsy |
|---|---|---|---|---|---|---|---|---|
| 1 | Mean | 34.3 | 34.2 | 32.7 | 36.8 | 37.4 | 27.2 | 29.0 |
|   | SD | 5.3 | 3.9 | 8.2 | 5.8 | 2.5 | 2.7 | 8.5 |
| 2 | Mean | 31.0 | 32.8 | 30.3 | 33.1 | 30.6 | 30.0 | 27.9 |
|   | SD | 2.8 | 5.8 | 4.7 | 3.8 | 3.4 | 4.1 | 10.0 |
| 3 | Mean | 32.3 | 38.1 | 36.9 | 32.2 | 33.1 | 27.6 | 25.6 |
|   | SD | 3.9 | 7.0 | 8.0 | 6.5 | 3.5 | 3.9 | 7.7 |
| 4 | Mean | 29.7 | 29.5 | 29.6 | 32.4 | 30.8 | 28.2 | 23.4 |
|   | SD | 2.0 | 1.7 | 3.5 | 5.5 | 6.9 | 11.2 | NA |

NA = not applicable, n is too small for SD

TABLE 5.18

| Group | Stat | Baseline | Week 1 | Week 2 | Week 3 | Week 4 | Week 8 | Pre-Necropsy |
|---|---|---|---|---|---|---|---|---|
| 1 | Mean | 51 | 53 | 54 | 54 | 55 | 54 | 51 |
|   | SD | 4 | 3 | 3 | 4 | 3 | 4 | 4 |
| 2 | Mean | 49 | 49 | 51 | 52 | 52 | 50 | 49 |
|   | SD | 2 | 2 | 3 | 3 | 4 | 3 | 3 |
| 3 | Mean | 49 | 52 | 51 | 50 | 52 | 51 | 50 |
|   | SD | 3 | 3 | 3 | 3 | 3 | 5 | 3 |
| 4 | Mean | 46 | 47 | 46 | 46 | 45 | 46 | 47 |
|   | SD | 2 | 2 | 2 | 2 | 1 | 2 | NA |

TABLE 5.19

| Group | Stat | Baseline | Week 1 | Week 2 | Week 3 | Week 4 | Week 8 | Pre-Necropsy |
|---|---|---|---|---|---|---|---|---|
| 1 | Mean | 16.4 | 17.0 | 17.1 | 17.3 | 17.2 | 16.8 | 16.6 |
|   | SD | 1.3 | 1.0 | 1.0 | 1.3 | 1.1 | 1.6 | 1.1 |
| 2 | Mean | 15.6 | 15.8 | 16.0 | 16.0 | 16.0 | 15.7 | 16.1 |
|   | SD | 0.6 | 0.8 | 0.8 | 0.9 | 1.0 | 1.2 | 0.9 |
| 3 | Mean | 15.8 | 16.2 | 16.4 | 16.2 | 16.4 | 16.1 | 15.6 |
|   | SD | 1.0 | 1.1 | 1.2 | 1.2 | 1.0 | 1.5 | 1.0 |
| 4 | Mean | 15.0 | 15.0 | 15.1 | 14.9 | 14.9 | 14.4 | 14.2 |

TABLE 5.20

| Group | Stat | Baseline | Week 1 | Week 2 | Week 3 | Week 4 | Week 8 | Pre-Necropsy |
|---|---|---|---|---|---|---|---|---|
| 1 | Mean | 419 | 404 | 510 | 418 | 379 | 559 | 322 |
|   | SD | 89 | 176 | 167 | 171 | 126 | 172 | 397 |
| 2 | Mean | 488 | 407 | 531 | 490 | 489 | 605 | 478 |
|   | SD | 61 | 143 | 163 | 151 | 208 | 286 | 435 |
| 3 | Mean | 558 | 434 | 357 | 404 | 453 | 563 | 509 |
|   | SD | 130 | 104 | 107 | 115 | 198 | 366 | 388 |
| 4 | Mean | 568 | 473 | 667 | 537 | 429 | 450 | 557 |
|   | SD | 126 | 95 | 159 | 199 | 103 | 14 | NA |

NA = not applicable, n is too small for SD

Table 5.21 shows the N-Values by Time Point.

TABLE 5.21

N-Values by Time Point:

| Group | Baseline | Week 1 | Week 2 | Week 3 | Week 4 | Week 8 | Pre-Necropsy |
|---|---|---|---|---|---|---|---|
| 1 | 8 | 8 | 7 | 7 | 6 | 4 | 7 |
| 2 | 8 | 8 | 8 | 8 | 8 | 6 | 6 |
| 3 | 8 | 8 | 7 | 7 | 7 | 5 | 6 |
| 4 | 8 | 7 | 7 | 6 | 5 | 3 | 2 |

Coagulation data is provided in Tables 5.22 (Prothrombin Time (seconds) Ref. Range 10-15.5); 5.23 (Activated Partial Thromboplastin Time (s) Ref. Range 18.4-27.7); and 5.24 (Fibrinogen (MG/DL) Ref. Range 100-500). This data is based on the individual values of the animals in each group (data not shown).

TABLE 5.22

| Group | Stat | Baseline | Week 1 | Week 2 | Week 3 | Week 4 | Week 8 | Pre-Necropsy |
|---|---|---|---|---|---|---|---|---|
| 1 | Mean | 11.5 | 11.8 | 11.7 | 12.0 | 11.5 | 11.4 | 16.3 |
|   | SD | 0.8 | 1.1 | 1.6 | 0.7 | 0.8 | 0.7 | 5.5 |
| 2 | Mean | 11.3 | 11.4 | 11.4 | 10.9 | 11.3 | 11.5 | 12.6 |
|   | SD | 0.8 | 0.4 | 0.5 | 0.4 | 0.3 | 0.4 | 1.2 |
| 3 | Mean | 11.4 | 11.2 | 11.7 | 10.9 | 11.4 | 11.3 | 12.2 |
|   | SD | 0.7 | 1.4 | 0.4 | 0.4 | 0.6 | 1.3 | 1.7 |
| 4 | Mean | 11.1 | 11.7 | 11.9 | 13.0 | 12.2 | 12.9 | 12.3 |
|   | SD | 0.3 | 0.2 | 0.7 | 0.9 | 0.6 | 2.0 | 0.6 |

TABLE 5.23

| Group | Stat | Baseline | Week 1 | Week 2 | Week 3 | Week 4 | Week 8 | Pre-Necropsy |
|---|---|---|---|---|---|---|---|---|
| 1 | Mean | 34.63 | 32.18 | 36.96 | 0.00 | 33.62 | 29.05 | 22.14 |
|   | SD | 9.47 | 9.06 | 15.08 | 0.00 | 10.19 | 8.09 | 7.70 |
| 2 | Mean | 33.88 | 32.89 | 39.53 | 37.20 | 29.95 | 20.57 | 20.18 |
|   | SD | 6.80 | 9.73 | 12.53 | 10.81 | 7.17 | 3.80 | 3.93 |
| 3 | Mean | 31.65 | 24.74 | 41.26 | 37.40 | 34.33 | 22.74 | 18.92 |
|   | SD | 6.36 | 5.47 | 17.12 | 14.67 | 14.41 | 7.61 | 5.20 |
| 4 | Mean | 40.51 | 41.66 | 30.29 | 36.10 | 30.52 | 38.00 | 29.05 |
|   | SD | 2.80 | 9.16 | 9.36 | 7.93 | 4.01 | 11.10 | NA |

TABLE 5.24

| Group | Stat | Baseline | Week 1 | Week 2 | Week 3 | Week 4 | Week 8 | Pre-Necropsy |
|---|---|---|---|---|---|---|---|---|
| 1 | Mean | 520 | 1561 | 837 | 1102 | 656 | 797 | 977 |
|   | SD | 155 | 2237 | 468 | 452 | 368 | 200 | 530 |
| 2 | Mean | 473 | 882 | 752 | 562 | 867 | 925 | 1218 |
|   | SD | 179 | 483 | 246 | 261 | 126 | 327 | 589 |
| 3 | Mean | 578 | 1140 | 591 | 610 | 1019 | 859 | 1339 |
|   | SD | 129 | 851 | 299 | 275 | 762 | 596 | 1276 |
| 4 | Mean | 700 | 1084 | 1908 | 1617 | 1051 | 1780 | 1496 |
|   | SD | 427 | 698 | 835 | 589 | 462 | 880 | NA |

NA = not applicable, n is too small for SD

Table 5.25 shows the N-Values by Time Point.

TABLE 5.25

| Group | Baseline | Week 1 | Week 2 | Week 3 | Week 4 | Week 8 | Pre-Necropsy |
|---|---|---|---|---|---|---|---|
| 1 | 8 | 8 | 7 | 7 | 6 | 4 | 7 |
| 2 | 8 | 8 | 8 | 8 | 8 | 6 | 6 |
| 3 | 8 | 8 | 7 | 7 | 7 | 5 | 6 |
| 4 | 8 | 7 | 7 | 6 | 5 | 3 | 2 |

Serum chemistry data is provided in Tables 5.26 (Sodium (MEQ/L) Ref. Range 135-150); 5.27 (Potassium (MEQ/L) Ref. Range 4.4-6.7); 5.28 (Chloride (MEQ/L) Ref. Range 93-106); 5.29 (Total Calcium (MEQ/L) Ref. Range 8.6-10.7); 5.30 (Phosphorous (MG/DL) Ref. Range 9.9-11.9); 5.31 (AST SGOT (U/L) Ref. Range 0-32); 5.32 (ALT SGPT (U/L) Ref. Range 0-0); 5.33 (ALP (U/L) Ref. Range 0-290); 5.34 (Gamma Glutamyl Transferase (U/L) Ref. Range 10-60); 5.35 (Glucose (MG/DL) Ref. Range 85-150); 5.36 (BUN (MG/DL) Ref. Range 10-30); 5.37 (Creatinine (MC/DL) 1-2.7); 5.38 (Cholesterol (MG/DL) Ref. Range 36-132); 5.39 (Triglyceride (MG/DL) Ref. Range 50-100); 5.40 (Total Bilirubin (MG/DL) Ref. Range 0.0-1.0); 5.41 (Albumin (MG/DL) Ref. Range 1.6-4.0); 5.42 (Total Protein (G/DL) Ref. Range 5.5-8.5); 5.43 (Globulin (G/DL) Ref. Range 1.5-6.9); and 5.44 (Albumin/Globulin Ratio (Ratio) Ref. Range 0.2-2.7). This data is based on the individual values of the animals in each group (data not shown).

TABLE 5.26

| Group | Stat | Baseline | Week 1 | Week 2 | Week 3 | Week 4 | Week 8 | Pre-Necropsy |
|---|---|---|---|---|---|---|---|---|
| 1 | Mean | 153 | 139 | 141 | 143 | 141 | 138 | 133 |
|   | SD | 15 | 3 | 2 | 5 | 4 | 4 | 15 |
| 2 | Mean | 147 | 141 | 136 | 139 | 139 | 137 | 137 |
|   | SD | 11 | 5 | 7 | 6 | 2 | 4 | 4 |
| 3 | Mean | 152 | 137 | 131 | 142 | 141 | 141 | 132 |
|   | SD | 12 | 6 | 8 | 3 | 4 | 4 | 11 |
| 4 | Mean | 140 | 138 | 136 | 131 | 136 | 135 | 140 |
|   | SD | 3 | 5 | 5 | 6 | 8 | 5 | NA |

TABLE 5.27

| Group | Stat | Baseline | Week 1 | Week 2 | Week 3 | Week 4 | Week 8 | Pre-Necropsy |
|---|---|---|---|---|---|---|---|---|
| 1 | Mean | 4.4 | 4.2 | 4.6 | 4.8 | 4.8 | 4.3 | 5.6 |
|   | SD | 0.4 | 0.3 | 1.0 | 0.4 | 1.2 | 0.5 | 1.1 |
| 2 | Mean | 4.2 | 4.1 | 4.0 | 4.7 | 4.4 | 4.7 | 5.0 |
|   | SD | 0.4 | 0.5 | 0.5 | 0.4 | 0.4 | 0.4 | 0.6 |
| 3 | Mean | 4.2 | 4.3 | 5.6 | 4.5 | 4.7 | 5.1 | 5.7 |
|   | SD | 0.2 | 0.9 | 2.3 | 0.4 | 0.3 | 0.7 | 1.7 |
| 4 | Mean | 3.9 | 4.1 | 5.3 | 4.3 | 5.0 | 4.3 | 4.6 |
|   | SD | 0.3 | 0.3 | 0.7 | 0.9 | 2.4 | 1.4 | NA |

TABLE 5.28

| Group | Stat | Baseline | Week 1 | Week 2 | Week 3 | Week 4 | Week 8 | Pre-Necropsy |
|---|---|---|---|---|---|---|---|---|
| 1 | Mean | 111 | 98 | 101 | 101 | 98 | 103 | 97 |
|   | SD | 14 | 2 | 2 | 2 | 3 | 4 | 23 |
| 2 | Mean | 105 | 100 | 97 | 99 | 101 | 99 | 99 |
|   | SD | 12 | 4 | 2 | 5 | 2 | 5 | 11 |
| 3 | Mean | 111 | 96 | 94 | 102 | 100 | 103 | 102 |
|   | SD | 12 | 7 | 7 | 5 | 5 | 4 | 11 |
| 4 | Mean | 98 | 97 | 94 | 89 | 94 | 87 | 98 |
|   | SD | 4 | 6 | 6 | 7 | 10 | 10 | NA |

TABLE 5.29

| Group | Stat | Baseline | Week 1 | Week 2 | Week 3 | Week 4 | Week 8 | Pre-Necropsy |
|---|---|---|---|---|---|---|---|---|
| 1 | Mean | 10.9 | 9.9 | 10.0 | 10.4 | 10.3 | 9.9 | 9.8 |
|   | SD | 0.7 | 0.4 | 0.9 | 0.5 | 0.5 | 0.3 | 0.8 |
| 2 | Mean | 10.7 | 9.6 | 9.8 | 10.3 | 9.9 | 10.0 | 9.6 |
|   | SD | 0.6 | 0.5 | 0.6 | 0.5 | 0.5 | 0.4 | 0.6 |
| 3 | Mean | 10.6 | 10.0 | 10.3 | 9.9 | 10.2 | 10.3 | 9.9 |
|   | SD | 0.7 | 0.6 | 0.8 | 0.4 | 0.5 | 0.4 | 0.9 |
| 4 | Mean | 10.4 | 10.3 | 10.3 | 10.0 | 10.2 | 10.6 | 10.4 |
|   | SD | 0.3 | 0.7 | 0.6 | 0.6 | 0.7 | 0.3 | NA |

NA = not applicable,
n is too small for SD

TABLE 5.30

| Group | Stat | Baseline | Week 1 | Week 2 | Week 3 | Week 4 | Week 8 | Pre-Necropsy |
|---|---|---|---|---|---|---|---|---|
| 1 | Mean | 9.5 | 6.1 | 6.2 | 6.8 | 6.8 | 6.5 | 11.6 |
|   | SD | 1.1 | 0.6 | 0.9 | 0.8 | 1.2 | 0.8 | 5.9 |
| 2 | Mean | 8.6 | 5.8 | 6.8 | 6.9 | 6.8 | 6.2 | 9.0 |
|   | SD | 0.9 | 1.5 | 0.8 | 0.8 | 0.7 | 0.4 | 5.4 |
| 3 | Mean | 8.5 | 7.2 | 8.4 | 6.6 | 6.6 | 6.8 | 8.3 |
|   | SD | 1.4 | 3.0 | 3.7 | 1.7 | 0.8 | 0.7 | 1.8 |
| 4 | Mean | 7.7 | 6.6 | 7.4 | 7.4 | 7.6 | 6.8 | 6.6 |
|   | SD | 0.5 | 0.8 | 0.7 | 2.2 | 2.2 | 2.1 | NA |

TABLE 5.31

| Group | Stat | Baseline | Week 1 | Week 2 | Week 3 | Week 4 | Week 8 | Pre-Necropsy |
|---|---|---|---|---|---|---|---|---|
| 1 | Mean | 108 | 41 | 33 | 22 | 21 | 17 | 301 |
|   | SD | 202 | 15 | 14 | 10 | 7 | 5 | 577 |
| 2 | Mean | 30 | 45 | 17 | 17 | 20 | 39 | 76 |
|   | SD | 13 | 30 | 3 | 4 | 7 | 17 | 106 |
| 3 | Mean | 34 | 44 | 34 | 41 | 27 | 31 | 47 |
|   | SD | 15 | 26 | 10 | 25 | 19 | 17 | 26 |
| 4 | Mean | 29 | 18 | 27 | 42 | 110 | 23 | 46 |
|   | SD | 19 | 7 | 9 | 38 | 112 | 2 | NA |

TABLE 5.32

| Group | Stat | Baseline | Week 1 | Week 2 | Week 3 | Week 4 | Week 8 | Pre-Necropsy |
|---|---|---|---|---|---|---|---|---|
| 1 | Mean | 61 | 56 | 48 | 30 | 29 | 23 | 29 |
|   | SD | 48 | 19 | 19 | 19 | 6 | 10 | 15 |
| 2 | Mean | 35 | 51 | 33 | 29 | 28 | 22 | 26 |
|   | SD | 7 | 5 | 12 | 10 | 12 | 7 | 6 |
| 3 | Mean | 63 | 46 | 55 | 53 | 36 | 30 | 24 |
|   | SD | 69 | 22 | 18 | 11 | 11 | 6 | 8 |
| 4 | Mean | 34 | 29 | 25 | 21 | 41 | 20 | 19 |
|   | SD | 4 | 9 | 4 | 5 | 25 | 3 | NA |

TABLE 5.33

| Group | Stat | Baseline | Week 1 | Week 2 | Week 3 | Week 4 | Week 8 | Pre-Necropsy |
|---|---|---|---|---|---|---|---|---|
| 1 | Mean | 113 | 76 | 59 | 66 | 88 | 63 | 68 |
|   | SD | 32 | 30 | 14 | 23 | 34 | 27 | 34 |
| 2 | Mean | 129 | 87 | 75 | 83 | 76 | 66 | 72 |
|   | SD | 33 | 31 | 15 | 31 | 27 | 10 | 45 |
| 3 | Mean | 96 | 99 | 63 | 65 | 64 | 62 | 65 |
|   | SD | 26 | 47 | 14 | 26 | 19 | 19 | 57 |

TABLE 5.33-continued

| Group | Stat | Baseline | Week 1 | Week 2 | Week 3 | Week 4 | Week 8 | Pre-Necropsy |
|---|---|---|---|---|---|---|---|---|
| 4 | Mean | 102 | 63 | 54 | 65 | 85 | 81 | 91 |
|   | SD | 25 | 16 | 9 | 23 | 24 | 14 | NA |

NA = not applicable,
n is too small for SD

TABLE 5.34

| Group | Stat | Baseline | Week 1 | Week 2 | Week 3 | Week 4 | Week 8 | Pre-Necropsy |
|---|---|---|---|---|---|---|---|---|
| 1 | Mean | 64 | 62 | 47 | 58 | 47 | 48 | 50 |
|   | SD | 15 | 16 | 8 | 14 | 5 | 4 | 17 |
| 2 | Mean | 65 | 47 | 46 | 48 | 63 | 47 | 51 |
|   | SD | 16 | 8 | 9 | 6 | 15 | 8 | 12 |
| 3 | Mean | 59 | 65 | 63 | 49 | 47 | 44 | 50 |
|   | SD | 12 | 25 | 18 | 17 | 16 | 12 | 27 |
| 4 | Mean | 68 | 44 | 65 | 47 | 55 | 43 | 84 |
|   | SD | 16 | 9 | 28 | 9 | 8 | 5 | NA |

TABLE 5.35

| Group | Stat | Baseline | Week 1 | Week 2 | Week 3 | Week 4 | Week 8 | Pre-Necropsy |
|---|---|---|---|---|---|---|---|---|
| 1 | Mean | 80 | 87 | 78 | 87 | 90 | 83 | 67 |
|   | SD | 19 | 16 | 29 | 17 | 24 | 15 | 33 |
| 2 | Mean | 87 | 75 | 86 | 75 | 74 | 76 | 58 |
|   | SD | 15 | 17 | 20 | 11 | 19 | 20 | 25 |
| 3 | Mean | 89 | 86 | 103 | 71 | 69 | 72 | 240 |
|   | SD | 22 | 14 | 43 | 7 | 7 | 17 | 390 |
| 4 | Mean | 77 | 92 | 96 | 69 | 92 | 100 | 76 |
|   | SD | 14 | 9 | 19 | 24 | 32 | 8 | NA |

TABLE 5.36

| Group | Stat | Baseline | Week 1 | Week 2 | Week 3 | Week 4 | Week 8 | Pre-Necropsy |
|---|---|---|---|---|---|---|---|---|
| 1 | Mean | 15 | 17 | 18 | 13 | 13 | 50 | 160 |
|   | SD | 8 | 10 | 11 | 6 | 2 | 30 | 138 |
| 2 | Mean | 12 | 29 | 16 | 19 | 14 | 27 | 140 |
|   | SD | 8 | 14 | 16 | 18 | 14 | 15 | 51 |
| 3 | Mean | 14 | 42 | 35 | 13 | 17 | 44 | 91 |
|   | SD | 7 | 40 | 46 | 10 | 12 | 34 | 59 |
| 4 | Mean | 7 | 13 | 30 | 49 | 33 | 76 | 44 |
|   | SD | 1 | 4 | 16 | 38 | 35 | 78 | NA |

TABLE 5.37

| Group | Stat | Baseline | Week 1 | Week 2 | Week 3 | Week 4 | Week 8 | Pre-Necropsy |
|---|---|---|---|---|---|---|---|---|
| 1 | Mean | 1.2 | 1.3 | 1.2 | 1.2 | 1.2 | 1.5 | 4.3 |
|   | SD | 0.4 | 0.3 | 0.3 | 0.2 | 0.2 | 0.5 | 4.2 |
| 2 | Mean | 1.1 | 1.6 | 1.1 | 1.1 | 1.0 | 1.2 | 2.0 |
|   | SD | 0.3 | 0.7 | 0.5 | 0.2 | 0.2 | 0.3 | 1.1 |
| 3 | Mean | 1.3 | 3.7 | 1.8 | 1.0 | 1.1 | 1.4 | 2.0 |
|   | SD | 0.4 | 5.6 | 1.3 | 0.2 | 0.4 | 0.4 | 1.1 |
| 4 | Mean | 1.1 | 1.1 | 1.5 | 1.9 | 1.8 | 6.3 | 3.5 |
|   | SD | 0.1 | 0.1 | 0.5 | 1.2 | 1.0 | 5.8 | NA |

TABLE 5.38

| Group | Stat | Baseline | Week 1 | Week 2 | Week 3 | Week 4 | Week 8 | Pre-Necropsy |
|---|---|---|---|---|---|---|---|---|
| 1 | Mean | 87 | 69 | 69 | 84 | 79 | 77 | 74 |
|   | SD | 38 | 14 | 12 | 13 | 16 | 19 | 38 |
| 2 | Mean | 71 | 80 | 83 | 92 | 79 | 74 | 71 |
|   | SD | 27 | 24 | 23 | 28 | 36 | 29 | 26 |
| 3 | Mean | 73 | 71 | 65 | 75 | 77 | 73 | 66 |
|   | SD | 35 | 10 | 26 | 16 | 17 | 17 | 24 |
| 4 | Mean | 72 | 83 | 87 | 84 | 87 | 120 | 130 |
|   | SD | 27 | 31 | 51 | 54 | 41 | 37 | NA |

TABLE 5.39

| Group | Stat | Baseline | Week 1 | Week 2 | Week 3 | Week 4 | Week 8 | Pre-Necropsy |
|---|---|---|---|---|---|---|---|---|
| 1 | Mean | 48 | 46 | 47 | 79 | 76 | 37 | 64 |
|   | SD | 49 | 11 | 30 | 57 | 62 | 19 | 24 |
| 2 | Mean | 40 | 47 | 132 | 41 | 25 | 45 | 57 |
|   | SD | 35 | 21 | 121 | 30 | 12 | 19 | 11 |
| 3 | Mean | 57 | 53 | 40 | 42 | 100 | 53 | 41 |
|   | SD | 55 | 12 | 20 | 17 | 55 | 27 | 25 |
| 4 | Mean | 21 | 27 | 34 | 48 | 45 | 97 | 45 |
|   | SD | 9 | 9 | 15 | 29 | 26 | 8 | NA |

TABLE 5.40

| Group | Stat | Baseline | Week 1 | Week 2 | Week 3 | Week 4 | Week 8 | Pre-Necropsy |
|---|---|---|---|---|---|---|---|---|
| 1 | Mean | 0.1 | 0.1 | 0.1 | 0.1 | 0.2 | 0.1 | 0.5 |
|   | SD | 0.0 | 0.1 | 0.1 | 0.1 | 0.1 | 0.0 | 0.5 |
| 2 | Mean | 0.1 | 0.2 | 0.1 | 0.2 | 0.1 | 0.1 | 0.3 |
|   | SD | 0.1 | 0.1 | 0.0 | 0.1 | 0.1 | 0.0 | 0.2 |
| 3 | Mean | 0.1 | 0.3 | 0.2 | 0.1 | 0.0 | 0.1 | 0.2 |
|   | SD | 0.1 | 0.2 | 0.1 | 0.1 | 0.0 | 0.0 | 0.1 |
| 4 | Mean | 0.1 | 0.2 | 0.1 | 0.1 | 0.2 | 0.4 | 0.1 |
|   | SD | 0.1 | 0.1 | 0.0 | 0.1 | 0.1 | 0.2 | NA |

TABLE 5.41

| Group | Stat | Baseline | Week 1 | Week 2 | Week 3 | Week 4 | Week 8 | Pre-Necropsy |
|---|---|---|---|---|---|---|---|---|
| 1 | Mean | 4.3 | 3.6 | 3.7 | 3.4 | 3.3 | 3.5 | 3.0 |
|   | SD | 0.4 | 0.3 | 0.6 | 0.3 | 0.2 | 0.3 | 0.4 |
| 2 | Mean | 4.1 | 3.5 | 3.4 | 3.5 | 3.4 | 3.2 | 3.1 |
|   | SD | 0.3 | 0.4 | 0.4 | 0.3 | 0.4 | 0.2 | 0.6 |
| 3 | Mean | 4.2 | 3.8 | 3.8 | 3.5 | 3.4 | 3.4 | 3.0 |
|   | SD | 0.4 | 0.4 | 0.3 | 0.3 | 0.5 | 0.3 | 0.9 |
| 4 | Mean | 4.2 | 3.7 | 3.8 | 3.4 | 3.4 | 3.0 | 3.1 |
|   | SD | 0.3 | 0.4 | 0.4 | 0.3 | 0.1 | 0.2 | NA |

TABLE 5.42

| Group | Stat | Baseline | Week 1 | Week 2 | Week 3 | Week 4 | Week 8 | Pre-Necropsy |
|---|---|---|---|---|---|---|---|---|
| 1 | Mean | 6.3 | 6.6 | 7.1 | 7.7 | 7.5 | 7.7 | 7.8 |
|   | SD | 0.6 | 0.7 | 0.8 | 0.6 | 0.7 | 0.8 | 0.9 |
| 2 | Mean | 5.7 | 6.4 | 6.6 | 6.9 | 6.8 | 7.1 | 7.0 |
|   | SD | 0.5 | 0.6 | 0.8 | 0.5 | 0.5 | 0.7 | 0.9 |
| 3 | Mean | 6.3 | 6.9 | 7.3 | 6.8 | 7.3 | 7.7 | 7.5 |
|   | SD | 0.7 | 0.6 | 1.0 | 0.7 | 0.7 | 0.5 | 1.4 |
| 4 | Mean | 6.1 | 6.3 | 7.5 | 7.4 | 7.7 | 8.6 | 8.1 |
|   | SD | 0.4 | 0.5 | 0.8 | 0.7 | 0.9 | 0.4 | NA |

TABLE 5.43

| Group | Stat | Baseline | Week 1 | Week 2 | Week 3 | Week 4 | Week 8 | Pre-Necropsy |
|---|---|---|---|---|---|---|---|---|
| 1 | Mean | 2.0 | 3.1 | 3.4 | 4.2 | 4.2 | 4.2 | 4.8 |
|   | SD | 0.3 | 0.5 | 0.5 | 0.7 | 0.6 | 0.9 | 0.7 |
| 2 | Mean | 1.6 | 2.9 | 3.2 | 3.3 | 3.4 | 3.8 | 3.9 |
|   | SD | 0.3 | 0.4 | 0.5 | 0.4 | 0.3 | 0.7 | 0.6 |
| 3 | Mean | 2.1 | 3.1 | 3.5 | 3.3 | 3.9 | 4.3 | 4.5 |
|   | SD | 0.3 | 0.3 | 0.9 | 0.5 | 0.5 | 0.3 | 0.6 |
| 4 | Mean | 1.9 | 2.6 | 3.7 | 4.0 | 4.3 | 5.6 | 5.0 |
|   | SD | 0.2 | 0.3 | 0.6 | 0.4 | 0.9 | 0.4 | NA |

TABLE 5.44

| Group | Stat | Baseline | Week 1 | Week 2 | Week 3 | Week 4 | Week 8 | Pre-Necropsy |
|---|---|---|---|---|---|---|---|---|
| 1 | Mean | 2.1 | 1.2 | 1.1 | 0.8 | 0.8 | 0.9 | 0.6 |
|   | SD | 0.3 | 0.2 | 0.2 | 0.2 | 0.1 | 0.2 | 0.1 |
| 2 | Mean | 2.7 | 1.2 | 1.1 | 1.1 | 1.0 | 0.9 | 0.8 |
|   | SD | 0.5 | 0.2 | 0.1 | 0.1 | 0.1 | 0.2 | 0.2 |
| 3 | Mean | 2.0 | 1.2 | 1.1 | 1.1 | 0.9 | 0.8 | 0.7 |
|   | SD | 0.2 | 0.2 | 0.2 | 0.2 | 0.2 | 0.0 | 0.1 |
| 4 | Mean | 2.3 | 1.4 | 1.1 | 0.9 | 0.8 | 0.5 | 0.6 |
|   | SD | 0.2 | 0.1 | 0.2 | 0.1 | 0.1 | 0.1 | NA |

NA = not applicable, n is too small for SD

Table 5.45 shows the N-Values by Time Point.

TABLE 5.45

| Group | Baseline | Week 1 | Week 2 | Week 3 | Week 4 | Week 8 | Pre-Necropsy |
|---|---|---|---|---|---|---|---|
| 1 | 8 | 8 | 7 | 7 | 6 | 4 | 7 |
| 2 | 8 | 8 | 8 | 8 | 8 | 6 | 6 |
| 3 | 8 | 8 | 7 | 7 | 7 | 5 | 6 |
| 4 | 8 | 7 | 7 | 6 | 5 | 3 | 2 |

Blood gas data is provided in Tables 5.46 (pH); 5.47 (PCO2 (mmHg)); 5.48 (PO2 (mmHg)); 5.49 (BEecf (mmol/L)); 5.50 (HCO3 (mmol/L)); 5.51 (TCO2 (mmol/L)); 5.52 (SO2 (Percent)); 5.53 (Sodium (mmol/L)); 5.54 (Potassium (mmol/L)); 5.55 (Ionized Calcium (mmol/L)); 5.56 (Glucose (mg/dL)); 5.57 (Hematocrit (Percent)), and 5.58 (Hb) below. This data is based on the individual values of the animals in each group (data not shown).

TABLE 5.46

| Group | Stat | Baseline |
|---|---|---|
| 1 | Mean | 7.327 |
|   | SD | 0.046 |
| 2 | Mean | 7.288 |
|   | SD | 0.050 |
| 3 | Mean | 7.329 |
|   | SD | 0.044 |
| 4 | Mean | 7.346 |
|   | SD | 0.048 |

TABLE 5.47

| Group | Stat | Baseline |
|---|---|---|
| 1 | Mean | 68.8 |
|   | SD | 11.0 |
| 2 | Mean | 72.1 |
|   | SD | 11.1 |

TABLE 5.47-continued

| Group | Stat | Baseline |
|---|---|---|
| 3 | Mean | 65.8 |
|   | SD   | 3.9 |
| 4 | Mean | 58.6 |
|   | SD   | 6.6 |

TABLE 5.48

| Group | Stat | Baseline |
|---|---|---|
| 1 | Mean | 267 |
|   | SD   | 201 |
| 2 | Mean | 220 |
|   | SD   | 218 |
| 3 | Mean | 222 |
|   | SD   | 244 |
| 4 | Mean | 287 |
|   | SD   | 200 |

TABLE 5.49

| Group | Stat | Baseline |
|---|---|---|
| 1 | Mean | 10 |
|   | SD   | 2 |
| 2 | Mean | 8 |
|   | SD   | 3 |
| 3 | Mean | 9 |
|   | SD   | 4 |
| 4 | Mean | 6 |
|   | SD   | 3 |

TABLE 5.50

| Group | Stat | Baseline |
|---|---|---|
| 1 | Mean | 35.7 |
|   | SD   | 2.8 |
| 2 | Mean | 34.3 |
|   | SD   | 3.2 |
| 3 | Mean | 34.7 |
|   | SD   | 3.2 |
| 4 | Mean | 32.0 |
|   | SD   | 2.1 |

TABLE 5.51

| Group | Stat | Baseline |
|---|---|---|
| 1 | Mean | 38 |
|   | SD   | 3 |
| 2 | Mean | 37 |
|   | SD   | 3 |
| 3 | Mean | 37 |
|   | SD   | 3 |
| 4 | Mean | 34 |
|   | SD   | 2 |

TABLE 5.52

| Group | Stat | Baseline |
|---|---|---|
| 1 | Mean | 93 |
|   | SD   | 11 |
| 2 | Mean | 84 |
|   | SD   | 19 |

TABLE 5.52-continued

| Group | Stat | Baseline |
|---|---|---|
| 3 | Mean | 85 |
|   | SD   | 13 |
| 4 | Mean | 98 |
|   | SD   | 5 |

TABLE 5.53

| Group | Stat | Baseline |
|---|---|---|
| 1 | Mean | 147 |
|   | SD   | 13 |
| 2 | Mean | 142 |
|   | SD   | 9 |
| 3 | Mean | 146 |
|   | SD   | 10 |
| 4 | Mean | 137 |
|   | SD   | 2 |

TABLE 5.54

| Group | Stat | Baseline |
|---|---|---|
| 1 | Mean | 4.3 |
|   | SD   | 0.5 |
| 2 | Mean | 4.0 |
|   | SD   | 0.4 |
| 3 | Mean | 4.2 |
|   | SD   | 0.3 |
| 4 | Mean | 3.9 |
|   | SD   | 0.2 |

TABLE 5.55

| Group | Stat | Baseline |
|---|---|---|
| 1 | Mean | 1.39 |
|   | SD   | 0.05 |
| 2 | Mean | 1.43 |
|   | SD   | 0.07 |
| 3 | Mean | 1.39 |
|   | SD   | 0.08 |
| 4 | Mean | 1.39 |
|   | SD   | 0.04 |

TABLE 5.56

| Group | Stat | Baseline |
|---|---|---|
| 1 | Mean | 80 |
|   | SD   | 18 |
| 2 | Mean | 85 |
|   | SD   | 13 |
| 3 | Mean | 88 |
|   | SD   | 20 |
| 4 | Mean | 78 |
|   | SD   | 11 |

TABLE 5.57

| Group | Stat | Baseline |
|---|---|---|
| 1 | Mean | 29 |
|   | SD   | 3 |
| 2 | Mean | 28 |
|   | SD   | 3 |
| 3 | Mean | 28 |
|   | SD   | 3 |

TABLE 5.57-continued

| Group | Stat | Baseline |
|---|---|---|
| 4 | Mean | 27 |
|   | SD | 2 |

TABLE 5.58

| Group | Stat | Baseline |
|---|---|---|
| 1 | Mean | 9.9 |
|   | SD | 1.1 |
| 2 | Mean | 9.6 |
|   | SD | 0.9 |
| 3 | Mean | 9.5 |
|   | SD | 0.9 |
| 4 | Mean | 9.3 |
|   | SD | 0.7 |

Table 5.59 shows the N-Values by Time Point.

TABLE 5.59

| Group | Baseline |
|---|---|
| 1 | 8 |
| 2 | 8 |
| 3 | 8 |
| 4 | 8 |

The quantitative microscopic urine analysis is provided in Tables 5.60 (Urine Glucose (MG/DL) Ref. Range) and 5.61 (Urine Total Protein (MG/DL) Ref. Range 0-100). This data is based on the individual values of the animals in each group (data not shown).

TABLE 5.60

| Group | Stat | Baseline | Pre-Necropsy |
|---|---|---|---|
| 1 | Mean | 12.9 | 3.3 |
|   | SD | 9.6 | 3.9 |
| 2 | Mean | 9.8 | 2.5 |
|   | SD | 3.6 | 2.1 |
| 3 | Mean | 11.9 | 38.0 |
|   | SD | 7.0 | 39.2 |
| 4 | Mean | 13.1 | 2.0 |
|   | SD | 25.0 | NA |

TABLE 5.61

| Group | Stat | Baseline | Pre-Necropsy |
|---|---|---|---|
| 1 | Mean | 38.5 | 278.0 |
|   | SD | 38.3 | 575.2 |
| 2 | Mean | 25.6 | 24.7 |
|   | SD | 21.0 | 54.8 |
| 3 | Mean | 34.5 | 20.5 |
|   | SD | 45.2 | 33.2 |
| 4 | Mean | 9.3 | 82.5 |
|   | SD | 11.4 | NA |

Table 5.62 provides the individual Profiles of the Bacteria (/HPF) Ref. Range for each animal.

TABLE 5.62

| ANIMAL # | Group | Sex | Baseline | Pre-Necropsy |
|---|---|---|---|---|
| 1 | 1 | F | TRACE | 3+ |
| 2 | 1 | F | TRACE | 1+ |
| 3 | 1 | F | TRACE | — |
| 4 | 1 | F | TRACE | — |
| 5 | 1 | M | TRACE | 1+ |
| 8 | 1 | M | TRACE | — |
| 6 | 1 | M | TRACE | Trace |
| 7 | 1 | M | TRACE | — |
| 9 | 2 | F | TRACE | — |
| 10 | 2 | F | TRACE | — |
| 11 | 2 | F | TRACE | none |
| 12 | 2 | F | TRACE | — |
| 13 | 2 | M | TRACE | — |
| 14 | 2 | M | TRACE | 1+ |
| 15 | 2 | M | TRACE | Trace |
| 16 | 2 | M | TRACE | — |
| 17 | 3 | F | TRACE | — |
| 18 | 3 | F | TRACE | 2+ |
| 19 | 3 | F | TRACE | — |
| 20 | 3 | F | TRACE | — |
| 22 | 3 | M | TRACE | — |
| 23 | 3 | M | TRACE | Trace |
| 21 | 3 | M | TRACE | none |
| 24 | 3 | M | TRACE | Trace |
| 25 | 4 | F | TRACE | Trace |
| 26 | 4 | F | TRACE | Trace |
| 27 | 4 | F | TRACE | — |
| 28 | 4 | F | TRACE | — |
| 29 | 4 | M | TRACE | — |
| 30 | 4 | M | TRACE | — |
| 31 | 4 | M | TRACE | — |
| 32 | 4 | M | TRACE | — |

Qualitative urine analysis was also performed for each animal: Specific Gravity (g/mL) Ref. Range 1.001-1.035; Blood (Ery/μL) Ref. Range Neg. (non-Haemolyzed); Trace-Spur (Haemolyzed); pH Ref. Range 4.6-8.0; Protein (mg/dL) Ref. Range <150 mg; Urobilinogen (mg/dL) Ref. Range ≤1; Nitrates (~Leu/μL) Ref. Range neg; and Leukocytes (~Leu/μL) Ref. Range neg (data not shown).

Urine bacterial culture and sensitivity results were obtained. Bacteria was cultured from two animals Animal 18 was found to have ESCHERICHIA COLI—greater than 100,000 organisms per ml; MORGANELLA MORGANIT—greater than 100,000 organisms per ml ENTEROCOCCUS SPECIES—2+ ENTEROCOCCUS SPECIES 2+ second strain. Animal 32 was found to have PROTEUS MIRABILIS—greater than 100,000 organisms per ml strain 1 PROTEUS MIRABILIS—greater than 100,000 organisms per ml strain 2 NON-ENTERIC GRAM NEG ROD unable to speciate—10,000-50,000 organisms per ml.

Hematology for 7 Surviving Animals. Postoperative blood collection for hematology revealed the development of leukocytosis for all groups. Leukocyte counts for the construct groups (Groups 1-3) rose from baseline to week 2-4 and then plateaued or decreased thereafter; however, leukocyte counts for the scaffold-only group (Group 4) continued to increase until necropsy (Table 5.63 Average WBC Count by Group for 7 Surviving Animals (reference range 11-22 THSN/UL)).

TABLE 5.63

| Group | Baseline | Week 1 | Week 2 | Week 3 | Week 4 | Week 8 | Pre-Necropsy |
|---|---|---|---|---|---|---|---|
| 1 (N = 2) | 7.3 | 29.4 | 47.6 | 23.6 | 24.0 | 19.1 | 13.2 |
| 2 (N = 1) | 5.7 | 10.3 | 17.9 | 31.4 | 15.1 | 17.7 | 12.3 |
| 3 (N = 2) | 9.5 | 15.6 | 17.0 | 12.9 | 22.0 | 19.6 | 13.2 |
| 4 (N = 2) | 10.3 | 11.9 | 14.8 | 28.1 | 25.4 | 27.6 | 34.5 |

Red blood cell counts (RBCs) were similar across all groups (Table 5.64). At necropsy, mean RBC was within the reference range for all groups except Group 3. (Table 5.64—Average RBC Count by Group for 7 Surviving Animals (reference range 5-8 MILL/UL).

TABLE 5.64

| Group | Baseline | Week 1 | Week 2 | Week 3 | Week 4 | Week 8 | Pre-Necropsy |
|---|---|---|---|---|---|---|---|
| 1 (N = 2) | 6.8 | 6.6 | 5.3 | 5.8 | 6.9 | 5.4 | 6.4 |
| 2 (N = 1) | 6.3 | 6.2 | 5.7 | 5.8 | 5.7 | 5.6 | 5.9 |
| 3 (N = 2) | 6.4 | 6.7 | 6.4 | 6.5 | 6.8 | 5.5 | 4.7 |
| 4 (N = 2) | 6.2 | 6.4 | 6.2 | 7.5 | 7.0 | 6.8 | 5.1 |

Hematocrit values for all groups were below or at the low end of reference at baseline and fluctuated during the study, with values in the lower limit of the reference range at week 8 and necropsy (Table 5.65—Average Hematocrit by Group for 7 Surviving Animals (reference range 32-50%)).

TABLE 5.65

| Group | Baseline | Week 1 | Week 2 | Week 3 | Week 4 | Week 8 | Pre-Necropsy |
|---|---|---|---|---|---|---|---|
| 1 (N = 2) | 34.0 | 35.0 | 27.9 | 30.5 | 37.1 | 28.2 | 30.8 |
| 2 (N = 1) | 31.0 | 32.1 | 30.5 | 31.4 | 31.0 | 29.4 | 28.8 |
| 3 (N = 2) | 32.0 | 36.0 | 34.4 | 33.9 | 36.2 | 28.6 | 24.1 |
| 4 (N = 2) | 29.3 | 30.6 | 29.0 | 35.0 | 32.2 | 32.1 | 23.4 |

Hematology for 12 non-PCV2 Unscheduled Deaths. Postoperative blood collection for hematology revealed the development of leukocytosis for all groups (Table 5.66—Average WBC Count by Group for 12 non-PCV2 Unscheduled Deaths (reference range 11-22 THNS/UL). Table 5.66

| Group | Baseline | Week 1 | Week 2 | Week 3 | Week 4 | Week 8 | Pre-Necropsy |
|---|---|---|---|---|---|---|---|
| 1 (N = 1)* | 7.6 | 42.4 | NA | NA | NA | NA | NA |
| 2 (N = 3) | 5.4 | 11.9 | 19.1 | 21.1 | 16.2 | 31.0 | 23.8 |
| 3 (N = 4) | 10.0 | 13.4 | 17.5 | 18.5 | 18.2 | 28.5 | 24.3 |
| 4 (N = 4) | 11.8 | 15.6 | 27.6 | 32.4 | 25.3 | 26.8 | NA |

NA = Not applicable
*Animal no. 8 euthanized on day 9.

Red blood cell counts (RBCs) were within normal ranges and similar across all groups (Table 5.67—Average RBC Count by Group for 12 non-PCV2 Unscheduled Deaths (reference range 5-8 MILL/UL).

TABLE 5.67

| Group | Baseline | Week 1 | Week 2 | Week 3 | Week 4 | Week 8 | Pre-Necropsy |
|---|---|---|---|---|---|---|---|
| 1 (N = 1)* | 6.6 | 8.4 | NA | NA | NA | NA | NA |
| 2 (N = 3) | 6.5 | 7.1 | 6.9 | 7.4 | 6.3 | 6.5 | 6.4 |
| 3 (N = 4) | 6.3 | 6.9 | 7.4 | 5.7 | 6.2 | 5.6 | 5.6 |
| 4 (N = 4) | 6.5 | 6.4 | 6.5 | 6.9 | 6.7 | 4.7 | NA |

NA = Not applicable
*Animal no. 8 euthanized on day 9.

Hematocrit values for the scaffold only group (Group 4) showed a significant drop in hematocrit values at week 8 (Table 5.68—Average Hematocrit by Group for 12 non-PCV2 Unscheduled Deaths (reference range 32-50%).

TABLE 5.68

| Group | Baseline | Week 1 | Week 2 | Week 3 | Week 4 | Week 8 | Pre-Necropsy |
|---|---|---|---|---|---|---|---|
| 1 (N = 1)* | 30.1 | 41.7 | NA | NA | NA | NA | NA |
| 2 (N = 3) | 31.5 | 34.4 | 33.8 | 36.4 | 31.0 | 31.8 | 30.2 |
| 3 (N = 4) | 30.8 | 35.6 | 37.6 | 28.9 | 31.5 | 28.8 | 28.1 |
| 4 (N = 4) | 29.6 | 29.2 | 29.2 | 31.1 | 29.9 | 20.5 | NA |

NA = Not applicable
*Animal no. 8 euthanized on day 9.

Coagulation for 7 Surviving Animals Coagulation panels revealed elevated fibrinogen for all groups throughout the study. The scaffold only group (Group 4) had the highest concentration and greatest elevation in fibrinogen from baseline (Table 5.69—Average Fibrinogen by Group for 7 Surviving Animals (reference range 100-500 mg/dL MG/DL).

TABLE 5.69

| Group | Baseline | Week 1 | Week 2 | Week 3 | Week 4 | Week 8 | Pre-Necropsy |
|---|---|---|---|---|---|---|---|
| 1 (N = 2) | 673 | 968 | 1606 | 1076 | 344 | 785 | 789 |
| 2 (N = 1) | 394 | 1116 | 381 | 947 | 1069 | 794 | 833 |
| 3 (N = 2) | 529 | 1148 | 502 | 716 | 629 | 1052 | 1027 |
| 4 (N = 2) | 419 | 546 | 1704 | 1469 | 868 | 1297 | 1496 |

The activated partial thromboplastin time was elevated or high normal throughout the study and related to the higher fibrinogen concentration (Table 5.70—Average APTT by Group for 7 Surviving Animals (reference range 18.4-27.2 Seconds).

TABLE 5.70

| Group | Baseline | Week 1 | Week 2 | Week 3 | Week 4 | Week 8 | Pre-Necropsy |
|---|---|---|---|---|---|---|---|
| 1 (N = 2) | 44.15 | 30.85 | 27.05 | 38.60 | 34.00 | 29.25 | 16.30 |
| 2 (N = 1) | 29.00 | 23.30 | 45.00 | 29.50 | 28.30 | 25.50 | 16.20 |
| 3 (N = 2) | 28.25 | 20.85 | 36.50 | 28.95 | 33.00 | 24.05 | 24.30 |
| 4 (N = 2) | 44.35 | 41.00 | 33.40 | 38.00 | 33.75 | 44.05 | 29.05 |

Coagulation for 12 non-PCV-2 Unscheduled Deaths. Coagulation panels revealed elevated fibrinogen for all groups throughout the study. The scaffold only group (Group 4) had the highest concentration and greatest elevation in fibrinogen from baseline (Table 5.71—Average Fibrinogen by Group for 12 non-PCV-2 Unscheduled Deaths (reference range 100-500 MG/DL).

TABLE 5.71

| Group | Baseline | Week 1 | Week 2 | Week 3 | Week 4 | Week 8 | Pre-Necropsy |
|---|---|---|---|---|---|---|---|
| 1 (N = 1)* | 282 | 7056 | NA | NA | NA | NA | NA |
| 2 (N = 3) | 406 | 1007 | 921 | 567 | 899 | 918 | 1531 |
| 3 (N = 4) | 603 | 682 | 518 | 603 | 1253 | 1051 | 1859 |
| 4 (N = 4) | 869 | 1432 | 1886 | 1691 | 1172 | 2745 | NA |

NA = Not applicable
*Animal no. 8 euthanized on day 9.

The activated partial thromboplastin time generally was elevated or high normal throughout the study for all groups. (Table 5.72—Average APTT by Group for 12 non-PCV-2 Unscheduled Deaths (reference range 18.4-27.7 Seconds).

TABLE 5.72

| Group | Baseline | Week 1 | Week 2 | Week 3 | Week 4 | Week 8 | Pre-Necropsy |
|---|---|---|---|---|---|---|---|
| 1 (N = 1)* | 18.90 | 32.40 | NA | NA | NA | NA | NA |
| 2 (N = 3) | 35.03 | 31.20 | 31.90 | 41.15 | 31.20 | 16.80 | 22.77 |
| 3 (N = 4) | 31.95 | 27.45 | 48.13 | 42.88 | 33.88 | 27.00 | 17.07 |
| 4 (N = 4) | 39.88 | 42.88 | 29.60 | 35.15 | 28.37 | 25.90 | NA |

NA = Not applicable
*Animal no. 8 euthanized on day 9.

Serum Chemistry for 7 Surviving Animals.

Increases in BUN are shown in Table 5.73—Average BUN by Group for 7 Surviving Animals (reference range 10-30 MG/DL.

TABLE 5.73

| Group | Baseline | Week 1 | Week 2 | Week 3 | Week 4 | Week 8 | Pre-Necropsy |
|---|---|---|---|---|---|---|---|
| 1 (N = 2) | 12 | 22 | 26 | 17 | 13 | 46 | 89 |
| 2 (N = 1) | 8 | 34 | 9 | 7 | 6 | 44 | 214 |
| 3 (N = 2) | 12 | 38 | 30 | 21 | 15 | 48 | 42 |
| 4 (N = 2) | 8 | 11 | 23 | 45 | 25 | 34 | 44 |

Increases in creatinine are shown in Table 5.74—Average Creatinine by Group for 7 Surviving Animals (reference range 1-2.7 MC/DL),

TABLE 5.74

| Group | Baseline | Week 1 | Week 2 | Week 3 | Week 4 | Week 8 | Pre-Necropsy |
|---|---|---|---|---|---|---|---|
| 1 (N = 2) | 1.1 | 1.4 | 1.2 | 1.1 | 1.2 | 1.3 | 1.9 |
| 2 (N = 1) | 0.9 | 0.9 | 0.8 | 0.8 | 0.7 | 0.9 | 1.5 |
| 3 (N = 2) | 1.4 | 2.3 | 1.5 | 1.3 | 1.3 | 1.6 | 1.2 |
| 4 (N = 2) | 1.1 | 1.2 | 1.2 | 2.5 | 1.9 | 3.1 | 3.2 |

Increases in potassium are shown in Table 5.75—Average Potassium by Group for 7 Surviving Animals (reference range 4.4-6.7 MEQ/L).

TABLE 5.75

| Group | Baseline | Week 1 | Week 2 | Week 3 | Week 4 | Week 8 | Pre-Necropsy |
|---|---|---|---|---|---|---|---|
| 1 (N = 2) | 4.1 | 4.4 | 4.5 | 5.1 | 6.3 | 4.1 | 6.2 |
| 2 (N = 1) | 4.6 | 3.2 | 4.4 | 4.1 | 4.4 | 4.4 | 4.8 |
| 3 (N = 2) | 4.3 | 3.3 | 5.2 | 4.2 | 5.1 | 5.2 | 5.2 |
| 4 (N = 2) | 3.7 | 3.9 | 4.9 | 4.2 | 3.6 | 3.8 | 4.6 |

Increases in total protein are shown in Table 5.76—Average Total Protein by Group for 7 Surviving Animals (reference range 5.5-8.5 G/DL).

TABLE 5.76

| Group | Baseline | Week 1 | Week 2 | Week 3 | Week 4 | Week 8 | Pre-Necropsy |
|---|---|---|---|---|---|---|---|
| 1 (N = 2) | 6.2 | 6.5 | 6.8 | 7.3 | 7.2 | 7.1 | 7.8 |
| 2 (N = 1) | 5.0 | 5.8 | 6.2 | 6.7 | 6.7 | 6.8 | 7.2 |
| 3 (N = 2) | 6.5 | 7.1 | 7.4 | 7.4 | 7.7 | 8.0 | 8.3 |
| 4 (N = 2) | 6.2 | 6.6 | 7.5 | 7.5 | 7.8 | 8.7 | 8.1 |

Decreases in sodium are shown in Table 5.77—Average Sodium by Group for 7 Surviving Animals (reference range 135-150 MEQ/L).

TABLE 5.77

| Group | Baseline | Week 1 | Week 2 | Week 3 | Week 4 | Week 8 | Pre-Necropsy |
|---|---|---|---|---|---|---|---|
| 1 (N = 2) | 154 | 137 | 143 | 140 | 144 | 138 | 141 |
| 2 (N = 1) | 147 | 131 | 145 | 144 | 140 | 133 | 140 |
| 3 (N = 2) | 146 | 139 | 136 | 139 | 144 | 142 | 140 |
| 4 (N = 2) | 138 | 139 | 135 | 129 | 138 | 135 | 140 |

Decreases in phosphorous are shown in Table 5.78—Average Phosphorous by Group for 7 Surviving Animals (reference range 9.9-11.9 MG/DL).

TABLE 5.78

| Group | Baseline | Week 1 | Week 2 | Week 3 | Week 4 | Week 8 | Pre-Necropsy |
|---|---|---|---|---|---|---|---|
| 1 (N = 2) | 8.9 | 6.0 | 5.5 | 7.0 | 7.9 | 6.5 | 6.4 |
| 2 (N = 1) | 8.3 | 3.1 | 7.9 | 6.2 | 6.9 | 6.4 | 5.7 |
| 3 (N = 2) | 7.6 | 6.4 | 7.7 | 6.9 | 7.2 | 7.3 | 7.1 |
| 4 (N = 2) | 7.5 | 6.6 | 7.5 | 7.5 | 6.8 | 5.7 | 6.6 |

Decreases in albumin are shown in Table 5.79—Average Albumin by Group for 7 Surviving Animals (reference range 1.6-4.0 MG/DL).

TABLE 5.79

| Group | Baseline | Week 1 | Week 2 | Week 3 | Week 4 | Week 8 | Pre-Necropsy |
|---|---|---|---|---|---|---|---|
| 1 (N = 2) | 4.0 | 3.3 | 3.2 | 3.1 | 3.1 | 3.4 | 3.1 |
| 2 (N = 1) | 3.8 | 2.9 | 3.2 | 3.3 | 3.2 | 3.4 | 3.9 |
| 3 (N = 2) | 4.3 | 4.0 | 4.0 | 3.8 | 3.7 | 3.5 | 3.6 |
| 4 (N = 2) | 4.4 | 4.0 | 4.0 | 3.5 | 3.4 | 3.1 | 3.1 |

The increases and decreases shown in Tables 5.73 to 5.79 were observed in all groups. In general, profiles for animals receiving construct implants (Groups 1-3) appear to be similar in magnitude and temporally across; however, the scaffold-only group (Group 4) appears to have earlier serum changes of greater magnitude that suggest more advanced and serious renal deterioration.

The serum chemistry for 12 non-PCV-2 Unscheduled Deaths was also examined.

Increases in BUN are provided in Table 5.80 Text Table 34: Average BUN by Group for 12 non-PCV-2 Unscheduled Deaths (reference range 10-30 MG/DL).

TABLE 5.80

| Group | Baseline | Week 1 | Week 2 | Week 3 | Week 4 | Week 8 | Pre-Necropsy |
|---|---|---|---|---|---|---|---|
| 1 (N = 1)* | 6 | 8 | NA | NA | NA | NA | NA |
| 2 (N = 3) | 12 | 28 | 24 | 19 | 9 | 35 | 124 |
| 3 (N = 4) | 11 | 22 | 42 | 11 | 21 | 32 | 126 |
| 4 (N = 4) | 6 | 13 | 31 | 51 | 39 | 162 | NA |

NA = Not applicable
*Animal no. 8 euthanized on day 9.

Increases in creatinine are provided in Table 5.81—Average Creatinine by Group for 12 non-PCV-2 Unscheduled Deaths (reference range 1-2.7 MC/DL).

TABLE 5.81

| Group | Baseline | Week 1 | Week 2 | Week 3 | Week 4 | Week 8 | Pre-Necropsy |
|---|---|---|---|---|---|---|---|
| 1 (N = 1)* | 1.0 | 0.9 | NA | NA | NA | NA | NA |
| 2 (N = 3) | 1.1 | 1.7 | 1.3 | 1.1 | 1.0 | 1.4 | 2.0 |
| 3 (N = 4) | 1.0 | 1.4 | 2.0 | 0.9 | 1.2 | 1.3 | 2.6 |
| 4 (N = 4) | 1.1 | 1.1 | 1.3 | 1.6 | 1.7 | 12.7 | NA |

NA = Not applicable
*Animal no. 8 euthanized on day 9.

Increases in potassium are provided in Table 5.82—Average Potassium by Group for 12 non-PCV-2 Unscheduled Deaths (reference range 4.4-6.7 MEQ/L).

TABLE 5.82

| Group | Baseline | Week 1 | Week 2 | Week 3 | Week 4 | Week 8 | Pre-Necropsy |
|---|---|---|---|---|---|---|---|
| 1 (N = 1)* | 4.2 | 3.9 | NA | NA | NA | NA | NA |
| 2 (N = 3) | 3.8 | 4.2 | 3.8 | 4.8 | 4.4 | 5.0 | 5.3 |
| 3 (N = 4) | 4.2 | 4.5 | 6.2 | 4.6 | 4.5 | 5.3 | 5.8 |
| 4 (N = 4) | 4.1 | 4.2 | 5.3 | 4.4 | 6.0 | 5.4 | NA |

NA = Not applicable;
*Animal no. 8 euthanized on day 9.

Increases in phosphorous are provided in Table 5.83—Average Phosphorous by Group for 12 non-PCV-2 Unscheduled Deaths (reference range 9.9-11.9MG/DL).

TABLE 5.83

| Group | Baseline | Week 1 | Week 2 | Week 3 | Week 4 | Week 8 | Pre-Necropsy |
|---|---|---|---|---|---|---|---|
| 1 (N = 1)* | 10.2 | 5.9 | NA | NA | NA | NA | NA |
| 2 (N = 3) | 9.3 | 5.8 | 6.9 | 6.8 | 6.9 | 6.5 | 11.1 |
| 3 (N = 4) | 8.6 | 6.4 | 9.3 | 6.5 | 6.4 | 6.8 | 9.4 |
| 4 (N = 4) | 7.5 | 6.9 | 7.1 | 7.3 | 8.2 | 9.2 | NA |

NA = Not applicable
*Animal no. 8 euthanized on day 9.

Increases in total protein are provided in Table 5.84—Average Total Protein by Group for 12 non-PCV-2 Unscheduled Deaths (reference range 5.5-8.5G/DL).

TABLE 5.84

| Group | Baseline | Week 1 | Week 2 | Week 3 | Week 4 | Week 8 | Pre-Necropsy |
|---|---|---|---|---|---|---|---|
| 1 (N = 1)* | 6.1 | 6.2 | NA | NA | NA | NA | NA |
| 2 (N = 3) | 6.0 | 6.8 | 7.2 | 7.3 | 7.2 | 7.7 | 7.6 |
| 3 (N = 4) | 6.0 | 6.9 | 7.2 | 6.5 | 7.2 | 7.6 | 7.1 |
| 4 (N = 4) | 6.1 | 6.3 | 7.4 | 7.3 | 7.6 | 8.4 | NA |

NA = Not applicable
*Animal no. 8 euthanized on day 9.

Decreases in sodium are provided in Table 5.85—Average Sodium by Group for 12 non-PCV-2 Unscheduled Deaths (reference range 135-150 MEQ/L).

TABLE 5.85

| Group | Baseline | Week 1 | Week 2 | Week 3 | Week 4 | Week 8 | Pre-Necropsy |
|---|---|---|---|---|---|---|---|
| 1 (N = 1)* | 140 | 139 | NA | NA | NA | NA | NA |
| 2 (N = 3) | 152 | 145 | 130 | 139 | 138 | 138 | 135 |
| 3 (N = 4) | 149 | 142 | 130 | 142 | 140 | 142 | 131 |
| 4 (N = 4) | 142 | 137 | 139 | 132 | 135 | 134 | NA |

NA = Not applicable
*Animal no. 8 euthanized on day 9.

Decreases in albumin are provided in Table 5.86—Average Albumin by Group for 12 non-PCV-2 Unscheduled Deaths (reference range 1.6-4.0 MG/DL).

TABLE 5.86

| Group | Baseline | Week 1 | Week 2 | Week 3 | Week 4 | Week 8 | Pre-Necropsy |
|---|---|---|---|---|---|---|---|
| 1 (N = 1)* | 4.3 | 3.5 | NA | NA | NA | NA | NA |
| 2 (N = 3) | 4.2 | 3.7 | 3.6 | 3.7 | 3.6 | 3.4 | 3.2 |
| 3 (N = 4) | 4.0 | 3.8 | 3.8 | 3.5 | 3.4 | 3.4 | 2.7 |
| 4 (N = 4) | 4.2 | 3.7 | 3.7 | 3.4 | 3.4 | 2.8 | NA |

NA = Not applicable
*Animal no. 8 euthanized on day 9.

The increases and decreases in Tables to 5.80 to 5.86 were observed in all groups. In general, profiles for animals receiving construct implants (Groups 1-3) appear to be similar in magnitude and temporally across; however, the scaffold-only group (Group 4) appears to have earlier serum changes of greater magnitude that suggest more advanced and serious renal deterioration.

Blood Gas Data for 7 Surviving Animals and 12 non-PCV-2 Unscheduled Deaths. All blood gas data were within normal limits for all 19 animals.

Urinalysis for 7 Surviving Animals and 12 non-PCV-2 Unscheduled Deaths For the 7 animals surviving to scheduled necropsy, the average urine protein values were within normal ranges of 0-100 mg/dL for all groups, although the scaffold only group (Group 4) had the highest value at necropsy (Table 5.87). Due to insufficient data available at necropsy for the 12 non-PCV-2 unscheduled deaths, comparisons could not be made. Table 5.87 provides the Average Urine Protein by Group for 7 Surviving Animals.

TABLE 5.87

| Group | Baseline | Pre-Necropsy |
|---|---|---|
| 1 (N = 2) | 22 | 23 |
| 2 (N = 1) | 15 | 12 |
| 3 (N = 2) | 19 | 47 |
| 4 (N = 2) | 2 | 83 |

Imaging. Intravenous pyelograms (IVPs) and loopograms (retrograde pyelograms) were performed for each animal. The IV Pyelogram visualization of one or both ureters and kidneys was inconsistent. In some cases kidneys, ureters and conduit were visible (radiopaque) while in other cases visibility was very limited or none. Due to the nature of the study a dilute contrast solution had to be used which resulted in limited visualization.

IVP for 7 Surviving Animals In 6/7 animals (nos. 1, 6, 15, 23, 25 and 26), the Week 8 pyelogram was possible. On Week 8, the pyelogram for animal no. 18 (Group 3) was (inadvertently) not obtained. The impact of this deviation, however, is limited to the single missing pyelogram for animal no. 18 (Group 3). Preeuthanasia pyelograms on all 7/7 animals were performed.

Figure 49A:
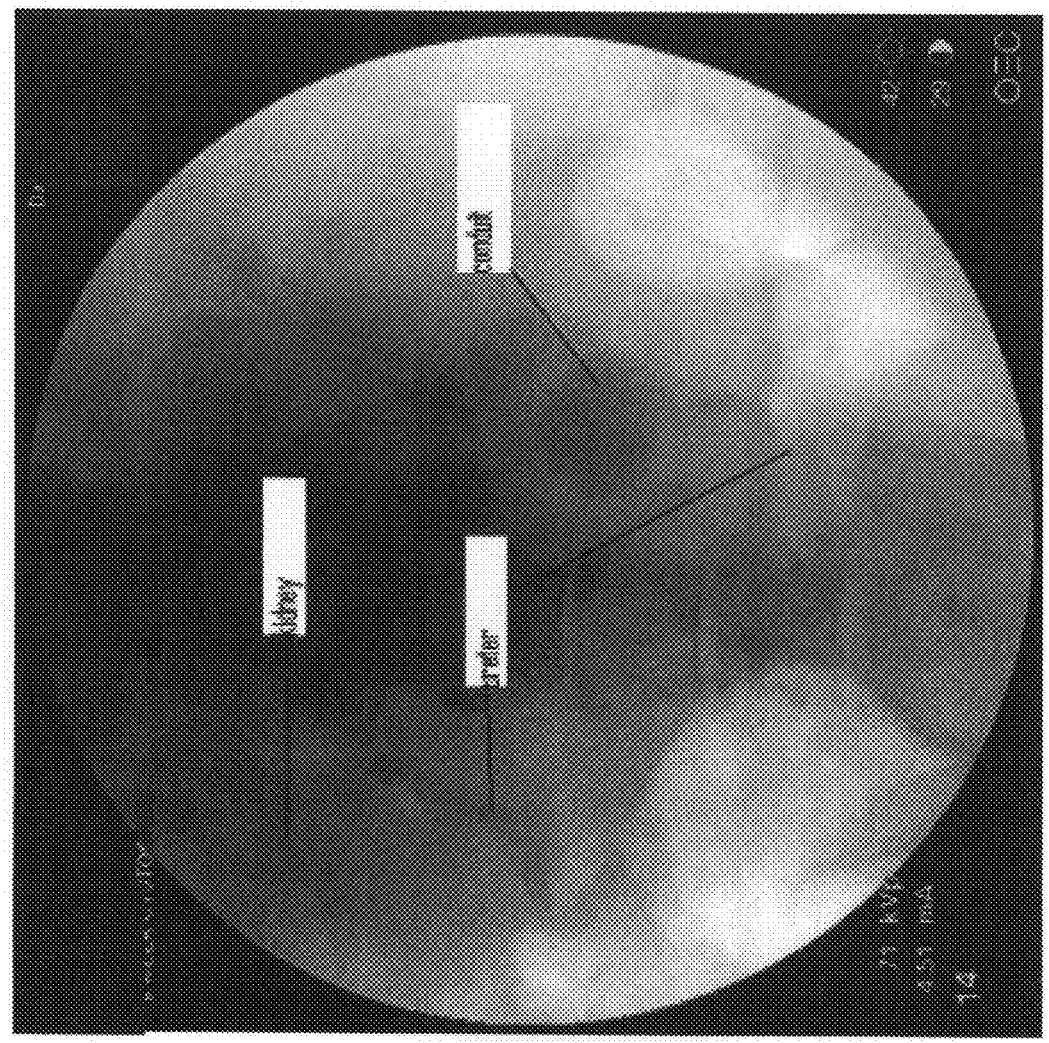
FIG. 49A-B shows pyelogram images for an animal implanted with a neo-urinary conduit (bladder SMC scaffold).
Figure 49B:
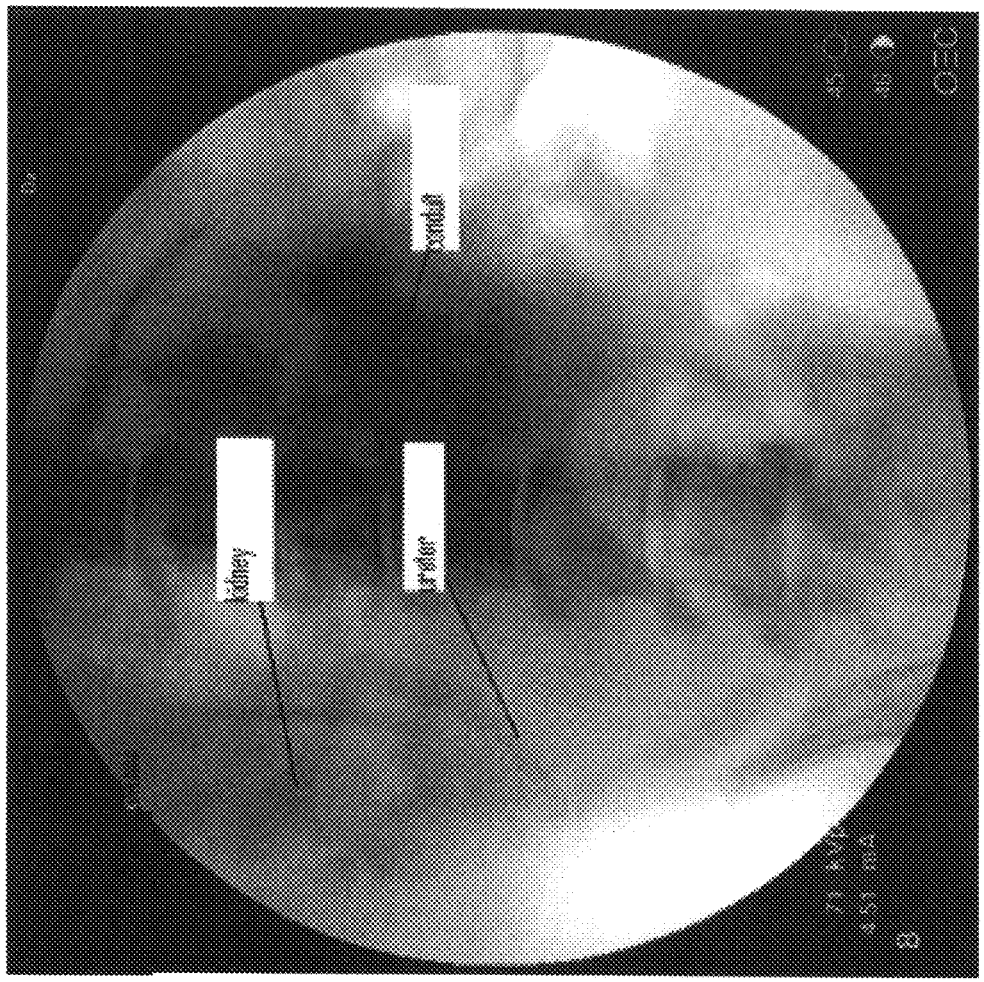
Figure 50A:
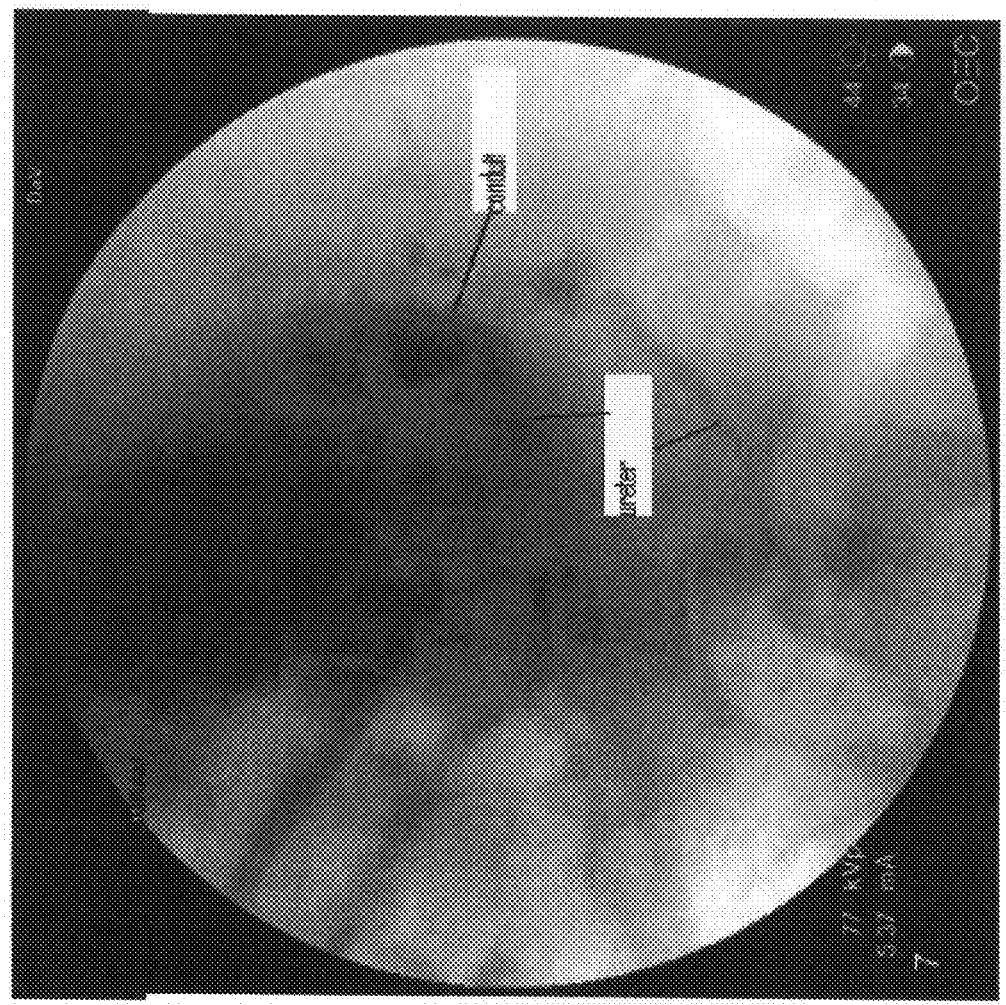
FIG. 50A-B shows pyelogram images for an animal implanted with a neo-urinary conduit (adipose SMC scaffold).
Figure 50B:
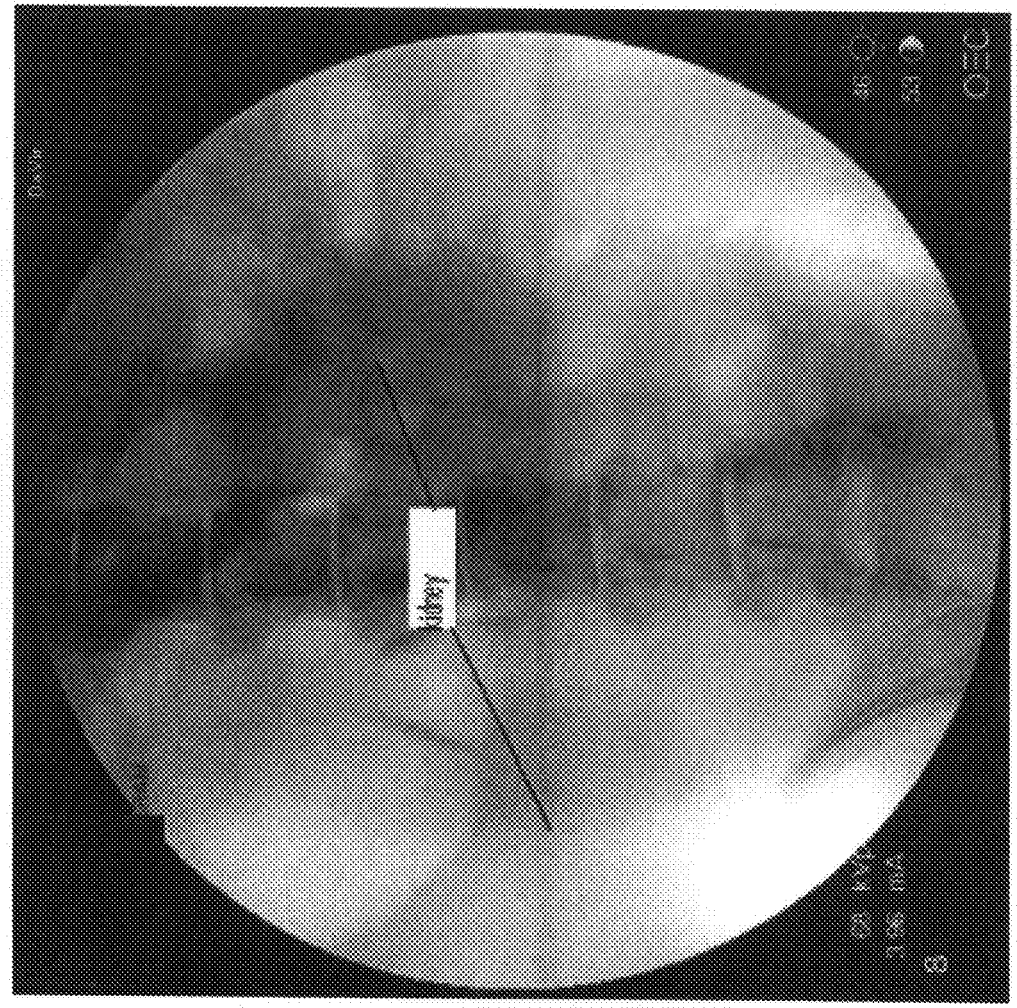
Figure 51:
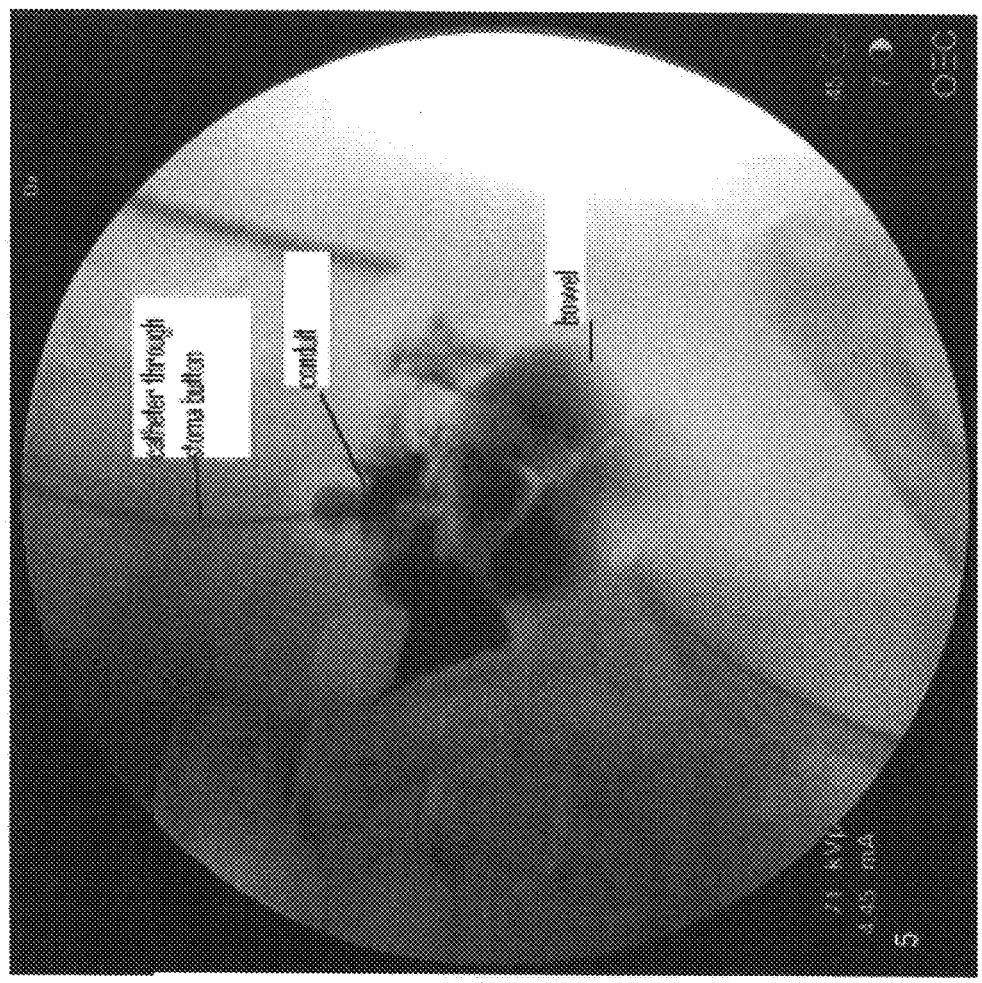
FIG. 51 shows a pyelogram image for an animal implanted with a neo-urinary conduit (adipose SMC scaffold).
Figure 52:
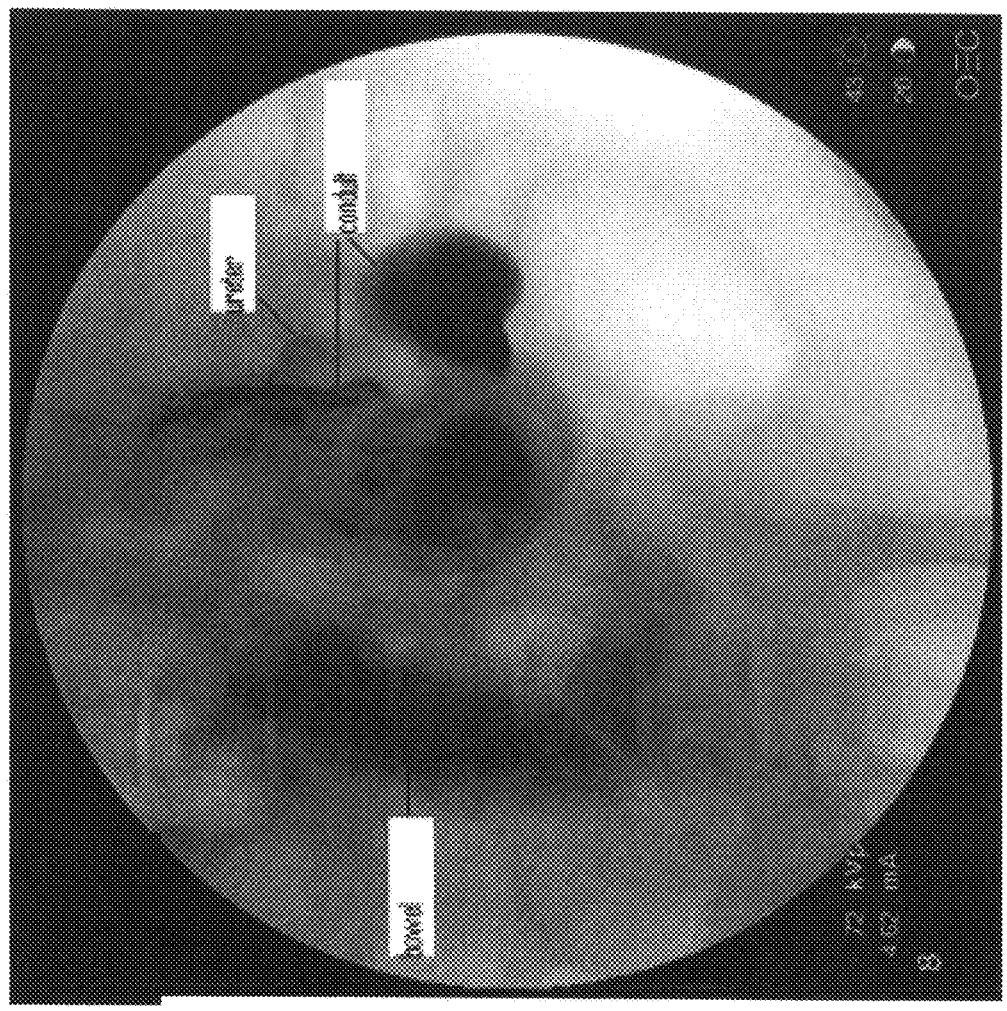
FIG. 52 shows a pyelogram image for an animal implanted with a neo-urinary conduit (blood SMC scaffold).
Figure 53:
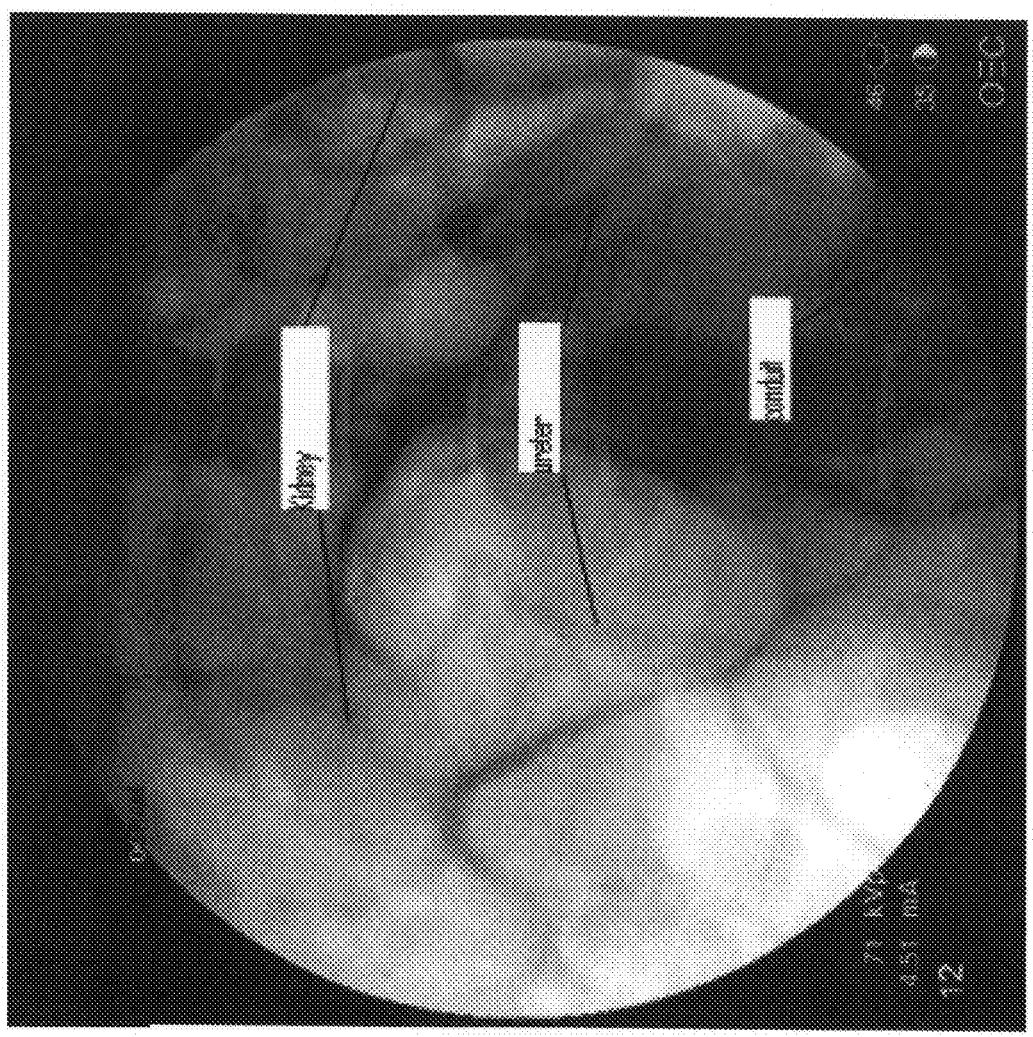
FIG. 53 shows a pyelogram image for an animal implanted with a neo-urinary conduit (blood SMC scaffold).
Figure 54:
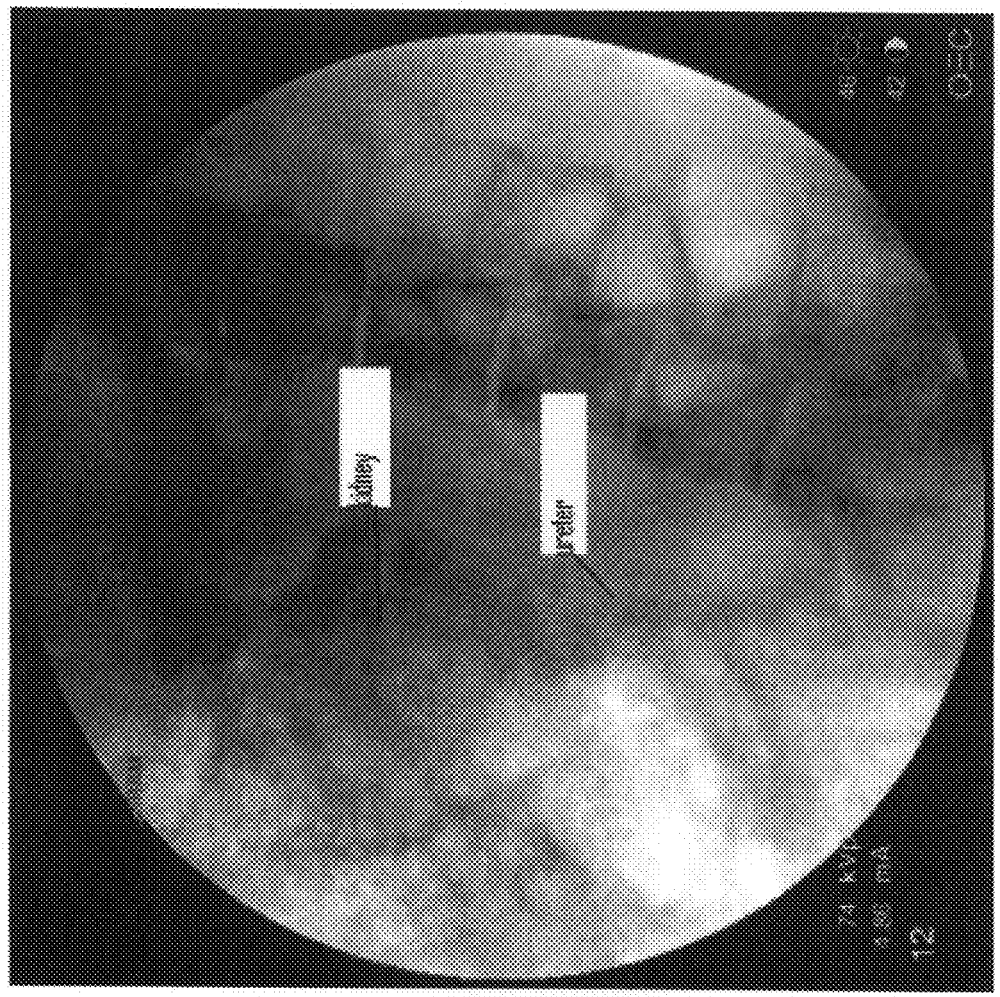
FIG. 54 shows a pyelogram image for an animal implanted with a neo-urinary conduit (blood SMC scaffold).
Figure 55A:
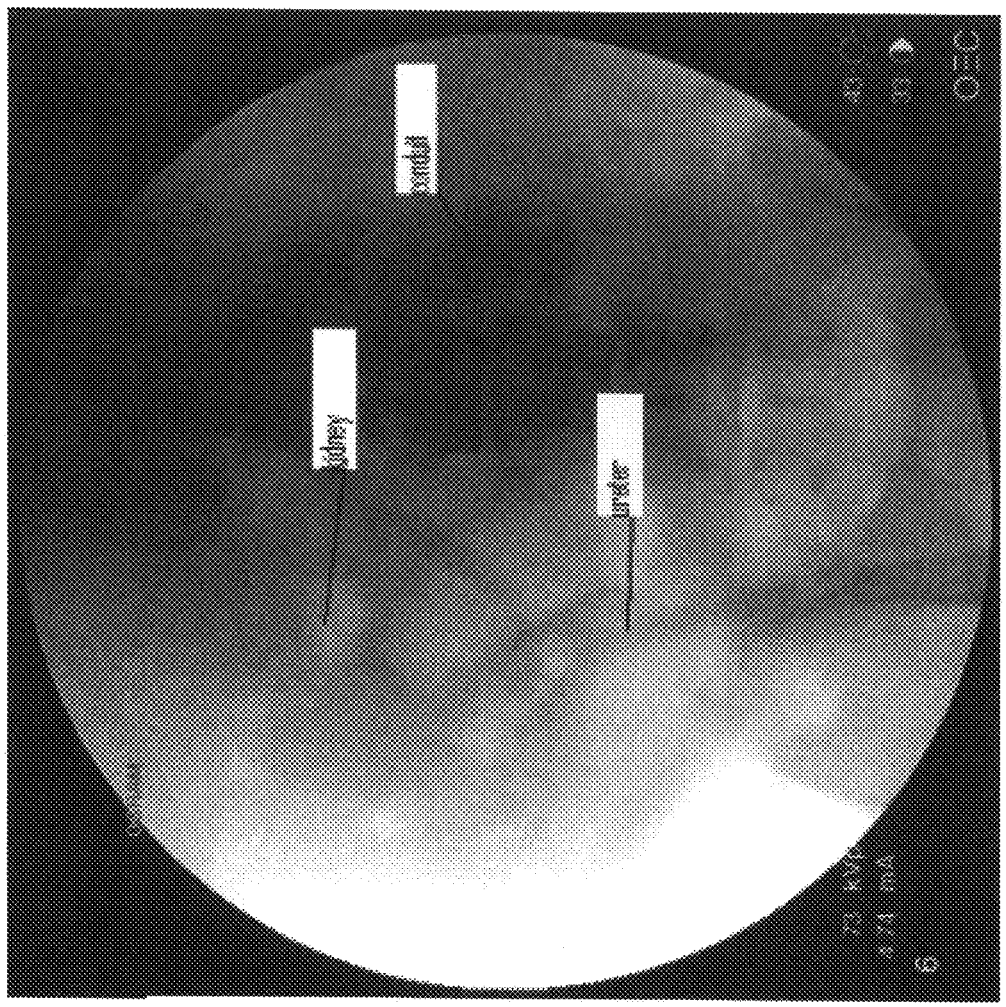
FIG. 55A-B shows pyelogram images for an animal implanted with a neo-urinary conduit (blood SMC scaffold).
Figure 55B:
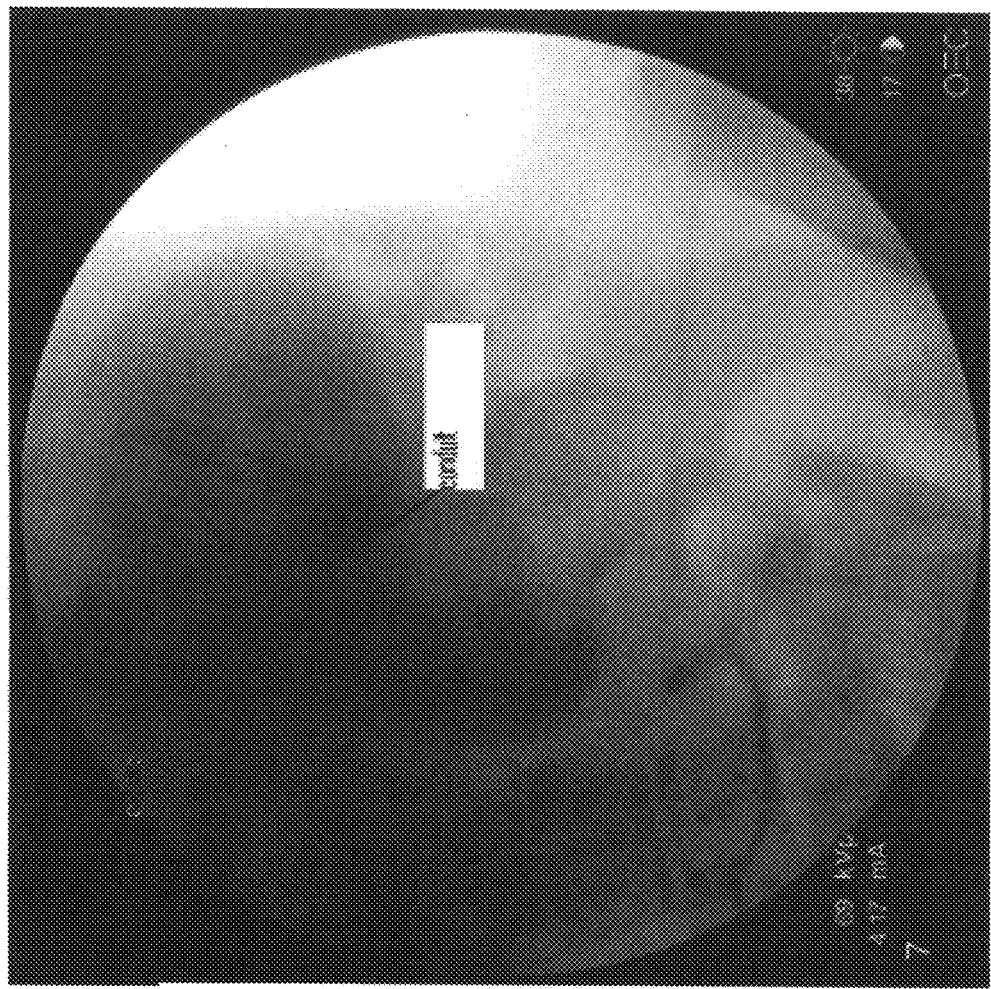
Figure 56A:
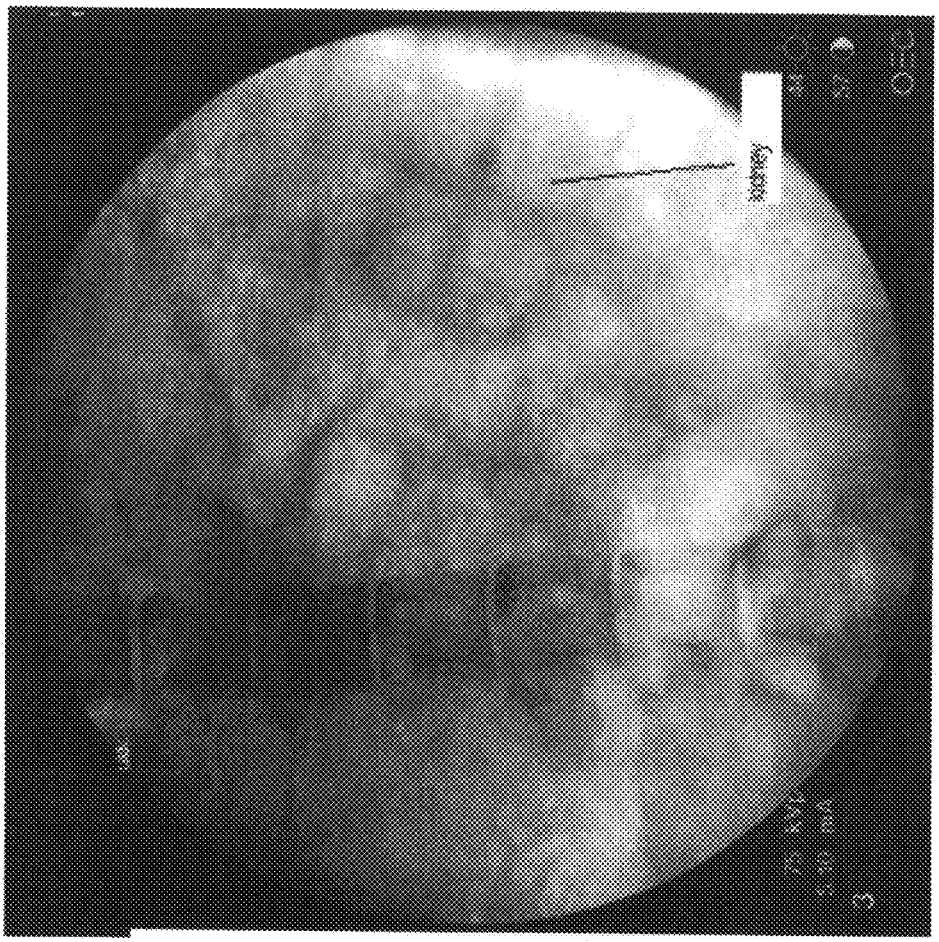
FIG. 56A-B shows pyelogram images for an animal implanted with a neo-urinary conduit (scaffold only).
Figure 56B:
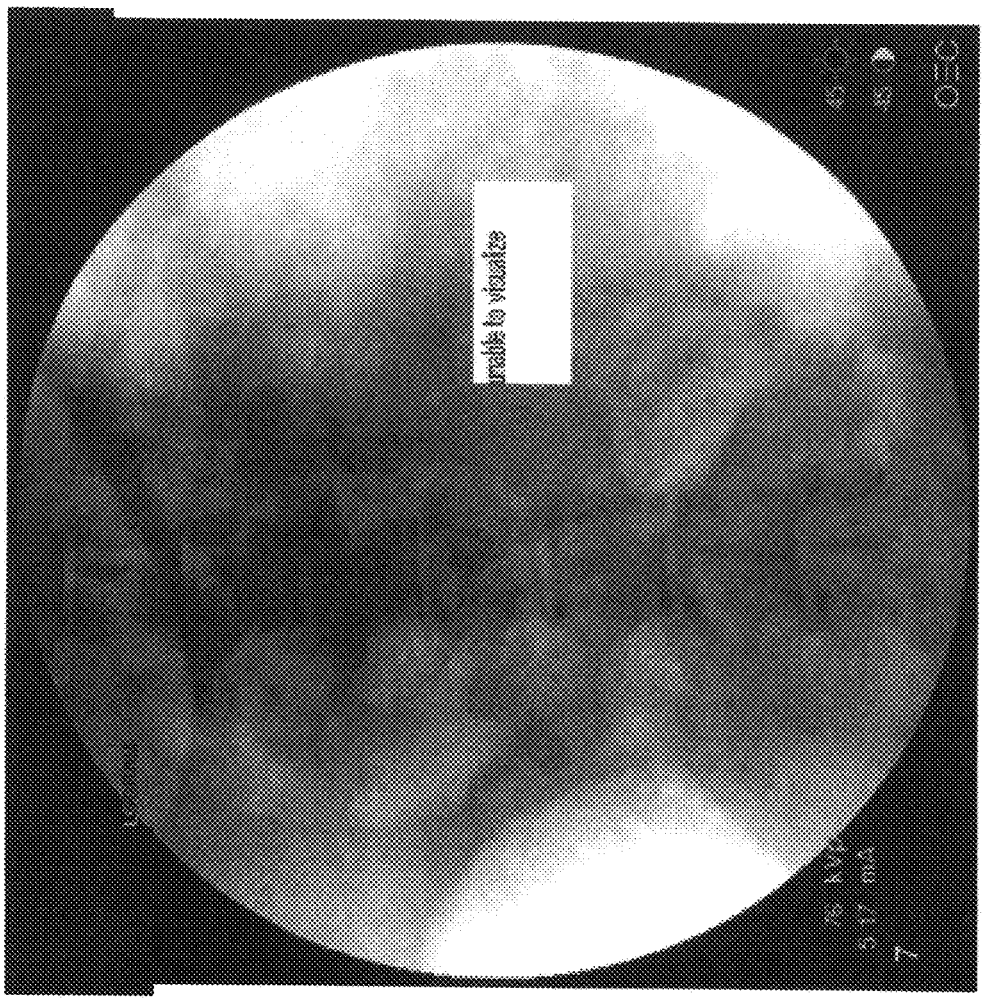
Figure 57A:
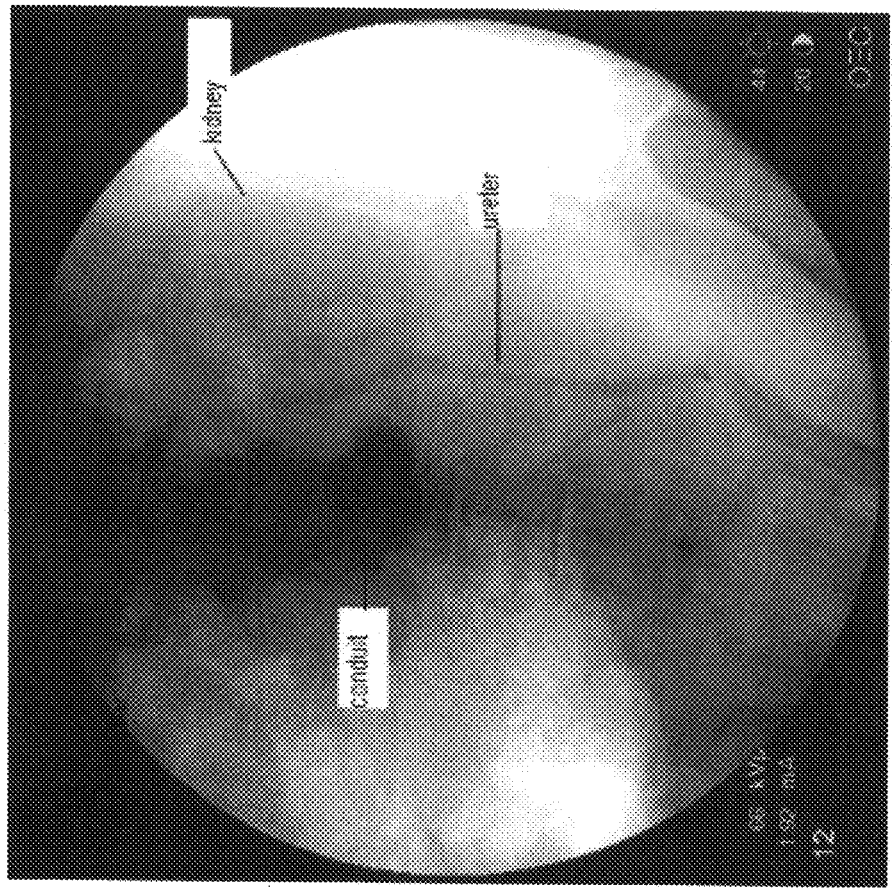
FIG. 57A-B shows pyelogram images for an animal implanted with a neo-urinary conduit (scaffold only).
Figure 57B:
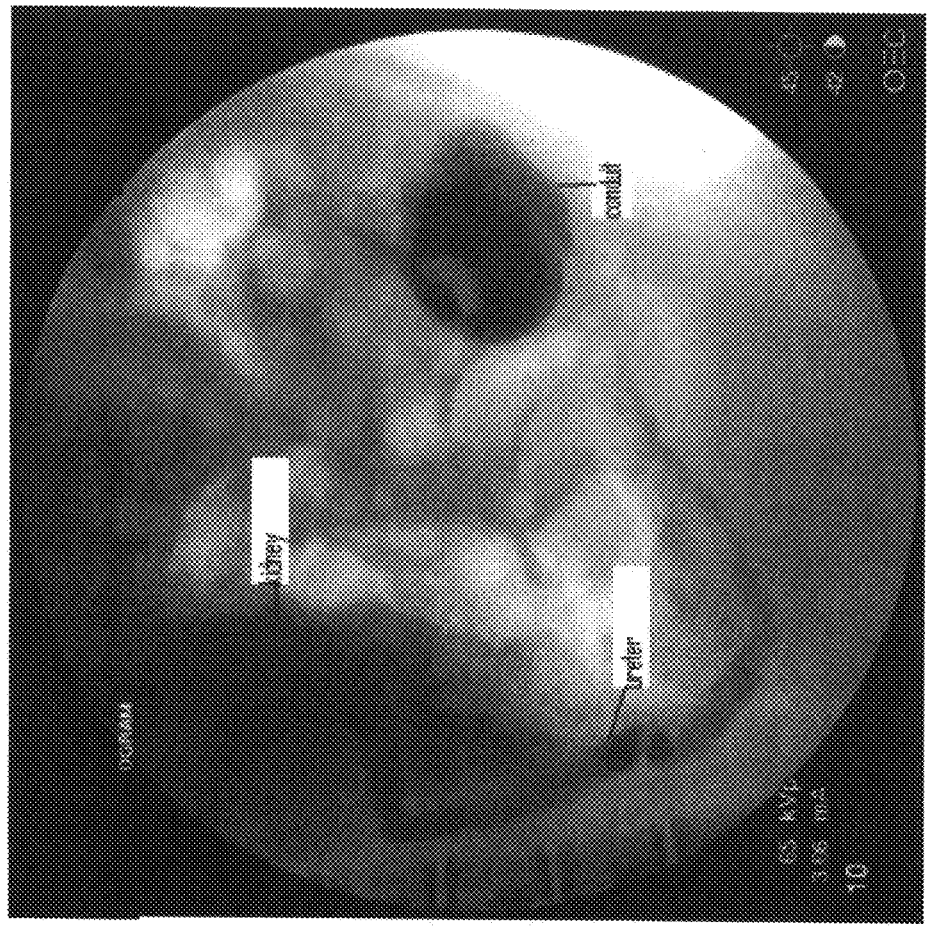
Figure 58A:
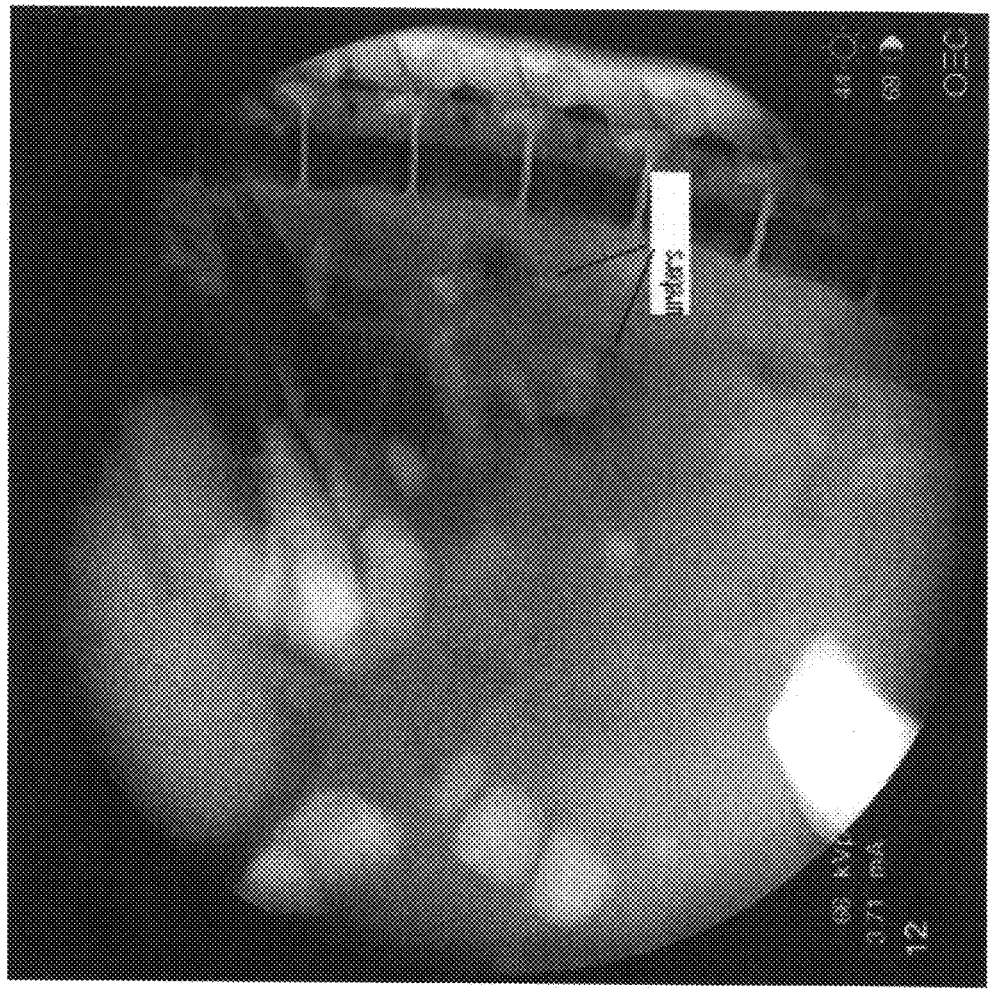
FIG. 58A-B shows pyelogram images for an animal implanted with a neo-urinary conduit (scaffold only).
Figure 58B:
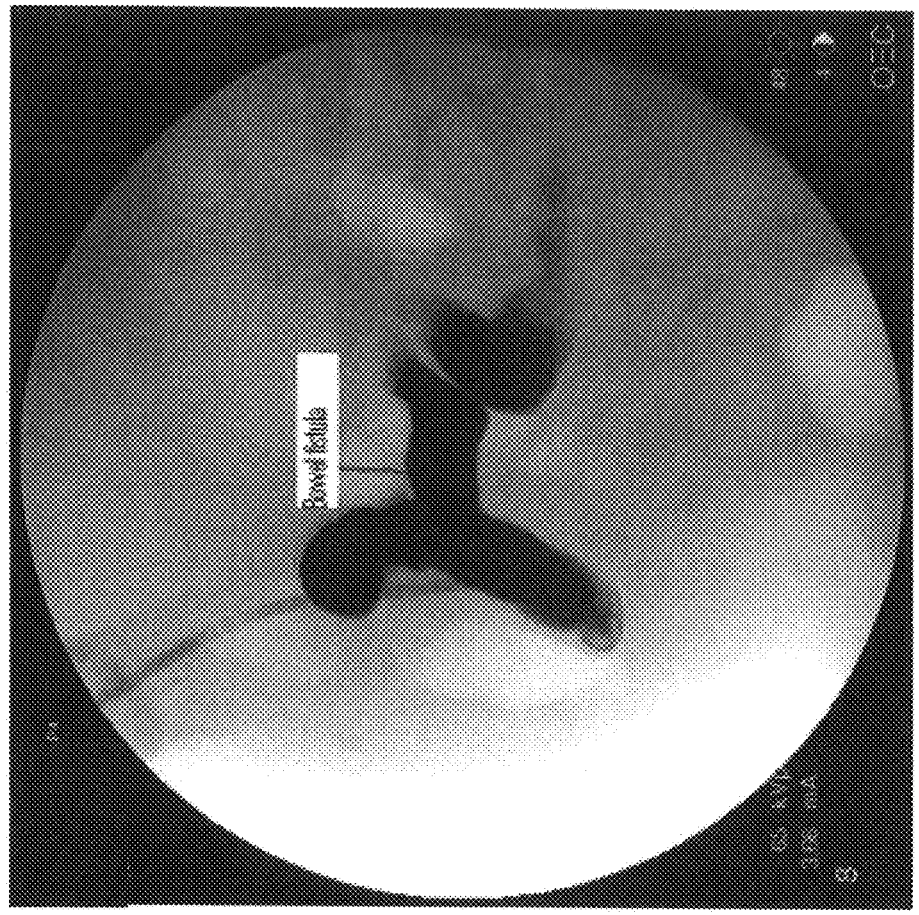

Representative pyelogram images are provided. FIG. 49 shows pyelogram images for animal 6 of Group 1 at week 8 (A) and pre-necropsy (B). FIG. 50 shows pyelogram images for animal 15 of Group 2 at week 8 (A) and pre-necropsy (B). FIG. 51 shows a pyelogram image for animal 9 of Group 2 at week 5 (loopogram: bowel illumination is indicative of a fistula). FIG. 52 shows a pyelogram image for animal 17 of Group 3 at week 7 (loopogram: bowel visualization is indicative of a fistula). FIG. 53 shows a pyelogram image for animal 21 of Group 3 at week 8 (both kidneys; respective ureters and conduit illuminated). FIG. 54 shows a pyelogram image for animal 24 of Group 2 at week 8 (one kidney and ureter visible). FIG. 55 shows pyelogram images for animal 23 of Group 2 at week 8 (A) and pre-necropsy—conduit with stoma port (B). FIG. 56 shows pyelogram images for animal 25 of Group 4 at week 8 (A) and pre-necropsy (B). FIG. 57 shows pyelogram images for animal 26 of Group 4 at week 8 (A) and pre-necropsy (B). FIG. 58 shows pyelogram images for animal 29 of Group 4 at week 4—ureters visible (A) and a week 4 loopogram—bowel fistula (B).

IVP for 12 Non-PCV-2 Unscheduled Deaths. These animals did not survive to the specified pyelogram. Several pre-necropsy pyelograms were not performed due to ill health, presence of conduit/bowel fistula and early euthanasia.

Loopograms (Retrograde Pyelograms) for 7 Surviving Animals Representative Loopograms are presented as described above. Of the 7 surviving animals one animal was evaluated for enteric-conduit fistula formation. The loopogram was performed on animal no. 25 during Week 3. The conduit was confirmed to be free of fistulas Animal was recovered and continued on study to successful completion.

Loopograms (Retrograde Pyelograms) for 12 non-PCV-2 Unscheduled Deaths Enteric-conduit fistulas were identified during the in-life position of the study in 4 of the 12 non-PCV-2 unscheduled death animals: Loopograms (retrograde pyelograms) were performed at varied timepoints to verify the presence of fistulas in Group 2 animal No. 9 (day 33); Group 3 animal No. 17 (day 48) and in Group 4 Animal Nos. 27 (day 20) and 29 (day 41). These animals were euthanized and necropsied at 20 to 48 days post-implantation.

Ultrasound for 7 Surviving Animals Individual and group ultrasonography data are presented in Appendix 11. Ultrasonography on the kidneys over the course of the study showed increases in surface area (length×width) indicating kidney changes (hydronephrosis) in all treatment groups. Group averages were similar over time for all groups for the right and left kidney (Table 5.88—Average Kidney Surface Area by Group for 7 Surviving Animals (L×W, cm2).

TABLE 5.88

| Group | Baseline | Week 2 | Week 6 | Week 10 | Pre-Necropsy |
|---|---|---|---|---|---|
| Left Kidney | | | | | |
| 1 (N = 2) | 26.7 | 19.8 | 21.3 | 41.2 | 29.2 |
| 2 (N = 1) | 16.2 | 18.4 | 27.8 | 21.0 | 39.3 |
| 3 (N = 2) | 14.3 | 16.1 | 19.2 | 26.5 | 38.3 |
| 4 (N = 2) | 14.7 | 15.2 | 23.5 | 39.8 | 17.1 |
| Right Kidney | | | | | |
| 1 (N = 2) | 22.1 | 20.3 | 26.0 | 35.8 | 23.7 |
| 2 (N = 1) | 15.4 | 14.2 | 25.4 | 25.4 | 22.9 |
| 3 (N = 2) | 13.4 | 13.5 | 13.5 | 43.2 | 24.8 |
| 4 (N = 2) | 17.0 | 18.7 | 28.5 | 27.3 | 27.9 |

Ultrasonography on the implant showed a decrease in wall thickness over time in all of the construct groups (Groups 1-3). The scaffold only group (Group 4) showed a slight increase in thickness (Table 5.89—Average Conduit Wall Thickness by Group for 7 Surviving Animals (cm).

TABLE 5.89

| Group | Week 2 | Week 6 | Week 10 | Pre-Necropsy |
|---|---|---|---|---|
| 1 (N = 2) | 0.327 | 0.227 | 0.152 | 0.181 |
| 2 (N = 1) | 0.172 | 0.169 | 0.099 | 0.114 |
| 3 (N = 2) | 0.333 | 0.239 | 0.169 | 0.145 |
| 4 (N = 2) | 0.196 | 0.248 | 0.179 | 0.222 |

Ultrasound for 12 non-PCV-2 Unscheduled Deaths. Individual and group ultrasonography data are presented in Table 5.90—Ultrasonography: Summary Results Kidney Measurements (cm)).

TABLE 5.90

| | | Pre-Biopsy | | | | Week 2 | | | | Week 6 | | | |
|---|---|---|---|---|---|---|---|---|---|---|---|---|---|
| | | Right | | Left | | Right | | Left | | Right | | Left | |
| Group | Stat | Len | Wid | Len | Wid | Len | Wid | Len | Wid | Len | Wid | Len | Wid |
| 1 | Mean | 6.29 | 2.93 | 6.08 | 2.92 | 6.68 | 3.17 | 6.88 | 3.12 | 7.14 | 3.38 | 6.49 | 3.19 |
| | Std. Dev | 1.09 | 0.40 | 1.00 | 0.63 | 0.69 | 0.30 | 1.23 | 0.25 | 0.39 | 0.26 | 0.89 | 0.34 |
| 2 | Mean | 5.36 | 2.73 | 5.66 | 2.70 | 5.98 | 2.83 | 5.96 | 2.79 | 6.66 | 3.77 | 7.36 | 3.91 |
| | Std. Dev | 0.79 | 0.29 | 0.92 | 0.33 | 0.93 | 0.30 | 0.77 | 0.40 | 0.66 | 0.50 | 0.56 | 0.55 |
| 3 | Mean | 6.08 | 2.91 | 6.31 | 2.99 | 6.02 | 2.99 | 5.87 | 2.99 | 6.40 | 2.97 | 7.69 | 3.38 |
| | Std. Dev | 0.84 | 0.52 | 0.95 | 0.41 | 0.85 | 0.44 | 0.80 | 0.14 | 1.21 | 0.48 | 1.58 | 0.55 |

TABLE 5.90-continued

| | | | | | | | | | | | | | |
|---|---|---|---|---|---|---|---|---|---|---|---|---|---|
| 4 | Mean | 5.83 | 2.62 | 5.93 | 2.58 | 6.32 | 3.89 | 5.37 | 2.72 | 7.95 | 4.05 | 7.66 | 3.99 |
| | Std. Dev | 0.74 | 0.26 | 0.42 | 0.21 | 1.78 | 1.30 | 0.88 | 0.37 | 1.98 | 1.58 | 1.51 | 0.43 |

| | | Week 10 | | | | Pre-Necropsy | | | |
|---|---|---|---|---|---|---|---|---|---|
| | | Right | | Left | | Right | | Left | |
| Group | Stat | Len | Wid | Len | Wid | Len | Wid | Len | Wid |
| 1 | Mean | 8.78 | 5.19 | 8.11 | 4.75 | 7.25 | 3.27 | 7.63 | 3.76 |
| | Std. Dev | 1.31 | 0.90 | 1.02 | 0.64 | 0.79 | 0.19 | 0.26 | 0.29 |
| 2 | Mean | 8.56 | 4.06 | 7.94 | 3.57 | 7.40 | 3.53 | 8.16 | 3.90 |
| | Std. Dev | 0.63 | 0.78 | 0.64 | 0.71 | 2.50 | 0.89 | 1.97 | 0.52 |
| 3 | Mean | 9.30 | 5.16 | 8.01 | 4.37 | 8.58 | 4.51 | 7.01 | 3.30 |
| | Std. Dev | 1.77 | 0.47 | 1.51 | 1.33 | 4.32 | 2.41 | 2.47 | 1.22 |
| 4 | Mean | 7.84 | 3.35 | 8.63 | 4.56 | 7.01 | 3.92 | 5.55 | 2.91 |
| | Std. Dev | NA | NA | NA | NA | NA | NA | NA | NA |

Len = length
Wid = width
NA = not applicable, n is too small for SD

TABLE 5.91 provides the N-Values by Time Point.

| Group | Baseline | Week 2 | Week 6 | Week 10 | Pre-Necropsy |
|---|---|---|---|---|---|
| 1 | 8 | 7 | 5 | 4 | 3 |
| 2 | 8 | 8 | 6 | 3 | 4 |
| 3 | 8 | 7 | 7 | 3 | 4 |
| 4 | 8 | 7 | 4 | 2 | 2 |

Ultrasonography on the kidneys over the course of the study showed increases in surface area (length×width) indicating kidney changes (hydronephrosis) in all treatment groups. Group averages were similar over time for all groups for the right and left kidney (Table 5.92—Average Kidney Surface Area by Group for 12 non-PCV-2 Unscheduled Deaths (L×W, cm2).

TABLE 5.92

| Group | Baseline | Week 2 | Week 6 | Week 10 | Pre-Necropsy |
|---|---|---|---|---|---|
| Left Kidney | | | | | |
| 1 (N = 1) | 21.0 | NA | NA | NA | NA |
| 2 (N = 3) | 14.5 | 19.8 | 15.5 | 13.1 | 18.8 |
| 3 (N = 4) | 19.5 | 20.9 | 22.3 | 14.4 | 42.5 |
| 4 (N = 4) | 13.9 | 21.7 | 20.2 | NA | NA |
| Right Kidney | | | | | |
| 1 (N = 1)* | 21.2 | NA | NA | NA | NA |
| 2 (N = 3) | 12.9 | 16.4 | 18.7 | 12.3 | 20.0 |
| 3 (N = 4) | 19.7 | 19.0 | 30.6 | 13.9 | 14.7 |
| 4 (N = 4) | 15.5 | 14.4 | 19.2 | NA | NA |

NA = Not applicable
*Animal no. 8 euthanized on day 9.

Ultrasonography on the implant showed a decrease in wall thickness over time in all of the construct groups (Groups 1-3). The scaffold only group (Group 4) showed a slight increase in thickness; however there are limited data points for analysis (Table 5.93—Average Conduit Wall Thickness by Group for 12 non-PCV-2 Unscheduled Deaths (cm).

TABLE 5.93

| Group | Week 2 | Week 6 | Week 10 | Pre-Necropsy |
|---|---|---|---|---|
| 1 (N = 1)* | NA | NA | NA | NA |
| 2 (N = 3) | 0.225 | 0.201 | 0.157 | 0.131 |

TABLE 5.93-continued

| Group | Week 2 | Week 6 | Week 10 | Pre-Necropsy |
|---|---|---|---|---|
| 3 (N = 4) | 0.291 | 0.184 | 0.228 | 0.144 |
| 4 (N = 4) | 0.203 | 0.358 | NA | NA |

NA = Not applicable
*Animal no. 8 euthanized on day 9.

Pathology. The pathology report appears in the Example below.

Viral infection and unscheduled deaths from consequences of obstruction reduced the number of animals surviving for study duration from 32 to a total of 7. For the animals surviving to sacrifice (N=7), adhesions were present in all animals and enteric-conduit fistulas were present in 4 of 7 animals (Pathology Example below). Hydroureter and hydronephrosis (unilateral or bilateral) were present in all animals, and pyelonephritis was present in 1 of 7 animals. The animal with pyelonephritis was in the scaffold-only treatment group (Group 4). For the non-PCV-2 unscheduled deaths (N=12), adhesions were present in all animals and fistulas were present in 7 of 12 animals (enteric-conduit) and 1 of 12 animals (ureter-intestine). Hydroureter and hydronephrosis (unilateral or bilateral) were present in 8 of 12 animals, and pyelonephritis was present in 4 of 12 animals. Three animals with pyelonephritis were in the scaffold only treatment group (Group 4), and 1 animal was in the blood-derived autologous SMC treatment group (Group 3). Despite complications that led to unscheduled deaths, the construct implants served as templates for a regenerative process that resulted in a tissue comprised of urothelium and smooth muscle layers. Regeneration was most prominent at the ureteral end of the implant. The tissue in the caudal implant and atrium segments of the conduit had a wall comprised of fibrous connective tissue without urothelial lining. The regenerative process at the ureteral end of the implant resulted in urinary tissue formation that was comparable among construct groups and distinct from the reparative healing which typified the scaffold-only group.

The scaffold-only test article was determined to be unsuitable for further development because the outcome was not consistent with normal urinary tissue and these animals had a higher incidence of bilateral renal complications. Outcomes observed in construct groups, regardless of cell source, were equivalent.

DISCUSSION. Of the 31 animals recovered from surgery, seven animals (23%; two from each of Groups 1, 3 and 4; and one from Group 2) successfully completed the full duration of the in-life portion of the study. Macroscopic pathology was evident in all groups and included evidence of viral infection, intermittent obstruction of urine flow, debris and detritus buildup in the conduit, abdominal and pelvic adhesions, fistulae, hydronephrosis, and hydroureter and pyelonephritis. Evidence of urinary tissue regeneration was observed to varying degrees in construct implants seeded with SMC from each source (Groups 1-3, bladder, adipose, and blood derived SMC, respectively). However, incomplete urinary tissue healing and increased incidence of upper urinary tract pathology were observed in the scaffold-only implanted animals (Group 4). Twelve of the 31 animals (39%) were infected with PCV-2 virus. Although a viral infection resulted in reduced survival, urinary tissue regeneration was also observed in the construct groups (Groups 1-3). The surgical placement of the test articles was designed for animal welfare purposes to achieve optimal voiding of urine by quadrupeds so as to avoid irritant contact dermatitis from urine and potential early morbidity and euthanasia. However, this surgical approach resulted in test articles being directly under the overlying abdominal organs and the weight of these organs and the pressure of the abdominal viscera caused intermittent conduit obstruction. This quadruped specific surgical placement may have also contributed to the observed adhesions, fistulae, and upper urinary tract complications (e.g., dilation, inflammation, and/or infection of ureters or kidney). However, intestinal obstruction was not observed in this study. The pig is commonly used as an animal model for studying the development and prevention of post-surgical adhesions therefore some incidence of adhesions was expected simply from the abdominal laparotomy for biopsy collection in construct animals (Groups 1-3). Animals in Groups 1-3 also underwent a second surgical procedure to implant the test article, substantially increasing the risk of adhesions compared to the animals receiving scaffold-only implants that underwent a single surgical procedure (test article implantation only). Adhesions observed in this study were considered a consequence of these surgical procedure(s).

All the adverse findings noted in the upper urinary tract (hydroureter, hydronephrosis, and pyelonephritis) were consequences of conditions that intermittently obstructed the flow of urine through the conduit. The pyelonephritis observed in the quadruped pigs of this study was considered secondary to the debris and detritus build-up and bacterial contamination of the stoma from feces and skin. Pyelonephritis was most frequently observed in the scaffold-only animals (Group 4). The surgical positioning of the test article for all animals and multiple surgeries for animals in Groups 1-3 (biopsy and test article implantation) promoted the formation of abdominal and pelvic adhesions. Furthermore, the intermittent obstruction, the debridement protocol used for stoma management (use of forceps in tranquilized animals to remove detritus buildup), viral infection, and adhesions of intestinal tract to the conduit contributed to enteric-conduit fistula formation and upper renal disease. Despite complications that led to unscheduled deaths, the construct implants (Groups 1-3) served as templates for a regenerative process that resulted in a tissue comprised of urothelium and smooth muscle layers (native urinary tissue components). Regeneration was most prominent at the ureteral end of the implant. The tissue in the atrium (peritoneal tissue only with no construct or scaffold) segments of the conduit had a wall comprised of fibrous connective tissue without urothelial lining, indicating the peritoneum alone was incapable of supporting regeneration of urinary tissue. The regenerative process at the ureteral end of the implant resulted in urinary tissue formation that was comparable among construct groups and distinct from the reparative healing which typified the scaffold-only group. The scaffold-only test article outcome was not consistent with normal urinary tissue and the wall was comprised of fibrovascular connective tissue that could be predisposed to scarring and/or stenosis of the lumen. The incomplete formation of urinary tissue in the animals receiving a scaffold-only implant exacerbated the upper urinary tract findings from intermittent obstruction discussed above; Group 4 animals had a higher incidence of the bilateral renal complications. Outcomes observed in construct groups, regardless of cell source, were equivalent.

Conclusion. The objective of this study was to evaluate the safety and functionality of a Neo-Urinary Conduit (NUC) seeded with autologous bladder-derived, adipose-derived or blood-derived smooth muscle cells (SMC), or scaffold-only (scaffold without SMC). Functionality assessments were urinary flow and urinary tissue regeneration. Only 7 of 31 (23%) animals completed this study. The primary safety findings underlying the 24 of 31 unscheduled deaths were PCV-2 viral infection and intermittent obstruction of the conduit resulting in upper urinary tract injury (hydronephrosis, hydroureter, and pyelonephritis). Obstruction was managed by debridement and saline flushing of the stoma. Urinary tissue-like regeneration characterized by mucosa, submucosa and smooth muscle with a fibrovascular stroma was observed after construct test article implantation regardless of SMC source (i.e. bladder, adipose, or blood). In contrast, a reparative process was observed following implantation of the scaffold-only test article characterized by an abnormal mucosa supported by fibrovascular stroma with limited smooth muscle. The predisposition of the pig to adhesion formation and the two surgical procedures related to tissue biopsy and test article implantation in all construct groups resulted in adhesions between the regenerated tissue and overlying bowel. Fistula formation was exacerbated by frequent stoma cleaning and the pig's quadruped stance. The absence of SMC in the scaffold-only test articles appears to have contributed to incomplete development of urinary tissue and an increase in mortality subsequent to obstruction, leading to the determination that the scaffold-only test article was unsuitable for further development.

Example 6

Pathology of Animals Following Implantation of Neo-urinary Conduit Constructs

At the conclusion of the study described in Example 5, the anatomic pathology of the test animals was assessed.

Tissue Collection. As per protocol, the abdominal cavity was opened and the conduit (the outcome of implanting a construct or scaffold-only test article), was visualized and digitally photographed in situ at the animal facility. The conduit was removed en bloc with the kidneys and ureters. The ureters were measured, and then detached from the conduit by transverse sectioning 3-4 cm away from the anastomoses. Representative sections of the kidneys, ureters, lymph nodes, and any other lesions observed grossly were obtained. All tissue samples were placed in 10% Neutral Buffered Formalin (NBF) for histological processing and evaluation.

Histological Processing. After fixation, the conduit was opened longitudinally (parallel with the outflow) and divided into dorsal and ventral halves as illustrated in the trimming diagram below.

Figure 59A:
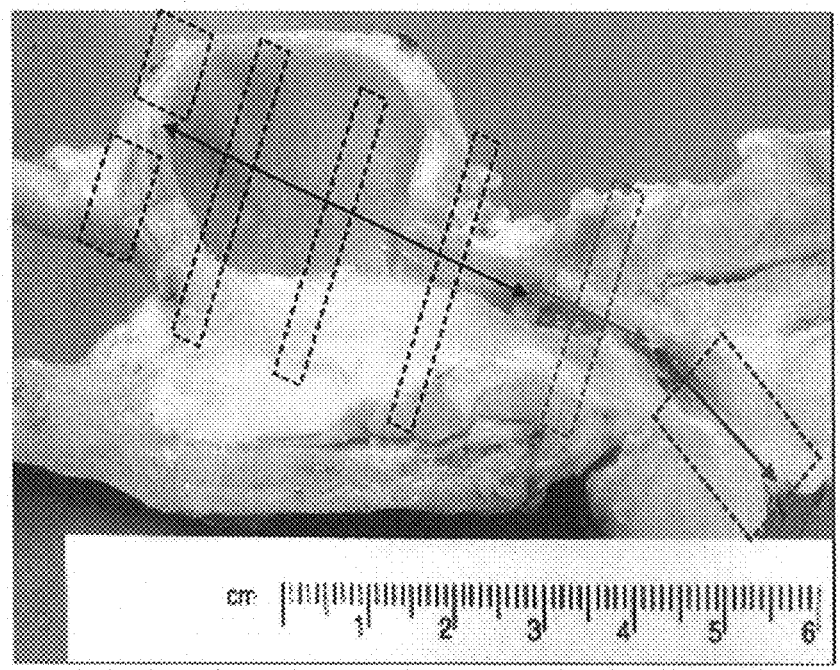
FIG. 59 shows a post-fixed conduit (A) and a trimming schematic (B).
FIG. 59C identifies areas of the conduit.
Figure 59B:
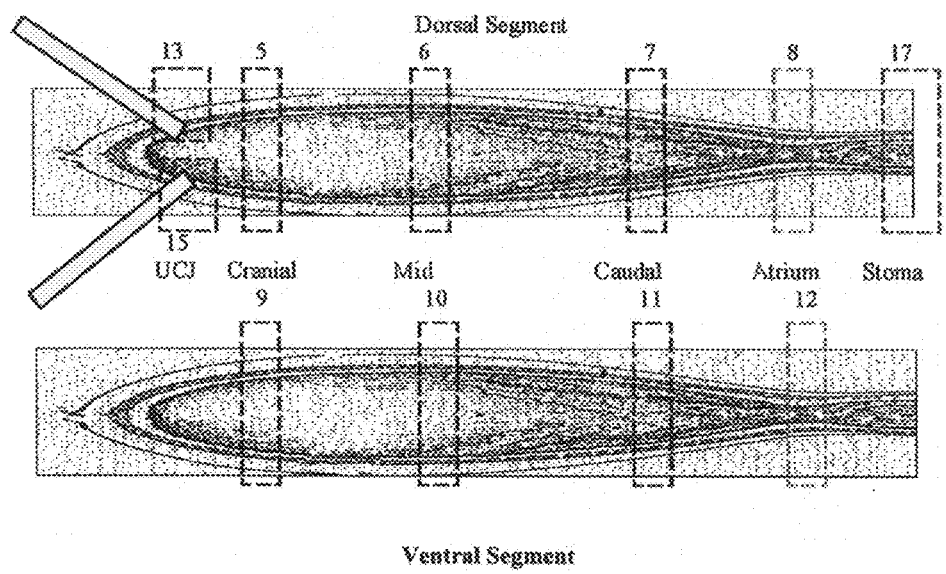
Figure 59C:
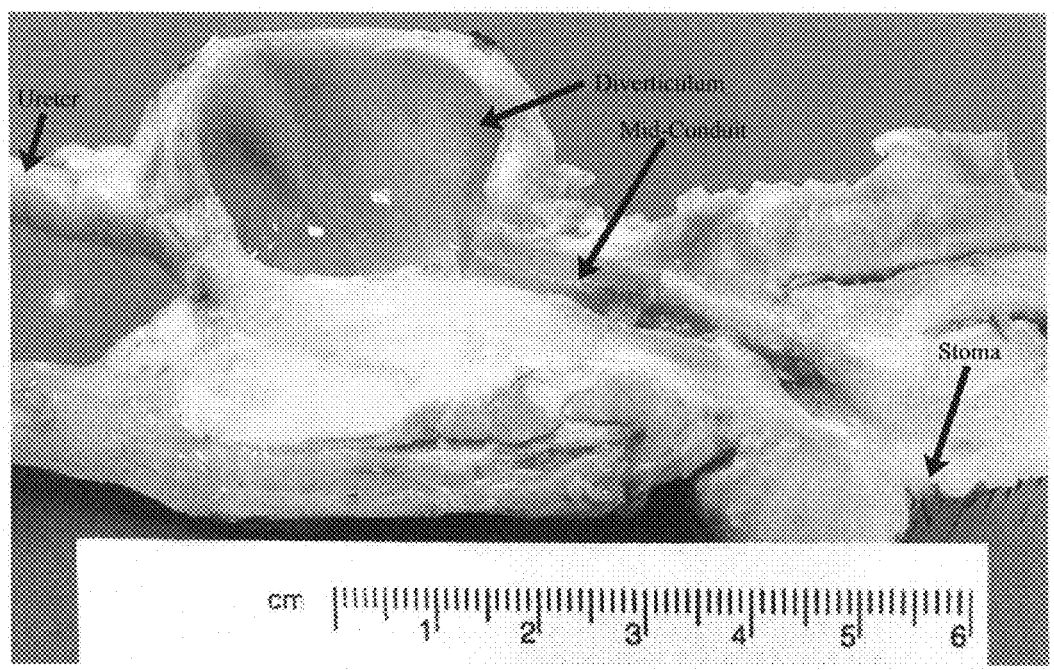

FIG. 59A-B shows a post-fixed conduit tissue from DB-252 Animal no 18 and a trimming schematic. FIG. 59C shows the position of the ureters, stoma, mid-conduit, and a diverticulum.

Three transverse sections were trimmed from the body of each half (cranial, mid and caudal captured on slides 5, 6, 7 on the dorsal half and 9, 10, 11 on the ventral half, respectively). One section from each half was taken from the atrium (captured on slide 8 on the dorsal half and 12 on the ventral half). An additional section was taken at each of the two ureter-conduit junctions (left captured on slide 13, right on slide 15). One other slide (number 17) was used to capture the stoma at the skin surface and the adjacent canal through the abdominal wall. When the size of the conduit permitted, this scheme resulted in 11 slides. Some conduits were too short in length to accommodate the trimming scheme, so the available conduit was divided into fewer sections. The sections collected from each animal include conduit doral cranial, conduit dorsal mid, conduit dorsal caudal, dorsal stomal conduit junction, conduit ventral cranial, conduit ventral mid, ventral conduit stomal junction, left ureter conduit stomal junction, right ureter-conduit junction, and conduit stoma-skin junction. In addition, the following tissue/organ sections were obtained and submitted for histology: left kidney (slide 1), right kidney (slide 2), left ureter (slide 14), right ureter (slide 16), lumbar lymph node (slide 3), mesenteric lymph nodes (slide 4) and any gross lesions (slides 18, 19 etc.). During trimming of tissues, digital photographs were taken for illustration purposes. Post fixation, tissues were processed routinely to microslides and stained with hematoxylin and eosin (H&E) and Masson's trichrome. Slides were evaluated microscopically. Where appropriate, microscopic observations for individual animal data were obtained and scored.

Results

Mortality. During definitive surgery, the ureters of Animal no 30 (Group 4) were perforated, thus preventing test article implantation. The animal was euthanized and not replaced, reducing the total N of animals implanted with test articles (construct or scaffold-only) to 31 and the N of Group 4 to 7 animals. Twenty-four animals were unscheduled deaths and seven animals survived until the scheduled sacrifice. Survival days post-implant and final disposition of each of the 31 animals implanted with the test article are shown in Appendix 1, Animal Information. Disposition (mortality classification) of the 24 unscheduled deaths is summarized by treatment group in Table 6.2—Unscheduled deaths by Group)

TABLE 6.2

| Mortality | Group 1 | Group 2 | Group 3 | Group 4 | Total |
| --- | --- | --- | --- | --- | --- |
| Group N | 8 | 8 | 8 | 7 | 31 |
| In-life procedure-related death | 0/8 | 0/8 | 1/8 | 0/7 | 1/31 |
| Found dead | 0/8 | 2/8 | 0/8 | 1/7 | 3/31 |
| Euthanized | 6/8 | 5/8 | 5/8 | 4/7 | 20/31 |
| Total Unscheduled Necropsies | 6/8 | 7/8 | 6/8 | 5/7 | 24/31 |
| Scheduled Necropsies | 2/8 | 1/8 | 2/8 | 2/7 | 7/31 |

The following sections discuss the underlying findings observed for unscheduled deaths.

Viral Related Mortalities. During in-life clinical observations, skin lesions consistent with PCV-2 infection were observed. Twelve unscheduled death animals developed one or more lesions, consistent with distinct pathological features ascribed to porcine dermatitis and nephropathy syndrome (PDNS), associated with PCV-2 infection Animals were classified as PCV-2-infected if any of the following were observed:

1) Clinically-observed purple skin discoloration
2) Microscopic vasculitis or vasculitis/perivasculitis affecting the kidney, skin or lung
3) Kidney findings of tubular necrosis/fluid/casts/glomerulonephritis, or viral inclusions of tubular epithelial cells
4) Lymphocyte depletion in lumbar lymph nodes in the presence of 1, 2, or 3

By these criteria, porcine PCV-2 infection was identified in 12 of the 24 unscheduled necropsy animals. These included 5 animals in Group 1 (animal nos. 5113342, 7, 2, 4 and 3); 4 animals in Group 2 (animal nos. 13, 16, 14 and 10); 2 animals in Group 3 (animal nos. 20 and 19); and 1 animal in Group 4 (animal no. 28). The microscopic findings from the PCV-2 animals will not be discussed in the results section as the PCV-2 condition was deemed an assignable cause of morbidity unrelated to the device.

Non-PCV-2 Associated Mortalities. A total of 12 unscheduled deaths were not associated with a detected PCV-2 virus infection (including the 1 in-life procedure-related death). The 12 unscheduled deaths not attributable to PCV-2 infection included 1 animal in Group 1 (animal no. 8); 3 animals in Group 2 (animal nos. 11, 9, and 12), 4 animals in Group 3 (animal nos. 24, 21, 22, and 17) and 4 animals in Group 4 (animal nos. 32, 31, 29, and 27). An important event in the clinical decline of these animals was obstruction of the outflow of urine and debris through the stoma. Obstruction appeared to have been facilitated by the placement of the test article in the ventral portion of the abdominal cavity where the weight of the overlying abdominal organs could lead to conduit closure, adhesion and fistula formation, and renal complications (e.g., dilation, inflammation, and/or infection of ureters or kidney). Surgical placement of the test article was the same in all study animals; therefore, obstruction-related complications had a similar pathobiological mechanism (i.e. abdominal viscera resting on the conduit because of the quadruped anatomy) in all groups.

Distribution of Unscheduled Deaths by Underlying Findings. A summary of underlying findings in the 24 unscheduled deaths is presented in Table 6.3—PCV-2 and Non-PCV-2 Associated Unscheduled Deaths by Group.

TABLE 6.3

| Mortality Categories | Group 1 | Group 2 | Group 3 | Group 4 | Total |
| --- | --- | --- | --- | --- | --- |
| Evidence of PCV-2 infection | 5 | 4 | 2 | 1 | 12 |
| Non-PCV-2 associated unscheduled deaths | 1 | 3 | 4 | 4 | 12 |
| Total unscheduled deaths | 6 | 7 | 6 | 5 | 24 |

Findings Pertinent to Safety. A comprehensive list of macroscopic findings and microscopic correlates for all animals was prepared (data not shown). Individual microscopic animal data was obtained (data not shown). Discussion of macroscopic and microscopic findings is focused to those relevant to the obstruction of urine outflow that was facilitated by the anatomical placement of test articles in the 7 animals surviving to scheduled sacrifice and the 12 non-PCV-2 associated unscheduled deaths (N=19). Conduits formed from implantation of a test article were variably sized and shaped tubes located in the retro-peritoneal space of the ventral abdomen. The ureters entered at the cranial end of the conduit (ureter-conduit junction, UCJ, FIG. 59). Urine flow was directed through the peritoneal wrapped implant and the atrium and emerged at the stoma. The cranial end of the conduit frequently had bilateral bulbous dilations, referred to as diverticula that were considered to be the consequence of intermittent obstruction.

Adhesions and Fistulas. The ventral side of the conduit was adhered to the fascia and skeletal muscle of the abdominal wall, and the dorsal side was covered with peritoneum. At necropsy, the conduit was often difficult to visualize because of marked adhesions (e.g., conduit to gastrointestinal tract, omentum, uterus, seminal vesicle, liver, pancreas, spleen, or reproductive organs). The lumen of the conduit was often filled with detritus. Fistulas were observed between conduit and adjacent hollow organs (e.g., intestine). Specifically, conduit-intestine or conduit-ureter fistulas were observed in the 19 animals evaluated.

Adhesions and Fistulas in 7 Surviving Animals. Adhesions were present in all 7 animals surviving to the scheduled sacrifice (Table 6.4). Fistulas between conduit and intestinal tract were observed in 4 of these 7 animals: 2/2 in Group 1 (animal nos. 1 and 6); 1/1 in Group 2 (animal no. 15) and 1/2 in Group 3 (animal no. 23). Table 6.4: Incidence of Adhesions and Fistulas in 7 Surviving Animals.

TABLE 6.4

| Macroscopic Finding | Group 1 N = 2 | Group 2 N = 1 | Group 3 N = 2 | Group 4 N = 2 | Total |
|---|---|---|---|---|---|
| Adhesions | 2/2 | 1/1 | 2/2 | 2/2 | 7/7 |
| Conduit-Intestine Fistula | 2/2 | 1/1 | 1/2 | 0/2 | 4/7 |

Adhesions and Fistulas in 12 Unscheduled Deaths. Adhesions were present in all 12 non-PCV-2 associated early deaths (Table 6.5). The presence of fistulas between conduit and intestinal tract was observed in 7 of 12 animals: 3/3 in Group 2 (animal nos. 11, 12 and 9), 3/4 in Group 3 (animal nos. 21, 22, and 17) and 1/4 in Group 4 (Animal No. 29). One fistula between intestine and ureter was observed in a Group 4 animal (animal no. 27). Table 6.5: Incidence of Adhesions and Fistulas in 12 non-PCV-2 Unscheduled Deaths.

TABLE 6.5

| Macroscopic Finding | Group 1 N = 1 | Group 2 N = 3 | Group 3 N = 4 | Group 4 N = 4 | Total |
|---|---|---|---|---|---|
| Adhesions | 1/1 | 3/3 | 4/4 | 4/4 | 12/12 |
| Conduit-Intestine Fistula | 0/1 | 3/3 | 3/4 | 1/4 | 7/12 |
| Ureter-Intestine Fistula | 0/1 | 0/3 | 0/4 | 1/4 | 1/12 |

Ureters and Kidneys. Thickened ureters observed macroscopically resulted from several underlying phenomena upon microscopic evaluation. Ureter dilatation (or hydroureter) was characterized by an expanded lumen with normal ureteral wall structure. Transitional cell hyperplasia was characterized by increased number of cells in the transitional epithelium, and vacuolation was characterized by round, clear vacuoles in the epithelium. Subacute/chronic inflammation of the peri-ureter mesentery occurred when the mesentery surrounding the ureter was expanded by collagen and fibroblasts, with occasional lymphocytes and macrophages. This inflammation did not usually affect the muscle tunics or urothelium of the ureter. Peri-ureter inflammation could be related to adhesion between ureter and intestinal or reproductive organs; but it could also occur without adhesion.

Microscopically, hydronephrosis was characterized by a dilatation of the renal pelvis with thinning and chronic inflammation (fibrosis, lymphocytes, plasma cells and occasional macrophages) of the renal cortex. Hydronephrosis was considered to be the result of full or partial obstruction in the lower urinary system (ureters, conduit or atrium/stoma). Chronic-active pyelonephritis, which was often associated with hydronephrosis, was characterized by infiltration of neutrophils and cellular debris into the renal pelvis, often spreading into the distal medulla.

Pyelonephritis was considered to be the result of bacterial infection of the lower urinary tract which ascended into the renal pelvis. Chronic nephritis (without hydronephrosis) was characterized by fibrosis with infiltration of inflammatory cells (lymphocytes, macrophages, plasma cells and occasionally neutrophils) in the renal cortex or medulla.

The cortex of kidneys with chronic nephritis looked similar to those in animals with hydronephrosis/chronic nephritis; however, in chronic nephritis the pelvis was not dilated. Chronic-active nephritis was similar in appearance to chronic nephritis, but with significant infiltration of neutrophils. Tubular necrosis/fluid/casts/glomerulonephritis was a constellation of changes characterized by neutrophils, lymphocytes and macrophages in glomeruli, necrosis of individual tubular epithelial cells, proteinaceous tubular casts and/or hemorrhage in tubular lumens.

Hydroureter and Hydronephrosis and/or Pyelonephritis in 7 Surviving Animals. Hydroureter and hydronephrosis were observed microscopically in all 7 surviving animals (Table 6.6). Unilateral hydroureter (2/7 animals): 2 animals in Group 3 (animal nos. 23 and 18). Bilateral hydroureter (5/7 animals): 2 animals in Group 1 (animal nos. 1 and 6), 1 animal in Group 2 (animal no. 15), and 2 animals in Group 4 (animal nos. 25 and 26). Unilateral hydronephrosis (6/7 animals): 2 animals in Group 1 (animal nos. 1 and 6), 1 animal in Group 2 (animal no. 15), 2 animals in Group 3 (animal nos. 18 and 23), and 1 animal in Group 4 (animal no. 26). Bilateral hydronephrosis (1/7 animals); Group 4 (animal no. 25). Pyelonephritis (unilateral) was observed in 1 of 7 animals; Group 4 animal no. 26. Table 6.6: Incidence of Hydroureter, Hydronephrosis and/or Pyelonephritis in 7 Surviving Animals. Table 6.6

| Finding | Group 1 N = 2 | Group 2 N = 1 | Group 3 N = 2 | Group 4 N = 2 | Total |
|---|---|---|---|---|---|
| Hydroureter, Unilateral | 0/2 | 0/1 | 2/2 | 0/2 | 2/7 |
| Hydroureter, Bilateral | 2/2 | 1/1 | 0/2 | 2/2 | 5/7 |
| Hydronephrosis, Unilateral | 2/2 | 1/1 | 2/2 | 1/2 | 6/7 |
| Hydronephrosis, Bilateral | 0/2 | 0/1 | 0/2 | 1/2 | 1/7 |
| Pyelonephritis, Unilateral | 0/2 | 0/1 | 0/2 | 1/2 | 1/7 |
| Pyelonephritis, Bilateral | 0/2 | 0/1 | 0/2 | 0/2 | 0/7 |

Hydroureter and Hydronephrosis and/or Pyelonephritis in 12 Unscheduled Deaths. Hydroureter and/or hydronephrosis were observed microscopically in 8/12 and 8/12 of the non-PCV-2 associated early deaths, respectively (Table 6.7). Unilateral hydroureter (3/12 animals): 1 animal in Group 2 (animal no. 12), 1 animal in Group 3 (animal no. 21) and 1 animal in Group 4 (animal no. 27). Bilateral hydroureter (5/12 animals): 2 animals in Group 3 (animal nos. 22 and 24), and 3 animals in Group 4 (animal nos. 32, 31 and 29). Unilateral hydronephrosis (5/12 animals): 2 animals in Group 2 (animal nos. 9 and 12), 1 animal in Group 3 (animal no. 21), and 2 animals in Group 4 (animal nos. 32 and 27). Bilateral hydronephrosis (3/12 animals): 1 animal in Group 3 (animal no. 24) and 2 animals in Group 4 (animal nos. 31, and 29).

Unilateral pyelonephritis was observed in 2 of 12 animals): 1 animal in Group 3 (animal no. 24) and 1 animal in Group 4 (animal no. 32). Bilateral pyelonephritis was observed in 2 of 12 animals): 2 animals in Group 4 (animal nos. 31 and 29). Table 6.7: Incidence of Hydroureter, Hydronephrosis and/or Pyelonephritis in 12 non-PCV-2 Unscheduled Deaths

TABLE 6.7

| Finding | Group 1 N = 1 | Group 2 N = 3 | Group 3 N = 4 | Group 4 N = 4 | Total |
|---|---|---|---|---|---|
| Hydroureter, Unilateral | 0/1 | 1/3 | 1/4 | 1/4 | 3/12 |
| Hydroureter, Bilateral | 0/1 | 0/3 | 2/4 | 3/4 | 5/12 |
| Hydronephrosis, Unilateral | 0/1 | 2/3 | 1/4 | 2/4 | 5/12 |
| Hydronephrosis, Bilateral | 0/1 | 0/3 | 1/4 | 2/4 | 3/12 |
| Pyelonephritis, Unilateral | 0/1 | 0/3 | 1/4 | 1/4 | 2/12 |
| Pyelonephritis, Bilateral | 0/1 | 0/3 | 0/4 | 2/4 | 2/12 |

Findings Pertinent to Regeneration of a Urinary Conduit. Tissue components from each section were observed (data not shown). The discussion of findings pertinent to regeneration below focuses on the sections obtained for histological evaluation (FIG. 59) from the 7 animals surviving to scheduled sacrifice and the 12 unscheduled deaths. The conduit that developed after surgical implantation of the test article consisted of a central lumen that coursed from ureters (cranial end) through the implant and atrium to the stomal opening in the skin of the ventral abdomen. The histological appearance of the conduit wall varied depending upon location of sample within the conduit and animal survival time.

Ureter-Conduit Junction and Cranial Portion of Conduit. The typical composition of tissue near the cranial end of the conduit encompassing the ureterconduit junction (UCJ; Sections 13 and 15 in FIG. 59) and the cranial portion (Sections 5 and 9 in FIG. 59) was urothelium overlying layers of smooth muscle fibers with interspersed connective tissue. UCJ and cranial sections of the conduit were morphologically similar to the ureters, although the conduit wall thickness was typically greater than that of the ureter, particularly within diverticula. Diverticula appeared as bi-compartmental portions of conduit projecting caudally from the left and right ureteral-conduit junctions. The typical appearance of urothelium was minimally-to-moderately vacuolated, and variable in thickness. Urothelium thickness varied between minimally-to-moderately attenuated (especially within a large diverticulum) and minimally-to-mildly hyperplastic. For the 7 animals surviving to scheduled sacrifice, incidence of urothelium and smooth muscle layers observed in Sections 5, 9, 13, and 15 was similar among all animals. Table 6.8: Incidence of Urothelium and Smooth Muscle in Cranial Conduit in 7 Surviving Animals

TABLE 6.8

| Histological Finding | Group 1 N = 1 | Group 2 N = 2 | Group 3 N = 2 | Group 4 N = 2 |
|---|---|---|---|---|
| Presence of Urothelium | | | | |
| UCJ (slides 13 or 15) | 2/2 | 1/1 | 2/2 | 2/2 |
| Cranial Conduit (slides 5 or 9) | 1/2* | 1/1 | 1/2* | 1/2 |
| Presence of Smooth Muscle | | | | |
| UCJ (slides 13 or 15) | 2/2 | 1/1 | 2/2 | 2/2 |
| Cranial Conduit (slides 5 or 9) | 1/2* | 1/1 | 1/2* | 1/2 |

*Due to size of regenerated conduit, insufficient tissue available to evaluate section(s) in 1 animal per group in Group 1 & 3.

For the 12 non-PCV-2 associated early deaths, the incidence of urothelium and smooth muscle layers in Sections 5, 9, 13, and 15 was similar among animals within and between groups receiving construct implants (Groups 1-3). The incidence of urothelium and smooth muscle layers in Sections 5, 9, 13, and 15 among animals receiving scaffold-only implants (Group 4) was lower than that observed in animals receiving a construct implant. Table 6.9: Incidence of Urothelium and Smooth Muscle in Cranial Conduit in 12 Unscheduled Deaths.

TABLE 6.9

| Histological Finding | Group 1* N = 1 | Group 2 N = 3 | Group 3 N = 4 | Group 4 N = 4 |
|---|---|---|---|---|
| Presence of Urothelium | | | | |
| UCJ (slides 13 or 15) | 0/1 | 3/3 | 4/4 | 3/4 |
| Cranial Conduit (slides 5 or 9) | 0/1 | 2/3 | 2/4^ | 0/4 |
| Presence of Smooth Muscle | | | | |
| UCJ (slides 13 or 15) | 0/1 | 2/3 | 4/4 | 2/4 |
| Cranial Conduit (slides 5 or 9) | 0/1 | 2/3 | 2/4^ | 0/4 |

*animal on study 9 days
^Due to size of regenerated conduit, in ufficient tissue available to evaluate section(s) in one animal in Group 3

Mid and Caudal Portions of Conduit. For all 19 animals, the typical appearance of the mid (Sections 6 and 10 in FIG. 59) and caudal (Sections 7 and 11 in FIG. 59) portions of the conduit differed from that observed in the UCJ and cranial sections. The point of transition from conduit to atrium varied between animals because the caudal end of the implant floated freely within the peritoneal wrapping making the transition from conduit to atrium difficult to define at necropsy. The typical composition of Sections 6, 7, 10, and 11 was organized collagen with associated fibroblasts. Internal to the collagenous wall and closest to the lumen was a layer of chronic-active inflammation comprised of loosely arranged collagen, capillaries and abundant neutrophils with fewer lymphocytes and macrophages. Internal to the inflammation, the lumen was often filled with detritus comprised of degenerate or necrotic inflammatory cells (primarily neutrophils) and cellular debris with admixed bacterial colonies.

Atrium and Stoma Portions of Conduit. At the region of the atrium-stomal end of the conduit (Sections 8, 12 and 17 in FIG. 59), the stoma-atrium junction was visible where the organized collagen and adnexa of the stomal dermis apposed the collagenous wall (without adnexa). For all 19 animals, these sections consisted mainly of squamous epithelium and chronic-active inflammation/detritus. Typically, the squamous epithelium (epidermis) of the skin extended cranially for a short distance over the atrium. The external surface of the atrium was comprised of loose connective tissue of peritoneum origin. This external covering was the equivalent of a serosal layer and contained nerves, blood vessels, adipose tissue, and some areas of fibrous connective tissue (collagen fibers and fibroblasts). At the site of one of the fistulas, ectopic intestinal mucosa was observed to cover a small segment of conduit adjacent to fistulas. This was noted in one of the 7 surviving Group 2 animals (animal no. 15).

Healing Outcomes in Animals Receiving Construct or Scaffold-Only Implants. Urinary tissue-like regeneration characterized by mucosa, submucosa and smooth muscle with a fibrovascular stroma was observed after construct test article implantation regardless of SMC source (i.e. bladder, adipose or blood). Areas of bladder-like tissue, comprised of continuous urothelium with underlying smooth muscle, were observed in 4 of 5 surviving animals and 4 of 8 unscheduled sacrifice animals implanted with construct test articles. In the majority of scaffold only animals, the conduit tissue morphology was compatible with a reparative process, characterized by urothelium extending only a short distance (approximately 1 mm) from the ureter-conduit junction without underlying smooth muscle.

Discussion. Seven of 31 animals survived to scheduled necropsy and over the course of the study 24/31 animals were euthanized off-schedule or found dead. Viral infections contributed to 12/24 unscheduled deaths. There were both clinical and pathological signs compatible with concurrently infection with PCV-2 during the course of this study. Macroscopic findings were ecchymoses (clinically, purple discoloration) of the skin and enlarged inguinal lymph nodes (macroscopic finding of viral infections were observed in 11/24 unscheduled deaths). Microscopic findings included renal changes consisting of tubular necrosis/fluid/casts/glomerulonephritis, eosinophilic intracellular inclusions in tubular epithelial cells in the kidney, and vasculitis/perivascular inflammation in the kidneys and ureters, and inflammation in the lungs (microscopic findings revealed an additional animal with PCV-2 infection at necropsy, bringing the total viral infection related unscheduled deaths to 12/24). These findings are among those commonly reported for pigs with PCV-2 infection. The infection with PCV-2 contributed to the poor clinical health of the animals (e.g. lethargy, diarrhea, loss of appetite) and subsequent humane early euthanasia. Twelve of 24 unscheduled deaths were non-PCV-2 associated: 1/24 unscheduled death was the result of an in-life procedural complication and obstruction contributed to 11/24 unscheduled deaths. Obstruction was caused by a combination of the surgical placement of the test article along the abdominal floor of the pig where the weight of abdominal viscera compressed the implant and the use of peritoneum to form an atrium segment connecting the conduit to the skin resulting in detritus buildup from the external environment and mucus in the urine (normal for swine).

Relevant postoperative complications that are inherent in this quadruped animal model include: (i) abdominal adhesions leading to potential fistula formation and (ii) location of the test article placement in relation to the abdominal organs.

When intestines were the adhered organ, the tunica muscularis of the adhered segment of intestine was often diminished or eroded at the point of adhesion, as was the atrium wall. Test articles were placed in the intra-abdominal cavity of the ventral abdomen with a peritoneum-derived tube extending from the caudal end of the test article through the abdominal wall to the skin. The test article was anchored at the cranial end to the ureters, but floated freely within the peritoneal wrapping at the caudal end. Healing resulted in a urinary conduit consisting of a central lumen that coursed from ureters (cranial end) to the stomal opening in the skin of the ventral abdomen (caudal end). Urothelium and layered smooth muscle formation were most frequently observed at the cranial end of the conduit where the implanted test article was present within the peritoneal wrap. The atrium formed from peritoneum only was comprised of fibrous connective tissue walls without urothelial covering.

The incidence of urothelium and/or smooth muscle layers in the cranial conduit (near the ureters) was higher in the construct groups (Groups 1, 2 and 3) than the scaffold-only group (Group 4). The extent of regeneration observed in sections taken near the caudal end of the implant was variable because the boundary between the caudal end of the implant and the cranial side of the atrium was difficult to discern at necropsy. Most sections presumed to be at the midsection of the implant (Sections 6 and 10, FIG. 59) had no urothelium present. Table 6.10 shows a summary of the findings by group for the neo-urinary conduit.

TABLE 6.10

| | Group Treatment | | | |
|---|---|---|---|---|
| | 1<br>Autologous<br>Bladder SMC's | 2<br>Autologous<br>Adipose SMC's | 3<br>Autologous<br>Blood SMC's | 4<br>Scaffold<br>Only |
| | Mean Days on Study | | | |
| | 53 | 60 | 61 | 48 |
| Incidence of Select Findings by Conduit Location (# animals with finding/# animals examined at that location) | | | | |
| Presence of Urothelium | | | | |
| Left Ureter Conduit Junction (Slide 13) | 5/8 | 6/8 | 7/8 | 3/7 |
| Right Ureter Conduit Junction (Slide 15) | 7/8 | 6/8 | 4/7 | 4/7 |
| Ureter End of Conduit Body (Slides 5 or 9) | 3/7 | 5/8 | 3/5 | 1/7 |
| Middle of Conduit Body (Slides 6 or 10) | 0/6 | 1/7 | 1/5 | 1/7 |
| Stoma End of Conduit Body (Slides 7, 8, 11 or 12) | 0/8 | 0/8 | 0/7 | 0/7 |
| Conduit-Stoma-Skin Junction (Slide 17) | 1/8 | 0/8 | 0/8 | 0/7 |
| Presence of Squamous Epithelium | | | | |
| Left Ureter Conduit Junction (Slide 13) | 0/8 | 0/8 | 0/8 | 0/7 |
| Right Ureter Conduit Junction (Slide 15) | 0/8 | 0/8 | 0/8 | 0/7 |
| Ureter End of Conduit Body (Slides 5 or 9) | 0/7 | 0/8 | 1/5 | 0/7 |
| Middle of Conduit Body (Slides 6 or 10) | 0/6 | 1/7 | 0/5 | 0/7 |
| Stoma End of Conduit Body (Slides 7, 8, 11 or 12) | 6/8 | 3/8 | 4/7 | 2/7 |
| Conduit-Stoma-Skin Junction (Slide 17) | 7/8 | 8/8 | 8/8 | 7/7 |

TABLE 6.10-continued

| | Group Treatment | | | |
|---|---|---|---|---|
| | 1 Autologous Bladder SMC's | 2 Autologous Adipose SMC's | 3 Autologous Blood SMC's | 4 Scaffold Only |
| | | Mean Days on Study | | |
| | 53 | 60 | 61 | 48 |
| Incidence of Select Findings by Conduit Location (# animals with finding/# animals examined at that location) | | | | |
| Presence of Smooth Muscle | | | | |
| Left Ureter Conduit Junction (Slide 13) | 4/8 | 4/8 | 7/8 | 2/7 |
| Right Ureter Conduit Junction (Slide 15) | 4/8 | 4/8 | 5/8 | 3/7 |
| Ureter End of Conduit Body (Slides 5 or 9) | 3/7 | 5/8 | 3/5 | 1/7 |
| Middle of Conduit Body (Slides 6 or 10) | 0/6 | 1/7 | 1/5 | 1/7 |
| Stoma End of Conduit Body (Slides 7, 8, 11 or 12) | 0/8 | 0/8 | 0/7 | 0/7 |
| Conduit-Stoma-Skin Junction (Slide 17) | 0/8 | 0/8 | 0/8 | 0/7 |
| Surface of chronic-active inflammation/detritus | | | | |
| Left Ureter Conduit Junction (Slide 13) | 5/8 | 5/8 | 1/8 | 6/7 |
| Right Ureter Conduit Junction (Slide 15) | 3/8 | 5/8 | 3/8 | 5/7 |
| Ureter End of Conduit Body (Slides 5 or 9) | 5/7 | 6/8 | 3/5 | 6/7 |
| Middle of Conduit Body (Slides 6 or 10) | 6/6 | 7/7 | 5/5 | 6/7 |
| Stoma End of Conduit Body (Slides 7, 8, 11 or 12) | 8/8 | 7/8 | 7/7 | 7/7 |
| Conduit-Stoma-Skin Junction (Slide 17) | 6/8 | 4/8 | 5/8 | 6/7 |
| Attenuation, Urothelium | 1/8 | 3/8 | 3/8 | 0/7 |
| Hyperplasia, Urothelium | 3/8 | 6/8 | 5/8 | 4/7 |
| Vacuolation, Urothelium | 6/8 | 6/8 | 6/8 | 4/7 |
| Ectopic GI mucosa | 1/8 | 2/8 | 0/8 | 0/7 |
| Heterotopic bone, sub-urothelial | 1/8 | 0/8 | 2/8 | 0/7 |
| Hemorrhage, conduit wall | 0/8 | 3/8 | 1/8 | 2/7 |
| Mineralization | 1/8 | 0/8 | 0/8 | 0/7 |
| Scaffold material | 1/8 | 0/8 | 1/8 | 1/7 |
| Adhered GI tract (P = present) | 6/8 | 6/8 | 1/8 | 5/7 |
| Adhered spleen (P = present) | 0/8 | 0/8 | 0/8 | 1/7 |
| Adhered seminal vesicle/uterus (P = present) | 0/8 | 0/8 | 2/8 | 0/7 |
| Vasculitis/vascular necrosis, small blood vessels | 3/8 | 0/8 | 2/8 | 1/7 |
| Acute inflammation/ulceration, skin near stoma | 1/8 | 0/8 | 0/8 | 0/7 |

Table 6.11 shows a summary of the findings by group for kidney, ureter and other tissues.

TABLE 6.11

| | Group Treatment | | | |
|---|---|---|---|---|
| | 1 Autologous Bladder SMC's | 2 Autologous Adipose SMC's | 3 Autologous Blood SMC's | 4 Scaffold Only |
| Left Kidney | | | | |
| Hydronephrosis/chronic nephritis | 3/8 | 2/8 | 2/8 | 6/7 |
| Chronic nephritis (without hydronephrosis) | 1/8 | 2/8 | 1/8 | 0/7 |
| Pyelonephritis | 2/8 | 0/8 | 0/8 | 3/7 |
| Chronic-active nephritis | 1/8 | 4/8 | 1/8 | 5/7 |
| Inflammation, acute/subacute | 1/8 | 1/8 | 0/8 | 0/7 |
| Regeneration, tubular epithelium | 5/8 | 6/8 | 4/8 | 1/7 |
| Tubular necrosis/fluid/casts/glomerulonephritis | 1/8 | 2/8 | 0/8 | 1/7 |
| Viral inclusions, tubular epithelial cells | 1/8 | 2/8 | 0/8 | 0/7 |
| Vasculitis/perivascular inflammation | 1/8 | 1/8 | 1/8 | 0/7 |
| Inflammation, subacute, pelvis | 2/8 | 0/8 | 1/8 | 0/7 |
| Hyperplasia, transitional epithelium, pelvis | 1/8 | 0/8 | 1/8 | 0/7 |
| Inflammation, chronic-active, capsule/peritoneum | 0/8 | 2/8 | 2/8 | 0/7 |

TABLE 6.11-continued

| | Group Treatment | | | |
|---|---|---|---|---|
| | 1 Autologous Bladder SMC's | 2 Autologous Adipose SMC's | 3 Autologous Blood SMC's | 4 Scaffold Only |
| Right Kidney | | | | |
| Hydronephrosis/chronic nephritis | 3/8 | 2/8 | 3/8 | 5/7 |
| Chronic nephritis (without hydronephrosis) | 2/8 | 1/8 | 2/8 | 0/7 |
| Pyelonephritis | 0/8 | 0/8 | 1/8 | 3/7 |
| Chronic-active nephritis | 1/8 | 2/8 | 0/8 | 1/7 |
| Inflammation, acute/subacute | 1/8 | 0/8 | 0/8 | 0/7 |
| Regeneration, tubular epithelium | 4/8 | 2/8 | 4/8 | 1/7 |
| Tubular necrosis/fluid/casts/glomerulonephritis | 1/8 | 2/8 | 0/8 | 0/7 |
| Viral inclusions, tubular epithelial cells | 1/8 | 1/8 | 0/8 | 0/7 |
| Vasculitis/perivascular inflammation | 3/8 | 0/8 | 2/8 | 0/7 |
| Inflammation, subacute, pelvis | 1/8 | 0/8 | 0/8 | 0/7 |
| Hyperplasia, transitional epithelium, pelvis | 1/8 | 0/8 | 1/8 | 1/7 |
| Inflammation, chronic-active, capsule/peritoneum | 1/8 | 2/8 | 0/8 | 0/7 |
| Left Ureter | | | | |
| Dilatation | 4/8 | 2/8 | 3/8 | 7/7 |
| Hyperplasia, transitional epithelium | 1/8 | 0/8 | 0/8 | 0/7 |
| Vacuolation, transitional epithelium | 1/8 | 0/8 | 1/8 | 0/7 |
| Inflammation, subacute/chronic, peri-ureter mesentery | 3/8 | 4/8 | 5/8 | 3/7 |
| Vasculitis/necrosis, mesenteric blood vessel | 4/8 | 1/8 | 1/8 | 1/7 |
| Neutrophils in lumen | 1/8 | 0/8 | 0/8 | 0/7 |
| Bacterial embolism, mesenteric blood vessel | 0/8 | 0/8 | 0/8 | 1/7 |
| Right Ureter | | | | |
| Dilatation | 4/8 | 2/8 | 4/8 | 6/7 |
| Hyperplasia, transitional epithelium | 1/8 | 0/8 | 0/8 | 0/7 |
| Vacuolation, transitional epithelium | 1/8 | 0/8 | 1/8 | 0/7 |
| Inflammation, subacute/chronic, peri-ureter mesentery | 1/8 | 3/8 | 6/8 | 1/7 |
| Vasculitis, mesenteric blood vessel | 4/8 | 1/8 | 2/8 | 1/7 |
| Lymph Node, Lumbar | | | | |
| Hyperplasia, lymphoid | 1/3 | 0/3 | 1/2 | U |
| Hemorrhage | 0/3 | 1/3 | 0/2 | U |
| Histiocytosis, sinus | 1/3 | 3/3 | 1/2 | U |
| Infiltrate, neutrophils | 2/3 | 1/3 | 0/2 | U |
| Depletion, lymphocytes | 1/3 | 3/3 | 1/2 | U |
| Lymph Node, Mesenteric | | | | |
| Hemorrhage | 0/2 | 1/2 | 0/2 | U |
| Histiocytosis, sinus | 0/2 | 1/2 | 1/2 | U |
| Depletion, lymphocytes | 0/2 | 0/2 | 1/2 | U |
| Congestion | 0/2 | 1/2 | 0/2 | U |
| Adhesions and Fistulas | | | | |
| Ahesion conduit to intestines | 8/8 | 8/8 | 5/8 | 5/7 |
| Fistula (macroscopic or clinical notes) | 5/8 | 7/8 | 6/8 | 2/7 |
| Fistula/neutrophil tract (microscopic) | 3/8 | 6/8 | 4/8 | 1/7 |
| Fistula (macroscopic or microscopic) | 5/8 | 8/8 | 6/8 | 3/7 |
| Adhesion ureter to intestines | 1/8 | 1/8 | 3/8 | 2/7 |
| Adhesion conduit to spleen | 0/8 | 0/8 | 0/8 | 2/7 |
| Adhesion conduit to seminal vesicle | 0/8 | 0/8 | 1/8 | 0/7 |
| Adhesion conduit to uterus | 0/8 | 0/8 | 1/8 | 0/7 |
| Adhesion ureter to uterus | 1/8 | 0/8 | 1/8 | 0/7 |
| GROSS LESIONS: | | | | |
| Abdominal Wall | | | | |
| Heterotopic bone, near stoma (P = present) | 4/4 | 3/5 | 2/2 | 1/1 |
| Inflammation, chronic-active, peritoneum | 1/4 | 2/5 | 0/2 | 0/1 |
| Fibrosis, fascia | 0/4 | 1/5 | 0/2 | 1/1 |

TABLE 6.11-continued

|  | Group Treatment | | | |
| --- | --- | --- | --- | --- |
|  | 1<br>Autologous<br>Bladder SMC's | 2<br>Autologous<br>Adipose SMC's | 3<br>Autologous<br>Blood SMC's | 4<br>Scaffold<br>Only |
| Gastrointestinal | | | | |
| Villous atrophy | 2/2 | 0/1 | 0/1 | U |
| Congestion | 0/2 | 1/1 | 0/1 | U |
| Mucous hyperplasia, stomach | 0/2 | 0/1 | 1/1 | U |
| Liver | | | | |
| Inflammation, chronic-active, capsule/peritoneum | U | 1/1 | U | U |
| Lung | | | | |
| Inflammation, acute/subacute, multifocal | 1/1 | 0/1 | 3/3 | U |
| Bacterial colonies, multifocal | 1/1 | 0/1 | 1/3 | U |
| Vasculitis, necrotizing/thrombi | 1/1 | 0/1 | 0/3 | U |
| Inflammation, chronic, pleura | 0/1 | 1/1 | 0/3 | U |
| Lymph Node, Inguinal | | | | |
| Hemorrhage | 1/1 | 0/2 | U | U |
| Infiltrate, neutrophils | 1/1 | 0/2 | U | U |
| Hyperplasia, lymphoid | 0/1 | 2/2 | U | U |
| Depletion, lymphocytes | 1/1 | 0/2 | U | U |
| Histiocytosis, sinus | 0/1 | 1/2 | U | U |
| Omentum | | | | |
| Inflammation, chronic-active | U | 3/3 | U | U |
| Pancreas | | | | |
| Autolysis (P = present) | 1/1 | 2/4 | U | U |
| Inflammation, chronic-active, peritoneum | 0/1 | 2/4 | U | U |
| Seminal Vesicle | | | | |
| Inflammation, chronic-active (with enlargement) | 1/2 | U | U | U |
| Skin, Ear | | | | |
| Vasculitis, necrotizing | U | 1/1 | U | U |
| Spleen | | | | |
| Inflammation, chronic, peritoneal surface | U | U | U | 1/1 |
| Uterus | | | | |
| Uterus adhered to ureters (P = present) | 1/1 | U | U | U |

Urothelium regeneration is not dependent on the presence of cells in the test article and was not expected to occur on the surface of the atrium facing the conduit lumen; therefore, assessment of urinary tissue regeneration was limited to the cranial end of the conduit (Sections 5, 9, 13, and 15).

The placement of the test article and the weight of the overlying abdominal organs may have contributed to poor drainage and detritus build-up in the lumen of all groups; however, there were distinct findings at necropsy in animals receiving a scaffold-only implant. The presence of upper urinary tract lesions was associated with intermittent or complete obstructions resulting in back pressure of the urine—as evidenced by the formation of diverticula in the cranial conduit and the incidence of ureter and kidney damage. No evidence of ureteral or conduit stenosis was observed in any group. However, group 4 animals had increased incidence of hydroureter and hydronephrosis relative to Group 1, 2, and 3 animals (100% and 69% combined, respectively). The absence of SMC in the scaffold-only test articles appears to have contributed to the increase in mortality subsequent to obstruction and incomplete development of urinary tissue, leading to the determination that the scaffold-only test article was unsuitable for further development.

Urinary tissue-like regeneration characterized by mucosa, submucosa and smooth muscle with a fibrovascular stroma was observed after construct test article implantation regardless of SMC source (i.e. bladder, adipose or blood). In contrast, a reparative process was observed following implantation of the scaffold-only test article characterized by an abnormal mucosa supported by fibrovascular stroma with limited smooth muscle. The extent of urinary-like tissue regeneration in the construct groups was influenced by duration of animal survival post-implantation.

Figure 60:
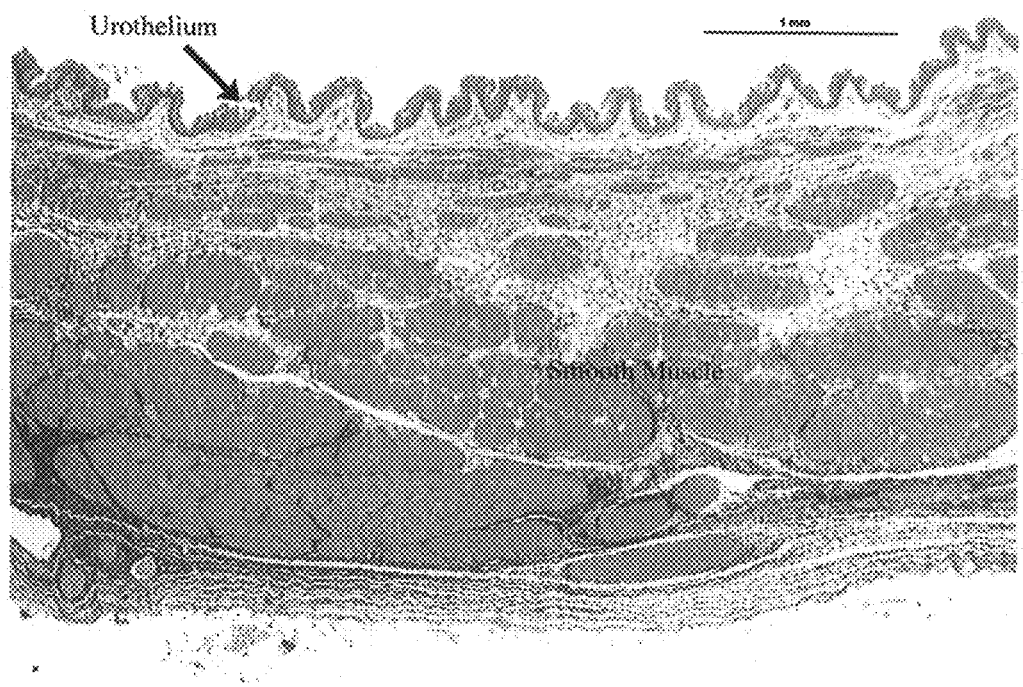
FIG. 60 shows a photomicrograph of an animal implanted with a neo-urinary conduit (Adipose SMC scaffold).

FIGS. 60-63 provide photomicrographs of the neo-urinary conduit. FIG. 60 shows a photomicrograph (Masson's trichome stain) of cranial portion of the NUC from Group 2 female animal 11. Urothelium is present over layers of smooth muscle.

Figure 61:
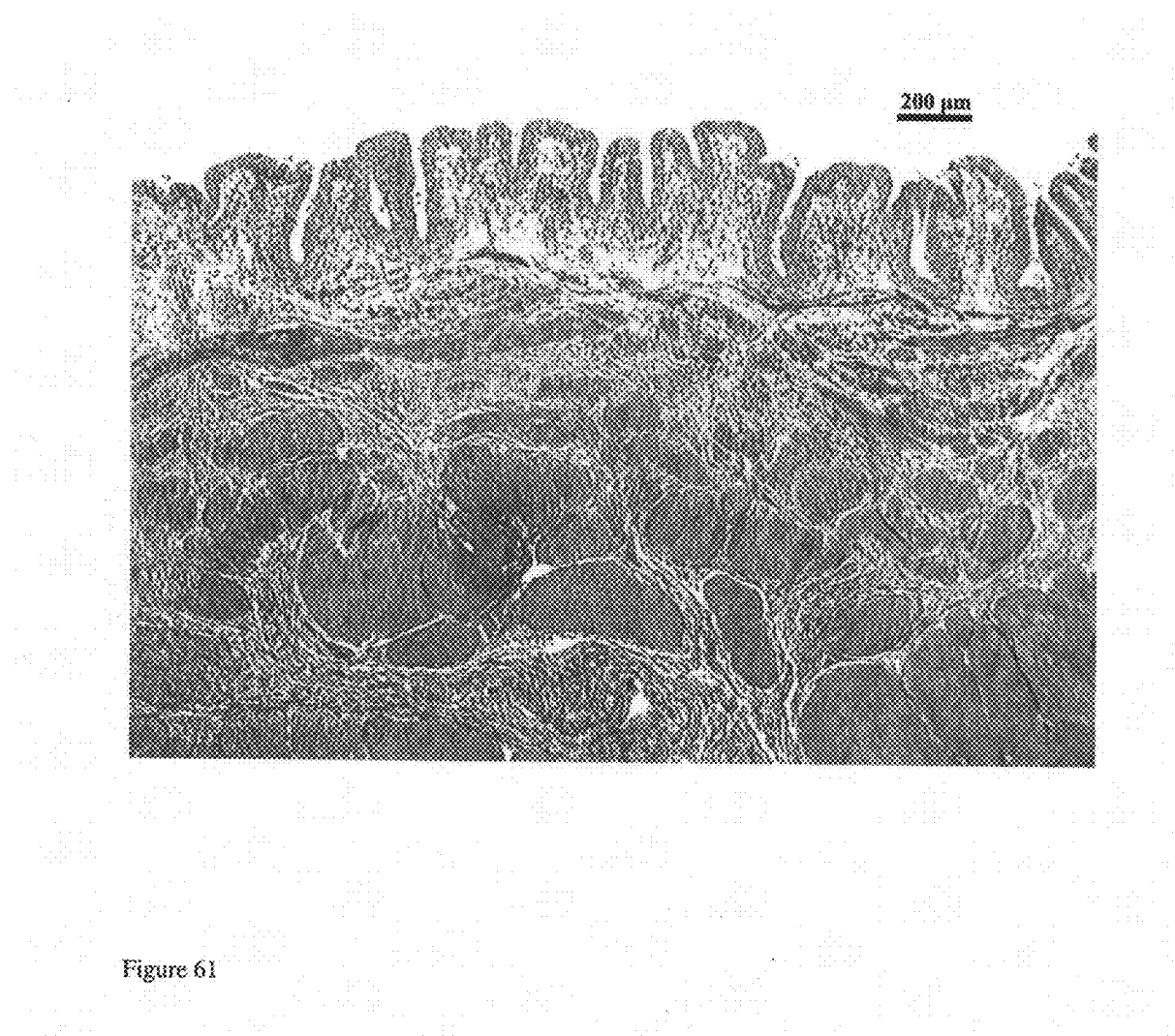
FIG. 61 shows a photomicrograph of an animal implanted with a neo-urinary conduit (Bladder SMC scaffold).

FIG. 61 shows a photomicrograph (Masson's trichome stain) of cranial portion of the NUC from Group 1 female animal 1. Urothelium is present over layers of smooth muscle.

Figure 62:
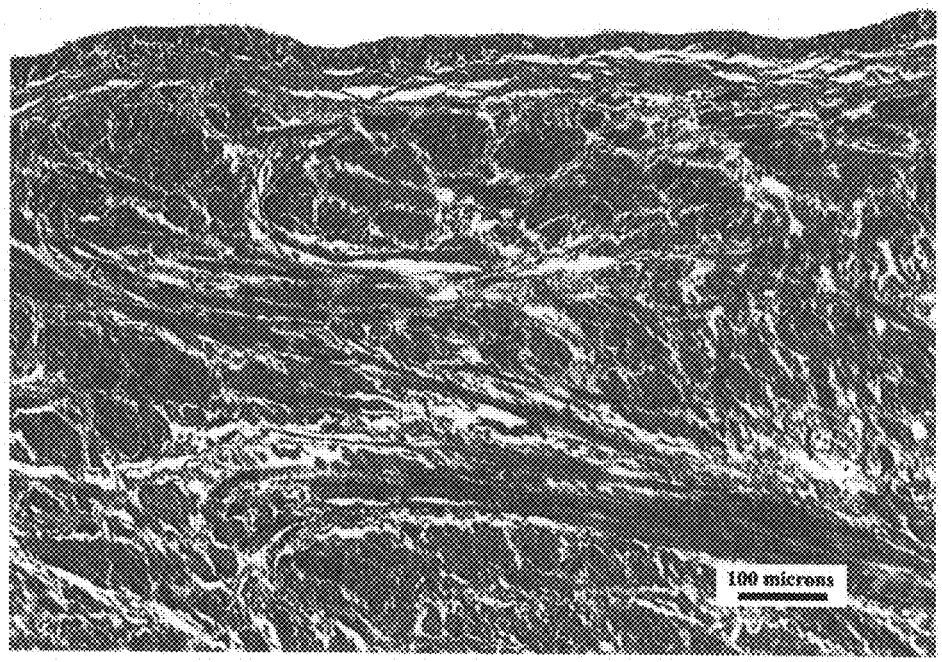
FIG. 62 shows a photomicrograph of an animal implanted with a neo-urinary conduit (Adipose SMC scaffold).

FIG. 62 shows a photomicrograph (Masson's trichome stain) of the NUC near the left ureter from Group 2 male animal 15. Urothelium is present over layers of smooth muscle.

Figure 63:
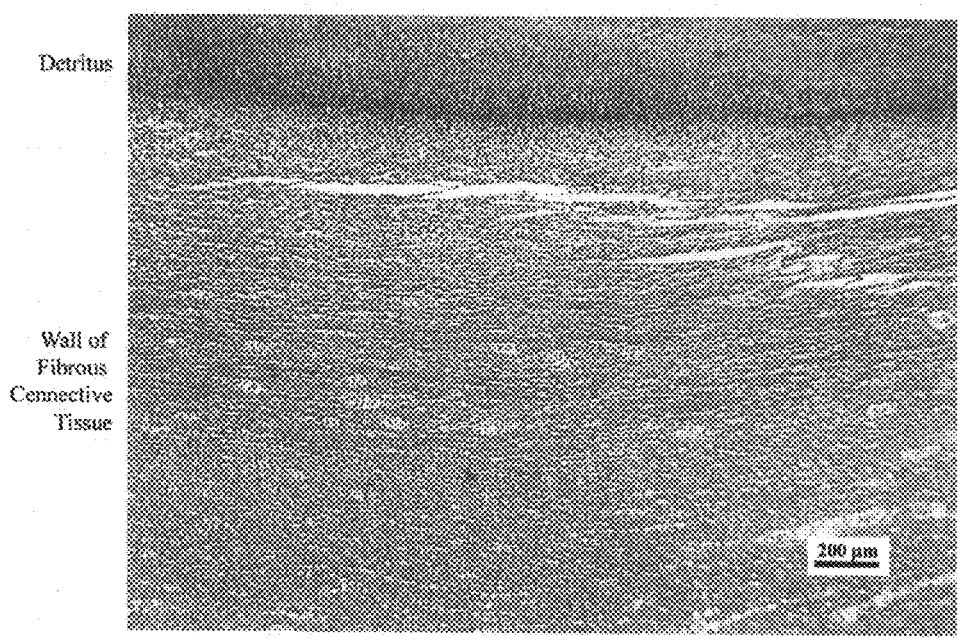
FIG. 63 shows a photomicrograph of an animal implanted with a neo-urinary conduit (Bladder SMC scaffold).

FIG. 63 shows a photomicrograph (Masson's trichome stain) of the NUC wall from Group 1 male animal 5. At this level, the wall of the conduit is comprised of fibrous connective tissue. Detritus covers the luminal surface. This appearance was most frequently observed in the caudal portion of the NUC.

Conclusions

PCV-2 viral infection and partial to full urinary obstruction of the urinary flow as a result of surgical implantation site and abdominal content compressing the lumen contributed to 23/24 unscheduled deaths. Findings related to compression of the lumen and urinary obstructions were adhesions, fistulas, hydroureter, hydronephrosis, and pyelonephritis. An in-life surgical procedure-related complication contributed to 1/24 unscheduled death.

Healing and regeneration was observed in portions of conduits derived from any of the construct test articles while healing and repair was observed in the conduits derived from the scaffold-only test article, demonstrating that construct implantation resulted in the formation of a conduit having a urinary-like tissue wall composed of mucosa and smooth muscle layers.

The difference in healing between the construct test articles (regeneration) and scaffoldonly test article (repair) contributed to a higher incidence of significant renal findings observed with the scaffold-only test article, leading to a determination that the scaffold-only test article was unsuitable for further development.

There were no differences observed in the regenerative process between construct test articles, suggesting equivalence between SMC sources in promoting regeneration.

Example 7

In Vivo Implantation of a Neo-urinary Conduit Scaffold Seeded with SMCs

A 3 month preclinical study using a porcine model to evaluate the potential of a synthetic scaffold (PGA) and cell-based constructs to create a regenerative Neo-Urinary Conduit (NUC) that would allow urine to flow from the ureters to outside the body without evidence of damage to the upper urinary tract or metabolic abnormalities has been performed (following Example 3 protocols).

The feasibility of using SMC-seeded PLGA-based biodegradable scaffolds, or Neo-Urinary Conduits (NUC), to establish an incontinent urinary diversion was evaluated. Scaffold-only controls and NUC seeded with autologous SMC isolated from blood, fat, or urinary bladders were evaluated in a percutaneous diversion porcine model for 3 months. Urine outflow was maintained by early post-operative management of the conduit lumen and stoma.

The constructs composed of smooth muscle cells (SMC) obtained from blood, fat, or bladder sources regenerated a patent conduit composed of a urothelial cell lining and smooth muscle layer that did not result in alterations to the upper urinary tract. No evidence was found for elevated creatinine, metabolic abnormalities or altered hematological parameters.

NUC diversions developed into conduits composed of regenerated urinary tissues (urothelial cell lining and vascular smooth muscle wall) regardless of cell source. No significant alterations to the upper urinary tract, creatinine elevations, or hematologic or metabolic abnormalities were observed. In contrast, scaffold-only implanted animals developed patent urothelial lined conduits composed primarily of fibrous connective tissue and limited smooth muscle development. This group also had a high frequency of hydroureter and hydronephrosis. In both groups, early post-operative management of the conduit lumen and stoma were required to maintain patency for the study duration.

Figure 64:
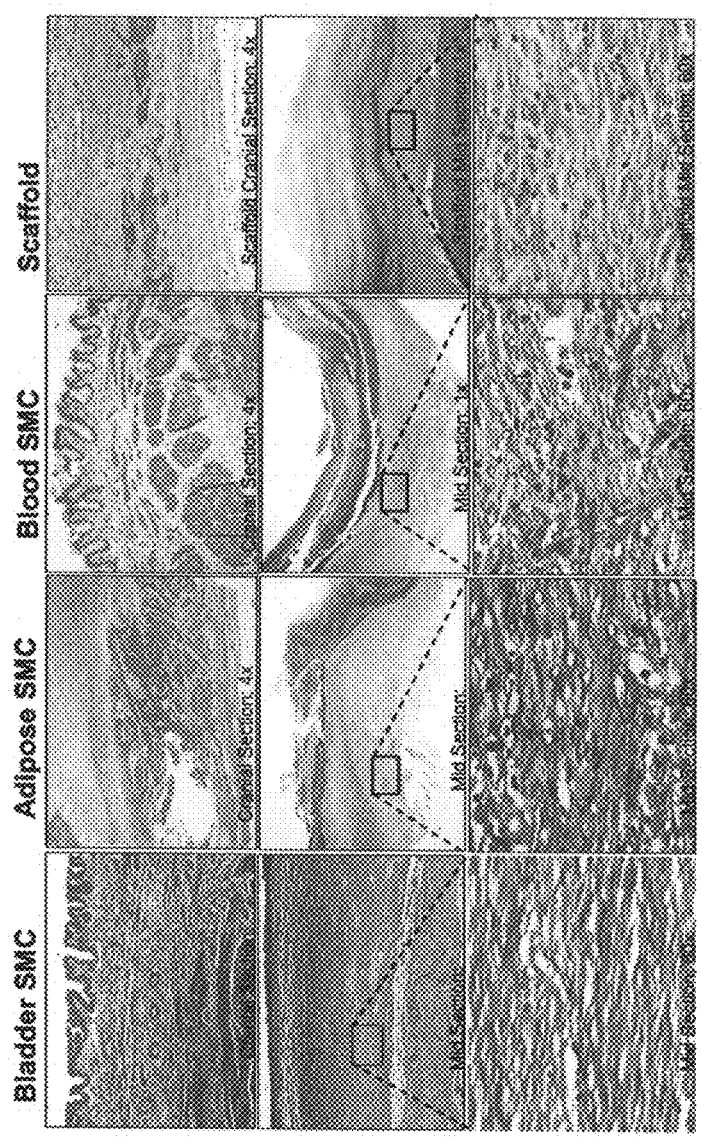
FIG. 64 shows histological characteristics of the regenerated urological tissue forming the neo-bladder conduit.

FIG. 64 shows the histological characteristics of the regenerated urological tissue forming the neo-bladder conduit was similar regardless of SMC origin. Analysis was performed at an interim analysis (48-days) and at end of study (3 mo terminal sacrifice).

These studies demonstrate that a synthetic Neo-Urinary Conduit (NUC) seeded with autologous SMC from various sources (blood, fat or bladder) is capable of establishing a patent incontinent urinary diversion for post-cystectomy management of urine elimination. NBC-implanted animals exhibited none of the sequelae commonly associated with GI-derived urinary diversions or scaffold-only implants. Neo-Bladder Conduit may represent an alternative to GI tissue for post-cystectomy management by incontinent urinary diversion.

Figure 65:
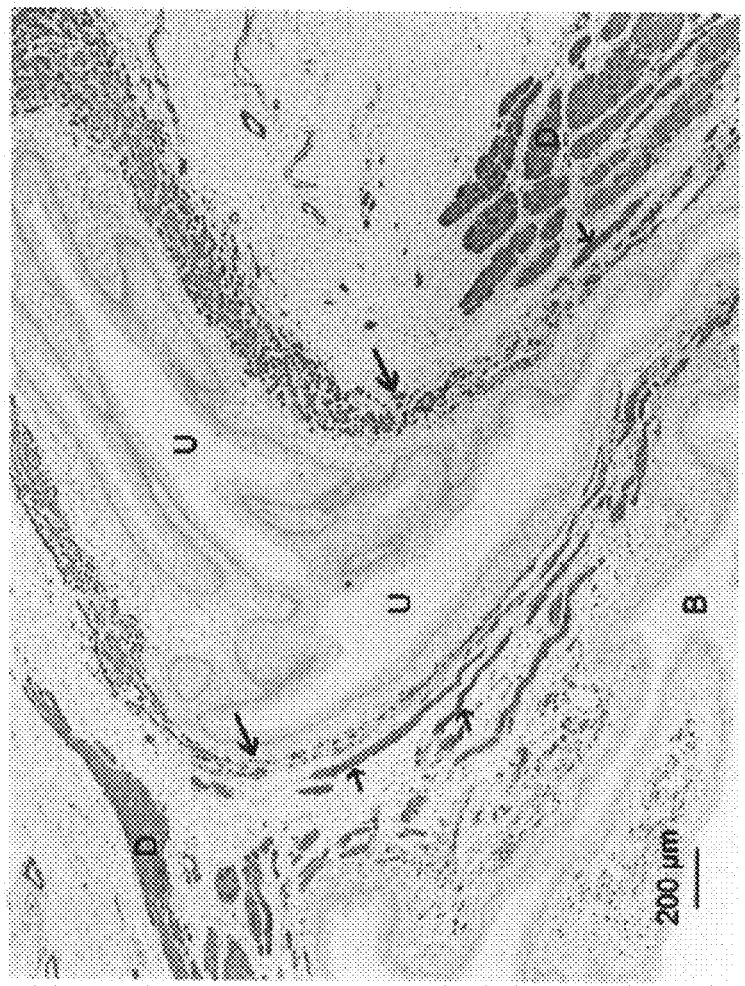
FIG. 65 shows the three muscle components of a native uretero-vesical junction.

According to Pirker et al. (2007) J. Urol. April; 177(4): 1546-51, the three muscle components of the uretero-vesical junction (UVJ) were readily distinguishable in porcine fetuses at gestational age 60 days. This included the 1) ureteral (U) smooth muscle, 2) detrusor (D) smooth muscle and 3) the periureteral sheath smooth muscle. The ureteral smooth muscle was characterized by numerous small diameter muscle fascicles (long arrows), while the detrusor muscle consisted of large diameter muscle bundles running in multiple directions, and the muscle fibers of the periureteral sheath distinguishable in all age groups by their intermediate fiber size, location, and orientation along the intramural ureter (short arrows). U=ureteral lumen; B=bladder lumen, α-SMA stain, reduced from x40. This is shown in FIG. 65.

Figure 66:
FIG. 66 shows the utero-conduit junction of a recipient of a conduit construct.

As shown in FIG. 66, after 82 days an adipose group animal showed similarities between the newly formed uretero-conduit junction (UCJ) and Pirker's depiction of the UVJ. Histologically, the UCJ section basically showed similarities to the embryological development of the 60 to 90 day-old porcine fetus. Masson's Trichrome-stained histological section of UCJ. Original total magnification 10×. U=ureteral lumen; C=conduit lumen, and arrows show a mixture of muscle fibers with ureteral and periureteral similarities.

Figure 67:
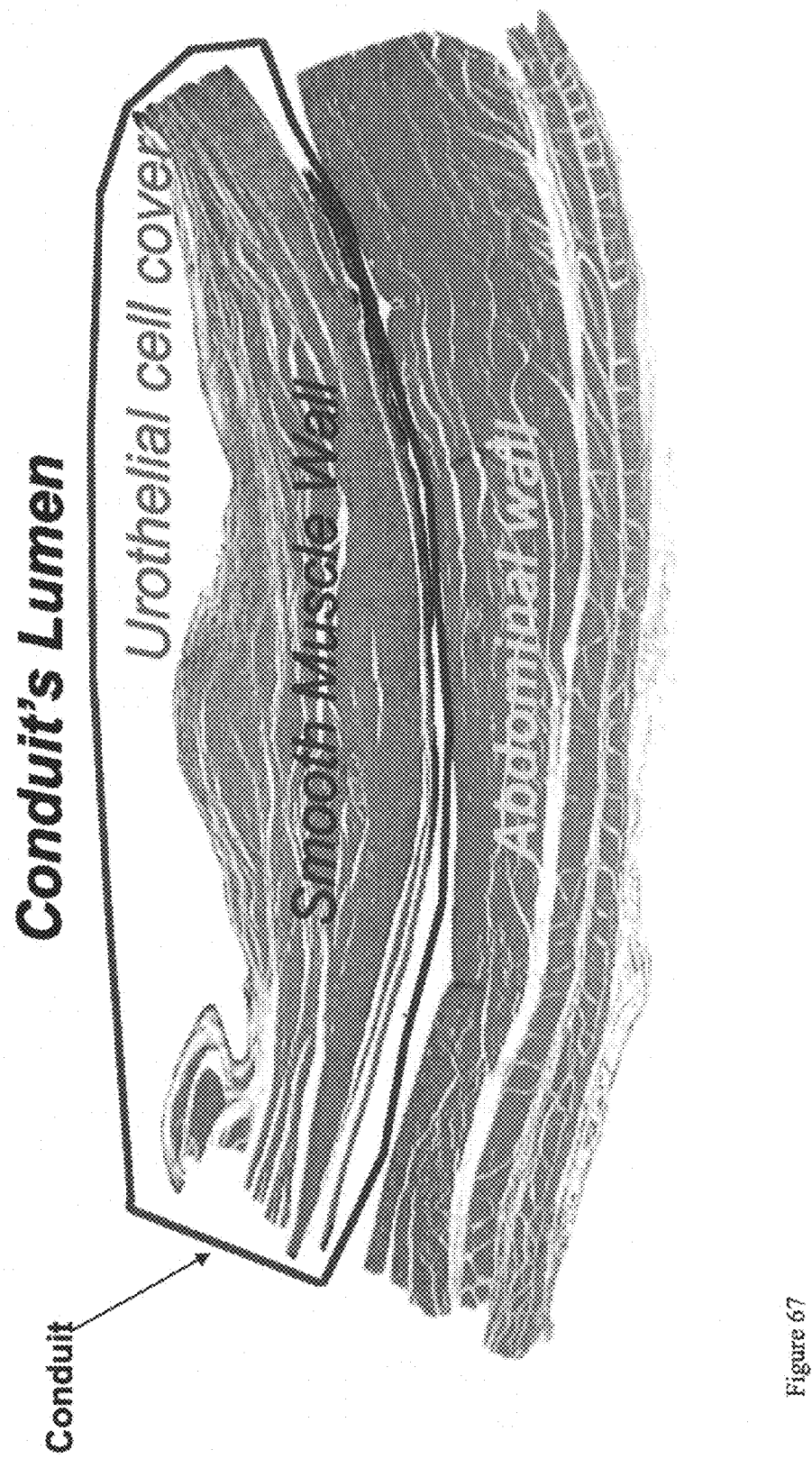
FIG. 67 shows the histology of an implanted conduit construct.

FIG. 67 shows the histology of an implanted conduit and indicates the smooth muscle cell wall, abdominal wall, urothelial cell cover, conduit, and conduit lumen locations.

Example 8

De Novo Functional Neo-urinary Conduit from Non-bladder Cell Sources

We describe here the isolation and characterization of smooth-muscle cells from porcine peripheral blood and adipose that are phenotypically and functionally indistinguishable from bladder-derived smooth muscle cells. We demonstrate that peripheral blood and adipose-derived smooth-muscle cells may be used to seed synthetic, biodegradeable tubular scaffold structures and that implantation of these seeded scaffolds into a porcine cystectomy model leads to successful regeneration of a neo-urinary conduit functionally indistinguishable from that seeded with bladder-derived smooth muscle cells. The ability to create urologic structures de novo from scaffolds seeded by peripheral blood- or adipose-derived smooth muscle cells will greatly facilitate the translation of urologic tissue engineering technologies into clinical practice.

Although smooth muscle cells have also been isolated from other tissue sources such as skeletal muscle and omentum (Wilschut et al. *J Cell Biochem* 105, 1228-1239 (2008); Hernando et al. *Eur J Vasc Surg* 8, 531-536 (1994)), we chose to focus on recovery of smooth muscle cells from peripheral blood and adipose, as these represent the source tissue with favorable potential clinical utility in terms of the ease of sample collection. A porcine cystectomy model was selected to evaluate the performance of peripheral blood- and adipose-derived smooth muscle cells relative to bladder-derived smooth muscle cells upon application in a cell/scaffold composite (Baldwin et al. *J. Endourol.* 17, 307-312 (2003); Akbal et al. *J Urol.* 176, 1706-1711 (2006).

FIG. 68 shows porcine (A) bladder-, (B) adipose-, and (C) peripheral blood-derived smooth muscle cells. Smooth muscle cells from all three tissue types share morphological features characteristic of fully differentiated smooth muscle cells, including a flattened, spindle-shaped fibroblastic appearance and whirling, "hill-and-valley" organization.

FIG. 69 shows RT-PCR analysis of smooth muscle cell associated markers from porcine bladder-, adipose-, and peripheral blood-derived smooth muscle cells. Expression of the smooth muscle cell associated markers SMαA, SM22, myocardin, SMMHC and calponin is comparable in all smooth muscle cell types, regardless of tissue source. Samples are normalized by mass of RNA and expression of β-actin. Numbers refer to individual swine from which primary cell cultures were derived.

FIG. 70 shows immuno-fluorescence analysis of smooth muscle cell associated markers from porcine bladder, adipose & peripheral blood-derived smooth muscle cells. Expression of the smooth muscle cell associated markers SMαA, SM22, SMMHC and calponin is comparable in all smooth muscle cell types, regardless of tissue source, with the exception of SM22 in adipose-derived SMC Negative controls (IgG isotypes) showed no detectable staining (data not shown).

Direct plating of the peripheral blood-derived mononuclear fraction from swine resulted in outgrowth of colonies with typical smooth muscle cell morphology (FIG. 68). All (100%) animals screened (n=24) generated smooth muscle cell colonies, with $2.44 \times 10^3$-$2.37 \times 10^6$ smooth muscle cells recovered at passage zero from 50 ml of peripheral blood. Recovery of smooth muscle cells was unaffected by changes in media formulation, cell density or surface coatings (data not shown). A similar approach was used to investigate the potential application of subcutaneous or lipoaspirate-derived adipose as a source of smooth muscle cells. The stromal-vascular fraction (SVF) of adipose represents a heterogenous population of cells including endothelial cells, smooth muscle cells as well as progenitor cells with limited mesenchymal potential[22]. We were able to generate colonies (expandable into monolayers) of smooth muscle cells from porcine adipose with 100% efficiency (n=24), (FIG. 68) with a cell recovery rate of $1.37 \times 10^5$-$4.36 \times 10^5$ cells/g adipose tissue. In comparison, smooth muscle cells could be isolated from bladder tissue with a recovery rate of $1.29 \times 10^6$-$9.3 \times 10^6$ cells/g bladder tissue. Expansion of smooth muscle cell colonies from peripheral blood or adipose resulted in the formation of a cell monolayer with a typical whirled, "hill-and-valley" organization characteristic of cultured bladder-derived smooth muscle cells (FIG. 68).

Enrichment of smooth muscle cells was facilitated by use of high cell densities and high glucose media, which has been shown to specifically select against the growth and expansion of mesenchymal stem cells (Lund et al. 2009 supra). To this end, a systematic comparative analysis demonstrating the key differences in phenotypic and functional properties between adipose-derived smooth muscle cells and mesenchymal stem cells was performed (see Example below).

Analysis of the functional properties of peripheral blood or adipose-derived smooth muscle cells in vitro demonstrates that they are indistinguishable from bladder-derived smooth muscle cells. Increased expression of proteins associated with smooth muscle contractility is a characteristic feature of smooth muscle cell differentiation and maturation (Jeon et al, 2006 supra; Ross et al., 2006 supra; Sinha et al., 2004 supra). Myocardin is a key transcription factor required for smooth muscle cell differentiation and acts to mediate the expression of smooth muscle markers essential for contractility including SM22, α-smooth muscle actin (SMαA), smooth muscle myosin heavy chain (SMMHC) and calponin (CNN). Expression of the smooth muscle markers SMMHC and CNN is generally regarded as diagnostic of mature smooth muscle cells. (Qiu et al., 2005 supra; Wang et al., 2003 supra; Yoshida et al., 2003 supra). As shown in FIG. 69, semi-quantitative RT-PCR analysis of the expression of these key smooth muscle cell markers demonstrates that blood and adipose-derived smooth muscle cells are directly comparable to bladder-derived smooth muscle cells.

These results were confirmed by immuno-fluorescence analysis of smooth muscle cell specific protein expression. αSMA, SM22, CNN and SMMHC were expressed in peripheral blood and adipose-derived smooth muscle cells with a localization pattern identical to that observed in bladder-derived smooth muscle cells (FIG. 70). Localization to stress fibers was observed as is typical for bladder-derived smooth muscle cells. Staining of SM22 was observed to be weak in adipose-derived smooth muscle cells.

FIG. 71 show contractility of porcine (A) bladder-, (B) adipose-, and (C) peripheral blood-derived smooth muscle cells. Smooth muscle cells from all three tissue sources show $Ca^{2+}$ dependant contractility in a collagen gel matrix. Numbers refer to cell lines derived from individual animals The functionality of peripheral blood and adipose-derived smooth muscle cells was further evaluated by a three dimensional $Ca^{2+}$-dependant contractility assay. Smooth muscle cells spontaneously induce contraction of a collagen matrix in a $Ca^{2+}$-dependant manner when embedded in a three-dimensional gel (Travis et al. 2001 supra). As shown in FIG. 71, while sample-to-sample variation was observed, peripheral blood and adipose-derived cells contract to a degree comparable to bladder-derived smooth muscle cells and this contractility is inhibited by EDTA, a known $Ca^{2+}$ chelator.

FIG. 72A-C shows the growth kinetics of porcine (A) bladder-, (B) adipose-, and (C) peripheral blood-derived smooth muscle cells. The numbers refer to cell lines derived from individual animals.

Application of adipose and peripheral blood-derived smooth muscle cells for urologic regenerative medicine is contingent on being able to secure adequate cell numbers within an acceptable time frame. Towards this end, we have observed that smooth muscle cell colonies (from a 50 ml sample of porcine peripheral blood or 7-25 g porcine adipose) are identifiable within 7 days post seeding, and may be passaged within 14 days. As shown in FIG. 72A-C, with the exception of one bladder smooth muscle sample which failed to proliferate for unknown reasons, one million to tens of millions of smooth muscle cells were recovered from bladder, peripheral blood or adipose within 2-4 weeks (n=24). Bladder and adipose-derived smooth muscle cells were expanded for 2 passages prior to harvesting of cells for seeding a synthetic, neo-urinary conduit scaffold. Peripheral blood-derived smooth muscle cells were expanded for 3-4 passages to generate equivalent cell numbers. On average, 30-40×10$^6$ smooth muscle cells were used to seed a neo-urinary conduit scaffold.

We have previously shown that bladder-derived smooth muscle cells may be used to seed a synthetic, biopolymer scaffold which upon implantation into an in vivo clinical model of bladder cystectomy resulted in the regeneration of a fully functional de novo bladder augment (Jayo I supra). However, because use of bladder-derived smooth muscle cells may not be clinically ideal, we proceeded to evaluate the in vivo clinical efficacy of peripheral blood and adipose-derived smooth muscle cells in a 3 month porcine clinical model of urinary incontinence Baldwin et al. 2003 supra; Akbal et al. 2006 supra). Bladder, adipose and peripheral blood-derived smooth muscle cells were used to seed PGA/PLGA-based scaffolds to create a regenerative, neo-urinary conduit permitting efflux of urine from the ureters directly to the external body surface. We observed that constructs composed of smooth muscle cells obtained from blood or bladder sources regenerated a patent conduit composed of an urothelial cell lining and smooth muscle layer that did not result in alterations to the upper urinary tract. No evidence was found for elevated creatinine, metabolic abnormalities or altered hematological parameters.

FIG. 73 shows the regeneration of neo-urinary conduit in porcine cystectomy model with adipose-, peripheral blood-, and bladder-derived smooth muscle cell-seeded synthetic scaffolds. Neo-urinary conduit composites seeded with adipose-, peripheral blood-, or bladder-derived smooth muscle cells led to regeneration of urinary-like tissue with urothelial and smooth muscle layers. Smooth muscle cell bundles were observed in the cranial dorsal/ventral aspect of the neo-urinary conduit, adjacent to the ureteral/scaffold junction. In all groups, fibroblasts and smooth muscle cells were observed in representative sections obtained from mid-portion of the conduit. The scaffold-only group developed neo-urinary conduits composed principally of fibrous connective tissue and limited smooth muscle bundles associated with repair. Masson's trichrome stain was used to identify regenerated smooth muscle bundles (red) and the presence of early cellular organization consisting of fibroblasts and smooth muscle cells in a collagen rich matrix (blue). Nuclei stain dark brown. In all groups, fibroblasts and smooth muscle cells were observed in representative sections obtained from mid-portion of the conduit. Higher concentration of collagen observed in the bladder and scaffold groups respectively, characterized by blue staining from Masson's trichrome stain. Scaffold only group developed neo-urinary conduits composed principally of fibrous connective tissue and limited smooth muscle bundles.

As shown in FIG. 73, the histological characteristics of the regenerated urological tissue forming the neo-urinary conduit was generally similar regardless of the origin of the smooth muscle cell population. In contrast, scaffold-only implanted animals developed patent urothelial-lined conduits composed primarily of fibrous connective tissue and limited smooth muscle development. In both groups, early post-operative management of the conduit lumen and stoma was required to maintain patency for the study duration.

This study demonstrates that a synthetic, biodegradable scaffold composite seeded with autologous smooth muscle cells derived from multiple potential cell sources (blood, fat or bladder) is capable of being used to re-create a patent neo-urinary conduit in a preclinical porcine model. This ability to create urologic structures de novo from synthetic scaffolds seeded by peripheral blood or adipose-derived smooth muscle cells will greatly facilitate the translation of urologic tissue engineering technologies into clinical practice.

Materials and Methods.

Generation of smooth muscle cells from porcine bladder, adipose and peripheral blood. Smooth muscle cells were isolated from bladder & adipose biopsies as well as peripheral blood draws for use in generation of an autologous Neo-Urinary Conduit construct. A 1 cm$^2$ bladder biopsy specimen, 2 cm$^2$ adipose biopsy specimen, and 50 mL of peripheral blood was obtained from each of 24 Gottingen swine approximately 8 weeks prior to the planned implantation of the final Neo-Urinary Conduit.

For isolation of bladder-derived smooth muscle cells, the urothelial cell layer was dissected away from the bladder biopsy and the remaining smooth muscle layer cut into 1 mm$^2$ pieces and arranged onto the surface of a tissue culture plate. Biopsy pieces were dried in a biosafety cabinet for 10-30 minutes. DMEM-HG (Gibco)+10% FBS was added to the biopsy samples and the plates incubated in a humidified 37° C. incubator at 5% $CO_2$.

Adipose tissue (7-25 g) was washed 3 times with PBS, minced with a scalpel and scissors, transferred into a 50 mL conical tube and incubated at 37° C. for 60 minutes in a solution of 0.3% collagenase (Worthington) and 1% BSA in DMEM-HG. The tubes were either continually rocked or periodically shaken to facilitate digestion. The stromal-vascular fraction was pelleted by centrifugation at 600 g for 10 minutes and resuspended in DMEM-HG+10% FBS. The stromal-vascular fraction was then used to seed passage zero.

25 ml of porcine peripheral blood was diluted 1:1 in PBS and layered with 25 ml Histopaque-1077 (Sigma) in a 50 mL conical tube. Following centrifugation (800 g, 30 min), the mononuclear fraction was collected, washed once with PBS and resuspended in α-MEM/10% FBS (Invitrogen) to seed passage zero.

Assembly of a Neo-Urinary Conduit cell/scaffold composite. Bladder, adipose and peripheral blood-derived smooth muscle cells were expanded separately for up to 7 weeks to generate the 10$^7$ cells required for seeding a NUC scaffold. Bladder and adipose-derived smooth muscle cells were expanded for 2 passages before harvesting of cells for seeding of scaffolds to produce the final construct. Peripheral blood-derived smooth muscle cell cultures were expanded to P3-4 before harvesting for scaffold seeding. To make the NUC scaffold, PGA felt was cut to size, sutured into the shape of a NUC, and coated with PLGA. This construct was then sterilized using ethylene oxide. On the day prior to cell seeding, the NUC scaffold was serially pre-wetted by saturation with 60% ethanol/40% D-PBS, 100% D-PBS, D-MEM/10% FBS or α-MEM/10% FBS followed by incubation in D-MEM/10% FBS or α-MEM/10% FBS at room temperature overnight. The NUC scaffold was then seeded with bladder-, adipose-, or peripheral blood-derived smooth muscle cells and the seeded construct matured in a humidified 37° C. incubator at 5% $CO_2$ until implantation in an autologous host pig by day 7.

Isolation of RNA and semi-quantitative RT-PCR analysis. RNA was isolated from porcine bladder, adipose and peripheral-blood derived smooth muscle cells using the RNeasy Plus RNA Mini isolation kit (Qiagen). 1 μg of RNA from each sample was reverse-transcribed using the Quantitect cDNA synthesis kit (Invitrogen). The following smooth muscle cell specific primers were used to set up RT-PCR reactions (5'-3'): β-actin (F: TTC TAC AAT GAG CTG CGT GTG (SEQ ID NO: 1), R: CGT TCA CAC TTC ATG ATG GAG T (SEQ ID NO: 2)), SM22 (transgelin) (F: GAT CCA ACT GGT TTA TGA AGA AAG C (SEQ ID NO: 3), R: TCT AAC TGA TGA TCT GCC GAG GTC (SEQ ID NO: 4)), SMαA (F: CCA GCA GAT GTG GAT CAG CA (SEQ ID NO: 5), R: AAG CAT TTG CGG TGG ACA AT (SEQ ID NO: 6)), SMMHC (F: GCT CAG AAA GTT TGC CAC CTC (SEQ ID NO: 7), R: TCC TGC TCC AGG ATG AAC AT (SEQ ID NO: 8)), CNN (calponin) (F: CAT GTC CTC TGC TCA CTT CAA C (SEQ ID NO: 9), R: CCC CTC GAT CCA CTC TCT CA (SEQ ID NO: 10)), MYOCD (F: AAG AGC ACA GGG TCT CCT CA (SEQ ID NO: 11), R: ACT CCG AGT CAT TTG CTG CT (SEQ ID NO: 12)). Cycling conditions: denature 95° (2 min), denature 95° (45s), anneal (45s), extension 72° (45s), final extension 72° (5 min). 35 cycles (myocardin 40 cycles). Annealing temps: β-actin=58°, SM22=56°, SMαA=55°, SMMHC=60°, CNN=51°, MYOCD=52°. PCR reactions were carried out using GoTaq Green PCR mix (Promega) and cycled on an iQcycler (Bio-Rad).

Immuno-fluorescence analysis. The following antibodies were used for immuno-fluorescence analysis: SMαA (Dako #M0851), CNN (Dako #M3556), SM-MHC (Sigma #M7786), myocardin (Santa Cruz #SC3428), SM22 (Abcam #ab28811-100), anti-msIgG1/Alexafluor 488 (Invitrogen #A21121), anti-msIgG2a/Alexafluor 488 (Invitrogen #A21131), anti-gtIgG/Alexafuor 488 (Invitrogen #A11055). All primary antibodies were used at a final concentration of 5 □g/ml, except SMMHC which was used at 10 μg/ml.

Contractility assay. Contractility assays were performed as described previously (Travis et al., 2001 supra).

Growth kinetics. Expansion of smooth muscle cells from tissue isolation to seeding of the Neo-Urinary Conduit scaffold was by serial passaging at a confluence >70%.

GLP preclinical analysis of de novo neo-urinary conduit formation in a porcine cystectomy model. 32 Gottingen swine with total cystectomy and incontinent ureterostomy (8 animals per data point composed of 4 males and 4 females each) were used in a GLP preclinical analysis to determine the safety and functionality of tissue-engineered NUC constructs seeded with autologous smooth muscle cells derived from the bladder, blood or adipose tissue. Of the 32 animals, the first group (4 males, 4 females) was implanted with NUC seeded with bladder-derived smooth muscle cells. A second group was implanted with NUC scaffold seeded with adipose-derived SMCs, a third group was implanted with a NUC scaffold seeded with blood-derived SMCs, and the 4th group was implanted with unseeded NUC scaffold only. Device effect and performance was monitored through ultrasound imaging, pyelogram, as well as urine and blood analysis at different time-points of the study. At the completion of the recovery period (Day 84+/−5), all animals were euthanized and a necropsy performed for harvesting the kidneys, conduits, and associated organs and tissues for histological preparation and pathological examination.

Example 9

Assessment of a Neo-Urinary Conduit in Swine

The objective of this study is to determine the safety and functionality of the use of Tengion's Neo-Urinary Conduit (NUC) Construct seeded with autologous smooth muscle cells derived from the bladder, blood or adipose for conduit implantation and tissue regeneration after surgical removal of the bladder (radical cystectomy) and diversion of the ureters to the inflow end of the NUC Construct implant system. Peritonewn will be used to wrap the whole construct. The draining outflow end of the construct will be directed and attached towards the surgically created stoma in order to pass urine. In this study, the performance of the Neo-Urinary Conduit Construct and the effects on the associated organs and tissues will be evaluated. The endpoint measurements include pyelogram, ultrasound, blood analysis, and histopathology.

Twenty animals (10 F, 10M) will be enlisted in the study. There is one (I) group with four animals (2F and 2M) with autologous bladder SMCs. There are 2 groups with eight animals (4F, 4M) each: autologous adipose SMCs and autologous blood SMCs. The first group will be implanted with a NUC scaffold seeded with bladder-derived SMCs, The second group will be implanted with a NUC scaffold seeded with adipose-derived SMC's, and the third group will be implanted with a Neo-Urinary Conduit scaffold seeded with blood-derived SMCs. Device effect and performance will be monitored through ultrasound imaging, pyelogram, and urine and blood analysis at different timepoints of the study. At the completion of the recovery period (Day 84 4-5), the animals shall be euthanized and a necropsy performed for harvesting the kidneys, conduits, and associated organs and tissues for histological preparation and pathological examination. Four out of twenty animals will be subjected to two major procedures. The first procedure will be a bladder biopsy. At a later date a second surgical procedure will be performed to implant the neo-urinary Conduit construct seeded with autologous bladder SMCs. The remaining 16 animals will undergo one minor surgical procedure to collect adipose tissue from the abdomen and venous blood collection. The tissues will be used for harvesting of autologous cells used in constructing the cell seeded Neo-urinary Conduit constructs. This procedure is required for sufficient autologous tissue samples needed for the constructs. The two tissues will be collected from the 16 animals to provide the optimal process for group selection. These same animals will be implanted with the autologous SMC seeded scaffold derived from the blood or adipose tissues. The utilization of peritoneum as a vascular source for the conduit implant will also be evaluated.

Test animals: Common Name: Yorkshire Swine; Breed/Class: *Sus Scrofa*; Number of Animals (by gender): 10 Females & 10 Males; Weight Range: 25±5 Kg.

Treatment Groups: The objective of the study is to assess Tengion's Neo-urinary Conduit Construct in Female and Male Yorkshire pig model over time for 12 weeks. Table 9.1 shows the five phases of the study.

| Summary | |
|---|---|
| Phase A | Baseline data collection, Tissue harvest for smooth muscle cells for scaffold |
| Phase B | Generation of Test Article (Construct) by Sponsor |
| Phase C | Surgical Implantation Procedure of 20 animals |
| Phase D | Survival: Post operative care and monitoring, Observation, Data Collection |
| Phase E | Pre-Necropsy follow up & necropsy with tissue harvest and histology |

Table 9.2 provides a summary of the study design. The body weight will be measured before pre-biopsy, pre-surgery, and pre-necropsy. Assessment of the incision site will be made daily for 14 days or until healed. Maintenance of the stoma button will be daily for the duration of the study as needed. Debridement will be performed on an as needed basis per animal.

TABLE 9.2

| Group No. | Treatment | No. of Animals M | F | Biopsy Procedure | Surgical Procedure (Day 0) | Postoperative procedures | Intended Necropsy Time Point |
|---|---|---|---|---|---|---|---|
| 1 | Autologous Bladder SMC | 2 | 2 | Collect from each animal: 2.5 cm² tissue sample | Complete cystectomy followed by transposition of the ureters to be attached to inflow end of NUC construct | Clinical health assessment, body weight, stoma button and incision site maintenance blood and urine analysis, pyelogram and ultrasound | Approximately 3 months after implantation (84 ± 5 days from implant) |
| 2 | Autologous adipose SMC | 4 | 4 | Collect from each animal: 25-50 g of adipose tissue sample 8 × 10 ml tubes of peripheral blood | Complete cystectomy followed by transposition of the ureters to be attached to inflow end of NUC construct Ureters are stented with a stent for ~7 days Peritoneum used to wrap and cover whole of construct Draining outflow end of the construct is attached through the abdominal wall and exiting to the skin without a continent stoma | | |
| 3 | Autologous Blood SMC | 4 | 4 | | Stoma button placed permanently to retain patency | | |

Test devices.

Test Article Group 1: PGA/PLGA Neo-urinary Conduit Construct with autologous bladder-derived SMCs. Description: Scaffold comprising of synthetic lactide/coglycolide acid polymers plus autologous bladder derived SMCs.

Test Article Group 2: PGA/PLGA Neo-urinary Conduit Construct with autologous adipose-derived SMCs. Description: Scaffold comprising of synthetic lactide/coglycolide acid polymers plus autologous adipose derived SMCs.

Test Article Group 3: PGA/PLGA Neo-urinary Conduit Construct with autologous blood-derived SMCs. Description: Scaffold comprising of synthetic lactide/coglycolide acid polymers plus autologous blood derived SMCs.

Pre-Surgery Fasting

Procedure Description: All animals will be fasted at least 8 hours prior to surgery. Food will be withheld the day prior to each surgery.

Duration/Frequency of the Procedure: Single event the night prior to each surgery with duration of approximately 8 hours.

Procedure Performance: Food withholding will be performed by DaVINCEs staff technician in animal pen.

Procedural Records: Data will be recorded on the DaVINCI Animal Room Maintenance Form, the Twice Daily Assessment Form or Animal Progress Notes.

Body Weight:

Procedure Description: The weight of the animal will be performed on a calibrated balance.

Duration/Frequency of the Procedure: Pre-Biopsy; Pre-Surgery and Pre-Necropsy. Additional body weights may be obtained at the discretion of the Veterinarian.

Procedure Performance: Body weights will be performed by trained technician.

Sedation/Anesthesia:

Procedure Description: Biopsy and Test Device Implantation Procedure: Each animal will be sedated and then anesthetized (in accordance with DaVINCI SOP DAV-SURG-003) prior to surgery preparation. Each animal will be sedated with Ketamine 20 mg/kg 1M, Xylazine 2 mg/kg (FYI) and Atropine (0.04 mg/Kg). Each animal will then be intubated and receive inhalant isoflurane at 2.5%-4% for induction and 0.5-2.5% for maintenance of anesthesia, delivered through either a volume-regulated respirator or rebreathing apparatus. An intravenous sheath will be placed in a peripheral vessel or right internal jugular vein. Lactated Ringer's solution will be administered at 10 mL/Kg/hr for the duration of the surgical procedures (Implantation animals only).

Ultrasound and Other Transient Procedures: Animal will be sedated as described in the paragraph immediately above. Alternatively animals may be sedated using Telazol (2-5 mg/kg) 1M and anesthetized using inhalant isoflurane Of needed) delivered through a cone. At the discretion of the Veterinarian or Surgeon animal may be intubated.

Duration/Frequency of the Procedure: Throughout each day of in-life procedures or surgery Procedure Performance: Anesthesia will be performed by a DaVINCI surgeon and assisted by trained technicians in DaVINCEs surgery room.

Procedural Records: Data will be recorded on DaVINCI Animal Surgery Forms.

Surgical Preparation:

Procedure Description: For all animals (on biopsy and implantation day), the hair will be clipped from 3 inches above the xiphoid to pubic symphysis. The animal will then be positioned in dorsal recumbency. The operative area(s) will then be cleaned with three alternating scrubs of povidone-iodine solution and 70% alcohol; once the alternating scrubs are complete, a final application of povidone-iodine solution will be applied and allowed to dry. The area(s) will be draped for aseptic surgery.

Duration/Frequency of the Procedure: Prior to Biopsy and prior to surgery. Surgical preparation will require approximately 30 minutes for each event.

Urine Sample Collection and Analysis:

Procedure Description: Two urine samples at pre-biopsy and pre-necropsy will be collected by catheterization or test tube caught method.

Urine sample of approximately 3.0 int volume (~1 mL for quantitative and 2 int qualitative testing) will be collected in a sterile container for qualitative analysis.

Smaller amounts may be sufficient for analysis; however, if urine collection is difficult the quantitative sample takes precedent over the qualitative sample. The collected urine will be decanted into 5 in L sterile tubes, refrigerated and shipped 24 hrs of collection.

Qualitative urinalysis: 0.5 mL of urine will be analyzed at DaVINCI on the day of collection. The qualitative measurement will be taken at time of collection using Multistixe 10 SG Test Strips.

Quantitative urinalysis: 1 mL or greater will be decanted into 5 mL sterile tubes, refrigerated and shipped in a cooler with an ice pack within 24 hrs of collection. Parameters of interest for both the qualitative and quantitative measurements include: Qualitative urinalysis: test strip-Glucose, Bilirubin, Ketones, Specific Gravity, Blood, pH, Protein, Urobilinogen, Nitrites and Leukocytes.

Quantitative urinalysis: qualitative amount of Bacteria, Glucose and total protein. Additional parameters may be requested at the discretion of the Facility Veterinarian. Specimens will be analyzed at AniLytics.

Duration/Frequency of the Procedure: Procedure lasts approximately 15 minutes per animal. Collection will be done pre-biopsy and prior to necropsy. Additional urine analyses may be performed to assess animal health at the discretion of the Facility Veterinarian and Study Director.

Procedure Performance: Urine collection procedures will be conducted by trained technicians.

Procedural Records: Collection information and qualitative results will be transcribed onto a DaVINCI prepared form. Quantitative urine results will be reported in hardcopy by analytical laboratory and filed with study raw data.

Blood Collection.

Hematology, Coagulation, Serum Chemistry, Blood Gases.

Hematology: Hematology samples will be collected in 2.0 ml EDTA tubes, and stored on wet ice or refrigerated (2-8° C.). Samples will be labeled and analysis will be performed within 24 hrs of collection. Blood samples will be evaluated for the parameters specified below: Total leukocyte count (WBC); Erythrocyte count (RBC); Hemoglobin concentration (HGB); Hematocrit value (HCT) 1; Mean corpuscular volume (MCV); Mean corpuscular hemoglobin (MCH) 1; Mean corpuscular hemoglobin concentration (MCHC) 1; Platelet count (PLT), wherein 1=Calculated values.

Coagulation.: A total of 1.8 mL blood will be collected into 1.8 mL sodium citrate tubes (0.2 mL of 3.8% sodium citrate). Citrated blood samples will be kept on ice until ready to be centrifuged at 1,000 to 1300×g for 10 to 15 minutes. Before freezing, divide plasma in 1/2 and freeze at −70° C. Citrated plasma samples need to be stored at −70° C. Samples will be evaluated for the following parameters: Prothrombin time (PT); Activated partial thromboplastin time (APTT); and Fibrinogen (FIB).

Serum Chemistry: Samples for Serum Chemistry will be collected in approximately 4.0 ml serum separation tubes. The blood samples will be centrifuged (1300-1600 zg for 10-15 minutes) and the serum extracted using sterile technique. Serum will then be frozen at −70° C. Samples were evaluated for the following serum chemistry parameters: Glucose (GLU); Urea nitrogen (BUN); Creatinine (CRE); Total protein (TPR); Albumin (ALB); Globulin (GLOB) 1; Albumin/Globulin ratio (A/G) 1; Calcium (CAL); Phosphorus (PHOS); Sodium (NA); Potassium (K); Chloride (CL); Total cholesterol (CHOL); Total bilirubin (TBIL); Triglycerides (TRG); Alanine aminotransferase (ALT); Aspartate aminotransferase (AST); Alkaline phosphatase (ALK); Gamma glutamyltransferase (GGT); where 1=Calculated values.

Blood Gases: Blood Gas/Spun Hematocrit/Total Protein Monitoring: Arterial blood samples (~1.0 mL) will be collected and analyzed using a calibrated i-STAT analyzer and the appropriate cartridge. Samples will be evaluated for the following blood gas parameters: Sodium (Na) (mmol/L) PCO2 (mm Hg); Potassium (K) (mmol/L) PO2 (mm Hg); Ionized Calcium (iCa) (mmol/L) TCO2 (mmol/L); Glucose (Glu) (mg/dL) HCO3 (mmol/L); Hematocrit (Hct) (%) BEecf (mmol/L); pH; and SO2 (%). Duration/Frequency of the Procedure. Collection of blood samples fore CBC, Clinical Chemistry and Coagulation will be conducted pre-biopsy, weeks 4 & 8 and pre-necropsy. Blood gases will be collected pre-biopsy. Each blood collection procedure lasts approximately 15 minutes per animal.

Vital Signs Monitoring Procedure:

Procedure Description: The following vitals will be monitored during implant surgery: animal will be monitored approximately every 20 minute for oxygen rate, SaO2, Pulse rate, Respiration, and body temperature.

Duration/Frequency of the Procedure: At approximately 20 minute intervals throughout the surgical procedure.

Procedure Performance: Vital signs monitoring procedures will be conducted by trained technicians in DaVINCI's surgery room.

Blood Collection, Adipose Tissue Collection and Bladder Tissue Collection for Cell Culture:

Procedure Description: Blood Collection (Group 2 & 3): Approximately 8×10 ml aliquots of venous blood collected from sixteen (16) animals (8M, 8F) in heparinized vacutainers. The blood will be packaged in the sponsor supplied shipper and shipped overnight to the Sponsor for processing. Adipose Tissue Collection (Group 2 & 3): To access the Adipose Tissue and the Bladder a midline incision will be made in the abdomen beginning immediately caudal to the umbilicus. From the same 16 animals that blood was collected, subcutaneous adipose tissue will be aseptically collected from the abdomen, corresponding to approximately 25-50 grams of tissue. The biopsy tissue will be immediately preserved aseptically in sponsor supplied jars containing tissue culture media and then packaged according to section 14.8 and shipped overnight to the Sponsor for processing.

Bladder Tissue Collection (Group 1): In the remaining four (4) animals, the urinary bladder will be exposed and emptied of urine. One apical dome piece (~2.5×2.5 cm) of urinary bladder tissue will be excised from the bladder. The urinary bladder tissue will be immediately preserved aseptically in the tissue culture media supplied by the Sponsor and then packaged according to section 14.8. The defect in the bladder will then be closed utilizing an appropriate technique, using absorbable suture material.

The abdominal incision will be closed in layers with absorbable suture material of an appropriate size. The skin will be closed in a subcuticular fashion, again using an appropriate size of absorbable suture material.

Duration/Frequency of the Procedure: Once per source animal lasting approximately 1 hour per animal.

Procedure Performance: Biopsy collection and preservation will be performed. The blood may be collected either in animal cage area or surgical suite as aseptic as possible.

Ureteral transposition through conduit with cystectomy:

Procedure Description Summary: The ureteral transposition procedure will be performed via laparotomy. A midline incision will be made in the abdomen beginning 5 cm cranial to the umbilicus extending approximately 15 cm caudal. The peritoneum will be identified, carefully separated from the abdominal space until the tissue is long enough to cover the Neo-urinary Conduit Construct and form a conduit that can exit through the body wall. The peritoneum will be measured and cut in order to wrap the construct and form a conduit that will extend out of the body wall. The peritoneum will be sutured around the construct with 3-0 Vicryl. Care will be taken to ensure the tissue remains intact and vascularized. The urinary bladder will then be exposed and emptied of urine taking care to avoid urine from entering into the abdominal cavity. The arteries and veins supplying the bladder will be identified and ligated. The ureters will be identified, two 7Fr 14 cm non-absorbable ureteral stents (DaVinci made) will be inserted in ascending fashion and the ureters will be carefully transected from the bladder. The urethra will be over sewn as it is transected. The bladder will then be removed. The left ureter will be carefully freed from the surrounding retroperitoneal fascia extending cranially until there is enough mobility to reach the right side. The right ureter will be dissected free to reach the end of the construct. The ureters will be sutured on to the construct with 3-0 Vicryl in a simple continuous pattern. A stoma will be created on the ventral abdominal wall lateral to the mammary glands. The peritoneal conduit will be exteriorized and sutured to the skin. Surgical adhesive will be placed along the suture line and where the peritoneum exits the body wall. The suture strands that are connected to the stents will be exteriorized through the stoma for future removal, and a DaVINCI made stoma button/catheter of appropriate length will be inserted into the stoma allowing adequate drainage for the duration of the survival period. Once secured, the abdominal incision will be closed with nonabsorbable Prolene suture. The skin will be closed in a routine fashion. The animal will then be recovered in animal's cage. NOTE: The peritoneum must be handled and manipulated with great care to prevent staunching blood flow through the vasculature. The ureteral non-degradable stents will be left in place for approximately 7 days unless diagnostic evaluations reveal a need to remove them prematurely (e.g., renal obstruction).

Duration/Frequency of the Procedure: Once per animal lasting approximately 2-4 hours per animal on Day 0.

Stoma Button Care and Maintenance & Incision Site Assessment

Procedure Description:

Stoma Button/Catheter (Foley or Equivalent): After the definitive surgery, the stoma catheter (DaVINCI generated stoma button or equivalent: 3-10 cm based on needed at various timepoints) will be reinserted and secured to the animal with sutures. Stoma button will be kept in place for the duration of the study. The catheter will be flushed with sterile saline when it is not dripping to assure patency. Note: Between days 7 and 21, scaffold material undergoes degradation and particulates (protein-associated) start to be shed in the urine. This may cause obstruction of the stoma button and retention of urine volume above or beyond the construct's capacity. Therefore, debridement of the stoma and or neo-conduit will be conducted as necessary.

Incision Site Assessment: The incision site will be evaluated daily for the initial 14 days or until healed. The stoma area and surrounding tissue will be cleaned twice a day. Stoma will be observed for urine drainage, incision site will be evaluated for dehiscence, abnormal discharge, odor, irritation or any abnormalities.

Stagnant stoma tissue debridement procedure: Animals with stagnant tissue within the stoma/conduit will undergo a debridement procedure Animal will be sedated according to protocol. A small incision may be made on the stoma to facilitate insertion of forceps for debridement. The stagnant issue will be visually identified and grasped with forceps and gently tugged. Once all stagnant tissue is removed, the stoma/conduit may be flushed with saline solution. The incision will be closed with a suture(s) and the stoma button will be reinserted and secured to the animal with sutures Animal will be recovered in individual cage.

Duration/Frequency of the Procedure: Following surgical procedure as follows: Stoma Button: Daily observations followed by maintenance as needed when catheter is observed not dripping. Time required for approximately 15 minutes. Incision Site Assessment: Daily for the initial 14 days or until healed and/or at the discretion of the Facility Veterinarian. Time required for approximately 15 minutes. 14.11.3 Procedure Performance: Catheter care and incision site assessment will be performed by either the Facility Veterinarian or trained technicians.

Clinical Observations:

Procedure Description: Recovery: Immediately following completion of each surgery, animal will be allowed to recover from anesthesia and transferred to the home cage. Clinical Observations Post-Implantation for a 4 Week Period: Postimplantation, individual animal evaluations of food intake and fecaUurine output will be conducted daily for 5 days per week (i.e., Monday Friday) post implantation for 4 weeks. Observation period may be extended at the discretion of the Facility Veterinarian and/or the Study Director. Survival: Post-implantation/reimplant surgery recovery animals will be survived for a period of 84+/−5 days.

Duration/Frequency of the Procedure: Recovery: will be performed at the end of any surgical procedure, approximately 1 hour. Clinical observations 5 days Post-implantation/reimplant surgery: Clinical observations will be conducted daily for 5 days per week.

Daily Animal Health Assessment: will be performed twice per day, approximately 8 hours apart for approximately 10 minutes for the duration of the study from quarantine to necropsy.

Pyelogram and ultrasound:

Procedure Description:

Pyelogram will be performed through a peripheral vein, or alternately via femoral artery catheterization under fluoroscopy injection of contrast directly into the renal artery. Ultrasound will be performed under general anesthesia on kidneys and Neo-urinary Conduit.

Duration/Frequency of the Procedure:

Pyelogram: Pre-necropsy. Procedures last approximately 30 minutes per animal. Ultrasound: Pre-biopsy (kidneys), week 4, 8 and pre-necropsy (kidneys and Neo-urinary Conduit). At the discretion of the Study Director and the Attending Veterinarian, additional ultrasound imaging may be obtained at other timepoints as needed to assess the animal's clinical health.

Animal Sacrifice and Necropsy.

Procedure Description:

Unscheduled Necropsy—Any animal found dead, moribund or undergoing an unscheduled euthanasia will be subjected to a limited necropsy. The exploratory necropsy will attempt to determine any potential cause(s) of death or issues leading to euthanasia. Tissue collection will be limited to the urogenital system. Microscopic analysis of the tissue will be decided through a joint discussion between Study Director and Sponsor Representative. Unscheduled and Scheduled Euthanasia—All animals will be injected with sodium pentobarbital (150 mg/kg, IV) to cause euthanasia in accordance with accepted American Veterinary Medical Association (AVMA) guidelines. Scheduled euthanasia is to be at week 12 (day 84±5) postimplantation.

Physical Examination—All animals will be evaluated by the Facility Veterinarian prior to euthanasia. The examination will include recording the general condition of the animal: rectal body temperature, respiratory rate, heart rate, and capillary refill time. Necropsy—All animals will be subjected to necropsy. There will be a specific focus on the kidneys, conduit, ureters, uretero-vesical junctions, midconduit, conduit-skin junction, and lymph nodes (lumbar and mesenteric). Gross evaluation will be performed on the kidneys, ureters, urethra (if present), conduit, stoma, thoracic, abdominal & pelvic cavities and their organs and tissues. If any gross lesions, adhesions and/or organ changes (including reproductive) are observed, they will be evaluated, photographed and collected for histopathological assessment. Major organs of the abdominal cavity will be collected and saved for possible future microscopic analysis. The major organs are the liver, spleen, pancreas, large intestine (cecum, colon, and rectum), small intestine (duodenum, jejunum and ileum) and the stomach (cardia, fundic and pyloric). The complete neo-urinary conduit area will be visualized and photographed in situ. Additional photographs and/or gross lesion may be taken at the discretion of the prosector. Fixation of conduit will be done with formalin by infusion of formalin into the stoma and inflating the conduit and ureters. This will be done with Foley (or equivalent) catheter while the stoma is tied off to hold pressure. 14.15.2 Duration/Frequency of the Procedure: Single event duration of approximately ½ hr per animal on Day 84 (±5 days)

Histology/Pathology Laboratory

Procedure Description: The fixed urinary organs (i.e., implanted neoconduit, kidneys, and associated tissues) will be collected, trimmed, examined, embedded in paraffin, and sectioned. Slides will be stained with hematoxylin and eosin (H & E) and Masson's Trichrome (elastin).

Example 10

Formation of a Conduit Having an Epithelialized Mucosa

Following the Example 9 protocols above, animals were implanted with a NUC scaffold seeded with adipose-, peripheral blood-, or bladder-derived smooth muscle cells.

Post-operative clinical observations were similar across all three treatment groups. All animals in all groups had urine flowing from the stoma immediately following post-operative procedures. All animals in all groups were clinically normal by one month. All animals in all groups required stoma button maintenance and debridement to maintain urine flow from stoma. Serum markers of renal function (blood urea nitrogen [BUN] and serum creatinine) were similar at baseline across all treatment groups. At week 4, the values increased for all groups (data not shown). Hematology indicators of inflammation and/or safety concerns (total white blood cells and fibrinogen) were simiar at baseline across all treatment groups. At week 4, the values increased for all animals (data not shown).

Figure 74:
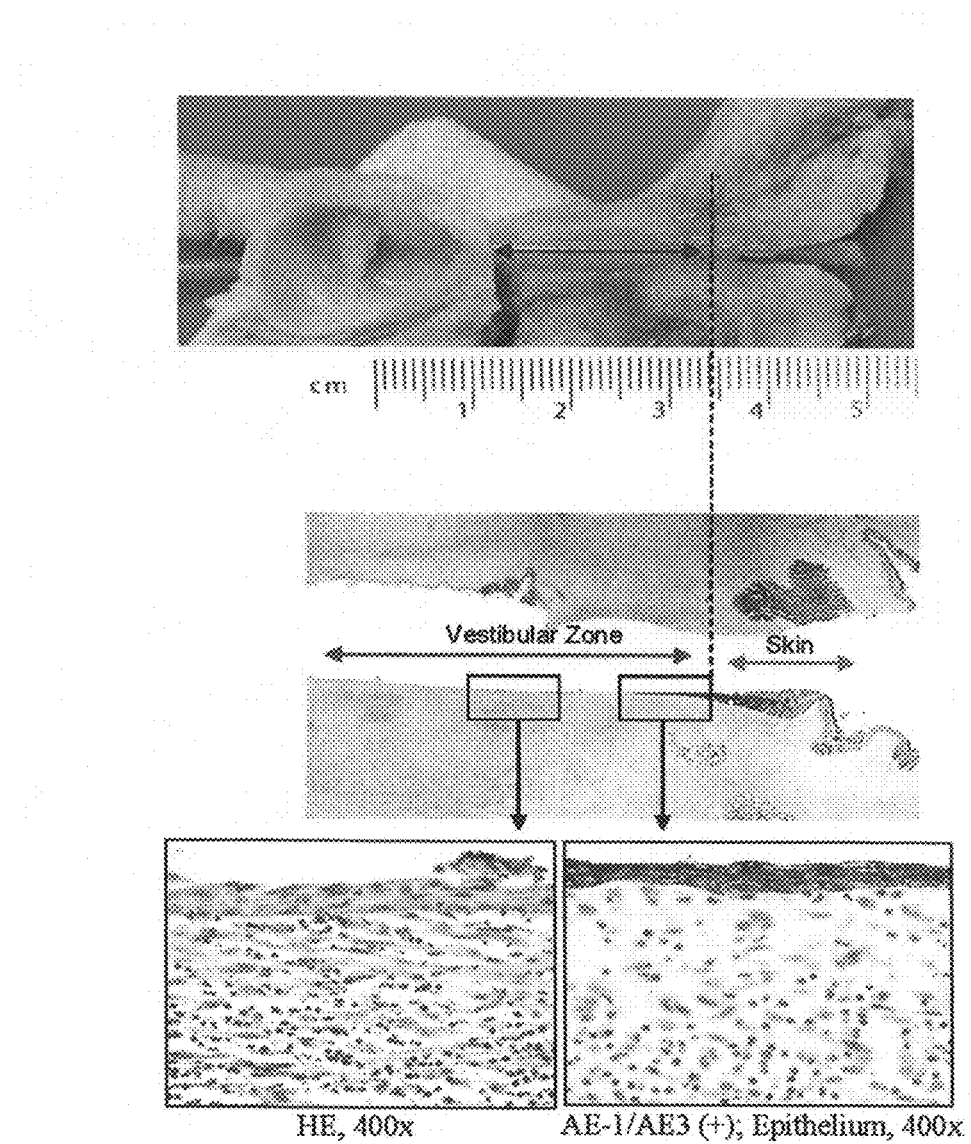
FIG. 74 shows the presence of an epithelizlized mucosa in an animal implanted with a urinary diversion construct.

Following necropsy, the fixed urinary organ (i.e., implanted neoconduit, kidneys, and associated tissues) was collected, trimmed, examined, embedded in paraffin, and sectioned. Slides were stained with hematoxylin and eosin (H & E) and Masson's Trichrome (elastin). The conduits formed in the animals were examined and found to be characterized by an epithelialized mucosa at the stomal end. As shown in FIG. 74, the epithelialized mucosa is located at the stomal end (Neo-urinary conduit seeded with adipose-derived SMC). AE-1/AE-3 was used to detect cytokeratin markers as an indicator of epithelium.

Example 11

Neo-bladder Augmentation Constructs after Trigone-sparing Cystectomy

The neo-bladder constructs of this study will be formed from a biodegradable scaffold on which a subject's own organ specific cells are grown. The goal is to construct a new urinary bladder for the subject that can be implanted in place of the diseased one, alleviating the need for creation of a "cloaca". The objective of this study is to determine the equivalency of neo-bladder constructs for urinary bladder augmentation.

Experimental design. Each of the 6 groups of canines will include 3 females and 3 males in which different densities of urothelial cells (UCs) and smooth muscle cells (SMCs) will be tested. Bladder augment scaffolds will be seeded with cells as follows.

| Group | Description | Cell source |
|---|---|---|
| 1 | $10 \times 10^6$ UC and $10 \times 10^6$ SMC | Bladder |
| 2 | $0.1 \times 10^6$ UC and $20 \times 10^6$ SMC | Bladder |
| 3 | $0.01 \times 10^6$ UC and $20 \times 10^6$ SMC | Bladder |
| 4 | 0 UC and $20 \times 10^6$ SMC | Bladder |
| 5 | 0 UC and $20 \times 10^6$ SMC | Blood |
| 6 | 0 UC and $20 \times 10^6$ SMC | Adipose tissue |

Tissue biopsy procedures. Groups 1-4 use SMCs and UCs derived from the bladder biopsy. Prior to the date or while the animal is anesthetized for the bladder biopsy procedure, each animal will be prepared for aseptic blood collection from a peripheral vessel and approximately 60 mL of venous blood will be aseptically collected (six 10 mL blood tubes with sodium heparin). Once the midline incision for urinary bladder biopsy is made in the abdomen, adipose tissue will be exposed and excised. The amount of adipose tissue collected aseptically from the abdomen will correspond to approximately 20-50 grams of tissue. If it is determined that there is not a sufficient amount of tissue collected, an incision will be made over the inguinal fat pad and subcutaneous tissues dissected to obtain adipose tissue. The urinary bladder will be exposed, and the bladder will be emptied of urine, should any be present. One, approximately 2 cm×1 cm piece of urinary bladder will then be excised from the apex of the bladder.

Surgical procedure (day 1)—a trigone-sparing cystectomy is performed followed by implantation of a neo-bladder construct. Postoperative procedure—cycling, compliance measurement, fluoroscopic examination, general health assessment, and clinical treatment are performed as necessary.

Necropsy time point—approximately 6 months after implantation (182±2 days from implantation).

Animals. The species *Canis familiaris* (strain—mongrel dog) is used. 12 males (plus one alternate) are used. 12 females (plus one alternative), which are nulliparous and nonpregnant are used. Animals are young adults at the biopsy stage and weigh between 15-25 kg.

Preoperative Procedures.

Analgesia and Anesthesia. Before induction of anesthesia the animal will be premedicated with atropine $SO_4$. (0.04 mg/kg, subcutaneously [SC]), buprenorphine (0.01 mg/kg, SC), and meloxicam (0.2 mg/kg, SC). An intravenous catheter will be placed in a peripheral vessel and at least 10 minutes after administering atropine, the animals will be anesthetized with Propofol® (4-10 mg/kg, intravenously [IV]). The animal will then be intubated and maintained in anesthesia with isoflurane inhalant anesthetic, delivered to effect through a volume-regulated ventilator. Lactated Ringer's solution will be administered during the procedure at a rate of approximately 5-20 mL/kg/hr. Each animal will receive a bupivacaine line block at the site of the abdominal incision (≤2 mg/kg, SC).

Antibiotic Therapy. To help prevent infection, the animals will be given cefotaxime (50 mg/kg, IV) immediately before the biopsy procedure. Additional doses may be administered as necessary. At the time of the definitive operation (Day 1), the animals will be given cefotaxime (50 mg/kg, IV) immediately before surgery and at its completion.

Animal Preparation. Lacrilube® (or other suitable ocular lubricant) will be applied to both eyes. Animals will be kept warm throughout the preparation and the surgical procedures. Hair will be clipped from the entire ventral abdomen. The surgical site will be prepared for aseptic surgery by first wiping the area with povidone-iodine scrub solution to remove all detritus, followed by wiping the area with sponges that have been soaked in 70% isopropyl alcohol. The area will then be allowed to dry. The animal will be taken to the operating room and placed in dorsal recumbency. A temperature probe will be inserted into the esophagus in order to monitor core temperature. At the time of biopsy surgery, the urinary bladder will be catheterized with a dual lumen catheter (or equivalent) to obtain a baseline compliance measurement. The catheter will be removed from the animals after the measurement. At the time of definitive surgery, the urinary bladder will be catheterized with a Foley catheter. Before both procedures, the surgical sites will again be washed thoroughly with povidone-iodine scrub solution, wiped with sponges that have been soaked in 70% isopropyl alcohol, and then allowed to dry. DuraPrep™ (or similar) solution will be applied to the area and also allowed to dry. The area will then be appropriately draped for strict aseptic surgery.

Surgical Procedures

Urinary Bladder Biopsy. A midline incision will be made in the abdomen, beginning immediately caudal to the umbilicus. The urinary bladder will be exposed, and the bladder will be emptied of urine, should any be present. One, approximately 2 cm×1 cm piece of urinary bladder will then be excised from the apex of the bladder. The urinary bladder tissue will be preserved in tissue culture media (DMEM or equivalent). The defect in the bladder will be closed in at least 2 layers, using absorbable suture material (PDS or equivalent). Alternatively, the bladder will be closed with surgical staples, oversewn with suture (PDS or equivalent). The abdominal incision will be closed in layers with absorbable suture material of an appropriate size. The skin will be closed in a subcuticular fashion, again using an appropriate size of absorbable suture material. Alternatively, the skin may be closed with staples.

Neo-bladder augment construct implantation. Neo-bladder augment scaffolds are seeded with UCs and/or SMCs as described above to form neo-bladder augment constructs for implantation. A midline incision will be made in the abdomen, beginning immediately caudal to the umbilicus. A self-retaining abdominal retractor may be placed to open the incision. The urinary bladder will be exposed, and the bladder will be emptied of urine, should any be present. The area of the trigone will be identified, and the urinary bladder will be resected in toto but leaving the trigone and ureteral valves intact. A catheter will then be advanced into what will be the construct's lumen by passing it through a submucosal/subserosal tunnel in the trigone region. This catheter will then be secured to the bladder serosa with the appropriate suture material, and will be brought to the outside of the animal by tunneling it through the abdominal musculature, subcutaneous tissues and skin, exiting near the umbilicus.

The construct will be anastomosed to the normal urinary bladder tissue using a series of suture patterns to be determined at the actual time of surgery with polyglactin 910 suture material. The lateral margins (both right and left) of the anastomotic site will be marked with a nonabsorbable suture to aid in identifying the anastomotic line at the time of necropsy. The omentum will be pulled over the bladder construct and secured with surgical adhesive.

The abdominal incision will be closed in layers with absorbable suture material of an appropriate size. The skin will be closed in a subcuticular fashion, again using an appropriate size of absorbable suture material. Alternatively, the skin may be closed with staples. The Foley catheter will be left in place to facilitate postoperative urine collection after the urinary bladder augmentation procedure with the test device.

Incision Site Observations. The surgical incision(s) will be observed and assessed at least once daily for at least 14 days (or until healed) for signs of infection, inflammation, and general integrity after surgery. Skin staples (if used) may be removed between 7 and 21 days after surgery. Appropriate therapy will be initiated as necessary.

Postoperative Urine Collection. After the definitive surgery, urine will be collected from the catheters until they are removed. All catheters will be connected to negative pressure reservoirs to collect urine from the animals. The reservoirs will be emptied as needed and the volume will be recorded. The reservoirs will be appropriately attached to the animal using a canine jacket, or equivalent, to prevent its disruption. The dogs may wear an Elizabethan or similar collar until adequately healed and continence has been achieved.

In the females, the perineal area, vulva, and vagina will be cleaned twice a day, and the vagina will be aseptically infused with antibiotic cream twice a day. The preputial area in the males will be similarly cleaned. In addition, the exit sites for the remaining catheters will be examined and cleaned at least twice daily. Catheters will be flushed as needed. If required, due to the suspected presence of urine in the peritoneal cavity, peritoneal lavage may be performed.

Appropriate measures to prevent disruption of the catheters and urine leakage will be performed during this period. The indwelling urethral catheter (ie, Foley) may be removed within approximately 7 days of placement. The suprapubic/subserosal/percutaneous catheter will be removed approximately 14-21 days after surgery. Once the Foley and suprapubic catheters have been removed, urine may be collected by catheterization or by a "pan caught" method.

Compliance Measurement. Before the biopsy procedure, monthly beginning approximately 30±3 days after implantation, and on the day of necropsy, a compliance measurement will be obtained. The urinary bladder will be catheterized with a dual-lumen catheter. All residual urine will be removed and the catheter size and placement length will be recorded to assure consistency for follow-up procedures. One lumen will be connected to the direct pressure cable and the other lumen will be used to infuse sterile saline (warmed by incubator) at a rate of 10-25 mL/min. The starting pressure of 0-10 mmHg will be achieved and recorded along with the start time. Time, volume delivered, and the pressure obtained will be recorded at the time leakage is observed around the catheter (aka leak point). The total infused amount of saline will then be aspirated to empty the bladder (either completely or partially depending on if cycling or fluoroscopic imaging follows) and the volume recovered will be recorded Animals will be tranquilized as outlined in Section 13.7. If a leak pressure of zero is obtained, the measurements will be repeated at least once, but not more than 3 times.

Cycling. Cycling will be performed every 2 weeks (14±2 day intervals) starting approximately 1 month after implantation and continuing until approximately Day 90. Cycling will be completed after compliance measurement and before fluoroscopic imaging. Cycling will be performed by re-inflating the bladder with sterile saline (warmed by incubator) after the completion of compliance measurement at a rate of 10-25 mL/min. The cycling will be repeated at least 5-10 times. The starting pressure of 0-10 mmHg will be achieved and recorded along with the start time. Time, volume of isotonic solution delivered, and the pressure obtained will be recorded for each cycle at the time leakage is observed around the catheter (aka leak point), or when the volume delivered is equal to that of the compliance measurement just performed, whichever comes first.

Fluoroscopic Imaging. Fluoroscopic imaging will be performed once monthly beginning approximately 30±3 days after implantation and on the day of necropsy. The fluoroscopic imaging will be conducted by infusing contrast media into the bladder and recording it. Fluoroscopic imaging will be performed after the completion of the compliance measurement or cycling (as appropriate to time point). Approximately half of the total infused saline will be aspirated and replaced with a 50/50 mixture of sterile saline (warmed by incubator) and a contrast media to inflate to the most recent leak volume of the bladder. Fluoroscopic imaging will be performed throughout the infusion of the 50/50 mixture. The volume used for the cystogram will be that volume at which the leak-point pressure was obtained.

In-life observations and measurements.

Moribundity/Mortality Check. Moribundity/mortality checks will be performed twice daily (AM and PM). All animals will be checked for general health, mortality, and moribundity.

Clinical Observations. After the biopsy procedure, clinical observations will be performed at least once weekly. After the implantation, clinical observations will be performed at least twice daily (at least 6 hours apart) for the first 2 weeks and then daily until Day 30. Clinical observations will be continued at least once weekly (7±1 day) thereafter. All animals will be observed; observations will be recorded.

Body Weights. Body weights will be recorded before animal assignment, within 5 days before the biopsy procedure, within 5 days before implantation, weekly thereafter (7±1 day) for the first 3 months (ie, until Day 90), and then monthly (intervals of 30±2 days) until necropsy.

Physical Examinations. A physical examination, including a record of general condition, rectal body temperature, respiratory rate, heart rate, and capillary refill time, will be performed for each animal before entry into the study and before necropsy.

Concurrent Therapy. In accordance with accepted veterinary practices, the animals may be administered concurrent therapy (such as antibiotics or fluid therapy) as required to maintain general good health of the animals. Concurrent therapy will be administered as necessary.

Sample Collection.

Blood. Blood will be collected from a peripheral vessel. Blood volumes represent whole blood and are approximate amounts. The following Blood Sample Collection Schedule will be followed.

| Time Point | Hematology | Serum Chemistry | Coagulation |
|---|---|---|---|
| Before biopsy and implantation (before Day 1) | X | X | X |
| Once weekly for first month after implantation (7 ± 1 day intervals), every 2 weeks thereafter (14 ± 2 day intervals), and on the day of necropsy | X | X | X |
| Volume of Whole Blood | 0.75 mL | 1.1 mL | 1.3 mL |
| Anticoagulant | EDTA | None | Sodium Citrate |

Urine. Urine samples will be collected via the Foley catheter (while it is indwelling), by catheterization after the Foley catheter has been removed, or by "pan caught" method. After collection, samples will be transferred to the appropriate laboratory for processing and analysis. The following Urine Sample Collection Schedule will be followed.

| Time Point | Urine |
|---|---|
| Before biopsy and before implantation (Day 1) | X |
| Once weekly for first month after implantation (7 ± 1 day intervals), every 2 weeks thereafter (14 ± 2 day intervals), and on the day of necropsy | X |
| Volume of Urine | 3.0 mL |
| Anticoagulant | None |

Clinical Pathology

Hematology. Blood samples will be evaluated for the following parameters: Red blood cell count; Hemoglobin concentration; Hematocrit; Mean corpuscular volume; Mean corpuscular hemoglobin concentration; Mean corpuscular hemoglobin; Reticulocyte count; Red blood cell morphology; Platelet count; Platelet morphology; White blood cell count; Neutrophil count; Lymphocyte count; Monocyte count; Eosinophil count; Basophil count; Other cells (as appropriate)

Coagulation. The blood samples will be centrifuged, the plasma will be extracted, and the plasma samples will be evaluated for the following parameters: Coagulation Parameters; Activated partial thromboplastin time; Prothrombin time; Fibrinogen.

Serum Chemistry. The blood samples will be centrifuged, the serum will be extracted, and the serum samples will be evaluated for the following parameters: Serum Chemistry Parameters; Alanine aminotransferase; Aspartate aminotransferase; Alkaline phosphatase; Gamma-glutamyltransferase; Total bilirubin; Blood urea nitrogen (BUN); Creatinine; Calcium; Phosphorus; Total protein; Albumin;

Globulin; Albumin/globulin ratio; Glucose; Cholesterol; Triglycerides; Sodium; Potassium; Chloride.

Urinalysis. Urine samples will be evaluated for the following parameters: Volume; Color; Clarity; Specific gravity; Microscopic evaluation of urine sediment; Urine test strip analysis, including: pH, Protein, Glucose, Bilirubin, Ketones, Blood, Urobilinogen, Nitrites, Leukocytes.

Euthanasia. On the day of euthanasia, the animals will initially be tranquilized and the compliance measurement and fluoroscopic imaging will be performed. Euthanasia (deep anesthesia of sodium pentobarbital, 35-60 mg/kg, intravenously, to effect, followed by exsanguination) will then be performed.

Gross Necropsy. A complete gross necropsy will be conducted on all animals. The necropsy will include examination of the carcass and musculoskeletal system, all external surfaces and orifices, cranial cavity and external surface of the brain, and all thoracic, abdominal, and pelvic cavities with their associated organs and tissues. There will be specific focus on the urinary bladder.

Tissue Collection and Preservation. The abdominal cavity will be opened and the augmented urinary bladder will be visualized and photographed in situ. The complete bladder will then be removed (trigone, anastomotic site, and neo-bladder), the ureters ligated, and the urethra appropriately catheterized to allow it to be fixed under pressure, similar to those generated during compliance measurements, with the appropriate fixative (ie, 10% neutral buffered formalin [NBF]) for the methods of evaluation (histopathology). After fixation in 10% NBF for 21-48 hours, the tissues will be transferred to 70% ethanol. In addition, organs (or samples of organs) and tissues listed below will be examined in situ, dissected free, and fixed in 10% NBF or other suitable fixative.

The following tissues will be collected: Adrenal gland (paired); Animal identification (collect at necropsy to retain identification); Aorta; Bone marrow; sternum; Brain (cerebrum, cerebellum, brain stem); Cervix; Epididymis (paired); Esophagus; Eye (paired) (Fixed in Davidson's Solution); Gallbladder; Heart; Intestine, cecum; Intestine, colon; Intestine, duodenum; Intestine, ileum (with Peyer's patch); Intestine, jejunum; Intestine, rectum; Kidney (paired); Lacrimal gland (paired); Liver; Lung; Lymph node, mandibular; Lymph node, mesenteric; Lymph node, iliac; Mammary gland; Nerve, optic (paired) (Fixed in Davidson's Solution); Nerve, sciatic; Ovary (paired); Pancreas; Parathyroid gland Pituitary gland; Prostate gland; Salivary gland, mandibular (paired); Skeletal muscle; Skin; Spinal cord (cervical, thoracic, lumbar); Spleen; Stomach (cardiac, fundic, pyloric); Testis (paired) (Fixed in Modified Davidson's Solution); Thymus; Thyroid gland (paired); Tongue; Trachea; Uterus; Vagina; Gross lesions/masses (Fixed in Modified Davidson's Solution).

Histology. The fixed urinary neo-bladder will be cut in half creating a dorsal half and a ventral half (the ureters enter the bladder on the dorsal surface). The bladder will again be cut in half along a cranial/caudal line creating 4 quadrants of bladder tissue. From each quadrant of tissue, 3 samples of up to ~0.5-cm wide will be collected (full thickness). As an identification aid, samples will decrease in length from Sample 1 (longest) to Sample 3 (shortest). In addition, to aid in orientation of tissue, a nick incision will be made in the serosal/adventitial portion of the caudal end of each sample.

When the surgical interface is apparent, two samples (i.e., Samples 1 and 2) from each quadrant will be collected from areas that span the surgical interface of the native bladder and neo-bladder. These samples will come from the area just above where the ureter inserts into the bladder (outside not inside). A third sample (ie, Sample 3) from each quadrant will be collected from the area cranial to the surgical interface representing the urinary neo-bladder samples and may not span the surgical interface.

When surgical interface is not apparent, three samples will be collected in a linear fashion from caudal (i.e., trigone) to cranial (i.e., apex).

A total of 12 samples will be collected from each augmented urinary bladder. Tissue samples will be trimmed, embedded in paraffin, and sectioned for histology evaluation. Regardless of sectioning scheme, the 3 samples from each quadrant will be embedded in 1 block so that there should be 4 blocks per bladder. The tissue samples will be embedded in such a way that when they are sectioned, the sections go through all layers of the tissue rather than en face (such as the epithelium only).

Slides for histopathology will be stained with hematoxylin and eosin (H & E) and Masson's Trichrome (elastin).

In addition, the ureters, urethra, kidneys, representative trigone samples, and local lymph nodes will be trimmed, embedded in paraffin, and sectioned. Slides will be stained with H & E.

Bladder Wall Thickness. Quantitative measurements of the wall thickness of each section will be performed with intra- and inter-group comparisons assessed. Blinded measurements of the primary constituent parts of the bladder wall, the combined urothelium/lamina propria (Uro/LP), and the tunica muscularis (TM), will be performed manually using an ocular micrometer at 4× magnification and denoted as reticules. The reticules will then be converted to millimeters and the average thicknesses of the Uro/LP, TM, and total wall will be calculated. Those sections which had been interpreted as approximating anatomic normalcy (ie, 'anatomic') during the histologic grading phase will be assessed for comparative analysis. These measurements will then be used to compare the relative thickness of the 3 noted regions of the bladder (ie, the trigone, mid, and apical bladder regions) as well as assess the overall consistency of the total wall thickness and the ratio and percentage of the constituent parts thereof. All values will be presented in the form of averages.

Statistical analysis. Data will be presented as individual values by animal and summary values with calculated means and standard deviations. Statistical analysis will be performed on body weights, hematology, coagulation, and serum chemistry. To determine the appropriate statistical test, each data set will be subjected to a statistical decision tree using the SASS System. A minimum of 3 animals per sex per group per interval will be required for statistical analysis. The data will initially be tested for normality using the Shapiro-Wilk test followed by the Levene's test for homogeneity of variance. A $p<0.05$ level of significance will be required for either test to reject the assumptions. If both assumptions are fulfilled, a single-factor ANOVA will be applied, with animal grouping as the factor, utilizing a $p<0.05$ level of significance. If the parametric ANOVA is significant at $p<0.05$, Dunnett's test will be used to identify statistically significant differences between the control group and each test article-treated group at the 0.05 level of significance. If either of the parametric assumptions is not satisfied, then the Kruskal-Wallis nonparametric ANOVA procedure will be used to evaluate intergroup differences ($p\le0.05$). The Dunn's multiple comparison test will be applied if this ANOVA is significant, again utilizing a significance level of $p\le0.05$.

Example 12

Figure 76A:
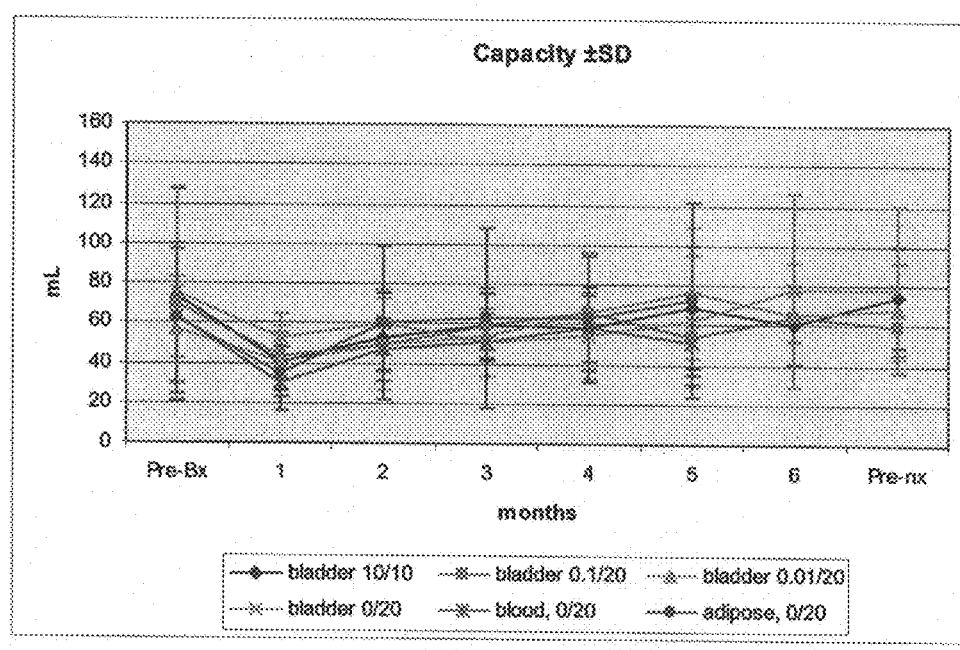
FIG. 76 shows the (A) capacity and (B) compliance of implanted neo-bladder constructs over time.
Figure 76B:
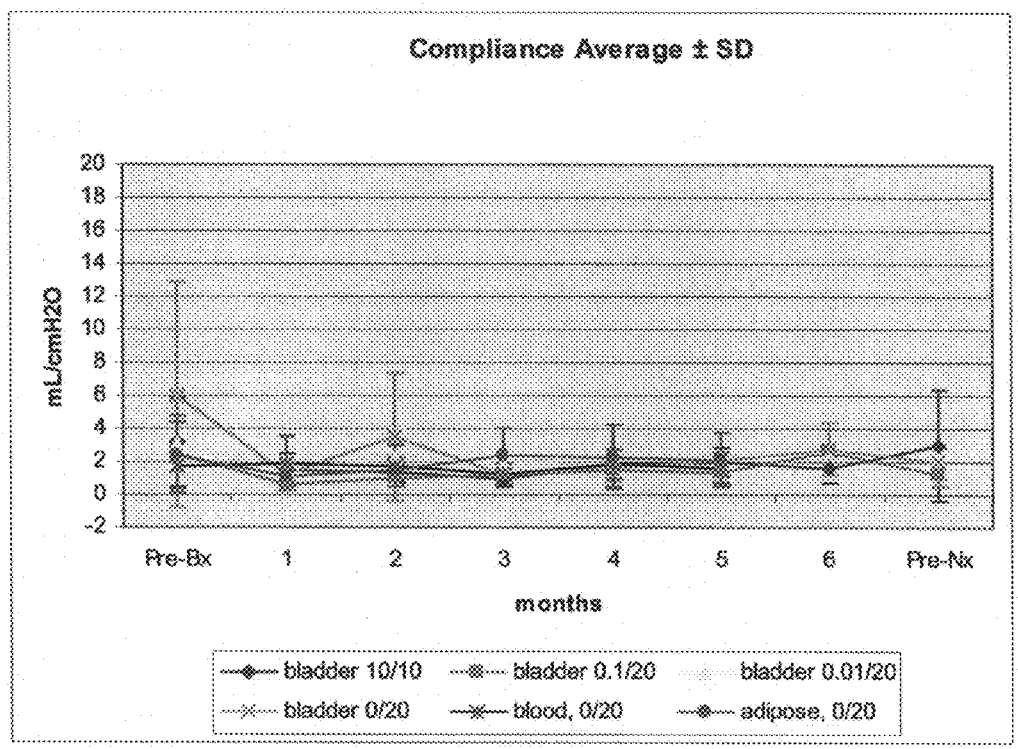

In Vivo Implantation of a Neo-bladder Augmentation Construct after Trigone-sparing Cystectomy Following implantation of neo-bladder augmentation constructs into canine subjects as described in the Example above, the implanted constructs were examined by fluoroscopic imaging, as well as for capacity and compliance. FIG. 75 shows cystograms for the implanted constructs at 4 months. A corresponds to a construct seeded with bladder-derived SMCs. B corresponds to a construct seeded with blood-derived SMCs; C corresponds to a construct seeded with adipose tissue-derived SMCs. D corresponds to native bladder baseline. FIG. 76 shows the (A) capacity and (B) compliance of the implanted neo-bladder constructs. All hematology and serum chemistries were found to be within normal limits for all bladder groups.

Figure 77:
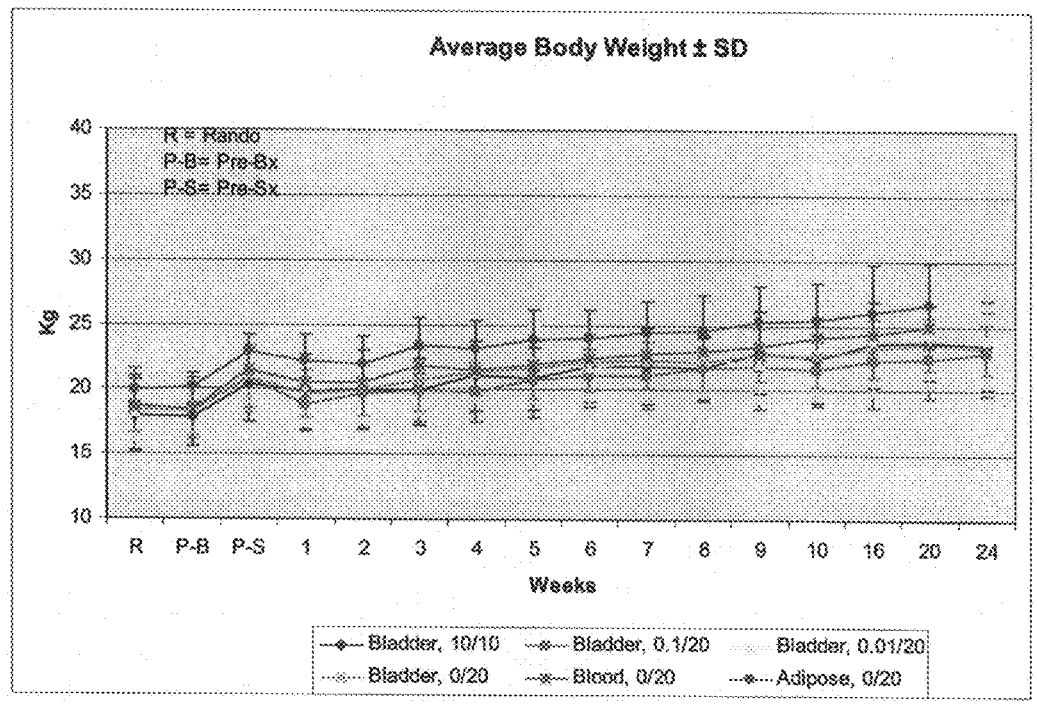
FIG. 77 shows the average body weight of the animals at greater than 4 months.
Figure 78:
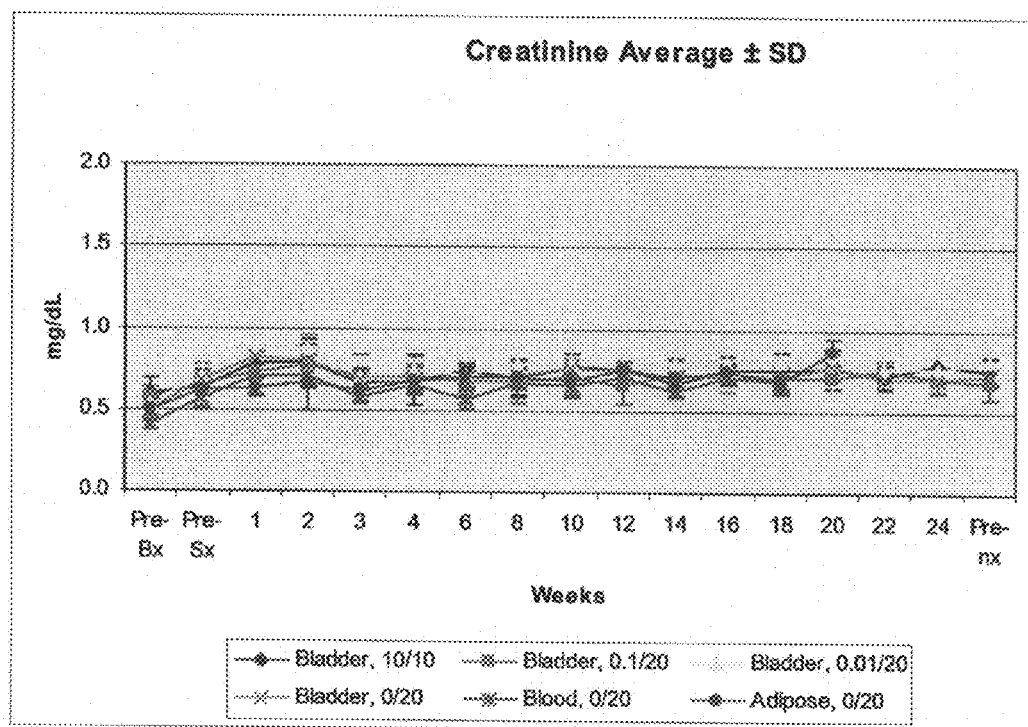
FIG. 78 shows the average serum creatinine of the animals at greater than 4 months.
Figure 79:
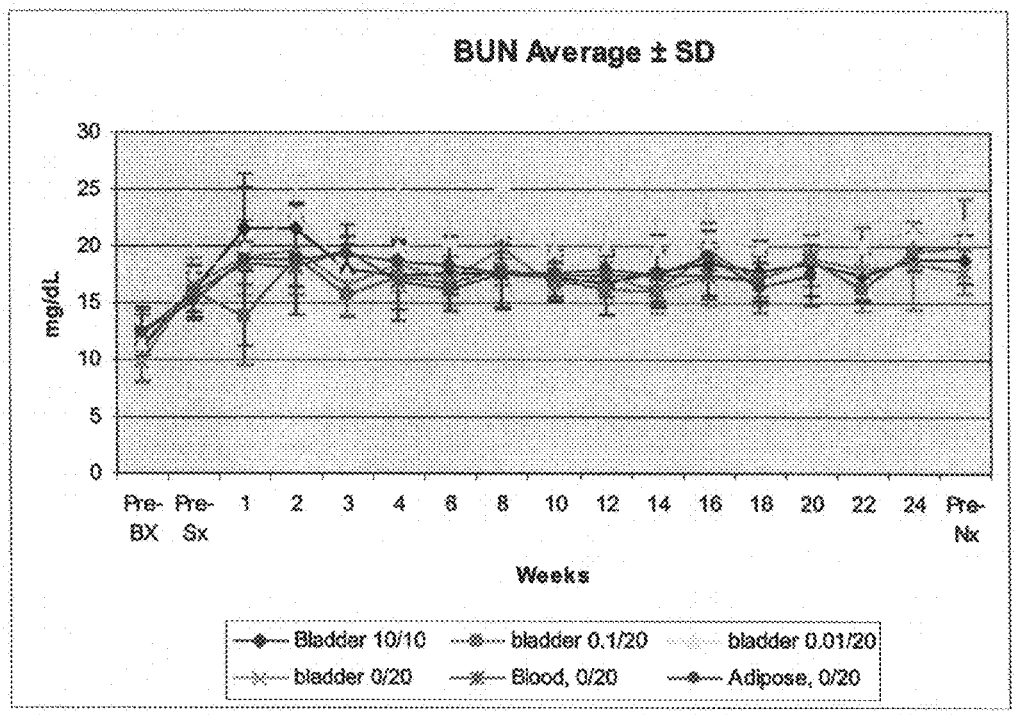
FIG. 79 shows the average BUN for the animals at greater than 4 months.
Figure 80:
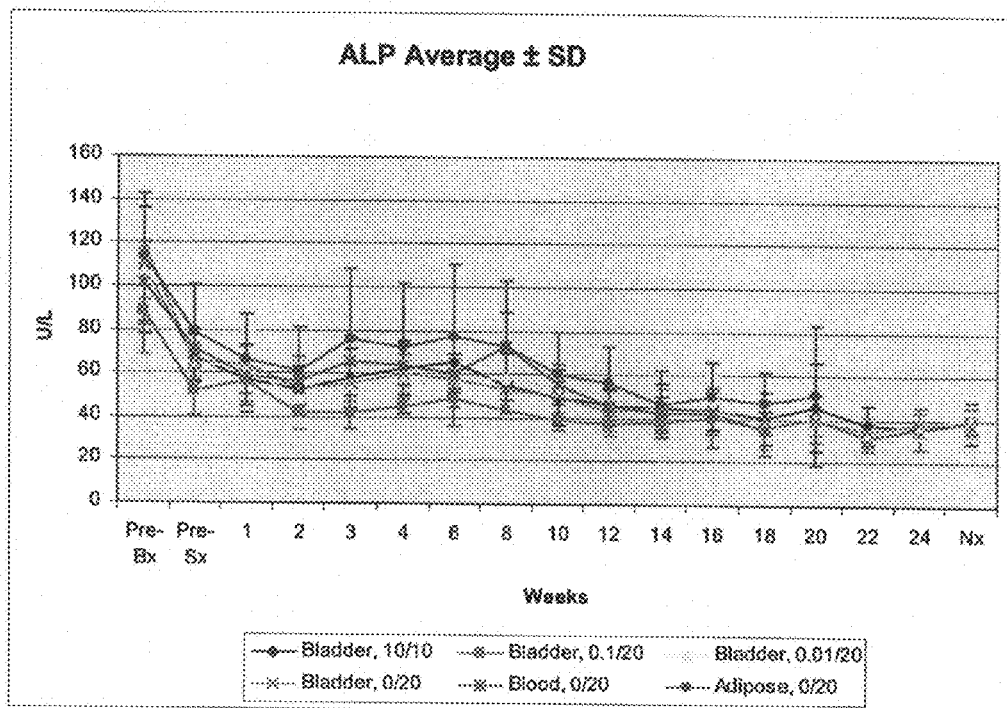
FIG. 80 shows the average alkaline phosphatase (ALP) for the animals at greater than 4 months.
Figure 81:
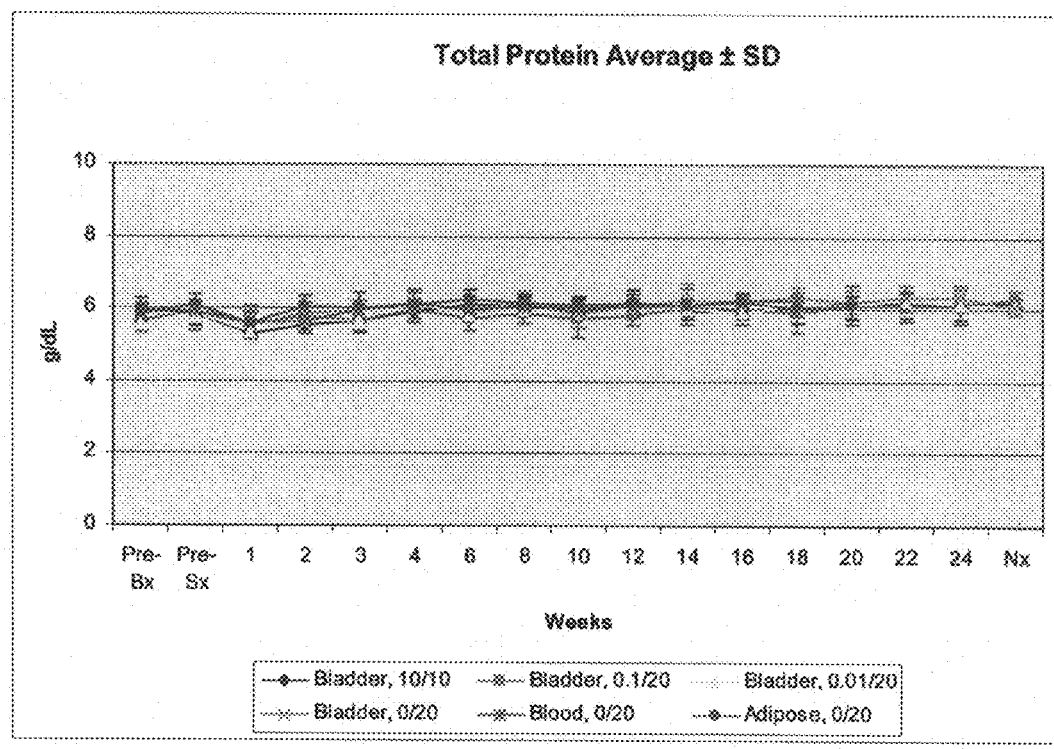
FIG. 81 shows the total protein average for the animals at greater than 4 months.
Figure 82:
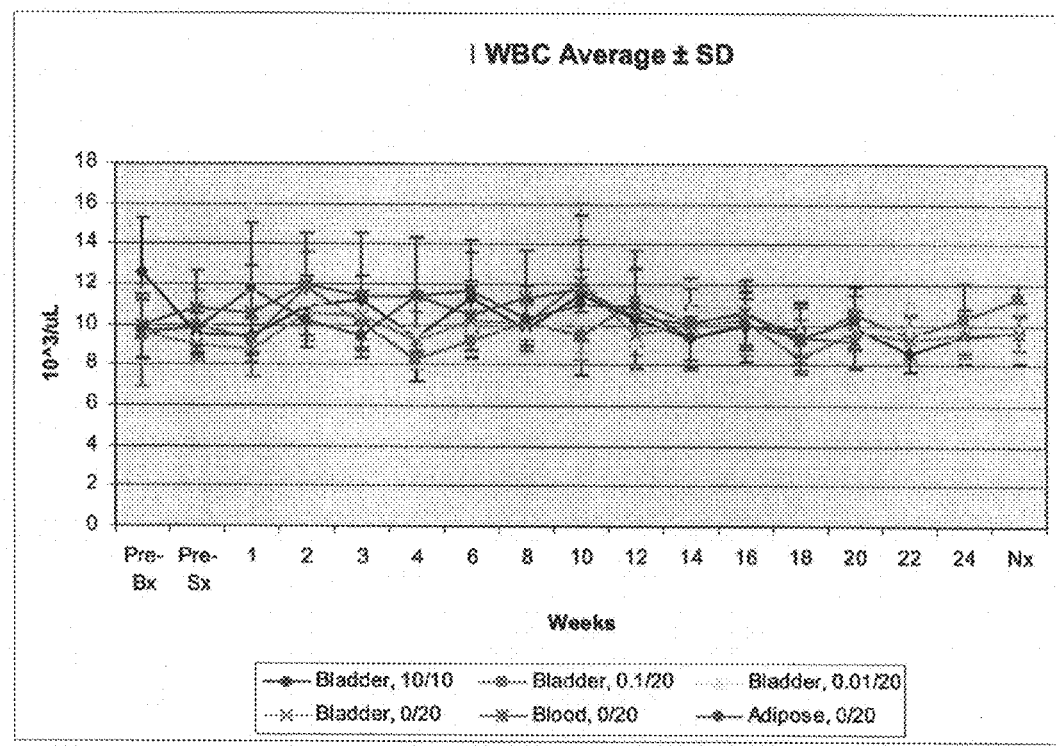
FIG. 82 shows the white blood cell (WBC) average for the animals at greater than 4 months.
Figure 83:
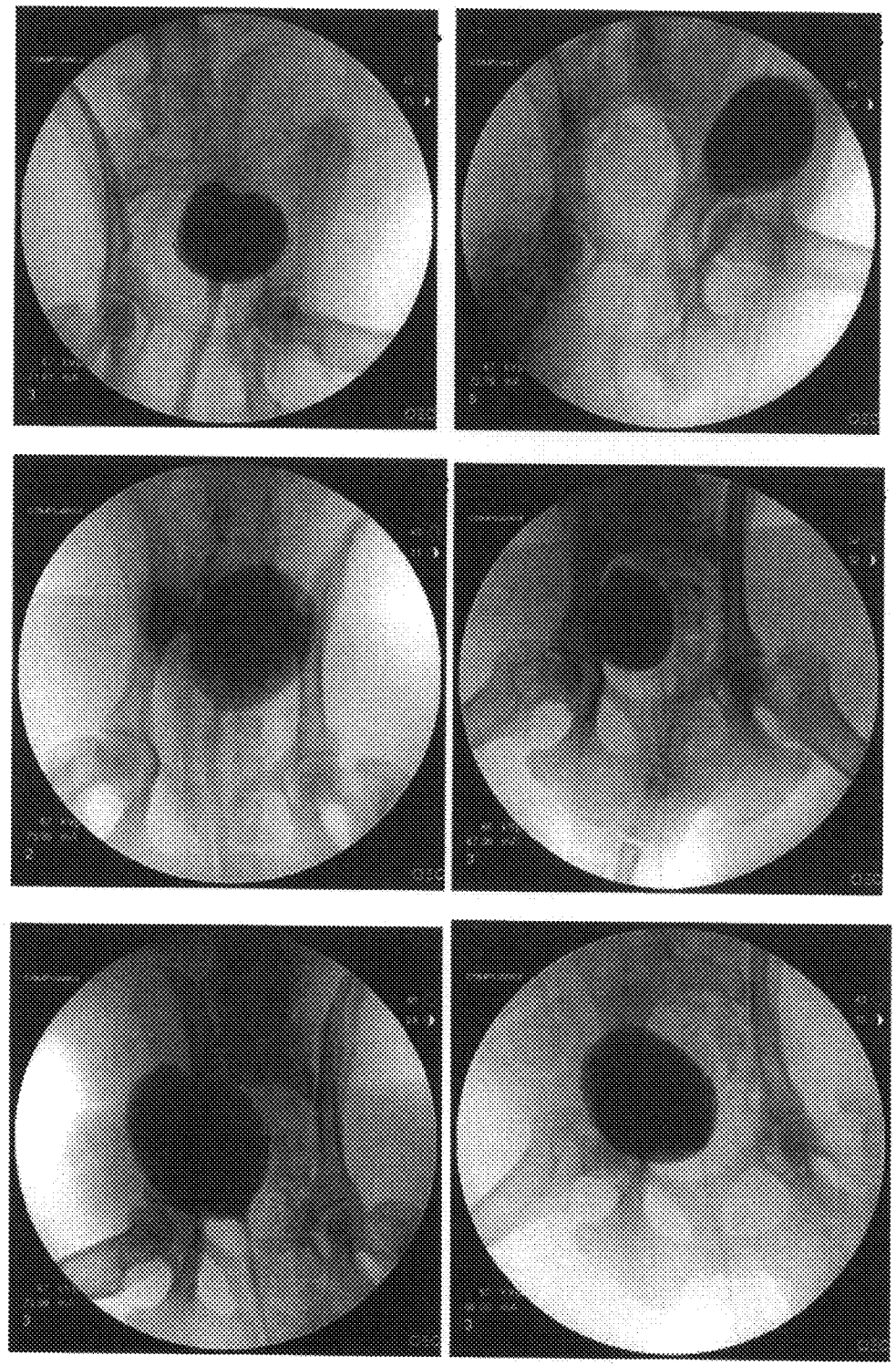
FIG. 83 shows cystograms for the implanted constructs at greater than 4 months (blood-derived SMCs).
Figure 84:
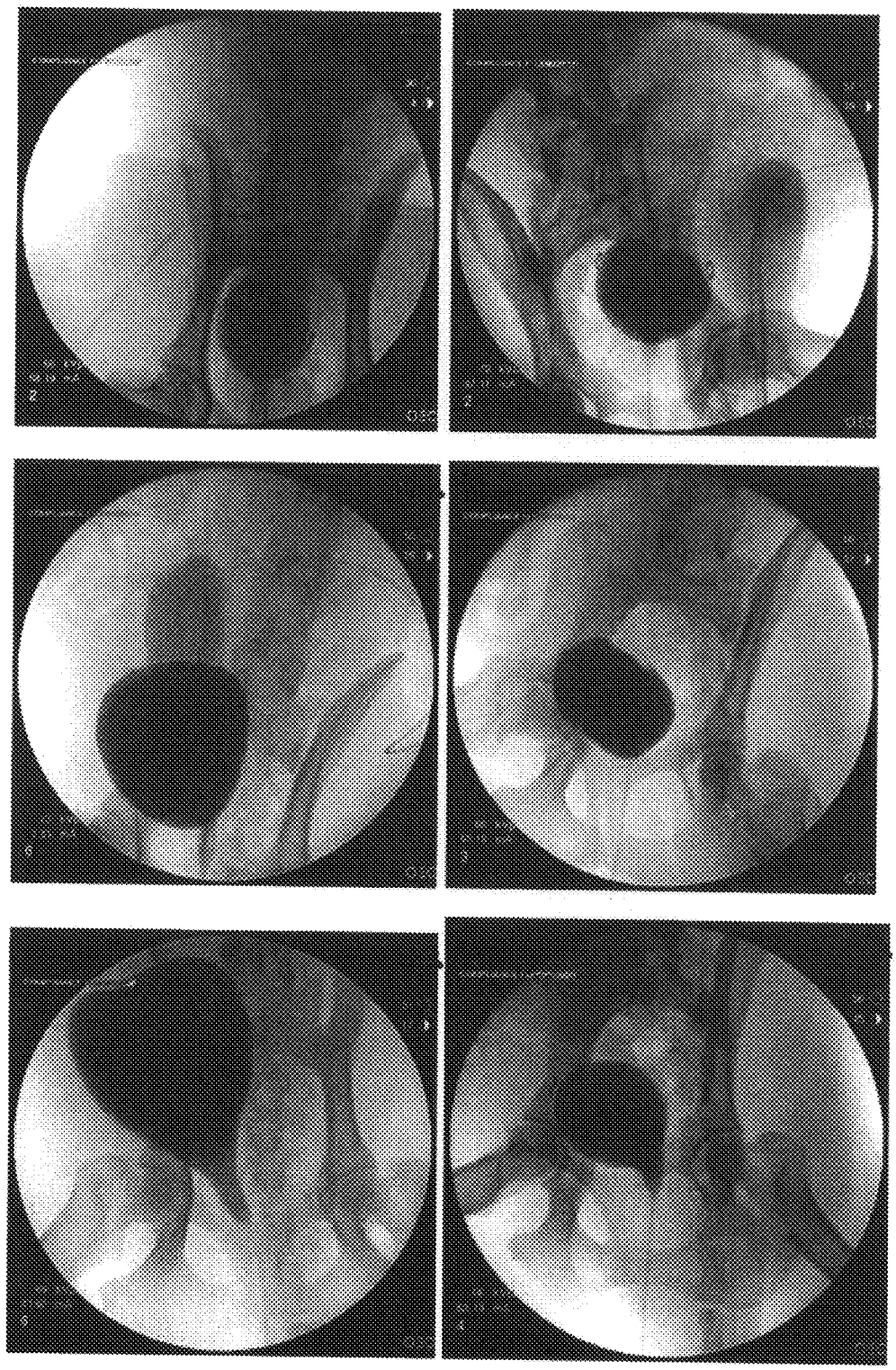
FIG. 84 shows cystograms for the implanted constructs at greater than 4 months (adipose-derived SMCs).

At 5 months, the animals appeared to be doing well clinically, gaining weight as expected, and all hematology and serum chemistries were found to be within normal limits for all bladder groups. In addition, no hydroureter/hydronephrosis was observed. The adipose-derived SMC group appeared to (i) have a higher mean bladder capacity versus the blood-derived SMC group, and (ii) be similar to the bladder-derived SMC group (10/10, 0.01/20 and 0/20) at 5 months. The compliance was similar between all groups at 5 months. FIG. 77 shows the average body weight of the animals. FIG. 78 shows the average serum creatinine of the animals. FIG. 79 shows the average BUN for the animals. FIG. 80 shows the average alkaline phosphatase (ALP) for the animals. FIG. 81 shows the total protein average for the animals. FIG. 82 shows the white blood cell count (WBC) average for the animals. FIG. 83 (blood) and FIG. 84 (adipose) shows cystograms for the implanted constructs. Table 12.3 shows the capacity of a native bladder versus a neo-bladder scaffold construct.

TABLE 12.3

| | | | | | | |
|---|---|---|---|---|---|---|
| Bladder 10, 10 (N = 6) | 5 | 5 | 4 | 5 | 4 | 4 |
| Bladder 0.1, 20 (N = 4) | 2 | 3 | 2 | 3 | 2 | 1 |
| Bladder 0.01, 20 (N = 6) | 6 | 5 | 5 | 4 | 5 | 4 |
| Bladder 0, 20 (N = 5) | 4 | 3 | 4 | 3 | 3 | 3 |
| Blood 0, 20 (N = 6) | 5 | 5 | 4 | 3 | 4 | 2 |
| Adipose 0, 20 (N = 6) | 5 | 4 | 4 | 3 | 3 | 2 |

Example 13

Characteristics of a Total Regenerated Urinary Bladder

Introduction and Objectives: Neo-bladder durability and functionality and the effect of total number smooth muscle cells (SMC) seeded onto a PLGA-based biodegradable polymer scaffold were evaluated in canines following radical cystectomy and implant of Autologous Neo-Bladder Replacement constructs (NBR).

Methods: NBR were seeded with SMC at 3 densities: 25, 12, and $4 \times 10^6$ cells/Construct (n=8/grp). A group (n=8) where radically cystectomized bladders were immediately reimplanted (R) served as a control. In-life assessments (radiographic, urinalysis, and urodyanamics) were performed for the 9 mo study duration. Ex-vivo pharmacological and histological studies were conducted on neo-bladder tissues at study termination.

Results: Animals were clinically healthy, continent, and able to urinate by 3 weeks post-implantation. At 9 mo post-implantation, all groups (NBR and R) had functional bladders with urodynamic compliance values and neo-bladder tissue histology (including mucosal and serosal linings, detrusor muscle, vasculature, and nerve components) consistent with native bladder. Contractile responses to various concentrations of carbachol (Car) and phenylephrine (PE) were similar among all groups. However, contractile responses to α-β-methylene-ATP (AA) were evident only with R and NBR implants seeded with $25 \times 10^6$ SMC. Logistic analysis of bladder tissue strips subjected to electrical field stimulation (EFS) revealed similar $EC_{50}$ and slope factor values for all groups.

Conclusions: An Autologous Neo-bladder Replacement Construct is capable of regenerating urinary bladder as a total organ that has structural, urodynamic, and pharmacological features similar to native bladder and is durable up to 9 mo after surgical implantation. There was no evidence of abnormal tissue development, immune response, or evidence of systemic response to the neo-bladder regeneration. Pharmacological and urodynamic responses suggest a positive correlation between number of autologous SMCs seeded per Neo-Bladder Replacement Construct and final regenerative outcome with $12 \times 10^6$ SMCs achieving tissue regeneration and urodynamic outcomes and $25 \times 10^6$ SMCs achieving tissue regeneration, urodynamic, and pharmacologic outcomes similar to R.

Example 14

Adaptive Regulation of Regenerated Bladder Size

Homeostatic regulation that maintains organ size and structure is a complex relationship between the specific organ, tissues, and body weight or size. Regulative development, or restoration of organ size and structure after cell or tissue loss, can be observed during tissue regeneration or organogenesis. Some goals for regenerative therapies include both restoration of structure and function and establishment of adaptive regulation specific for the recipient. Adaptive regulation in cystectomized animals implanted with cell-seeded PLGA-based scaffolds was compared with adaptive regulation based on early results from a Phase II clinical trial of the Tengion Autologous NEO-BLADDER AUGMENT™ (NBA) in children with neurogenic bladder due to spina bifida.

Neo-bladder capacity and body weight were measured in cystectomized animals implanted with cell-seeded PLGA-based scaffolds for 6 months post-implantation (p.i.). Cystometric capacity and voiding intervals (VI) were measured and formula predicted bladder capacity (FPBC) was calculated at baseline and 12 months after NBA implant in two age- and weight-matched Phase II NBA clinical trial subjects (PT1 and PT2).

Implanted animals remained healthy and continent for study duration and achieved neo-bladder capacities consistent with body weight as early as 6 months p.i. Histology and immunohistochemistry of neo-bladder tissue revealed a native bladder-like structure and function, indicative of bladder regeneration. PT1's baseline capacity was 33% of FPBC. At 12 months p.i., PT1's capacity had increased 84% from baseline and achieved 60% of FPBC. PT2 had capacities of 100% of FPBC at baseline and 12 months p.i. VI increased for both PT1 and PT2.

These results demonstrate that autologous neo-bladders regenerated and grew appropriately to the recipient's body size in animals and humans. These data support the conclusion that neo-bladders elicited by Tengion Autologous NEO-BLADDER AUGMENT™ implantation are bioresponsive to the needs of the recipient.

Example 15

Role of Biomechanical Stimulation (Cycling) in Neo-bladder Regeneration

Biomechanical stimulation is a process known to promote tissue regeneration and optimal healing. Bladder regeneration is biomechanically stimulated by cycling (filling, storage and evacuation), a process that begins in utero and contributes to the development of a functional bladder in humans by early childhood. Interruption of cycling in patients with neurogenic bladder from either congenital (i.e., spina bifida) or acquired (i.e. spinal cord injury) impairment leads to significant functional and structural alternations.

Cycling impacts on bladder tissue regeneration in cystectomized animals implanted with cell-seeded PLGA-based scaffolds were evaluated and learnings applied to outcomes of a Phase II clinical trial of the Tengion Autologous NEO-BLADDER AUGMENT™ (NBA) in patients with neurogenic bladder due to spina bifida.

Post-implantation (p.i.) neo-bladder cycling was initiated in animals at 2 weeks p.i. for 3 days/week. Three cycling parameters were collected: total weeks, hr/day, and total hrs. Urodynamic assessments from three cycling cohorts based on mean parameters were evaluated: HIGH (10 weeks, >3.75 hr/day, >60 hrs), LOW (10 weeks, <2.25 hr/day, <25 hrs), and NO cycling. The HIGH cohort developed neo-bladders with improved compliance and capacities that were on average 3-fold higher than the LOW cohort (p<0.0001). The HIGH cohort achieved 90% of native baseline capacity by 6 mo p.i., while the LOW cohort regained only 40%. Animals not cycled (incontinent) developed tubularized urinary tissue diversions. Histology of neo-bladder wall revealed more native-like tissue structure and extracellular matrix composition (e.g., elastin) in cycled bladders. Early Phase II data studying the NBA suggest that patients with challenges in postoperative cycling (e.g. open bladder necks, low pressure high grade reflux) had inferior clinical and urodynamic outcomes to patients without those challenges.

Early post-implantation cycling is essential for promoting regenerative healing following implantation of autologous cell-seeded PLGA-based scaffolds in animals and humans. Insights from Preclinical studies are consistent with early insights from Phase II NBA trial and confirm the importance of cycling in bladder regeneration.

Figure 85:
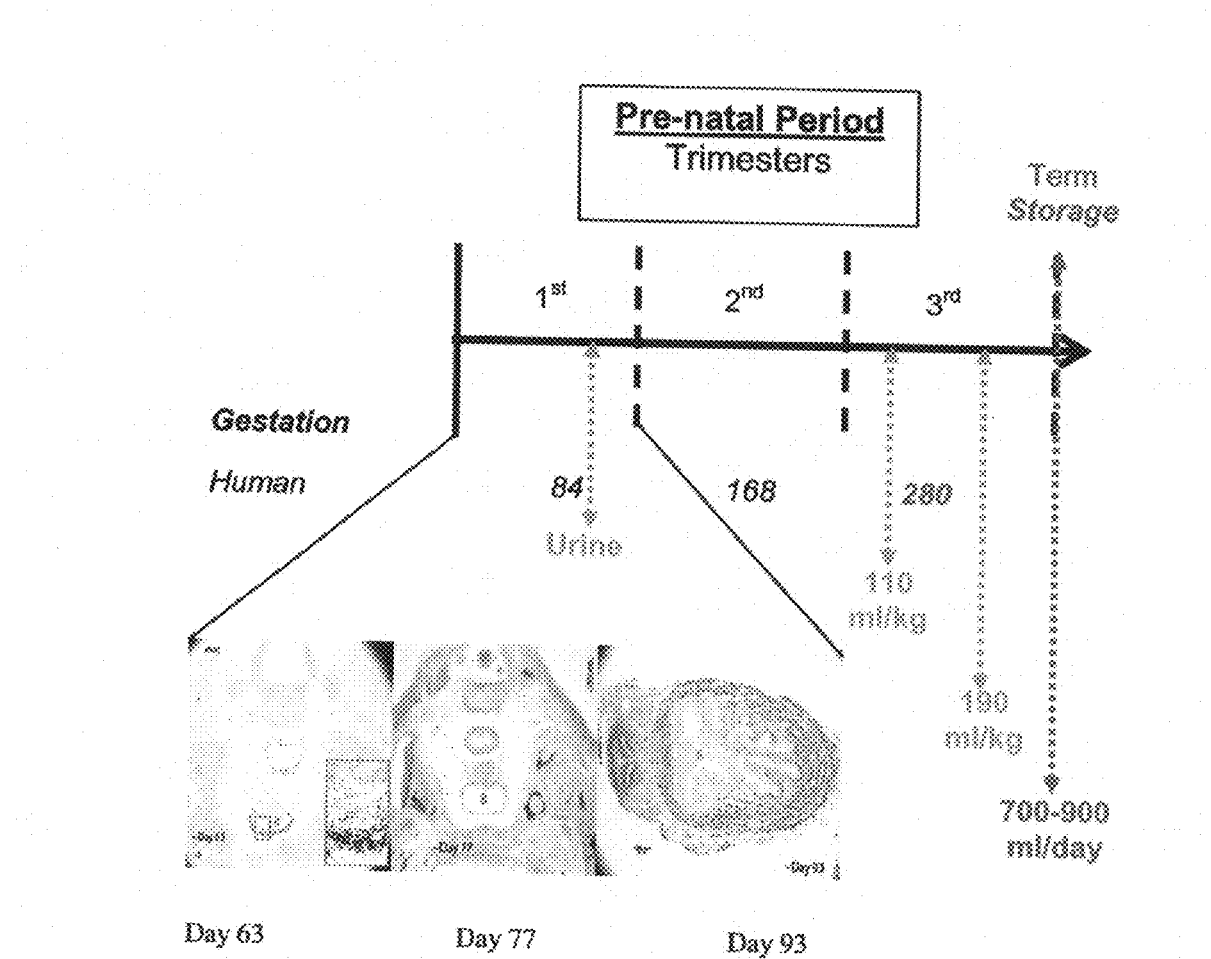
FIG. 85 demonstrates the role of cycling in human urinary bladder development.
Figure 86:
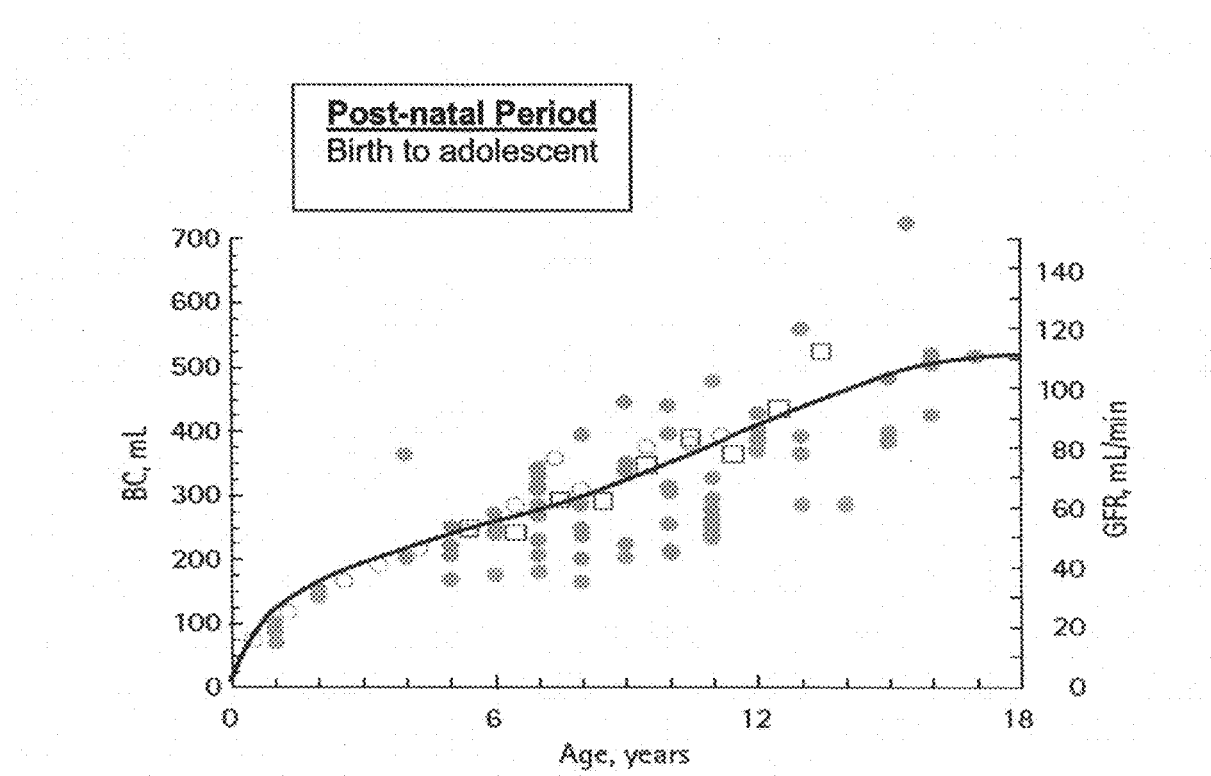
FIG. 86 demonstrates that bladder capacity increases with age and urine output.

FIG. 85 demonstrates the role of cycling in human urinary bladder development. Muscle and elastic fibers were found to increase while collagen was reduced. Sphincter tone develops near term to facilitate cycling dynamics (Wahl et al. BJU Int., 2003. 91:255). FIG. 86 demonstrates that bladder capacity increases with age and urine output. An increase in urine production drives increased bladder capacity (Kim et al. J. Urol., 1991; 146:524).

Figure 87A:
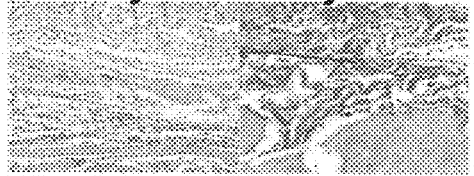
FIG. 87A-C demonstrates that cycling influences regenerative outcome.
Figure 87B:
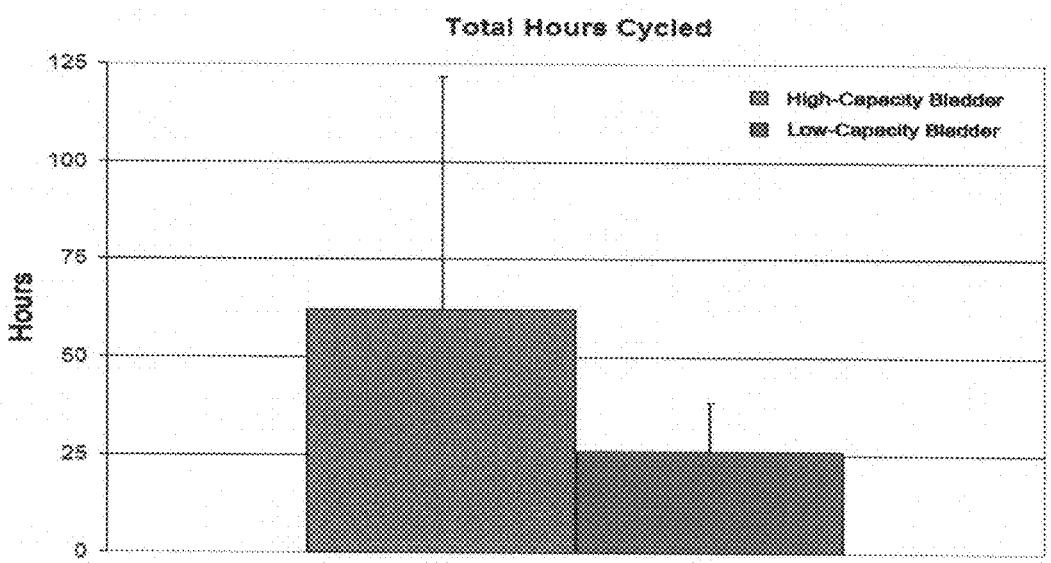
Figure 87C:
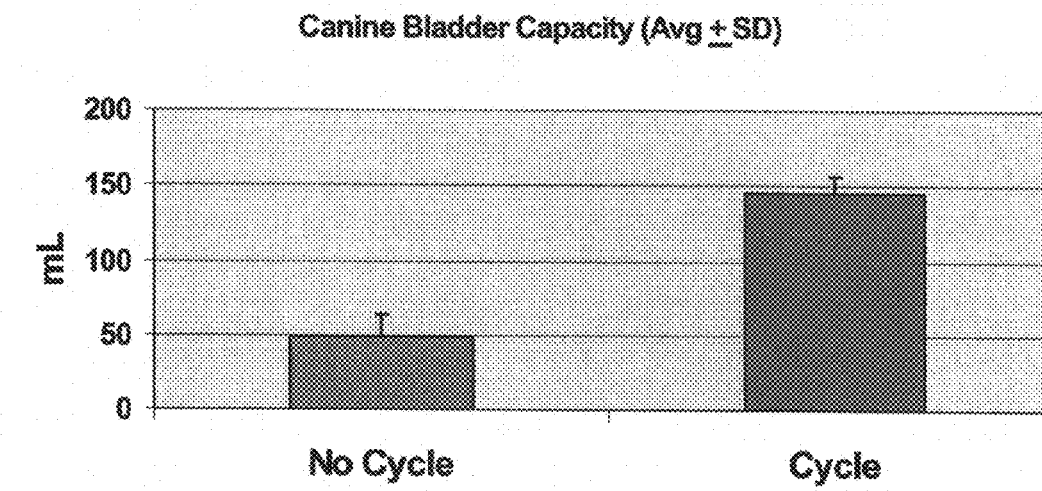

FIG. 87A-C demonstrates that cycling influences regenerative outcome. Two canine groups with similar sized neo-bladder scaffolds were examined and it was found that increased cycling resulted in higher capacity bladders. FIG. 87A depicts a histological comparison between an implanted neo-bladder that had been cycled versus an implanted neo-bladder that had not been cycled. Elastin fibers were observable in the cycled bladder. FIG. 87B depicts the difference in capacity between two different bladders based on the amount of time cycled. FIG. 87C depicts bladder capacity of a cycled bladder versus a non-cycled bladder.

Figure 88:
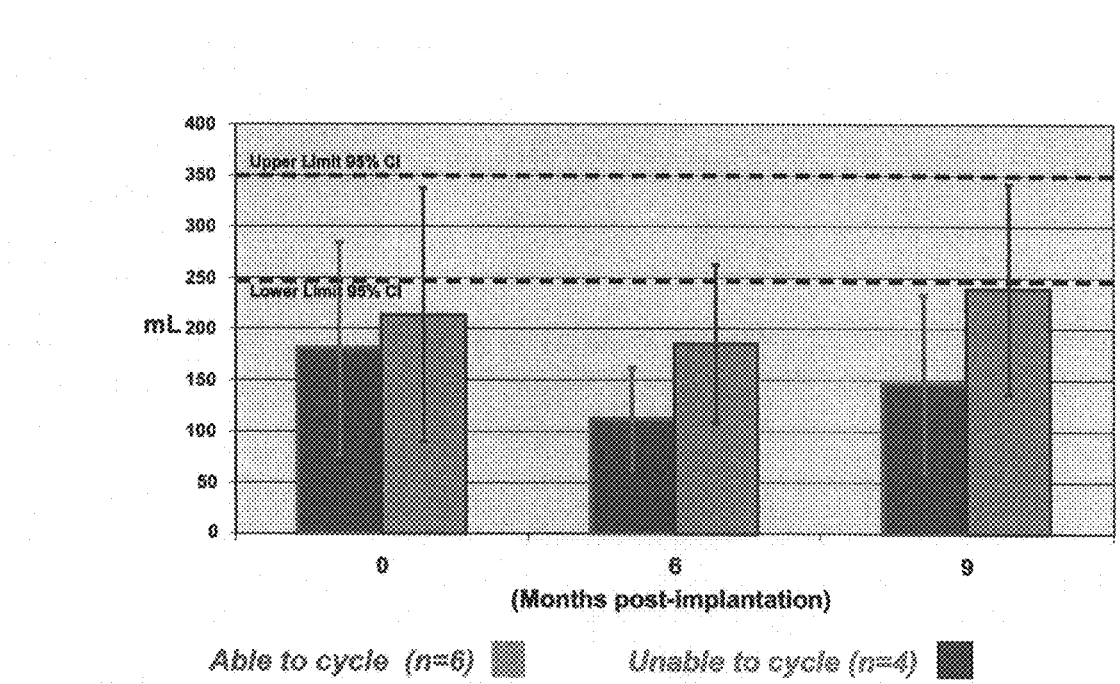
FIG. 88 depicts the translation of regeneration-enhancing effects of cycling to clinical outcomes.

FIG. 88 depicts the translation of regeneration-enhancing effects of cycling to clinical outcomes. Human patients that had received a neo-bladder implant and were able to undergo cycling were observed to have improved bladder capacity as compared to patients who were unable to undergo cycling. This suggests that cycling or biomechanical stimulation promotes regeneration and is important for improving clinical outcomes.

Example 16

Muscle Equivalent Constructs

Three-dimensional (3-D) constructs were fabricated from PGA/PLGA felt material. Specifically, a porous degradable scaffold, constructed of PGA felt coated with PLGA, was formed into a 3-D bladder-like shape, and seeded with cells. FIGS. 9A-E depict additional constructs.

In order to determine optimal scaffold formations, seven different scaffold constructs were pre-formed and surgically tested for preference. Qualitative scores were assigned to each construct using a scale of 1 to 10 (1=least liked; 10=most liked and preferred). The scaffold constructs consisted of the seven scaffold constructs outlined in Table 16.1 below.

TABLE 16.1

Scaffold constructs.

Figure 8:
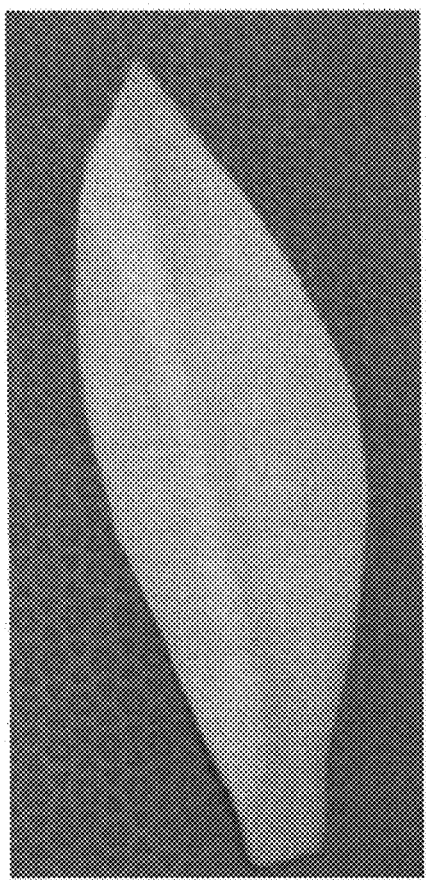
FIG. 8 depicts a pre-folded accordion style scaffold sheet to facilitate insertion through a laparoscope port.
Figure 9A:
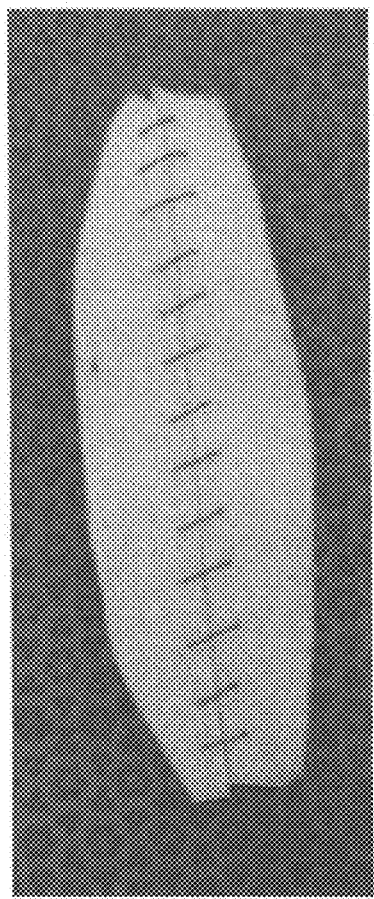
FIG. 9A depicts scaffold pre-cut into strips, then sutured together to allow stacking and insertion into the laparoscope port and secured in place in the abdominal cavity.

| Scaffold No. | Scaffold Name | Dimensions & Characteristics* |
| --- | --- | --- |
| 1 | Pre-rolled, regular-sized, flat scaffold | Ellipsoid 10 cm long × 3.7 cm wide (see top conformation of FIG. 5a); 2D surface area of 29.1 cm² Pre-rolled conformation is depicted in FIGS. 6c and 6d |
| 2 | 2 of 2 pre-rolled scaffold | Two scaffolds, same length as scaffold No.1, each of half width of scaffold No. 1, totaling the same surface area (see FIG. 8d) Pre-rolled conformation |
| 3 | Regular-sized scaffold | Ellipsoid 10 cm long × 3.7 cm wide (see top conformation of FIG. 5a); 2D surface area of 29.1 cm² |
| 4 | Piece of scaffold sterilized at 50° C. | Sterilized at a higher temperature, which may result in more degradation and more pliability. |
| 5 | 2 of 2 regular-sized scaffold | Two scaffolds, same length as scaffold No.1, each of half width of scaffold No. 1, totaling the same surface area (see FIG. 8d) |
| 6 | Regular-sized scaffold cut in half | Same shape as scaffold No. 1, cut down center and sutured, in a manner similar to FIG. 8 |

TABLE 16.1-continued

Scaffold constructs.

| Scaffold No. | Scaffold Name | Dimensions & Characteristics* |
|---|---|---|
| 7 | Rectangular sheet from which to cut desired shape | Rectangle for surgeon to cut down as surgeon saw fit. |

*Except where indicated otherwise, all scaffolds were sterilized at 30° C.

The results of the surgical preference testing are provided below in Table 16.2.

Study Design: The study design is shown below in Table 17.1

TABLE 17.1

Study Design

| Group # | Number of Animals | Test Device | SMC Source | Vascular Source | Blood & Urine Collection | Cystogram | Biopsy | Implant | Necropsy |
|---|---|---|---|---|---|---|---|---|---|
| 1 | 2 male | Source[a] | NA | NA | NA | NA | ~20 days pre-implant | NA | NA |
| 2 | 2 female | Construct[b] | Bladder | Omentum | Baseline; Periodically for first 48 hours[c] Wks 1, 2, 3, 4[d] & 8; Pre-Necropsy | Baseline, Post-Sx, Wks 4[d] & 8, Pre-Necropsy | NA | Day 0 | 1F Day 30 +/− 3 1F Day 84 +/− 3 |
| 3 | 2 female | Construct[b] | Bladder | Peritoneum | Baseline; Periodically for first 48 hours[c] Wks 1, 2, 3, 4[d] & 8; Pre-Necropsy | Baseline, Post-Sx, Wks 4[d] & 8, Pre-Necropsy | NA | Day 0 | 1F Day 30 +/− 3 1F Day 84 +/− 3 |

([a]Tissue Donor and Practice Animal [b]Scaffold mesh of poly(lactic-co-glycolic acid) + Autologous Smooth Muscle Cells [c]Urine Only [d]Pre-necropsy sample for 30d animals (e) Smooth Muscle Cells = SMC).

TABLE 16.2

Surgical Preference Test Results

| Scaffold Number | Rating (1-10) | Comments |
|---|---|---|
| 1 | 6 | Pre rolled ok will be difficult to lay flat |
| 2 | 2 | Too stiff will be difficult to manipulate |
| 3 | 8 | Good stiffness, easy to manipulate |
| 4* | 8 | Good stiffness, easy to manipulate |
| 5 | 10 | Easy to handle, good memory |
| 6 | 9 | Easy to handle, good memory, feels thin |
| 7 | 1 | Too stiff difficult to handle, creases easy |

*Sterilized at a higher temperature than the other scaffolds.

Example 17

In Vivo

Study Schedule—in vivo: Pre-Study Procedures (Biopsy): Day (−20)-(−30); Study Start (Day 0): Approximately 20-30 Days Post Pre-Study Biopsy; Necropsy Start: Day 30±3d and Day 84±3d; Preliminary Report: 2-3 weeks after receipt of pathology report; Final Report Issued: 2 weeks after approval of preliminary report; In-Vivo Study Completion: Day 84±3d Study Animal: Common Name: Yorkshire Pig; Breed/Class: Sus Scrofa; Number of Animals (by gender): 12 Female minimum; 2 Male minimum; Age Range: On File; Weight Range: >45 kg Test Device: Neo-bladder Enlargement Construct w/Bladder Smooth Muscle Cells (SMC); Description: Scaffold No. 1, as described above in the Example above (Ellipsoid 10 cm long×3.7 cm wide (see top conformation of FIG. 5A); 2D surface area of 29.1 cm$^2$), comprising of synthetic lactide/coglycolide acid polymers plus autologous bladder smooth muscle cells. Label Concentration: SMC number seeded on construct were provided on certificate of analysis. Storage Temperature: 22° C.±5.

Technical and Analytical Procedures

Pre-Surgery Fasting:

Procedure Description: All animals were fasted at least 8 hours prior to surgery. Food was withheld the day prior to each surgery.

Duration/Frequency of the Procedure: Single event the night prior to each surgery with duration of approximately 8 hours.

Body Weight:

Procedure Description: The weight of the animal was performed on a calibrated balance.

Duration/Frequency of the Procedure: Baseline, prior to implant surgery, weekly for the first month, then monthly thereafter (±2 days) and pre-necropsy.

Sedation/Anesthesia:

Procedure Description: Each animal was sedated and then anesthetized prior to surgery preparation. Each animal was sedated with Ketamine 20 mg/kg 1M, and Xylazine 2 mg/kg (IM). Each animal was intubated and received inhalant isoflurane at 2.5%-4% for induction and 0.5-2.5% for maintenance of anesthesia, delivered through either a volume-regulated respirator or rebreathing apparatus. An intravenous sheath was placed in a peripheral vessel or right internal jugular vein. Lactated Ringer's solution was administered at 10 ml/kg/hr for the duration of the surgical procedures (augmentation animals only).

Duration/Frequency of the Procedure: Throughout each day of in-life procedures or surgery.

Surgical Preparation:

Procedure Description: For all animals (biopsy and augmentation), the hair over the entire abdominal region was clipped. The animal was positioned in dorsal recumbency. A sterile urinary catheter was gently inserted into the bladder and the bladder emptied of urine prior to the start of procedure.

Care was taken to ensure the bladder was not traumatized during the evacuation procedure. The operative area was then cleaned with three alternating scrubs of povidone-iodine solution and 70% alcohol; once the alternating scrubs were complete, a final application of povidone-iodine solution was applied and allowed to dry. The area(s) was draped for aseptic surgery.

Duration/Frequency of the Procedure: Single event prior to surgery

Biopsy (source male porcine only): Procedure Description: A midline incision was made in the abdomen to allow access to the bladder. Prior to collecting the bladder tissue, the bladder was emptied of urine and one 2 cm×2 cm (approximate) piece of urinary bladder tissue was excised.

The biopsy tissues were immediately preserved aseptically in jars containing tissue culture media and then packaged. Additionally, >35 mL of venous or arterial blood was collected aseptically into an EtO sterilized plastic jar fortified with 0.05% heparin of total volume of blood collected.

Duration/Frequency of the Procedure: Once per source animal lasting approximately 1 hour per animal.

Catheter Implantation (Female Porcine Only):

Procedure Description: An indwelling catheter was placed within the jugular vein and within the bladder to facilitate blood and urine collection in each animal.

Urinary Bladder Catheterization: A midline incision was made in the abdomen to allow access to the bladder. The bladder was emptied of urine and one 8-9.5Fr open lumen catheter was inserted and sutured into the bladder to prevent movement. The insertion point was on the dorsal side of the bladder away from the expected ventral enlargement site. Once secured to the bladder, the catheter was tunneled to the flank of the animal where the port was attached and implanted in a subcutaneous pocket.

Jugular Vein Catheterization: The area surrounding the right or left jugular vein was shaved and aseptically prepared. A 9.5Fr silicon catheter was inserted into the vein and secured by suture to prevent movement. Once secured, an extra large DaVINCI port was attached and implanted in a subcutaneous pocket.

Duration/Frequency of the Procedure: Performed a minimum of 10 days prior to enlargement surgery. The procedure will be performed once per animal, approximately 1 hour per animal.

Urine Sample Collection and Analysis (Female Porcine Only):

Procedure Description: Two urine samples were collected by catheterization or a pan caught method. Approximately 1.0 mL and 3.0 mL samples were collected in sterile containers for qualitative and quantitative analysis, respectively. Smaller amounts were sufficient for analysis; however, if urine collection was difficult, the quantitative sample took precedent over the qualitative sample. The collected quantitative urine was decanted into 5 mL sterile tubes, refrigerated and shipped within 24 hrs of collection. The qualitative measurement was taken at time of collection using Multistix® 10 SG Test Strips. Parameters of interest for both the qualitative and quantitative measurements include: Glucose, Bilirubin, Blood, pH, Protein, Ketones, Urobilinogen, Specific Gravity, Nitrites, Bacteria 1 (quantitative only), and Leukocytes.

Duration/Frequency of the Procedure: Baseline, periodically for first 48 hours, Weeks 1, 2, 3, 42 & 8 following implantation and prior to necropsy. Procedure lasted approximately 15 minutes per animal.

Cystogram:

Procedure Description: The bladder of each animal was prepared for fluoroscopic imaging by: Placing a sterilized open lumen Foley catheter into the bladder access site; •Attaching a syringe and drawing out urine to empty the bladder; Injecting 3:1 saline:contrast medium via the open lumen catheter and filling the bladder; Performing fluoroscopic imaging.

Duration/Frequency of the Procedure: Baseline, post-surgery, Week 42, 8 and pre necropsy. Procedure lasted approximately 10-30 minutes per animal.

Blood Collection (female porcine only):

Hematology, Coagulation, Serum Chemistry and Blood Gases Hematology: Hematology samples were collected in 2.0 ml EDTA tubes, and stored on wet ice or refrigerated (2-8° C.). Samples were labeled and packaged on ice. Analysis was performed within 24 hrs of collection. Blood samples were evaluated for the parameters specified below: Total leukocyte count (WBC); Erythrocyte count (RBC); Hemoglobin concentration (HGB); Hematocrit value (HCT)a; Mean corpuscular volume (MCV); Mean corpuscular hemoglobin (MCH) a; Mean corpuscular hemoglobin concentration (MCHC)a; Platelet count (PLT); Reticulocyte count (RTC); White blood cell differential; a=Calculated values.

Coagulation: A total of 1.8 mL blood was collected into 1.8 mL sodium citrate tubes (0.2 mL of 3.8% sodium citrate). Citrated blood samples were kept on ice until ready to be centrifuged at 1,700×g for 15 minutes. Before freezing, plasma was divided in half and freezon at −70° C. One vial was sent to designated laboratory and the other was kept as a back-up until end of study. Citrated plasma samples were stored at −70° C.

Coagulation parameters measured include: Prothrombin time (PT); Activated partial thromboplastin time (APTT); •Fibrinogen (FIB).

Serum Chemistry: Samples for Serum Chemistry were collected in approximately 4.0 ml serum separation tubes. The blood samples were centrifuged (10,000 RPM for 10 minutes) and the serum extracted using sterile technique. Serum was evenly split among two separate labeled vials. Serum was frozen at −70° C. Serum samples were evaluated for the following parameters: Glucose (GLU); Urea nitrogen (BUN); Creatinine (CRE); Total protein (TPR); Albumin (ALB); Globulin (GLOB) 1; Albumin/Globulin ratio (A/G) 1; Calcium (CAL); Phosphorus (PHOS); Electrolytes: Sodium (NA), Potassium (K), and Chloride (CL); Total cholesterol (CHOL); Total bilirubin (TBIL); Triglycerides (TRG); Alanine aminotransferase (ALT); Aspartate aminotransferase (AST); Alkaline phosphatase (ALK); Gamma glutamyltransferase (GGT); 1=Calculated values Blood Gases: Blood Gas/Spun Hematocrit/Total Protein Monitoring: Arterial blood samples (~1.0 mL) were collected and analyzed using a calibrated i-STAT analyzer and the appropriate cartridge. Samples were evaluated for the following blood gas parameters: Sodium (Na) (mmol/L); Potassium (K) (mmol/L); Ionized Calcium (iCa) (mmol/L); Glucose (Glu) (mg/dL); Hematocrit (Hct) (%); pH, PCO2 (mm Hg); PO2 (mm Hg); TCO2 (mmol/L); HCO3 (mmol/L); BEecf (mmol/L); pH; and SO2 (%).

Duration/Frequency of the Procedure Collection of blood samples were conducted as follows: Baseline, Weeks 1, 2, 3, 4 (pre-necropsy sample for 30 day animals) & 8 following implantation and prior to necropsy. Procedure lasted approximately 15 minutes per animal.

Vital Signs Monitoring Procedure: Procedure Description: The following vitals were monitored during implant surgery:

Body Temperature: Body temperature was monitored through an esophageal probe.

Direct Blood Pressure and Heart Rate: A blood pressure line was connected to monitor systolic arterial pressure (SAP), diastolic arterial pressure (DAP), and mean arterial pressure (MAP). An introducing sheath was placed in the carotid artery for blood pressure monitoring.

Expired gases: CO2 and SaO2

ECG: Lead II ECG was monitored

Duration/Frequency of the Procedure: At approximately 20 minute intervals throughout the surgical procedure.

Laparoscopic Bladder Enlargement:

Procedure Description:

Positioning and Port Placement: A four port transperitoneal technique was employed to gain laparoscopic access to the bladder and intraperitonal space. Four punctures were made: a 12-mm primary port was inserted ~1 cm above the umbilicus; two 12-mm secondary ports were inserted ~7-10 cm lateral to and ~3-4 cm below the umbilicus; a 5-mm suprapubic port was inserted to establish pneumoperitoneum using CO2 and/or facilitate laparoscopic handling of the omentum, peritoneum and manipulation of neo-bladder. Alternatively, a fifth abdominal puncture below the umbilicus was performed using a Veress needle to establish pneumoperitoneum using $CO_2$ until the pressure reaches approximately 15 mm Hg.

Bladder Enlargement: Three bladder enlargement techniques were performed depending on the vascular source being utilized (i.e., omentum or peritoneum).

Bladder Enlargement Using Peritoneum: A suitable segment of peritoneum able to exceed the distance to the primary 12-mm port without tension was carefully isolated from the abdominal wall intracorporeally. A segment of peritoneum larger than the size of the construct was then externalized through one of the 12-mm ports and the peritoneum carefully spread out to accommodate the construct. The seeded construct was then removed from the media and the construct number matched to the animal documentation for verification. The construct was then secured to the peritoneum via surgical adhesive or suture allowing peritoneum to overlap the entire construct. The construct was maintained moist during the procedure using a sterile syringe and gently infusing sterile physiological pH saline. Once the construct was secured, the peritoneum/construct unit was carefully internalized through a 12-mm port into the intraperitonal space and positioned longitudinally on the bladder dome to just above the urethra on the ventral side of the bladder (opposite to the ureter orifices). One side of the construct was tacked to the bladder using appropriately sized staples, e.g., 0.45 cm horizontal dimension×0.47 cm vertical dimension. Once securely attached to the bladder, a longitudinal incision was made into the bladder mimicking the position of the construct and the incised bladder tissue stapled to the non secured side of the construct. Preventive measures were taken to limit the amount of residual urine within the incised bladder from reaching the abdominal cavity. Any peritoneum overlapping the construct was then secured to the bladder using surgical adhesive.

Bladder Enlargement using Omentum: A suitable segment of terminal omentum able to reach the entire length of the bladder without tension was gently grasped using endoscopic clamps and carefully isolated from the abdominal cavity intracorporeally. The omental segment was positioned longitudinally on the bladder dome to just above the urethra on the ventral side of the bladder (opposite to the ureter orifices). One side of the omentum vascular was tacked to the bladder surface using surgical adhesive. Once the omentum segment was securely attached to the bladder, the seeded construct was then removed from the media and the construct number matched to the animal documentation for verification. The construct was carefully internalized through a 12-mm port into the intraperitonal space and positioned longitudinally on the bladder mimicking the secured omentum line. The construct side nearer the secured omentum was tacked longitudinally onto the bladder using appropriately sized staples. A longitudinal incision was made into the bladder along the same line as the secured construct. The incised bladder tissue was stapled to the non secured side of the construct. Preventive measures were taken to limit the amount of residual urine within the incised bladder from reaching the abdominal cavity. Any omentum overlapping the construct was then secured to the bladder using surgical adhesive. Using a lumen catheter, the augmented bladder was checked for leaks to assure adequate closure and water-tightness. The 4 laparoscopic ports were removed and the abdominal punctures were then closed with absorbable suture material of an appropriate size. The skin was closed in a subcuticular fashion, using an appropriate size of absorbable suture material.

Duration/Frequency of the Procedure: Once per animal lasting approximately 5 hours per animal on Day 0.

Bladder Enlargement using Omentum via Laparotomy: The omentum bladder enlargement procedure outlined above was altered from laparoscopy to laparotomy. For comparison purposes, two peritoneum bladder enlargement procedures were performed as a laparotomy, as shown below in Table 17.2.

TABLE 17.2

Laparotomy Study Design

| DB-Pig | Scaffold | Cell Origin & # | Tissue Wrap | Necropsy Post-Implant Time |
|---|---|---|---|---|
| 1 | Scaffold No. 1* | Pig Bladder-derived SMCs ($10 \times 10^6$) | Omentum | 30 ± 2 days |
| 2 | | | Omentum | 84 ± 5 days |
| 3 | | | Peritoneum | 30 ± 2 days |
| 4 | | | Peritoneum | 84 ± 5 days |

*as described above

Briefly, a midline incision was made in the abdomen beginning immediately caudal to the umbilicus. The omentum and peritoneum were identified, carefully separated from the abdominal space until the tissue is long enough to cover the enlarged bladder section. Care was taken to ensure the tissue remained vascularized. The urinary bladder was then exposed and the bladder carefully emptied of urine taking care to avoid urine from entering into the abdominal cavity. The augmentation of the construct to the bladder followed the same procedure outlined above. Once secured, the abdominal incision was closed in layers with absorbable suture material of an appropriate size. The skin was closed in a subcuticular fashion, using an appropriate size of absorbable suture material.

Duration of the Procedure: Once per animal lasting ~5 hours per animal on Day 0.

Post-Surgery and Recovery Analgesia:

Procedure Description: Survival animals receive the following: Antibiotic Therapy—Approximately 2 mg/kg Naxcel (ceftiofur) or equivalent antibiotic was provided intramuscularly to each animal prior to and following enlargement surgery beginning on Day 0. Treatment continued once daily until Day 3 or until the facility veterinarian deemed appropriate.

Postoperative Analgesia—Approximately 0.1 mg/kg, IM given 8-12 hours apart, of Buprenorphine was administered following surgery (enlargement procedure [Day 0]) for a total of two injections. Analgesic therapy continued twice a day for up to 3 days following the definitive surgery (Days 1-3) for a total of six injections.

Concurrent Therapy—As prescribed by the Facility Veterinarian and Study Director, animals were provided concurrent therapy (e.g., antibiotics or fluid therapy) in order to maintain general good health. Duration/Frequency of the Procedure: Immediately following surgical procedures and daily thereafter at the discretion of the Facility Veterinarian.

Animal Sacrifice and Necropsy

Procedure Description:

Unscheduled and Scheduled Euthanasia—All animals were injected with sodium pentobarbital (150 mg/kg, IV) to cause euthanasia. Scheduled euthanasia was day of biopsy (male porcine only), Day 30 and Day 84 post-enlargement procedure.

Necropsy—All female animals will be subjected to necropsy. There was a specific focus on the urinary bladder. The complete bladder (trigone, anastomotic site, and neobladder) was visualized and photographed in situ and then excised en bloc and fixed in 10% NBF.

Duration/Frequency of the Procedure: Single event duration of approximately ½ hr per animal on Day 30 & 84 (±3 days).

Histology/Pathology Laboratory

Procedure Description: The fixed urinary bladder (i.e., enlarged neobladder) was trimmed to include separate sections across the interface between the normal bladder and the construct. Tissue samples were trimmed, embedded in paraffin, and sectioned. Slides will be stained with hematoxylin and eosin (H & E) and Masson's Trichrome (elastin).

Duration/Frequency of the Procedure: Histology and Pathology were conducted within 3 months of receipt of samples.

Results: As shown in Tables 17.3 and 17.4 below, the implantation did not affect the animals' capacity for growth as measured by body weight and the associated increase in the bladder's volumetric capacity. FIG. 8f shows a cystogram of the implanted patch of the instant invention at 4 weeks.

TABLE 17.3

Body Weight.
Body Weight (Kg)

| Animal Number | Implant | 28 Days | 55 Days |
|---|---|---|---|
| 1 | 60.0 | 71.7 | — |
| 2 | 55.9 | 67.8 | 81.6 |
| 3 | 63.1 | 71.2 | 89.7 |
| 4 | 56.8 | 68.0 | — |

TABLE 17.4

Bladder Capacity.
Bladder Capacity (mL)

| Animal Number | Implant | 28 Days | 55 Days |
|---|---|---|---|
| 1 | 700 | 1200 | — |
| 2 | 750 | 1100 | 2350 |
| 3 | 775 | 1250 | 2650 |
| 4 | 1100 | 1400 | — |

Figure 89:
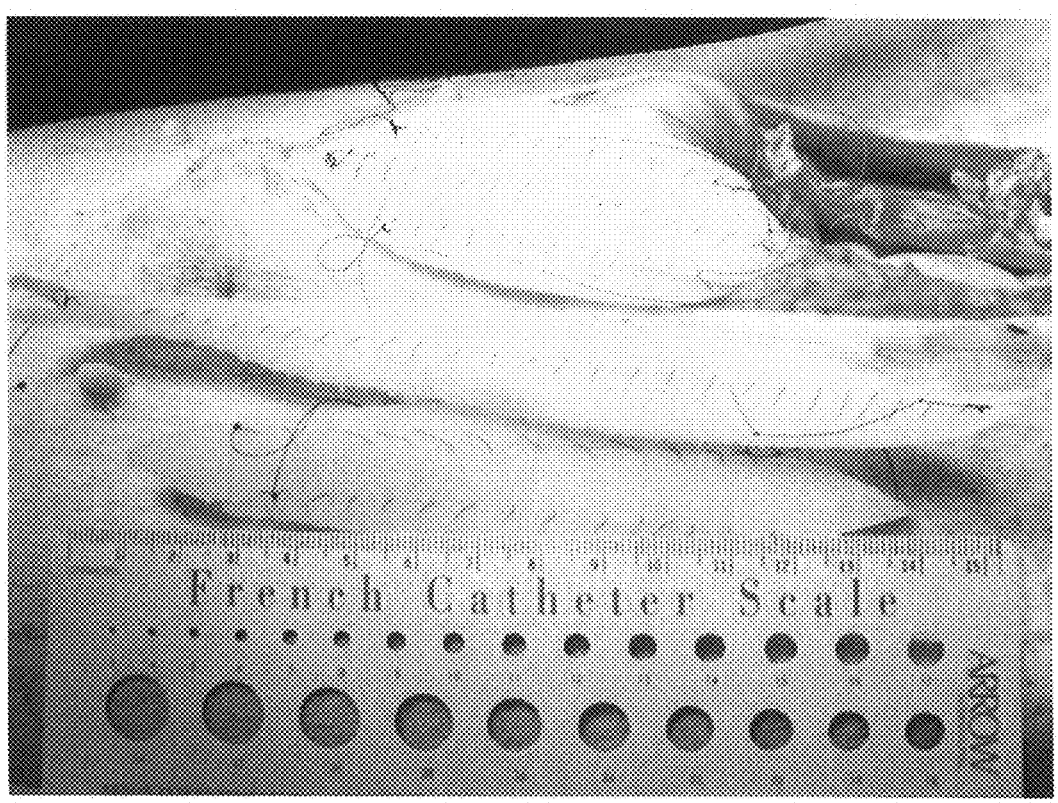
FIG. 89 shows the implantation of a muscle equivalent scaffold.
Figure 90:
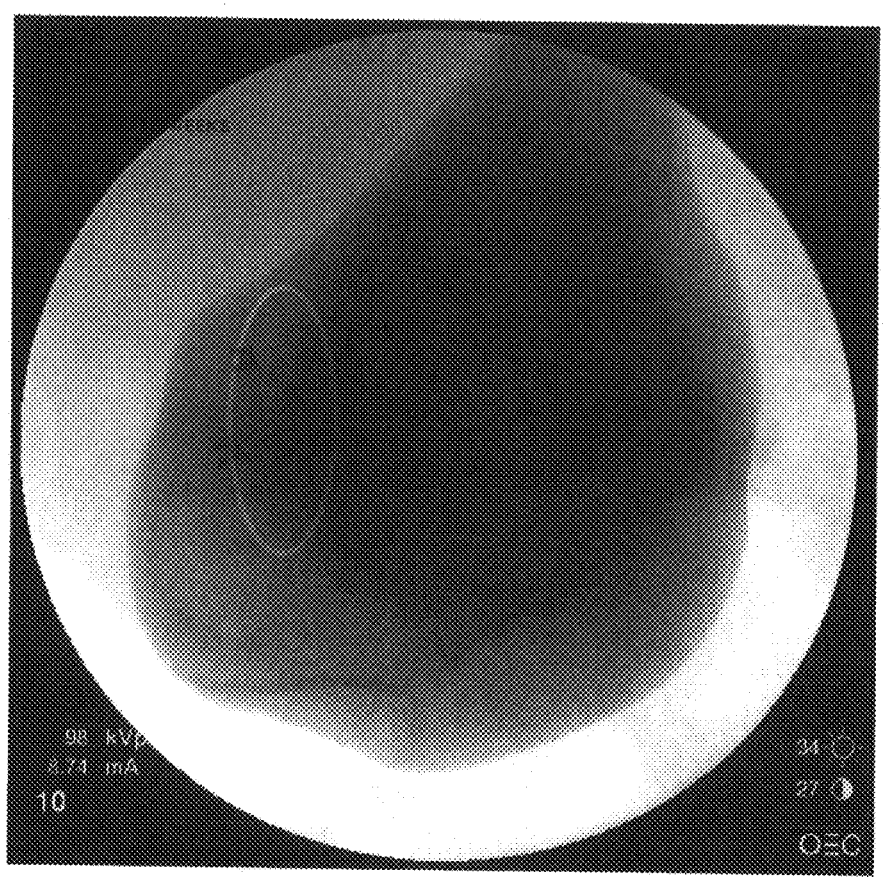
FIG. 90 shows a cystogram of an animal following implantation of a muscle equivalent scaffold at 4 weeks.

FIG. 89 shows the implantation of a scaffold.
FIG. 90 shows a cystogram of an implanted patch scaffold at 4 weeks.

Example 18

Adipose-derived Smooth Muscle Cells Versus Mesenchymal Stem Cells (MSCs)

Adipose tissue represents a heterogenous cell population composed of endothelial cells, adipocytes, smooth muscle cells and progenitor cells with limited mesenchymal differentiation potential. We have used quantitative RT-PCR, antigen expression, protein fingerprinting, growth kinetics and functional analysis to evaluate the cellular composition of the adherent, stromal vascular fraction (SVF) derived from human adipose. We show that enrichment for the smooth muscle cell compartment of adipose SVF is directly dependant on media formulation. These human adipose-derived smooth muscle cells (Ad-SMC) are functionally indistinguishable from human bladder-derived smooth muscle cells and phenotypically and functionally distinct from mesenchymal stem cells (MSC) or other adipose-derived progenitor populations.

We have investigated the cellular composition of the initial "passage zero" adherent human SVF-derived cell population using quantitative real-time PCR methods (TaqMan). We show that though this starting adherent SVF-derived cell population is composed of cells expressing endothelial, smooth muscle and adipocyte-associated markers, we have been able to identify and culture a cell population with markedly distinctive biological properties through the expansion of SVF-derived cells under defined media conditions that select against the growth of MSC (Gong et al. Tissue Eng Part A 2008; 15:319-330; Lund et al. Cytotherapy 2009; 11:189-

197). Despite partial overlap in differentiation potential and expression of markers historically associated with MSC, this cell population clearly has a more pronounced smooth muscle cell phenotype relative to MSC based on FACS and RT-PCR (reverse transcription PCR) analysis of the expression of key nuclear and cell surface markers. This population also expresses noticeably fewer endothelial-specific genes when compared to MSC. Manifestation of a smooth muscle cell phenotype is independent of passage number, adipose donor source or the requirement for directed differentiation with recombinant cytokines and growth factors. Additionally, this smooth muscle cell enriched population has a distinctive proteomic signature which unambiguously discriminates it from MSC. Finally, we have leveraged the diametrically opposing responses of this smooth muscle cell like population and MSC towards the thromboxane A2 mimetic U46619 to document a clear functional dichotomy between the two cell types. Taken together, these data support the conclusion that this population is more accurately described as adipose-derived smooth muscle cells (Ad-SMC), and represents a separate and distinctive cellular species compared to other classes of adipose-derived cells including adipocytes, endothelial cells and MSC.

Methods and Materials.

Preparation of Adipose Tissue. Human adipose samples were obtained either subcutaneously or through lipoaspiration (Zen-Bio, Research Triangle Park, N.C.), and washed 3-5 times with an equal volume of PBS/gentamycin (Gibco) (5 µg/ml). Adipose was digested with filter-sterilized collagenase I (Worthington) (0.1%, 1% BSA in DMEM-HG (Gibco)) at 37° C. for 1 hour, then centrifuged for 5 minutes at 300 g in 50 ml conical tubes. The stromal vascular fraction was resuspended in PBS/1% BSA and filtered through a 100 µm Steriflip vacuum filter. The cell population was pelleted again at 300 g for 5 minutes and resuspended in DMEM-HG+ 10% FBS+gentamycin 5 µg/ml. Bone marrow derived MSC at the end of passage two was obtained from a commercial supplier (Lonza). For studies on the effect of media type on expression of smooth muscle cell markers, the SVF-derived cells were alternatively resuspended in α-MEM (Gibco)+ 10% FBS, SMCM (ScienCell) or L15 (Sigma).

Taq-Man qRT-PCR. RNA was purified from MSC or Ad-SMC using the RNeasy Plus Mini Kit (Qiagen) according to the manufacturer's instructions. cDNA was generated from 2 µg of RNA using the SuperScript VILO cDNA Synthesis Kit (Invitrogen) according to the manufacturer's instructions. Following cDNA synthesis, each sample was diluted 1:10. qRT-PCR was setup as follows using the TaqMan primers and probes listed below: 10 µl master mix (2×), 1 µl primer/probe, 9 µl cDNA (diluted 1:10).

The following TaqMan primers were used for evaluation of smooth muscle, endothelial and adipogenic gene expression: SmαA (smooth muscle alpha actin): Hs00909449_m1, SM22: Hs00162558_m1, myocardin: Hs00538076_m1, SMMHC (smooth muscle myosin heavy chain): Hs00224610_m1, calponin: Hs00154543_m1, adiponectin: Hs00605917_m1, FABP-4 (fatty acid binding protein #4): Hs1086177_m1, CDH5/VECAD (vascular endothelial cadherin): Hs00174344_m1, vWF (von Willebrand factor): Hs00169795_m1, PECAM1 (platelet endothelial cell adhesion molecule #1): Hs00169777_m1, FLT1/VEGFR (VEGF receptor): Hs01052936_m1, KDR/FLK1 (fetal liver kinase #1): Hs00176676_m1, TEK (tyrosine kinase, endothelial): Hs00945155_m1. 18s rRNA was used as endogenous control and all samples were calibrated against bladder smooth muscle cell cDNA. All primer/probes were secured from Applied Biosystems. All reactions were carried out in an ABI 7300 real time thermal cycler using default cycling parameters. Analysis of PCR data was performed using the method of Relative Quantitation (RQ) by Comparative Ct.

Array-RT-PCR. Real time array-based qRT-PCR analysis was performed for 35 cycles using the SABiosciences MSC (PAHS-082A) and Cell Surface Marker PCR array platform (PAHS-055A) according to the manufacturer's instructions.

FACs Analysis. $0.5 \times 10^6$-$1 \times 10^6$ cells per data point were fixed in 2% paraformaldehyde and $F_c$ receptors blocked to prevent non-specific binding. Cells were then incubated with a directly conjugated antibody for the cell surface markers CD31, CD45, CD54, CD56, CD73, CD90, CD105, CD117 or CD133 (BD Biosciences) as recommended by the manufacturer. Subsequent to final washing (PBS, 0.1% Triton X-100), antigen detection was performed utilizing the BD FACS Aria 1 or Guava EasyCyte Mini Express Assay system using the appropriate fluorescent channel A minimum of 5000-10,000 events were acquired from each sample.

2D Proteomic Analysis. Passage controlled (end of P2) bone marrow derived MSC and Ad-SMC were lysed in Lysis Buffer (50 mM Tris pH 8; 150 mM NaCl; 0.5% NP40 and protease inhibitors, Roche) and 40 µg of protein lysate from each cell type was run out on a pH 4.0-7.0 Zoom IEF strip (Invitrogen) according to the manufacturer's instructions. Each strip was then loaded onto a 4-12% Bis/Tris acrylamide gel and run out on the $2^{nd}$ dimension. The gels were stained with SYPRO Ruby stain (Invitrogen) according to the manufacturer's instructions.

Passage controlled (end of P2) bone marrow derived MSC and Ad-SMC were lysed in Lysis Buffer (50 mM Tris pH 8; 150 mM NaCl; 0.5% NP40 and protease inhibitors, Roche) and 40 µg of protein lysate from each cell type was run out on a pH 4.0-7.0 Zoom IEF strip (Invitrogen) according to the manufacturer's instructions. Each strip was then loaded onto a 4-12% Bis/Tris acrylamide gel and run out on the $2^{nd}$ dimension. The gels were stained with SYPRO Ruby stain (Invitrogen) according to the manufacturer's instructions.

Results

Figure 91A:
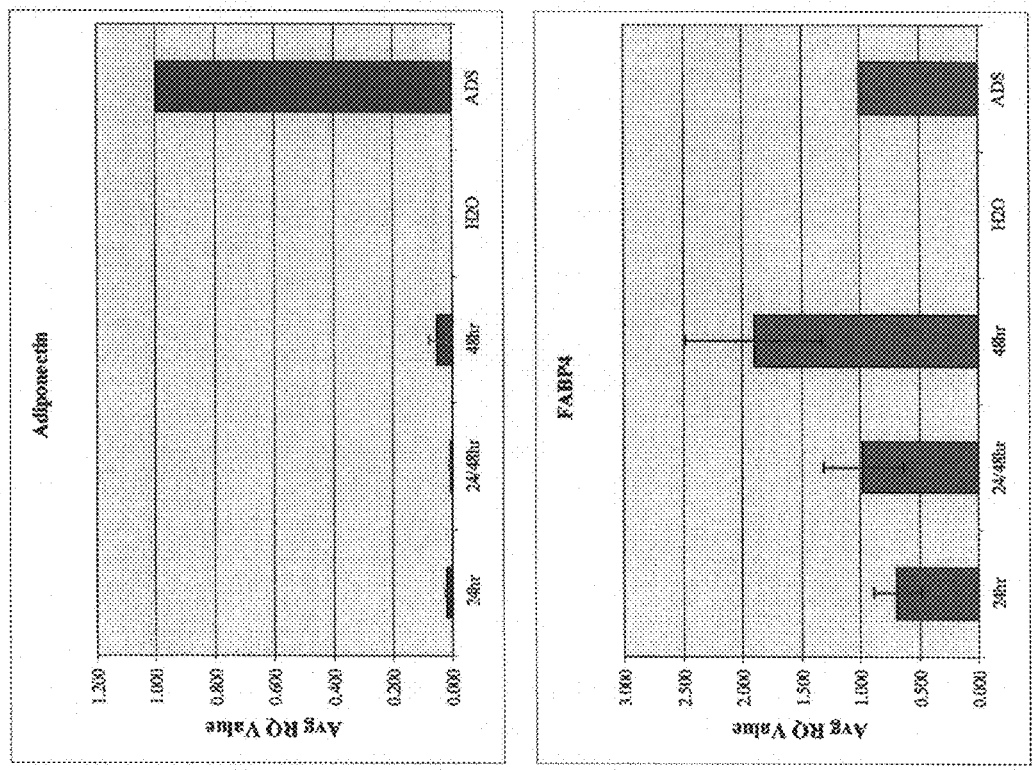
FIG. 91 shows expression levels of various markers in adipose-derived cell populations: (A) adiponection and FABP-4, (B) SMαA, SM22, myocardin, SMMHC; (C) calponin; (D) VECAD, vWF, PECAM, FLT1; and (E) FLK and TEK.
Figure 91B:
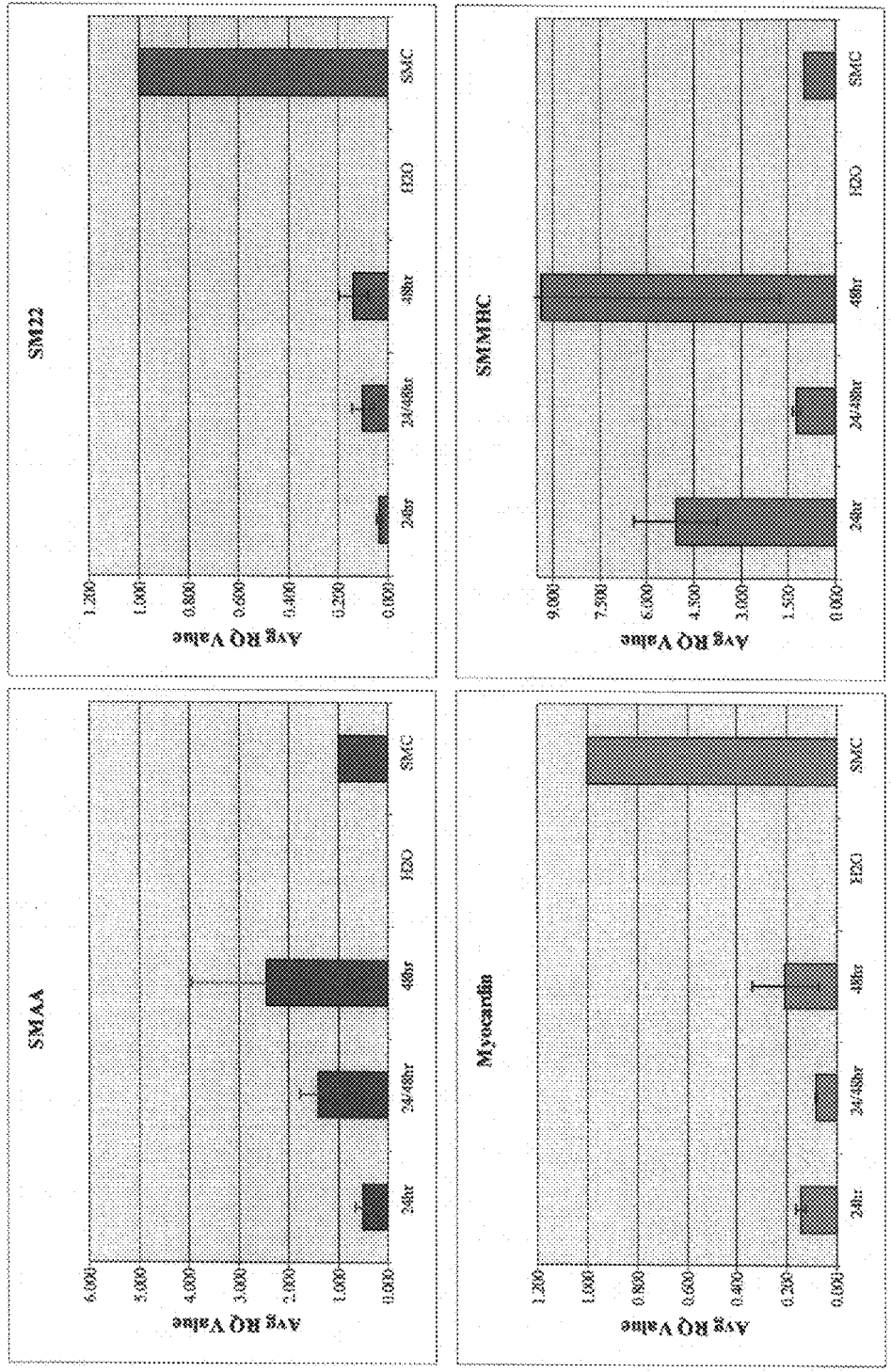
Figure 91C:
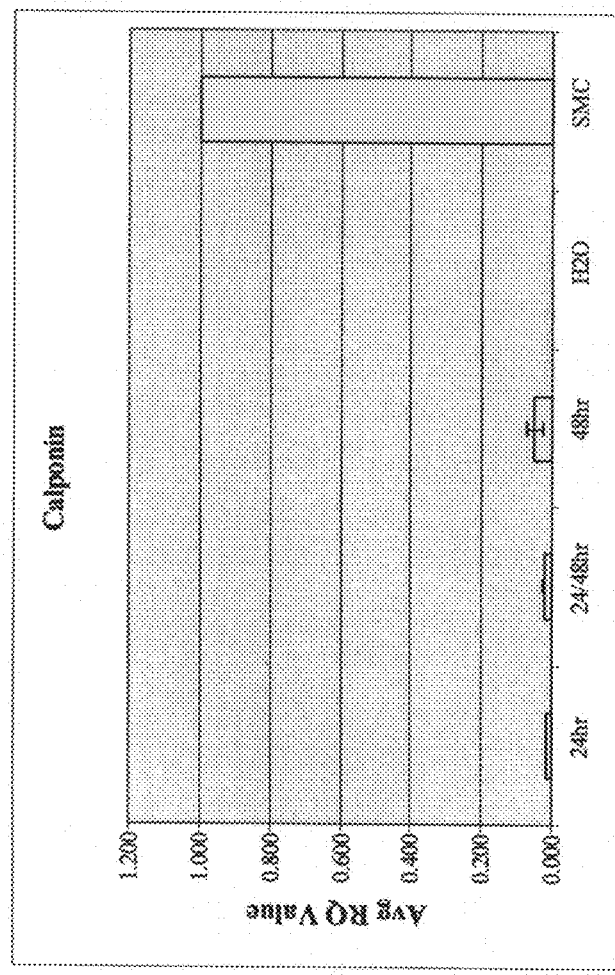
Figure 91D:
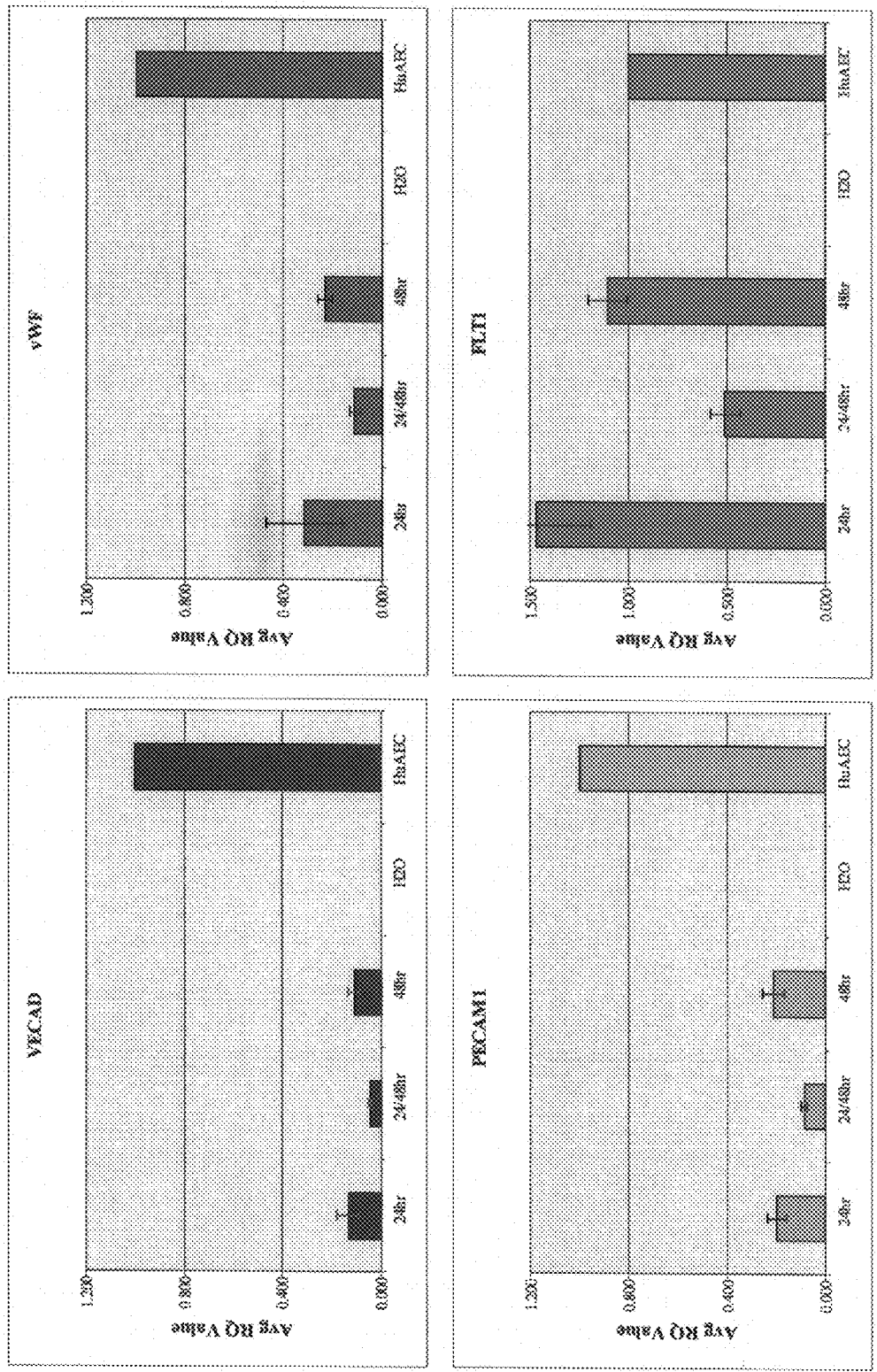
Figure 91E:
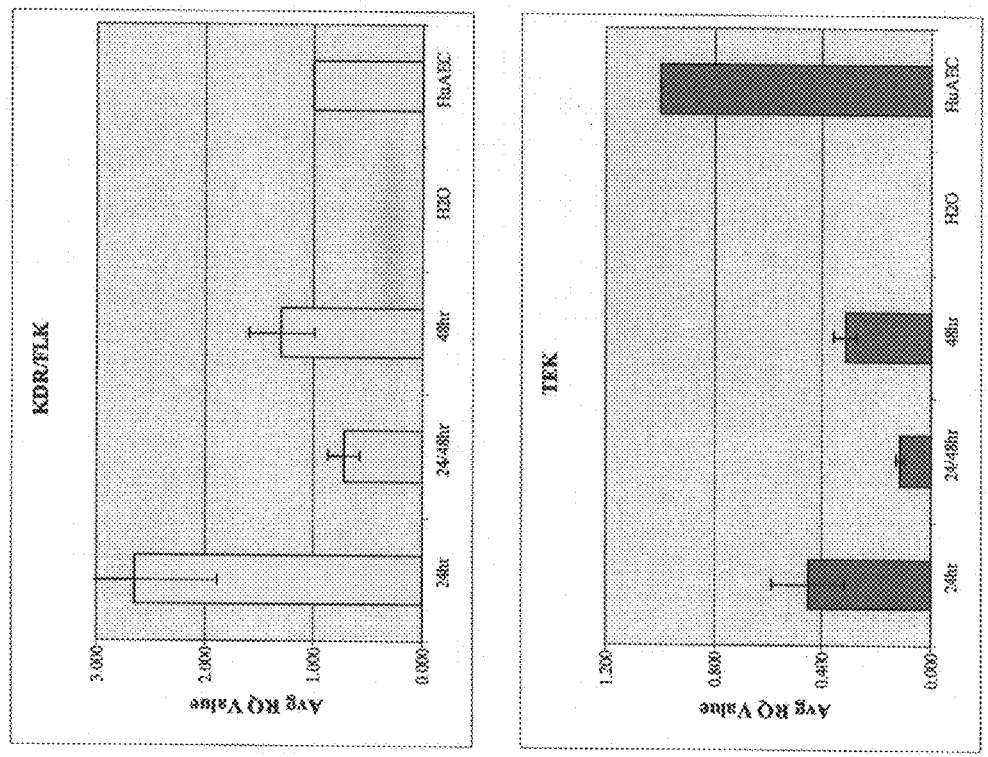

Expression markers in Ad-SVF. We performed a quantitative TaqMan RT-PCR analysis of the cell population derived from the stromal-vascular fraction of adipose tissue adherent on the tissue culture flask within the initial 24-48 hours subsequent to plating, using a panel of defined endothelial, adipocytic and smooth muscle cell specific TaqMan primers. This served to analyze expression markers in the initial adherent cell population as well as establishing a baseline for subsequent analysis of the effects of passage, time and media formulation upon expression of smooth muscle cell specific genes. As shown in FIG. 91A, low but detectable levels of FABP-4 and adiponectin were observed in the adherent cell population within the first 24 hours, consistent with the presence of residual adipocytes. Similarly, an endothelial population defined by expression of VECAD, vWF, PECAM, FLT1, FLK and TEK was present at this time point (FIG. 91D-E). A smooth muscle cell population defined by expression of SMαA, SM22, myocardin, SMMHC and calponin was also observed within the earliest adherent cell population (FIG. 91B-C). We were able to detect all three cell populations at comparable levels within 24-48 hrs of plating. As discussed below, smooth muscle cells were isolated from this mixture of cell populations.

Figure 92A:
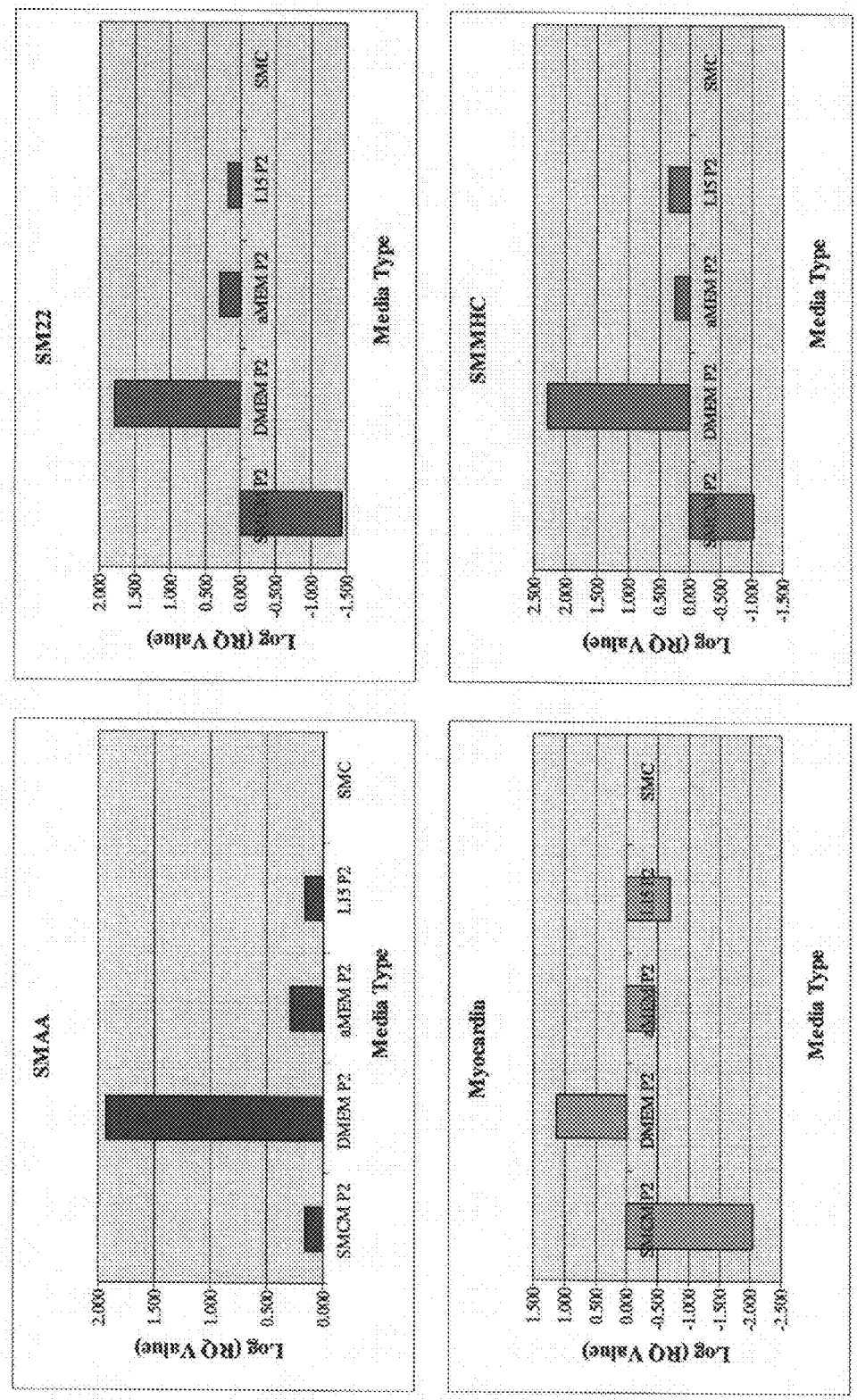
FIG. 92 shows the dependence of smooth muscle markers on media type: (A) SMαA, SM22, myocardin, SMMHC; and (B) calponin.
Figure 92B:
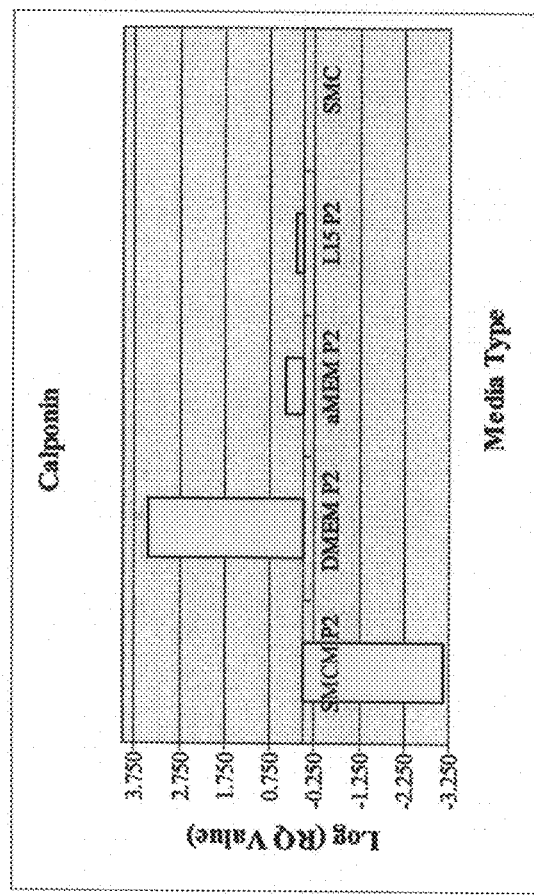

Expression of smooth muscle markers is dependent on media type. As adipose is a heterogenous tissue composed of multiple cell types, it is reasonable to expect that enrichment for smooth muscle cells over endothelial cells or MSCs may be affected by media formulation. Isolation of undifferentiated MSCs from bone-marrow and adipose is closely dependant on media composition (Gong et al. 2009 supra). In particular, the presence of elevated levels of glucose in the media or growth at high density appears to select against the expansion of MSC (Lund et al. 2009 supra; Stolzing et al. Rejuv Res 2006; 9:31-35). We reasoned that modulation of media formulation may be useful in enrichment for smooth muscle cells at the expense of MSC and other cell populations. As shown in FIG. 92A-B (Taqman analysis of SMC marker expression by media type), the expansion of a smooth muscle cell enriched population from adipose-SVF is tightly dependent upon growth in DMEM-HG media. Expansion in α-MEM, SMCM or L15 is associated with a markedly reduced smooth muscle cell phenotype as shown by decreased expression of SMαA, SM22, myocardin, SMMHC and calponin.

Figure 93:
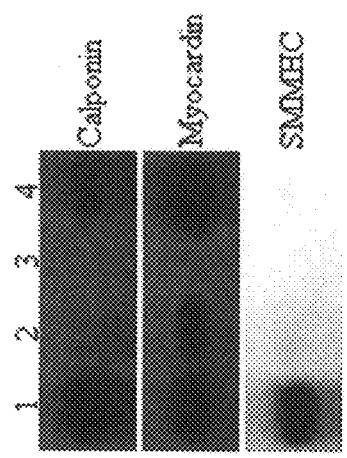
FIG. 93 shows a comparison of the expression of smooth muscle markers calponin, myocardin and SMMHC in adipose-derived cells and mesenchymal stem cells.
Figure 94:
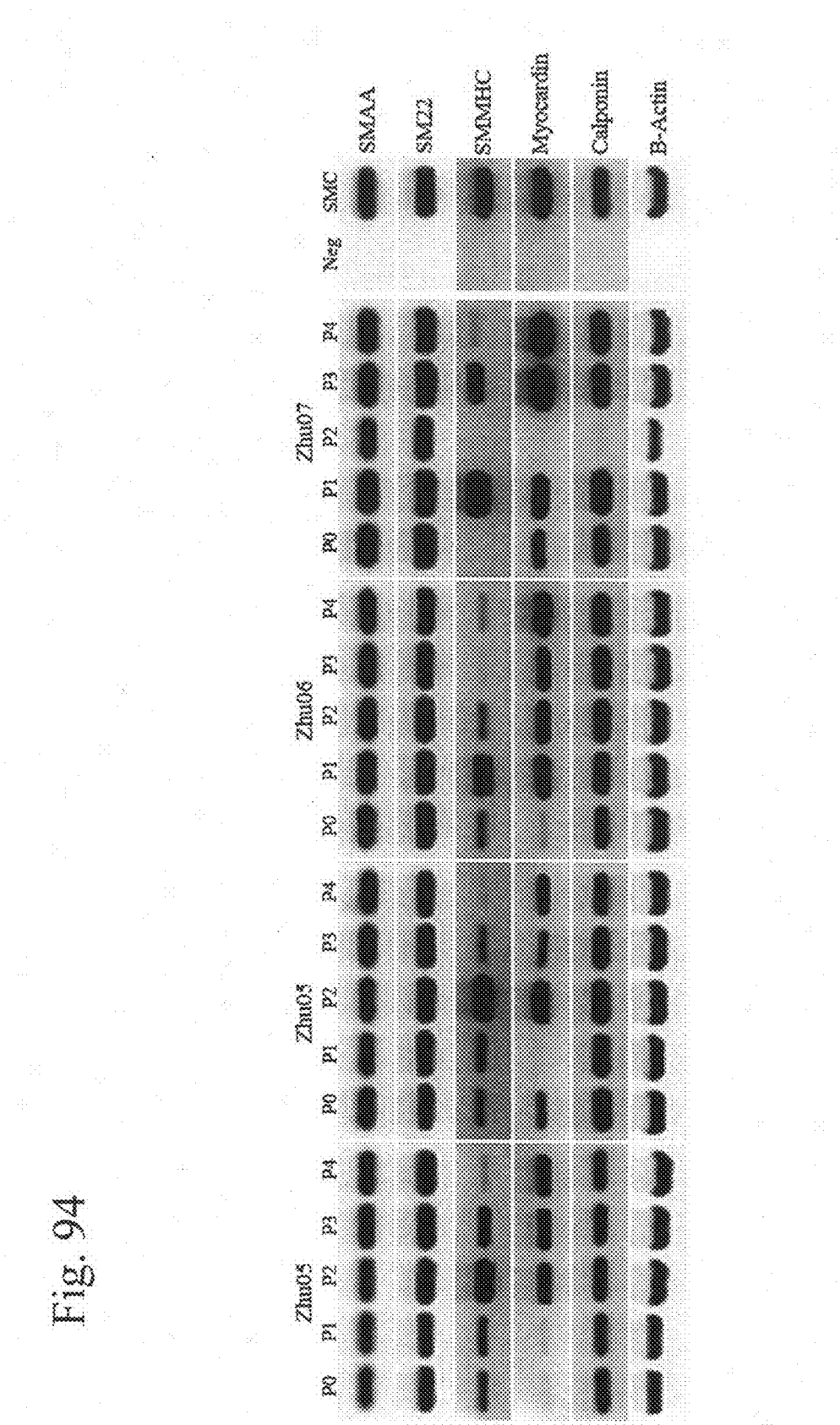
FIG. 94 shows the expression of SMαA, SM22, myocardin and calponin in adipose-derived cells over time.

Ad-SMC more closely resemble smooth muscle cells than MSC. We used semi-quantitative RT-PCR to assess the smooth muscle cell associated gene expression signatures of Ad-SMC and MSC. As shown in FIG. 93, the expression of the key smooth muscle markers calponin, myocardin and SMMHC is noticeably more pronounced in Ad-SMC when compared to MSC, supporting our hypothesis that this cell population is more similar to smooth muscle cells than to MSC. We then evaluated the stability of expression of SMC specific markers across multiple independent adipose preparations (n=4) and over 5 passages in culture. As shown in FIG. 94 (RT-PCR of Ads across passage), the expression of SMαA, SM22, SMMHC, myocardin and calponin is remarkably constant across passage and is independent of donor, demonstrating that expression of a smooth muscle cell phenotype is stable over time. These observations are consistent with Ad-SMC being a more fully differentiated, phenotypically stable cell population.

Array-based RT-PCR analysis demonstrates significant differences in gene expression of key markers between Ad-SMC and MSC. We have used the SABiosciences MSC Marker Array panel to systematically identify differences in gene expression between passage controlled (P2) Ad-SMC and MSC. This panel profiles the expression status of 84 genes involved in MSC pluripotency and self-renewal. A summary of the key markers identified as distinct between Ad-SMC and MSC is shown in Table 18.1.

TABLE 18.1

| Symbol | Description | MSC Ct | Hu Ad-SMC P4 Ct | Fold Regulation Ad-SMC vs MSC |
|---|---|---|---|---|
| BMP6 | Bone morphogenetic protein 6 | 34.09 | 28.57 | 35.5555 |
| CD44 | CD44 molecule (Indian blood group) | 31.87 | 23.06 | 347.7725 |
| IL1B | Interleukin 1, beta | 35 | 29.62 | 32.2673 |
| GDF5 | Growth differentiation factor 5 | 25.34 | 31.89 | −120.9276 |
| HGF | Hepatocyte growth factor (hepapoietin A; scatter factor) | 27.95 | 32.77 | −36.4539 |
| LIF | Leukemia inhibitory factor (cholinergic differentiation factor) | 29.37 | 35 | −63.9113 |
| MCAM | Melanoma cell adhesion molecule | 27.99 | 33.67 | −66.1652 |
| RUNX2 | Runt related transcription factor 2 | 27.69 | 30.58 | −12.1426 |
| VCAM1 | Vascular cell adhesion molecule 1 | 24.36 | 34.1 | −1103.5987 |

| Historically Defined Cell Surface Markers | | | | |
|---|---|---|---|---|
| Symbol | Description | MSC Ct | Hu Ads P4 Ct | Fold Regulation MSC vs. Ads |
| ALCAM | Activated leukocyte cell adhesion molecule (CD166) | 24.88 | 24.44 | 1.0512 |
| ENG | Endoglin (CD105) | 23.06 | 22.57 | 1.0882 |
| NT5E | 5'-nucleotidase, ecto (CD73) | 25.2 | 24.38 | 1.3679 |
| THY1 | Thy-1 cell surface antigen (CD90) | 29.54 | 29.68 | −1.4221 |

Significant (at least ten fold) down-regulation in Ad-SMC relative to MSC was observed for GDF5, HGF, LIF, MCAM, RUNX2 and VCAM1. Significant (at least ten fold) up-regulation in Ad-SMC compared to MSC was observed for BMP6, CD44, and IL1β. These key differences in gene expression were observed to remain consistent independent of passage or cell sample (n=6, data not shown).

Gene expression analysis was continued using the SABiosciences Surface Marker Array. A summary of the key results is presented in Table 18.2, where we have examined Ad-SMC at P0 and P4.

TABLE 18.2

PCR Array Catalog # PAHS-055A Human Cell Surface Markers on Human Adipose Zhu05 SQ RT 300xg DMEM

| Cell Type | Symbol | Description | Ct P0 | Ct P4 | Fold Regulation P0 to P4 |
|---|---|---|---|---|---|
| SMC | MYH9 | Myosin, heavy chain 9, non-muscle | 23.59 | 24.2 | −2.5245 |
|  | MYH10 | Myosin, heavy chain 10, non-muscle | 25.94 | 26.05 | −1.7851 |
|  | MYOCD | Myocardin | 35 | 33.09 | 2.2721 |
| Endo-thelial | ENG | Endoglin (Osler-Rendu-Weber syndrome 1) | 23.84 | 22.73 | 1.305 |
|  | ICAM2 | Intercellular adhesion molecule 2 | 27.35 | 29.02 | −5.2634 |
|  | NOS3 | Nitric oxide synthase 3 (endothelial cell) | 30.01 | 31.66 | −5.191 |
|  | PECAM1* | Platelet/endothelial cell adhesion molecule (CD31 antigen) | 29.07 | 35 | −100.8453 |
|  | SELP | Selectin P (granule membrane protein 140kDa, antigen CD62) | 35 | 35 | N/A |
|  | TEK* | TEK tyrosine kinase, endothelial (venous malformations, multiple cutaneous and mucosal) | 31.27 | 25.68 | 29.1212 |
|  | VCAM1* | Vascular cell adhesion molecule 1 | 25.88 | 34.16 | −514.1338 |
|  | VWF* | Von Willebrand factor | 27.2 | 31.49 | −32.3569 |
| Adipocyte | RETN | Resistin | 35 | 35 | N/A |
| Fibroblast | ALCAM | Activated leukocyte cell adhesion molecule | 28.6 | 24.98 | 7.4333 |
|  | COL1A1 | Collagen, type I, alpha 1 | 20.26 | 20.65 | −2.1675 |
|  | COL1A2 | Collagen, type I, alpha 2 | 19.36 | 18.2 | 1.351 |
| HLA | HLA-A | Major histocompatibility complex, class I, A | 24.53 | 24.7 | −1.8609 |
|  | HLA-DRA* | Major histocompatibility complex, class II, DR alpha | 26.57 | 34.12 | −309.9733 |
|  | CD74* | CD74 molecule, major histocompatibility complex, class II invariant chain | 28.13 | 35 | −193.4746 |
| Other | NT5E | 5'-nucleotidase, ecto (CD73) | 27.43 | 24.24 | 5.5174 |
|  | NCAM1 | Neural cell adhesion molecule 1 | 35 | 35 | N/A |

*= Change in Fold Regulation > |10.01|

Figure 95:
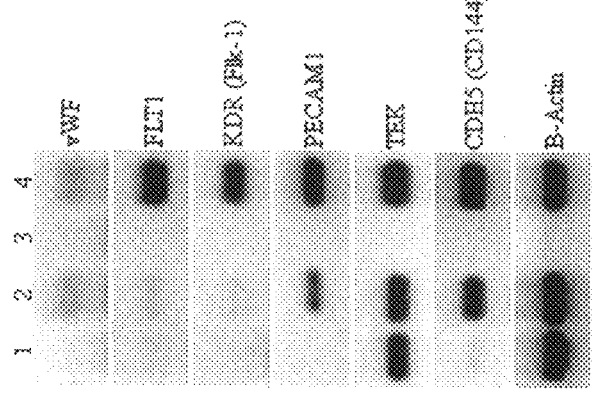
FIG. 95 shows the expression of endothelial markers in adipose-derived cells and mesenchymal stem cells.

Expression of the fibroblastic/stromal markers ALCAM, COL1A1 and COL1A2 is maintained across passage, as are the smooth muscle cell specific markers MYH10, MYH9 and MYOCD. The population is negative for the adipocyte marker RETN, indicating that there is minimal contamination with adherent adipocytes. Importantly, although Ad-SMC acquire an HLA MHC II negative status within 4 passages they are initially HLA MHC II positive, a key distinction with MSC which are MHC II negative. Another interesting observation is that Ad-SMC becomes progressively less endothelial with passage, as judged by the general trend in down-regulation of the endothelial markers ENG, ICAM2, NOS3, PECAM1, SELP, TEK, VECAM and VWF. This data is independently confirmed by the RT-PCR analysis in FIG. 95.

To further compare the gene expression profiles between the adipose-derived smooth muscle cells (Ad-SMC) and mesenchymal stem cells (MSC), a PCR-based gene array analysis was performed for human mesenchymal stem cell markers (SABiosciences; PCR Array Catalog #PAHS-082A) (data not shown). The results illustrated the extent of homologous gene expression among Ad-SMC, MSC, and a well characterized non-MSC cell type, human aortic endothelial cells (HuAEC). Of the 84 human MSC genes analyzed, human Ad-SMC share only 27% homology (23 of 84 genes) with human MSC at initial isolation (data not shown). In contrast, the well characterized, non-MSC, HuAEC share 49% homology (41 of 84 genes) with MSC (data not shown). This supports the conclusion that the Ad-SMC share significantly less homology with MSC than HuAEC, which is a well-known non-MSC cell type. Thus, the Ad-SMC are even less like MSCs than HuAEC are, further supporting the conclusion that the Ad-SMC cells isolated from adipose tissue are Ad-SMC and not MSC.

Figure 96:
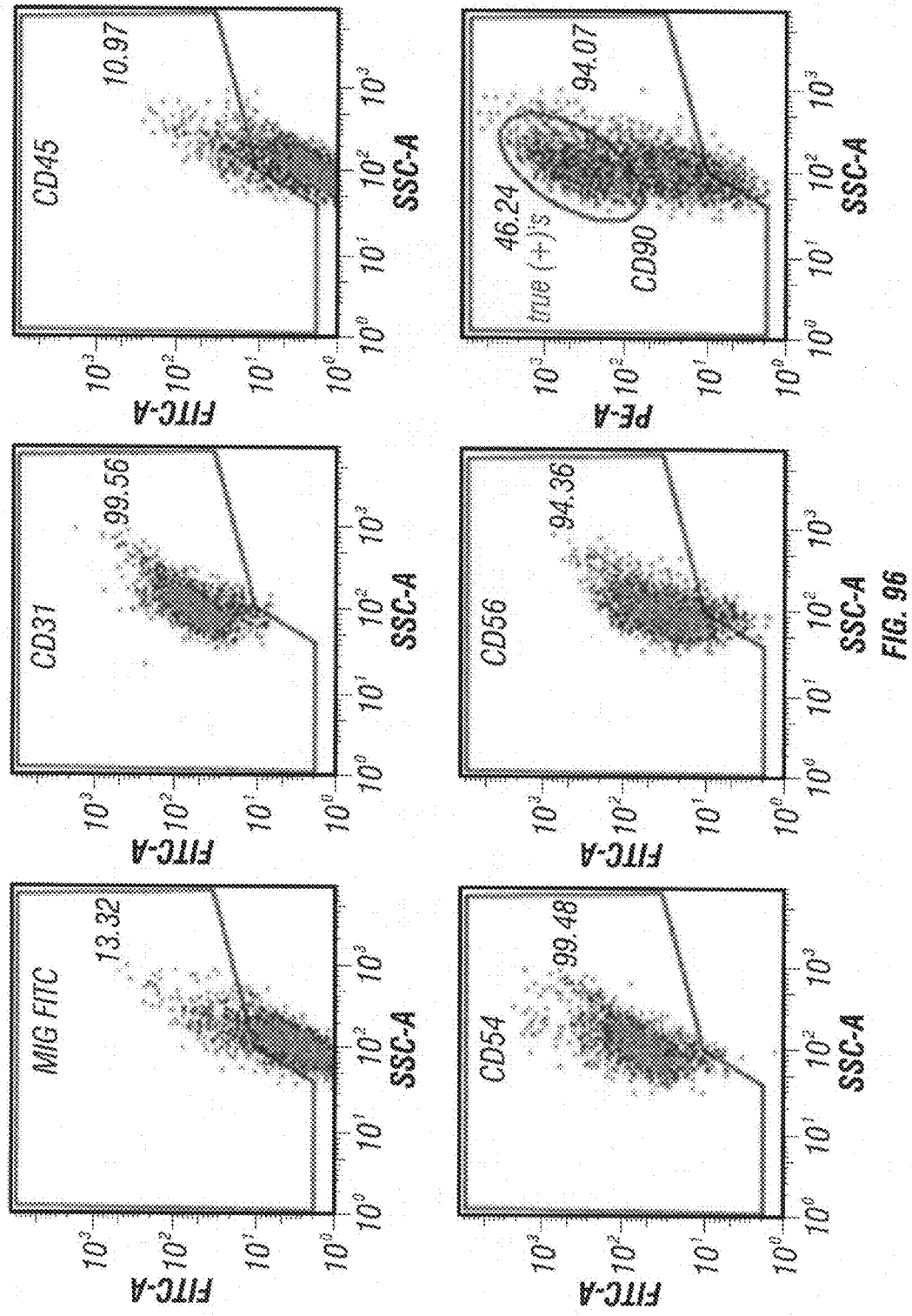
FIG. 96 shows the expression of cell surface markers in adipose-derived cells.
Figure 96:
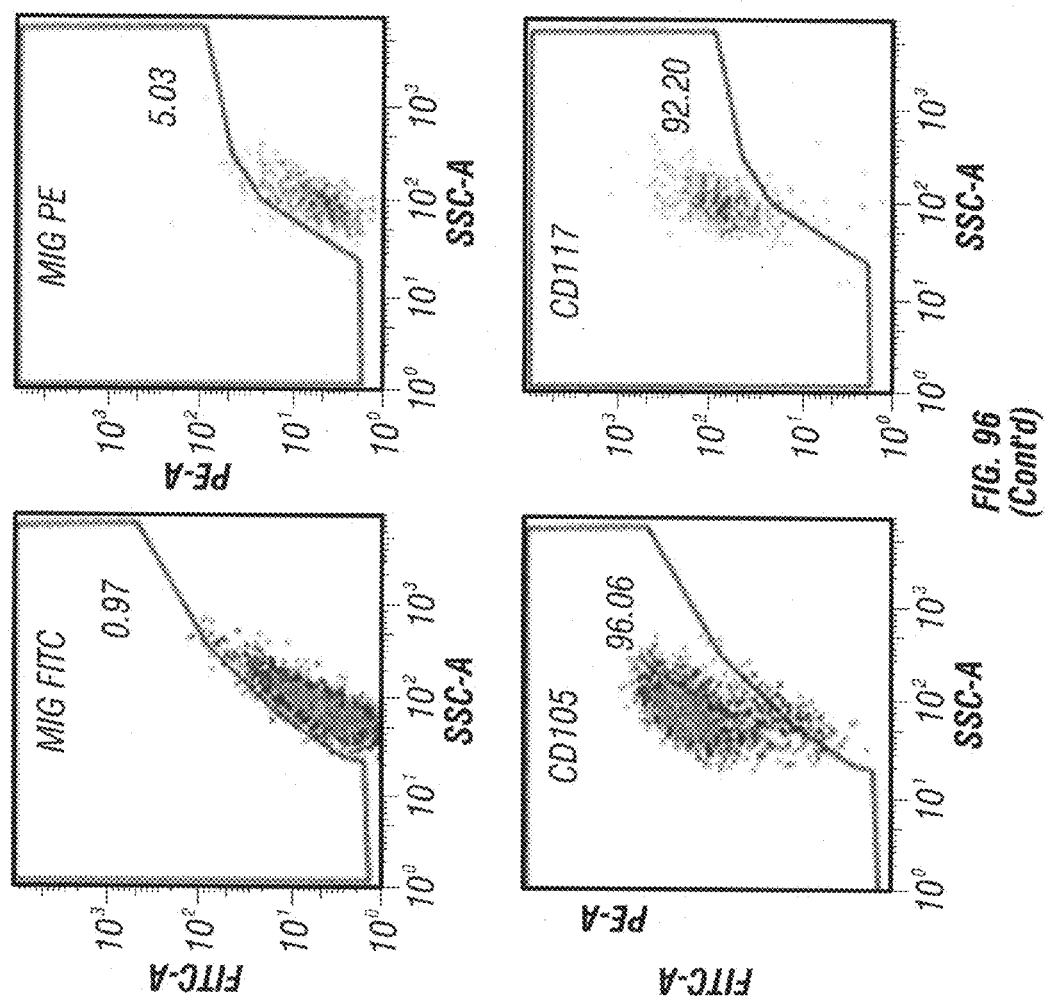
Figure 96:
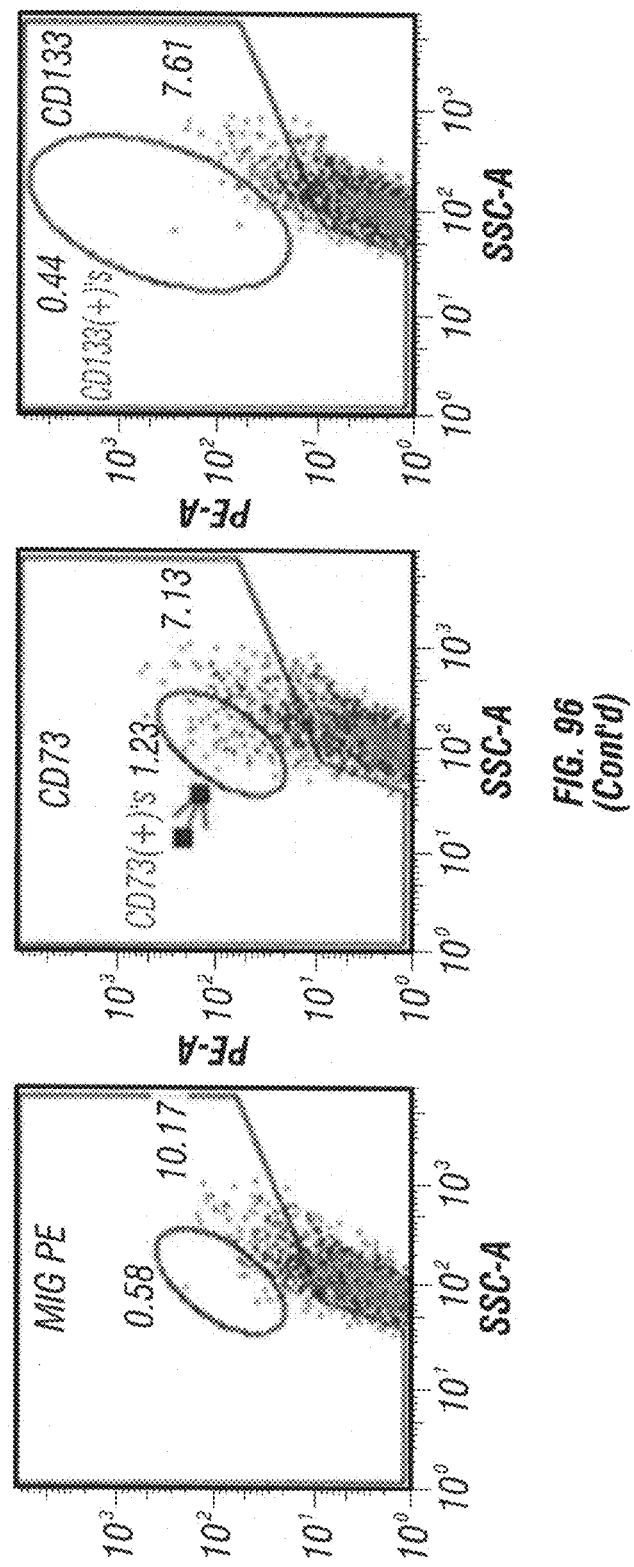
Figure 97:
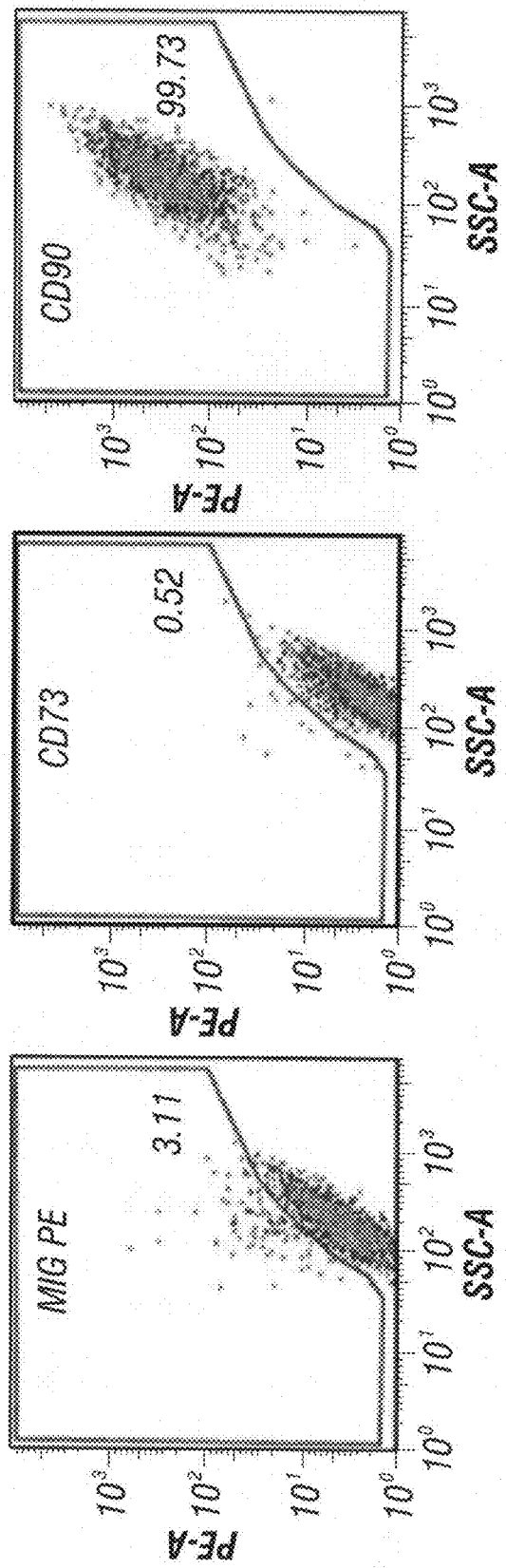
FIG. 97 shows the expression of cell surface markers in mesenchymal stem cells.
Figure 97:
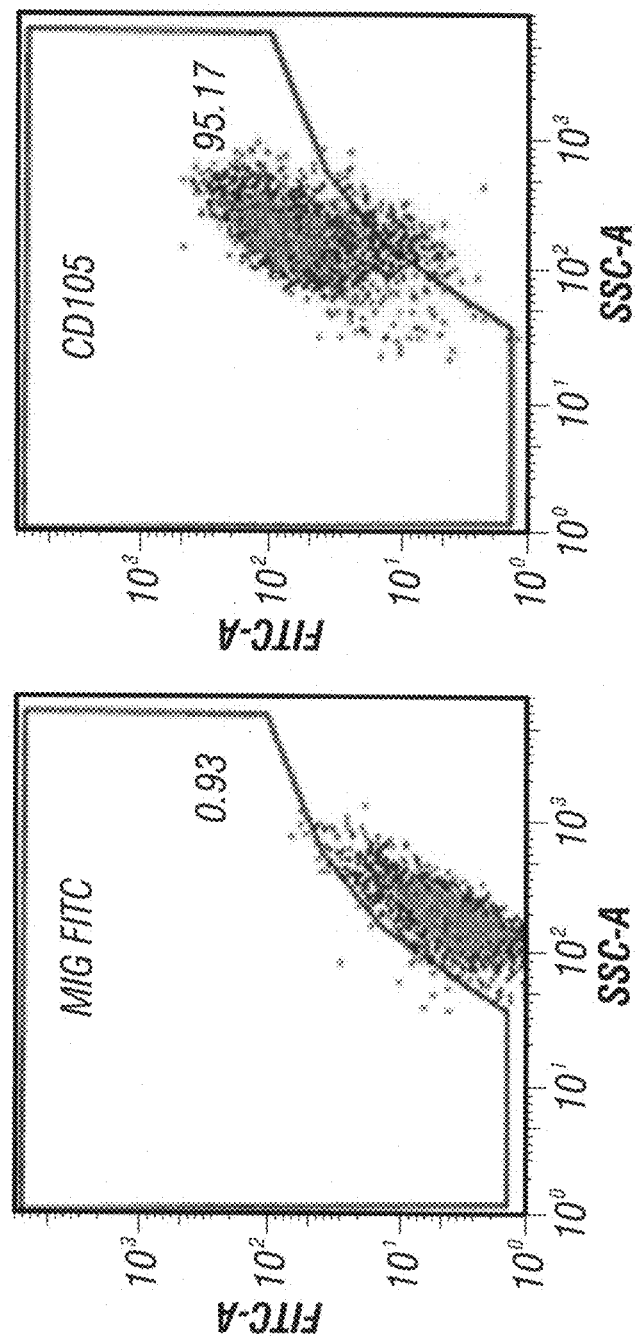

The cell surface profile of Ad-SMC is significantly different from that defined for MSC. We observed that both MSC and Ad-SMC share expression of the surface markers CD73, CD90, CD105 and CD166 which are traditionally associated with MSC (Table 18.1). However, as discussed below, these markers have no intrinsic biological significance beyond their historical association with MSC. The gene expression results from the cell surface marker RT-PCR analysis were generally reflected in the comparative FACs analysis presented in FIG. 96A-C (Ad-SMCs) and FIG. 97A-B (MSCs), which shows that Ad-SMC are CD31+, CD45+, CD54+, CD56+, CD90+, CD105+. Importantly, Ad-SMC was CD45+and CD117+, a clear distinction from MSC, which are CD45− CD117−. Expression of CD73 is consistent with that previously reported for adipose stromal vascular fraction (da Silva Meirelles et al. J Cell Sci., 119:2204 (2006)), but differs from that reported for bone-marrow derived MSC. We were also able to observe a small but distinct population of CD133+cells, possibly reflecting a small, pluripotent cell sub-population.

Figure 98:
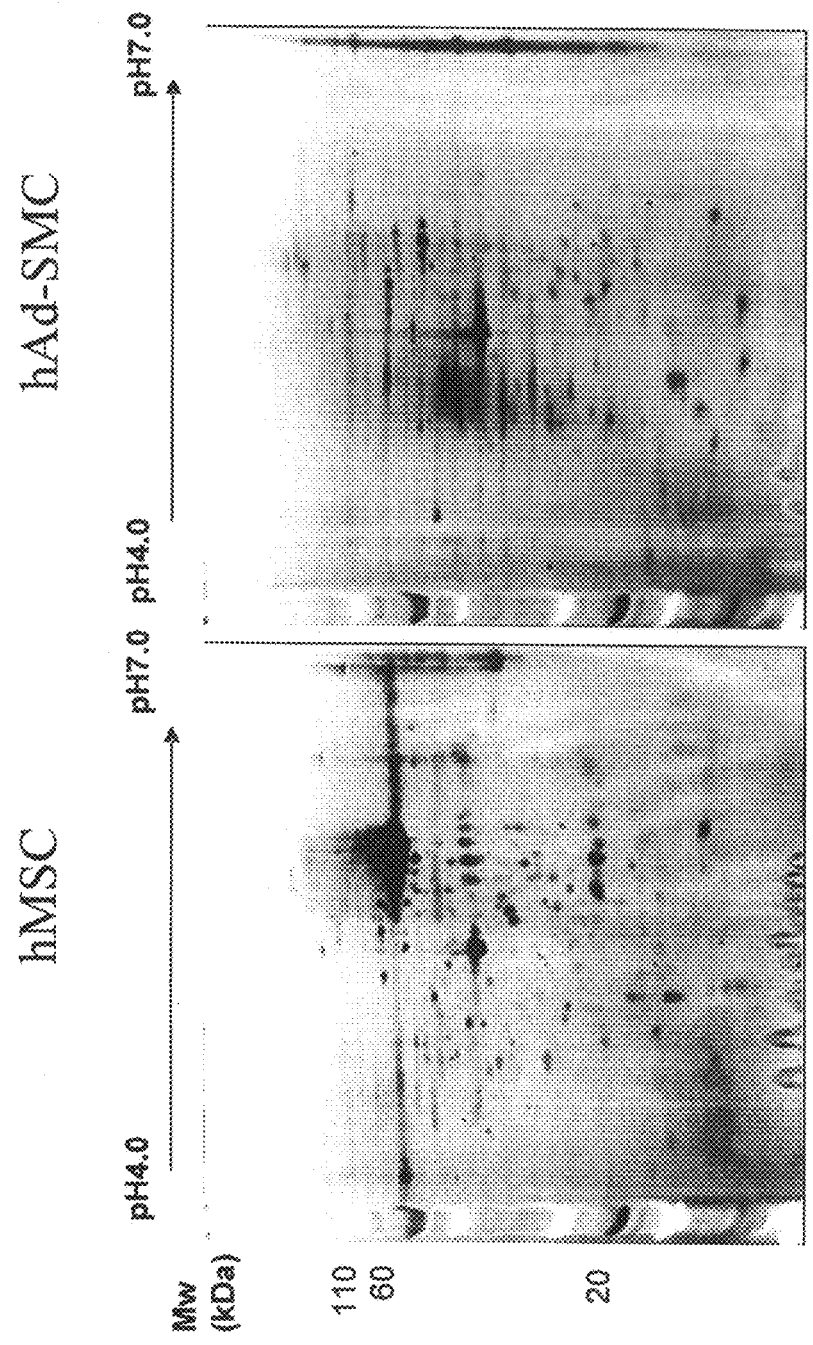
FIG. 98 shows a comparative analysis of the proteomic signatures of MSCs, bladder-derived SMCs, Ad-SMCs, and human aortic smooth muscle cells.

Passage controlled MSC and Ad-SMC have unique proteomic signatures. FIG. 98 shows a comparative analysis of the whole proteomic signatures of MSC, bladder-derived SMC, Ad-SMC, and human aortic smooth muscle cells. The top two panels demonstrate that Ad-SMCs are distinct from MSC and are also clearly different from MSC isolated from adipose tissue as well as other classes of stem and progenitor cells (Roche et al; Proteomics 2009; 9:223-232; Noel et al. Exp Cell Res 2008; 314:1575-1584). The arrows on both gels highlight one difference between MSCs and AdSMCs; concentration of proteins at different and distinct locations within the pH gradient and molecular weight range. MSC have this protein concentration closer to a pH of 7.0, and greater than or equal to 60,000 molecular weight. In contrast, AdSMC have this protein concentration closer to a pH of 4.0, and less than 60,000 in molecular weight. AdSMC also had more protein present with pI above 7 than MSC, as indicated by the smear along the right outside edge of the gel at pH 7.0. Bladder smooth muscle cells were analyzed as a control. The boxes indicate areas of similarity among all samples. It is clear that the AdSMC protein profile is most like the profile for bladder-derived SMC (lower left panel), which is distinct from the pattern observed for MSC. Aortic smooth muscle cells were also analyzed as an additional smooth muscle cell control (lower right panel). The proteomic signature of the aortic smooth muscle cells and bladder smooth muscle cells are almost identical. Taken together, the high degree of similarity among the profiles for AdSMC, bladder and aortic smooth muscle cells, which are distinctly different from the profile of the MSC, supports the conclusion that SMCs, not MSCs, are being isolated from adipose tissue. All gels were stained with SPRYO Ruby stain to visualize the protein pattern.

Figure 99:
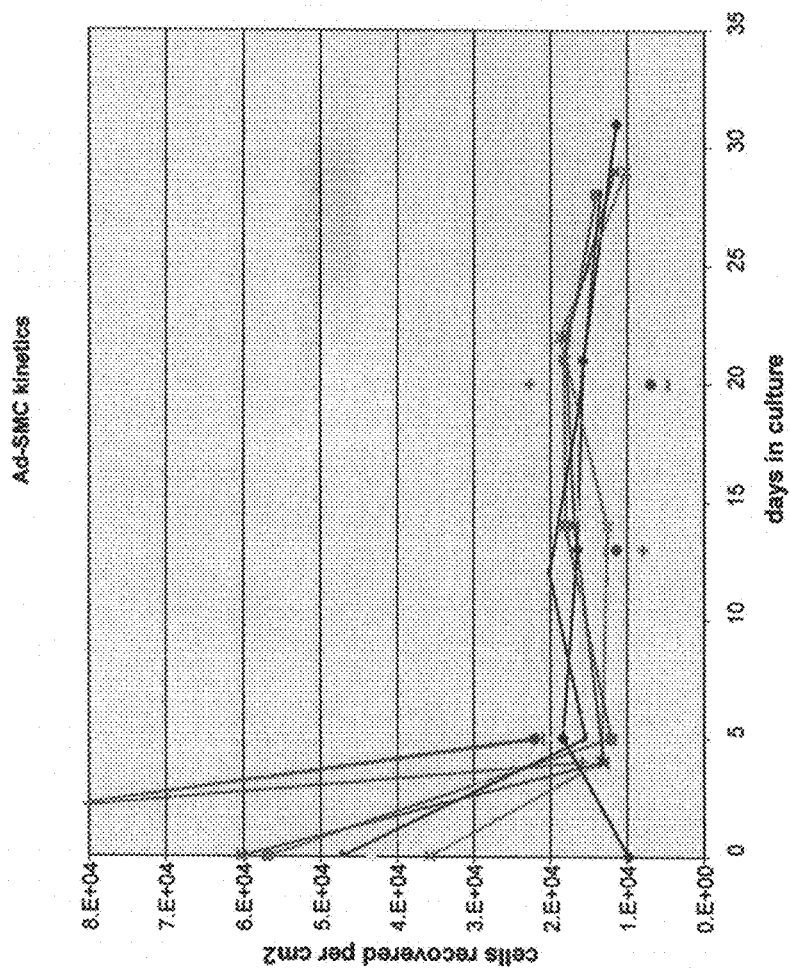
FIG. 99 shows the proliferative capacity of adipose-derived cells over time in culture.

Growth kinetics of Ad-SMC differ markedly from MSC. The proliferative potential of Ad-SMC differs markedly from MSC which have been successfully expanded to up to 40 passages (Bruder et al., J Cell Biochem., 64:278-294 (1997)). As shown in FIG. 99, Ad-SMC show a marked decline in proliferative capacity after the 4th-5th day in culture. We have also observed that unlike MSC, Ad-SMC exhibit contact dependant inhibition of proliferation. These observations demonstrate that Ad-SMC have no capacity for self-renewal and therefore by definition are not stem or progenitor cells. MSCs do not exhibit contact inhibition of proliferation and they can be observed piling on top of each other, similar to foci formation in transformed cell cultures. This is consistent with previous observations (Zhou et al. 2006 supra).

Figure 100:
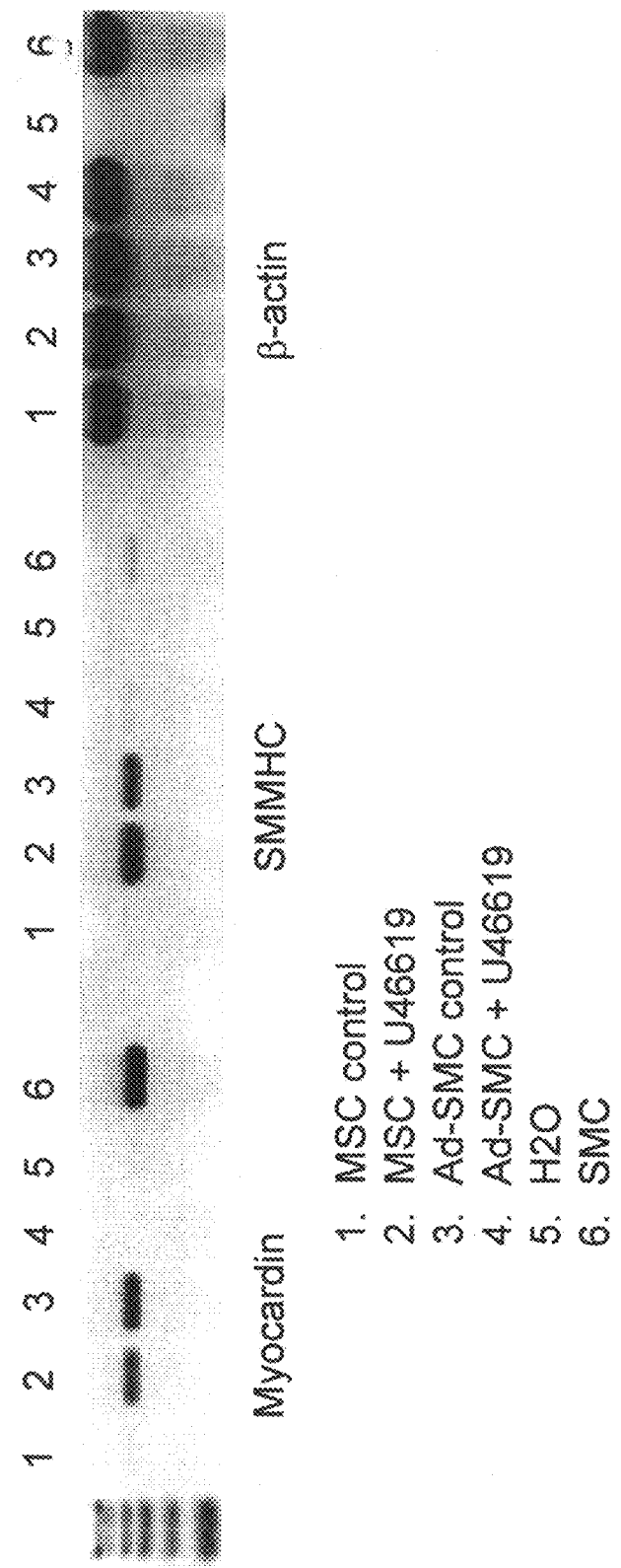
FIG. 100 shows the response of adipose-derived cells and mesenchymal stem cells to U46619.

Ad-SMC and MSC have distinctly opposing responses to treatment with U46619. As part of our efforts to evaluate the effects of small molecules targeting signaling cascades involved in the activation of smooth muscle cell related developmental pathways, we have focused on U46619, a thromboxane A2 mimetic whose effects include increasing intracellular $Ca^{2+}$ levels and activation of RhoA, CaM and MLC kinase signaling cascades. As reported previously (Kim et al. 2009, Stem Cells. 27(1):191-199), we have confirmed that treatment with U46619 (11.1M) led to up-regulation of the key smooth muscle cell markers myocardin and SMMHC in MSC. However, Ad-SMC responded to the same treatment by unambiguous downregulation of myocardin and SMMHC expression as shown in FIG. 100. These results provide clear evidence for a functional dichotomy between Ad-SMC and MSC.

Expression of functional markers. FIG. 101 provides results of RT-PCR analysis of mesodermal differentiation markers. Lane contents: 1: MSC control; 2:MSC experimental; 3: AdSMC control; 4: AdMSC experimental; 5: Peripheral blood control; 6: Peripheral blood experimental; and 7: $H_2O$. The expression of markers of mesodermal differentiation in MSC and AdSMCs undergoing adipogenic differentiation. AdSMC shows significantly greater expression of ostepontin relative to MSC during growth under standard conditions (n=1). Expression of Oct4B, a splice-variant of Oct4A, an established marker for pluripotentiality (Kotoula et al., 2008, Stem Cells 26(1): 290-1), is significantly upregulated in adipose-derived cells relative to MSC. Neither MSC nor adipose-derived cells show expression of Oct4A.

FIG. 102 shows the results of RT-PCR analysis of Oct4A/Oct4B expression in MSC/AdSMC. Lane contents: 1: Bladder SMC; 2: HFF-1 (human fibroblast); 3: MSC; 4: AdSMC; 5: peripheral blood; 6: $H_2O$. Expression of the closely related transcriptional isoforms Oct4A and Oct4B was evaluated in MSC, AdSMC, fibroblast and SMC lines. No expression of the pluripotency marker Oct4A (Gong et al. 2009 supra) was observed, though all cell lines evaluated expressed Oct4B (n=1).

Discussion. In this report, we have evaluated the marker expression of adipose-derived cell populations. Adipose tissue represents a heterogenous mix of cell types, including endothelial cells, pericytes, smooth muscle cells, adipocytes and MSC (Lin et al., Stem Cells Dev 2008; 17:1053-1063). Adherent cells from the stromal vascular fraction of adipose isolated under different conditions and expanded at different densities and media formulations are often grouped together as MSC, with no systematic approach towards establishing cellular composition across disparate conditions (Rebelatto et al., 2008 supra; Liu et al. 2007 supra; Jack et al. Biomaterials 2009; 30:3259-3270). Similarly, adherent cells from the mononuclear fraction of bone marrow are typically referred to collectively as MSC. However, multiple laboratories claim to have isolated distinct bone-marrow derived stem cell or progenitor populations with disparate but overlapping phenotypic and functional properties, though it remains to be determined whether or not these represent unique cell types in vivo (Ulloa-Montoya et al., J Biosci Bioeng 2005; 100:12-27; Ratajczak et al. Folia Histochem et Cyto 2004; 42:139-146; Lodie et al. Tissue Eng 2002; 8:739-751). Likewise, a number of studies have reported conflicting conclusions regarding the degree of functional and phenotypic similarity between adipose and bone-marrow derived MSC (Roche et al. Proteomics 2009; 9:223-232; Noel et al. Exp Cell Res 2008; 314:1575-1584). The identification of any non-bone marrow derived stromal cell population as MSC has been questioned through the application of in vivo heterotopic ossicle formation assays, which indicate that only bone marrow derived stromal cells may be labeled as MSC (Kalz et al. Stem Cells 2008; 26:2419-24). These data notwithstanding, it may be reasonably concluded from evaluation of the published literature that adipose-derived MSC and bone-marrow derived MSC share overlapping but distinctive differentiation potentials, as evaluated by quantitative PCR-based lineage analysis (Roche et al. 2009 supra; Noel et al. 2008 supra; Rebelatto et al. 2008 supra; Liu et al. 2007 supra).

We began our analysis of the initial, adherent adipose stromal vascular fraction-derived cells using TaqMan Q-RTPCR. As shown in FIGS. 91 & 92, we were able to isolate a cell population that consistently displays a smooth muscle cell phenotype as shown by expression of SMαA, SM22, SMMHC, calponin and myocardin. Although endothelial and adipocytic markers are also detectable within the initial 24-48 hour window subsequent to plating, the population retains smooth muscle characteristics as the incidence of other cell characteristics decrease with passage (FIGS. 91, 92, Table 7). Expression of adipogenic markers was observed to rapidly decline (Table 7). Unlike other reports describing the isolation of MSCs from adipose and their subsequent applications in tissue engineering, no inductive cytokines or additional, exogenous growth factors are required to direct differentiation of a smooth muscle associated gene expression signature (Jack et al. 2009 supra).

Ad-SMCs are directly comparable to bladder-derived smooth muscle cells as defined by gene and protein expression of smooth muscle cell associated markers and $Ca^{2+}$ dependant contractility (Basu et al., 2009 in preparation; Basu et al. International Society for Stem Cell Research, $7^{th}$ Annual Meeting, Jul. 8-11, 2009). Isolation of Ad-SMCs is directly dependant upon isolation in a particular media formulation—as shown in FIG. 91B, expression of smooth muscle cell markers is contingent upon expansion in DMEM-HG media. Growth in other media types leads to loss of smooth muscle cell associated characteristics and possibly leads to enrichment for more mesenchymal progenitor populations (Gong et al. 2009 supra). To this end, the presence of high glucose levels in media or expansion at high density has been shown to be detrimental to the manifestation of a robust MSC differentiation potential (Lund et al. 2009 supra). Additional studies have shown increased osteogenic differentiation potential of MSC in low glucose media compared to high glucose media (Jager et al. Biomed Tech (Berl) 2003; 48:241-244). It has been suggested that the presence of advanced glycation end products related to glucose and other sugars may lead to loss of differentiation potential in MSC (Kume et al. J Bone Miner Res 2005; 20:1647-1658). Taken together, these observations demonstrate that expansion of adipose-SVF derived cells under conditions of high density and high glucose leads to selection for a smooth muscle cell phenotype and against acquisition of MSC characteristics.

Continuing with the gene expression approach, we have used the Array PCR data panel in Tables 18.1 and 18.2 to identify a core group of markers that consistently and unambiguously discriminates Ad-SMC from MSC. BMP6, CD44 and IL-1β show at least 30 fold greater expression in Ad-SMC compared to MSC, whereas GDF5, HGF, LIF, MCAM, RUNX2 and VCAM1 demonstrate at least 30 fold greater expression in MSC relative to Ad-SMC. These results are consistent across multiple donor samples (n=3), suggesting that our observations are not a consequence of donor variability or random fluctuations in gene expression levels. BMP6 is a member of the TGF-β superfamily which which has been implicated in the regulation of chrondrogenesis and osteogenesis during MSC differentiation (Henning et al. J Cell Physiol 2007; 211:682-291; Friedman et al. J Cell Biochem 2006; 98:538-554). Our data showing up-regulation of BMP6 expression clearly discriminates Ad-SMC from adipose-derived MSC where down-regulation of BMP6 expression was observed relative to bone marrow derived MSC (Henning et al. 2007 supra). Interestingly, induction of adipose-derived MSC with exogenous BMP6 led to an up-regulation in expression of the TGF-β1 receptor (Henning et al. 2007 supra). The TGF-β signaling pathway is well established to have a critical role in activation of smooth muscle cell specific developmental pathways Owens et al. Acta Physiol Scand 1998; 164:623-635. CD44 is a well known marker of MSC-like cells and has been widely implicated in cell growth, migration and homing (Khaldoyanidi S. Cell Stem Cell 2008; 2:198-200). Expression of CD44 between adipose and bone-marrow derived MSCs has been shown to be similar in terms of overall expression, regulation of transcriptional splice variants and the overall stability of gene expression (Peroni et al. Exp Cell Res 2008; 314:603-615).

Genes found to be up-regulated in MSC over Ad-SMC include GDF5, which has been shown to be important in the regulation of chondrogenic and osteogenic differentiation in MSC, and HGF. HGF and its cognate receptor c-met have been identified with the regulation of motility and proliferation in bone-marrow derived MSC (Neuss et al. Stem Cells 2004; 22:405-414). Consistent with earlier reports, we have observed expression of the pro-inflammatory cytokine LIF to be a key distinguishing feature separating MSCs and Ad-SMCs (Majumdar et al. J Hematother Stem Cell Res 2000; 9:841-8). Importantly, LIF acts as a key marker of progenitor status in MSC, serving as a proxy for maximum differentiation potential (Whitney et al. Tissue Eng Part A 2009; 15:1). This observation is in agreement with our interpretation that Ad-SMC represents a smooth muscle cell population. MCAM (CD146) is a cell surface marker closely associated with MSC derived from the perivascular niche of adipose (Zannettino et al. J Cell Physiol 2008; 214:413-421) and bone-marrow (Baksh et al. Stem Cells 2007; 25:1384-92). The expression of CD146 appears to be closely correlated with the stem cell potential of MSC-like cell populations from adipose or bone-marrow (Zannettino et al. 2008 supra; Baksh et al. 2007 supra; Gronthos et al. J Cell Physiol 2001; 189: 54-63). RUNX2 is a transcription factor involved in regulation of osteogenesis during differentiation of MSC (Isenmann et al., Stem Cells 2009). Expression of the cell-adhesion marker VCAM1 (CD106) is also characteristic of MSC isolated from adipose (Zannettino et al. 2008 supra) or bone-marrow (Brooke et al. Stem Cells Dev 2008; 17:929-40). Finally, Ad-SMC show strong expression of MHC Class II, unlike MSC isolated from either adipose or bone marrow (Niemeyer et al. Tissue Eng 2007; 13:111-121).

Taken together, the gene expression data suggest that Ad-SMC represent a more fully differentiated SMC population, rather than an MSC-like cell population. This interpretation is corroborated by the 2D whole proteome comparison of Ad-SMC with MSC shown in FIG. 39, which demonstrates that Ad-SMC and MSC have distinctive and unique proteomic signatures. Additional comparison of the Ad-MSC proteomic profile with that reported for adipose-derived MSC and other classes of stem or progenitor cell shows little, if any, significant overlap (Noel et al. 2008 supra; Rebelatto et al. 2008 supra). Given the associated expression of multiple mature smooth muscle cell markers and loss of endothelial markers as well as functional contractility comparable to bladder-derived smooth muscle cells (Basu et al., 2009; in preparation; Basu et al. International Society for Stem Cell Research, $7^{th}$ Annual Meeting, Jul. 8-11, 2009), these data strongly suggest that Ad-SMC are in fact smooth muscle cells rather than MSCs.

In parallel with the gene expression studies discussed above, we have examined the expression of key MSC-associated cell surface markers on both bone-marrow derived MSC and Ad-SMC by FACS. Both cell types were consistently positive for CD90+ and CD105+ but were negative for CD73, a well established marker for MSC, suggesting the potential for considerable heterogeneity in the expression of standard MSC markers (Chamberlain et al. Stem Cells 2007; 25:2739-49). Furthermore, Ad-SMC were observed to be CD45+ CD117+, (FIG. 96) which unambiguously discriminates them from MSC derived from either adipose or bone marrow sources (Lee et al. Cell Physiol Biochem 2004; 14:311-324). Identification of a CD45+ compartment suggests the existence of a sub-population of hematopoeitic origin, unlike MSC. These observations notwithstanding, we believe that the identification of cell surface markers such as CD73, CD90 and CD105 with MSC has no intrinsic biological significance, and may be viewed as an artifact created during the historical progression of the field (Dominici et al. 2006 supra). Although AD-SMC may share some of these archetypal cell surface markers with MSCs (for example, CD90 and CD105), they are clearly distinct from MSC in the expression of other established markers (such as CD34, CD45 and CD117). It is therefore challenging to believe that these markers have discriminatory value, as we and others have observed multiple, fully differentiated cell types to robustly express many of the same markers commonly associated with MSC (Jones et al. Rheumatology 2008; 47:126-131). The combined transcriptomic, proteomic and functional analysis of MSC and Ad-SMC presented in the current report will likely be more useful in evaluating whether or not MSC and Ad-SMC represent biologically distinct cell populations (Lodie et al. 2002 supra; Gong et al. 2009 supra).

Our functional comparison of Ad-SMC and MSC focused on the analysis of growth kinetics, smooth muscle phenotype and response to small molecule drugs targeting smooth muscle cell specific signaling pathways. A key feature of stem cells is the capacity for self-renewal. MSC have the capacity for self-renewal as demonstrated by the ability to expand for at least 25-40 passages while retaining the potential for multilineage differentiation (Tintut et al. Circulation 2003; 108: 2505-2510; Reyes et al. Blood 2001; 98:2615-2625; Bruder et al. J Cell Biochem 1997; 64:278-294). In contrast, as shown in FIG. 99, Ad-SMC demonstrate a sharp drop in growth potential within 4-5 days initial plating, consistent with their identification as a terminally differentiated smooth muscle cell type. There is no indication of any capacity for self-renewal.

Another characteristic of stem and progenitor cell populations is the requirement for directed differentiation along defined developmental lineages using a combination of exogenous growth factors, ECM and other controllable components of the extracellular milieu. A number of reports have focused on the regulated differentiation of MSC from adipose or bone marrow for applications in tissue engineering and regenerative medicine. For example, adipose-derived MSC were differentiated into smooth muscle like cells using inductive media containing 100 U/ml heparin for up to 6 weeks prior to seeding polymeric bladder dome-like scaffold structures that demonstrated evidence of functionality in a rat cystectomy model (Jack et al. 2009 supra). In addition, TGF-β or small molecule agonists targeting the TGF-β signaling pathway including sphingosylphosphorylcholine, bradykinin and angiotensin II have also been used for induction of a smooth muscle like phenotype from adipose or bone marrow derived MSC (Gong et al. 2009 supra; Kim et al. Cell Signal 2008; 20:1882-1889; Jeon et al. 2006 supra; Kim et al. Int J Biochem Cell Biol 40; 2482-2491). A less targeted approach, epigenomic reprogramming with the DNA demethylating agent 5-azaC, has been used to direct bone marrow-derived MSC towards a cardiomyocyte-like phenotype (Xu et al. Exp Biol Med 2004; 229:623-631). Dedifferentiated adipocytes may also be driven along a smooth muscle lineage using TGF-β and have been reported to contribute towards bladder tissue regeneration in a mouse bladder injury model (Sakuma et al. J Urol 2009 July; 182(1):355-65. Epub 2009 May 20). Finally, methods for TGF-β induced differentiation of smooth muscle cells from bone-marrow derived cells have been described (Kanematsu et al. Am J Pathol 2005; 166:565-573; Becker et al. Int J Artif Organs 2008; 31:951-9). Taken together, these reports typically present a MSC-like population with little or no expression of any smooth muscle cell associated markers prior to treatment with an inductive cytokine or small molecule agonist.

In marked contrast, we have been able to directly isolate and expand a smooth muscle cell population from adipose expressing all key smooth muscle associated markers including those typically associated with mature smooth muscle cells (SmαA, SM22, SMMHC, calponin and myocardin) without the requirement for directed differentiation by any exogenous agent (Owens et al. Physiol Rev 2004; 84:767-801). This observation strongly suggests that Ad-SMC represent a cell population that is already more fully differentiated from initial isolation and fundamentally distinct from MSC. The acquisition of smooth muscle like features by porcine bone-marrow derived MSC after multiple passaging at high density without the addition of exogenous growth factors has been recently presented (Shukla et al. World J Urol 2008; 26:341-349). However, in contrast to this report, we are able to isolate Ad-SMC with a clear smooth muscle cell phenotype from the earliest passage across multiple, independent preparations, (n=174 as demonstrated in FIG. 94). There is no requirement for "differentiation" through prolonged growth at confluence.

Co-ordinate regulation of multiple smooth muscle cell specific gene expression pathways with signaling cascades regulating contractility through disparate independent kinases, so-called "excitation-transcription" coupling (Wamhoff et al. Circ Res 2006; 98:868-878) is modulated by U46619, a stable analog of thromboxane A2 (TxA2). Treatment with U46619 has been shown to lead to increased expression of SRF and myocardin in adipose-derived MSC and associated up-regulation of the smooth muscle cell specific markers SMαA, calponin, smoothelin and SMMHC (Kim et al. 2009 supra). The effect of TxA2 on excitation-transcription coupling appears to serve as a functional fingerprint for MSC, regardless of the tissue of origin. We have observed that bone-marrow derived MSC recapitulates the up-regulation of smooth muscle markers upon treatment with U46619 as observed for adipose-derived MSC (Kim et al. 2009 supra). However, as shown in FIG. 100, Ad-SMC respond to U46619 in a diametrically opposing manner, showing unambiguous down-regulation of the key functional smooth muscle markers myocardin and SMMHC. Clearly, the organization and regulation of signaling cascades involved in excitation-transcriptional coupling as observed in MSC is fundamentally different in Ad-SMC. This observation provides definitive evidence that Ad-SMC is functionally distinct from adipose or bone-marrow derived MSC and in fact represents a biologically unique cell population.

From where do Ad-SMCs originate and what is their relationship to MSC? Adipose is a heavily vascularized tissue and a number of studies have implicated the perivascular niche as a potential source of both MSC as well as smooth muscle and endothelial cells (Caplan J Pathol 2009; 217:318-324). Pericytes with MSC differentiation potential have been isolated directly from blood vessels as well as from multiple organ systems throughout the body (da Silva Meirelles et al. 2006 supra; da Silva Meirelles et al. Tissue Eng Part A 2009February; 15(2):221-9; Tintut et al. 2003 supra). However, although SMαA+cells have been localized to all capillaries, arterioles and venules of the adipose-derived vascular bed, expression of STRO-1, a key MSC-specific marker, is tightly associated with endothelium and additionally found only within a subset of blood vessels (Lin et al. Stem Cells Dev 2008; 17:1053-1063). Furthermore, expression of the stem cell-specific markers Oct4 and telomerase was observed only rarely, suggesting that truly pluripotent progenitors are uncommon within adipose (Lin et al. 2008 supra). In their entirety, these observations point to MSC, endothelium and smooth muscle occupying distinct spaces within the broader perivascular niche. Nevertheless, there remains the potential for considerable ebb-and-flow across developmental lineages. For example, endothelial cells appear capable of lineage switching towards a smooth muscle cell like phenotype in response to TGF-β or the depletion of pro-angiogenic factors and loss of endothelial cell-cell contact (Krenning et al. Trends Cardiovasc Med 2008; 18:312-323; Krenning et al. Biomaterials 2008; 29:3703-3711).

Finally, adherent cell types with endothelial and smooth muscle phenotypes as well as limited mesenchymal differentiation potential have been identified to circulate in adult peripheral blood (He et al. Stem Cells 2007; 25:69-77). Such circulating smooth muscle cells may contribute to the population of adipose-derived smooth muscle cells, although we have been unable to purify them directly from human adult peripheral blood in meaningful numbers (our unpublished observations). Given that MSC in long term culture also follow a smooth muscle cell like differentiation pathway (Dennis et al. Stem Cells 2002; 20:205-214), we believe that taken together, the published data as well as our observations are consistent with the perivascular niche as a source for a broad continuum of smooth muscle, endothelial and MSC cell types with variable degrees of proliferative and differentiation potential. Although smooth muscle cells generated by the directed differentiation of MSC or isolated directly from adipose continue to show evidence of mesenchymal differentiation plasticity (Kim et al. 2009 supra; our unpublished observations), nonetheless, we believe a clear distinction may be drawn between opposing ends of the spectrum, with adipose-derived smooth muscle cells having unambiguous functional and phenotypic differences relative to MSC of bone-marrow or adipose SVF origin.

In closing, we have demonstrated that the isolation of Ad-SMCs directly from the PO adherent stromal vascular fraction of adipose is tightly dependant on media formulation. Expression of smooth muscle cell markers is robust and consistent and is independent of donor source and across passage. We have shown that Ad-SMCs are phenotypically distinct from MSC as demonstrated by gene expression, proteomic and surface marker analysis, and are functionally distinct from MSC as evaluated by their response to pharmacologic agents targeting smooth muscle cell associated signaling pathways. In contrast to other published reports, isolation of these smooth muscle cells does not require directed differentiation with TGF-β or related small molecules. Ad-SMC may be expanded to up to $10^7$ cells within 4-5 passages, express the full range of smooth muscle cell associated markers and are functionally comparable to bladder-derived SMC both in vitro ($Ca^{2+}$-dependant contractility) and in vivo (regeneration of neo-urinary conduit in swine cystectomy model) (Basu et al., 2009 in preparation; Basu et al. International Society for Stem Cell Research, 7th Annual Meeting, Jul. 8-11, 2009). These data support the conclusion that this population is more accurately described as adipose-derived smooth muscle cells (Ad-SMC), and represents a separate and distinct population compared to other classes of adipose-derived cells including endothelial cells and MSC.

What is claimed is:

1. An implantable construct for replacement of a defective bladder in a human subject comprising
   a) a tubular scaffold having a first open end configured for anastomosis to an opening in the subject's abdominal wall, a second open end configured to connect to a ureter; and
   b) an autologous cell population that is not derived from the defective bladder, deposited on or in a surface of the tubular scaffold,
   wherein the cell population is a smooth muscle cell population derived from adipose tissue or peripheral blood, and wherein the implantable construct is adapted for temporary storage and passage of urine.

2. The implantable construct of claim 1, wherein the first open end is configured to connect to an abdominal wall section.

3. The implantable construct of claim 1, wherein the first open end is configured to form a stoma.

4. The implantable construct of claim 1, wherein the first open end is configured to be positioned flush with the abdominal wall.

5. The implantable construct of claim 1, wherein the first open end is configured to be sutured to the skin of the subject.

6. The implantable construct of claim 1, wherein the first open end is configured to be anastomosed to the skin.

7. The implantable construct of claim 3, wherein the stoma further comprises a stoma button.

8. The implantable construct of claim 1, wherein the tubular scaffold further comprises a side opening configured to connect to a second ureter.

9. The implantable construct of claim 1, wherein the biocompatible scaffold is biodegradable.

10. The implantable construct of claim 1, wherein the scaffold comprises a material selected from the group consisting of polyglycolic acid, polylactic acid, and a copolymer of polyglycolic acid and polylactic acid.

11. The implantable construct of claim 1, wherein the diversion is free of urothelial cells.

12. The implantable construct of claim 1, wherein the smooth muscle cell (SMC) population is not derived from in vitro differentiation of mesenchymal stem cells (MSCs).

13. The implantable construct of claim 1, wherein the tubular scaffold is coated with a biocompatible and biodegradable shape-setting material.

14. The implantable construct of claim 13, wherein the shape-setting material comprises a poly-lactide-co-glycolide copolymer.

* * * * *